United States Patent
Liu et al.

(10) Patent No.: US 8,716,292 B2
(45) Date of Patent: May 6, 2014

(54) RIMINOPHENAZINES WITH 2-(HETEROARYL)AMINO SUBSTITUENTS AND THEIR ANTI-MICROBIAL ACTIVITY

(75) Inventors: Kai Liu, Beijing (CN); Christopher B. Cooper, Lawrenceville, NJ (US); Haihong Huang, Beijing (CN); Chun Li, Beijing (CN); Binna Liu, Beijing (CN); Yang Liu, Beijing (CN); Zhenkun Ma, Westfield, NJ (US); Jingbin Wang, Beijing (CN); Dali Yin, Beijing (CN); Dongfeng Zhang, Beijing (CN); Gang Zhang, Beijing (CN); Hao Zhang, Beijing (CN)

(73) Assignee: Global Alliance for TB Drug Development, New York, NY (US)

( * ) Notice: Subject to any disclaimer, the term of this patent is extended or adjusted under 35 U.S.C. 154(b) by 0 days.

(21) Appl. No.: 13/171,102

(22) Filed: Jun. 28, 2011

(65) Prior Publication Data
US 2012/0071472 A1    Mar. 22, 2012

Related U.S. Application Data

(60) Provisional application No. 61/359,638, filed on Jun. 29, 2010.

(51) Int. Cl.
*A61K 31/495*    (2006.01)

(52) U.S. Cl.
USPC ........... 514/250; 544/115; 544/333; 544/348; 544/405; 546/200; 546/268.1; 549/13; 549/356

(58) Field of Classification Search
USPC ................. 514/250; 544/115, 333, 348, 405; 546/200, 268.1; 549/13, 356
See application file for complete search history.

(56) References Cited

U.S. PATENT DOCUMENTS

| | | | |
|---|---|---|---|
| 2,875,204 A | 2/1959 | Barry et al. |
| 2,943,089 A | 6/1960 | Barry et al. |
| 2,946,792 A | 7/1960 | Barry et al. |
| 2,948,726 A | 8/1960 | Barry et al. |
| 3,499,899 A | 3/1970 | Girard et al. |
| 3,592,814 A | 7/1971 | Barry et al. |
| 4,859,667 A | 8/1989 | Lau et al. |
| 5,763,443 A | 6/1998 | Medlen et al. |

FOREIGN PATENT DOCUMENTS

| | | |
|---|---|---|
| EP | 0374991 A1 | 6/1990 |
| WO | 97/45120 A1 | 12/1997 |
| WO | 2009/042114 A2 | 4/2009 |

OTHER PUBLICATIONS

Barry, V.C., et al; A New Series of Phenazines (Rimino-Compounds) With High Antituberculosis Activity; Nature, No. 4568, pp. 1013-1015, May 18, 1957.
Jagannath, C., et al.; Chemotherapeutic Activity of Clofazimine and Its Analogues Against *Mycobacterium tuberculosis*; American Journal of Respiratory and Critical Care Medicine, vol. 151, pp. 1083-1086, 1995.
Martins, M., et al; Inhibitors of Ca2+ and K+ Transport Enhance Intracellular Killing of M. Tuberculosis by Non-Killing Macrophages; In Vivo: International Journal of Experimental and Clinical Pathophysiology and Drug Research, vol. 22, No. 1, pp. 69-75, Jan. 1, 2008.
O'Sullivan, J.F., et al; Clofazimine Analogues Active Against a Clofazimine-Resistant Organism; Journal of Medicinal Chemistry; vol. 31, No. 3, pp. 567-572, Mar. 1, 1988.
Reddy, V.M, et al; Antituberculosis Activities of Clofazimine and Its New Analogs B4154 and B4157, Antimicrobial Agents and Chemotherapy, vol. 40, No. 3, pp. 633-636, Mar. 1996.
Reddy, V.M, et al; Antimycobacterial Activities of Riminophenazines, Journal of Antimicrobial Chemotherapy (1999) 43, 615-623.
European Patent Office; International Search Report and Written Opinion; PCT Application No. PCT/US2011/042221, Aug. 22, 2011.
Ma, Z., et al; Toward an Optimized Therapy for Tuberculosis? Drugs in Clinical Trials and in Preclinical Development; Clin Chest Med 30 (2009) 755-768.
European Patent Office, Second Written Opinion; PCT Application No. PCT/US2011/042221, May 25, 2012.
European Patent Office, International Preliminary Report on Patentability; PCT Application No. PCT/US2011/042221, Aug. 14, 2012.
European Patent Office, Response to Office Action; European Application No. 11731600.0, 5 pages; Apr. 22, 2013.
Chinese Patent Office; First Office Action (in Chinese); Chinese Patent Application No. 201180032107.9; Aug. 26, 2013, 7 pages.
Chinese Patent Office; First Office Action (in English); Chinese Patent Application No. 201180032107.9; Aug. 26, 2013, 10 pages.

*Primary Examiner* — Douglas M Willis
(74) *Attorney, Agent, or Firm* — Jackson Walker L.L.P.

(57) ABSTRACT

The present invention relates to riminophenazines having heteroaromatic substitutions, including those with 2-heteroaryl-amino substituents, to their preparation, and to their use as drugs for treating *Mycobacterium tuberculosis* and other microbial infections, either alone or in combination with other anti-infective treatments. A general representation of the 2-(heteroaryl)amino-riminophenazines is shown below.

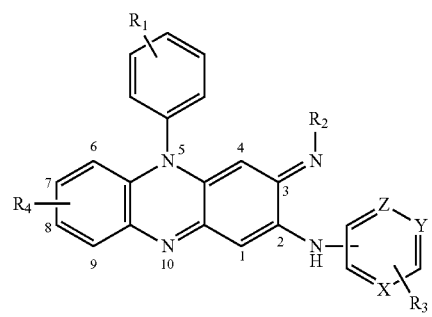

7 Claims, 1 Drawing Sheet

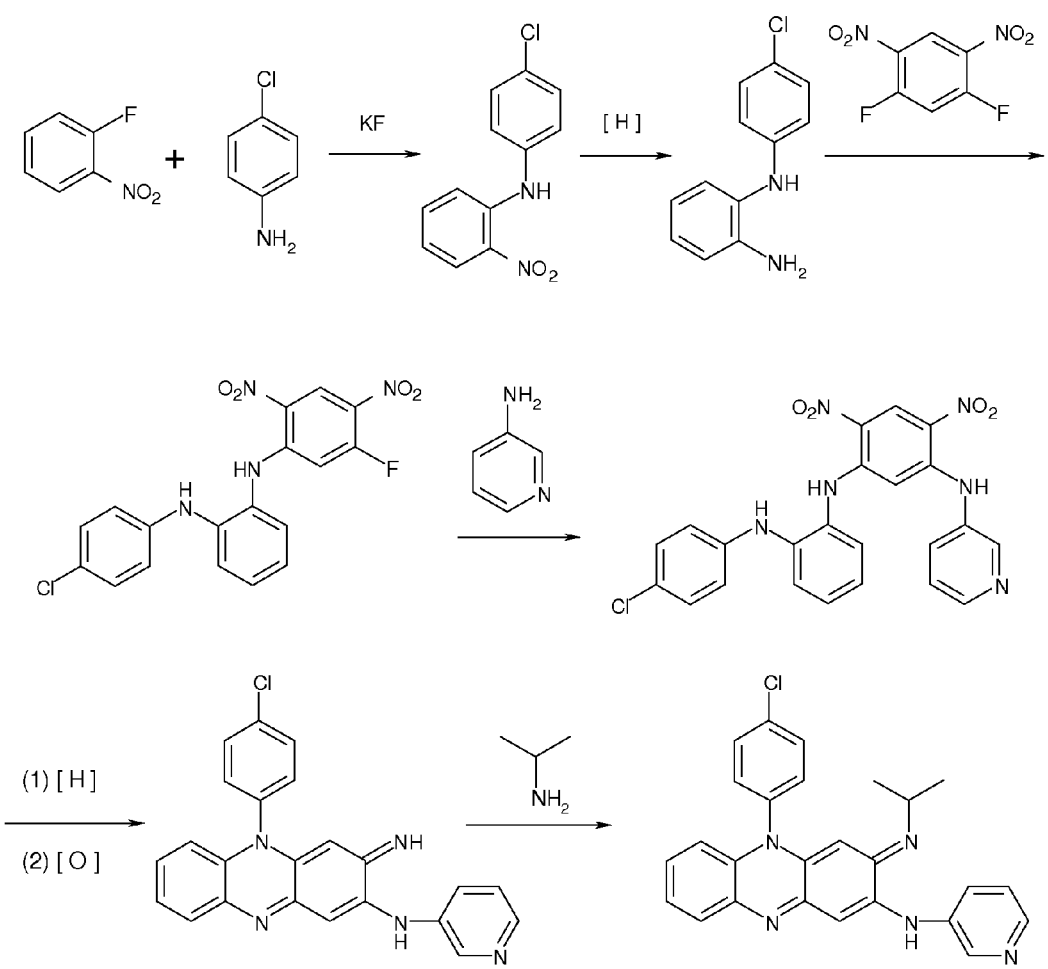

RIMINOPHENAZINES WITH 2-(HETEROARYL)AMINO SUBSTITUENTS AND THEIR ANTI-MICROBIAL ACTIVITY

RELATED APPLICATION

This application claims priority to U.S. Provisional Patent Application No. 61/359,638, filed Jun. 29, 2010, the entire content of which is hereby incorporated by reference.

BACKGROUND

The present invention relates to riminophenazines having heteroaromatic substitutions, to their preparation, and to their use as drugs for treating *Mycobacterium tuberculosis* and other microbial infections, either alone or in combination with other anti-infective treatments.

*Mycobacterium tuberculosis* ("M.tb") is the causative agent of tuberculosis ("TB"), a devastating infectious disease. It is estimated that about 2 million TB patients die each year globally. There are urgent needs for new drugs to fight the increasing threat of tuberculosis.

Current first-line drug therapy for tuberculosis is long and complex, involving multidrug combinations (usually isoniazid, rifampin, pyrazinamide and ethambutol) given daily for 6 to 9 months. Furthermore, these drugs are relatively ineffective against the resistant form of the disease and difficult to use to treat TB/HIV co-infected patients due to drug-drug interactions (Ma et al., 2009).

Clofazimine was first reported in 1957 by Barry and was found to possess potent antituberculosis activity (Barry, V. C., 1957). It demonstrated in vivo anti-TB activity in mice and hamsters, but failed to show efficacy in guinea pig and monkey models. The major drawbacks of clofazimine are skin discoloration, high fat tissue distribution, and very long half-life (70 days). New riminophenazine analogues have been synthesized to identify compounds with improved activity, lower side effects, and better solubility. Among those compounds, B4154 and B4157 showed improved in vitro activity (V. M. Reddy, 1996).

The structures of clofazimine, B4154, and B4157 are shown below.

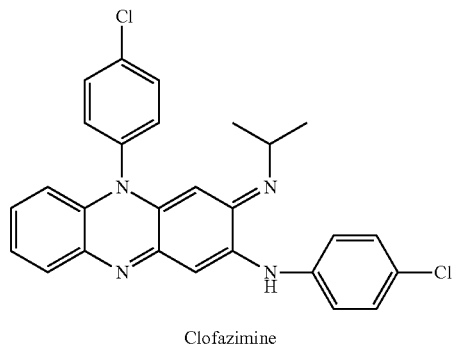
Clofazimine

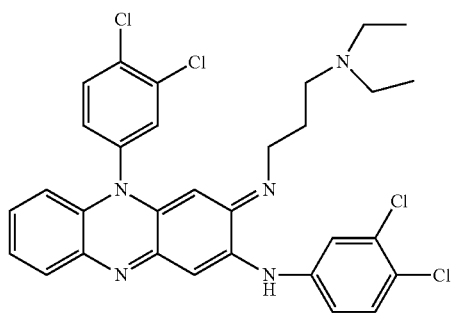
B4154

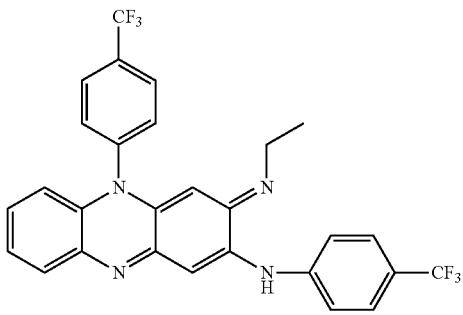
B4157

One of the major advantages of the riminophenazine class is their low frequency for resistance development. They are highly potent against various forms of drug-resistant TB. New and improved riminophenazines could potentially contribute to the treatment of both drug-susceptible and drug-resistant tuberculosis.

SUMMARY

The current invention pertains to riminophenazines with 2-(heteroaryl)amino substituents, their methods of preparation, and their use as treatments for tuberculosis and other microbial infections.

In the current riminophenazine molecules, the phenylamino group attached to the 2-position of the riminophenazine core can be replaced by a heteroarylamino group as shown in general formula (I) below.

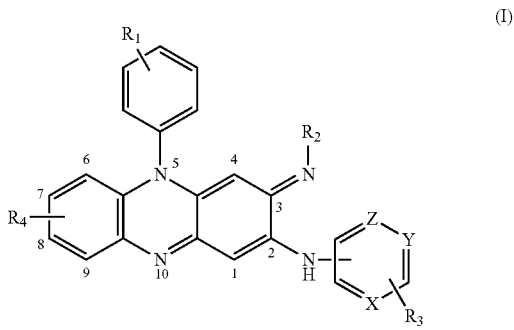
(I)

In this structure, $R_1$, $R_2$, $R_3$ and $R_4$ can be a variety of substituents. The heteroaromatic ring represents a nitrogen-containing heteroaromatic group. It can be substituted or non-substituted pyridyl wherein X=N and Y=Z=CH, or it can be pyrimidyl wherein X=Y=N and Z=CH, or it can be pyrazinyl wherein X=Z=N and Y=CH. The most preferred compounds include a group of riminophenazines with the 2-phenylamino group replaced by a 2-(3-pyridyl)amino substitution.

The synthesis of riminophenazines of formula (I) follows a modified synthetic procedure reported in U.S. Pat. No. 3,499,899. For example riminophenazines with 2-(3-pyridyl)amino substitutions can be prepared by the following route: 1,5-Difluoro-2,4-dinitrobenzene (DFDNB) was used to ensure easier substitution of the two fluoro by amines, as shown in FIG. 1. The synthesis is started with 1-fluoro-2-nitrobenzene and anilines. The reaction mixture is then heated at 180-190° C. to give 1-anilino-2-nitrobenzene. After reduction of the nitro group, it is coupled with 1,5-difluoro-2,4-dinitrobenzene and then the second fluoro is replaced by 3-aminopyridines. The two nitro groups are reduced either by Zn/acetic acid or by catalytic hydrogenation over Pd—C. After reduction, the tetra-amino compound (without isolation) is stirred and oxidized by air to form the corresponding riminophenazine. The imino group is further derivatized by different aliphatic and heteroaliphatic amines to give the final products. A general representation of the 2-N-(3-pyridyl)-riminophenazines is shown as general formula (II) below.

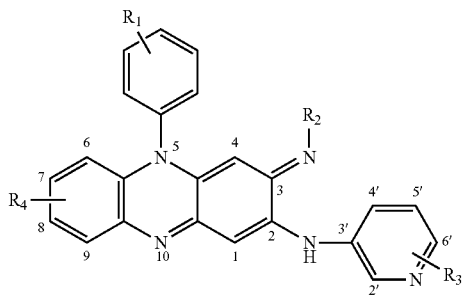

In this representation shown as general formula (II), $R_1$ can be H, alkyl, alkoxyl, cycloalkyl, heterocycloalkyl, Cl, F, Br, $CF_3$, $OCH_3$, $OCF_3$, $SCH_3$, $SOCH_3$, or a combination of any two or three of them, the same or different. $R_3$ can be H, alkyl, alkoxyl, cycloalkyl, heterocycloalkyl, halo (F, Cl, Br), NAc, or a combination of any two or three of them, the same or different. $R_4$ can be H, halo (Cl, Br, F), alkyl, alkoxyl, or mono-, di-, or cycloalkylamino with or without an additional O, S or NR' in the ring, where R' is an alkyl or substituted alkyl group; and $R_2$ can be alkyl, cycloalkyl, substituted alkyl or substituted cycloalkyl; cycloalkyl herein could have an additional O, S, or NR' in the ring, where R' is as defined above. A "substituted alkyl or cycloalkyl" is defined as alkyl or cycloalkyl substituted by the groups selected from H, alkyl, alkyoxy, halo, or mono-, di- or cycloalkylamino.

The anti-tuberculosis activity of the compounds was tested against H37Rv strains both in vitro and in vivo. In the in vitro assay, most of the compounds in this class showed equal or better activity when compared with clofazimine, rifampicin, or isoniazid.

BRIEF DESCRIPTION OF THE DRAWINGS

FIG. 1 shows a general synthetic scheme for the synthesis of riminophenazines with 2-(3-pyridyl)-amino substitutions.

DETAILED DESCRIPTION

The current invention pertains to riminophenazines with 2-(heteroaryl)amino substituents, their methods of preparation, and uses of the compounds as treatment for tuberculosis and other microbial infections.

A general representation of the 2-(heteroaryl)amino-riminophenazines is shown as general formula (I) below.

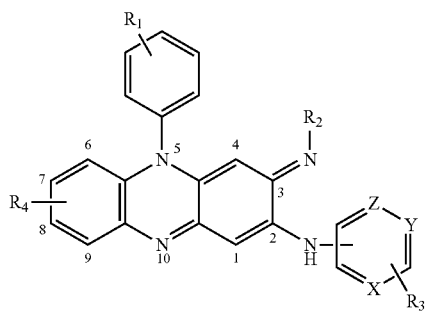

In this structure, $R_1$, $R_2$, $R_3$ and $R_4$ can be a variety of substituents. $R_1$ can be a substituent selected from the group consisting of H, alkyl, substituted alkyl, alkoxyl, substituted alkoxyl, monoalkylamino, dialkylamino, cycloalkylamino, substituted cycloalkylamino, halo, $CF_3$, $OCF_3$, $SCH_3$, $SOCH_3$, and combinations of any two or three of these listed substitutents, wherein the two or three substituents are the same or different. $R_3$ can be a substituent selected from the group consisting of H, alkyl, substituted alkyl, alkoxyl, substituted alkoxyl, monoalkylamino, dialkyl amino, cycloalkylamino, substituted cycloalkylamino, halo, NAc, and combinations of any two or three of these listed substituents, wherein the two or three substituents are the same or different. $R_4$ can be a substituent selected from the group consisting of H, alkyl, substituted alkyl, alkoxyl, substituted alkoxyl, halo, or monoalkylamino, dialkylamino, and cycloalkylamino. The heteroaromatic ring containing X, Y, and Z represents a N-containing heteroaromatic group. It can be substituted or non-substituted pyridyl wherein X=N and Y=Z=CH, pyrimidyl wherein X=Y=N and Z=CH, or pyrazinyl wherein X=Z=N and Y=CH.

Additionally, with regard to $R_1$, $R_3$, and $R_4$, if they are cycloalkylamino rings, they can also include O, S, or NR' in the ring, wherein R' is an alkyl or substituted alkyl group. These cycloalkylamino rings can also be further substituted. With regard to $R_2$, if it is a cycloalkyl ring, then it can also include O, S, or NR' in the ring, wherein R' is an alkyl or substituted alkyl group. The cycloalkyl ring can also be further substituted.

The preferred compounds include a group of riminophenazines with 2-phenylamino replaced by a 2-(3-pyridyl)-amino substitution. A general representation of the 2-(3-pyridyl) amino-riminophenazines is shown as general formula (II) below.

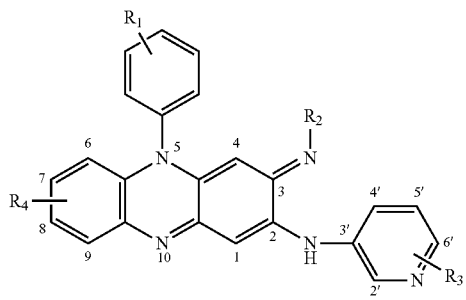

In this representation shown as general formula (II), $R_1$ can be H, alkyl, alkoxyl, cycloalkyl, heterocycloalkyl, Cl, F, Br, $CF_3$, $OCH_3$, $OCF_3$, $SCH_3$, $SOCH_3$, or a combination of any two or three of them, the same or different. $R_3$ can be H, alkyl, alkoxyl, cycloalkyl, heterocycloalkyl, halo (F, Cl, Br), NAc, or a combination of any two or three of them, the same or different. $R_4$ can be H, halo (Cl, Br, F), alkyl, alkoxyl, or mono-, di-, or cycloalkylamino with or without an additional O, S or NR' in the ring, where R' is an alkyl or substituted alkyl group. $R_2$ can be a alkyl, cycloalkyl, substituted alkyl or substituted cycloalkyl. If it is cycloalkyl, it could have an additional O, S, or NR' in the ring, where R' is as defined above. A "substituted alkyl or cycloalkyl" is defined as alkyl or cycloalkyl substituted by the groups selected from H, alkyl, alkyoxy, halo, or mono-, di- or cycloalkylamino.

Table 1 below shows a variety of examples of the 2-(3-pyridyl)amino-riminophenazines by indicating the structures shown as general formula (II) present at $R_1$, $R_2$, $R_3$ and $R_4$ of the FIGURE above, as well as their in vitro activity against *Mycobacterium tuberculosis* H37Rv strains, described in Example 2 below.

TABLE 1

| Compds | R₁ | R₂ | R₃ | R₄ | MIC (μg/mL) against H37Rv |
|---|---|---|---|---|---|
| TBI-054 | H | isopropyl | H | H | 0.03 |
| TBI-055 | H | 1-methylpiperidin-4-yl-methyl | H | H | 0.5 |
| TBI-056 | H | 3-morpholinopropyl | H | H | 0.25 |
| TBI-057 | H | (1-isobutylpiperidin-4-yl)methyl | H | H | 0.125 |
| TBI-058 | H | (tetrahydro-2H-pyran-4-yl)methyl | H | H | 0.06 |
| TBI-059 | H | (4-methoxycyclohexyl)methyl | H | H | 0.125 |
| TBI-060 | H | (1-cyclopentylpiperidin-4-yl)methyl | H | H | 1.0 |
| TBI-300 | 4-CH₃ | isopropyl | H | H | 0.03 |
| TBI-301 | 4-CH₃ | (4-methoxycyclohexyl)methyl | H | H | 0.06 |
| TBI-302 | 4-CH₃ | 3-morpholinopropyl | H | H | 0.125 |
| TBI-303 | 4-CH₃ | (tetrahydro-2H-pyran-4-yl)methyl | H | H | 0.03 |
| TBI-304 | 4-CH₃ | 1-methylpiperidin-4-yl-methyl | H | H | 0.25 |
| TBI-305 | 4-CH₃ | (1-isobutylpiperidin-4-yl)methyl | H | H | 0.125 |
| TBI-307 | 4-CH₃ | (1-cyclopentylpiperidin-4-yl)methyl | H | H | 0.125 |
| TBI-416 | 4-Cl | isopropyl | H | H | 0.03 |

TABLE 1-continued

| Compds | R₁ | R₂ | R₃ | R₄ | MIC (µg/mL) against H37Rv |
|---|---|---|---|---|---|
| TBI-427 | 4-Cl | N-methylpiperidin-4-yl | H | H | 0.125 |
| TBI-428 | 4-Cl | 1-methylpiperidin-4-yl ethyl | H | H | 0.25 |
| TBI-433 | 4-Cl | 3-morpholinopropyl | H | H | 0.25 |
| TBI-434 | 4-Cl | tetrahydro-2H-pyran-4-yl | H | H | 0.03 |
| TBI-435 | 4-Cl | 1-isobutylpiperidin-4-yl | H | H | 0.25 |
| TBI-436 | 4-Cl | 4-methoxycyclohexyl | H | H | 0.03 |
| TBI-437 | 4-Cl | 1-cyclopentylpiperidin-4-yl | H | H | 0.125 |
| TBI-422 | 4-Cl | cyclohexyl | H | H | 0.06 |
| TBI-458 | 4-Cl | tetrahydro-2H-thiopyran-4-yl | H | H | 0.018 |
| TBI-679 | 4-F | isopropyl | H | H | 0.03 |
| TBI-680 | 4-F | 3-morpholinopropyl | H | H | 0.5 |
| TBI-681 | 4-F | tetrahydro-2H-pyran-4-yl | H | H | 0.06 |
| TBI-682 | 4-F | 1-methylpiperidin-4-yl | H | H | 0.25 |
| TBI-683 | 4-F | 1-isobutylpiperidin-4-yl | H | H | 0.125 |
| TBI-684 | 4-F | 1-cyclopentylpiperidin-4-yl | H | H | 0.5 |

TABLE 1-continued
| Compds | R₁ | R₂ | R₃ | R₄ | MIC (μg/mL) against H37Rv |
|---|---|---|---|---|---|
| TBI-685 | 4-F | 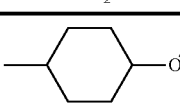 | H | H | 0.125 |
| TBI-920 | 4-F | 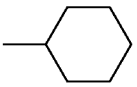 | H | H | 0.029 |
| TBI-921 | 4-F |  | H | H | 0.434 |
| TBI-922 | 4-F |  | H | H | 0.012 |
| TBI-923 | 4-F |  | H | H | 0.021 |
| TBI-678 | 4-CF₃ |  | H | H | 0.03 |
| TBI-686 | 4-CF₃ | 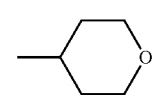 | H | H | 0.125 |
| TBI-687 | 4-CF₃ | 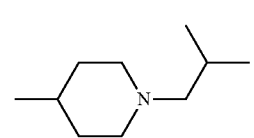 | H | H | 0.06 |
| TBI-688 | 4-CF₃ |  | H | H | 0.03 |
| TBI-689 | 4-CF₃ | 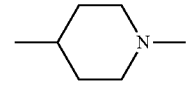 | H | H | 0.125 |
| TBI-690 | 4-CF₃ | 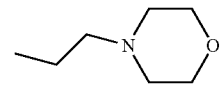 | H | H | 0.125 |
| TBI-691 | 4-CF₃ | 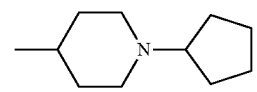 | H | H | 0.06 |
| TBI-157 | 4-OCF₃ |  | H | H | 0.03 |
| TBI-158 | 4-OCF₃ | 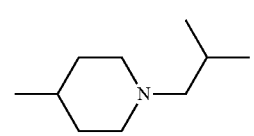 | H | H | 0.03 |
| TBI-159 | 4-OCF₃ | 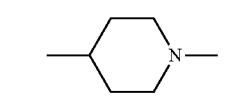 | H | H | 0.25 |

TABLE 1-continued
| Compds | R$_1$ | R$_2$ | R$_3$ | R$_4$ | MIC (μg/mL) against H37Rv |
|---|---|---|---|---|---|
| TBI-160 | 4-OCF$_3$ | 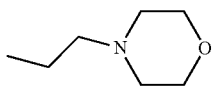 | H | H | 0.125 |
| TBI-161 | 4-OCF$_3$ | 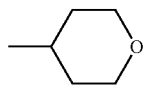 | H | H | 0.03 |
| TBI-162 | 4-OCF$_3$ | 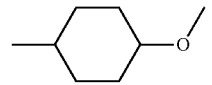 | H | H | 0.03 |
| TBI-163 | 4-OCF$_3$ | 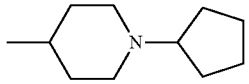 | H | H | 0.06 |
| TBI-061 | H |  | 2'-MeO | H | 0.06 |
| TBI-062 | H |  | 2'-MeO | H | 0.061 |
| TBI-063 | H | 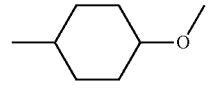 | 2'-MeO | H | 0.06 |
| TBI-064 | H | 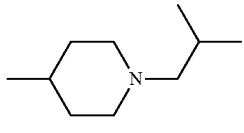 | 2'-MeO | H | 0.057 |
| TBI-065 | H | 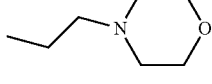 | 2'-MeO | H | 0.080 |
| TBI-066 | H | 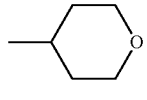 | 2'-MeO | H | 0.026 |
| TBI-079 | H | 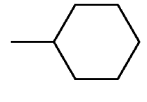 | 2'-MeO | H | 0.068 |
| TBI-087 | H | 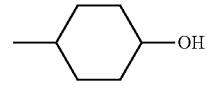 | 2'-MeO | H | 0.466 |
| TBI-097 | H |  | 2'-MeO | H | 0.032 |
| TBI-505 | H | 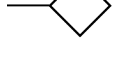 | 2'-MeO | H | 0.043 |
| TBI-073 | H |  | 2'-Me | H | 0.058 |
| TBI-075 | H | 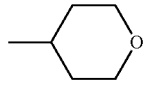 | 2'-Me | H | 0.328 |

TABLE 1-continued

| Compds | R₁ | R₂ | R₃ | R₄ | MIC (μg/mL) against H37Rv |
|---|---|---|---|---|---|
| TBI-076 | H | cyclohexyl-OMe | 2'-Me | H | 0.042 |
| TBI-077 | H | cyclohexyl | 2'-Me | H | 0.016 |
| TBI-092 | H | cyclohexyl-OH | 2'-Me | H | 0.5 |
| TBI-078 | H | Me | 2'-Me | H | 0.019 |
| TBI-067 | H | isopropyl | 6'-Me | H | 0.048 |
| TBI-068 | H | 4-(isobutyl)piperidinyl | 6'-Me | H | 0.156 |
| TBI-069 | H | 4-(N-methyl)piperidinyl | 6'-Me | H | 0.219 |
| TBI-072 | H | cyclohexyl-OMe | 6'-Me | H | 0.091 |
| TBI-070 | H | tetrahydropyranyl | 6'-Me | H | 0.080 |
| TBI-086 | H | cyclohexyl-OH | 6'-Me | H | 0.5 |
| TBI-095 | H | cyclopropyl | 6'-Me | H | 0.048 |
| TBI-506 | H | cyclobutyl | 6'-Me | H | 0.05 |
| TBI-080 | H | cyclohexyl | 6'-Me | H | 0.243 |
| TBI-081 | H | isopropyl | 5'-Me | H | 0.117 |
| TBI-082 | H | cyclohexyl | 5'-Me | H | 0.111 |
| TBI-083 | H | tetrahydropyranyl | 5'-Me | H | 0.049 |

TABLE 1-continued

| Compds | R₁ | R₂ | R₃ | R₄ | MIC (μg/mL) against H37Rv |
|---|---|---|---|---|---|
| TBI-084 | H | 4-methoxycyclohexyl | 5'-Me | H | 0.059 |
| TBI-085 | H | 4-hydroxycyclohexyl | 5'-Me | H | 0.5 |
| TBI-096 | H | cyclopropyl | 5'-Me | H | 0.069 |
| TBI-510 | H | isopropyl | 6'-MeO | H | 0.5 |
| TBI-511 | H | cyclopropyl | 6'-MeO | H | 0.177 |
| TBI-512 | H | cyclobutyl | 6'-MeO | H | 0.41 |
| TBI-513 | H | cyclohexyl | 6'-MeO | H | 0.244 |
| TBI-514 | H | 4-methoxycyclohexyl | 6'-MeO | H | 0.243 |
| TBI-515 | H | tetrahydropyran-4-yl | 6'-MeO | H | 0.233 |
| TBI-088 | 4-Br | isopropyl | H | H | 0.023 |
| TBI-089 | 4-Br | cyclohexyl | H | H | 0.021 |
| TBI-090 | 4-Br | cyclopropyl | H | H | 0.016 |
| TBI-091 | 4-Br | 4-methoxycyclohexyl | H | H | 0.062 |
| TBI-093 | 4-Br | tetrahydropyran-4-yl | H | H | 0.163 |
| TBI-094 | 4-Br | 4-hydroxycyclohexyl | H | H | 0.5 |
| TBI-098 | 4-Br | cyclobutyl | H | H | 0.028 |
| TBI-099 | 4-Br | isopropyl | 6'-Me | H | 0.049 |

TABLE 1-continued
| Compds | R₁ | R₂ | R₃ | R₄ | MIC (µg/mL) against H37Rv |
|---|---|---|---|---|---|
| TBI-100 | 4-Br |  | 6'-Me | H | 0.011 |
| TBI-501 | 4-Br |  | 6'-Me | H | 0.09 |
| TBI-502 | 4-Br | 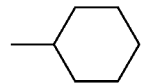 | 6'-Me | H | 0.217 |
| TBI-503 | 4-Br | 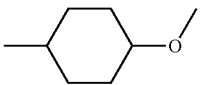 | 6'-Me | H | 0.097 |
| TBI-504 | 4-Br | 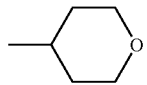 | 6'-Me | H | 0.044 |
| TBI-507 | 4-Br |  | 2'-Me | H | 0.062 |
| TBI-508 | 4-Br | 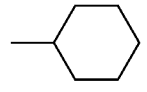 | 2'-Me | H | 0.021 |
| TBI-509 | 4-Br | 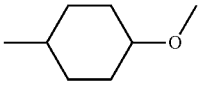 | 2'-Me | H | 0.015 |
| TBI-516 | 4-Br |  | 2'-MeO | H | 0.049 |
| TBI-517 | 4-Br | 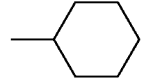 | 2'-MeO | H | 0.029 |
| TBI-308 | 4-CH₃ |  | 2'-MeO | H | 0.125 |
| TBI-309 | 4-CH₃ | 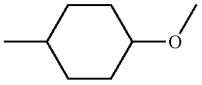 | 2'-MeO | H | 0.06 |
| TBI-310 | 4-CH₃ | 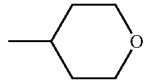 | 2'-MeO | H | 0.03 |
| TBI-311 | 4-CH₃ | 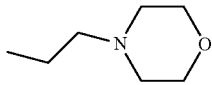 | 2'-MeO | H | 0.125 |
| TBI-313 | 4-CH₃ | 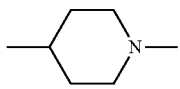 | 2'-MeO | H | 0.016 |
| TBI-314 | 4-CH₃ | 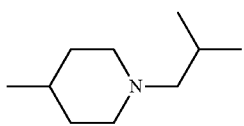 | 2'-MeO | H | 0.024 |

TABLE 1-continued

| Compds | R₁ | R₂ | R₃ | R₄ | MIC (μg/mL) against H37Rv |
|---|---|---|---|---|---|
| TBI-312 | 4-CH₃ | cyclohexyl-methyl | 2'-Me | H | 0.053 |
| TBI-321 | 4-CH₃ | isobutyl | 2'-Me | H | 0.419 |
| TBI-322 | 4-CH₃ | 4-methoxycyclohexyl-methyl | 2'-Me | H | 0.092 |
| TBI-323 | 4-CH₃ | tetrahydropyran-4-yl-methyl | 2'-Me | H | 0.057 |
| TBI-324 | 4-CH₃ | morpholinopropyl | 2'-Me | H | 0.120 |
| TBI-325 | 4-CH₃ | 1-isobutylpiperidin-4-yl-methyl | 2'-Me | H | 0.056 |
| TBI-326 | 4-CH₃ | 1-methylpiperidin-4-yl-methyl | 2'-Me | H | 0.100 |
| TBI-306 | 4-CH₃ | cyclohexyl | 6'-Me | H | 0.106 |
| TBI-315 | 4-CH₃ | isobutyl | 6'-Me | H | 0.057 |
| TBI-316 | 4-CH₃ | 4-methoxycyclohexyl-methyl | 6'-Me | H | 0.028 |
| TBI-317 | 4-CH₃ | tetrahydropyran-4-yl-methyl | 6'-Me | H | 0.055 |
| TBI-318 | 4-CH₃ | morpholinopropyl | 6'-Me | H | 0.087 |
| TBI-319 | 4-CH₃ | 1-methylpiperidin-4-yl-methyl | 6'-Me | H | 0.173 |
| TBI-320 | 4-CH₃ | 1-isobutylpiperidin-4-yl-methyl | 6'-Me | H | 0.110 |
| TBI-693 | 4-F | isobutyl | 2'-Me | H | 0.03 |

TABLE 1-continued
| Compds | R₁ | R₂ | R₃ | R₄ | MIC (μg/mL) against H37Rv |
|---|---|---|---|---|---|
| TBI-1012 | 4-F | 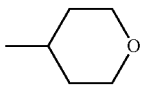 | 2'-Me | H | 0.026 |
| TBI-1013 | 4-F |  | 2'-Me | H | 0.019 |
| TBI-1014 | 4-F |  | 2'-Me | H | 0.025 |
| TBI-1015 | 4-F |  | 2'-Me | H | 0.387 |
| TBI-1018 | 4-F | 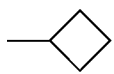 | 2'-Me | H | 0.028 |
| TBI-1023 | 4-F | 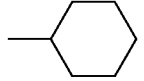 | 2'-Me | H | 0.0075 |
| TBI-1002 | 4-F |  | 2'-MeO | H | 0.016 |
| TBI-1003 | 4-F | 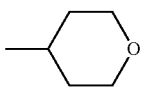 | 2'-MeO | H | 0.039 |
| TBI-1004 | 4-F |  | 2'-MeO | H | 0.038 |
| TBI-1005 | 4-F |  | 2'-MeO | H | 0.213 |
| TBI-1008 | 4-F | 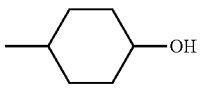 | 2'-MeO | H | 0.248 |
| TBI-1009 | 4-F | 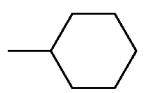 | 2'-MeO | H | 0.03 |
| TBI-1010 | 4-F |  | 2'-MeO | H | 0.011 |
| TBI-1016 | 4-F | 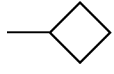 | 2'-MeO | H | 0.037 |
| TBI-692 | 4-F |  | 6'-Me | H | 0.06 |
| TBI-1001 | 4-F | 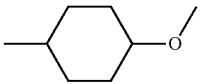 | 6'-Me | H | 0.06 |

TABLE 1-continued
| Compds | R₁ | R₂ | R₃ | R₄ | MIC (μg/mL) against H37Rv |
|---|---|---|---|---|---|
| TBI-900 | 4-F | 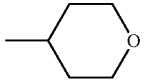 | 6'-Me | H | 0.125 |
| TBI-901 | 4-F | 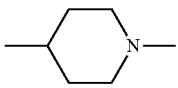 | 6'-Me | H | 0.102 |
| TBI-902 | 4-F | 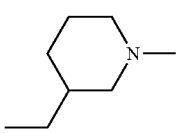 | 6'-Me | H | 0.058 |
| TBI-904 | 4-F | 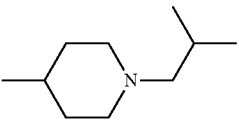 | 6'-Me | H | 0.016 |
| TBI-1017 | 4-F | 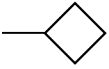 | 6'-Me | H | 0.056 |
| TBI-905 | 4-F | 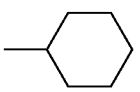 | 6'-Me | H | 0.057 |
| TBI-906 | 4-F | 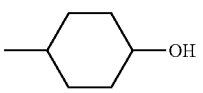 | 6'-Me | H | 0.5 |
| TBI-907 | 4-F | 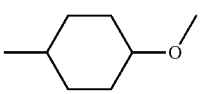 | 6'-Me | H | 0.063 |
| TBI-908 | 4-F |  | 6'-Me | H | 0.03 |
| TBI-90B | 4-F | 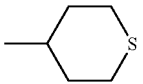 | 6'-Me | H | 0.397 |
| TBI-910 | 4-F |  | 6'-NAc | H | 0.147 |
| TBI-911 | 4-F | 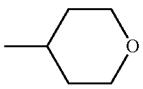 | 6'-NAc | H | 0.360 |
| TBI-912 | 4-F |  | 6'-NAc | H | 0.351 |
| TBI-913 | 4-F | 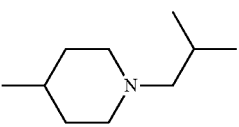 | 6'-NAc | H | 0.144 |
| TBI-915 | 4-F | 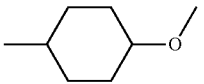 | 6'-NAc | H | 0.211 |

TABLE 1-continued

| Compds | R₁ | R₂ | R₃ | R₄ | MIC (μg/mL) against H37Rv |
|---|---|---|---|---|---|
| TBI-916 | 4-F | cyclohexyl | 6'-NAc | H | 0.014 |
| TBI-917 | 4-F | 4-hydroxycyclohexyl | 6'-NAc | H | 1.0 |
| TBI-438 | 4-Cl | isobutyl | 2'-MeO | H | 0.03 |
| TBI-439 | 4-Cl | propyl-morpholine | 2'-MeO | H | 0.06 |
| TBI-440 | 4-Cl | 1-methylpiperidin-4-yl | 2'-MeO | H | 0.06 |
| TBI-442 | 4-Cl | 1-isobutylpiperidin-4-yl | 2'-MeO | H | 0.016 |
| TBI-443 | 4-Cl | tetrahydropyran-4-yl | 2'-MeO | H | 0.016 |
| TBI-444 | 4-Cl | 4-methoxycyclohexyl | 2'-MeO | H | 0.016 |
| TBI-451 | 4-Cl | cyclohexyl | 2'-MeO | H | 0.057 |
| TBI-441 | 4-Cl | isobutyl | 6'-Me | H | 0.06 |
| TBI-445 | 4-Cl | propyl-morpholine | 6'-Me | H | 0.076 |
| TBI-446 | 4-Cl | 1-methylpiperidin-4-yl | 6'-Me | H | 0.016 |
| TBI-447 | 4-Cl | 1-isobutylpiperidin-4-yl | 6'-Me | H | 0.028 |
| TBI-449 | 4-Cl | tetrahydropyran-4-yl | 6'-Me | H | 0.030 |
| TBI-450 | 4-Cl | 4-methoxycyclohexyl | 6'-Me | H | 0.016 |

TABLE 1-continued
| Compds | R₁ | R₂ | R₃ | R₄ | MIC (μg/mL) against H37Rv |
|---|---|---|---|---|---|
| TBI-448 | 4-Cl |  | 2'-Me | H | 0.055 |
| TBI-452 | 4-Cl | 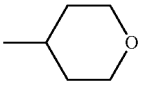 | 2'-Me | H | 0.168 |
| TBI-453 | 4-Cl | 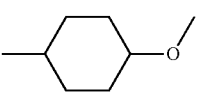 | 2'-Me | H | 0.011 |
| TBI-699 | 4-CF₃ |  | 2'-MeO | H | 0.029 |
| TBI-700 | 4-CF₃ | 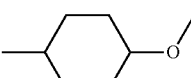 | 2'-MeO | H | 0.016 |
| TBI-701 | 4-CF₃ | 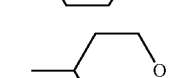 | 2'-MeO | H | 0.016 |
| TBI-702 | 4-CF₃ | 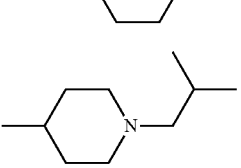 | 2'-MeO | H | 0.016 |
| TBI-703 | 4-CF₃ | 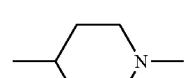 | 2'-MeO | H | 0.020 |
| TBI-704 | 4-CF₃ | 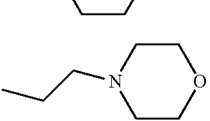 | 2'-MeO | H | 0.061 |
| TBI-710 | 4-CF₃ | 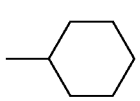 | 2'-MeO | H | 0.03 |
| TBI-718 | 4-CF₃ |  | 2'-MeO | H | 0.015 |
| TBI-719 | 4-CF₃ | 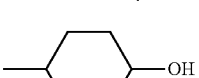 | 2'-MeO | H | 0.204 |
| TBI-728 | 4-CF₃ | 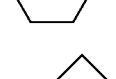 | 2'-MeO | H | 0.033 |
| TBI-694 | 4-CF₃ |  | 2'-MeO | H | 0.03 |
| TBI-695 | 4-CF₃ | 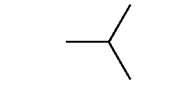 | 2'-MeO | H | 0.016 |
| TBI-696 | 4-CF₃ | 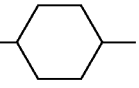 | 6'-Me | H | 0.032 |

TABLE 1-continued
| Compds | R₁ | R₂ | R₃ | R₄ | MIC (μg/mL) against H37Rv |
|---|---|---|---|---|---|
| TBI-697 | 4-CF₃ |  | 6'-Me | H | 0.053 |
| TBI-698 | 4-CF₃ | 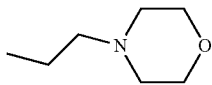 | 6'-Me | H | 0.108 |
| TBI-716 | 4-CF₃ |  | 6'-Me | H | 0.041 |
| TBI-717 | 4-CF₃ | 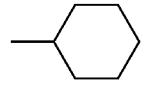 | 6'-Me | H | 0.015 |
| TBI-738 | 4-CF₃ | 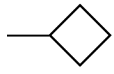 | 6'-Me | H | 0.029 |
| TBI-164 | 4-OCF₃ | 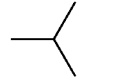 | 2'-MeO | H | 0.028 |
| TBI-165 | 4-OCF₃ | 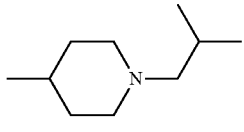 | 2'-MeO | H | 0.016 |
| TBI-166 | 4-OCF₃ | 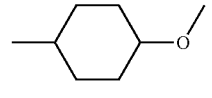 | 2'-MeO | H | 0.016 |
| TBI-167 | 4-OCF₃ | 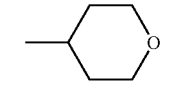 | 2'-MeO | H | 0.016 |
| TBI-168 | 4-OCF3 | 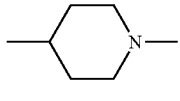 | 2'-MeO | H | 0.109 |
| TBI-169 | 4-OCF3 | 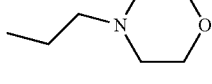 | 2'-MeO | H | 0.060 |
| TBI-359 | 3,4-dichloro | 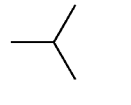 | 2'-MeO | H | 0.099 |
| TBI-361 | 3,4-dichloro | 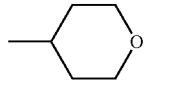 | 2'-MeO | H | 0.08 |
| TBI-362 | 3,4-dichloro | 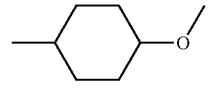 | 2'-MeO | H | 0.059 |
| TBI-363 | 2,4-dichloro | 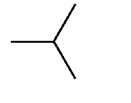 | H | H | 0.03 |
| TBI-1019 | 3-OCF₃ | 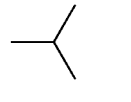 | H | H | 0.057 |

TABLE 1-continued
| Compds | R₁ | R₂ | R₃ | R₄ | MIC (μg/mL) against H37Rv |
|---|---|---|---|---|---|
| TBI-1020 | 3-OCF₃ | 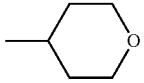 | H | H | 0.058 |
| TBI-1021 | 3-OCF₃ |  | H | H | 0.054 |
| TBI-1022 | 3-OCF₃ | 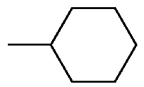 | H | H | 0.074 |
| TBI-1027 | 3-OCF₃ |  | H | H | 0.383 |
| TBI-1024 | 3-OCF₃ | 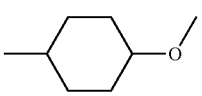 | H | H | 0.112 |
| TBI-1032 | 3-OCF₃ |  | 2'-Me | H | 0.107 |
| TBI-1033 | 3-OCF₃ | 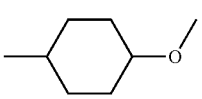 | 2'-Me | H | 0.242 |
| TBI-1034 | 3-OCF₃ | 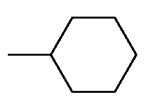 | 2'-Me | H | 0.059 |
| TBI-1035 | 3-OCF₃ | 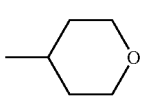 | 2'-Me | H | 0.062 |
| TBI-1038 | 3-OCF₃ |  | 2'-MeO | H | 0.118 |
| TBI-1039 | 3-OCF₃ | 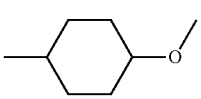 | 2'-MeO | H | 0.059 |
| TBI-1040 | 3-OCF₃ | 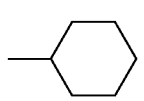 | 2'-MeO | H | 0.086 |
| TBI-1041 | 3-OCF₃ | 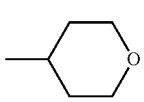 | 2'-MeO | H | 0.115 |
| TBI-1025 | 4-F |  | 5'-Me | H | 0.122 |
| TBI-1026 | 4-F | 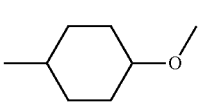 | 5'-Me | H | 0.121 |
| TBI-1028 | 4-F | 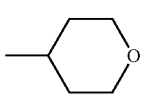 | 5'-Me | H | 0.06 |

TABLE 1-continued

| Compds | R₁ | R₂ | R₃ | R₄ | MIC (μg/mL) against H37Rv |
|---|---|---|---|---|---|
| TBI-1029 | 4-F | cyclohexyl | 5'-Me | H | 0.027 |
| TBI-1030 | 4-F | cyclopropyl | 5'-Me | H | 0.012 |
| TBI-1031 | 4-F | cyclobutyl | 5'-Me | H | 0.028 |
| TBI-930 | 4-F | isopropyl | 6'-MeO | H | 0.494 |
| TBI-931 | 4-F | cyclopropyl | 6'-MeO | H | 0.238 |
| TBI-932 | 4-F | cyclohexyl | 6'-MeO | H | 0.148 |
| TBI-933 | 4-F | 4-methoxycyclohexyl | 6'-MeO | H | 0.175 |
| TBI-934 | 4-F | cyclobutyl | 6'-MeO | H | 0.3 |
| TBI-935 | 4-F | tetrahydropyran-4-yl | 6'-MeO | H | 0.205 |
| TBI-940 | 4-F | cyclopropyl | 4'-Me | H | 0.062 |
| TBI-705 | 4-CF₃ | isopropyl | 2'-Me | H | 0.014 |
| TBI-706 | 4-CF₃ | 4-methoxycyclohexyl | 2'-Me | H | 0.011 |
| TBI-707 | 4-CF₃ | tetrahydropyran-4-yl | 2'-Me | H | 0.011 |
| TBI-708 | 4-CF₃ | cyclohexyl | 2'-Me | H | 0.028 |
| TBI-709 | 4-CF₃ | 4-hydroxycyclohexyl | 2'-Me | H | 0.108 |
| TBI-729 | 4-CF₃ | cyclopropyl | 2'-Me | H | 0.186 |
| TBI-734 | 4-CF₃ | cyclobutyl | 2'-Me | H | 0.014 |

TABLE 1-continued

| Compds | R₁ | R₂ | R₃ | R₄ | MIC (μg/mL) against H37Rv |
|---|---|---|---|---|---|
| TBI-711 | 4-CF₃ | isopropyl | 6'-NAc | H | 0.11 |
| TBI-712 | 4-CF₃ | tetrahydropyran-4-yl | 6'-NAc | H | 0.158 |
| TBI-713 | 4-CF₃ | cyclohexyl | 6'-NAc | H | 0.022 |
| TBI-714 | 4-CF₃ | 4-hydroxycyclohexyl | 6'-NAc | H | 0.686 |
| TBI-715 | 4-CF₃ | 4-methoxycyclohexyl | 6'-NAc | H | 0.06 |
| TBI-721 | 4-CF₃ | isopropyl | 5'-Me | H | 0.082 |
| TBI-722 | 4-CF₃ | cyclohexyl | 5'-Me | H | 0.031 |
| TBI-723 | 4-CF₃ | tetrahydropyran-4-yl | 5'-Me | H | 0.041 |
| TBI-724 | 4-CF₃ | 4-methoxycyclohexyl | 5'-Me | H | 0.03 |
| TBI-725 | 4-CF₃ | cyclopropyl | 5'-Me | H | 0.031 |
| TBI-726 | 4-CF₃ | cyclobutyl | 5'-Me | H | 0.058 |
| TBI-727 | 4-CF₃ | 4-hydroxycyclohexyl | 5'-Me | H | 0.405 |
| TBI-731 | 4-CF₃ | isopropyl | 6'-MeO | H | 0.348 |
| TBI-732 | 4-CF₃ | cyclohexyl | 6'-MeO | H | 0.113 |
| TBI-733 | 4-CF₃ | tetrahydropyran-4-yl | 6'-MeO | H | 0.111 |
| TBI-735 | 4-CF₃ | 4-methoxycyclohexyl | 6'-MeO | H | 0.186 |

TABLE 1-continued

| Compds | R₁ | R₂ | R₃ | R₄ | MIC (μg/mL) against H37Rv |
|---|---|---|---|---|---|
| TBI-736 | 4-CF₃ | cyclopropyl | 6'-MeO | H | 0.224 |
| TBI-737 | 4-CF₃ | cyclobutyl | 6'-MeO | H | 0.119 |
| TBI-891 | 2-Cl | cyclohexyl | H | H | 0.036 |
| TBI-892 | 2-Cl | cyclopropyl | H | H | 0.028 |
| TBI-870 | 2-Cl | tetrahydropyran-4-yl | 2'-MeO | H | 0.084 |
| TBI-820 | 3-Cl | cyclohexyl | 2'-MeO | H | 0.057 |
| TBI-811 | 3-Cl | 4-hydroxycyclohexyl | H | H | 0.5 |
| TBI-812 | 3-Cl | cyclopropyl | H | H | 0.013 |
| TBI-814 | 3-Cl | cyclobutyl | H | H | 0.04 |
| TBI-880 | 4-Cl | tetrahydropyran-4-yl | 5'-Br | H | 0.036 |
| TBI-881 | 4-Cl | 4-methoxycyclohexyl | 5'-Br | H | 0.052 |
| TBI-720 | 2-CF₃ | isopropyl | H | H | 0.214 |
| TBI-739 | 2-CF₃ | 4-methoxycyclohexyl | H | H | 0.239 |
| TBI-730 | 3-CF₃ | isopropyl | H | H | 0.205 |
| TBI-454 | 3-CH₃S | isopropyl | H | H | 0.213 |
| TBI-455 | 3-CH₃SO | isopropyl | H | H | 0.5 |
| TBI-456 | 4-CH₃S | isopropyl | H | H | 0.05 |

TABLE 1-continued

| Compds | R₁ | R₂ | R₃ | R₄ | MIC (μg/mL) against H37Rv |
|---|---|---|---|---|---|
| TBI-457 | 4-CH₃SO | isopropyl | H | H | 0.469 |
| TBI-327 | 4-CH₃ | isopropyl | 5'-CH₃ | H | 0.109 |
| TBI-328 | 4-CH₃ | tetrahydropyran-4-yl | 5'-CH₃ | H | 0.037 |
| TBI-329 | 4-CH₃ | cyclohexyl | 5'-CH₃ | H | 0.092 |
| TBI-330 | 4-CH₃ | 4-methoxycyclohexyl | 5'-CH₃ | H | 0.035 |
| TBI-331 | 4-CH₃ | cyclohexyl | 2'-MeO | H | 0.047 |
| TBI-332 | 4-CH₃ | 4-hydroxycyclohexyl | 2'-MeO | H | 0.294 |
| TBI-333 | 4-CH₃ | cyclohexyl | H | H | 0.061 |
| TBI-334 | 4-CH₃ | 4-hydroxycyclohexyl | 6'-CH₃ | H | 0.372 |
| TBI-335 | 4-CH₃ | 4-hydroxycyclohexyl | 2'-CH₃ | H | 0.336 |
| TBI-336 | 3,4-dichloro | isopropyl | H | H | 0.055 |
| TBI-337 | 4-CH₃ | 4-hydroxycyclohexyl | 5'-CH₃ | H | 0.452 |
| TBI-338 | 4-CH₃ | 4-hydroxycyclohexyl | H | H | 0.5 |
| TBI-339 | 4-CH₃ | cyclopropyl | 2'-MeO | H | 0.033 |
| TBI-340 | 4-CH₃ | cyclopropyl | 6'-CH₃ | H | 0.149 |
| TBI-341 | 4-CH₃ | cyclopropyl | 2'-CH₃ | H | 0.014 |
| TBI-342 | 4-CH₃ | cyclopropyl | 5'-CH₃ | H | 0.022 |

TABLE 1-continued

| Compds | R₁ | R₂ | R₃ | R₄ | MIC (μg/mL) against H37Rv |
|---|---|---|---|---|---|
| TBI-343 | 3,4-dichloro | cyclopropyl | H | H | 0.014 |
| TBI-344 | 4-CH₃ | cyclobutyl | 2'-MeO | H | 0.04 |
| TBI-345 | 4-CH₃ | cyclobutyl | H | H | 0.221 |
| TBI-346 | 4-CH₃ | cyclobutyl | 6'-CH₃ | H | 0.058 |
| TBI-347 | 4-CH₃ | cyclobutyl | 2'-CH₃ | H | 0.042 |
| TBI-348 | 4-CH₃ | cyclobutyl | 5'-CH₃ | H | 0.118 |
| TBI-349 | 4-CH₃ | cyclopropyl | H | H | 0.0075 |
| TBI-350 | 3,4-dichloro | cyclohexyl | H | H | 0.031 |
| TBI-351 | 3,4-dichloro | tetrahydropyranyl | H | H | 0.079 |
| TBI-352 | 3,4-dichloro | 4-methoxycyclohexyl | H | H | 0.096 |
| TBI-353 | 3,4-dichloro | isopropyl | 6'-CH₃ | H | 0.025 |
| TBI-354 | 3,4-dichloro | cyclohexyl | 6'-CH₃ | H | 0.229 |
| TBI-355 | 3,4-dichloro | 4-methoxycyclohexyl | 6'-CH₃ | H | 0.09 |
| TBI-356 | 4-CH₃ | isopropyl | 6'-MeO | H | 0.459 |
| TBI-357 | 4-CH₃ | cyclohexyl | 6'-MeO | H | 0.228 |
| TBI-358 | 4-CH₃ | 4-methoxycyclohexyl | 6'-MeO | H | 0.202 |
| TBI-360 | 4-CH₃ | tetrahydropyranyl | 6'-MeO | H | 0.2 |

TABLE 1-continued
| Compds | R₁ | R₂ | R₃ | R₄ | MIC (μg/mL) against H37Rv |
|---|---|---|---|---|---|
| TBI-364 | 4-OCF₃ |  | 2'-MeO | H | 0.015 |
| TBI-365 | 4-OCF₃ | 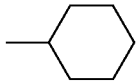 | 2'-MeO | H | 0.018 |
| TBI-366 | 3,4-dichloro |  | 2'-MeO | H | 0.025 |
| TBI-367 | 2,4-dichloro |  | H | H | 0.023 |
| TBI-368 | 2,4-dichloro | 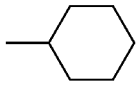 | H | H | 0.054 |
| TBI-369 | 2,4-dichloro |  | 2'-MeO | H | 0.104 |
| TBI-370 | 2,4-dichloro |  | 2'-MeO | H | 0.052 |
| TBI-371 | 2,4-dichloro |  | 2'-MeO | H | 0.044 |
| TBI-372 | 4-OCF₃ | 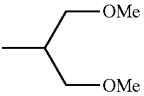 | 2'-MeO | H | 0.098 |
| TBI-373 | 4-CH₃ | 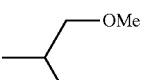 | 2'-MeO | H | 0.125 |
| TBI-374 | 4-CH₃ | 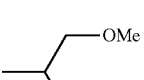 | 6'-CH₃ | H | 0.125 |
| TBI-375 | 3,4-dichloro | 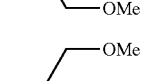 | 2'-MeO | H | 0.125 |
| TBI-518 | 4-Br | 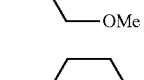 | 2'-MeO | H | 0.02 |
| TBI-519 | 4-Br |  | 2'-MeO | H | 0.015 |
| TBI-520 | 4-Br |  | 2'-MeO | H | 0.043 |
| TBI-521 | 4-Br | 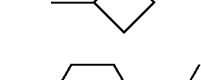 | 2'-MeO | H | 0.031 |
| TBI-522 | 3-F | 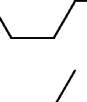 | H | H | 0.062 |

TABLE 1-continued

| Compds | R₁ | R₂ | R₃ | R₄ | MIC (μg/mL) against H37Rv |
|---|---|---|---|---|---|
| TBI-523 | 3-F | isopropyl | 2'-MeO | H | 0.06 |
| TBI-524 | 3-F | tetrahydropyran-4-yl | 2'-MeO | H | 0.061 |
| TBI-525 | 3,4-difluoro | isopropyl | H | H | 0.058 |
| TBI-526 | 3,4-difluoro | cyclobutyl | H | H | 0.079 |
| TBI-527 | 3,4-difluoro | cyclohexyl | H | H | 0.039 |
| TBI-528 | 3,4-difluoro | CH(CH₂OMe)₂ | H | H | 0.216 |
| TBI-529 | 3,4-difluoro | isopropyl | 2'-MeO | H | 0.066 |
| TBI-530 | 3,4-difluoro | cyclobutyl | 2'-MeO | H | 0.04 |
| TBI-531 | 3,4-difluoro | cyclohexyl | 2'-MeO | H | 0.03 |
| TBI-532 | 3,4-difluoro | tetrahydropyran-4-yl | 2'-MeO | H | 0.067 |
| TBI-1042 | 4-F | tetrahydrothiopyran-4-yl | 2'-MeO | H | 0.034 |
| TBI-1043 | 4-F | tetrahydrothiopyran-4-yl | 2'-CH₃ | H | 0.021 |
| TBI-1044 | 2-OCF₃ | 4-methoxycyclohexyl | 2'-MeO | H | 0.25 |
| TBI-1045 | 2-OCF₃ | tetrahydropyran-4-yl | 2'-MeO | H | 0.4 |
| TBI-1046 | 2-OCF₃ | isopropyl | 2'-MeO | H | 0.44 |
| TBI-1047 | 2-OCF₃ | cyclohexyl | 2'-MeO | H | 0.465 |

TABLE 1-continued

| Compds | R₁ | R₂ | R₃ | R₄ | MIC (μg/mL) against H37Rv |
|---|---|---|---|---|---|
| TBI-1048 | 4-F | CH(CH₂OMe)₂ | 2'-MeO | H | 0.226 |
| TBI-1049 | 4-F | CH(OMe)CH₂OMe | 2'-MeO | H | 0.162 |
| TBI-744 | 4-CF₃ | CH(OMe)CH₂OMe | 2'-MeO | H | 0.059 |
| TBI-825 | 3-Cl | CH(CH₂OMe)₂ | 2'-MeO | H | 0.125 |
| TBI-871 | 4-Cl | CH(CH₂OMe)₂ | 2'-MeO | H | 0.03 |
| TBI-80C | 3-Cl | CH(CH₂OMe)₂ | 6'-CH₃ | H | 0.327 |
| TBI-826 | 3-Cl | CH(OMe)CH₂OMe | 2'-MeO | H | 0.125 |
| TBI-872 | 4-Cl | CH(OMe)CH₂OMe | 2'-MeO | H | 0.06 |
| TBI-810 | 3-Cl | isopropyl | H | H | 0.103 |
| TBI-890 | 2-Cl | isopropyl | H | H | 0.476 |
| TBI-882 | 4-Cl | cyclopropyl | 5'-Br | H | 0.015 |
| TBI-883 | 4-Cl | cyclobutyl | 5'-Br | H | 0.03 |
| TBI-821 | 3-Cl | isopropyl | 2'-MeO | H | 0.25 |
| TBI-822 | 3-Cl | tetrahydropyran-4-yl | 2'-MeO | H | 0.125 |
| TBI-823 | 3-Cl | cyclopropyl | 2'-MeO | H | 0.03 |
| TBI-824 | 3-Cl | cyclobutyl | 2'-MeO | H | 0.06 |

TABLE 1-continued
| Compds | R₁ | R₂ | R₃ | R₄ | MIC (μg/mL) against H37Rv |
|---|---|---|---|---|---|
| TBI-80A | 3-Cl | 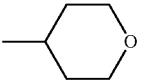 | 6'-CH₃ | H | 0.125 |
| TBI-80B | 3-Cl | 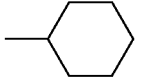 | 6'-CH₃ | H | 0.125 |
| TBI-950 | 4-OCF₃ | 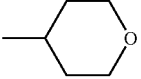 | 6'-CH₃ | H | 0.035 |
| TBI-741 | 4-Cl |  | 2'-MeO | 7-F | 0.035 |
| TBI-914 | 4-Cl |  | 6'-Me | 7-F | >0.5 |
| TBI-918 | 4-Cl | 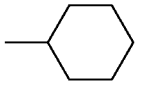 | 6'-Me | 7-F | 0.253 |
| TBI-925 | 4-Cl | 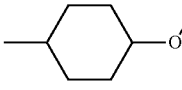 | 6'-Me | 7-F | 0.078 |
| TBI-924 | 4-Cl |  | 2'-MeO | 7-F | 0.06 |
| TBI-926 | 4-Cl |  | 2'-MeO | 7-F | 0.103 |
| TBI-927 | 4-Cl | 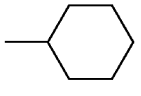 | 2'-MeO | 7-F | 0.04 |
| TBI-928 | 4-Cl | 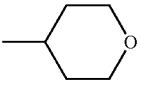 | 2'-MeO | 7-F | 0.5 |
| TBI-938 | 4-Cl | 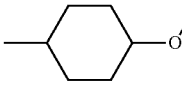 | 6'-Me | 8-F | 0.125 |
| TBI-943 | 4-Cl |  | 6'-Me | 8-F | 0.06 |
| TBI-929 | 4-Cl |  | 2'-MeO | 8-F | 0.125 |
| TBI-936 | 4-Cl | 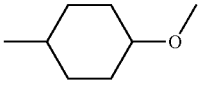 | 2'-MeO | 8-F | 0.06 |
| TBI-937 | 4-Cl | 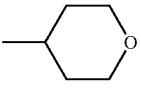 | 2'-MeO | 8-F | 0.125 |

TABLE 1-continued
| Compds | R₁ | R₂ | R₃ | R₄ | MIC (µg/mL) against H37Rv |
|---|---|---|---|---|---|
| TBI-939 | 4-Cl |  | 2'-MeO | 7-MeO | 0.125 |
| TBI-941 | 4-Cl |  | 2'-MeO | 7-MeO | 0.06 |
| TBI-942 | 4-Cl | 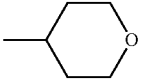 | 2'-MeO | 7-MeO | 0.125 |
| TBI-894 | 4-Cl |  | 2'-MeO | 7-MeO | 0.06 |
| TBI-895 | 4-Cl | 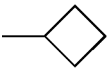 | 2'-MeO | 7-MeO | 0.125 |
| TBI-944 | 3,4-dichloro |  | 6'-Me | H | 0.06 |
| TBI-945 | 3,4-dichloro | 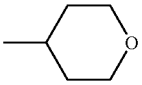 | 6'-Me | H | 0.25 |
| TBI-948 | 3,4-dichloro | 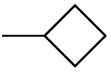 | 6'-Me | H | 0.125 |
| TBI-946 | 3,4-dichloro | 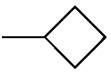 | 2'-MeO | H | 0.06 |
| TBI-947 | 2,4-dichloro | 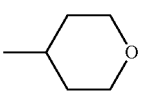 | 2'-MeO | H | 0.06 |
| TBI-893 | 2,4-dichloro | 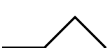 | 2'-MeO | H | 0.06 |
| TBI-949 | 3,4-dichloro | 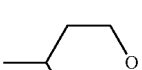 | 6'-Me | 7-F | 0.816 |
| TBI-896 | 3,4-dichloro |  | 6'-Me | 7-F | 0.25 |
| TBI-897 | 3,4-dichloro | 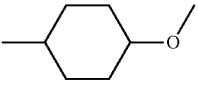 | 6'-Me | 7-F | 0.25 |
| TBI-899 | 3,4-dichloro |  | 2'-MeO | 7-F | 0.125 |
| TBI-884 | 3,4-dichloro | 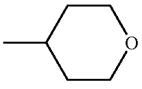 | 2'-MeO | 7-F | 0.5 |
| TBI-885 | 3,4-dichloro |  | 2'-MeO | 7-F | 0.06 |

TABLE 1-continued
| Compds | R₁ | R₂ | R₃ | R₄ | MIC (μg/mL) against H37Rv |
|---|---|---|---|---|---|
| TBI-886 | 3,4-dichloro | 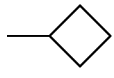 | 2'-MeO | 7-F | 0.06 |
| TBI-887 | 3,4-dichloro |  | 6'-Me | 8-F | 0.062 |
| TBI-888 | 3,4-dichloro |  | 6'-Me | 8-F | 0.028 |
| TBI-873 | 3,4-dichloro | 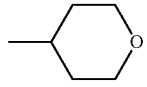 | 6'-Me | 8-F | 0.076 |
| TBI-878 | 3,4-dichloro | 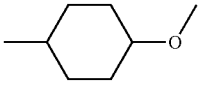 | 6'-Me | 8-F | 0.029 |
| TBI-874 | 3,4-dichloro |  | 2'-MeO | 8-F | 0.129 |
| TBI-875 | 3,4-dichloro |  | 2'-MeO | 8-F | 0.047 |
| TBI-877 | 3,4-dichloro | 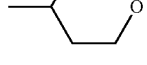 | 2'-MeO | 8-F | 0.091 |
| TBI-879 | 3,4-dichloro | 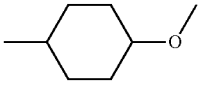 | 2'-MeO | 8-F | 0.109 |
| TBI-861 | 4-OCF₃ | 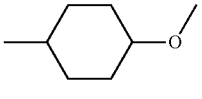 | 2'-MeO | 8-F | 0.058 |
| TBI-862 | 4-OCF₃ | 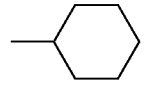 | 2'-MeO | 8-F | 0.088 |
| TBI-863 | 4-OCF₃ |  | 6'-Me | 8-F | 0.061 |
| TBI-864 | 4-OCF₃ |  | 6'-Me | 8-F | 0.057 |
| TBI-865 | 4-OCF₃ | 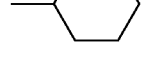 | 6'-Me | 8-F | 0.031 |
| TBI-866 | 4-OCF₃ | 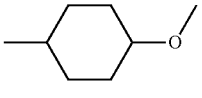 | 6'-Me | 8-F | 0.027 |
| TBI-898 | 4-Cl |  | 6'-Me | 8-MeO | 0.25 |
| TBI-859 | 4-Cl |  | 2'-MeO | 8-F | 0.015 |

TABLE 1-continued

| Compds | R₁ | R₂ | R₃ | R₄ | MIC (μg/mL) against H37Rv |
|---|---|---|---|---|---|
| TBI-867 | 4-Cl | 4-methoxycyclohexyl | 6'-Me | 8-MeO | 0.058 |
| TBI-868 | 4-Cl | cyclopropyl | 6'-Me | 7-MeO | 0.028 |
| TBI-869 | 4-Cl | cyclohexyl | 6'-Me | 7-MeO | 0.056 |
| TBI-858 | 4-OCF₃ | isopropyl | 2'-MeO | 7-F | 0.08 |
| TBI-857 | 4-OCF₃ | cyclopropyl | 2'-MeO | 7-F | 0.045 |
| TBI-856 | 4-OCF₃ | cyclohexyl | 2'-MeO | 7-F | 0.029 |
| TBI-855 | 4-OCF₃ | tetrahydropyranyl | 2'-MeO | 7-F | 0.193 |
| TBI-854 | 4-OCF₃ | isopropyl | 6'-Me | 7-F | 0.067 |
| TBI-853 | 4-OCF₃ | cyclohexyl | 6'-Me | 7-F | 0.025 |
| TBI-852 | 4-OCF₃ | 4-methoxycyclohexyl | 6'-Me | 7-F | 0.024 |
| TBI-1220 | 4-NHAc | isopropyl | 2'-MeO | H | >0.5 |
| TBI-1221 | 4-NHAc | cyclopropyl | 2'-MeO | H | 0.900 |
| TBI-1222 | 4-NHAc | 4-methoxycyclohexyl | 2'-MeO | H | 0.925 |
| TBI-1223 | 4-NHAc | cyclohexyl | 2'-MeO | H | 1.488 |
| TBI-1224 | 4-NHAc | tetrahydropyranyl | 6'-Me | H | TBD |
| TBI-1225 | 4-NHAc | tetrahydropyranyl | 2'-MeO | H | TBD |

TABLE 1-continued

| Compds | R$_1$ | R$_2$ | R$_3$ | R$_4$ | MIC (μg/mL) against H37Rv |
|---|---|---|---|---|---|
| TBI-1227 | 4-NHAc | CH(CH$_2$OMe)$_2$ | 2'-MeO | H | TBD |
| TBI-1228 | 4-NHAc | isopropyl | 6'-Me | H | 2.398 |
| TBI-1229 | 4-NHAc | 4-methoxycyclohexyl | 6'-Me | H | 0.482 |
| TBI-1230 | 4-NHAc | cyclopropyl | 6'-Me | H | TBD |
| TBI-1231 | 4-NHAc | cyclohexyl | 6'-Me | H | TBD |
| TBI-1236 | 4-COOCH$_3$ | isopropyl | 2'-MeO | H | TBD |
| TBI-1237 | 4-COOCH$_3$ | cyclopropyl | 2'-MeO | H | TBD |
| TBI-1426 | 3,4-difluoro | cyclopropyl | 2'-MeO | H | 0.014 |
| TBI-1427 | 3,4-difluoro | 4-methoxycyclohexyl | 2'-MeO | H | 0.056 |
| TBI-1428 | 3,4-difluoro | tetrahydropyranyl | 2'-MeO | H | 0.054 |
| TBI-1429 | 3,4-difluoro | cyclopropyl | H | H | 0.011 |
| TBI-1430 | 3,4-difluoro | 4-methoxycyclohexyl | H | H | 0.059 |
| TBI-1432 | 3,4-difluoro | tetrahydropyranyl | H | H | 0.088 |
| TBI-1064 | 4-F | isopropyl | 2'-MeO | 8-CN | 0.24 |
| TBI-1065 | 4-F | 4-methoxycyclohexyl | 2'-MeO | 8-CN | >16 |
| TBI-1066 | 4-F | tetrahydropyranyl | 2'-MeO | 8-CN | >6.639 |

TABLE 1-continued

| Compds | R₁ | R₂ | R₃ | R₄ | MIC (μg/mL) against H37Rv |
|---|---|---|---|---|---|
| TBI-1067 | 4-F | isobutyl | 6'-Me | 8-CN | 0.117 |
| TBI-1068 | 4-F | 4-methoxycyclohexyl-methyl | 6'-Me | 8-CN | 0.165 |
| TBI-1092 | 4-F | isobutyl | 2'-MeO, 6'-Me | H | 0.424 |

Table 2 below shows a variety of examples of the 2-(heteroaryl)amino-riminophenazines shown as general formula (I) by indicating the structures present at R1, R2, R3, R4, X, Y and Z of the FIGURE above, as well as their in vitro activity against *Mycobacterium tuberculosis* H37Rv strains, described in Example 2 below. In these examples, R₄ is H.

TABLE 2

| Compds | R₁ | R₂ | X-Y-Z ring | R₃ | MIC (μg/mL) against H37Rv |
|---|---|---|---|---|---|
| TBI-952 | 4-OCF₃ | isobutyl | 2-pyridyl | H | 0.093 |
| TBI-954 | 4-OCF₃ | isobutyl | 2-pyridyl | 3'-NO₂ | 0.030 |
| TBI-1050 | 4-Cl | isobutyl | 2-pyridyl | 3'-NO₂ | 0.025 |
| TBI-951 | 4-OCF₃ | isobutyl | 2-pyrimidyl | H | 0.019 |
| TBI-830 | 4-OCF₃ | tetrahydropyran-4-yl | 2-pyrimidyl | H | 0.014 |
| TBI-860 | 4-Cl | tetrahydropyran-4-yl | 2-pyrimidyl | H | 0.029 |
| TBI-960 | 4-Cl | tetrahydropyran-4-yl | 5-pyrimidyl | H | 0.03 |
| TBI-961 | 4-Cl | cyclohexyl | 5-pyrimidyl | H | 0.015 |

TABLE 2-continued
| Compds | R$_1$ | R$_2$ |  | R$_3$ | MIC (μg/mL) against H37Rv |
|---|---|---|---|---|---|
| TBI-980 | 3-Cl | 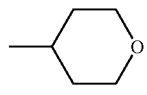 | 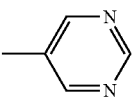 | H | 0.06 |
| TBI-953 | 4-OCF$_3$ |  | 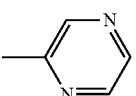 | H | 0.015 |
| TBI-1051 | 4-Cl |  | 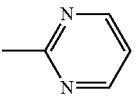 | H | 0.015 |
| TBI-1052 | 4-F |  | 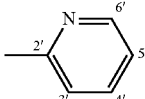 | 3'-NO$_2$ | 0.022 |
| TBI-1053 | 4-F |  | 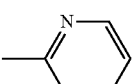 | H | 0.015 |
| TBI-1054 | 4-F |  | 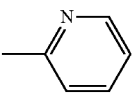 | H | 0.446 |
| TBI-1055 | 4-F |  | 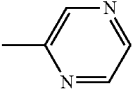 | H | 0.022 |
| TBI-1057 | 4-F |  | 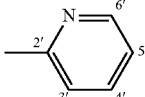 | 3'-CN | 0.015 |
| TBI-1075 | 4-Cl |  | 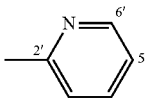 | 3'-CN | 0.016 |
| TBI-1076 | 4-Cl |  | 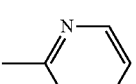 | H | 0.014 |
| TBI-1077 | 4-Cl |  | 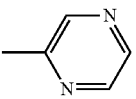 | H | <0.0075 |
| TBI-1078 | 4-F | 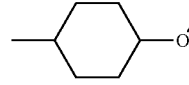 | 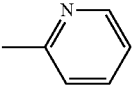 | H | 0.028 |
| TBI-1079 | 4-F | 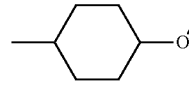 | 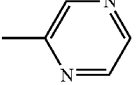 | H | 0.037 |

TABLE 2-continued
| Compds | R$_1$ | R$_2$ |  | R$_3$ | MIC (µg/mL) against H37Rv |
|---|---|---|---|---|---|
| TBI-1080 | 4-F | 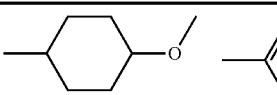 |  | H | 0.029 |
| TBI-1082 | 4-F | 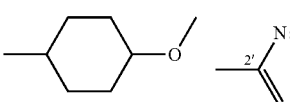 | 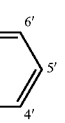 | 3'-CN | 0.029 |
| TBI-1083 | 4-F | 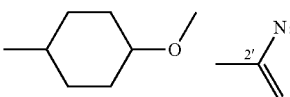 | 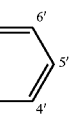 | 3'-NO$_2$ | 5.814 |
| TBI-1084 | 4-F | 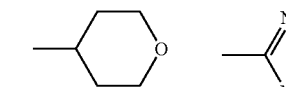 |  | H | 0.043 |
| TBI-1085 | 4-F | 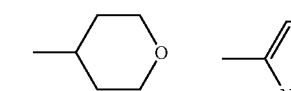 |  | H | 0.038 |
| TBI-1086 | 4-F | 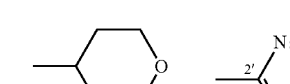 | 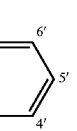 | 3'-CN | 0.04 |
| TBI-1087 | 4-F | 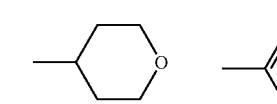 |  | H | 0.028 |
| TBI-1088 | 4-F | 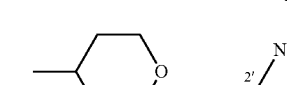 | 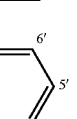 | 3'-NO$_2$ | 0.028 |
| TBI-1090 | 4-Cl | 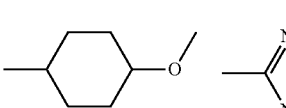 |  | H | <0.0075 |
| TBI-1091 | 4-Cl | 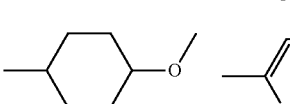 |  | H | 0.018 |
| TBI-1433 | 3,4-difluoro | 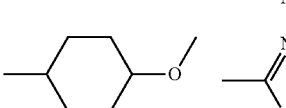 |  | H | 0.086 |
| TBI-1436 | 3,4-difluoro |  | 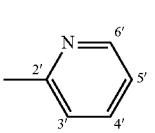 | H | 0.028 |
| TBI-1437 | 3,4-difluoro |  | 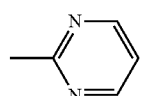 | H | 0.02 |

TABLE 2-continued

| Compds | R₁ | R₂ | (ring structure) | R₃ | MIC (µg/mL) against H37Rv |
|---|---|---|---|---|---|
| TBI-1438 | 3,4-difluoro | 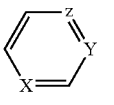 |  | 3'-CN | 0.053 |
| TBI-1444 | 3,4-difluoro | 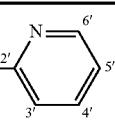 | 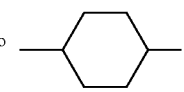 | 5'-NO2 | 0.114 |
| TBI-1445 | 3,4-difluoro | 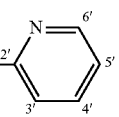 | 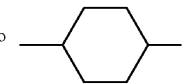 | H | 0.056 |
| TBI-1446 | 3,4-difluoro | 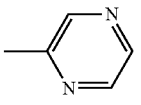 |  | H | 0.03 |

The riminophenazines with 2-(heteroaryl)amino substituents may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

The current invention also pertains to methods of prevention or therapy for microbial infections, such as *Mycobacterium tuberculosis*, including the step of administering a riminophenazine with 2-(heteroaryl)amino substituents.

In another aspect of the present invention there is provided a pharmaceutical composition including a therapeutically effective amount of a riminophenazine with 2-(heteroaryl) amino substituents as defined above and a pharmaceutically acceptable excipient, adjuvant, carrier, buffer or stabiliser. A "therapeutically effective amount" is to be understood as an amount of a riminophenazine with 2-(heteroaryl)amino substituents that is sufficient to show antibacterial or antimicrobial effects. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilisers, buffers, antioxidants and/or other additives may be included as required.

The pharmaceutical composition can further comprise one or more additional anti-infective treatments. These anti-infective treatments can be any suitable treatment available commercially or from other sources that are known to effectively prevent or treat microbial infections, such as *Mycobacterium tuberculosis*.

In another aspect, there is provided the use in the manufacture of a medicament of a therapeutically effective amount of a riminophenazine with 2-(heteroaryl)amino substituents as defined above for administration to a subject. There is also provided a method of making riminophenazines with 2-(heteroaryl)amino substituents.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.
Some preferred examples of the riminophenazines with 2-(3-pyridyl)amino substituents include compounds having the following structures:
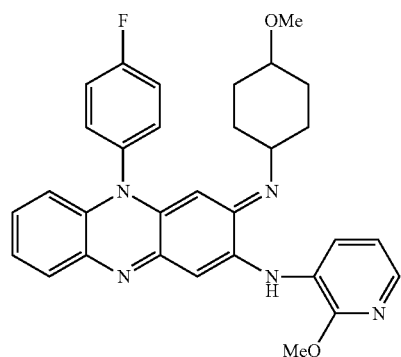
TBI-1002
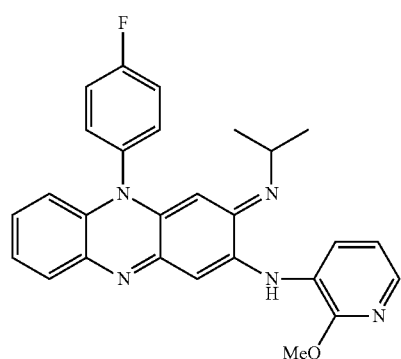
TBI-1004
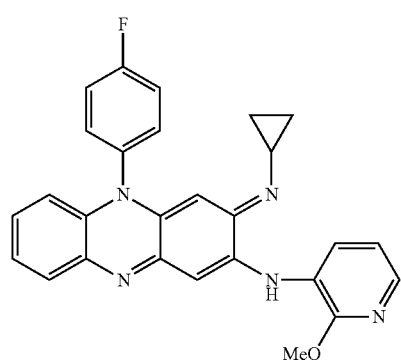
TBI-1010
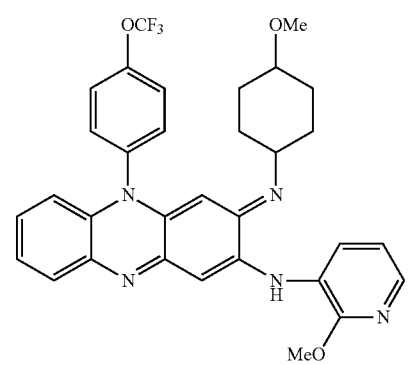
TBI-166
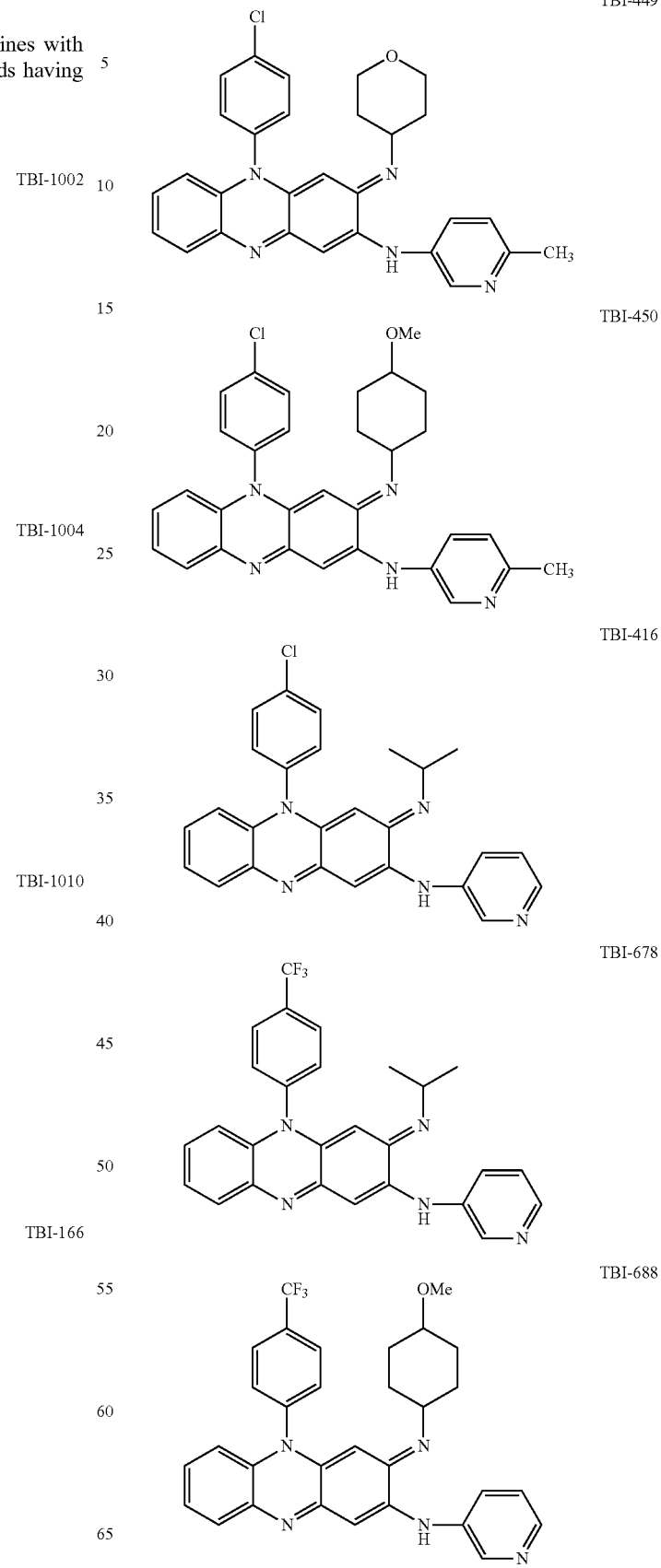

-continued

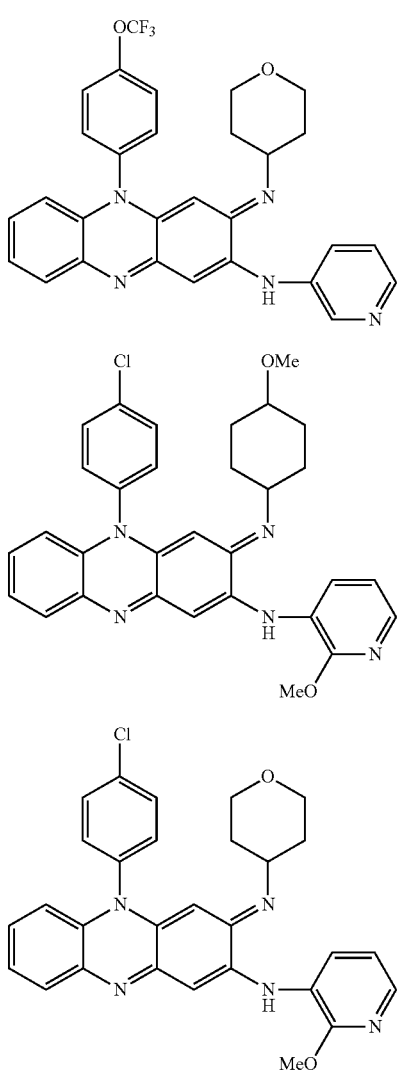

TBI-161

TBI-444

TBI-443

Further aspects of the present invention will become apparent from the following description given by way of example only and with reference to the accompanying synthetic schemes.

Example 1

General Synthetic Methods

General procedures for the preparation of 5-(4-chlorophenyl)-3-(1 methylethyl)imino-2-(3-pyridyl)amino-3,5-dihydrophenazine (TBI-416), or the current riminophenazine compounds, are provided below.

Step A: 2-(4-chloroanilino)-nitrobenzene. A mixture of 2-fluoro-nitrobenzene (33.7 g), 4-chloroaniline (61.0 g) and anhydrous potassium fluoride (13.9 g) was stirred at 180° C. for 10 h. After being cooled to rt, 3 M HCl was added and the mixture was stirred at 100° C. for 30 min. Then cooled to rt, filtered by suction, washed with water to give a brown solid. The solid was dissolved in $CH_2Cl_2$ and filtered through a thin pad of silica gel, washed with $CH_2Cl_2$. The filtrate was concentrated to dryness, and the residue was recrystallized with 95% ethanol to give 57.0 g of orange solid.

Step B: 2-(4-chloroanilino)-aniline. To a solution of 2-(4-chloroanilino)-nitrobenzene (57.0 g) in $CH_2Cl_2$ (40 mL) was added AcOH (90 mL), then Zn (105 g) was added in small portions. After Zn was added, the color of the mixture became light green, filtered by suction, washed with $CH_2Cl_2$. The filtrate was concentrated to dryness. Water was added, filtered, and washed with water to give a brown solid. This solid was used directly in the next step without further purification.

Step C: 1-[2-(4-chloroanilino)anilino]-3-fluoro-4,6-dinitrobenzene. The solid from step B was added to a solution of 1,3-difluoro-4,6-dinitrobenzene (46 g) in methanol (200 L), then triethylamine (31.4 mL) was added, and stirred at rt for 4 h. The reaction mixture was filtered, and the cake was washed with methanol to give 80.6 g of red solid.

Step D: 1-[2-(4-chloroanilino)anilino]-3-(3-pyridyl)amino-4,6-dinitrobenzene, shown below.

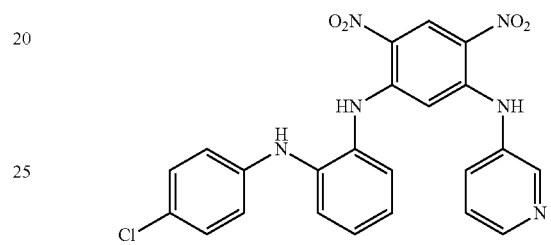

A mixture of 1-[2-(4-chloroanilino)anilino]-3-fluoro-4,6-dinitrobenzene (40.3 g), 3-aminopyridine (14.12 g), triethylamine (14 mL) and THF (200 mL) was heated to reflux for 28 h. then about 150 mL of THF was distilled out. To the residue was added $CH_2Cl_2$, the solid was filtered, and washed with $CH_2Cl_2$ to give 31.2 g of red solid. $^1$H NMR (300 MHz, DMSO-$d_6$) δ: 9.72 (s, 1H), 9.50 (s, 1H), 9.00 (s, 1H), 8.40-8.37 (m, 2H), 7.77 (s, 1H), 7.63-7.59 (m, 1H), 7.37-7.33 (m, 1H), 7.21-7.09 (m, 5H), 6.92-6.83 (m, 1H), 6.82-6.78 (m, 2H), 5.92 (s, 1H); ESI-MS (m/z): 477 (M+H$^+$).

Step E: 5-(4-chlorophenyl)-3-imino-2-(3-pyridyl)amino-3,5-dihydrophenazine, shown below.

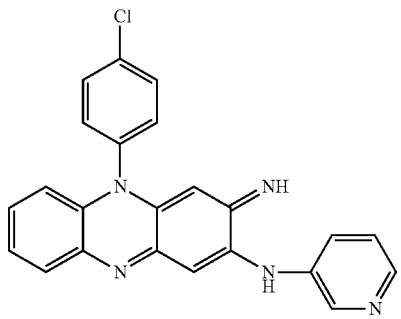 [SMILES: N=c1cc2n(-c3ccc(Cl)cc3)c3ccccc3nc-2cc1Nc1cccnc1]

Method A. To a suspension of 1-[2-(4-chloroanilino)anilino]-3-(3-pyridyl)amino-4,6-dinitrobenzene (28.6 g) in AcOH (150 mL) was added Zn powder (69 g) in small portions. After Zn was added, the color of the mixture became light green. The mixture was filtered, washed with AcOH and methanol. The filtrate was concentrated to dryness, water and ammonia was added. After being filtered, the cake was washed with water to give a dark solid. The solid was dissolved in methanol and $CH_2Cl_2$, stirred at rt in contact with air overnight. The solution was concentrated to a small volume, and filtered, washed with methanol to give 23.1 g of dark solid. $^1$H NMR (300 MHz, CDCl₃) δ: 8.63 (d, J=2.7 Hz, 1H), 8.37 (dd, J=4.8 Hz, 1.2 Hz, 1H), 7.81-7.70 (m, 4H), 7.34-7.28 (m, 3H), 7.24-7.18 (m, 2H), 6.94 (s, 1H), 6.54-6.51 (m, 1H), 5.23 (s, 1H). Method B. 9.49 g (21 mmol) of 1-[2-(4-chloroanilino)anilino]-3-(3-pyridyl)amino-4,6-dinitrobenzene was suspended in 100 ml of anhydrous methanol. The mixture was hydrogenation with 0.97 g of 10% Pd—C at 45 psi. Then the Pd—C was removed by filtration. The filtrate was opened in the air and stirred at r.t. over night. The solid separated was filtered out to give the title compound 4.83 g.

Step F: 5-(4-chlorophenyl)-3-(1-methylethyl)imino-2-(3-pyridyl)amino-3,5-dihydrophenazine, shown below.

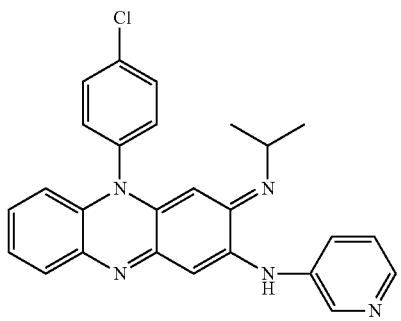

To a sealed bomb was added 5-(4-chlorophenyl)-3-imino-2-(3-pyridyl)amino-3,5-dihydrophenazine (23.1 g), isopropylamine (99.4 mL) and dioxane (120 mL). The mixture was stirred at 110° C. in the bomb for 7 h. After being cooled to rt, water was added, suction filtered, washed with water to give a dark solid. The solid was purified by flash column chromatography (EtOAc/hexane 1:2) to give 11.2 g of red solid. mp: 194-196° C., ¹H NMR (300 MHz, DMSO-d₆) (δ: 8.63 (brs, 1H), 8.61 (d, J=2.4 Hz, 1H), 8.32 (dd, J=4.8 Hz, 1.2 Hz, 1H), 7.90-7.84 (m, 3H), 7.65-7.58 (m, 3H), 7.25-7.18 (m, 2H), 6.66 (s, 1H), 6.47-6.44 (m, 1H), 5.76 (s, 1H), 3.43-3.35 (m, 1H), 1.06 (d, J=6.3 Hz, 6H), ¹³C NMR (100 MHz, DMSO-d₆) (δ: 150.2, 149.9, 144.1, 143.8, 143.5, 136.8, 135.8, 135.3, 134.4, 131.6, 131.1, 130.9, 128.3, 128.0, 127.8, 123.9, 122.9, 114.1, 98.8, 88.3, 48.9, 23.3, HRMS (ESI-TOF⁺): [M+H]⁺ calcd for C₂₆H₂₃ClN₅: 440.1641; found: 440.1643.

General procedures for the preparation of 5-(4-chlorophenyl)-3-(1-methylethyl)imino-2-(pyrimidin-2-yl)amino-3,5-dihydrophenazine (TBI-1051), or the current riminophenazine compounds, are provided below.

Step A: 2-(4-chloroanilino)-nitrobenzene. A mixture of 2-fluoro-nitrobenzene (33.7 g), 4-chloroaniline (61.0 g) and anhydrous potassium fluoride (13.9 g) was stirred at 180° C. for 10 h. After being cooled to rt, 3 M HCl was added and the mixture was stirred at 100° C. for 30 min. Then cooled to rt, filtered by suction, washed with water to give a brown solid. The solid was dissolved in CH₂Cl₂ and filtered through a thin pad of silica gel, washed with CH₂Cl₂. The filtrate was concentrated to dryness, and the residue was recrystallized with 95% ethanol to give 57.0 g of orange solid.

Step B: 2-(4-chloroanilino)-aniline. To a solution of 2-(4-chloroanilino)-nitrobenzene (57.0 g) in CH₂Cl₂ (40 mL) was added AcOH (90 mL), then Zn powder (105 g) was added in small portions. After Zn powder was added, the color of the mixture became light green, filtered by suction, washed with CH₂Cl₂. The filtrate was concentrated to dryness. Water was added, filtered, and washed with water to give a brown solid. This solid was used directly in the next step without further purification.

Step C: 1-[2-(4-chloroanilino)-anilino]-3-fluoro-4,6-dinitrobenzene. The solid from step B was added to a solution of 1,3-difluoro-4,6-dinitrobenzene (46 g) in methanol (200 mL), then triethylamine (31.4 mL) was added, and stirred at rt for 4 h. The reaction mixture was filtered, and the cake was washed with methanol to give 80.6 g of red solid.

Step D: 1-[2-(4-chloroanilino)-anilino]-3-amino-4,6-dinitrobenzene, shown below.

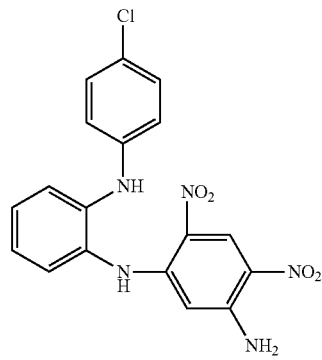 [SMILES: Nc1cc(Nc2ccccc2Nc2ccc(Cl)cc2)c([N+](=O)[O-])cc1[N+](=O)[O-]]

A mixture of 1-[2-(4-chloroanilino)-anilino]-3-fluoro-4,6-dinitrobenzene (40.3 g), ammonia (50 ml) and THF (80 mL) was heated to 80□ for 12 h in a sealed bomb, then about 70 mL of THF was distilled out. The suspension was filtered by suction, and the filter cake was washed with CH₂Cl₂ to give 37.6 g of yellow solid. ¹H NMR (300 MHz, DMSO-d₆) δ: 8.92 (1H, s), 7.77 (3H, m), 7.28 (5H, m), 7.06 (1H, m), 7.00 (2H, m), 6.15 (1H, s), 5.76 (1H, s).

Step E: 5-(4-chlorophenyl)-3-imino-2-amino-3,5-dihydrophenazine, shown below.

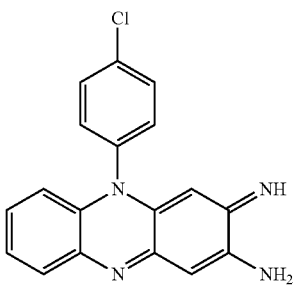 [SMILES: N=c1cc2n(-c3ccc(Cl)cc3)c3ccccc3nc-2cc1N]

Method A: To a suspension of 1-[2-(4-chloroanilino)-anilino]-3-amino-4,6-dinitrobenzene (24.0 g) in AcOH (150 mL) was added Zn powder (69.0 g) in small portions. After Zn powder was added, the color of the mixture became light green. The mixture was filtered, washed with AcOH and methanol. The filtrate was concentrated to dryness, water and ammonia was added. After being filtered, the cake was washed with water to give a dark solid. The solid was dissolved in methanol and CH₂Cl₂, stirred at rt in contact with air overnight. The solution was concentrated to a small volume, and filtered, washed with methanol to give 16.9 g of dark solid. ¹H NMR (300 MHz, DMSO-d₆) δ: 7.86 (2H, d, J=8.7 Hz), 7.76 (1H, m), 7.59 (2H, d, J=8.7 Hz), 7.31 (2H, m), 6.78 (2H, br s), 6.57 (1H, m), 6.49 (1H, s), 5.45 (1H, s).

Method B: 8.40 g (21 mmol) of 1-[2-(4-chloroanilino)-anilino]-3-amino-4,6-dinitrobenzene was suspended in 100 mL of anhydrous methanol. The mixture was hydrogenation with 0.97 g of 10% Pd—C at 45 psi. Then the Pd—C was removed by filtration. The filtrate was stirred at rt in contact with air overnight. The solid separated was filtered out to give the title compound 3.90 g.

Step F: 5-(4-chlorophenyl)-3-(1-methylethyl)imino-2-amino-3,5-dihydrophenazine, shown below.

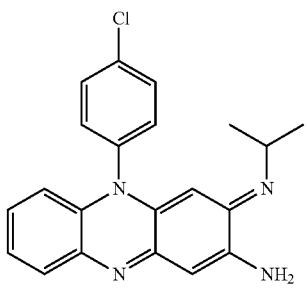 [SMILES: CC(C)/N=c1\cc2n(-c3ccc(Cl)cc3)c3ccccc3nc-2cc1N]

To a sealed bomb was added 5-(4-chlorophenyl)-3-imino-2-amino-3,5-dihydro-phenazine (18.6 g), isopropylamine (99.4 mL) and dioxane (120 mL). The mixture was stirred at 110° C. in the bomb for 24 h. After being cooled to rt, water was added, suction filtered, washed with water to give a dark solid. The solid was purified by flash column chromatography (EtOAc/hexane 1:2) to give 5.6 g of red solid. $^1$H NMR (300 MHz, DMSO-$d_6$) δ: 7.84 (2H, d, J=8.4 Hz), 7.59 (1H, m), 7.55 (2H, d, J=8.4 Hz), 7.14 (2H, m), 6.39 (3H, m), 6.27 (1H, s), 5.11 (1H, s), 3.29 (1H, m), 0.98 (6H, d, J=6.3 Hz).

Step G: 5-(4-Chlorophenyl)-3-(1-methylethyl)imino-2-(pyrimidin-2-yl)amino-3,5-dihydrophenazine, shown below.

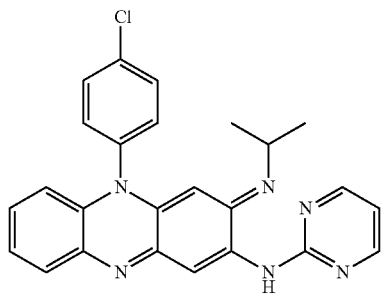 [SMILES: CC(C)/N=c1\cc2n(-c3ccc(Cl)cc3)c3ccccc3nc-2cc1Nc1ncccn1]

Under an atmosphere of $N_2$, toluene (50 mL), 2-bromopyrimidine (4.7 g), 5-(4-chlorophenyl)-3-(1-methylethyl)imino-2-amino-3,5-dihydrophenazine (7.2 g), $Pd_2(dba)_3$ (0.4 g), DPPF (0.9 g) and $Cs_2CO_3$ (9.8 g) were added in turn to a two-necked round-bottomed flask with a reflux condenser. The mixture was refluxed for 2 h, allowed to cool, and filtered. After filtration, the filtrate was concentrated under reduced pressure and the residue was purified by flash silica gel chromatography (EtOAc/hexane 1:2) to give 8.4 g of red solid. mp: 232-235☐, $^1$H NMR (300 MHz, CDCl$_3$) δ: 9.76 (1H, br s), 8.56 (2H, d, J=4.5 Hz), 8.49 (s, 1H), 7.77 (1H, d, J=6.9 Hz), 7.71 (2H, m), 7.32 (2H, m), 7.17 (2H, m), 6.83 (1H, m), 6.44 (1H, d, J=6.9 Hz), 5.28 (1H, s), 3.47 (1H, m), 1.10 (6H, d, J=6.0 Hz), $^{13}$C NMR (100 MHz, CDCl$_3$) δ: 159.3, 157.9, 151.8, 150.1, 140.2, 136.0, 135.7, 135.0, 132.0, 131.7, 130.5, 128.8, 128.3, 122.8, 113.7, 113.5, 108.4, 89.0, 49.4, 23.6. HRMS (ESI-TOF$^+$): m/z [M+H]$^+$ calcd for $C_{25}H_{22}ClN_6$: 441.1589; found: 441.1589.

Example 2

In Vitro Assay for Antimicrobial Susceptibility

Antimicrobial susceptibility testing was performed in 96-well microplates. Initial drug dilutions (6.4 mg/ml) were prepared in dimethyl sulfoxide, and subsequent two-fold dilutions were performed in 0.1 ml of 7H9 in the microplates. The final drug concentrations were about 0.008 μg/ml. Every concentration of test compounds was added to two wells. Control wells consisted of bacteria and positive drug (Clofazimine). Plates were incubated at 37° C. The final bacterial titers were 1×10$^6$ CFU/ml for H$_{37}$Rv. Starting at day 7 of incubation, 20 μl of 10× Alamar blue solution and 12.5 μl of 20% Tween 80 were added to each well and the plates were reincubated at 37° C. Wells were observed at 24 h and the colors of all were recorded. Visual MICs were defined as the lowest of drug that prevented a color change from blue to pink. Fluorescence was measured in a microplate fluorometer in bottom-reading mode with excitation at 530 nm and emission at 590 nm. For fluorometric MICs, the lowest drug concentration effecting an inhibition of ≥90% was considered the MIC. The results are shown Table 1 and 2 above.

Example 3

In Vivo Testing

Male BALB/c mice (18~20 g) were infected intravenously with 0.2 ml portions containing 1×10$^5$ CFU of H$_{37}$Rv. One day after the infection, four mice were sacrificed and the numbers of CFU in the spleens and lungs were determined. Organs were removed and homogenized in Middlebrook 7H9 broth. To enumerate CFU, appropriate dilutions of the homogenates were plated onto Middlebrook 7H10 agar and colonies were counted after 3 to 4 weeks of incubation at 37° C. The remaining mice were allocated either to untreated groups or to various drug treated groups (six mice per group). The dose of every test compound was 20 mg/kg. The positive control groups were treated by isoniazid and clofazimine. The test compounds and clofazimine were administered by gavage 5 times weekly. Untreated mice were administered by gavage with CMC. Thirty days postinfection, both untreated and treated mice were sacrificed and lung tissue CFU counts were determined. The significance of the CFU count and organ weight difference was assessed by a two-tailed Student t test. P≤0.01 was considered significant. The results of twelve exemplary compounds are shown Table 3 below.

TABLE 3

| | Compound | | | | | |
| --- | --- | --- | --- | --- | --- | --- |
| | TBI-1002 | TBI-1004 | TBI-1010 | TBI-166 | TBI-416 | TBI-443 |
| Untreated Control | 8.53 | 8.53 | 8.53 | 8.53 | 8.53 | 8.53 |
| Log CFU (CLF-treated) | 6.33 | 6.33 | 6.33 | 6.33 | 6.33 | 6.33 |
| Log CFU Reduction (CLF) | 2.20 | 2.20 | 2.20 | 2.20 | 2.20 | 2.20 |
| Log CFU (TBI treated) | 4.85 | 4.28 | 4.86 | 4.66 | 3.83 | 5.13 |

TABLE 3-continued

| | | | | | | |
|---|---|---|---|---|---|---|
| Log CFU Reduction (TBI treated) | 3.68 | 4.25 | 3.67 | 3.87 | 4.70 | 3.40 |
| Fold X CLF (log) | 1.48 | 2.05 | 1.47 | 1.67 | 2.50 | 1.20 |
| Fold X CLF | 30.2 | 112.2 | 29.5 | 46.8 | 316.2 | 15.8 |

| | Compound | | | | | |
|---|---|---|---|---|---|---|
| | TBI-444 | TBI-449 | TBI-450 | TBI-678 | TBI-688 | TBI-161 |
| Untreated Control | 8.53 | 8.53 | 8.53 | 8.82 | 8.82 | 8.82 |
| Log CFU (CLF-treated) | 6.33 | 6.33 | 6.33 | 5.99 | 5.99 | 5.99 |
| Log CFU Reduction (CLF) | 2.20 | 2.20 | 2.20 | 2.83 | 2.83 | 2.83 |
| Log CFU (TBI treated) | 4.71 | 3.87 | 3.64 | 5.82 | 5.99 | 6.05 |
| Log CFU Reduction (TBI treated) | 3.82 | 4.66 | 4.89 | 3.00 | 2.83 | 2.77 |
| Fold X CLF (log) | 1.62 | 2.46 | 2.69 | 0.17 | 0.00 | −0.06 |
| Fold X CLF | 41.7 | 288.4 | 489.8 | 1.5 | 1.0 | 0.9 |

Example 5

Compounds Synthesized According to General Methods

TBI-054, 5-Phenyl-3-(1-methy ethyl)imino-2-(3-pyridyl)amino-3,5-dihydrophenazine:

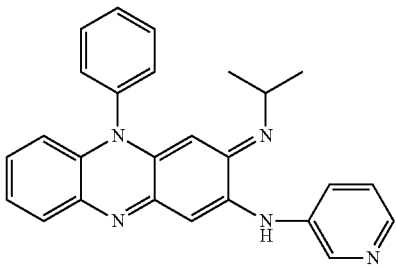 [SMILES: CC(C)/N=c1\cc2n(-c3ccccc3)c3ccccc3nc-2cc1Nc1cccnc1]

$^1$H NMR (300 MHz, CDCl$_3$) δ: 1.06-1.08 (6H, d, J=6.0 Hz, CH(CH$_3$)$_2$), 3.38-3.46 (1H, m, J=6.0 Hz, CH(CH$_3$)$_2$), 5.28 (1H, s, CH═C═N), 6.48-6.50 (1H, d, J=7.5 Hz, PhH$_6$), 6.85 (1H, s, CH═C—NH), 7.10-7.19 (2H, m, PhH$_{7,8}$), 7.29-7.35 (3H, m, PhH$_9$, Ph'H$_{2,6}$), 7.62-7.80 (5H, m, Ph'H$_{3,4,5}$, PyH$_6$, PyH$_5$), 8.32-8.33 (1H, d, J=3.9 Hz, PyH$_4$), 8.59 (1H, d, J=2.4 Hz, PyH$_2$). $^{13}$C NMR (100 MHz, CDCl$_3$) δ: 23.49, 49.28, 89.08, 99.40, 114.16, 122.78, 123.60, 127.64, 127.82, 128.18, 128.79, 129.72, 131.25, 131.74, 135.08, 135.64, 136.96, 137.59, 143.66, 143.92, 144.15, 150.57, 150.96. HRMS (ESI-TOF$^+$): m/z [M+H]$^+$ calcd for C$_{26}$H$_{24}$N$_5$: 406.2031; found: 406.2041.

TBI-055, 5-Phenyl-3-(N-methyl-4-piperidyl)imino-2-(3-pyridyl)amino-3,5-dihydrophenazine:

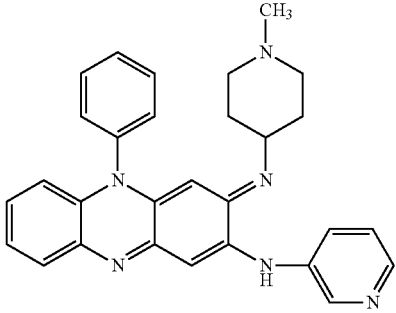 [SMILES: CN1CCC(/N=c2\cc3n(-c4ccccc4)c4ccccc4nc-3cc2Nc2cccnc2)CC1]

$^1$H NMR (300 MHz, CDCl$_3$) δ: 1.66 (4H, brs, (CH$_2$CH$_2$N)$_2$), 1.96-2.04 (2H, m, CH$_2$CH$_2$N), 2.27 (3H, s, CH$_3$), 2.75-2.79 (2H, m, CH$_2$CH$_2$N), 3.06-3.10 (1H, m, NCHCH$_2$CH$_2$N), 5.24 (1H, s, CH═C═N), 6.52-6.54 (1H, d, J=7.8 Hz, PhH$_6$), 6.87 (1H, s, CH═C—NH), 7.12-7.21 (2H, m, PhH$_{7,8}$), 7.27-7.34 (3H, m, PhH$_9$, Ph'H$_{2,6}$), 7.64-7.80 (5H, m, PyH$_6$, PyH$_5$), 8.32-8.34 (1H, d, J=4.8 Hz, PyH$_4$), 8.58 (1H, d, J=1.8 Hz, PyH$_2$). $^{13}$C NMR (100 MHz, CDCl$_3$) δ: 32.64, 46.38, 54.05, 89.13, 99.51, 114.23, 122.93, 123.64, 127.89, 128.29, 128.69, 129.76, 131.25, 131.60, 135.09, 135.68, 136.80, 137.51, 143.53, 143.96, 144.29, 150.81, 151.25. HRMS (ESI-TOF$^+$): m/z [M+H]$^+$ calcd for C$_{29}$H$_{29}$N$_6$: 461.2453; found: 461.2436.

TBI-056, 5-Phenyl-3-(2-morpholinoethyl)imino-2-(3-pyridyl)amino-3,5-dihydrophenazine:

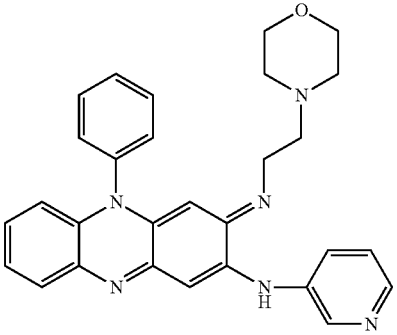 [SMILES: c1ccc(-n2c3c/c(=N\CCN4CCOCC4)c(Nc4cccnc4)cc-3nc3ccccc32)cc1]

$^1$H NMR (300 MHz, CDCl$_3$) δ: 2.44-2.47 (4H, t, J=4.5 Hz, (OCH$_2$CH$_2$N)$_2$), 2.66-2.71 (2H, t, J=7.5 Hz, CH$_2$CH$_2$), 3.30-3.35 (2H, t, J=7.5 Hz, CH$_2$CH$_2$), 3.68-3.71 (4H, t, J=4.8 Hz, (OCH$_2$CH$_2$N)$_2$), 5.30 (1H, s, CH—C═N), 6.48-6.51 (1H, d, J=7.8 Hz, PhH$_6$), 6.89 (1H, s, CH═C—NH), 7.13-7.23 (2H, m, PhH$_{7,8}$), 7.29-7.35 (3H, m, PhH$_9$, Ph'H$_{2,6}$), 7.62-7.80 (5H, m, Ph'H$_{3,4,5}$, PyH$_6$, PyH$_5$), 8.34-8.35 (1H, d, J=3.9 Hz, PyH$_4$), 8.59 (1H, d, J=2.1 Hz, PyH$_2$). $^{13}$C NMR (100 MHz, CDCl$_3$) δ: 47.70, 54.02, 59.78, 66.91, 88.94, 99.54, 114.36, 123.09, 123.66, 127.92, 128.32, 128.62, 129.82, 131.43, 135.11, 135.69, 136.70, 137.48, 143.34, 143.90, 144.36, 150.68, 152.92. HRMS (ESI-TOF$^+$): m/z [M+H]$^+$ calcd for C$_{29}$H$_{29}$N$_6$O: 477.2397; found: 477.2399.

TBI-057, 5-phenyl-3-(N-isobutyl-4-piperidyl)imino-2-(3-pyridyl)amino-3,5-dihydrophenazine:

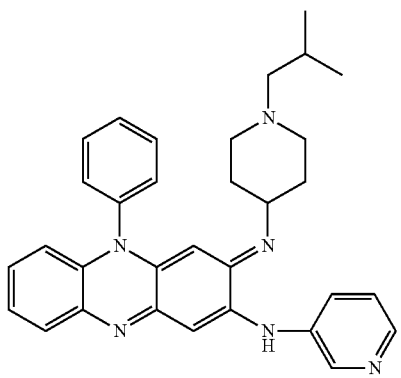 [SMILES: CC(C)CN1CCC(/N=c2\cc3n(-c4ccccc4)c4ccccc4nc-3cc2Nc2cccnc2)CC1]

¹H NMR (300 MHz, CDCl₃) δ: 0.88-0.90 (6H, d, J=6.6 Hz, CH(CH₃)₂), 1.60-1.91 (7H, m, (CH₂CH₂N)₂, CH(CH₃)₂, CH₂CH₂N), 2.03-2.05 (2H, d, J=7.5 Hz, CH₂CH), 2.75-2.79 (2H, m, CH₂CH₂N), 3.05-3.08 (1H, m, NCHCH₂CH₂N), 5.24 (1H, s, CH=C=N), 6.51-6.54 (1H, d, J=7.5 Hz, PhH₆), 6.86 (1H, s, CH=C—NH), 7.11-7.20 (2H, m, PhH₇,₈), 7.29-7.35 (3H, m, PhH₉, Ph'H₂,₆), 7.63-7.80 (5H, m, Ph'H₃,₄,₅, PyH₆, PyH₅), 8.32-8.33 (1H, d, J=4.2 Hz, PyH₄), 8.58 (1H, d, J=2.4 Hz, PyH₂). ¹³C NMR (100 MHz, CDCl₃) δ: 20.96, 25.70, 32.78, 52.51, 56.01, 67.11, 89.22, 99.43, 114.18, 122.84, 123.63, 127.74, 128.24, 128.74, 129.70, 131.23, 131.67, 135.06, 135.67, 136.90, 137.55, 143.58, 143.88, 144.18, 151.06. HRMS (ESI-TOF⁺): m/z [M+H]⁺ calcd for C₃₂H₃₅N₆: 503.2923; found: 503.2962.

TBI-058, 5-Phenyl-3-(4-tetrahydropyranyl)imino-2-(3-pyridyl)amino-3,5-dihydrophenazine:

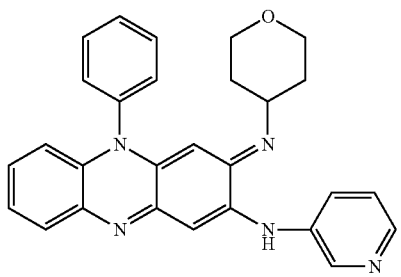 [SMILES: c1ccc(-n2c3c/c(=N\C4CCOCC4)c(Nc4cccnc4)cc-3nc3ccccc32)cc1]

¹H NMR (300 MHz, CDCl₃) 1.60 (4H, m), 3.27-3.41 (3H, m), 3.94-3.97 (2H, 5.24 (1H, s, CH=C=N), 6.52-6.55 (1H, d, J=7.5 Hz, PhH₆), 6.88 (1H, s, CH=C—NH), 7.13-7.22 (2H, m, PhH₇,₈), 7.28-7.35 (3H, m, PhH₉, Ph'H₂,₆), 7.63-7.80 (5H, m, Ph'H₃,₄,₅, PyH₆, PyH₅), 8.33-8.35 (1H, d, J=4.2 Hz, PyH₄), 8.59 (1H, d, J=2.4 Hz, PyH₂). ¹³C NMR (100 MHz, CDCl₃) δ: 33.37, 54.43, 66.20, 88.96, 99.58, 114.24, 122.97, 123.64, 127.87, 127.94, 128.31, 128.6, 129.77, 131.25, 131.56, 135.16, 135.65, 136.72, 137.51, 143.55, 143.95, 144.35, 150.71, 151.28. HRMS (ESI-TOF⁺): m/z [M+H]⁺ calcd for C₂₈H₂₆N₅O: 448.2137; found: 448.2100.

TBI-059, 5-Phenyl-3-(4-methoxycyclohexyl)imino-2-(3-pyridyl)amino-3,5-dihydrophenazine:

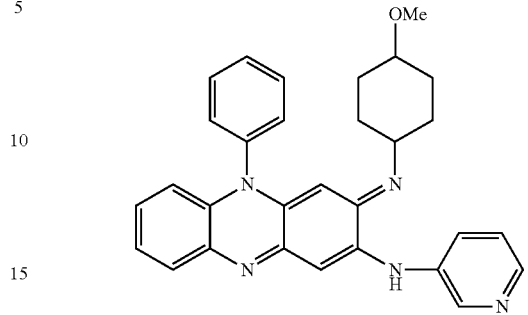

¹H NMR (300 MHz, CDCl₃) δ: 1.07-1.18 (2H, q), 1.33-1.45 (2H, q), 1.66-1.69 (2H, d), 2.04-2.07 (2H, q), 2.99-3.06 (1H, m), 3.13-3.21 (1H, m), 3.35 (3H, s), 5.23 (1H, s, CH—C=N), 6.52-6.55 (1H, d, J=7.5 Hz, PhH₆), 6.85 (1H, s, CH=C—NH), 7.12-7.20 (2H, m, PhH₇,₈), 7.28-7.33 (3H, m, PhH₉, Ph'H₂,₆), 7.61-7.80 (5H, m, Ph'H₃,₄,₅, PyH₆, PyH₅), 8.32-8.33 (1H, d, J=4.2 Hz, PyH₄), 8.57 (1H, d, J=2.4 Hz, PyH₂). ¹³C NMR (100 MHz, CDCl₃) δ: 30.04, 31.15, 55.85, 57.45, 78.56, 89.17, 99.50, 114.20, 122.85, 123.61, 127.79, 128.25, 128.68, 129.82, 131.22, 131.65, 135.06, 135.64, 136.82, 137.46, 143.52, 143.90, 144.22, 150.88, 151.35. HRMS (ESI-TOF⁺): m/z [M+H]⁺ calcd for C₃₀H₃₀N₅O: 476.2450; found: 476.2427.

TBI-060, 5-Phenyl-3-(N-cyclopentyl-4-piperidyl)imino-2-(3-pyridyl)amino-3,5-dihydrophenazine:

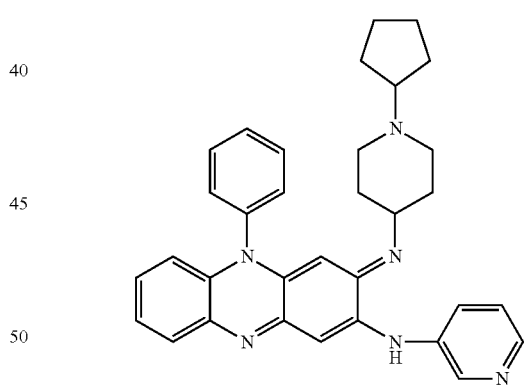

¹H NMR (300 MHz, CDCl₃) δ: 1.23-2.04 (14H, m), 2.45 (1H, brs), 2.91 (2H, brs), 3.12 (1H, brs), 5.24 (1H, s, CH—C=N), 6.51-6.54 (1H, d, J=7.8 Hz, PhH₆), 6.87 (1H, s, CH=C—NH), 7.15-7.19 (2H, m, PhH₇,₈), 7.28-7.34 (3H, m, PhH₉, Ph'H₂,₆), 7.64-7.79 (5H, m, Ph'H₃,₄,₅, PyH₆, PyH₅), 8.32-8.34 (1H, d, J=4.8 Hz, PyH₄), 8.57 (1H, s, PyH₂). ¹³C NMR (125 MHz, CDCl₃) δ: 24.15, 30.66, 32.62, 50.95, 55.48, 67.70, 89.13, 99.51, 114.23, 122.91, 123.64, 127.79, 128.30, 128.70, 129.77, 131.26, 131.63, 135.12, 135.70, 136.86, 137.54, 143.53, 143.92, 144.25, 151.11. HRMS (ESI-TOF⁺): m/z [M+H]⁺ calcd for C₃₃H₃₅N₆: 515.2918; found: 515.2913.

TBI-061, 5-Phenyl-3-(1-methylethyl)imino-2-(2-methoxy-3-pyridyl)amino-3,5-dihydrophenazine:

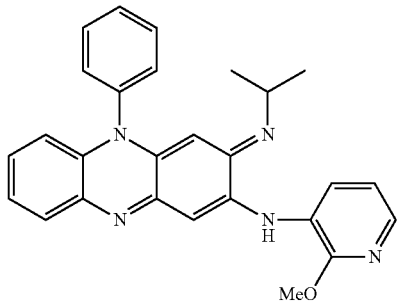 [SMILES: COc1ncccc1Nc1cc2nc3ccccc3n(-c3ccccc3)c-2c/c1=N\C(C)C]

$^1$H NMR (300 MHz, CDCl$_3$) δ: 1.07-1.09 (6H, d, J=6.0 Hz, CH(CH$_3$)$_2$), 3.36-3.45 (1H, m, J=6.0 Hz, CH(CH$_3$)$_2$), 4.03 (3H, s, CH$_3$), 5.27 (1H, s, CH—C=N), 6.45-6.48 (1H, d, J=7.5 Hz, PhH$_6$), 6.88-6.91 (1H, m, PhH$_9$), 6.93 (1H, s, CH=C—NH), 7.08-7.18 (2H, m, PhH$_{7,8}$), 7.32-7.35 (2H, m, Ph'H$_{2,6}$), 7.61-7.66 (1H, m, PyH$_5$), 7.68-7.75 (3H, m, Ph'H$_{3,4,5}$), 7.80-7.83 (1H, d, J=4.8 Hz, PyH$_6$), 7.84-7.87 (1H, d, J=7.8 Hz, PyH$_4$). $^{13}$C NMR (100 MHz, CDCl$_3$) δ: 23.50, 49.29, 53.69, 89.27, 100.10, 114.07, 116.78, 122.64, 124.84, 124.96, 127.53, 128.07, 128.85, 129.65, 131.23, 131.87, 134.96, 135.61, 137.65, 138.69, 142.91, 150.81, 151.29, 155.47. HRMS (ESI-TOF$^+$): m/z [M+H]$^+$ calcd for C$_{27}$H$_{26}$N$_5$O: 436.2137; found: 436.2172.

TBI-062, 5-Phenyl-3-(N-methyl-4-piperidyl)imino-2-(2-methoxy-3-pyridyl)amino-3,5-dihydrophenazine:

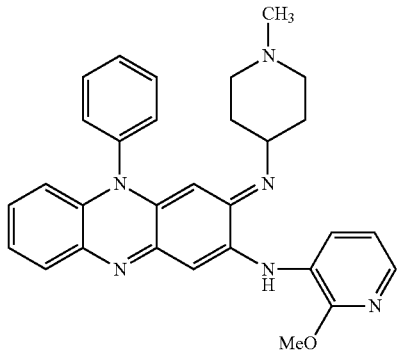 [SMILES: COc1ncccc1Nc1cc2nc3ccccc3n(-c3ccccc3)c-2c/c1=N\C1CCN(C)CC1]

$^1$H NMR (300 MHz, CDCl$_3$) δ: 1.66 (4H, brs, (CH$_2$CH$_2$N)$_2$), 2.10 (2H, m, CH$_2$CH$_2$N), 2.29 (3H, s, CH$_3$), 2.73-2.77 (2H, m, CH$_2$CH$_2$N), 3.16 (1H, m, NCHCH$_2$CH$_2$N), 4.03 (3H, s, CH$_3$), 5.23 (1H, s, CH—C=N), 6.48-6.51 (1H, d, J=7.5 Hz, PhH$_6$), 6.89-6.93 (1H, m, PhH$_9$), 6.97 (1H, s, CH=C—NH), 7.10-7.19 (2H, m, PhH$_{7,8}$), 7.31-7.34 (2H, m, Ph'H$_{2,6}$), 7.62-7.75 (4H, m, PyH$_5$, Ph'H$_{3,4,5}$), 7.78-7.80 (1H, d, J=4.8 Hz, PyH$_6$), 7.84-7.87 (1H, d, J=7.8 Hz, PyH$_4$), 9.08 (1H, s, NH). $^{13}$C NMR (100 MHz, CDCl$_3$) δ: 32.63, 46.51, 53.52, 53.67, 89.10, 100.19, 114.14, 116.82, 122.76, 124.10, 125.03, 127.65, 128.15, 128.77, 128.89, 129.69, 131.24, 131.76, 135.08, 135.64, 137.56, 138.46, 142.60, 151.18, 155.25. HRMS (ESI-TOF$^+$): m/z [M+H]$^+$ calcd for C$_{30}$H$_{31}$N$_6$O: 491.2554; found: 491.2556.

TBI-063, 5-Phenyl-3-(4-methoxycyclohexyl)imino-2-(2-methoxy-3-pyridyl)amino-3,5-dihydrophenazine:

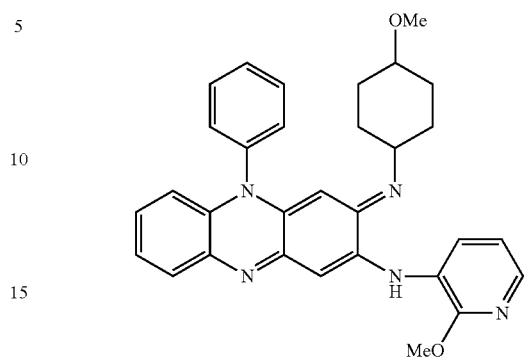

$^1$H NMR (300 MHz, CDCl$_3$) δ: 1.06-1.22 (2H, q), 1.35-1.47 (2H, q), 1.68-1.71 (2H, d), 2.04-2.07 (2H, d), 3.02-3.08 (1H, m), 3.18-3.24 (1H, m), 3.35 (3H, s), 4.02 (3H, s, CH$_3$), 5.22 (1H, s, CH—C=N), 6.51-6.53 (1H, d, J=7.5 Hz, PhH$_6$), 6.88-6.91 (1H, m, PhH$_9$), 6.94 (1H, s, CH=C—NH), 7.10-7.19 (2H, m, PhH$_{7,8}$), 7.31-7.33 (2H, m, Ph'H$_{2,6}$), 7.60-7.65 (1H, m, PyH$_5$), 7.68-7.71 (3H, m, Ph'H$_{3,4,5}$), 7.79-7.81 (1H, d, J=4.8 Hz, PyH$_6$), 7.84-7.86 (1H, d, J=7.8 Hz, PyH$_4$), 8.93 (1H, s, NH). $^{13}$C NMR (100 MHz, CDCl$_3$) δ: 29.66, 30.83, 53.68, 55.82, 57.08, 78.42, 89.32, 100.21, 114.13, 116.82, 122.72, 124.61, 124.94, 127.65, 128.15, 128.74, 129.75, 131.21, 131.77, 134.99, 135.64, 137.52, 138.64, 142.74, 151.19, 151.53, 155.35. HRMS (ESI-TOF$^+$): m/z [M+H]$^+$ calcd for C$_{31}$H$_{32}$N$_5$O$_2$: 506.2556; found: 506.2585.

TBI-064, 5-Phenyl-3-(N-isobutyl-4-piperidyl)imino-2-(2-methoxy-3-pyridyl)amino-3,5-dihydrophenazine:

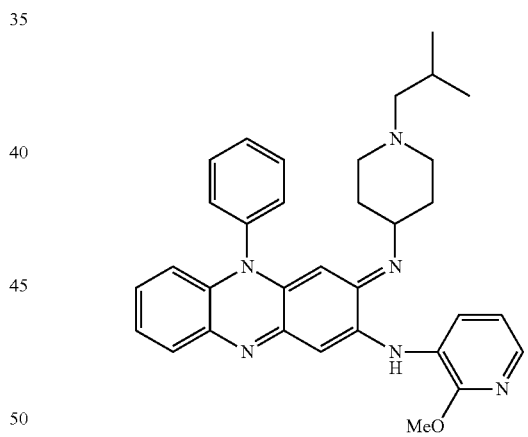

$^1$H NMR (300 MHz, CDCl$_3$) δ: 0.89-0.91 (6H, d, J=6.6 Hz, CH(CH$_3$)$_2$), 1.62-1.82 (5H, m, (CH$_2$CH$_2$N)$_2$, CH(CH$_3$)$_2$), 1.96 (2H, m, CH$_2$CH$_2$N), 2.05-2.07 (2H, d, J=7.5 Hz, CH$_2$CH), 2.74-2.77 (2H, m, CH$_2$CH$_2$N), 3.10-3.12 (1H, m, NCHCH$_2$CH$_2$N), 4.03 (3H, s, CH$_3$), 5.24 (1H, s, CH—C=N), 6.48-6.51 (1H, d, J=7.2 Hz, PhH$_6$), 6.89-6.93 (1H, m, PhH$_9$), 6.96 (1H, s, CH=C—NH), 7.10-7.19 (2H, m, PhH$_{7,8}$), 7.31-7.34 (2H, d, J=7.2 Hz, PhH$_{2,6}$), 7.62-7.75 (4H, m, PyH$_5$, Ph'H$_{3,4,5}$), 7.79-7.80 (1H, d, J=4.8 Hz, PyH$_6$), 7.84-7.87 (1H, d, J=8.1 Hz, PyH$_4$), 9.06 (1H, s, NH). $^{13}$C NMR (100 MHz, CDCl$_3$) δ: 21.04, 25.68, 32.75, 52.18, 53.68, 55.32, 67.38, 89.28, 100.17, 114.10, 116.80, 122.70, 124.26, 125.03, 127.59, 128.13, 128.80, 129.64, 131.21, 131.80, 135.01, 135.64, 137.60, 138.49, 142.70, 151.12, 151.28, 155.31. HRMS (ESI-TOF$^+$): m/z [M+H]$^+$ calcd for C$_{33}$H$_{37}$N$_6$O: 533.3023; found: 533.3019.

TBI-065, 5-Phenyl-3-(2-morpholinoethyl)imino-2-(2-methoxy-3-pyridyl)amino-3,5-dihydrophenazine:

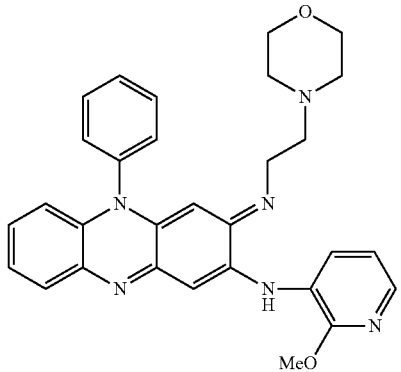 [SMILES: COc1ncccc1Nc1cc2nc3ccccc3n(-c3ccccc3)c-2c/c1=N\CCN1CCOCC1]

$^1$H NMR (300 MHz, CDCl$_3$) δ: 2.49-2.52 (4H, t, J=4.5 Hz, (OCH$_2$CH$_2$N)$_2$), (2H, t, J=6.9 Hz, CH$_2$CH$_2$), 3.30-3.34 (2H, t, J=7.2 Hz, CH$_2$CH$_2$), 3.68-3.71 (4H, t, J=4.8 Hz, (OCH$_2$CH$_2$N)$_2$), 4.03 (3H, s, CH$_3$), 5.27 (1H, s, CH—C=N), 6.47-6.49 (1H, d, J=7.5 Hz, PhH$_6$), 6.89-6.94 (1H, m, PhH$_9$), 6.98 (1H, s, CH=C—NH), 7.11-7.22 (2H, m, PhH$_{7,8}$), 7.31-7.34 (2H, d, J=7.2 Hz, Ph'H$_{2,6}$), 7.61-7.74 (4H, m, PyH$_5$, Ph'H$_{3,4,5}$), 7.80-7.82 (1H, d, J=4.5 Hz, PyH$_6$), 7.85-7.88 (1H, d, J=7.5 Hz, PyH$_4$), 8.85 (1H, s, NH). $^{13}$C NMR (100 MHz, CDCl$_3$) δ: 48.31, 53.72, 54.18, 59.80, 67.00, 89.10, 100.17, 114.30, 116.85, 122.96, 124.64, 124.81, 127.79, 128.21, 128.68, 129.75, 131.41, 131.72, 135.03, 135.69, 137.54, 138.76, 142.51, 151.01, 153.05, 155.31. HRMS (ESI-TOF$^+$): m/z [M+H]$^+$ calcd for C$_{30}$H$_{31}$N$_6$O$_2$: 507.2503; found: 507.2505.

TBI-066, 5-Phenyl-3-(4-tetrahydropyranyl)imino-2-(2-methoxy-3-pyridyl)amino-3,5-dihydrophenazine:

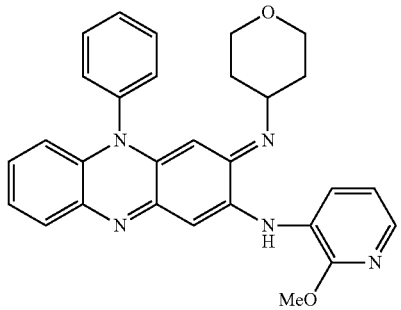 [SMILES: COc1ncccc1Nc1cc2nc3ccccc3n(-c3ccccc3)c-2c/c1=N\C1CCOCC1]

$^1$H NMR (300 MHz, CDCl$_3$) δ: 1.60-1.66 (4H, m), 3.34-3.48 (3H, m), 3.96-4.05 (5H, m), 5.23 (1H, s, CH—C=N), 6.49-6.53 (1H, d, J=7.5 Hz, PhH$_6$), 6.90-6.94 (1H, m, PhH$_9$), 6.98 (1H, s, CH=C—NH), 7.11-7.21 (2H, m, PhH$_{7,8}$), 7.32-7.35 (2H, m, Ph'H$_{2,6}$), 7.62-7.75 (4H, m, PyH$_5$, Ph'H$_{3,4,5}$), 7.80-7.82 (1H, d, J=4.8 Hz, PyH$_6$), 7.84-7.87 (1H, d, J=7.8 Hz, PyH$_4$). $^{13}$C NMR (100 MHz, CDCl$_3$) δ: 33.29, 53.47, 53.674, 89.02, 100.30, 114.19, 116.83, 122.87, 124.32, 124.93, 127.74, 128.21, 128.75, 129.73, 131.25, 131.68, 135.15, 135.65, 137.55, 138.63, 142.63, 151.02, 151.37, 155.30. HRMS (ESI-TOF$^+$): m/z [M+H]$^+$ calcd for C$_{29}$H$_{28}$N$_5$O$_2$: 478.2243; found: 478.2272.

TBI-067, 5-Phenyl-3-(1-methylethyl)imino-2-(6-methyl-3-pyridyl)amino-3,5-dihydrophenazine:

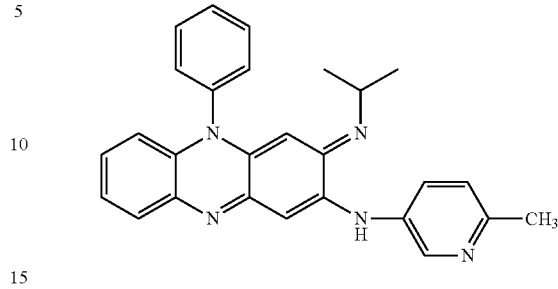

$^1$H NMR (300 MHz, CDCl$_3$) δ: 1.06-1.08 (6H, d, J=6.0 Hz, CH(CH$_3$)$_2$), 2.55 (1H, s, CH$_3$), 3.37-3.45 (1H, m, J=6.0 Hz, CH(CH$_3$)$_2$), 5.27 (1H, s, CH—C=N), 6.46-6.49 (1H, d, J=7.8 Hz, PhH$_6$), 6.73 (1H, s, CH=C—NH), 7.08-7.18 (3H, m, PhH$_{7,8,9}$), 7.32-7.34 (2H, d, J=7.2 Hz, Ph'H$_{2,6}$), 7.61-7.74 (5H, m, Ph'H$_{3,4,5}$, PyH$_{4,5}$), 8.44-8.45 (1H, d, J=2.4 Hz, PyH$_2$). $^{13}$C NMR (100 MHz, CDCl$_3$) δ: 23.49, 23.81, 49.28, 89.07, 98.80, 114.10, 122.70, 123.12, 127.43, 128.07, 128.80, 129.33, 129.67, 131.21, 131.67, 134.16, 135.00, 135.62, 137.64, 143.71, 144.38, 150.61, 151.00, 153.20. HRMS (ESI-TOF$^+$): m/z [M+H]$^+$ calcd for C$_{27}$H$_{26}$N$_5$: 420.2183; found: 420.2181.

TBI-068, 5-Phenyl-3-(N-isobutyl-4-piperidyl)imino-2-(6-methyl-3-pyridyl)amino-3,5-dihydrophenazine:

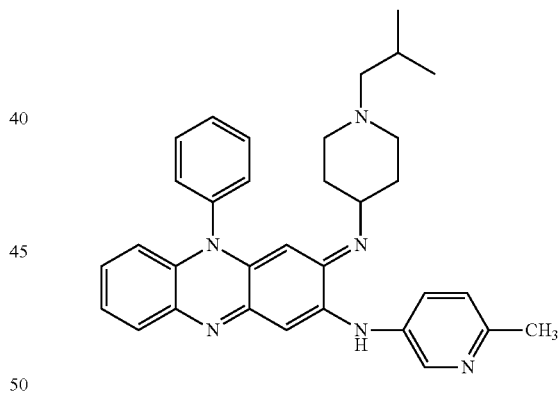

$^1$H NMR (300 MHz, CDCl$_3$) δ: 0.87-0.89 (6H, d, J=6.6 Hz, CH(CH$_3$)$_2$), 1.59-1.89 (7H, (CH$_2$CH$_2$N)$_2$, CH(CH$_3$)$_2$, CH$_2$CH$_2$N), 2.02-2.04 (2H, d, J=6.9 Hz, CH$_2$CH), 2.55 (3H, s, CH$_3$), 2.74-2.78 (2H, m, CH$_2$CH$_2$N), 3.04-3.07 (1H, m, NCHCH$_2$CH$_2$N), 5.23 (1H, s, CH—C=N), 6.50-6.53 (1H, d, J=7.8 Hz, PhH$_6$), 6.74 (1H, s, CH=C—NH), 7.09-7.19 (3H, m, PhH$_{7,8,9}$), 7.31-7.33 (2H, d, J=6.9 Hz, Ph'H$_{2,6}$), 7.62-7.75 (5H, m, Ph'H$_{3,4,5}$, PyH$_{4,5}$), 8.43-8.44 (1H, d, J=2.4 Hz, PyH$_2$). $^{13}$C NMR (100 MHz, CDCl$_3$) δ: 20.96, 23.83, 25.71, 32.79, 52.54, 56.07, 67.10, 89.21, 98.82, 114.14, 122.76, 123.14, 127.50, 128.14, 128.76, 129.26, 129.65, 131.20, 131.60, 134.14, 135.00, 135.67, 137.61, 143.69, 144.32, 151.11, 153.23. HRMS (ESI-TOF$^+$): m/z [M+H]$^+$ calcd for C$_{33}$H$_{37}$N$_6$: 517.3074; found: 517.3076.

TBI-069, 5-Phenyl-3-(N-methyl-4-piperidyl)imino-2-(6-methyl-3-pyridyl)amino-3,5-dihydrophenazine:

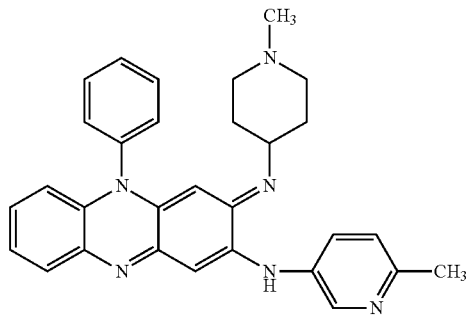 [SMILES: Cc1ccc(Nc2cc3nc4ccccc4n(-c4ccccc4)c-3c/c2=N\C2CCN(C)CC2)cn1]

$^1$H NMR (300 MHz, CDCl$_3$) δ: 1.65 (4H, brs, (CH$_2$CH$_2$N)$_2$), 2.04 (2H, m, CH$_2$CH$_2$N), 2.27 (3H, s, CH$_3$), 2.56 (3H, s, CH$_3$), 2.75-2.79 (2H, m, CH$_2$CH$_2$N), 3.07 (1H, m, NCHCH$_2$CH$_2$N), 5.23 (1H, s, CH—C=N), 6.51-6.53 (1H, d, J=7.5 Hz, PhH$_6$), 6.74 (1H, s, CH=C—NH), 7.15-7.17 (3H, m, PhH$_{7, 8, 9}$), 7.31-7.34 (2H, d, J=7.5 Hz, Ph'H$_{2, 6}$), 7.66-7.75 (5H, m, Ph'H$_{3, 4, 5}$, PyR$_{4, 5}$), 8.45-8.46 (1H, d, J=2.1 Hz, PyH$_2$). $^{13}$C NMR (100 MHz, CDCl$_3$) δ: 23.83, 32.38, 32.61, 46.37, 54.08, 54.48, 89.12, 98.89, 114.21, 122.87, 123.17, 127.60, 128.20, 128.71, 129.49, 129.72, 131.22, 131.52, 134.06, 135.04, 135.71, 137.58, 143.81, 144.31, 151.32, 153.38. HRMS (ESI-TOF$^+$): m/z [M+H]$^+$ calcd for C$_{30}$H$_{31}$N$_6$: 475.2610; found: 475.2597.

TBI-070, 5-Phenyl-3-(4-tetrahydropyranyl)imino-2-(6-methyl-3-pyridyl)amino-3,5-dihydrophenazine:

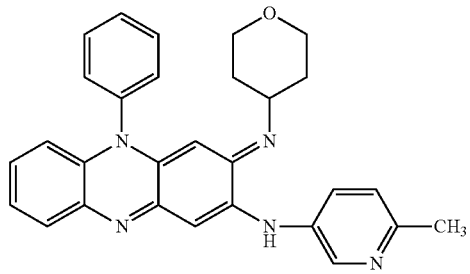 [SMILES: Cc1ccc(Nc2cc3nc4ccccc4n(-c4ccccc4)c-3c/c2=N\C2CCOCC2)cn1]

$^1$H NMR (300 MHz, CDCl$_3$) δ: 1.61-1.67 (4H, m), 2.56 (3H, s, CH$_3$), 3.30-3.47 (3H, 3.93-3.97 (2H, m), 5.23 (1H, s, CH—C=N), 6.51-6.54 (1H, d, J=7.5 Hz, PhH$_6$), 6.75 (1H, s, CH=C—NH), 7.11-7.21 (3H, m, PhH$_{7, 8, 9}$), 7.32-7.34 (2H, d, J=7.5 Hz, Ph'H$_{2, 6}$), 7.63-7.75 (5H, m, Ph'H$_{3, 4, 5}$, PyH$_{4, 5}$), 8.46 (1H, s). $^{13}$C NMR (100 MHz, CDCl$_3$) δ: 23.82, 33.39, 54.46, 66.23, 88.95, 98.97, 114.22, 122.92, 123.19, 127.66, 128.22, 128.72, 129.51, 129.74, 131.24, 131.49, 134.00, 135.12, 135.67, 137.58, 143.79, 144.34, 150.76, 151.36, 153.46. HRMS (ESI-TOF$^+$): m/z [M+H]$^+$ calcd for C$_{29}$H$_{28}$N$_5$O: 462.2293; found: 462.2316.

TBI-072, 5-Phenyl-3-(4-methoxycyclohexyl)imino-2-(6-methyl-pyridyl)amino-3,5-dihydrophenazine:

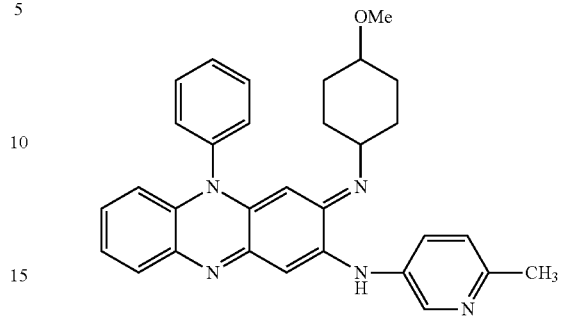

$^1$H NMR (300 MHz, CDCl$_3$) δ: 1.06-1.18 (2H, q), 1.34-1.45 (2H, q), 1.65-1.69 (2H, d), 2.04-2.07 (2H, d), 2.55 (3H, s, CH$_3$), 2.98-3.05 (1H, m), 3.13-3.20 (1H, m), 3.35 (3H, s), 5.22 (1H, s, CH—C=N), 6.51-6.54 (1H, d, J=8.1 Hz, PhH$_6$), 6.73 (1H, s, CH=C—NH), 7.10-7.19 (3H, m, PhH$_{7, 8, 9}$), 7.30-7.33 (2H, d, J=6.9 Hz, Ph'H$_{2, 6}$), 7.60-7.73 (5H, m, Ph'H$_{3, 4, 5}$, PyH$_{4, 5}$), 8.43-8.44 (1H, d, J=2.4 Hz, PyH$_2$). $^{13}$C NMR (125 MHz, CDCl$_3$) δ: 23.81, 30.07, 31.18, 55.84, 57.50, 78.60, 89.16, 98.91, 114.17, 122.77, 123.14, 127.58, 128.17, 128.71, 129.33, 129.78, 131.20, 131.59, 134.09, 135.01, 135.68, 137.54, 143.74, 144.32, 150.92, 151.43, 153.30. HRMS (ESI-TOF$^+$): m/z [M+H]$^+$ calcd for C$_{31}$H$_{32}$N$_5$O: 490.2606; found: 490.2586.

TBI-073, 5-Phenyl-3-(1-methylethyl)imino-2-(2-methyl-3-pyridyl)amino-3,5-dihydrophenazine:

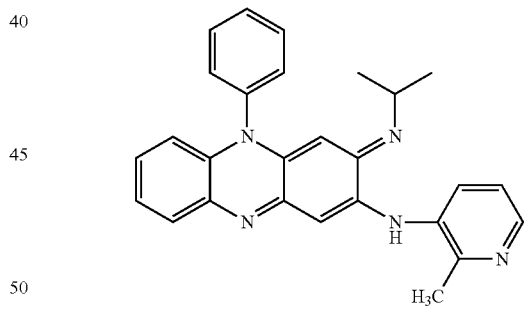

$^1$H NMR (300 MHz, CDCl$_3$) δ: 1.07-1.09 (6H, d, J=6.0 Hz, CH(CH$_3$)$_2$), 2.55 (1H, s, CH$_3$), 3.39-3.47 (1H, m, J=6.0 Hz, CH(CH$_3$)$_2$), 5.28 (1H, s, CH—C=N), 6.47-6.50 (1H, d, J=7.8 Hz, PhH$_6$), 6.60 (1H, s, CH=C—NH), 7.09-7.20 (3H, m, PhH$_{7, 8, 9}$), 7.33-7.36 (2H, d, J=7.8 Hz, Ph'H$_{2, 6}$), 7.62-7.76 (4H, m, Ph'H$_{3, 4, 5}$, PyH$_5$), 7.81-7.84 (1H, d, J=8.1 Hz, PyH$_4$), 8.44-8.45 (1H, d, J=4.5 Hz, PyH$_6$). $^{13}$C NMR (100 MHz, CDCl$_3$): 20.92, 23.52, 49.18, 89.03, 98.82, 114.14, 121.63, 122.74, 127.47, 128.07, 128.80, 128.95, 129.71, 131.24, 131.69, 134.87, 135.07, 135.61, 137.65, 144.02, 144.12, 150.53, 151.01, 152.12. HRMS (ESI-TOF$^+$): m/z [M+H]$^+$ calcd for C$_{27}$H$_{26}$N$_5$: 420.2188; found: 420.2167.

TBI-075, 5-Phenyl-3-(4-tetrahydropyranyl)imino-2-(2-methyl-3-pyridyl)amino-3,5-dihydrophenazine:

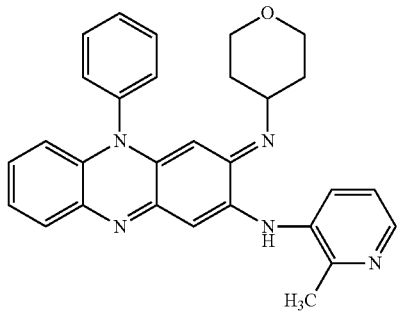 [SMILES: Cc1ncccc1Nc1cc2nc3ccccc3n(-c3ccccc3)c-2c/c1=N\C1CCOCC1]

$^1$H NMR (300 MHz, CDCl$_3$) δ: 1.60-1.66 (4H, m), 2.56 (3H, s, CH$_3$), 3.33-3.46 (3H, m), 3.93-3.99 (2H, m), 5.25 (1H, s, CH—C=N), 6.51-6.55 (1H, d=7.5 Hz, PhH$_6$), 6.65 (1H, s, CH=C—NH), 7.12-7.21 (3H, m, PhH$_{7, 8, 9}$), 7.33-7.35 (2H, d, J=6.9 Hz, Ph'H$_{2, 6}$), 7.64-7.76 (4H, m, Ph'H$_{3, 4, 5}$, PyH$_5$), 7.83-7.86 (1H, d, J=8.1 Hz, PyH$_4$), 8.27-8.29 (1H, d, J=4.8 Hz, PyH$_6$). $^{13}$C NMR (100 MHz, CDCl$_3$) δ: 20.95, 33.19, 53.82, 65.96, 88.90, 99.01, 114.24, 121.67, 122.95, 127.71, 128.21, 128.71, 128.90, 129.77, 131.26, 131.52, 134.68, 135.19, 135.64, 137.56, 143.94, 144.13, 150.75, 151.27, 152.04. HRMS (ESI-TOF$^+$): m/z [M+H]$^+$ calcd for C$_{29}$H$_{28}$N$_5$O: 462.2293; found: 462.2278.

TBI-076, 5-Phenyl-3-(4-methoxycyclohexyl)imino-2-(2-ethyl-3-pyridyl)amino-3,5-dihydrophenazine:

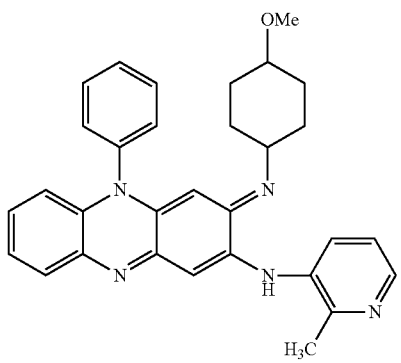

$^1$H NMR (300 MHz, CDCl$_3$) δ: 1.09-1.22 (2H, q), 1.32-1.45 (2H, q), 1.68-1.71 (2H, d), 2.03-2.06 (2H, d), 2.53 (3H, s, CH$_3$), 3.02-3.09 (1H, m), 3.16-3.22 (1H, m), 3.35 (3H, s, CH$_3$), 5.24 (1H, s, CH—C=N), 6.52-6.55 (1H, d, J=7.8 Hz, PhH$_6$), 6.61 (1H, s, CH=C—NH), 7.11-7.20 (3H, m, PhH$_{7, 8, 9}$), 7.31-7.34 (2H, d, J=7.2 Hz, Ph'H$_{2, 6}$), 7.61-7.74 (4H, m, Ph'H$_{3, 4, 5}$, PyH$_5$), 7.81-7.84 (1H, d, J=8.1 Hz, PyH$_4$), 8.26-8.27 (1H, d, J=4.5 Hz, PyH$_6$). $^{13}$C NMR (100 MHz, CDCl$_3$) δ: 20.91, 29.82, 31.03, 55.83, 57.13, 89.12, 98.92, 114.19, 121.65, 122.80, 127.62, 128.14, 128.69, 128.88, 129.79, 131.21, 131.59, 134.76, 135.06, 135.62, 137.52, 143.96, 144.04, 150.91, 151.33, 152.01. HRMS (ESI-TOF$^+$): m/z [M+H]$^+$ calcd for C$_{31}$H$_{32}$N$_5$O: 490.2606; found: 490.2591.

TBI-077, 5-Phenyl-3-cyclohexylimino-2-(2-methyl-3-pyridyl)amino-3,5-dihydrophenazine:

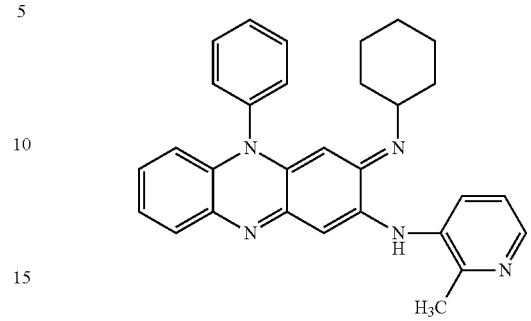

$^1$H NMR (300 MHz, CDCl$_3$) δ: 1.15-1.42 (5H, m), 1.58-1.63 (3H, m), 1.70-1.73 (2H, m), 2.54 (3H, s, CH$_3$), 3.05-3.11 (1H, m), 5.26 (1H, s, CH—C=N), 6.50-6.53 (1H, d, J=7.5 Hz, PhH$_6$), 6.62 (1H, s, CH=C—NH), 7.09-7.20 (3H, m, PhH$_{7, 8, 9}$), 7.32-7.35 (2H, d, J=7.2 Hz, Ph'H$_{2, 6}$), 7.62-7.75 (4H, m, Ph'H$_{3, 4, 5}$, PyH$_5$), 7.81-7.84 (1H, d, J=7.8 Hz, PyH$_4$), 8.25-8.27 (1H, d, J=4.5 Hz, PyH$_6$). $^{13}$C NMR (100 MHz, CDCl$_3$) δ: 20.94, 24.46, 25.88, 33.57, 57.44, 89.28, 98.80, 114.12, 121.63, 122.72, 127.46, 128.07, 128.68, 128.78, 129.61, 131.19, 131.66, 134.94, 135.01, 135.64, 137.65, 143.88, 144.06, 150.64, 151.07, 151.94. HRMS (ESI-TOF$^+$): m/z [M+H]$^+$ calcd for C$_{30}$H$_{30}$N$_5$: 460.2501; found: 460.2486.

TBI-078, 5-Phenyl-3-methylimino-2-(2-ethyl-3-pyridyl)amino-3,5-dihydrophenazine:

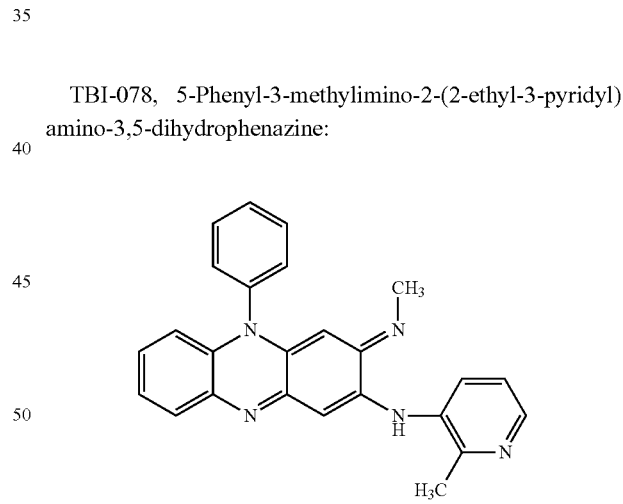

$^1$H NMR (300 MHz, CDCl$_3$) δ: 2.55 (3H, s, CH$_3$), 3.06 (3H, s, CH$_3$), 5.33 (1H, s, CH—C=N), 6.51-6.53 (2H, m, CH=C—NH, PhH$_6$), 7.13-7.23 (3H, m, PhH$_{7, 8, 9}$), 7.33-7.36 (2H, d, J=7.5 Hz, Ph'H$_{2, 6}$), 7.63-7.79 (5H, m, Ph'H$_{3, 4, 5}$, PyH$_5$, PyH$_4$), 8.31-8.32 (1H, d, J=3.6 Hz, PyH$_6$). $^{13}$C NMR (100 MHz, CDCl$_3$) δ: 21.01, 37.21, 88.52, 99.01, 114.40, 121.72, 123.12, 127.79, 128.23, 128.56, 129.85, 130.23, 131.37, 134.49, 135.02, 135.79, 137.52, 144.24, 144.76, 152.95, 154.23. HRMS (ESI-TOF$^+$): m/z [M+H]$^+$ calcd for C$_{25}$H$_{22}$N$_5$: 392.1875; found: 392.1861.

TBI-079, 5-Phenyl-3-cyclohexylimino-2-(2-methoxy-3-pyridyl)amino-3,5-dihydrophenazine:

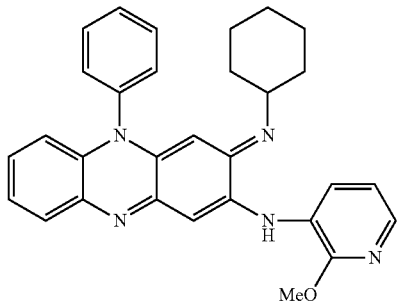 [SMILES: COc1ncccc1Nc1cc2nc3ccccc3n(-c3ccccc3)c-2c/c1=N\C1CCCCC1]

$^1$H NMR (300 MHz, CDCl$_3$) δ: 1.16-1.76 (10H, m), 3.05-3.08 (1H, m), 4.03 (3H, s, CH$_3$), 5.25 (1H, s, CH—C=N), 6.49-6.52 (1H, d, J=8.1 Hz, PhH$_6$), 6.89-6.94 (2H, m, PhH$_9$, CH=C—NH), 7.09-7.19 (2H, m, PhH$_{7, 8}$), 7.32-7.35 (2H, d, J=7.5 Hz, Ph'H$_{2, 6}$), 7.61-7.75 (4H, m, PyH$_5$, Ph'H$_{3, 4, 5}$), 7.79-7.81 (1H, d, J=4.8 Hz, PyH$_6$), 7.84-7.87 (1H, d, J=7.8 Hz, PyH$_4$). $^{13}$C NMR (100 MHz, CDCl$_3$) δ: 24.33, 25.97, 33.49, 53.68, 57.41, 89.49, 100.12, 114.04, 116.80, 122.61, 124.47, 125.05, 127.52, 128.07, 128.84, 129.55, 131.18, 131.86, 134.91, 135.62, 137.64, 138.53, 142.84, 150.81, 151.38, 155.37. HRMS (ESI-TOF$^+$): m/z [M+H]$^+$ calcd for C$_{30}$H$_{30}$N$_5$O: 476.2450; found: 476.2432.

TBI-081, 5-Phenyl-3-(1-methylethyl)imino-2-(5-methyl-3-pyridyl)amino-3,5-dihydrophenazine:

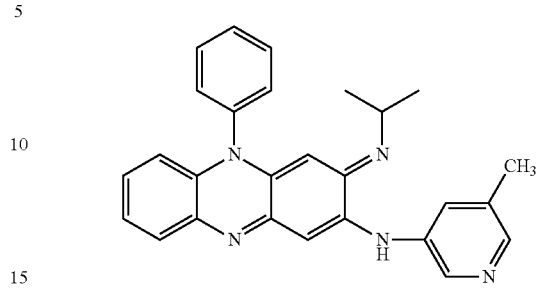

$^1$H NMR (300 MHz, CDCl$_3$) δ: 1.05-1.08 (6H, d, J=6.3 Hz, CH(CH$_3$)$_2$), 2.04 (3H, s, CH$_3$), 3.37-3.45 (1H, m, J=6.0 Hz, CH(CH$_3$)$_2$), 5.27 (1H, s, CH—C=N), 6.47-6.50 (1H, d, J=7.8 Hz, PhH$_6$), 6.84 (1H, s, CH=C—NH), 7.09-7.19 (2H, m, PhH$_{7, 8}$), 7.32-7.35 (2H, d, J=7.2 Hz, Ph'H$_{2, 6}$), 7.59-7.75 (5H, m, Ph'H$_{3, 4, 5}$, PyH$_4$, PhH$_9$), 8.16 (1H, s, PyH$_6$), 8.39-8.40 (1H, d, J=2.1 Hz, PyH$_2$). $^{13}$C NMR (100 MHz, CDCl$_3$) δ: 18.47, 23.49, 49.28, 89.10, 99.32, 114.15, 122.75, 127.58, 128.10, 128.28, 128.80, 129.71, 131.25, 131.74, 133.46, 135.05, 135.61, 136.53, 137.61, 141.08, 143.75, 144.83, 150.55, 151.06. HRMS (ESI-TOF$^+$): m/z [M+H]$^+$ calcd for C$_{27}$H$_{26}$N$_5$: 420.2188; found: 420.2178.

TBI-080, 5-Phenyl-3-cyclohexylimino-2-(6-methyl-3-pyridyl)amino-3,5-dihydrophenazine:

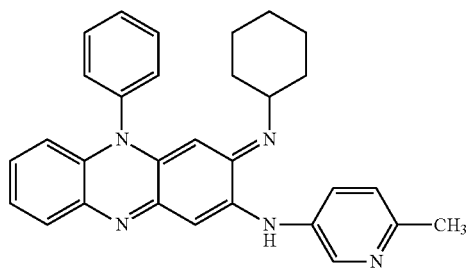 [SMILES: Cc1ccc(Nc2cc3nc4ccccc4n(-c4ccccc4)c-3c/c2=N\C2CCCCC2)cn1]

$^1$H NMR (300 MHz, CDCl$_3$) δ: 1.07-1.41 (5H, m), 1.58-2.04 (5H, m), 2.55 (3H, s, CH$_3$), 2.99-3.06 (1H, m), 5.24 (1H, s, CH—C=N), 6.50-6.52 (1H, d, J=7.5 Hz, PhH$_6$), 6.73 (1H, s, CH=C—NH), 7.09-7.18 (3H, m, PhH$_{7, 8, 9}$), 7.32-7.34 (2H, d, J=7.2 Hz, Ph'H$_{2, 6}$), 7.61-7.75 (5H, m, Ph'H$_{3, 4, 5}$, PyH$_{4, 5}$), 8.43-8.44 (1H, d, J=2.4 Hz, PyH$_2$). $^{13}$C NMR (100 MHz, CDCl$_3$) δ: 23.80, 24.71, 25.82, 33.60, 57.97, 89.36, 98.78, 114.08, 122.68, 123.13, 127.42, 128.08, 128.79, 129.28, 129.57, 131.17, 131.64, 134.20, 134.93, 135.5, 137.65, 143.67, 144.40, 150.76, 151.07, 153.15. HRMS (ESI-TOF$^+$): m/z [M+H]$^+$ calcd for C$_{30}$H$_{30}$N$_5$: 460.2501; found: 460.2485.

TBI-082, 5-Phenyl-3-cyclohexylimino-2-(5-methyl-3-pyridyl)amino-3,5-dihydrophenazine:

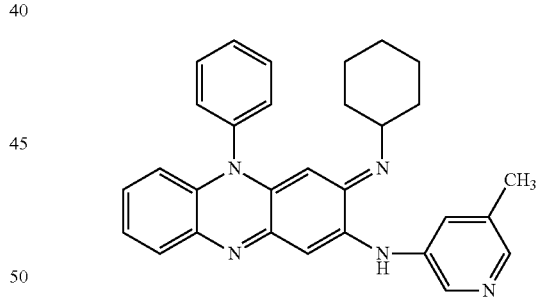

$^1$H NMR (300 MHz, CDCl$_3$) δ: 1.07-1.41 (5H, m), 1.56-1.74 (5H, m), 2.37 (3H, s, CH$_3$), 2.99-3.06 (1H, m), 5.24 (1H, s, CH—C=N), 6.50-6.53 (1H, d, J=7.5 Hz, PhH$_6$), 6.83 (1H, s, CH=C—NH), 7.10-7.19 (2H, m, PhH$_{7, 8}$), 7.32-7.34 (2H, d, J=6.9 Hz, Ph'H$_{2, 6}$), 7.58-7.75 (5H, m, Ph'H$_{3, 4, 5}$, PyH$_4$, PhH$_9$), 8.16 (1H, s, PyH$_6$), 8.38-8.39 (1H, d, J=1.8 Hz, PyH$_2$). $^{13}$C NMR (100 MHz, CDCl$_3$) δ: 18.46, 24.67, 25.82, 33.58, 57.90, 89.38, 99.28, 114.11, 122.72, 127.56, 128.09, 128.21, 128.78, 129.60, 131.19, 131.69, 133.45, 134.96, 135.63, 136.58, 137.61, 141.03, 143.76, 144.75, 150.69, 151.11. HRMS (ESI-TOF$^+$): m/z [M+H]$^+$ calcd for C$_{30}$H$_{30}$N$_5$: 460.2501; found: 460.2498.

TBI-083, 5-Phenyl-3-(4-tetrahydropyranyl)imino-2-(5-methyl-3-pyridyl)amino-3,5-dihydrophenazine:

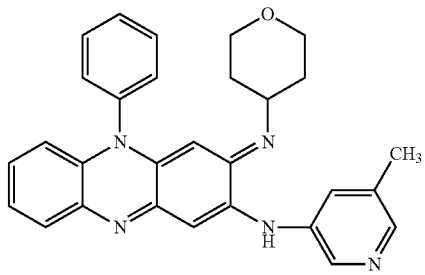 [SMILES: Cc1cncc(Nc2cc3nc4ccccc4n(-c4ccccc4)c-3c/c2=N\C2CCOCC2)c1]

$^1$H NMR (300 MHz, CDCl$_3$) δ: 1.60-1.66 (4H, m), 2.38 (3H, s, CH$_3$), 3.28-3.39 (3H, m), 3.93-3.97 (2H, m), 5.24 (1H, s, CH—C=N), 6.52-6.54 (1H, d, J=7.8 Hz, PhH$_6$), 6.87 (1H, s, CH=C—NH), 7.12-7.22 (2H, m, PhH$_{7,8}$), 7.32-7.34 (2H, d, J=7.5 Hz, Ph'H$_{2,6}$), 7.58-7.76 (5H, m, Ph'H$_{3,4,5}$, PyH$_4$, PhH$_9$), 8.18 (1H, s, PyH$_6$), 8.38-8.39 (1H, s, PyH$_2$). $^{13}$C NMR (100 MHz, CDCl$_3$) δ: 18.46, 33.36, 54.39, 66.19, 88.98, 99.48, 114.24, 122.96, 127.80, 128.23, 128.43, 128.71, 129.76, 131.25, 131.54, 133.53, 135.15, 135.63, 136.34, 137.53, 141.08, 143.65, 144.99, 150.79, 151.29. HRMS (ESI-TOF$^+$): m/z [M+H]$^+$ calcd for C$_{29}$H$_{28}$N$_5$O: 462.2293; found: 462.2297.

TBI-084, 5-Phenyl-3-(4-methoxycyclohexyl)imino-2-(5-methyl-3-pyridyl)amino-3,5-dihydrophenazine:

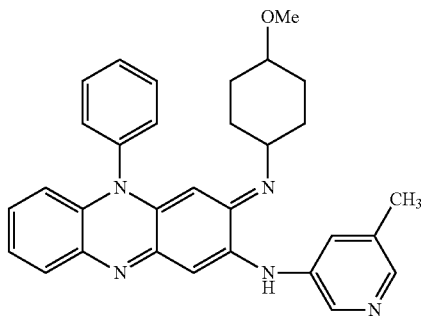 [SMILES: COC1CCC(/N=c2\cc3n(-c4ccccc4)c4ccccc4nc-3cc2Nc2cncc(C)c2)CC1]

$^1$H NMR (300 MHz, CDCl$_3$) δ: 1.07-1.18 (2H, q), 1.34-1.45 (2H, q), 1.66-1.69 (2H, d), 2.05-2.07 (2H, d), 2.38 (3H, s, CH$_3$), 2.99-3.06 (1H, m), 3.14-3.21 (1H, m), 3.36 (3H, s, CH$_3$), 5.23 (1H, s, CH—C=N), 6.53-6.56 (1H, d, J=7.8 Hz, PhH$_6$), 6.85 (1H, s, CH=C—NH), 7.12-7.21 (2H, m, PhH$_{7,8}$), 7.32-7.34 (2H, d, J=6.9 Hz, Ph'H$_{2,6}$), 7.59-7.74 (5H, m, Ph'H$_{3,4,5}$, PyH$_4$, PhH$_9$), 8.17 (1H, s, PyH$_6$), 8.38-8.39 (1H, s, J=1.8 Hz, PyH$_2$). $^{13}$C NMR (100 MHz, CDCl$_3$) δ: 18.45, 30.03, 31.11, 55.85, 57.41, 78.54, 89.21, 99.41, 114.21, 122.85, 127.75, 128.18, 128.66, 129.83, 131.23, 131.61, 133.51, 135.03, 135.64, 136.41, 137.45, 141.06, 143.60, 144.87, 150.91, 151.37. HRMS (ESI-TOF$^+$): m/z [M+H]$^+$ calcd for C$_{31}$H$_{32}$N$_5$O: 490.2606; found: 490.2613.

TBI-085, 5-Phenyl-3-(4-hydroxycyclohexyl)imino-2-(5-methyl-3-pyridyl)amino-3,5-dihydrophenazine:

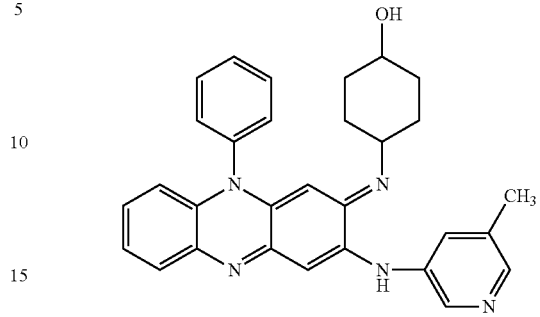

$^1$H NMR (300 MHz, CDCl$_3$) δ: 1.15-1.26 (2H, q), 1.38-1.49 (2H, q), 1.64-1.68 (2H, d), 1.95-1.99 (2H, q), 2.38 (3H, s, CH$_3$), 2.98-3.05 (1H, m), 3.65-3.72 (1H, m), 5.23 (1H, s, CH—CN), 6.52-6.56 (1H, d, J=7.8 Hz, PhH$_6$), 6.85 (1H, s, CH=C—NH), 7.12-7.21 (2H, m, PhH$_{7,8}$), 7.32-7.35 (2H, d, J=7.2 Hz, Ph'H$_{2,6}$), 7.59-7.75 (5H, m, Ph'H$_{3,4,5}$, PyH$_4$, PhH$_9$), 8.16 (1H, s, PyH$_6$), 8.38-8.39 (1H, d, J=2.1 Hz, PyH$_2$). $^{13}$C NMR (100 MHz, CDCl$_3$) δ: 18.46, 31.21, 33.73, 57.20, 70.01, 89.15, 99.40, 114.20, 122.85, 127.74, 128.17, 128.29, 128.71, 129.78, 131.23, 131.62, 133.51, 135.04, 135.62, 136.41, 137.51, 141.03, 143.62, 144.85, 150.93, 151.39. HRMS (ESI-TOF$^+$): m/z [M+H]$^+$ calcd for C$_{30}$H$_{30}$N$_5$O: 476.2450; found: 476.2467.

TBI-086, 5-Phenyl-3-(4-hydroxycyclohexyl)imino-2-(6-ethyl-3-pyridyl amino-3,5-dihydrophenazine:

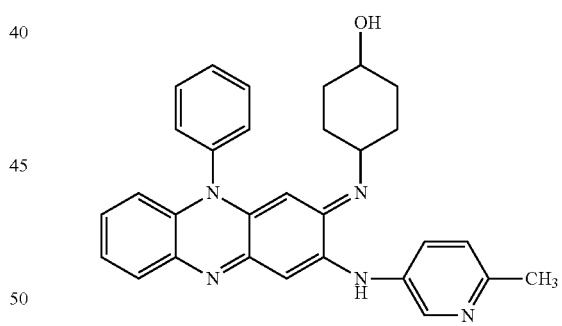

$^1$H NMR (300 MHz, CDCl$_3$) δ: 1.14-1.28 (2H, q), 1.38-1.49 (2H, q), 1.64-1.68 (2H, d), 1.95-1.98 (2H, q), 2.55 (3H, s, CH$_3$), 2.98-3.05 (1H, m), 3.64-3.71 (1H, m), 5.22 (1H, s, CH—C=N), 6.51-6.54 (1H, d, J=7.8 Hz, PhH$_6$), 6.73 (1H, s, CH=C—NH), 7.11-7.19 (3H, m, PhH$_{7,8,9}$), 7.31-7.34 (2H, d, J=7.2 Hz, Ph'H$_{2,6}$), 7.62-7.75 (5H, m, Ph'H$_{3,4,5}$, PyH$_{4,5}$), 8.43 (1H, d, J=2.1 Hz, PyH$_2$), $^{13}$C NMR (100 MHz, CDCl$_3$) 23.78, 31.23, 33.76, 57.24, 70.01, 89.12, 98.87, 114.17, 122.80, 123.18, 127.60, 128.14, 128.71, 129.35, 129.75, 131.21, 131.56, 134.08, 135.01, 135.63, 137.54, 143.63, 144.26, 150.87, 151.45, 153.26. HRMS (ESI-TOF$^+$): m/z [M+H]$^+$ calcd for C$_{30}$H$_{30}$N$_5$O: 476.2450; found: 476.2458.

TBI-087, 5-Phenyl-3-(4-hydroxycyclohexyl)imino-2-(2-methoxy-3-pyridyl)amino-3,5-dihydrophenazine:

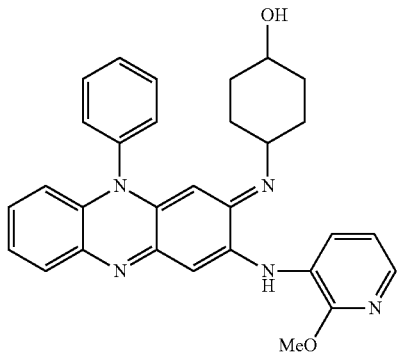 [SMILES: COc1ncccc1Nc1cc2nc3ccccc3n(-c3ccccc3)c-2c/c1=N\C1CCC(O)CC1]

$^1$H NMR (300 MHz, CDCl$_3$) δ: 1.17-1.28 (2H, q), 1.40-1.52 (2H, q), 1.67-1.70 (2H, d), 1.97-1.99 (2H, q), 3.00-3.07 (1H, m), 3.67-3.75 (1H, m), 4.02 (3H, s, CH$_3$), 5.22 (1H, s, CH—C=N), 6.51-6.53 (1H, d, J=8.7 Hz, PhH$_6$), 6.89-6.95 (2H, m, PhH$_9$, CH=C—NH), 7.10-7.19 (2H, m, PhH$_{7, 8}$), 7.32-7.34 (2H, d, J=7.2 Hz, Ph'H$_{2, 6}$), 7.62-7.74 (4H, m, PyH$_5$, Ph'H$_{3, 4, 5}$), 7.79-7.81 (1H, d, J=3.9 Hz, PyH$_6$), 7.84-7.86 (1H, d, J=7.8 Hz, PyH$_4$). $^{13}$C NMR (100 MHz, CDCl$_3$) δ: 30.91, 33.43, 53.70, 56.91, 69.92, 89.28, 100.18, 114.13, 116.82, 122.75, 124.67, 124.90, 127.67, 128.14, 128.76, 129.73, 131.22, 131.75, 134.99, 135.62, 137.54, 138.68, 142.74, 151.16, 151.60, 155.36. HRMS (ESI-TOF$^+$) [M+H]$^+$ calcd for C$_{30}$H$_{30}$N$_5$O$_2$: 492.2399; found: 492.2386.

TBI-088, 5-(4-Bromophenyl)-3-(1-methylethyl)imino-2-(3-pyridyl)amino-3,5-dihydrophenazine:

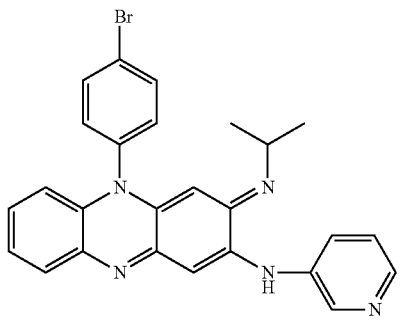 [SMILES: CC(C)/N=c1\cc2n(-c3ccc(Br)cc3)c3ccccc3nc-2cc1Nc1cccnc1]

$^1$H NMR (300 MHz, CDCl$_3$) δ: 1.10-1.12 (6H, d, J=6.3 Hz, CH(CH$_3$)$_2$), 3.44-3.52 (1H, m, J=6.0 Hz, CH(CH$_3$)$_2$), 5.30 (1H, s, CH—C=N), 6.44-6.46 (1H, d, J=7.5 Hz, PhH$_6$), 6.83 (1H, s, CH=C—NH), 7.11-7.18 (2H, m, PhH$_{7, 8}$), 7.23-7.27 (2H, d, J=9.0 Hz, Ph'H$_{2, 6}$), 7.30-7.32 (1H, m, PyH$_5$), 7.67-7.70 (1H, d, J=7.5 Hz, PyH$_4$), 7.77-7.80 (1H, d, J=8.1 Hz, PhH$_9$), 7.86-7.89 (2H, d, J=8.1 Hz, Ph'H$_{3, 5}$), 8.33-8.34 (1H, d, J=4.5 Hz, PyH$_6$), 8.59 (1H, s, PyH$_2$). $^{13}$C NMR (100 MHz, CDCl$_3$) δ: 23.56, 49.40, 89.07, 99.43, 113.87, 123.00, 123.62, 123.79, 127.73, 127.93, 128.31, 130.71, 131.44, 134.70, 135.58, 136.57, 136.81, 143.68, 143.96, 144.28, 150.31, 150.95. HRMS (ESI-TOF$^+$): [M+H]$^+$ calcd for C$_{26}$H$_{23}$BrN$_5$: 484.1136; found: 484.1126.

TBI-089, 5-(4-Bromophenyl)-3-cyclohexylimino-2-(3-pyridyl)amino-3,5-dihydrophenazine:

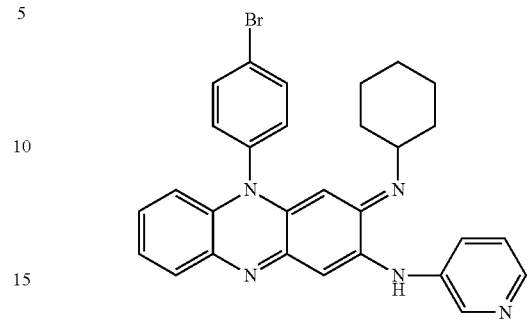

$^1$H NMR (300 MHz, CDCl$_3$) δ: 1.09-1.41 (5H, m), 1.60-1.76 (5H, 3.10 (1H, brs), 5.26 (1H, s, CH—C=N), 6.47-6.49 (1H, d, J=7.2 Hz, PhH$_6$), 6.82 (1H, s, CH=C—NH), 7.11-7.31 (5H, m, PhH$_{7, 8}$, Ph'H$_{2, 6}$, PyH$_5$), 7.67-7.69 (1H, d, 19.0 Hz, PyH$_4$), 7.76-7.79 (1H, d, J=8.7 Hz, PhH$_9$), 7.86-7.88 (2H, d, J=8.1 Hz, Ph'H$_{3, 5}$), 8.32-8.33 (1H, d, J=4.2 Hz, PyH$_6$), 8.57 (1H, d, J=2.1 Hz, PyH$_2$). $^{13}$C NMR (100 MHz, CDCl$_3$) δ: 24.57, 25.82, 33.62, 57.84, 89.35, 99.40, 113.84, 122.98, 123.62, 127.72, 127.85, 128.31, 130.70, 131.39, 134.60, 134.72, 135.61, 136.56, 136.84, 143.68, 143.92, 144.22, 150.43, 150.99. HRMS (ESI-TOF$^+$): m/z [M+H]$^+$ calcd for C$_{29}$H$_{27}$BrN$_5$: 524.1449; found: 524.1448.

TBI-090, 5-(4-Bromophenyl)-3-cyclopropylimino-2-(3-pyridyl)amino-3,5-dihydrophenazine:

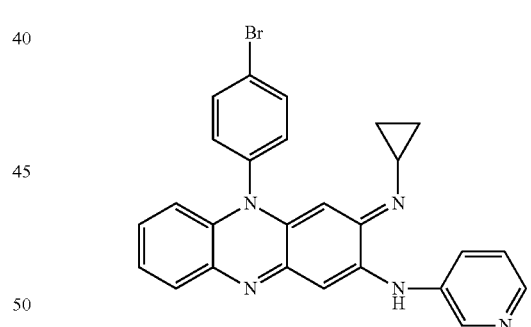

$^1$H NMR (300 MHz, CDCl$_3$) δ: 0.83 (2H, brs), 0.91-0.93 (2H, m), 2.76 (1H, brs), 5.56 (1H, s, CH—C=N), 6.42-6.44 (1H, d=7.8 Hz, PhH$_6$), 6.78 (1H, s, CH=C—NH), 7.10-7.17 (2H, m, PhH$_{7, 8}$), 7.25-7.31 (3H, m, Ph'H$_{2, 6}$, PyH$_5$), 7.66-7.68 (1H, d, J=7.2 Hz, PyH$_4$), 7.75-7.77 (1H, d, J=7.5 Hz, PhH$_9$), 7.86-7.88 (2H, d, J=8.4 Hz, Ph'H$_{3, 5}$), 8.33-8.34 (1H, d, J=4.2 Hz, PyH$_6$), 8.57 (1H, s, PyH$_2$). $^{13}$C NMR (100 MHz, CDCl$_3$) δ: 10.04, 32.94, 89.47, 99.41, 113.82, 122.97, 123.64, 123.75, 127.75, 128.12, 128.26, 130.81, 131.60, 134.60, 134.75, 135.68, 136.56, 136.62, 143.43, 144.03, 144.39, 151.18, 152.25. HRMS (ESI-TOF$^+$): m/z [M+H]$^+$ calcd for C$_{26}$H$_{21}$BrN$_5$: 482.0980; found: 482.0970.

TBI-091, 5-(4-Bromophenyl)-3-(4-methoxycyclohexyl)imino-2-(3-pyridyl)amino-3,5-dihydrophenazine:

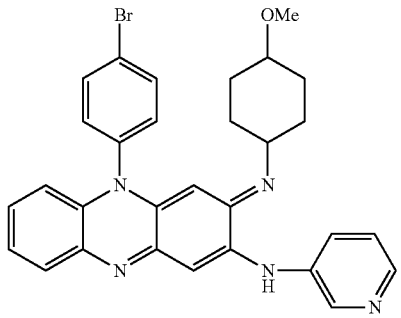

$^1$H NMR (300 MHz, CDCl$_3$) δ: 1.16-1.26 (2H, q), 1.37-1.49 (2H, q), 1.69-1.72 (2H, d), 2.06-2.09 (2H, d), 3.08-3.24 (2H, m), 3.37 (3H, s, CH$_3$), 5.27 (1H, s, CH—C=N), 6.47-6.49 (1H, d, J=7.8 Hz, PhH$_6$), 6.84 (1H, s, CH=C—NH), 7.12-7.32 (5H, m, PhH$_{7,8}$, Ph'H$_{2,6}$, PyH$_5$), 7.68-7.71 (1H, d, J=9.0 Hz, PyH$_4$), 7.76-7.79 (1H, d, J=8.4 Hz, PhH$_9$), 7.85-7.88 (2H, d, J=8.4 Hz, Ph'H$_{3,5}$), 8.33-8.34 (1H, d, J=3.9 Hz, PyH$_6$), 8.57 (1H, d, J=2.4 Hz, PyH$_2$). $^{13}$C NMR (100 MHz, CDCl$_3$) δ: 29.83, 31.11, 55.83, 57.21, 78.45, 89.09, 99.53, 113.94, 123.08, 123.64, 123.86, 127.88, 128.37, 130.59, 131.37, 134.64, 134.79, 135.60, 136.41, 136.72, 143.54, 143.92, 144.31, 150.83, 151.03. HRMS (ESI-TOF$^+$): m/z [M+H]$^+$ calcd for C$_{30}$H$_{29}$BrN$_5$O: 554.1555; found: 554.1536.

TBI-092, 5-Phenyl-3-(4-hydroxycyclohexyl)imino-2-(2-ethyl-3-pyridyl)amino-3,5-dihydrophenazine:

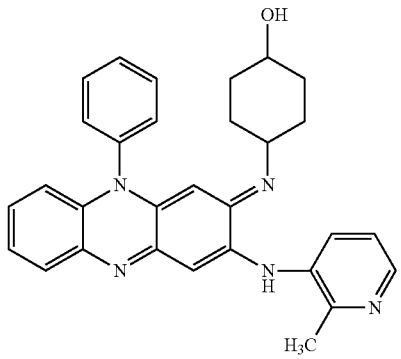 [SMILES: Cc1ncccc1Nc1cc2nc3ccccc3n(-c3ccccc3)c-2c/c1=N\C1CCC(O)CC1]

$^1$H NMR (300 MHz, CDCl$_3$) δ: 1.17-1.28 (2H, q), 1.37-1.49 (2H, q), 1.67-1.70 (2H, d), 1.95-1.99 (2H, q), 2.53 (3H, s), 3.01-3.08 (1H, m), 3.66-3.74 (1H, m), 5.24 (1H, s, CH—C=N), 6.52-6.55 (2H, d, J=7.8 Hz, PhH$_6$), 6.61 (1H, s, CH=C—NH), 7.11-7.20 (3H, m, PhH$_{7,8,9}$), 7.32-7.35 (2H, d, J=7.2 Hz, Ph'H$_{2,6}$), 7.63-7.75 (5H, m, Ph'H$_{3,4,5}$, PyH$_5$), 7.81-7.83 (1H, d, J=7.5 Hz, PyH$_4$), 8.26-8.27 (1H, d, 13.9 Hz, PyH$_6$). $^{13}$C NMR (100 MHz, CDCl$_3$) δ: 20.87, 31.12, 33.56, 56.94, 69.86, 89.08, 98.91, 114.19, 121.67, 122.83, 127.64, 128.13, 128.69, 128.96, 129.78, 131.23, 131.57, 134.76, 135.06, 135.59, 137.53, 144.02, 150.87, 151.38, 152.04. HRMS (ESI-TOF$^+$): m/z [M+H]$^+$ calcd for C$_{30}$H$_{30}$N$_5$O: 476.2450; found: 476.2455.

TBI-093, 5-(4-Bromophenyl)-3-(4-tetrahydropyranyl)imino-2-(3-pyridyl)amino-3,5-dihydrophenazine:

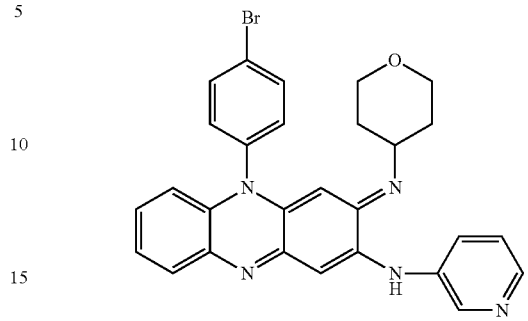

$^1$H NMR (300 MHz, CDCl$_3$) δ: 1.63-1.69 (4H, m), 3.37-3.49 (3H, m), 3.97-4.01 (2H, m), 5.25 (1H, s, CH—C=N), 6.48-6.51 (1H, d, J=7.8 Hz, PhH$_6$), 6.86 (1H, s, CH=C—NH), 7.16-7.33 (5H, m, PhH$_{7,8}$, Ph'H$_{2,6}$, PyH$_5$), 7.70-7.73 (1H, d, J=7.5 Hz, PyH$_4$), 7.77-7.79 (1H, d, J=8.4 Hz, PhH$_9$), 7.87-7.89 (2H, d, J=8.1 Hz, Ph'H$_{3,5}$), 8.34-8.36 (1H, d, J=4.2 Hz, PyH$_6$), 8.60 (1H, d, J=1.8 Hz, PyH$_2$). $^{13}$C NMR (100 MHz, CDCl$_3$) δ: 33.37, 54.27, 66.06, 88.92, 99.60, 113.96, 123.20, 123.67, 123.85, 127.96, 128.04, 128.44, 130.61, 131.24, 134.68, 134.92, 135.61, 136.46, 136.63, 143.56, 143.96, 144.44, 150.66, 151.04. HRMS (ESI-TOF$^+$): m/z [M+H]$^+$ calcd for C$_{28}$H$_{25}$BrN$_5$O: 526.1242; found: 526.1236.

TBI-094, 5-(4-Bromophenyl)-3-(4-hydroxycyclohexyl)imino-2-(3-pyridyl)amino-3,5-dihydrophenazine:

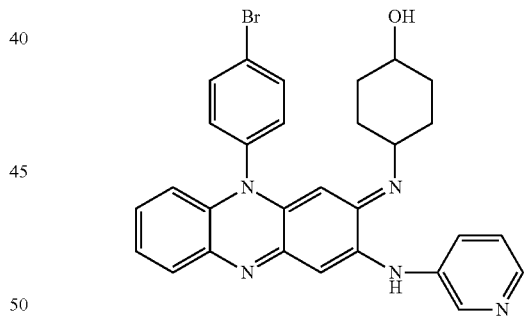

$^1$H NMR (300 MHz, CDCl$_3$) δ: 1.22-1.33 (2H, q), 1.41-1.52 (2H, q), 1.67-1.70 (2H, d), 1.98-2.02 (2H, d), 3.06-3.13 (1H, m), 3.67-3.73 (1H, m), 5.25 (1H, s, CH—C=N), 6.47-6.49 (1H, d, J=7.5 Hz, PhH$_6$), 6.83 (1H, s, CH=C—NH), 7.12-7.32 (5H, m, PhH$_{7,8}$, Ph'H$_{2,6}$, PyH$_5$), 7.68-7.71 (1H, d, J=7.2 Hz, PyH$_4$), 7.76-7.79 (1H, d, J=8.1 Hz, PhH$_9$), 7.86-7.88 (2H, d, J=8.4 Hz, Ph'H$_{3,5}$), 8.32-8.33 (1H, d, J=3.9 Hz, PyH$_6$), 8.56 (1H, d, J=2.4 Hz, PyH$_2$). $^{13}$C NMR (100 MHz, CDCl$_3$) δ: 31.23, 33.63, 57.06, 69.97, 89.07, 99.52, 113.93, 123.10, 123.66, 123.83, 127.91, 128.37, 130.62, 131.35, 134.65, 134.81, 135.59, 136.45, 136.71, 143.54, 143.88, 144.29, 150.80, 151.09. HRMS (ESI-TOF$^+$): m/z [M+H]$^+$ calcd for C$_{29}$H$_{27}$BrN$_5$O: 540.1398; found: 540.1378.

TBI-095, 5-Phenyl-3-cyclopropylimino-2-(6-ethyl-3-pyridyl)amino-3,5-dihydrophenazine:

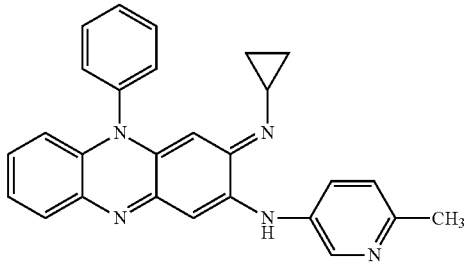 [SMILES: Cc1ccc(Nc2cc3nc4ccccc4n(-c4ccccc4)c-3c/c2=N\C2CC2)cn1]

$^1$H NMR (300 MHz, CDCl$_3$) δ: 0.78-0.87 (4H, m), 2.55 (3H, s, CH$_3$), 2.68 (1H, brs), 5.55 (1H, s, CH=C=N), 6.44-6.47 (1H, d, J=7.81 Hz, PhH$_6$), 6.68 (1H, s, CH=C—NH), 7.08-7.16 (3H, m, PhH$_{7, 8, 9}$), 7.34-7.37 (2H, d, J=7.5 Hz, Ph'H$_{2, 6}$), 7.60-7.75 (5H, m, Ph'H$_{3, 4, 5}$, PhH$_{4, 5}$), 8.41 (1H, s, PyH$_2$). $^{13}$C NMR (100 MHz, CDCl$_3$) δ: 9.73, 23.80, 32.72, 89.47, 98.85, 114.11, 122.73, 123.18, 127.51, 128.05, 128.87, 129.65, 131.28, 131.83, 133.97, 134.85, 135.74, 137.63, 143.80, 144.14, 151.21, 152.78, 153.37. HRMS (ESI-TOF$^+$): m/z [M+H]$^+$ calcd for C$_{27}$H$_{24}$N$_5$: 418.2031; found: 418.2022.

TBI-096, 5-Phenyl-3-cyclopropylimino-2-(5-methyl-3-pyridyl)amino-3,5-dihydrophenazine:

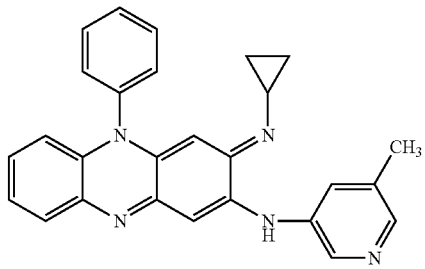 [SMILES: Cc1cncc(Nc2cc3nc4ccccc4n(-c4ccccc4)c-3c/c2=N\C2CC2)c1]

$^1$H NMR (300 MHz, CDCl$_3$) 0.77-0.84 (4H, m), 2.36 (3H, s, CH$_3$), 2.68 (1H, brs), 5.54 (1H, s, CH=C=N), 6.44-6.46 (1H, d, J=7.5 Hz, PhH$_6$), 6.79 (1H, s, CH=C—NH), 7.11-7.15 (2H, m, PhH$_{7, 8}$), 7.34-7.37 (2H, d, J=7.2 Hz, Ph'H$_{2, 6}$), 7.56-7.75 (5H, m, Ph'H$_{3, 4, 5}$, PyH$_4$, PhH$_9$), 8.16 (1H, s, PyH$_6$), 8.35 (1H, s, PyH$_2$). $^{13}$C NMR (100 MHz, CDCl$_3$) δ: 9.79, 18.45, 32.73, 89.49, 99.33, 114.13, 122.75, 127.63, 128.06, 128.51, 128.87, 129.67, 131.31, 131.89, 133.51, 134.87, 135.70, 136.32, 137.60, 141.18, 143.51, 144.97, 151.28, 152.66. HRMS (ESI-TOF$^+$): m/z [M+H]$^+$ calcd for C$_{27}$H$_{24}$N$_5$: 418.2031; found: 418.2014.

TBI-097, 5-Phenyl-3-cyclopropylimino-2-(2-methoxy-3-pyridyl)amino-3,5-dihydrophenazine:

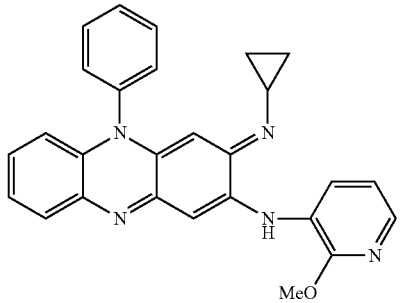 [SMILES: COc1ncccc1Nc1cc2nc3ccccc3n(-c3ccccc3)c-2c/c1=N\C1CC1]

$^1$H NMR (300 MHz, CDCl$_3$) δ: 0.79-0.88 (4H, m), 2.70 (1H, brs), 4.00 (3H, s, CH$_3$), 5.55 (1H, s, CH=C—N), 6.43-6.46 (1H, d, J=7.8 Hz, PhH$_6$), 6.88-6.92 (2H, m, PhH$_9$, CH=C—NH), 7.08-7.17 (2H, m, PhH$_{7, 8}$), 7.34-7.37 (2H, d, J=7.2 Hz, Ph'H$_{2, 6}$), 7.60-7.75 (4H, m, PyH$_5$, Ph'H$_{3, 4, 5}$), 7.79-7.81 (1H, d, J=4.5 Hz, PyH$_6$), 7.83-7.85 (1H, d, J=7.8 Hz, PyH$_4$). $^{13}$C NMR (100 MHz, CDCl$_3$) δ: 9.90, 32.77, 53.67, 89.62, 100.09, 114.06, 116.81, 122.65, 124.83, 124.97, 127.54, 128.03, 128.93, 129.61, 131.28, 132.02, 134.82, 135.73, 137.64, 138.75, 142.63, 151.49, 152.87, 155.40. HRMS (ESI-TOF$^+$): m/z [M+H]$^+$ calcd for C$_{27}$H$_{24}$N$_5$O: 434.1980; found: 434.1963.

TBI-098, 5-(4-Bromophenyl)-3-cyclobutylimino-2-(3-pyridyl)amino-3,5-dihydrophenazine:

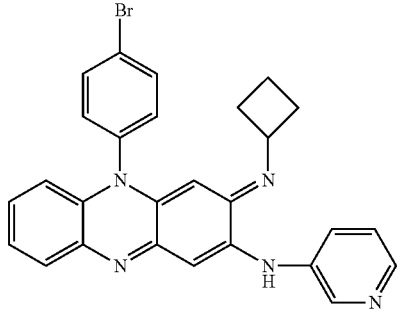 [SMILES: Brc1ccc(-n2c3c/c(=N\C4CCC4)c(Nc4cccnc4)cc-3nc3ccccc32)cc1]

$^1$H NMR (300 MHz, CDCl$_3$) δ: 1.71-1.82 (2H, m), 2.01-2.08 (2H, m), 2.18-2.21 (2H, m), 3.88-3.94 (1H, p, J=7.5 Hz), 5.10 (1H, s, CH—C=N), 6.47-6.49 (1H, d, J=7.5 Hz, PhH$_6$), 6.84 (1H, s, CH=C—NH), 7.12-7.32 (5H, m, PhH$_{7, 8}$, Ph'H$_{2, 6}$, PyH$_5$), 7.69-7.71 (1H, d, J=7.5 Hz, PyH$_4$), 7.77-7.79 (1H, d, J=8.1 Hz, PhH$_9$), 7.86-7.89 (2H, d, J=8.1 Hz, Ph'H$_{3, 5}$), 8.34-8.35 (1H, d, J=3.9 Hz, PyH$_6$), 8.60 (1H, s, PyH$_2$). $^{13}$C NMR (100 MHz, CDCl$_3$) δ: 16.06, 31.96, 54.78, 90.55, 99.51, 113.95, 123.15, 123.66, 123.83, 127.88, 128.05, 128.40, 130.72, 131.28, 134.39, 134.66, 135.67, 136.51, 136.68, 143.60, 144.03, 144.41, 150.87, 151.13. HRMS (ESI-TOF$^+$): m/z [M+H]$^+$ calcd for C$_{27}$H$_{23}$BrN$_5$: 496.1136; found: 496.1114.

TBI-099, 5-(4-Bromophenyl)-3-(1-methylethyl)imino-2-(6-methyl-3-pyridyl)amino-3,5-dihydrophenazine:

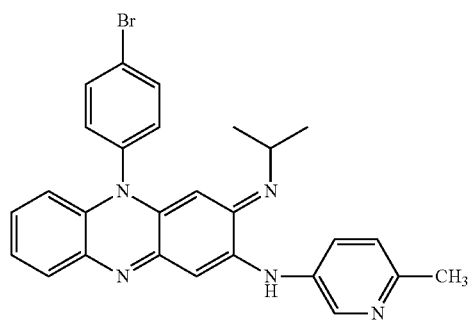

$^1$H NMR (300 MHz, CDCl$_3$) δ: 1.09-1.11 (6H, d, J=6.3 Hz, CH(CH$_3$)$_2$), 2.56 (3H, s, CH$_3$), 3.45-3.49 (1H, m, J=6.0 Hz, CH(CH$_3$)$_2$), 5.28 (1H, s, CH—C=N), 6.42-6.45 (1H, d, J=7.5 Hz, PhH$_6$), 6.71 (1H, s, CH=C—NH), 7.09-7.25 (5H, m, PhH$_{7, 8}$, Ph'H$_{2, 6}$, PyH$_5$), 7.66-7.68 (2H, m, PyH$_4$, PhH$_9$), 7.84-7.87 (2H, d, J=8.4 Hz, Ph'H$_{3, 5}$), 8.44 (1H, s, PyH$_2$). $^{13}$C NMR (100 MHz, CDCl$_3$) δ: 23.56, 23.82, 49.40, 89.60, 98.83, 113.84, 122.94, 123.16, 123.75, 127.53, 128.22, 129.47, 130.73, 131.36, 134.04, 134.68, 135.60, 136.63, 137.72, 143.77, 144.43, 150.37, 150.97, 153.36. HRMS (ESI-TOF$^+$): m/z [M+H]$^+$ calcd for C$_{27}$H$_{25}$BrN$_5$: 498.1293; found: 498.1267.

TBI-100, 5-(4-Bromophenyl)-3-cyclopropylimino-2-(6-methyl-3-pyridyl)amino-3,5-dihydrophenazine:

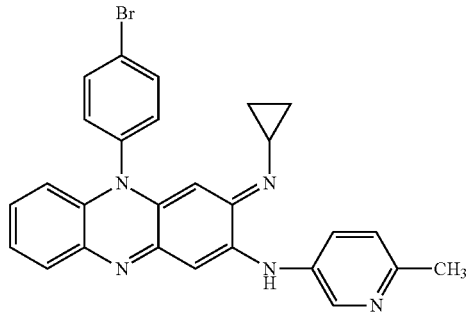

$^{1}$H NMR (300 MHz, CDCl$_{3}$) δ: 0.81-0.92 (4H, m), 2.55 (3H, s, CH$_{3}$), 2.75 (1H, brs), 5.54 (1H, s, CH—C=N), 6.40-6.43 (1H, d, J=7.5 Hz, PhH$_{6}$), 6.65 (1H, s, CH=C—NH), 7.08-7.16 (3H, m, PhH$_{7,8}$, PyH$_{5}$) 7.24-7.27 (2H, d, J=8.4 Hz, Ph'H$_{2,6}$), 7.63-7.66 (2H, d, J=8.1 Hz, PyH$_{4}$, PhH$_{9}$), 7.84-7.87 (2H, d, J=8.4 Hz, Ph'H$_{3,5}$), 8.40-8.41 (1H, d, J=2.4 Hz, PyH$_{2}$). $^{13}$C NMR (100 MHz, CDCl$_{3}$) δ: 9.99, 23.82, 32.92, 89.45, 98.82, 113.80, 122.93, 123.18, 123.71, 127.54, 128.17, 129.68, 130.83, 131.51, 133.90, 134.57, 134.73, 135.72, 136.63, 143.90, 144.23, 151.20, 152.36, 153.52. HRMS (ESI-TOF$^{+}$): m/z [M+H]$^{+}$ calcd for C$_{27}$H$_{23}$BrN$_{5}$: 496.1136; found: 496.11130.

TBI-501, 5-(4-Bromophenyl)-3-cyclobutylimino-2-(6-methyl-3-pyridyl)amino-3,5-dihydrophenazine:

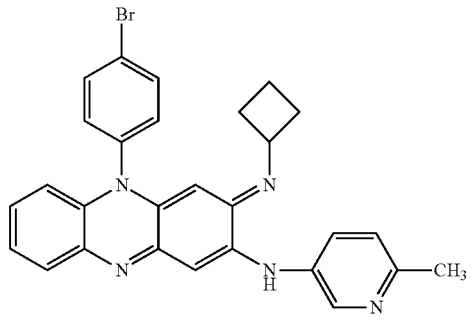

$^{1}$H NMR (300 MHz, CDCl$_{3}$) δ: 1.72-1.82 (2H, 2.02-2.08 (2H, m), 2.15-2.20 (2H, m), 2.56 (3H, s, CH$_{3}$), 3.88-3.93 (1H, p, J=7.8 Hz), 5.09 (1H, s, CH—C=N), 6.46-6.48 (1H, d, J=7.8 Hz, PhH$_{6}$), 6.71 (1H, s, CH=C—NH), 7.15-7.24 (5H, m, PhH$_{7,8}$, Ph'H$_{2,6}$, PyH$_{5}$), 7.67-7.70 (2H, d, J=8.1 Hz, PyH$_{4}$, PhH$_{9}$), 7.86-7.88 (2H, d, J=8.4 Hz, Ph'H$_{3,5}$), 8.46 (1H, s, PyH$_{2}$). HRMS (ESI-TOF$^{+}$): m/z [M+H]$^{+}$ calcd for C$_{28}$H$_{25}$BrN$_{5}$: 510.1293; found: 510.1267.

TBI-502, 5-(4-Bromophenyl)-3-cyclohexylimino-2-(6-methyl-3-pyridyl)amino-3,5-dihydrophenazine:

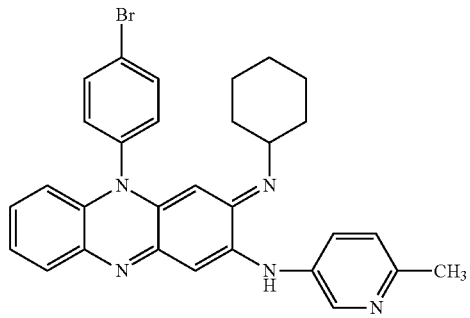

$^{1}$H NMR (300 MHz, CDCl$_{3}$) δ: 1.18-1.44 (5H, m), 1.59-1.76 (5H, m), 2.55 (3H, s, CH$_{3}$), 3.06-3.13 (1H, m), 5.25 (1H, s, CH—C=N), 6.45-6.48 (1H, d, J=7.8 Hz, PhH$_{6}$), 6.70 (1H, s, CH=C—NH), 7.09-7.24 (5H, m, PhH$_{7,8}$, Ph'H$_{2,6}$, PyH$_{5}$), 7.66-7.69 (2H, m, PyH$_{4}$, PhH$_{9}$), 7.85-7.88 (2H, d, J=8.7 Hz, Ph'H$_{3,5}$), 8.44 (1H, d, J=2.4 Hz, PyH$_{2}$). $^{13}$C NMR (100 MHz, CDCl$_{3}$) δ: 23.81, 24.61, 25.84, 33.64, 57.91, 89.35, 98.81, 113.80, 122.91, 123.16, 123.63, 127.51, 128.21, 129.38, 130.73, 131.33, 134.07, 134.58, 134.67, 135.62, 136.64, 143.71, 144.43, 150.50, 151.04, 153.31. HRMS (ESI-TOF$^{+}$): m/z [M+H]$^{+}$ calcd for C$_{30}$H$_{29}$BrN$_{5}$: 538.1606; found: 538.1593.

TBI-503, 5-(4-Bromophenyl)-3-(4-methoxycyclohexyl)imino-2-(6-methyl-3-pyridyl)amino-3,5-dihydrophenazine:

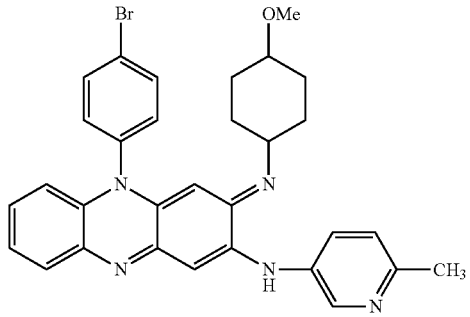

$^{1}$H NMR (300 MHz, CDCl$_{3}$) δ: 1.18-1.28 (2H, q), 1.38-1.50 (2H, q), 1.69-1.72 (2H, d), 2.05-2.09 (2H, q), 2.56 (3H, s, CH$_{3}$), 3.08-3.24 (2H, m), 3.37 (3H, s, CH$_{3}$), 5.26 (1H, s, CH—C=N), 6.46-6.48 (1H, d, J=7.8 Hz, PhH$_{6}$), 6.72 (1H, s, CH=C—NH), 7.11-7.24 (5H, m, PhH$_{7,8}$, Ph'H$_{2,6}$, PyH$_{5}$), 7.66-7.70 (2H, m, PyH$_{4}$, PhH$_{9}$), 7.85-7.87 (2H, d, J=8.7 Hz, Ph'H$_{3,5}$), 8.44 (1H, d, J=2.1 Hz, PyH$_{2}$). $^{13}$C NMR (100 MHz, CDCl$_{3}$) δ: 23.82, 29.87, 31.15, 55.82, 57.25, 78.50, 89.08, 98.92, 113.90, 123.01, 123.17, 123.81, 127.65, 128.26, 129.43, 130.61, 131.30, 133.99, 134.61, 134.75, 135.62, 136.49, 143.75, 144.33, 150.86, 151.09, 153.42. HRMS (ESI-TOF$^{+}$): [M+H]$^{+}$ calcd for C$_{31}$H$_{31}$BrN$_{5}$O: 568.1711; found: 568.1703.

TBI-504, 5-(4-Bromophenyl)-3-(4-tetrahydropyranyl)imino-2-(6-methyl-3-pyridyl)amino-3,5-dihydrophenazine:

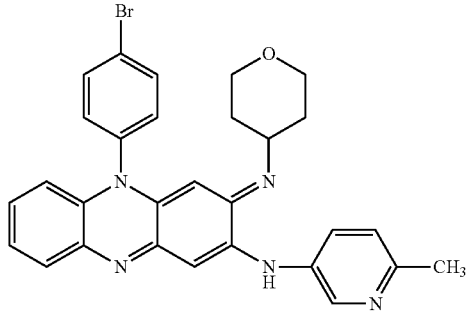

$^{1}$H NMR (300 MHz, CDCl$_{3}$) δ: 1.62-1.69 (4H, m), 2.56 (3H, s, CH$_{3}$), 3.35-3.48 (3H, m), 3.95-4.00 (2H, m), 5.24 (1H, s, CH—C=N), 6.47-6.50 (1H, d, J=8.1 Hz, PhH$_{6}$), 6.73 (1H, s, CH=C—NH), 7.12-7.24 (5H, m, PhH$_{7,8}$, Ph'H$_{2,6}$, PyH$_{5}$), 7.66-7.70 (2H, m, PyH$_{4}$, PhH$_{9}$), 7.86-7.89 (2H, d, J=8.4 Hz, Ph'H$_{3,5}$), 8.45 (1H, d, J=2.4 Hz, PyH$_{2}$). $^{13}$C NMR (100 MHz, CDCl$_{3}$) δ: 23.84, 33.40, 54.32, 66.10, 88.91, 98.99, 113.94, 123.15, 123.21, 123.81, 127.73, 128.35, 129.60, 130.64, 131.17, 133.90, 134.66, 134.89, 135.64, 136.54, 143.83, 144.36, 150.70, 151.10, 153.59. HRMS (ESI-TOF$^{+}$): m/z [M+H]$^{+}$ calcd for C$_{29}$H$_{27}$BrN$_{5}$O: 540.1398; found: 540.1380.

TBI-505, 5-Phenyl-3-cyclobutylimino-2-(2-methoxy-3-pyridyl)amino-3,5-dihydrophenazine:

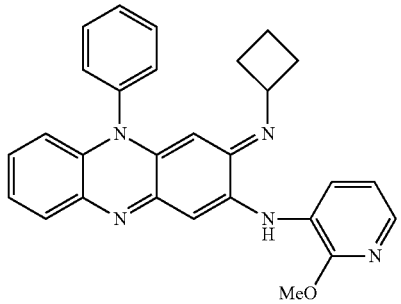 [SMILES: COc1ncccc1Nc1cc2nc3ccccc3n(-c3ccccc3)c-2c/c1=N\C1CCC1]

$^1$H NMR (300 MHz, CDCl$_3$) δ: 1.62-1.77 (2H, m, 1.94-2.16 (4H, m), 3.79-3.90 (1H, p, J=7.5 Hz), 4.04 (3H, s, CH$_3$), 5.07 (1H, s, CH—C=N), 6.49-6.52 (1H, d, J=7.8 Hz, PhH$_6$), 6.89-6.94 (2H, m, PhH$_9$, H=C—NH), 7.10-7.20 (2H, m, PhH$_{7, 8}$), 7.31-7.34 (2H, d, J=7.5 Hz, Ph'H$_{2, 6}$), 7.62-7.75 (4H, m, PyH$_5$, Ph'H$_{3, 4, 5}$), 7.80-7.81 (1H, d, J=4.8 Hz, PyH$_6$), 7.84-7.87 (1H, d, J=7.8 Hz, PyH$_4$). $^{13}$C NMR (100 MHz, CDCl$_3$) δ: 15.99, 31.96, 53.71, 54.88, 90.80, 100.28, 114.17, 116.81, 122.80, 124.76, 127.68, 128.15, 128.87, 129.70, 131.21, 131.71, 134.56, 135.69, 137.59, 138.75, 142.74, 151.63, 155.41. HRMS (ESI-TOF$^+$): m/z [M+H]$^+$ calcd for C$_{28}$H$_{26}$N$_5$O: 448.2137; found: 448.2131.

TBI-506, 5-Phenyl-3-cyclobutylimino-2-(6-methyl-3-pyridyl)amino-3,5-dihydrophenazine:

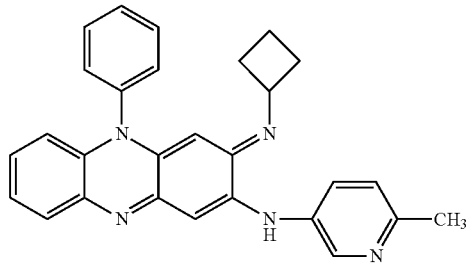 [SMILES: Cc1ccc(Nc2cc3nc4ccccc4n(-c4ccccc4)c-3c/c2=N\C2CCC2)cn1]

$^1$H NMR (300 MHz, CDCl$_3$) δ: 1.62-1.77 (2H, m), 1.95-2.18 (4H, m), 2.56 (3H, s, CH$_3$), 3.79-3.89 (1H, p, J=7.8 Hz), 5.08 (1H, s, CH—C=N), 6.50-6.53 (1H, d, J=7.8 Hz, PhH$_6$), 6.73 (1H, s, CH=C—NH), 7.10-7.20 (3H, m, PhH$_{7, 8, 9}$), 7.31-7.33 (2H, d, J=7.2 Hz, Ph'H$_{2, 6}$), 7.63-7.75 (5H, m, Ph'H$_{3, 4, 5}$, PyH$_{4, 5}$), 8.45 (1H, d, J=2.1 Hz, PyH$_2$). $^{13}$C NMR (100 MHz, CDCl$_3$) 15.99, 23.83, 31.93, 54.84, 90.60, 98.89, 114.21, 122.88, 123.17, 127.60, 128.17, 128.82, 129.48, 129.73, 131.21, 131.51, 134.02, 134.61, 135.72, 137.59, 143.78, 144.30, 150.92, 151.43, 153.36. HRMS (ESI-TOF$^+$): m/z [M+H]$^+$ calcd for C$_{28}$H$_{26}$N$_5$: 432.2188; found: 432.2188.

TBI-507, 5-(4-Bromophenyl)-3-(1-methylethyl)imino-2-(2-methyl-3-pyridyl)amino-3,5-dihydrophenazine:

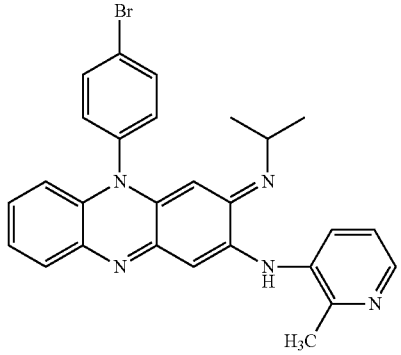

$^1$H NMR (300 MHz, CDCl$_3$) δ: 1.09-1.11 (6H, d, J=6.0 Hz, CH(CH$_3$)$_2$), 2.54 (3H, s, CH$_3$), 3.45-3.53 (1H, p, J=6.0 Hz, CH(CH$_3$)$_2$), 5.29 (1H, s, CH—C=N), 6.43-6.46 (1H, d, J=8.1 Hz, Ph'H$_6$), 6.57 (1H, s, CH=C—NH), 7.09-7.25 (5H, m, PhH$_{7, 8}$, Ph'H$_{2, 6}$, PyH$_5$), 7.65-7.68 (1H, d, J=0.8 Hz, PyH$_4$), 7.79-7.82 (1H, d, J=8.1 Hz, PhH$_9$), 7.85-7.88 (2H, d, J=8.4 Hz, Ph'H$_{3, 5}$), 8.27-8.28 (1H, d, J=3.6 Hz, PyH$_6$). $^{13}$C NMR (100 MHz, CDCl$_3$) δ: 20.91, 23.59, 49.29, 89.01, 98.82, 113.85, 121.64, 122.96, 123.77, 127.55, 128.19, 129.17, 130.72, 131.37, 134.68, 134.79, 135.56, 136.62, 144.18, 150.29, 150.97, 152.27. HRMS (ESI-TOF$^+$): m/z [M+H]$^+$ calcd for C$_{27}$H$_{25}$BrN$_5$: 498.1293; found: 498.1273.

TBI-508, 5-(4-Bromophenyl)-3-cyclohexylimino-2-(2-methyl-3-pyridyl)amino-3,5-dihydrophenazine:

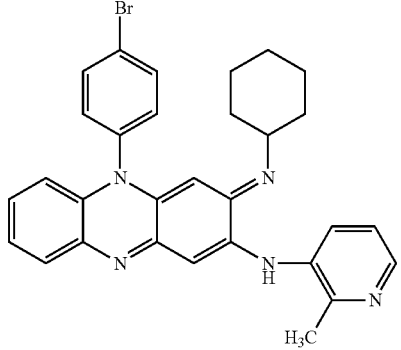

$^1$H NMR (300 MHz, CDCl$_3$) δ: 1.26-1.41 (5H, 1.60-1.76 (5H, m), 2.54 (3H, s, CH$_3$), 3.15 (1H, brs), 5.26 (1H, s, CH—C=N), 6.46-6.48 (1H, d, J=7.5 Hz, Ph'H$_6$), 6.60 (1H, s, CH=C—NH), 7.10-7.25 (5H, m, PhH$_{7, 8}$, Ph'H$_{2, 6}$, PyH$_5$), 7.66-7.68 (1H, d, J=7.5 Hz, PyH$_4$), 7.81-7.83 (1H, d, J=8.4 Hz, PhH$_9$), 7.85-7.88 (2H, d, J=8.4 Hz, Ph'H$_{3, 5}$), 8.26-8.27 (1H, d, J=3.6 Hz, PyH$_6$). $^{13}$C NMR (100 MHz, CDCl$_3$) δ: 20.93, 24.33, 25.89, 33.60, 57.35, 89.28, 98.82, 113.83, 121.64, 122.94, 123.67, 127.55, 128.20, 128.82, 130.72, 131.35, 134.61, 134.75, 134.80, 135.60, 136.63, 144.02, 144.09, 150.38, 151.04, 152.03. HRMS (ESI-TOF$^+$): m/z [M+H]$^+$ calcd for C$_{30}$H$_{29}$BrN$_5$: 538.1606; found: 538.1603.

TBI-509, 5-(4-Bromophenyl)-3-(4-methoxycyclohexyl)imino-2-(2-methyl-3-pyridyl)amino-3,5-dihydrophenazine:

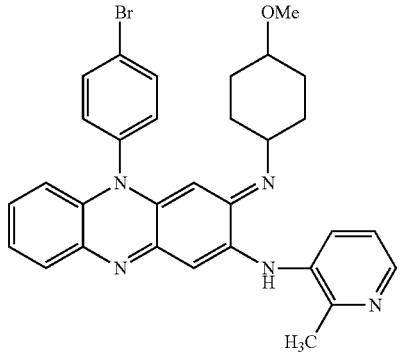

$^1$H NMR (300 MHz, CDCl$_3$) δ: 1.19-1.30 (2H, q), 1.36-1.47 (2H, q), 1.71-1.74 (2H, d), 2.04-2.08 (2H, q), 2.58 (3H, s, CH$_3$), 3.11-3.25 (2H, m), 3.36 (3H, s, CH$_3$), 5.27 (1H, s, CH—C=N), 6.46-6.48 (1H, d, J=7.5 Hz, Ph'H$_6$), 6.59 (1H, s, CH=C—NH), 7.11-7.24 (5H, m, PhH$_{7, 8}$, Ph'H$_{2, 6}$, PyH$_5$), 7.66-7.69 (1H, d, J=7.5 Hz, PyH$_4$), 7.80-7.83 (1H, d, J=8.4 Hz, PhH$_9$), 7.85-7.87 (2H, d, J=8.7 Hz, Ph'H$_{3, 5}$), 8.26-8.27 (1H, d, J=3.6 Hz, PyH$_6$). $^{13}$C NMR (100 MHz, CDCl$_3$) δ: 20.89, 29.57, 30.95, 55.80, 56.84, 89.04, 98.94, 113.92, 121.66, 123.03, 123.83, 127.68, 128.24, 128.95, 130.60, 131.30, 134.63, 134.79, 135.57, 136.46, 143.98, 144.13, 150.85, 151.00, 152.05. HRMS (ESI-TOF$^+$): m/z [M+H]$^+$ calcd for C$_{31}$H$_{31}$BrN$_5$O: 568.1711; found: 568.1691.

TBI-510, 5-Phenyl-3-(1-methylethyl)imino-2-(6-methoxy-3-pyridyl)amino-3,5-dihydrophenazine:

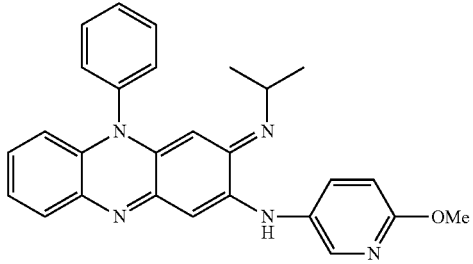 [SMILES: COc1ccc(Nc2cc3nc4ccccc4n(-c4ccccc4)c-3c/c2=N\C(C)C)cn1]

$^1$H NMR (300 MHz, CDCl$_3$) δ: 1.06-1.08 (6H, d, J=6.0 Hz, CH(CH$_3$)$_2$), 3.37-3.44 (1H, p, J=5.7 Hz, CH(CH$_3$)$_2$), 3.95 (1H, s, CH$_3$), 5.27 (1H, s, CH—C=NH), 6.46-6.48 (1H, d, J=8.1 Hz, PhH$_6$), 6.51 (1H, s, CH=C—NH), 6.76-6.79 (1H, d, J=8.7 Hz, PyH$_5$), 7.07-7.17 (2H, m, PhH$_{7, 8}$), 7.32-7.34 (2H, J=7.5 Hz, Ph'H$_{2, 6}$), 7.61-7.74 (5H, m, PyH$_4$, PhH$_9$), 8.14-8.15 (1H, d, J=2.4 Hz, PyH$_2$). $^{13}$C NMR (125 MHz, CDCl$_3$) δ: 23.52, 49.30, 53.60, 89.04, 98.04, 110.96, 114.08, 122.65, 127.20, 127.99, 128.85, 129.64, 130.34, 131.20, 131.60, 134.99, 135.10, 135.66, 137.76, 142.45, 145.99, 150.70, 151.03, 161.17. HRMS (ESI-TOF$^+$): m/z [M+H]$^+$ calcd for C$_{27}$H$_{26}$N$_5$O: 436.2137; found: 436.2154.

TBI-511, 5-Phenyl-3-cyclopropylimino-2-(6-methoxy-3-pyridyl)amino-3,5-dihydrophenazine:

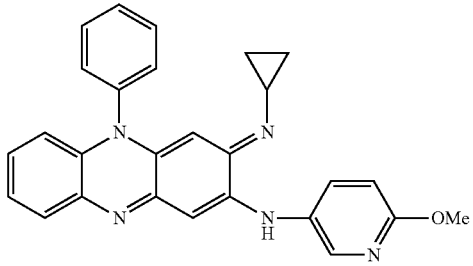 [SMILES: COc1ccc(Nc2cc3nc4ccccc4n(-c4ccccc4)c-3c/c2=N\C2CC2)cn1]

$^1$H NMR (300 MHz, CDCl$_3$) δ: 0.77-0.84 (4H, m), 2.70 (1H, brs), 3.95 (1H, s, CH$_3$), 5.54 (1H, s, CH—C=NH), 6.43-6.45 (2H, m, PhH$_6$, CH=C—NH), 6.76-6.78 (1H, d, J=8.4 Hz, PyH$_5$), 7.06-7.16 (2H, m, PhH$_{7, 8}$), 7.34-7.36 (2H, d, J=7.5 Hz, Ph'$_{2, 6}$), 7.59-7.74 (5H, m, Ph'H$_{3, 4, 5}$, PyH$_4$, PhH$_9$), 8.11 (1H, d, J=2.1 Hz, PyH$_2$). $^{13}$C NMR (125 MHz, CDCl$_3$) δ: 9.69, 32.75, 53.60, 89.39, 98.06, 111.01, 114.06, 122.64, 127.23, 127.93, 128.90, 129.59, 130.08, 131.25, 131.74, 134.81, 135.24, 135.73, 137.74, 142.56, 145.72, 151.22, 152.85, 161.25. HRMS (ESI-TOF$^+$): m/z calcd for C$_{27}$H$_{24}$N$_5$O: 434.1980; found: 434.1969.

TBI-512, 5-Phenyl-3-cyclobutylimino-2-(6-methoxy-3-pyridyl)amino-3,5-dihydrophenazine:

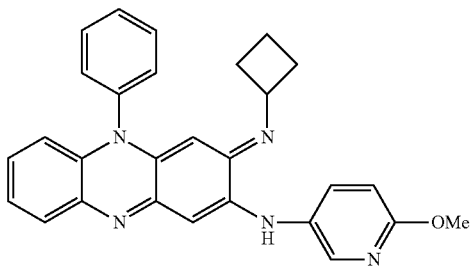 [SMILES: COc1ccc(Nc2cc3nc4ccccc4n(-c4ccccc4)c-3c/c2=N\C2CCC2)cn1]

$^1$H NMR (300 MHz, CDCl$_3$) δ: 1.65-1.76 (2H, m), 1.98-2.15 (4H, m), 3.82-3.87 (1H, p, J=8.1 Hz), 3.95 (3H, s, CH$_3$), 5.07 (1H, s, CH—C=NH), 6.50-6.52 (2H, m, PhH$_6$, CH=C—NH), 6.77-6.79 (1H, d, J=8.7 Hz, PyH$_5$), 7.09-7.19 (2H, m, PhH$_{7, 8}$), 7.31-7.33 (2H, d, J=7.2 Hz, Ph'H$_{2, 6}$), 7.62-7.75 (5H, m, Ph'H$_{3, 4, 5}$, PyH$_4$, PhH$_9$), 8.15 (1H, d, J=2.4 Hz, PyH$_2$). $^{13}$C NMR (75 MHz, CDCl$_3$) δ: 15.99, 31.96, 53.62, 54.88, 90.57, 98.09, 111.04, 114.18, 122.81, 127.35, 128.04, 128.85, 129.69, 130.15, 131.19, 131.42, 134.56, 135.23, 135.70, 137.67, 142.57, 145.92, 150.92, 151.52, 161.26. HRMS (ESI-TOF$^+$): m/z [M+H]$^+$ calcd for C$_{28}$H$_{26}$N$_5$O: 448.2137; found: 448.2125.

TBI-513, 5-Phenyl-3-cyclohexylimino-2-(6-methoxy-3-pyridyl)amino-3,5-dihydrophenazine:

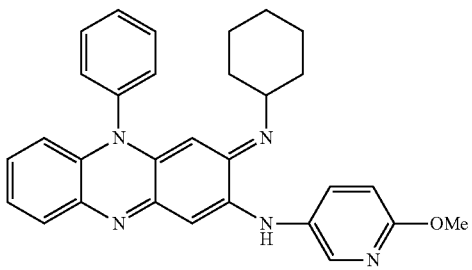 [SMILES: COc1ccc(Nc2cc3nc4ccccc4n(-c4ccccc4)c-3c/c2=N\C2CCCCC2)cn1]

$^1$H NMR (300 MHz, CDCl$_3$) δ: 1.07-1.41 (5H, m), 1.58-1.74 (5H, m), 3.00-3.06 (1H, m), 3.95 (3H, s, CH$_3$), 5.24 (1H, s, CH—C=NH), 6.50-6.52 (2H, m, PhH$_6$, CH=C—NH), 6.77-6.79 (1H, d, J=8.7 Hz, PyH$_5$), 7.07-7.17 (2H, m, PhH$_{7, 8}$), 7.31-7.34 (2H, d, J=7.5 Hz, Ph'H$_{2, 6}$), 7.61-7.74 (5H, m, PyH$_4$, PhH$_9$), 8.14 (1H, d, J=2.7 Hz, PyH$_2$). $^{13}$C NMR (75 MHz, CDCl$_3$) δ: 24.74, 25.84, 33.62, 53.62, 58.03, 89.33, 97.96, 102.96, 109.74, 110.96, 114.08, 122.62, 127.20, 127.98, 128.82, 129.55, 130.35, 131.16, 131.55, 134.90, 135.08, 135.66, 137.73, 142.42, 145.99, 150.85, 151.09, 154.65. HRMS (ESI-TOF$^+$): m/z [M+H]$^+$ calcd for C$_{30}$H$_{30}$N$_5$O: 476.2444; found: 476.2453.

TBI-514, 5-Phenyl-3-(4-methoxycyclohexyl)imino-2-(6-methoxy-3-pyridyl)amino-3,5-dihydrophenazine:

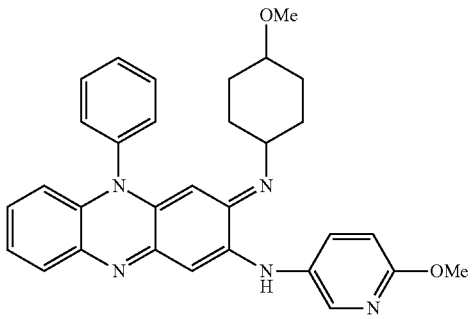 [SMILES: COc1ccc(Nc2cc3nc4ccccc4n(-c4ccccc4)c-3c/c2=N\C2CCC(OC)CC2)cn1]

$^1$H NMR (300 MHz, CDCl$_3$) δ: 1.06-1.17 (2H, q), 1.33-1.45 (2H, q), 1.66-1.70 (2H, d), 2.04-2.07 (2H, q), 2.99-3.05 (1H, m), 3.11-3.20 (1H, m), 3.35 (3H, s, CH$_3$), 3.95 (3H, s, CH$_3$), 5.21 (1H, s, CH—C=NH), 6.50-6.53 (2H, m, PhH$_6$, CH=C—NH), 6.76-6.79 (1H, d, 8.7 Hz, PyH$_5$), 7.09-7.18 (2H, m, PhH$_{7, 8}$), 7.30-7.32 (2H, d, J=7.5 Hz, Ph'H$_{2, 6}$), 7.60-7.73 (5H, m, Ph'H$_{3, 4, 5}$, PyH$_4$, PhH$_9$), 8.13 (1H, d, J=2.1 Hz, PyH$_2$). $^{13}$C NMR (75 MHz, CDCl$_3$) δ: 30.08, 31.18, 53.62, 55.85, 57.51, 78.60, 89.10, 98.05, 110.98, 114.14, 122.71, 127.34, 128.01, 128.70, 129.74, 130.19, 131.17, 131.45, 134.94, 135.08, 135.63, 137.57, 142.42, 145.84, 150.89, 151.49, 161.16. HRMS (ESI-TOF+): m/z [M+H]+ calcd for $C_{31}H_{32}N_4O_2$: 506.2550; found: 506.2552.

TBI-515, 5-Phenyl-3-(4-tetrahydropyranyl)imino-2-(6-methoxy-3-pyridyl)amino-3,5-dihydrophenazine:

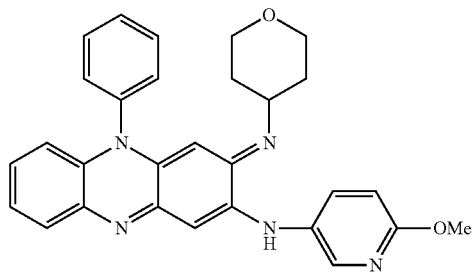 [SMILES: COc1ccc(Nc2cc3nc4ccccc4n(-c4ccccc4)c-3c/c2=N\C2CCOCC2)cn1]

$^1$H NMR (300 MHz, CDCl$_3$) d: 1.61-1.67 (4H, m), 3.29-3.40 (3H, m), 3.94-3.96 (5H, m), 5.23 (1H, s, CH—C=NH), 6.50-6.53 (2H, m, PhH$_6$, CH=C—NH), 6.77-6.80 (1H, d, J=9.0 Hz, PyH$_5$), 7.12-7.17 (2H, m, PhH$_{7, 8}$), 7.31-7.34 (2H, d, J=7.2 Hz, Ph'H$_{2, 6}$), 7.62-7.75 (5H, m, Ph'H$_{3, 4, 5}$, PyH$_4$, PhH$_9$), 8.15 (1H, d, J=2.7 Hz, PyH$_2$). $^{13}$C NMR (75 MHz, CDCl$_3$) δ: 33.41, 53.63, 54.47, 66.24, 88.91, 98.19, 111.04, 114.20, 122.87, 127.42, 128.12, 128.74, 129.71, 130.15, 131.22, 131.40, 135.14, 135.69, 137.67, 142.51, 145.88, 150.77, 151.41, 161.27. HRMS (ESI-TOF+): m/z [M+H]+ calcd for $C_{29}H_{28}N_5O_2$: 478.2237; found: 478.2249.

TBI-516, 5-(4-Bromophenyl)-3-(1-methylethyl)imino-2-(2-methoxy-3-pyridyl)amino-3,5-dihydrophenazine:

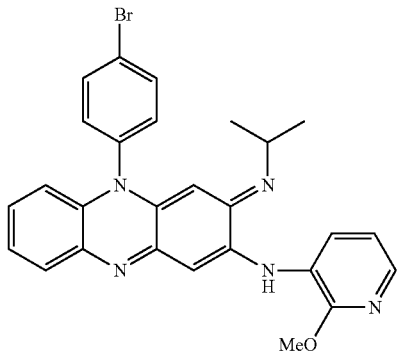

$^1$H NMR (300 MHz, CDCl$_3$) 1.10-1.12 (6H, d, J=6.0 Hz, CH(CH$_3$)$_2$), 3.45-3.49 (1H, 6.0 Hz, CH(CH$_3$)$_2$), 4.03 (3H, s, CH$_3$), 5.28 (1H, s, CH—C=N), 6.42-6.44 (1H, d, J=8.1 Hz, Ph'H$_6$), 6.89-6.93 (2H, m, PyH$_5$, CH=C—NH), 7.09-7.19 (2H, m, PhH$_{7, 8}$), 7.22-7.25 (2H, d, J=8.4 Hz, Ph'H$_{2, 6}$), 7.67-7.69 (1H, d, J=7.8 Hz, PyH$_4$), 7.80-7.87 (4H, m, Ph'H$_{3, 5}$, PhH$_9$, PyH$_6$). $^{13}$C NMR (100 MHz, CDCl$_3$) d: 23.56, 49.39, 53.71, 89.25, 100.08, 113.79, 116.78, 122.87, 123.71, 124.84, 124.93, 127.60, 128.19, 130.77, 131.54, 134.67, 135.57, 136.62, 138.83, 142.92, 150.55, 151.23, 155.49. HRMS (ESI-TOF+): m/z [M+H]+ calcd for $C_{27}H_{25}BrN_5O$: 514.1242; found: 514.1219.

TBI-517, 5-(4-Bromophenyl)-3-cyclohexylimino-2-(2-methoxy-3-pyridyl)amino-3,5-dihydrophenazine:

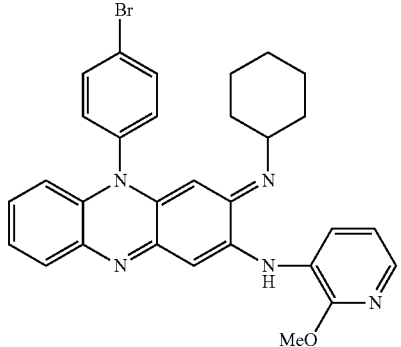

$^1$H NMR (300 MHz, CDCl$_3$) δ: 1.22-1.48 (5H, m), 1.59-1.79 (5H, m), 3.12-3.17 (1H, m), 4.03 (3H, s, CH$_3$), 5.25 (1H, s, CH—C=N), 6.44-6.48 (1H, d, J=7.8 Hz, PhH$_6$), 6.89-6.93 (2H, m, PyH$_5$, CH=C—NH), 7.10-7.19 (2H, m, PhH$_{7, 8}$), 7.22-7.25 (2H, d, J=8.4 Hz, Ph'H$_{2, 6}$), 7.67-7.70 (1H, d, J=7.8 Hz, PyH$_4$), 7.79-7.88 (4H, m, Ph'H$_{3, 5}$, PhH$_9$, PyH$_6$). $^{13}$C NMR (100 MHz, CDCl$_3$) δ: 24.18, 25.99, 33.52, 53.70, 57.27, 89.48, 100.12, 113.77, 116.80, 122.86, 123.61, 124.52, 124.95, 127.60, 128.20, 130.77, 131.52, 134.59, 134.66, 135.60, 136.63, 138.64, 142.85, 150.54, 151.32, 155.38. HRMS (ESI-TOF+): m/z [M+H]+ calcd for $C_{30}H_{29}BrN_5O$: 554.1555; found: 554.1561.

TBI-518, 5-(4-Bromophenyl)-3-(4-tetrahydropyranyl)imino-2-(2-methoxy-3-pyridyl)amino-3,5-dihydrophenazine:

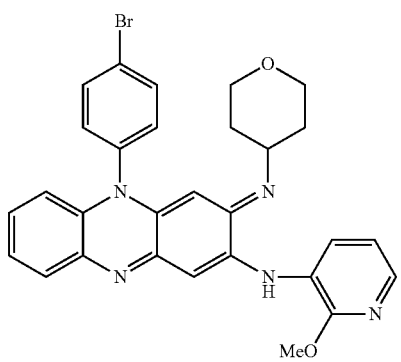 [SMILES: COc1ncccc1Nc1cc2nc3ccccc3n(-c3ccc(Br)cc3)c-2c/c1=N\C1CCOCC1]

mp: 225-227□. $^1$H NMR (300 MHz, CDCl$_3$) δ: 1.58-1.72 (4H, m), 3.43-3.56 (3H, m), 3.99-4.06 (5H, m), 5.25 (1H, s, CH—C=N), 6.46-6.49 (1H, d, J=8.1 Hz, PhH$_6$), 6.90-6.95 (2H, m, PyH$_5$, CH=C—NH), 7.12-7.25 (4H, m, PhH$_{7, 8}$, Ph'H$_{2, 6}$), 7.70-7.73 (1H, d, J=7.5 Hz, PyH$_4$), 7.81-7.91 (4H, m, PhH$_9$, Ph'H$_{3, 5}$, PyH$_6$). $^{13}$C NMR (100 MHz, CDCl$_3$) δ: 33.29, 53.26, 53.76, 65.56, 88.97, 100.30, 113.92, 116.83, 123.11, 123.81, 124.34, 124.84, 127.81, 128.33, 129.35, 129.87, 130.67, 131.35, 134.68, 134.92, 135.62, 136.51, 138.74, 142.63, 150.96, 151.09, 155.30. HRMS (ESI-TOF+): m/z [M+H]+ calcd for $C_{29}H_{27}BrN_5O_2$: 556.1348; found: 556.1358.

TBI-519, 5-(4-Bromophenyl)-3-cyclopropylimino-2-(2-methoxy-3-pyridyl)amino-3,5-dihydrophenazine:

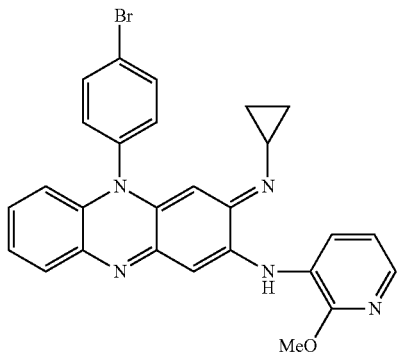 [SMILES: COc1ncccc1Nc1cc2nc3ccccc3n(-c3ccc(Br)cc3)c-2c/c1=N\C1CC1]

mp: 217-218□. ¹H NMR (300 MHz, CDCl₃) δ: 0.83-0.92 (4H, m), 2.75 (1H, brs), 4.05 (3H, s, CH₃), 5.54 (1H, s, CH—C=N), 6.40-6.42 (1H, d, J=7.8 Hz, PhH₆), 6.87-6.92 (2H, m, PyH₅, CH=C—NH), 7.08-7.18 (2H, m, PhH₇,₈), 7.24-7.27 (2H, d, J=8.4 Hz, Ph'H₂,₆), 7.65-7.67 (1H, d, J=7.5 Hz, PyH₄), 7.79-7.87 (4H, m, PhH₉, Ph'H₃,₅, PyH₆). ¹³C NMR (100 MHz, CDCl₃) δ: 10.11, 32.90, 53.69, 89.66, 100.07, 113.78, 116.82, 122.89, 123.71, 124.71, 125.13, 127.62, 128.16, 130.86, 131.66, 134.53, 134.74, 135.73, 136.60, 138.91, 142.63, 151.42, 152.50, 155.43. HRMS (ESI-TOF⁺): m/z [M+H]⁺ calcd for C₂₇H₂₃BrN₅O: 512.1085; found: 512.1075.

TBI-520, 5-(4-Bromophenyl)-3-cyclobutylimino-2-ethoxy-3-pyridyl)amino-3,5-dihydrophenazine:

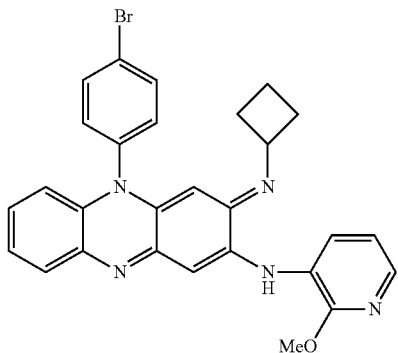 [SMILES: COc1ncccc1Nc1cc2nc3ccccc3n(-c3ccc(Br)cc3)c-2c/c1=N\C1CCC1]

mp: >250□. ¹H NMR (300 MHz, CDCl₃) δ: 1.70-1.82 (2H, m), 2.00-2.24 (4H, m), 3.85-3.96 (1H, p, J=8.1 Hz), 4.00 (3H, s, CH₃), 5.09 (1H, s, CH—C=N), 6.45-6.48 (1H, d, J=7.5 Hz, PhH₆), 6.89-6.93 (2H, m, PyH₅, CH=C—NH), 7.11-7.18 (2H, m, PhH₇,₈), 7.21-7.24 (2H, d, J=8.7 Hz, Ph'H₂,₆), 7.68-7.71 (1H, d, J=7.5 Hz, PyH₄), 7.81-7.88 (4H, m, PhH₉, Ph'H₃,₅, PyH₆). ¹³C NMR (100 MHz, CDCl₃) δ: 16.06, 32.00, 53.73, 54.85, 90.75, 100.26, 113.87, 116.80, 123.02, 123.74, 124.76, 124.84, 127.73, 128.27, 130.79, 131.38, 134.28, 134.61, 135.66, 136.56, 138.87, 142.76, 151.14, 151.39, 155.43. HRMS (ESI-TOF⁺): m/z [M+H]⁺ calcd for C₂₈H₂₅N₅OBr: 526.1236; found: 526.1244.

TBI-521, 5-(4-Bromophenyl)-3-(4-methoxycyclohexyl)imino-2-(2-methoxy-3-pyridyl)amino-3,5-dihydrophenazine:

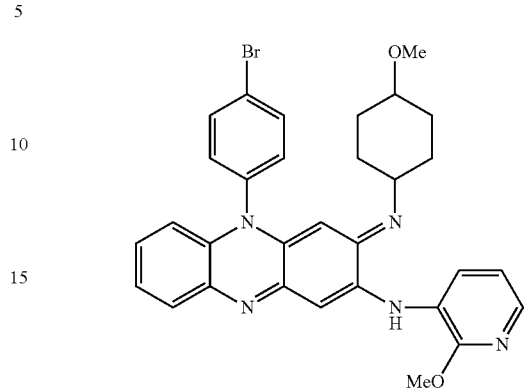

mp: 234-236□. ¹H NMR (300 MHz, CDCl₃) δ: 1.23-1.32 (2H, q), 1.39-1.49 (2H, q), 1.71-1.74 (2H, d), 2.04-2.09 (2H, q), 3.12-3.18 (1H, m), 3.22-3.28 (1H, m), 3.36 (3H, s, CH₃), 4.02-4.05 (4H, m), 5.26 (1H, s, CH—C=N), 6.45-6.48 (1H, d, J=7.5 Hz, PhH₆), 6.89-6.93 (2H, m, PyH₅, CH=C—NH), 7.13-7.24 (4H, m, PhH₇,₈, Ph'H₂,₆), 7.68-7.71 (1H, d, J=6.9 Hz, PyH₄), 7.80-7.87 (4H, m, PyH₆). ¹³C NMR (100 MHz, CDCl₃) δ: 29.35, 30.69, 53.71, 55.79, 56.73, 78.24, 89.24, 100.22, 113.87, 116.84, 122.96, 123.79, 124.61, 124.86, 127.72, 128.26, 129.88, 130.65, 131.47, 134.63, 134.73, 135.61, 136.47, 138.74, 142.72, 151.18, 155.36. HRMS (ESI-TOF⁺): m/z [M+H]⁺ calcd for C₃₁H₃₁N₅O₂Br: 584.1655; found: 584.1667.

TBI-522, 5-(3-Fluorophenyl)-3-(1-methylethyl)imino-2-(3-pyridyl)amino-3,5-dihydrophenazine:

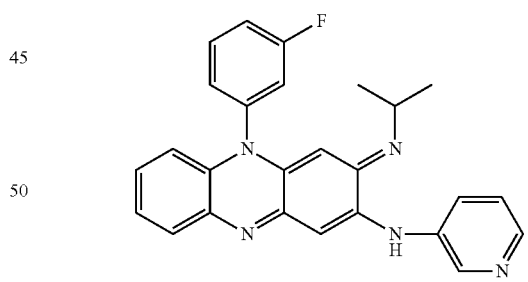

mp: 164-166□. ¹H NMR (300 MHz, CDCl₃) δ: 1.14 (6H, brs), 3.42-3.48 (1H, m), 5.28 (1H, s), 6.46-6.48 (1H, d, J=8.1 Hz), 6.83 (1H, s), 7.09-7.17 (4H, m), 7.29-7.39 (2H, m), 7.68-7.79 (3H, m), 8.32-8.33 (1H, d, J=5.2 Hz), 8.58 (1H, s). ¹³C NMR (100 MHz, CDCl₃) δ: 23.48, 23.59, 49.40, 89.11, 99.44, 113.85, 116.40, 116.62, 117.01, 117.22, 123.03, 123.63, 124.79, 127.77, 127.95, 128.31, 131.32, 132.62, 132.71, 134.70, 136.82, 138.88, 143.68, 143.97, 144.28, 150.38, 150.95. HRMS (ESI-TOF⁺): m/z [M+H]⁺ calcd for C₂₆H₂₃FN₅: 424.1937; found: 424.1921.

TBI-523, 5-(3-Fluorophenyl)-1-methylethyl)imino-2-ethoxy-3-pyridyl)amino-3,5-dihydrophenazine:

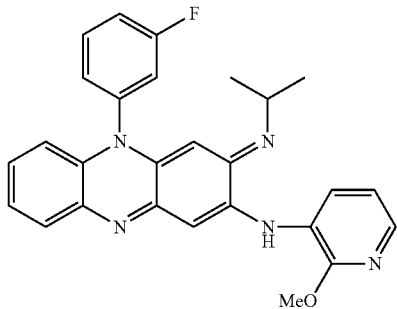 [SMILES: COc1ncccc1Nc1cc2nc3ccccc3n(-c3cccc(F)c3)c-2c/c1=N\C(C)C]

$^1$H NMR (300 MHz, CDCl$_3$) δ: 1.11 (6H, brs), 3.42-3.50 (1H, m), 4.04 (3H, s), 5.29 (1H, s), 6.46-6.48 (1H, d, J=8.1 Hz), 6.93 (2H, brs), 7.10-7.20 (4H, m), 7.34-7.40 (1H, t, J=8.1 Hz), 7.69-7.76H, m), 7.81-7.86 (2H, m). $^{13}$C NMR (100 MHz, CDCl$_3$) δ: 23.47, 49.39, 53.70, 89.28, 100.10, 113.77, 116.45, 116.67, 116.78, 116.93, 117.14, 122.89, 124.84, 124.91, 127.62, 128.19, 131.42, 132.58, 132.67, 134.58, 135.54, 138.81, 138.94, 142.90, 150.61, 151.25, 155.49, 162.95, 165.44. HRMS (ESI-TOF$^+$): m/z [M+H]$^+$ calcd for C$_{27}$H$_{25}$FN$_5$O: 454.2038; found: 454.2043.

TBI-524, 5-(3-Fluorophenyl)-3-(4-tetrahydropyranyl)imino-2-ethoxy-3-pyridyl)amino-3,5-dihydrophenazine:

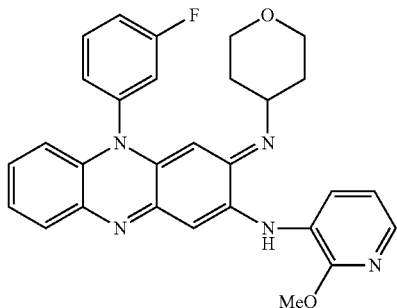 [SMILES: COc1ncccc1Nc1cc2nc3ccccc3n(-c3cccc(F)c3)c-2c/c1=N\C1CCOCC1]

$^1$H NMR (300 MHz, CDCl$_3$) δ: 1.67 (4H, brs), 3.41-3.50 (3H, m), 4.01-4.04 (5H, m), 5.26 (1H, s), 6.49-6.52 (1H, d, J=8.1 Hz), 6.90-6.94 (1H, m), 6.97 (1H, s), 7.09-7.22 (4H, m), 7.36-7.41 (1H, t, J=8.7 Hz), 7.69-7.76 (2H, m), 7.81-7.86 (2H, m). $^{13}$C NMR (100 MHz, CDCl$_3$) δ: 33.26, 33.36, 53.46, 53.75, 65.66, 88.99, 100.31, 113.89, 116.39, 116.61, 116.82, 116.99, 117.20, 123.12, 124.36, 124.75, 124.84, 127.83, 128.32, 131.24, 132.61, 132.70, 134.78, 135.59, 138.74, 138.92, 142.63, 150.98, 151.17, 155.31, 162.95, 165.44. HRMS (ESI-TOF$^+$): m/z [M+H]$^+$ calcd for C$_{29}$H$_{27}$FN$_5$O$_7$: 496.2143; found: 496.2152.

TBI-525, 5-(3,4-Difluorophenyl)-3-(1-methylethyl)imino-2-(3-pyridyl)amino-3,5-dihydrophenazine:

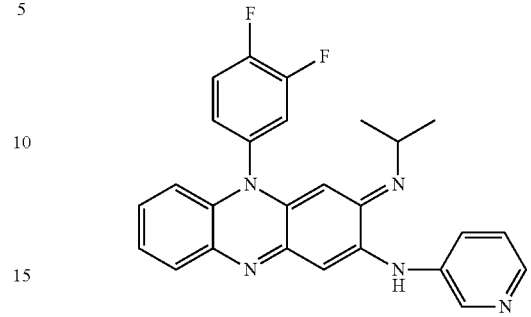

$^1$H NMR (300 MHz, CDCl$_3$) 1.10-1.14 (6H, t, J=6.9 Hz), 3.48-3.52 (1H, m, J=6.6 Hz), 5.29 (1H, s, CH—C=N), 6.44-6.47 (1H, d, J=8.1 Hz), 6.82 (1H, s, CH=C—NH), 7.13-7.32 (5H, m), 7.50-7.56 (1H, dd, J=9.0 Hz), 7.67-7.70 (1H, d, J=7.8 Hz), 7.76-7.79 (1H, d, J=8.4 Hz), 8.33 (1H, d, J=4.5 Hz), 8.59 (1H, d, J=2.1 Hz). $^{13}$C NMR (100 MHz, CDCl$_3$) δ: 23.50, 23.63, 49.48, 89.06, 99.44, 113.62, 118.63, 118.80, 119.89, 120.08, 123.16, 123.62, 125.72, 127.81, 127.99, 128.41, 131.32, 133.63, 134.77, 135.53, 136.70, 143.67, 144.00, 144.37, 150.21, 150.96. HRMS (ESI-TOF$^+$): m/z [M+H]$^+$ calcd for C$_{26}$H$_{22}$F$_2$N$_5$: 442.1838; found: 442.1844.

TBI-526, 5-(3,4-Difluorophenyl)-3-cyclobutylimino-2-(3-pyridyl)amino-3,5-dihydrophenazine:

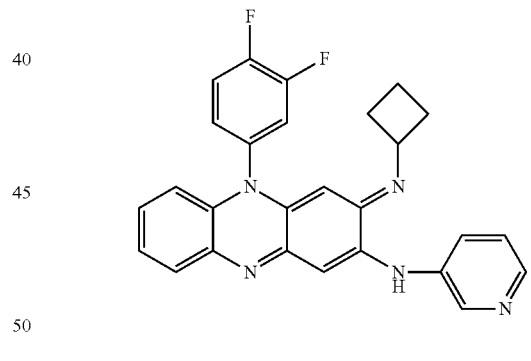

$^1$H NMR (300 MHz, CDCl$_3$) 1.74-1.83 (2H, 2.02-2.21 (4H, m), 3.90-3.96 (1H, p, J=7.8 Hz), 5.10 (1H, s, CH—C=N), 6.47-6.49 (1H, d, J=6.9 Hz), 6.82 (1H, s, CH=C—NH), 7.14-7.33 (5H, m), 7.51-7.60 (1H, dd, J=9.0 Hz), 7.69-7.71 (1H, d, J=7.5 Hz), 7.76-7.79 (1H, d, J=8.1 Hz), 8.34-8.35 (1H, d, J=4.5 Hz), 8.60 (1H, d, J=2.1 Hz). $^{13}$C NMR (100 MHz, CDCl$_3$) δ: 16.07, 32.00, 54.83, 90.55, 99.52, 113.70, 118.65, 118.83, 119.85, 120.03, 123.31, 123.66, 125.74, 127.94, 128.10, 128.49, 131.18, 133.61, 134.35, 135.62, 136.60, 143.60, 144.05, 144.49, 149.64, 150.50, 150.64, 150.90, 151.04, 152.28, 153.03, 153.17. HRMS (ESI-TOF$^+$): m/z [M+H]$^+$ calcd for C$_{27}$H$_{22}$F$_2$N$_5$: 454.1838; found: 454.1852.

TBI-527, 5-(3,4-Difluorophenyl)-3-cyclohexylimino-2-(3-pyridyl)amino-3,5-dihydrophenazine:

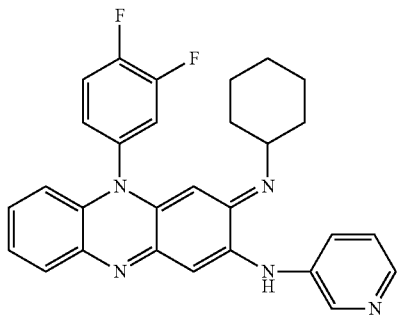

¹H NMR (300 MHz, CDCl₃) 1.25-1.41 (5H, m), 1.62-1.78 (5H, m), 3.10-3.17 (1H, m), 5.27 (1H, s, CH—C=N), 6.46-6.48 (1H, d, J=7.8 Hz), 6.82 (1H, s, CH=C—NH), 7.15-7.32 (5H, m), 7.51-7.60 (1H, dd, J=8.7 Hz), 7.67-7.70 (1H, d, J=7.2 Hz), 7.76-7.79 (1H, d, J=8.1 Hz), 8.33-8.34 (1H, d, J=4.8 Hz), 8.58 (1H, s). ¹³C NMR (100 MHz, CDCl₃) δ: 24.54, 24.62, 25.79, 33.60, 33.71, 57.96, 89.30, 99.44, 113.60, 118.66, 118.84, 119.78, 119.96, 123.15, 123.62, 125.72, 127.79, 127.91, 128.41, 131.31, 133.65, 134.68, 135.57, 136.74, 143.69, 143.97, 144.33, 149.71, 150.31, 150.50, 151.03, 153.17. HRMS (ESI-TOF⁺): m/z [M+H]⁺ calcd for $C_{29}H_{26}F_2N_5$: 482.2151; found: 482.2152.

TBI-528, 5-(3,4-Difluorophenyl)-3-(1,3-dimethoxyisopropyl)imino-2-(3-pyridyl)amino-3,5-dihydrophenazine:

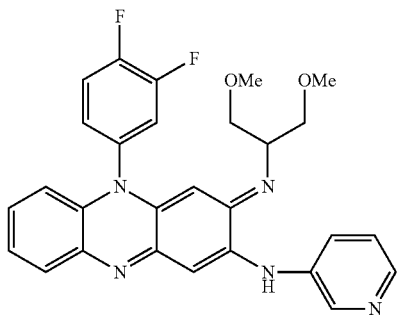 [SMILES: COCC(COC)/N=c1\cc2n(-c3ccc(F)c(F)c3)c3ccccc3nc-2cc1Nc1cccnc1]

¹H NMR (300 MHz, CDCl₃) δ: 3.29 (6H, s), 3.35-3.43 (2H, m), 3.53-3.58 (2H, m), 3.70-3.76 (1H, m), 5.50 (1H, s, CH—C=N), 6.47-6.50 (1H, d, J=7.8 Hz), 6.84 (1H, s, CH=C—NH), 7.12-7.32 (5H, m), 7.48-7.60 (1H, dd, J=8.4 Hz), 7.70-7.72 (1H, d, J=7.2 Hz), 7.76-7.79 (1H, d, J=8.4 Hz), 8.33-8.35 (1H, d, J=4.5 Hz), 8.58 (1H, d, J=2.1 Hz). ¹³C NMR (100 MHz, CDCl₃) δ: 58.75, 59.07, 59.11, 74.50, 74.62, 90.31, 99.61, 113.74, 118.60, 118.78, 119.81, 119.99, 123.26, 123.63, 125.64, 127.99, 128.16, 128.52, 131.25, 133.49, 134.65, 135.55, 136.58, 143.57, 144.14, 144.48, 149.66, 149.78, 150.50, 150.71, 152.18, 153.03, 153.16, 153.26. HRMS (ESI-TOF⁺): m/z [M+H]⁺ calcd for $C_{28}H_{26}F_2N_5O_2$: 502.2049; found: 502.2042.

TBI-529, 5-(3,4-Difluorophenyl)-3-(1-methylethyl)imino-2-(2-methoxy-3-pyridyl)amino-3,5-dihydrophenazine:

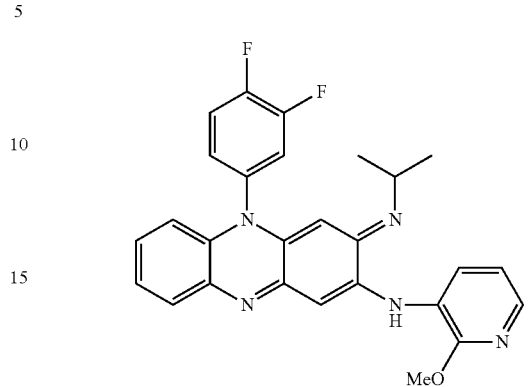

¹H NMR (300 MHz, CDCl₃) 1.10-1.15 (6H, t, J=6.9 Hz), 3.45-3.53 (1H, m, J=6.3 Hz), 4.04 (3H, s), 5.28 (1H, s, CH—C=NH), 6.42-6.45 (1H, d, J=7.5 Hz), 6.89-6.93 (2H, m), 7.13-7.25 (4H, m), 7.49-7.59 (1H, dd, J=9.0 Hz), 7.67-7.70 (1H, d, J=7.2 Hz), 7.81-7.84 (2H, m), 8.92 (1H, s). ¹³C NMR (100 MHz, CDCl₃) δ: 23.48, 23.62, 49.46, 53.71, 89.23, 100.10, 113.55, 116.78, 118.68, 118.86, 119.86, 120.04, 123.05, 124.77, 124.96, 125.75, 127.66, 128.29, 131.41, 133.69, 134.67, 135.54, 138.90, 142.90, 149.59, 149.71, 150.47, 150.67, 151.23, 152.11, 152.23, 153.06, 153.19, 155.49. HRMS (ESI-TOF⁺): m/z [M+H]⁺ calcd for $C_{27}H_{24}F_2N_5O$: 472.1943; found: 472.1937.

TBI-530, 5-(3,4-Difluorophenyl)-3-cyclobutylimino-2-(2-methoxy-3-pyridyl)amino-3,5-dihydrophenazine:

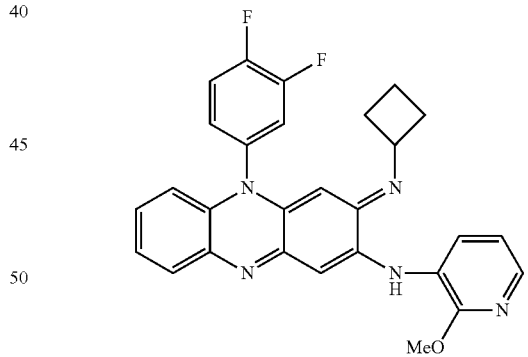

¹H NMR (300 MHz, CDCl₃) δ: 1.70-1.82 (2H, m), 2.03-2.20 (4H, m), 3.90-3.95 (1H, p, J=7.8 Hz), 4.04 (3H, s), 5.08 (1H, s, CH—C=N), 6.45-6.47 (1H, d, J=7.5 Hz), 6.89-6.93 (2H, m), 7.12-7.23 (4H, m), 7.50-7.59 (1H, dd, J=8.7 Hz), 7.68-7.70 (1H, d, J=7.5 Hz), 7.82-7.84 (2H, m). ¹³C NMR (100 MHz, CDCl₃) δ: 16.07, 32.04, 53.73, 54.87, 90.74, 100.26, 113.63, 116.78, 118.69, 118.86, 119.81, 119.99, 123.19, 124.68, 124.86, 125.77, 127.79, 128.35, 131.26, 133.60, 134.24, 135.61, 138.94, 142.74, 150.48, 150.62, 151.14, 151.31, 155.43. HRMS (ESI-TOF⁺): m/z [M+H]⁺ calcd for $C_{28}H_{24}F_2N_5O$: 484.1943; found: 484.1933.

TBI-531, 5-(3,4-Difluorophenyl)-3-cyclohexylimino-2-(2-methoxy-3-pyridyl)amino-3,5-dihydrophenazine:

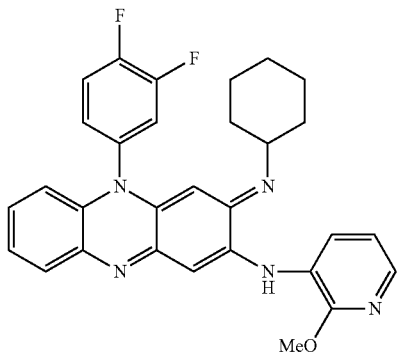

¹H NMR (300 MHz, CDCl₃) δ: 1.23-1.79 (10H, m), 3.14-3.20 (1H, m), 4.03 (3H, s), 5.26 (1H, s, CH—C=N), 6.43-6.46 (1H, d, J=7.5 Hz), 6.88-6.93 (2H, m), 7.11-7.25 (4H, m), 7.49-7.58 (1H, dd, J=8.7 Hz), 7.67-7.70 (1H, d, J=7.5 Hz), 7.80-7.84 (2H, m). ¹³C NMR (100 MHz, CDCl₃) δ: 24.21, 25.95, 33.50, 33.61, 53.71, 57.38, 89.42, 100.14, 113.53, 116.80, 118.71, 118.89, 119.75, 119.94, 123.03, 124.54, 124.89, 125.77, 127.65, 128.29, 131.41, 133.67, 134.62, 135.56, 138.71, 142.84, 149.56, 150.42, 151.34, 152.19, 153.02, 155.38. HRMS (ESI-TOF⁺): m/z [M+H]⁺ calcd for $C_{30}H_{28}F_2N_5O$: 512.2256; found: 512.2263.

TBI-532, 5-(3,4-Difluorophenyl)-3-(4-tetrahydropyranyl)imino-2-(2-methoxy-3-pyridyl)amino-3,5-dihydrophenazine:

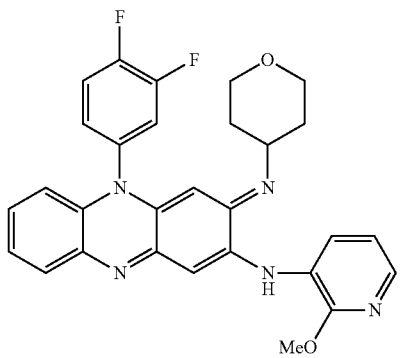 [SMILES: COc1ncccc1Nc1cc2nc3ccccc3n(-c3ccc(F)c(F)c3)c-2c/c1=N\C1CCOCC1]

¹H NMR (300 MHz, CDCl₃) 1.65-1.68 (4H, m), 3.46-3.55 (3H, m), 4.05 (5H, m), 5.25 (1H, s, CH—C=N), 6.45-6.48 (1H, d, J=9.0 Hz), 6.90-6.95 (2H, m), 7.13-7.24 (4H, m), 7.51-7.60 (1H, dd, J=9.0 Hz, 8.7 Hz), 7.70-7.72 (1H, d, J=7.5 Hz), 7.81-7.85 (2H, m), 9.08 (1H, s). HRMS (ESI-TOF⁺): m/z [M+H]⁺ calcd for $C_{29}H_{26}F_2N_5O_7$: 514.2049; found: 514.2042.

TBI-300, 5-(4-Methylphenyl)-3-(1-methylethyl)imino-2-(3-pyridyl)amino-3,5-dihydrophenazine:

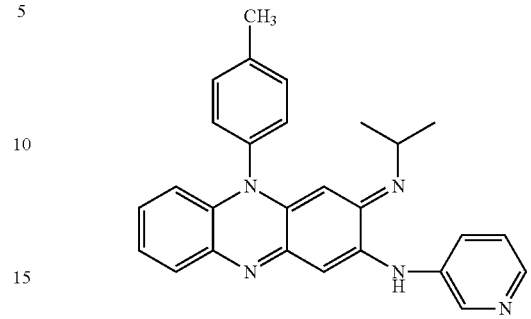

¹H NMR (300 MHz, CDCl₃) δ: 1.05 (6H, d, J=6.3 Hz, —CH(CH₃)₂), 2.58 (3H, s, —CH₃), 3.41 (1H, m, —CH(CH₃)₂), 5.38 (1H, s, 4-H), 6.50 (1H, d, J=7.8 Hz, 6-H), 6.85 (1H, s, 1-H), 7.13 (2H, q, J₁=8.1 Hz, J₂=7.8 Hz, 7-H, 8-H), 7.20 (2H, d, J=7.5 Hz, 2"-H, 6"-H), 7.28 (1H, d, J=8.1 Hz, 9-H), 7.50 (2H, d, J=7.5 Hz, 3"-H, 5"-H), 7.68 (1H, d, J=7.2 Hz, 4'-H), 7.78 (1H, d, J=7.8 Hz, 5'-H), 7.32 (1H, d, J=4.2 Hz, 6'-H), 8.58 (1H, s, 2'-H). ¹³C NMR (100 MHz, CDCl₃) δ: 21.43, 23.51, 49.21, 89.03, 99.43, 114.29, 122.72, 123.60, 127.59, 127.81, 128.13, 128.37, 131.83, 134.85, 135.19, 135.69, 137.03, 139.74, 143.66, 143.91, 144.10, 150.63, 150.91. HRMS (ESI-TOF⁺): m/z [M+H]⁺ calcd for $C_{27}H_{26}N_5$: 420.2157; found: 420.2156.

TBI-301, 5-(4-Methylphenyl)-3-(4-methoxycyclohexyl)imino-2-(3-pyridyl)amino-3,5-dihydrophenazine:

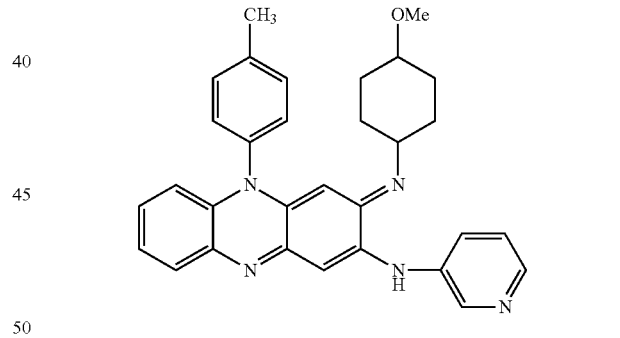

¹H NMR (300 MHz, CDCl₃) δ: 1.12 (2H, m, —CH₂—CH₂—OCH₃), 1.41 (2H, m, —CH₂CH₂—OCH₃), 1.70 (2H, m, CH—CH₂), 2.09 (2H, m, CH—CH₂), 2.58 (3H, s, —CH₃), 3.05 (1H, m, —CH—OCH₃), 3.18 (1H, m, —N—CH), 3.18 (3H, s, —OCH₃), 5.35 (1H, s, 4-H), 6.55 (1H, d, J=7.2 Hz, 6-H), 6.87 (1H, s, 1-H), 7.14 (2H, J=8.1 Hz, J=7.2 Hz, 7-H, 8-H), 7.19 (2H, d, J=7.8 Hz, 2"-H, 6"-H), 7.28 (1H, d, J=8.1 Hz, 9-H), 7.50 (2H, J=7.8 Hz, 3"-H, 5"-H), 7.60 (1H, d, J=6.6 Hz, 4'-H), 7.69 (1H, d, J=8.1 Hz, 5'-H), 8.32 (1H, d, J=4.2 Hz, 6'-H), 8.57 (1H, s, 2'-H). ¹³C NMR (100 MHz, CDCl₃) δ: 21.44, 29.97, 31.09, 55.87, 57.19, 78.57, 89.08, 99.58, 114.58, 122.81, 123.62, 127.77, 128.28, 131.76, 134.73, 135.17, 135.71, 136.87, 139.94, 143.51, 143.89, 144.18, 150.81, 151.36. HRMS (ESI-TOF⁺): m/z [M+H]⁺ calcd for $C_{31}H_{32}N_5O$: 490.2589; found: 490.2587.

TBI-302, 5-(4-Methylphenyl)-3-(2-morpholinoethyl)imino-2-(3-pyridyl)amino-3,5-dihydro-phenazine:

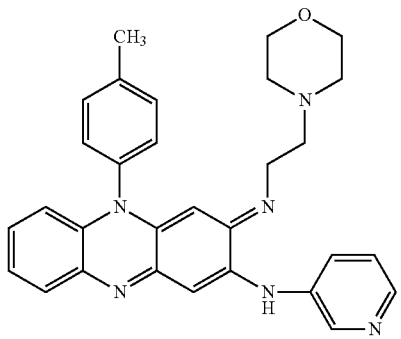 [SMILES: Cc1ccc(-n2c3c/c(=N\CCN4CCOCC4)c(Nc4cccnc4)cc-3nc3ccccc32)cc1]

$^1$H NMR (300 MHz, CDCl$_3$) δ: 2.20-2.30 (8H, m, —CH$_2$CH$_2$OCH$_2$CH$_2$—), 2.70 (2H, CH$_2$CH$_2$), 3.25 (2H, CH$_2$CH$_2$), 3.65 (3H, s, —CH$_3$), 5.35 (1H, s, 4-H), 6.51 (1H, d, J=7.2 Hz, 6-H), 6.85 (1H, s, 1-H), 7.10 (2H, q, J=8.1 Hz, J=7.2 Hz, 7-H, 8-H), 7.19 (2H, d, J=7.8 Hz, 2″-H, 6″-H), 7.32 (1H, m, 9-H), 7.51 (2H, d, J=7.8 Hz, 3″-H, 5″-H), 7.71 (1H, d, J=5.4 Hz, 4′-H), 7.79 (1H, d, J=6.9 Hz, 5′-H), 8.32 (1H, 6′-H), 8.57 (1H, s, 2′-H). $^{13}$C NMR (100 MHz, CDCl$_3$) δ: 21.41, 54.07, 66.93, 88.95, 99.58, 114.52, 123.04, 123.68, 127.91, 128.21, 132.02, 124.76, 135.25, 135.74, 136.74, 139.94, 143.33, 143.92, 144.35, 152.99. HRMS (ESI-TOF$^+$): m/z [M+H]$^+$ calcd for C$_{30}$H$_{31}$N$_6$O: 491.2583; found: 491.2582.

TBI-303, 5-(4-Methylphenyl)-3-(4-tetrahydropyranyl)imino-2-(3-pyridinyl)amino-3,5-dihydrophenazine:

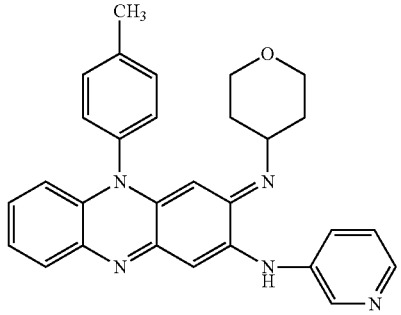 [SMILES: Cc1ccc(-n2c3c/c(=N\C4CCOCC4)c(Nc4cccnc4)cc-3nc3ccccc32)cc1]

$^1$H NMR (300 MHz, CDCl$_3$) δ: 1.63 (4H, m, —CH$_2$—CH—CH$_2$—), 2.57 (3H, s, —CH$_3$), 3.29 (1H, m-CH$_2$—CH—CH$_2$—), 3.40 (2H, m, —CH$_2$—O), 3.99 (2H, m, —CH$_2$—O), 5.27 (1H, s, 4-H), 6.58 (1H, d, J=7.5 Hz, 6-H), 6.87 (1H, s, 1-H), 7.15 (2H, q, J=7.8 Hz, J=7.5 Hz, 7-H, 8-H), 7.19 (2H, d, J=8.1 Hz, 2″-H, 6″-H), 7.35 (1H, d, J=7.8 Hz, 9-H), 7.51 (2H, d, J=8.1 Hz, 3″-H, 5″-H), 7.68 (1H, d, J=6.9 Hz, 4′-H), 7.81 (1H, d, J=8.4 Hz, 5′-H), 8.37 (1H, d, J=3.9 Hz, 6′-H), 8.60 (1H, s, 2′-H). $^{13}$C NMR (100 MHz, CDCl$_3$) δ: 21.41, 33.40, 54.32, 66.21, 88.96, 99.63, 114.38, 122.92, 123.67, 127.86, 127.93, 128.35, 131.81, 134.84, 135.31, 135.72, 136.80, 139.90, 143.57, 143.97, 144.35, 150.74, 151.37. HRMS (ESI-TOF$^+$): m/z [M+H]$^+$ calcd for C$_{29}$H$_{28}$N$_5$O: 462.2584; found: 462.2582.

TBI-304, 5-(4-Methylphenyl)-3-(N-methyl-4-piperidyl)imino-2-(3-pyridinyl)amino-3,5-dihydro-phenazine:

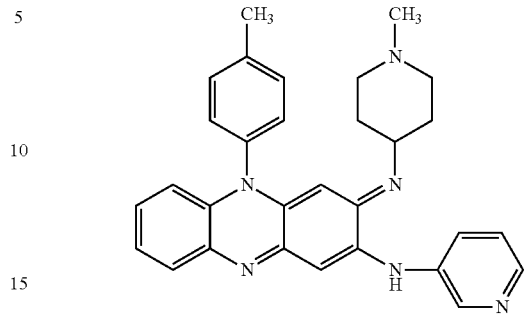

$^1$H NMR (300 MHz, CDCl$_3$) δ: 1.66 (4H, m, —CH$_2$—CH—CH$_2$—), 2.20 (2H, m, —CH$_2$—N), 2.27 (3H, s, N—CH$_3$), 2.53 (3H, s, —CH$_3$), 2.78 (2H, m, —CH$_2$—N), 3.11 (1H, m-CH$_2$—CH—CH$_2$—), 5.53 (1H, s, 4-H), 6.57 (1H, d, J=7.2 Hz, 6-H), 6.83 (1H, s, 1-H), 7.13 (2H, q, J=7.2 Hz, J=8.4 Hz, 7-H, 8-H), 7.20 (2H, d, J=8.1 Hz, 2″-H, 6″-H), 7.30 (1H, d, J=8.4 Hz, 9-H), 7.52 (2H, d, J=7.2 Hz, 3″-H, 5″-H), 7.70 (1H, d, J=6.6 Hz, 4′-H), 7.78 (1H, d, J=8.4 Hz, 5′-H), 8.33 (1H, d, J=4.8 Hz, 6′-H), 8.59 (1H, s, 2′-H). $^{13}$C NMR (100 MHz, CDCl$_3$) δ: 21.41, 26.39, 32.46, 46.28, 53.86, 89.12, 99.61, 114.45, 123.68, 127.92, 128.29, 131.82, 134.79, 135.25, 136.85, 143.50, 144.02, 144.34, 151.38. HRMS (ESI-TOF$^+$): m/z. [M+H]$^+$ calcd for C$_{30}$H$_{31}$N$_6$: 475.2548; found: 475.2546.

TBI-305, 5-(4-Methylphenyl)-3-(N-isobutyl-4-piperidyl)imino-2-(3-pyridyl)amino-3,5-dihydrophenazine:

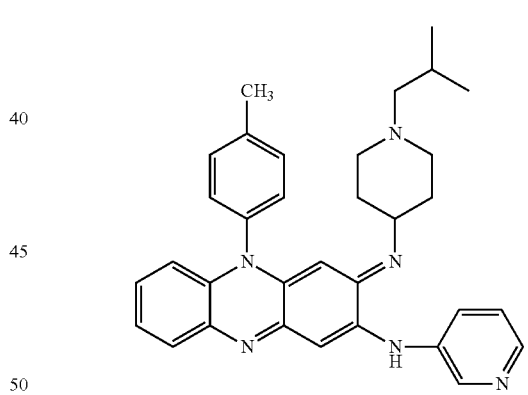

$^1$H NMR (300 MHz, CDCl$_3$) δ: 0.89 (6H, d, J=6.9 Hz, (CH$_3$)$_2$—CH—), 1.58-1.99 (8H, —CH$_2$—CH$_2$—CH—CH$_2$—CH$_2$—), 2.07 (2H, d, J=5.4 Hz, CH$_2$—CH), 2.55 (3H, s, —CH$_3$), 2.78 (1H, m, (CH$_3$)$_2$—CH—), 3.11 (1H, m, N—CH—CH$_2$—), 5.31 (1H, s, 4-H), 6.55 (1H, d, J=7.8 Hz, 6-H), 6.88 (1H, s, 1-H), 7.14 (2H, m, 7-H, 8-H), 7.20 (2H, d, J=7.8 Hz, 2″-H, 6″-H), 7.30 (1H, m, 9-H), 7.51 (2H, d, J=7.8 Hz, 3″-H, 5″-H), 7.69 (1H, d, J=6.0 Hz, 4′-H), 7.78 (1H, d, J=6.0 Hz, 5′-H), 8.28 (1H, d, J=4.5 Hz, 6′-H), 8.58 (1H, s, 2′-H). $^{13}$C NMR (100 MHz, CDCl$_3$) δ: 20.98, 21.40, 25.72, 31.85, 32.72, 52.43, 55.78, 67.11, 89.16, 99.47, 109.76, 114.34, 122.79, 123.64, 127.72, 128.35, 131.35, 135.79, 135.79, 136.95, 139.77, 143.87, 144.14, 151.12, 155.00. HRMS (ESI-TOF$^+$): m/z [M+H]$^+$ calcd for C$_{33}$H$_{37}$N$_6$: 517.3156; found: 517.3157.

TBI-306, 5-(4-Methylphenyl)-3-cyclohexylimino-2-(6-methyl-3-pyridyl)amino-3,5-dihydrophenazine:

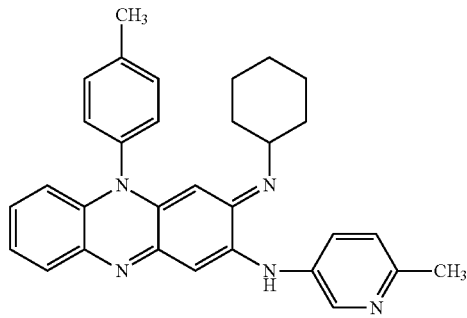

$^1$H NMR (300 MHz, CDCl$_3$) δ: 1.13-1.75 (10H, m, —CH$_2$—CH$_2$—CH$_2$—CH$_2$—CH$_2$—), 2.53 (6H, s-CH$_3$, py-CH$_3$), 3.06 (1H, m, —CH$_2$—CH—CH$_2$—), 5.28 (1H, s, 4-H), 6.53 (1H, d, J=7.5 Hz, 6-H), 6.72 (1H, s, 1-H), 7.08-7.16 (3H, m, 7-H, 8-H, 9-H), 7.19 (2H, d, J=7.8 Hz, 2"-H, 6"-H), 7.50 (2H, d, J=7.8 Hz, 3"-H, 5"-H), 7.67 (1H, d, J=2.7 Hz, 4'-H), 7.61 (1H, d, J=2.7 Hz, 5'-H), 8.45 (1H, s, 2'-H). $^{13}$C NMR (100 MHz, CDCl$_3$) δ: 21.36, 23.80, 24.68, 25.86, 33.58, 57.81, 89.32, 98.79, 114.21, 122.21, 123.12, 127.39, 128.04, 128.39, 129.28, 131.69, 134.28, 134.93, 135.05, 135.71, 139.65, 143.67, 144.41, 120.83, 151.03, 153.11. HRMS (ESI-TOF$^+$): [M+H]$^+$ calcd for C$_{31}$H$_{32}$N$_5$: 474.3848; found: 474.3846.

TBI-307, 5-(4-Methylphenyl)-3-(N-cyclopentyl-4-piperidyl)imino-2-(3-pyridyl)amino-3,5-dihydrophenazine:

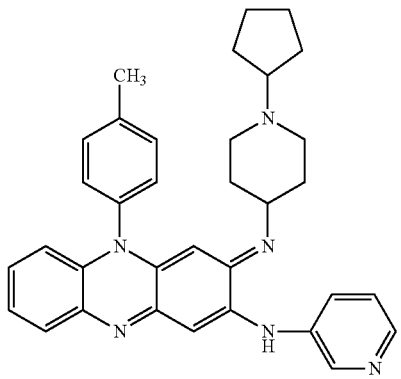 [SMILES: Cc1ccc(-n2c3c/c(=N\C4CCN(C5CCCC5)CC4)c(Nc4cccnc4)cc-3nc3ccccc32)cc1]

$^1$H NMR (300 MHz, CDCl$_3$) 1.35-2.15 (16H, m, —CH$_2$—CH$_2$—N—CH$_2$—CH$_2$—, —CH$_2$—CH$_2$—CH$_2$—CH$_2$—), 2.52 (3H, s, —CH$_3$), 2.91 (1H, m, —CH$_2$—CH—CH$_2$—), 3.12 (1H, m, N—CH—CH$_2$), 5.28 (1H, s, 4-H), 6.55 (1H, d, J=6.6 Hz, 6-H), 6.89 (1H, s, 1-H), 7.12 (2H, m, 7-H, 8-H), 7.19 (2H, d, J=7.8 Hz, 2"-H, 6"-H), 7.31 (1H, m, 9-H), 7.52 (2H, d, J=7.8 Hz, 3"-H, 5"-H), 7.62 (1H, d, J=5.4 Hz, 4'-H), 7.80 (1H, d, J=6.9 Hz, 5'-H), 8.32 (1H, d=3.9 Hz, 6'-H), 8.57 (1H, s, 2'-H). $^{13}$C NMR (100 MHz, CDCl$_3$) δ: 21.41, 24.15, 30.64, 32.69, 50.81, 67.71, 89.19, 99.56, 114.38, 122.85, 123.67, 127.77, 128.28, 131.83, 135.28, 136.86, 143.50, 143.93, 150.04. HRMS (ESI-TOF$^+$): m/z [M+H]$^+$ calcd for C$_{34}$H$_{37}$N$_6$: 529.2046; found: 529.3054.

TBI-308, 5-(4-Methylphenyl)-3-(1-methylethyl)imino-2-(2-methoxy-3-pyridyl)amino-3,5-dihydrophenazine:

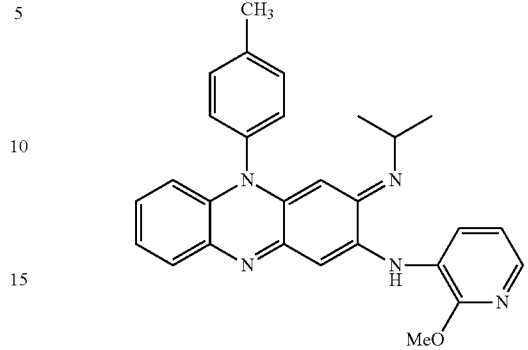

$^1$H NMR (300 MHz, CDCl$_3$) δ: 1.19 (6H, d, J=6.3 Hz, —CH(CH$_3$)$_2$), 2.54 (3H, s, —CH$_3$), 3.43 (1H, m, —CH(CH$_3$)$_2$), 4.03 (3H, s, —OCH$_3$), 5.32 (1H, s, 4-H), 6.48 (1H, d, J=7.8 Hz, 6-H), 6.90 (1H, J=8.1 Hz, 9-H), 6.92 (1H, s, 1-H), 7.12 (2H, m, 7-H, 8-H), 7.20 (2H, d, J=7.8 Hz, 2"-H, 6"-H), 7.49 (2H, d, J=7.8 Hz, 3"-H, 5"-H), 7.68 (1H, d, J=7.2 Hz, 4'-H), 7.80 (1H, d, J=5.1 Hz, 5'-H), 7.85 (1H, d, J=7.8 Hz, 6'-H). $^{13}$C NMR (100 MHz, CDCl$_3$) δ: 21.42, 23.51, 49.23, 53.68, 89.21, 100.14, 114.19, 116.79, 122.56, 124.88, 124.99, 127.49, 128.03, 128.44, 131.80, 132.07, 134.90, 135.06, 138.67, 139.65, 142.90, 150.86, 151.26, 155.49. HRMS (ESI-TOF$^+$): m/z [M+H]$^+$ calcd for C$_{28}$H$_{28}$N$_5$O: 450.2334; found: 450.2330.

TBI-309, 5-(4-Methylphenyl)-3-(4-methoxycyclohexyl)imino-2-(2-methoxy-3-pyridyl)amino-3,5-dihydrophenazine:

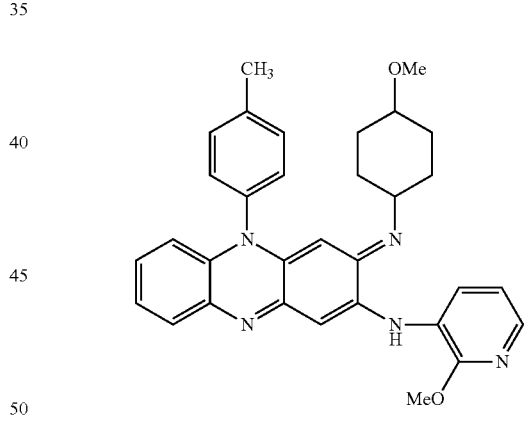

$^1$H NMR (300 MHz, CDCl$_3$) δ: 1.21 (2H, m, —CH$_2$—CH$_2$—), 1.42 (2H, m, —CH$_2$—CH$_2$—), 1.70 (2H, m, —CH—CH$_2$—), 2.08 (2H, m, —CH—CH$_2$—), 2.58 (3H, s, —CH$_3$), 3.10 (1H, m, —CH$_2$—CH—CH$_2$—), 3.24 (1H, m, —CH$_2$—CH—CH$_2$—), 3.38 (3H, s, —OCH), 4.05 (3H, s, —OCH$_3$), 5.23 (1H, s, 4-H), 6.52 (1H, d, J=6.2 Hz, 6-H), 6.91 (1H, m, 9-H), 6.95 (1H, s, 1-H), 7.12 (2H, m, 7-H, 8-H), 7.17 (2H, d, J=8.1 Hz, 2"-H, 6"-H), 7.49 (2H, d, J=8.1 Hz, 3"-H, 5"-H), 7.68 (1H, d, J=8.1 Hz, 4'-H), 7.80 (1H, d, J=6.3 Hz, 5'-H), 7.87 (1H, d, J=8.1 Hz, 6'-H). $^{13}$C NMR (100 MHz, CDCl$_3$) δ: 21.43, 29.54, 30.77, 53.6, 55.83, 56.82, 78.43, 89.21, 100.25, 114.24, 116.83, 122.63, 124.54, 124.98, 127.60, 128.09, 128.35, 131.74, 132.00, 134.80, 135.66, 138.58, 139.82, 139.82, 142.72, 151.19, 151.50, 155.34. HRMS (ESI-TOF$^+$): [M+H]$^+$ calcd for C$_{32}$H$_{34}$N$_5$O$_2$: 520.2750; found: 520.2751.

TBI-310, 5-(4-Methylphenyl)-3-(4-tetrahydropyranyl)imino-2-(2-methoxy-3-pyridyl)amino-3,5-dihydrophenazine:

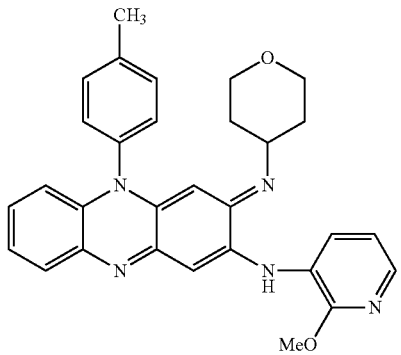 [SMILES: COc1ncccc1Nc1cc2nc3ccccc3n(-c3ccc(C)cc3)c-2c/c1=N\C1CCOCC1]

¹H NMR (300 MHz, CDCl₃) δ: 1.64 (2H, —CH₂—CH₂—), 2.57 (3H, s, —CH₃), 3.42-3.91 (4H, m, —CH₂—CH₂—), 4.02 (1H, m, —CH₂—CH—CH₂—), 4.13 (3H, s, —OCH₃), 5.23 (1H, s, 4-H), 6.53 (1H, d, J=9.3 Hz, 6-H), 6.91 (1H, m, 9-H), 6.95 (1H, s, 1-H), 7.14 (2H, m, 7-H, 8-H), 7.18 (2H, d, J=8.1 Hz, 2"-H, 6"-H), 7.51 (2H, d, J=8.1 Hz, 3"-H, 5"-H), 7.71 (1H, d, J=6.0 Hz, 4'-H), 7.81 (1H, d, J=5.1 Hz, 5'-H), 7.87 (1H, d, J=8.1 Hz, 6'-H). ¹³C NMR (100 MHz, CDCl₃) δ: 21.39, 33.29, 53.29, 53.73, 65.68, 88.97, 100.32, 114.29, 116.83, 122.83, 124.24, 124.98, 128.16, 128.36, 131.78, 131.89, 134.84, 135.26, 135.68, 138.56, 139.79, 142.62, 151.02, 151.41, 155.28. HRMS (ESI-TOF⁺): m/z [M+H]⁺ calcd for $C_{30}H_{30}N_5O_2$: 492.2514; found: 492.2513.

TBI-311, 5-(4-Methylphenyl)-3-(2-morpholinoethyl)imino-2-(2-methoxy-3-pyridyl)amino-3,5-dihydrophenazine:

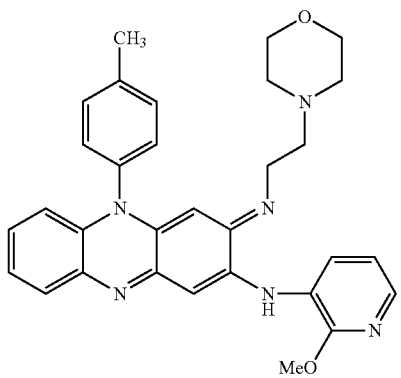 [SMILES: COc1ncccc1Nc1cc2nc3ccccc3n(-c3ccc(C)cc3)c-2c/c1=N\CCN1CCOCC1]

¹H NMR (300 MHz, CDCl₃) δ: 2.51 (3H, s, —CH₃), 2.52 (4H, m, —CH₂—CH₂—), 2.78-2.83 (4H, m, —CH₂—N—CH₂—), 3.30-3.38 (4H, m, —CH₂—O—CH₂—), 4.05 (3H, s, —OCH₃), 5.25 (1H, s, 4-H), 6.52 (1H, d, J=6.9 Hz, 6-H), 6.93 (1H, m, 9-H), 6.98 (1H, s, 1-H), 7.12 (2H, m, 7-H, 8-H), 7.18 (2H, d, J=7.8 Hz, 2"-H, 6"-H), 7.30 (2H, d, J=7.8 Hz, 3"-H, 5"-H), 7.71 (1H, d, J=6.6 Hz, 4'-H), 7.82 (1H, d, J=4.5 Hz, 5'-H), 7.86 (1H, d, J=7.8 Hz, 6'-H). ¹³C NMR (100 MHz. CDCl₃) δ: 21.40, 48.29, 53.71, 54.20, 59.83, 67.00, 89.09, 100.22, 114.43, 116.86, 122.80, 124.65, 127.79, 128.24, 131.99, 134.78, 135.15, 138.83, 139.83, 142.48, 153.10. HRMS (ESI-TOF⁺): m/z [M+H]⁺ calcd for $C_{31}H_{33}N_6O_7$: 521.2713; found: 521.2712.

TBI-312, 5-(4-Methylphenyl)-3-cyclohexylimino-2-(2-methyl-3-pyridyl)amino-3,5-dihydrophenazine:

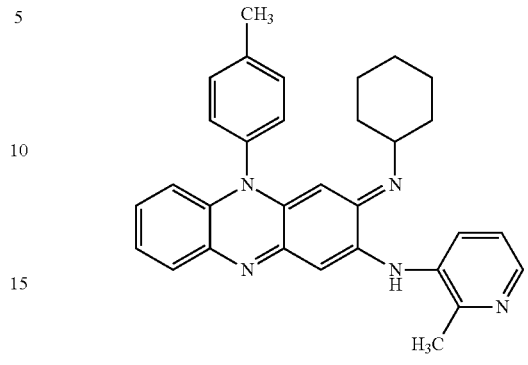

¹H NMR (300 MHz, CDCl₃) δ: 1.17-1.74 (10H, m, —CH₂—CH₂—CH₂—CH₂—CH₂—), 2.54 (6H, s, —CH₃, py-CH₃), 3.12 (1H, m, —CH₂—CH—CH₂—), 5.30 (1H, s, 4-H), 6.53 (1H, d, J=7.5 Hz, 6-H), 6.61 (1H, s, 1-H), 7.11-7.17 (3H, m, 7-H, 8-H, 9-H), 7.20 (2H, d=8.1 Hz, 2"-H, 6"-H), 7.51 (2H, d, J=8.1 Hz, 3-H, 5"-H), 7.66 (1H, d, J=6.9 Hz, 4'-H), 7.82 (1H, d, J=7.8 Hz, 5'-H), 8.24 (1H, d, J=3.6 Hz, 6'-H). ¹³C NMR (100 MHz, CDCl₃) δ: 20.92, 21.37, 24.40, 25.91, 33.54, 57.25, 89.24, 98.81, 114.24, 121.63, 122.65, 127.42, 128.02, 128.38, 131.72, 134.92, 135.02, 135.13, 139.68, 143.80, 144.05, 150.70, 151.04, 151.89. HRMS (ESI-TOF⁺): m/z [M+H]⁺ calcd for $C_{31}H_{32}N_5$: 474.2645; found: 474.2642.

TBI-313, 5-(4-Methylphenyl)-3-(N-methyl-4-piperidyl)imino-2-(2-methoxy-3-pyridyl)amino-3,5-dihydrophenazine:

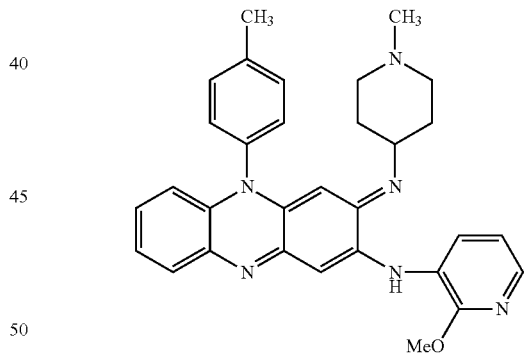

¹H NMR (300 MHz, CDCl₃) δ: 1.63 (4H, —CH₂—CH—CH₂—), 2.08 (2H, m, —CH₂—N—CH₂—), 2.37 (3H, s, —CH₃), 2.59 (3H, s, —N—CH₃), 2.78 (2 m, —CH₂—N—CH₂—), 3.21 (1H, m, —CH₂—CH—CH₂—), 4.03 (3H, s, —OCH₃), 5.23 (1H, s, 4-H), 6.53 (1H, d, J=9.0 Hz, 6-H), 6.92 (1H, m, 9-H), 6.98 (1H, s, 1-H), 7.14 (2H, m, 7-H, 8-H), 7.20 (2H, d, J=8.4 Hz, 2"-H, 6"-H), 7.51 (2H, d, J=8.4 Hz, 3"-H, 5"-H), 7.70 (1H, d, J=6.0 Hz, 4'-H), 7.79 (1H, d, J=6.0 Hz, 5"-H), 7.86 (1H, d, J=6.0 Hz, 6'-H). ¹³C NMR (100 MHz, CDCl₃) δ: 21.40, 32.50, 46.45, 53.36, 53.67, 89.04, 100.24, 114.26, 116.84, 122.69, 124.03, 125.07, 127.63, 128.11, 128.37, 131.79, 131.96, 134.84, 135.22, 135.67, 138.40, 139.75, 142.57, 151.21, 155.22. HRMS (ESI-TOF⁺): m/z [M+H]⁺ calcd for $C_{31}H_{33}N_6O$: 505.2753; found: 505.2751.

TBI-314, 5-(4-Methylphenyl)-3-(N-isobutyl-4-piperidyl)imino-2-(2-methoxy-3-pyridyl)amino-3,5-dihydrophenazine:

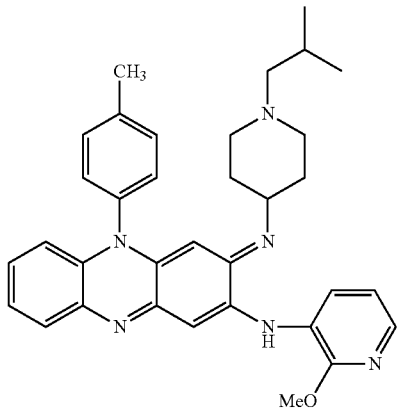 [SMILES: COc1ncccc1Nc1cc2nc3ccccc3n(-c3ccc(C)cc3)c-2c/c1=N\C1CCN(CC(C)C)CC1]

$^1$H NMR (300 MHz, CDCl$_3$) δ: 0.92 (6H, d, J=6.6 Hz, (CH$_3$)$_2$—CH), 1.62 (4H, m, —CH$_2$—CH—CH$_2$—), 1.79 (1H, m, —CH$_2$—CH—CH$_2$—), 2.05 (4H, m, —CH$_2$—N—CH$_2$—), 2.57 (3H, s, —CH$_3$), 2.76 (2H, m, —N—CH$_2$—CH—), 3.38 (1H, m, —CH$_2$—CH—CH$_2$—), 4.02 (3H, s, —OCH$_3$), 5.24 (1H, s, 4-H), 6.53 (1H, d, J=7.8 Hz, 6-H), 6.91 (1H, m, 9-H), 6.97 (1H, s, 1-H), 7.14 (2H, m, 7-H, 8-H), 7.20 (2H, d, J=8.4 Hz, 2''-H, 6''-H), 7.51 (2H, d, J=8.4 Hz, 3''-H, 5''-H), 7.69 (1H, d, J=5.4 Hz, 4'-H), 7.79 (1H, d, J=4.8 Hz, 5'-H), 7.85 (1H, d, J=6.2 Hz, 6'-H). $^{13}$C NMR (100 MHz, CDCl$_3$) δ: 21.08, 21.39, 32.68, 51.98, 53.68, 89.20, 100.20, 114.23, 122.63, 124.18, 125.06, 127.58, 128.09, 128.39, 131.77, 131.99, 134.86, 135.15, 135.66, 134.86, 135.15, 135.66, 138.43, 139.71, 142.65, 151.19. HRMS (ESI-TOF$^+$): m/z [M+H]$^+$ calcd for C$_{34}$H$_{39}$N$_6$O: 547.3116; found: 547.3115.

TBI-315, 5-(4-Methylphenyl)-3-(1-methylethyl)imino-2-(6-methyl-3-pyridyl)amino-3,5-dihydrophenazine:

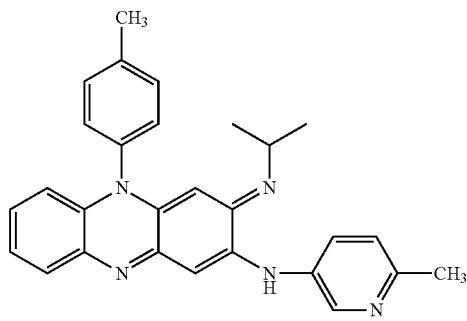 [SMILES: Cc1ccc(-n2c3c/c(=N\C(C)C)c(Nc4ccc(C)nc4)cc-3nc3ccccc32)cc1]

$^1$H NMR (300 MHz, CDCl$_3$) δ: 1.15 (6H, d, J=6.3 Hz, (CH$_3$)$_2$—CH—), 2.57 (6H, s, —CH$_3$, py-CH$_3$), 3.48 (1H, m, (CH$_3$)$_2$—CH—), 5.45 (1H, s, 4-H), 6.61 (1H, d, J=7.2 Hz, 6-H), 6.83 (1H, s, 1-H), 7.15-7.18 (3H, m, 7-H, 8-H, 9-H), 7.22 (2H, d, J=8.4 Hz, 2''-H, 6''-H), 7.53 (2H, d, J=8.4 Hz, 3''-H, 5''-H), 7.61 (1H, d, J=6.9 Hz, 4'-H), 7.78 (1H, d, J=6.9 Hz, 5'-H), 8.50 (1H, s, 2'-H). $^{13}$C NMR (100 MHz, CDCl$_3$) δ: 21.44, 22.90, 23.81, 48.83, 89.15, 99.84, 114.73, 123.29, 128.10, 128.45, 129.96, 131.86, 134.21, 134.60, 135.20, 136.31, 140.17, 144.00, 151.09, 153.50, 176.99. HRMS (ESI-TOF$^+$): m/z [M+H]$^+$ calcd for C$_{28}$H$_{28}$N$_5$: 434.2303; found: 434.2305.

TBI-316, 5-(4-Methylphenyl)-3-(4-methoxycyclohexyl)imino-2-(6-methyl-3-pyridyl)amino-3,5-dihydrophenazine:

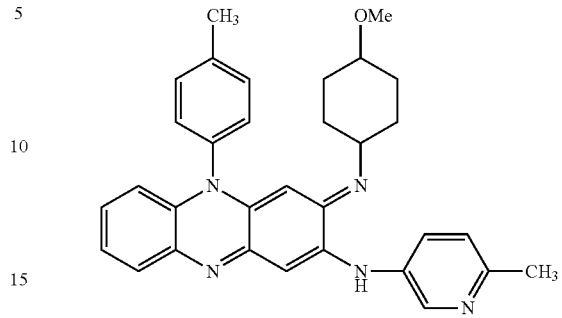

$^1$H NMR (300 MHz, CDCl$_3$) δ: 1.15 (2H, m, —CH$_2$—CH—CH$_2$—), 1.41 (2H, m, —CH$_2$—CH—CH$_2$—), 1.70 (2H, —CH$_2$—CH—CH$_2$—), 2.08 (2H, m, —CH$_2$—CH—CH$_2$—), 2.53 (6H, s, py-CH$_3$), 3.08 (1H, m, —CH$_2$—CH—CH$_2$—), 3.18 (1H, m, —CH$_2$—CH—CH$_2$—), 3.38 (3H, s, —OCH$_3$), 5.25 (1H, s, 4-H), 6.52 (1H, d, J=8.4 Hz, 6-H), 6.74 (1H, s, 1-H), 7.09-7.14 (3H, m, 7-H, 8-H, 9-H), 7.19 (2H, d, J=7.8 Hz, 2''-H, 6''-H), 7.50 (2H, d, J=7.8 Hz, 3''-H, 5''-H), 7.67 (1H, d, J=4.5 Hz, 4'-H), 7.70 (1H, d, J=4.5 Hz, 5'-H), 8.43 (1H, s, 2'-H). $^{13}$C NMR (100 MHz, CDCl$_3$) δ: 21.43, 23.81, 30.00, 31.16, 55.86, 57.26, 78.63, 89.05, 98.91, 114.28, 122.69, 123.13, 127.52, 128.09, 128.31, 129.28, 131.72, 134.11, 134.81, 135.11, 125.68, 139.86, 143.68, 144.27, 150.90, 151.39, 153.22. HRMS (ESI-TOF$^+$): m/z [M+H]$^+$ calcd for C$_{32}$H$_{34}$N$_5$O: 504.2719; found: 504.2718.

TBI-317, 5-(4-Methylphenyl)-3-(4-tetrahydropyranyl)imino-2-(6-methyl-3-pyridyl)amino-3,5-dihydrophenazine:

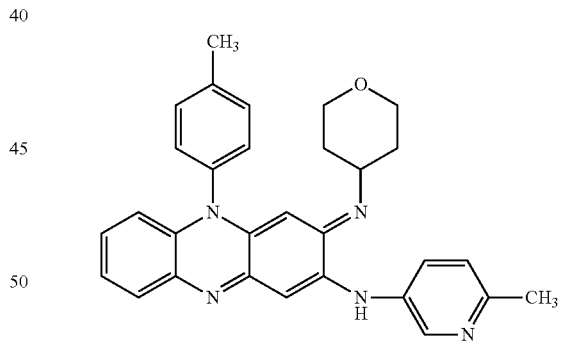

$^1$H NMR (300 MHz, CDCl$_3$) δ: 1.61 (4H, m, —CH$_2$—CH$_2$—), 2.58 (6H, s, —CH$_3$, py-CH$_3$), 3.11-3.52 (4H, m, —CH$_2$—CH$_2$—), 3.98 (1H, m, —CH$_2$—CH—CH$_2$—), 5.23 (1H, s, 4-H), 6.53 (1H, d, J=7.8 Hz, 6-H), 6.77 (1H, s, 1-H), 7.11-7.18 (3H, m, 7-H, 8-H, 9-H), 7.20 (2H, d, J=7.8 Hz, 2''-H, 6''-H), 7.51 (2H, d, J=7.8 Hz, 3''-H, 5''-H), 7.67 (1H, d, J=2.7 Hz, 4'-H), 7.81 (1H, d, J=2.7 Hz, 5'-H), 8.46 (1H, s, 2'-H). $^{13}$C NMR (100 MHz, CDCl$_3$) δ: 21.36, 23.82, 33.02, 33.38, 54.31, 66.19, 88.92, 98.98, 114.32, 122.82, 123.17, 127.61, 128.16, 128.33, 129.45, 131.75, 134.02, 135.22, 135.70, 139.82, 143.75, 144.30, 150.72, 151.40, 153.39. HRMS (ESI-TOF$^+$): m/z [M+H]$^+$ calcd for C$_{30}$H$_{30}$N$_5$O: 476.2527; found: 476.2526.

TBI-318, 5-(4-Methylphenyl)-3-(2-morpholinoethyl)imino-2-(6-methyl-3-pyridyl)amino-3,5-dihydrophenazine:

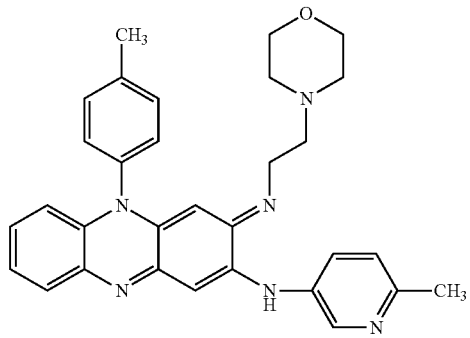

¹H NMR (300 MHz, CDCl₃) δ: 2.51 (3H, s, —CH₃), 2.52 (4H, m, —CH₂—CH₂—), 2.78 (2H, q, CH₂—CH₂—N—), 3.35 (2H, q, —CH₂—CH₂—N—), 2.53 (6H, s, py-CH₃), 5.25 (1H, s, 4-H), 6.52 (1H, d, J=8.4 Hz, 6-H), 6.74 (1H, s, 1-H), 7.09-7.14 (3H, m, 7-H, 8-H, 9-H), 7.19 (2H, d, J=7.8 Hz, 2"-H, 6"-H), 7.50 (2H, d, J=7.8 Hz, 3"-H, 5"-H), 7.67 (1H, d, J=4.5 Hz, 4'-H), 7.70 (1H, d, J=4.5 Hz, 5'-H), 8.43 (1H, s, 2'-H). ¹³C NMR (100 MHz, CDCl₃) δ: 21.40, 48.29, 53.71, 54.20, 59.83, 67.00, 98.91, 114.28, 122.69, 123.13, 127.52, 128.09, 128.31, 129.28, 131.72, 134.11, 134.81, 135.11, 125.68, 139.86, 143.68, 144.27, 150.90, 151.39, 153.22. HRMS (ESI-TOF⁺): [M+H]⁺ calcd for C₃₁H₃₃N₆O: 505.2724; found: 505.2726.

TBI-319, 5-(4-Methylphenyl)-3-(N-methyl-4-piperidyl)imino-2-(6-methyl-3-pyridyl)amino-3,5-dihydrophenazine:

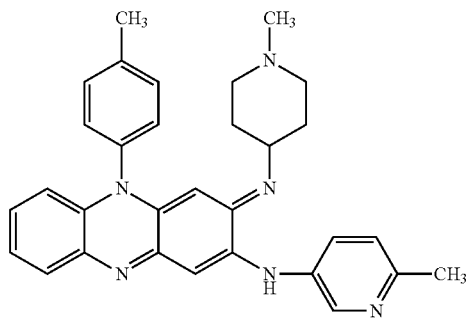 [SMILES: Cc1ccc(-n2c3c/c(=N\C4CCN(C)CC4)c(Nc4ccc(C)nc4)cc-3nc3ccccc32)cc1]

¹H NMR (300 MHz, CDCl₃) δ: 1.65 (4H, m, —CH₂—CH₂—), 2.01 (2H, m, —CH₂—N—CH₂—), 2.27 (3H, s, —NCH₃), 2.55 (6H, s, —CH₃, -py-CH₃), 2.77 (2H, m, —CH₂—N—CH₂—), 3.13 (1H, m, —CH₂—CH—CH₂—), 5.27 (1H, s, 4-H), 6.53 (1H, d, J=7.5 Hz, 6-H), 6.75 (1H, s, 1-H), 7.10-7.17 (3H, m, 7-H, 8-H, 9-H), 7.19 (2H, d, J=8.1 Hz, 2"-H, 6"-H), 7.52 (2H, d, J=8.1 Hz, 3"-H, 5"-H), 7.68 (1H, d, J=2.7 Hz, 4'-H), 7.61 (1H, d, J=2.7 Hz, 5'-H), 8.45 (1H, s, 2'-H). ¹³C NMR (100 MHz, CDCl₃) δ: 21.38, 23.82, 32.61, 64.39, 54.00, 89.08, 98.92, 114.31, 122.75, 123.17, 127.54, 128.33, 129.40, 131.75, 134.10, 134.87, 135.17, 135.71, 139.77, 143.76, 144.29, 151.35, 153.33. HRMS (ESI-TOF⁺): m/z [M+H]⁺ calcd for C₃₁H₃₃N₆: 489.2776; found: 489.2775.

TBI-320, 5-(4-Methylphenyl)-3-(N-isobutyl-4-piperidyl)imino-2-(6-methyl-3-pyridyl)amino-3,5-dihydrophenazine:

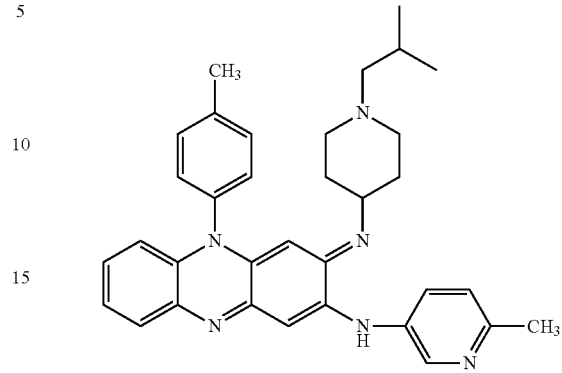

¹H NMR (300 MHz, CDCl₃) δ: 0.89 (6H, d, J=6.6 Hz, (CH₃)₂—CH), 1.61-2.08 (9H, m, —CH₂—CH—)—CH—CH, —CH₂), 2.55 (6H, s, —CH₃, -py-CH₃, 2.77 (2H, m, —N—CH₂—CH), 3.10 (1H, m, —CH—(CH₃)₂), 5.23 (1H, s, 4-H), 6.74 (1H, d, J=7.5 Hz, 6-H), 6.75 (1H, s, 1-H), 7.09-7.18 (3H, m, 7-H, 8-H, 9-H), 7.20 (2H, d, J=7.8 Hz, 2"-H, 6"-H), 7.51 (2H, d, J=7.8 Hz, 3"-H, 5"-H), 7.67 (1H, d, J=7.8 Hz, 4'-H), 7.61 (1H, d, J=7.8 Hz, 5'-H), 8.45 (1H, s, 2'-H). ¹³C NMR (100 MHz, CDCl₃) δ: 20.97, 21.38, 23.82, 25.73, 32.77, 52.48, 55.86, 67.11, 89.15, 98.83, 114.24, 122.67, 123.14, 127.45, 128.09, 128.37, 129.22, 131.73, 134.18, 134.91, 135.12, 135.69, 139.69, 143.66, 144.31, 151.13, 153.17. HRMS (ESI-TOF⁺): m/z [M+H]⁺ calcd for C₃₄H₃₉N₆: 531.3403; found: 531.3400.

TBI-321, 5-(4-Methylphenyl)-3-(1-methylethyl)imino-2-(2-methyl-3-pyridyl)amino-3,5-dihydrophenazine:

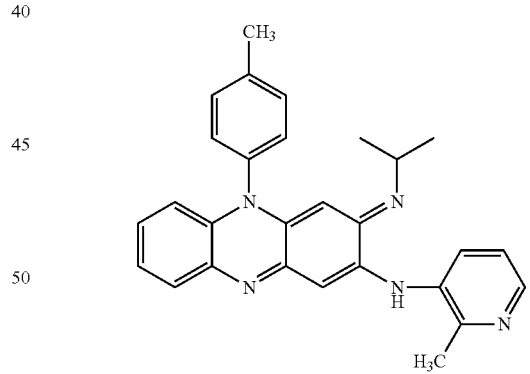

¹H NMR (300 MHz, CDCl₃) δ: 1.13 (6H, d, J=5.7 Hz, (CH₃)₂—CH—), 2.53 (6H, s, —CH₃, py-CH₃), 3.47 (1H, m, —CH—(CH₃)₂), 5.41 (1H, s, 4-H), 6.53 (1H, s, 6-H), 6.59 (1H, s, 1-H), 7.15-7.18 (3H, m, 7-H, 8-H, 9-H), 7.20 (2H, d, J=8.1 Hz, 2"-H, 6"-H), 7.52 (2H, d, J=8.1 Hz, 3"-H, 5"-H), 7.71 (1H, d, J=6.6 Hz, 4'-H), 7.81 (1H, d, J=8.1 Hz, 5'-H), 8.30 (1H, d=4.2 Hz, 6'-H). ¹³C NMR (100 MHz, CDCl₃) δ: 20.94, 21.44, 23.14, 48.87, 89.07, 99.42, 114.57, 121.74, 123.19, 128.20, 129.70, 131.85, 134.71, 135.21, 136.02, 141.02, 144.07, 144.36, 150.83. HRMS (ESI-TOF⁺): m/z [M+H]⁺ calcd for C₂₈H₂₈N₅: 434.2330; found: 434.2334.

TBI-322, 5-(4-Methylphenyl)-3-(4-methoxycyclohexyl)imino-2-(2-methyl-3-pyridyl)amino-3,5-dihydrophenazine:

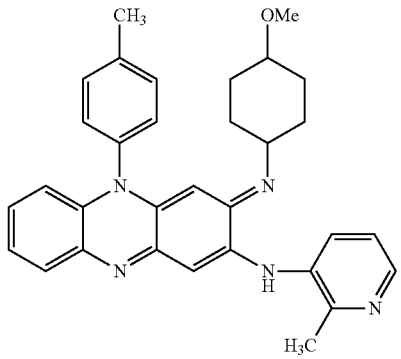

$^1$H NMR (300 MHz, CDCl$_3$) δ: 1.21 (2H, m, —CH$_2$—CH$_2$—), 1.41 (2H, m, —CH$_2$—CH$_2$—), 1.17 (2H, m, —CH$_2$—CH$_2$—), 2.05 (2H, m, —CH$_2$—CH$_2$—), 2.52 (6H, s, —CH$_3$, py-CH$_3$), 3.10 (1H, m, —CH$_2$—CH—CH$_2$—), 3.35 (1H, m, —CH$_2$—CH—CH$_2$—), 3.75 (3H, s, —OCH$_3$), 5.25 (1H, s, 4-H), 6.52 (1H, d, J=8.4 Hz, 6-H), 6.61 (1H, s, 1-H), 7.08-7.15 (3H, m, 7-H, 8-H, 9-H), 7.18 (2H, d, J=7.8 Hz, 2"-H, 6"-H), 7.50 (2H, d, J=7.8 Hz, 3"-H, 5"-H), 7.68 (1H, d, J=7.5 Hz, 4'-H), 7.72 (1H, d, J=7.2 Hz, 5'-H), 8.27 (1H, d, J=3.6 Hz, 6'-H). $^{13}$C NMR (100 MHz, CDCl$_3$) δ: 20.91, 21.44, 29.73, 30.99, 55.85, 56.88, 78.45, 89.01, 98.96, 114.32, 121.65, 122.73, 127.57, 128.09, 128.30, 128.81, 131.75, 134.82, 135.17, 135.66, 139.89, 143.97, 150.90, 151.32, 151.97. HRMS (ESI-TOF$^+$): m/z [M+H]$^+$ calcd for C$_{32}$H$_{34}$N$_5$O: 504.2765; found: 504.2767.

TBI-323, 5-(4-Methylphenyl)-3-(4-tetrahydropyranyl)imino-2-(2-methyl-3-pyridyl)amino-3,5-dihydrophenazine:

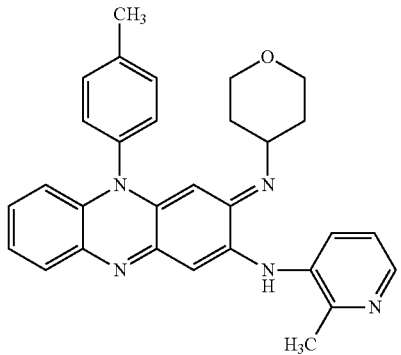

$^1$H NMR (300 MHz, CDCl$_3$) δ: 1.67 (4H, m, —CH$_2$—CH$_2$—), 2.52 (6H, s, —CH$_3$, py-CH$_3$), 3.32-3.51 (3H, m, —CH$_2$—CH—CH$_2$—), 3.92-4.01 (2H, m, —CH$_2$—CH—CH$_2$—), 5.23 (1H, s, 4-H), 6.44 (1H, d, J=8.7 Hz, 6-H), 6.63 (1H, s, 1-H), 7.10-7.18 (3H, m, 7-H, 8-H, 9-H), 7.20 (2H, d, J=8.1 Hz, 2"-H, 6"-H), 7.32 (2H, d, J=8.1 Hz, 3"-H, 5"-H), 7.68 (1H, d, J=7.5 Hz, 4'-H), 7.72 (1H, d, J=7.8 Hz, 5'-H), 8.28 (1H, d, J=3.9 Hz, 6'-H). $^{13}$C NMR (100 MHz, CDCl$_3$) δ: 20.95, 21.38, 33.03, 33.34, 53.65, 65.91, 88.86, 99.03, 114.36, 121.67, 122.86, 127.67, 128.16, 128.32, 128.82, 131.79, 134.72, 134.85, 135.67, 139.86, 143.92, 144.07, 150.73, 151.32, 151.98. HRMS (ESI-TOF$^+$): m/z [M+H]$^+$ calcd for C$_{30}$H$_{30}$N$_5$O: 476.2453; found: 476.2450.

TBI-324, 5-(4-Methylphenyl)-3-(2-morpholinoethyl)imino-2-(2-methyl-3-pyridyl)amino-3,5-dihydrophenazine:

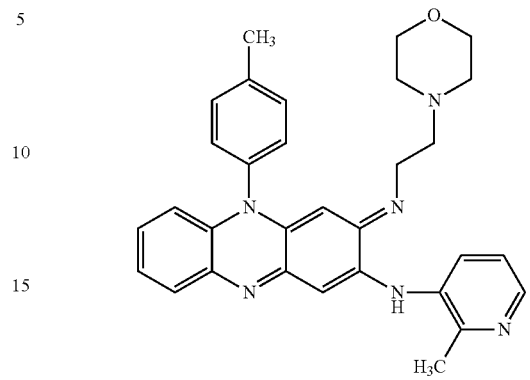

$^1$H NMR (300 MHz, CDCl$_3$) δ: 2.48 (4H, m, —CH$_2$—O—CH$_2$—), 2.57 (6H, s, —CH$_3$, py-CH$_3$), 2.73 (2H, m, —CH$_2$—CH$_2$—), 3.36 (2H, m, —CH$_2$—CH$_2$—), 3.70 (4H, m, —CH$_2$—N—CH$_2$—), 5.33 (1H, s, 4-H), 6.57 (1H, s, 6-H), 6.62 (1H, s, 1-H), 7.10-7.15 (3H, m, 7-H, 8-H, 9-H), 7.18 (2H, d, J=6.9 Hz, 2"-H, 6"-H), 7.51 (2H, d, J=6.9 Hz, 3"-H, 5"-H), 7.71 (1H, s, 4'-H), 7.81 (1H, d, J=7.8 Hz, 5'-H), 8.30 (1H, s, 6'-H). $^{13}$C NMR (100 MHz, CDCl$_3$) δ: 20.98, 21.41, 47.96, 54.15, 60.02, 66.95, 88.95, 98.98, 114.48, 121.72, 122.97, 127.71, 128.22, 129.24, 132.02, 134.82, 135.23, 135.72, 139.88, 143.89, 144.28, 152.92. HRMS (ESI-TOF$^+$): m/z [M+H]$^+$ calcd for C$_{31}$H$_{33}$N$_6$O: 505.2847; found: 505.2846.

TBI-325, 5-(4-Methylphenyl)-3-(N-isobutyl-4-piperidyl)imino-2-(2-methyl-3-pyridyl)amino-3,5-dihydrophenazine:

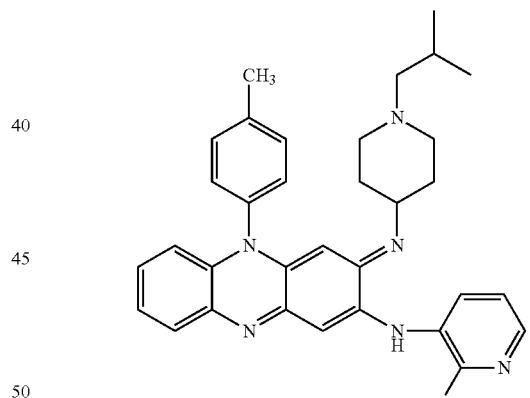

$^1$H NMR (300 MHz, CDCl$_3$) δ: 0.79 (6H, d, J=6.2 Hz, (CH$_3$)$_2$—CH—), 1.62 (4H, m, —CH$_2$—CH—CH$_2$—), 1.75 (1H, m, CH$_2$—CH—CH$_2$—), 1.92-2.09 (4H, m, —CH$_2$—N—CH$_2$—), 2.57 (6H, s, —CH$_3$, py-CH$_3$), 2.71 (2H, q, —CH$_2$—CH—), 3.15 (1H, m, (CH$_3$)$_2$—CH—), 5.25 (1H, s, 4-H), 6.54 (1H, d, J=7.8 Hz, 6-H), 6.65 (1H, s, 1-H), 7.08-7.18 (3H, m, 7-H, 8-H, 9-H), 7.21 (2H, d, J=8.1 Hz, 2"-H, 6"-H), 7.51 (2H, d, J=8.1 Hz, 3"-H, 5"-H), 7.68 (1H, d, J=8.4 Hz, 4'-H), 7.86 (1H, d, J=7.8 Hz, 5'-H), 8.25 (1H, d, J=3.6 Hz, 6'-H). $^{13}$C NMR (100 MHz, CDCl$_3$) δ: 21.01, 21.38, 25.69, 32.76, 52.20, 55.15, 67.25, 89.08, 98.89, 114.28, 121.63, 122.71, 127.51, 128.08, 128.36, 131.76, 134.89, 135.19, 135.66, 139.74, 143.79, 151.04, 151.77. HRMS (ESI-TOF$^+$): m/z calcd for C$_{34}$H$_{39}$N$_6$: 531.3357; found: 531.3359.

TBI-326, 5-(4-Methylphenyl)-3-(N-methyl-4-piperidyl)imino-2-(2-methyl-3-pyridyl)amino-3,5-dihydrophenazine:

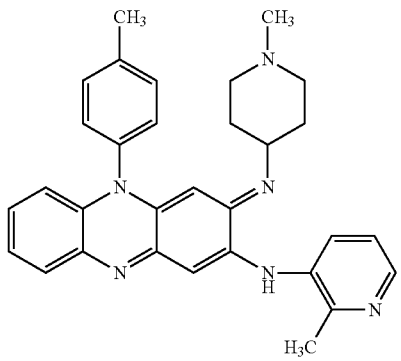 [SMILES: Cc1ccc(-n2c3c/c(=N\C4CCN(C)CC4)c(Nc4cccnc4C)cc-3nc3ccccc32)cc1]

$^1$H NMR (300 MHz, CDCl$_3$) δ: 1.60-1.78 (4H, m, —CH$_2$—CH—CH$_2$—), 2.05-2.15 (2H, m, —CH$_2$—CH$_2$—), 2.29 (3H, s, —N—CH$_3$), 2.53 (6H, s, —CH$_3$, py-CH$_3$), 2.70-2.80 (2H, m, —CH$_3$—CH$_2$—), 3.19 (1H, m, —CH$_2$—CH—CH$_2$—), 5.28 (1H, s, 4-H), 6.52 (1H, d, J=7.2 Hz, 6-H), 6.68 (1H, s, 1-H), 7.09-7.15 (3H, m, 7-H, 8-H, 9-H), 7.20 (2H, d, J=8.4 Hz, 2"-H, 6"-H), 7.52 (2H, d, J=8.4 Hz, 3"-H, 5"-H), 7.70 (1H, d, J=6.9 Hz, 4'-H), 7.85 (1H, d, J=8.1 Hz, 5'-H), 8.28 (1H, d, J=3.9 Hz, 6'-H). $^{13}$C NMR (100 MHz, CDCl$_3$) δ: 20.98, 21.40, 32.43, 46.36, 53.54, 88.98, 98.96, 114.38, 121.68, 122.88, 127.67, 128.28, 131.80, 134.81, 135.26, 139.86, 143.77, 151.20. HRMS (ESI-TOF$^+$): m/z [M+H]$^+$ calcd for C$_{31}$H$_{33}$N$_6$: 489.2862; found: 489.2860.

TBI-327, 5-(4-Methylphenyl)-3-(1-methylethyl)imino-2-(5-methyl-3-pyridyl)amino-3,5-dihydrophenazine:

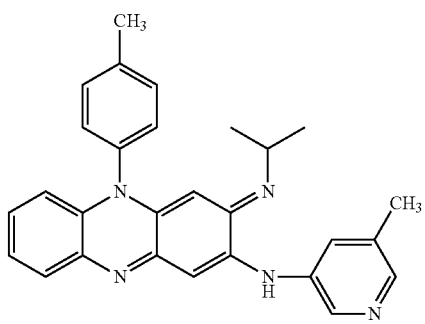 [SMILES: Cc1ccc(-n2c3c/c(=N\C(C)C)c(Nc4cncc(C)c4)cc-3nc3ccccc32)cc1]

$^1$H NMR (300 MHz, CDCl$_3$) δ: 1.09 (6H, d, J=6.0 Hz, (CH$_3$)$_2$—CH—), 2.37 (3H, s, —CH$_3$), 2.52 (3H, s, py-CH$_3$), 3.34 (1H, m, (CH$_3$)$_2$—CH—), 5.33 (1H, s, 4-H), 6.51 (1H, d, 18.4 Hz, 6-H), 6.83 (1H, s, 1-H), 7.08-7.17 (2H, m, 7-H, 8-H), 7.20 (2H, d, J=7.5 Hz, 2"-H, 6"-H), 7.49 (2H, d, J=7.5 Hz, 3"-H, 5"-H), 7.59 (1H, s, 4'-H), 7.69 (1H, d, J=7.5 Hz, 9-H), 8.18 (1H, s, 6'-H), 8.39 (1H, s, 2'-H). $^{13}$C NMR (100 MHz, CDCl$_3$) δ: 18.46, 21.43, 23.52, 49.23, 89.04, 99.33, 114.26, 122.68, 127.53, 128.05, 128.26, 128.40, 131.82, 133.44, 134.88, 135.15, 135.65, 136.60, 139.72, 141.08, 143.75, 144.78, 150.61, 151.04. HRMS (ESI-TOF$^+$): m/z [M+H]$^+$ calcd for C$_{28}$H$_{28}$N$_5$: 434.2331; found: 434.2330.

TBI-328, 5-(4-Methylphenyl)-3-(4-tetrahydropyranyl)imino-2-(5-methyl-3-pyridyl)amino-3,5-dihydrophenazine:

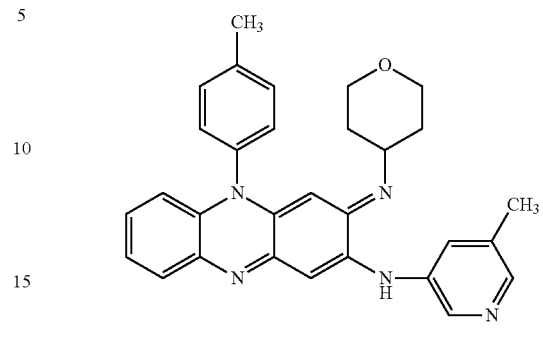

$^1$H NMR (300 MHz, CDCl$_3$) δ: 1.57-1.67 (4H, m, —CH$_2$—CH—CH$_2$—), 2.38 (3H, s, —CH$_3$), 2.53 (3H, s, py-CH$_3$), 3.32-3.43 (3H, m, —CH$_2$—CH—CH$_2$—), 3.93-4.02 (2H, m, —CH—CH$_2$—CH$_2$—), 5.24 (1H, s, 4-H), 6.58 (1H, d, J=7.5 Hz, 6-H), 6.87 (1H, s, 1-H), 7.11-7.18 (2H, m, 7-H, 8-H), 7.21 (2H, d, J=7.5 Hz, 2"-H, 6"-H), 7.42 (2H, d, J=7.5 Hz, 3"-H, 5"-H), 7.58 (1H, s, 4'-H), 7.72 (1H, d, J=7.5 Hz, 9-H), 8.18 (1H, s, 6'-H), 8.41 (1H, s, 2'-H). $^{13}$C NMR (100 MHz, CDCl$_3$) δ: 18.44, 21.37, 33.36, 54.24, 66.16, 88.94, 99.49, 114.35, 122.87, 127.76, 128.18, 128.32, 131.77, 133.53, 134.82, 135.25, 135.67, 136.38, 139.86, 141.06, 143.3, 144.95, 150.77, 151.35. HRMS (ESI-TOF$^+$): m/z [M+H]$^+$ calcd for C$_{30}$H$_{30}$N$_5$O: 476.2450; found: 476.2453.

TBI-329, 5-(4-Methylphenyl)-3-cyclohexylimino-2-(5-methyl-3-pyridyl)amino-3,5-dihydrophenazine:

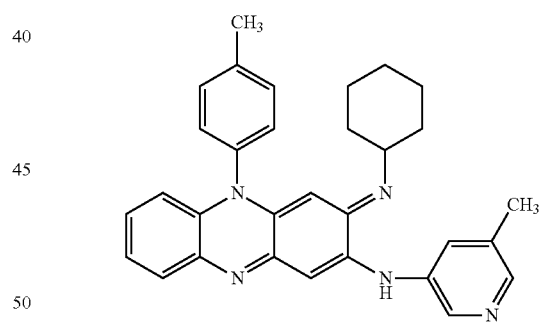

$^1$H NMR (300 MHz, CDCl$_3$) δ: 1.38-1.78 (10H, m, —CH$_2$—CH$_2$—CH$_2$—CH$_2$—CH$_2$—), 2.38 (3H, s, —CH$_3$), 2.53 (3H, s, py-CH$_3$), 3.06 (1H, m, —CH$_2$—CH—CH$_2$—), 5.28 (1H, s, 4-H), 6.54 (1H, d, J=8.1 Hz, 6-H), 6.83 (1H, s, 1-H), 7.08-7.18 (2H, m, 7-H, 8-H), 7.20 (2H, d, 17.2 Hz, 2"-H, 6"-H), 7.31 (2H, d, J=7.2 Hz, 3"-H, 5"-H), 7.59 (1H, s, 4'-H), 7.69 (1H, d, J=7.5 Hz, 9-H), 8.15 (1H, s, 6'-H), 8.38 (1H, s, 2'-H). $^{13}$C NMR (100 MHz, CDCl$_3$) δ: 18.46, 21.37, 24.64, 25.87, 33.57, 57.74, 89.34, 99.29, 114.23, 122.65, 127.51, 128.04, 128.19, 128.39, 131.71, 133.45, 134.90, 135.09, 135.68, 136.65, 139.68, 141.03, 143.77, 144.71, 150.75, 151.09. HRMS (ESI-TOF$^+$): m/z [M+H]$^+$ calcd for C$_{31}$H$_{32}$N$_5$: 474.2811; found: 474.2810.

TBI-330, 5-(4-Methylphenyl)-3-(4-methoxycyclohexyl)imino-2-(5-methyl-3-pyridyl)amino-3,5-dihydrophenazine:

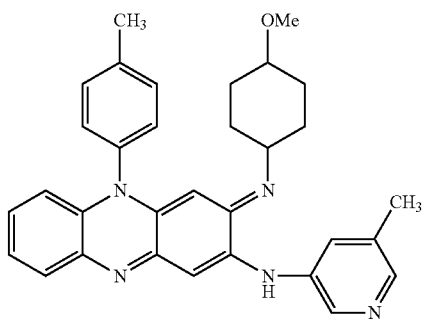 [SMILES: COC1CCC(/N=c2\cc3n(-c4ccc(C)cc4)c4ccccc4nc-3cc2Nc2cncc(C)c2)CC1]

$^1$H NMR (300 MHz, CDCl$_3$) δ: 1.10-1.46 (4H, m, —CH$_2$—CH—CH$_2$—), 1.68 (2H, m, —CH$_2$—CH$_2$—), 2.08 (2H, m, —CH$_2$—CH$_2$—), 2.38 (3H, s, —CH$_3$), 2.54 (3H, s, py-CH3), 3.05 (1H, m, —CH$_2$—CH—CH$_2$—), 3.18 (1H, m, —CH$_2$—CH—CH$_2$—), 3.36 (3H, s, —OCH$_3$), 5.29 (1H, s, 4-H), 6.53 (1H, d, J=7.8 Hz, 6-H), 6.85 (1H, s, 1-H), 7.11-7.15 (2H, m, 7-H, 8-H), 7.19 (2H, d, 18.1 Hz, 2"-H, 6"-H), 7.50 (2H, d, J=8.1 Hz, 3"-H, 5"-H), 7.59 (1H, s, 4'-H), 7.69 (1H, d, J=7.5 Hz, 9-H), 8.18 (1H, s, 6'-H), 8.28 (1H, s, 2'-H). $^{13}$C NMR (100 MHz, CDCl$_3$) δ: 18.46, 21.44, 29.95, 31.11, 55.86, 57.20, 78.59, 89.08, 99.43, 114.32, 122.74, 127.67, 128.10, 128.29, 131.75, 133.48, 135.15, 135.65, 136.48, 139.90, 141.03, 143.62, 144.81, 150.93, 151.34. HRMS (ESI-TOF$^+$): m/z [M+H]$^+$ calcd for C$_{32}$H$_{34}$N$_5$O: 504.2765; found: 504.2767.

TBI-331, 5-(4-ethylphenyl)-3-cyclohexylimino-2-(2-methoxy-3-pyridyl)amino-3,5-dihydrophenazine:

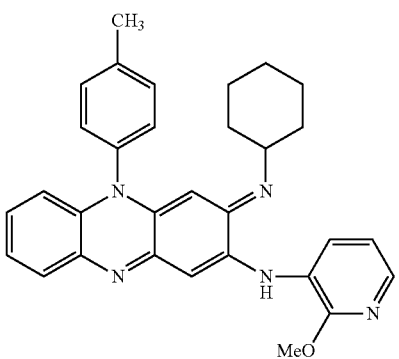

$^1$H NMR (300 MHz, CDCl$_3$) δ: 1.18-1.78 (10H, m, —CH$_2$—CH$_2$—CH$_2$—CH$_2$—CH$_2$—), 2.54 (3H, s, —CH$_3$), 3.12 (1H, m, —CH$_2$—CH—CH$_2$—), 4.03 (3H, s, —OCH$_3$), 5.28 (1H, s, 4-H), 6.52 (1H, d, J=8.4 Hz, 6-H), 6.90 (1H, m, 9-H), 6.94 (1H, s, 1-H), 7.08-7.15 (2H, m, 7-H, 8-H), 7.20 (2H, d, J=7.8 Hz, 2"-H, 6"-H), 7.48 (2H, d, J=7.8 Hz, 3"-H, 5"-H), 7.68 (1H, d, J=4.5 Hz, 4'-H), 7.78 (1H, d, J=4.5 Hz, 5'-H), 7.85 (1H, d, J=7.5 Hz, 6'-H). $^{13}$C NMR (100 MHz, CDCl$_3$) δ: 21.36, 24.26, 26.01, 33.47, 53.67, 89.45, 100.14, 114.15, 116.81, 122.52, 124.42, 125.09, 127.48, 128.02, 128.44, 131.71, 132.05, 134.92, 135.02, 135.64, 138.47, 139.60, 142.83, 150.84, 151.36, 155.35. HRMS (ESI-TOF$^+$): m/z [M+H]$^+$ calcd for C$_{31}$H$_{32}$N$_5$O: 490.4489; found: 490.4486.

TBI-332, 5-(4-Methylphenyl)-3-(4-hydroxycyclohexyl)imino-2-(2-methoxy-3-pyridyl)amino-3,5-dihydrophenazine:

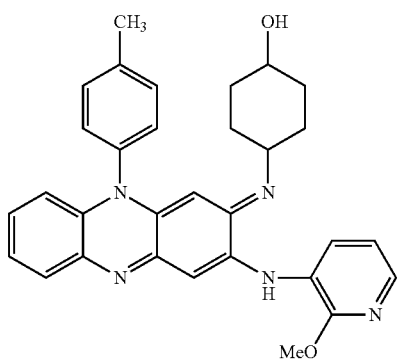

$^1$H NMR (300 MHz, CDCl$_3$) δ: 1.14-1.31 (4H, m, —CH$_2$—CH—CH$_2$—), 1.45-1.73 (4H, m, —CH$_2$—CH—CH$_2$—), 2.55 (3H, s, —CH$_3$), 3.10 (1H, m, —CH$_2$—CH—CH$_2$—), 3.72 (1H, m, —CH$_2$—CH—CH$_2$—), 4.04 (3H, s, —OCH$_3$), 5.27 (1H, s, 4-H), 6.55 (1H, d, J=6.9 Hz, 6-H), 6.95 (1H, m, 9-H), 6.94 (1H, s, 1-H), 7.03-7.15 (2H, m, 7-H, 8-H), 7.20 (2H, d, J=7.8 Hz, 2"-H, 6"-H), 7.48 (2H, d, J=7.8 Hz, 3"-H, 5"-H), 7.70 (1H, d, J=6.9 Hz, 4'-H), 7.80 (1H, d, J=4.2 Hz, 5'-H), 7.85 (1H, d, J=2.7 Hz, 6'-H). $^{13}$C NMR (100 MHz, CDCl$_3$) δ: 21.43, 30.85, 33.33, 53.59, 56.69, 69.88, 89.21, 100.22, 114.26, 122.66, 124.62, 124.94, 127.63, 128.10, 128.35, 131.75, 134.81, 135.10, 135.66, 136.53, 138.62, 139.81, 142.72, 151.60. HRMS (ESI-TOF$^+$): m/z [M+H]$^+$ calcd for C$_{31}$H$_{32}$N$_5$O$_2$: 506.2957; found: 506.2958.

TBI-333, 5-(4-Methylphenyl)-3-cyclohexylimino-2-(3-pyridyl)amino-3,5-dihydrophenazine:

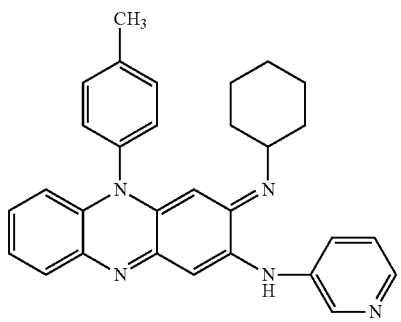

$^1$H NMR (300 MHz, CDCl$_3$) δ: 1.10-1.60 (10H, m, —CH$_2$—CH$_2$—CH$_2$—CH$_2$—CH$_2$—), 2.54 (3H, s, —CH$_3$), 3.07 (1H, m, —CH$_2$—CH—CH$_2$—), 5.29 (1H, s, 4-H), 6.53 (1H, d, J=8.1 Hz, 6-H), 6.91 (1H, s, 1-H), 7.10-7.14 (2H, m, 7-H, 8-H), 7.18 (2H, d, J=8.4 Hz, 2"-H, 6"-H), 7.30 (1H, m, 9-H), 7.51 (2H, d, J=8.4 Hz, 3"-H, 5"-H), 7.68 (1H, d, J=4.8 Hz, 4'-H), 7.79 (1H, d, J=7.8 Hz, 5'-H), 8.32 (1H, d, J=4.8 Hz, 6'-H), 8.57 (1H, d, J=2.4 Hz, 2'-H). $^{13}$C NMR (100 MHz, CDCl$_3$) δ: 21.37, 24.64, 25.87, 33.57, 57.74, 89.32, 99.37, 114.25, 122.68, 123.60, 127.57, 127.72, 128.13, 128.38, 131.72, 131.89, 134.89, 135.12, 135.71, 137.09, 143.69, 143.86, 144.05, 150.77, 151.00. HRMS (ESI-TOF$^+$): m/z [M+H]$^+$ calcd for C$_{30}$H$_{30}$N$_5$: 460.2753; found: 460.2752.

TBI-334, 5-(4-Methylphenyl)-3-(4-hydroxycyclohexyl)imino-2-(6-methyl-3-pyridyl)amino-3,5-dihydrophenazine:

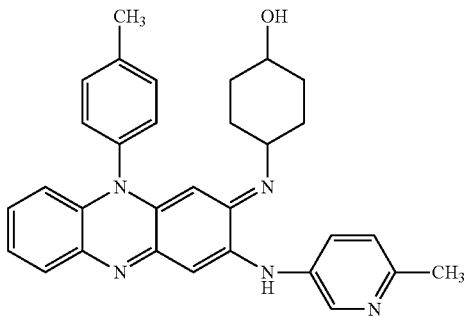 [SMILES: Cc1ccc(-n2c3c/c(=N\C4CCC(O)CC4)c(Nc4ccc(C)nc4)cc-3nc3ccccc32)cc1]

$^1$H NMR (300 MHz, CDCl$_3$) δ: 1.17-1.51 (4H, m, —CH$_2$—CH—CH$_2$—), 1.67-2.04 (4H, m, —CH$_2$—CH—CH$_2$—), 2.54 (6H, s, —CH$_3$, -py-CH$_3$), 3.06 (1H, m, —CH$_2$—CH—CH$_2$—), 3.56 (1H, m, —CH$_2$—CH—CH$_2$—), 5.28 (1H, s, 4-H), 6.53 (1H, d, J=8.7 Hz, 6-H), 6.73 (1H, s, 1-H), 7.10-7.18 (3H, m, 7-H, 8-H, 9-H), 7.23 (2H, d, J=8.1 Hz, 2''-H, 6''-H), 7.50 (2H, d, J=8.1 Hz, 3''-H, 5''-H), 7.67 (1H, d, J=8.1 Hz, 4'-H), 7.61 (1H, d, J=8.1 Hz, 5'-H), 8.45 (1H, s, 2'-H). $^{13}$C NMR (100 MHz, CDCl$_3$) δ: 21.43, 23.78, 31.21, 33.69, 57.05, 70.04, 89.03, 98.90, 114.29, 122.29, 123.17, 127.54, 128.09, 128.33, 129.31, 131.74, 134.13, 135.12, 135.67, 139.83, 143.65, 144.27, 150.89, 151.46, 153.23. HRMS (ESI-TOF$^+$): m/z [M+H]$^+$ calcd for C$_{31}$H$_{32}$N$_5$O: 490.2673; found: 490.2672.

TBI-335, 5-(4-Methylphenyl)-3-(4-hydroxycyclohexyl)imino-2-(2-methyl-3-pyridyl)amino-3,5-dihydrophenazine:

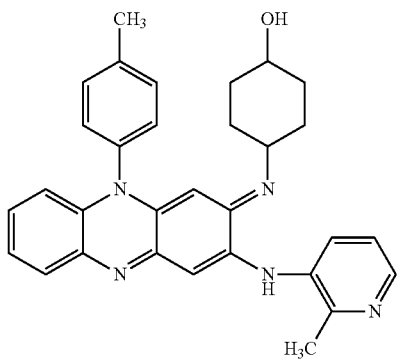

$^1$H NMR (300 MHz, CDCl$_3$) δ: 1.13-1.46 (4H, m, —CH$_2$—CH$_2$—), 1.49-2.04 (4H, m, —CH$_2$—CH$_2$—), 2.54 (6H, s, —CH$_3$, py-CH$_3$), 3.71 (1H, m, —CH$_2$—CH—CH$_2$—), 4.21 (1H, m, —CH$_2$—CH—CH$_2$—), 5.30 (1H, s, 4-H), 6.53 (1H, d, J=7.8 Hz, 6-H), 6.61 (1H, s, 1-H), 7.11-7.17 (3H, m, 7-H, 8-H, 9-H), 7.24 (2H, d, J=8.1 Hz, 2''-H, 6''-H), 7.50 (2H, d, J=8.1 Hz, 3''-H, 5''-H), 7.68 (1H, d, 7.2 Hz, 4'-H), 7.82 (1H, d, J=7.8 Hz, 5'-H), 8.26 (1H, d, J=4.2 Hz, 6'-H). $^{13}$C NMR (100 MHz, CDCl$_3$) δ: 20.90, 21.43, 31.05, 33.47, 56.70, 69.84, 89.01, 98.99, 114.35, 121.69, 122.79, 127.62, 127.62, 128.11, 128.93, 131.77, 134.80, 135.18, 139.90, 143.99, 151.39. HRMS (ESI-TOF$^+$): m/z [M+H]$^+$ calcd for C$_{31}$H$_{32}$N$_5$O: 490.2842; found: 490.2845.

TBI-336, 5-(3,4-Dichlorophenyl)-3-(1-methylethyl)imino-2-(3-pyridyl)amino-3,5-dihydrophenazine:

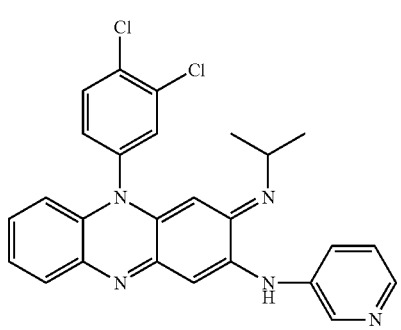

$^1$H NMR (300 MHz, CDCl$_3$) δ: 1.13 (6H, d, J=7.9 Hz, —CH—(CH$_3$)$_2$), 3.50 (1H, m, —CH—(CH$_3$)$_2$), 5.30 (1H, s, 4-H), 6.45 (1H, d, J=7.5 Hz, 6-H), 6.82 (1H, s, 1-H), 7.17-7.24 (2H, m, 7-H, 8-H), 7.29-7.32 (2H, m, 5''-H, 6''-H), 7.51 (1H, s, 2''-H), 7.70 (1H, d, J=7.5 Hz, 4'-H), 7.72 (1H, d, J=7.8 Hz, 5'-H), 7.82 (1H, d, J=7.8 Hz, 9-H), 8.34 (1H, d, J=4.5 Hz, 6'-H), 8.59 (1H, s, 2'-H). $^{13}$C NMR (100 MHz, CDCl$_3$) δ: 23.61, 49.49, 89.18, 99.46, 113.66, 123.23, 123.64, 127.83, 128.03, 128.44, 128.56, 131.21, 133.12, 134.38, 134.58, 135.52, 136.76, 143.69, 144.01, 144.37, 150.16, 150.94. HRMS (ESI-TOF$^+$): m/z [M+H]$^+$ calcd for C$_{26}$H$_{22}$Cl$_2$N$_5$: 475.1295; found: 475.1296.

TBI-337, 5-(4-Methylphenyl)-3-(4-hydroxycyclohexyl)imino-2-(5-methyl-3-pyridyl)amino-3,5-dihydrophenazine:

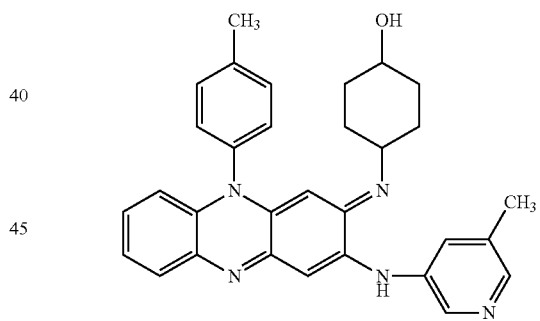

$^1$H NMR (300 MHz, CDCl$_3$) δ: 1.17-1.50 (4H, m, —CH$_2$—CH—CH$_2$—), 1.66-1.70 (2H, m, —CH$_2$—CH—CH$_2$—), 1.95-2.04 (2H, m, —CH$_2$—CH—CH$_2$—), 2.27 (3H, s, —CH$_3$), 2.54 (3H, s, py-CH$_3$), 3.06 (1H, m, —CH$_2$—CH—CH$_2$—), 3.70 (1H, m, —CH$_2$—CH—CH$_2$—), 5.29 (1H, s, 4-H), 6.53 (1H, d, J=7.5 Hz, 6-H), 6.84 (1H, s, 1-H), 7.13-7.18 (2H, m, 7-H, 8-H), 7.19 (2H, d, J=7.8 Hz, 2''-H, 6''-H), 7.51 (2H, d, J=7.8 Hz, 3''-H, 5''-H), 7.58 (1H, s, 4'-H), 7.70 (1H, d, J=7.8 Hz, 9-H), 8.16 (1H, s, 6'-H), 8.38 (1H, s, 2'-H). $^{13}$C NMR (100 MHz, CDCl$_3$) 18.45, 21.44, 31.18, 33.65, 57.01, 70.02, 89.07, 99.43, 114.32, 122.77, 127.68, 128.31, 131.77, 133.51, 134.80, 135.16, 135.66, 136.47, 139.87, 141.02, 143.61, 144.82, 150.93, 151.41. HRMS (ESI-TOF$^+$): m/z [M+H]$^+$ calcd for C$_{31}$H$_{32}$N$_5$O: 490.2843; found: 490.2845.

TBI-338, 5-(4-Methylphenyl)-3-(4-hydroxycyclohexyl)imino-2-(3-pyridyl)amino-3,5-dihydrophenazine:

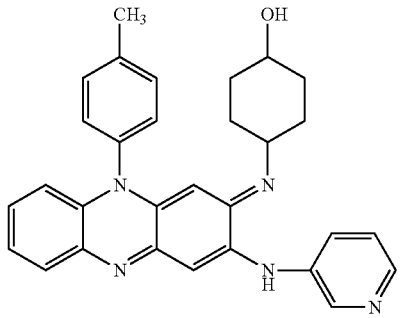

$^1$H NMR (300 MHz, CDCl$_3$) δ: 1.21-1.50 (4H, m, —CH$_2$—CH—CH$_2$—), 1.67-1.99 (4H, m, —CH$_2$—CH—CH$_2$—), 2.54 (3H, s, —CH$_3$), 3.06 (1H, m, —CH$_2$—CH—CH$_2$—), 3.69 (1H, m, —CH$_2$—CH—CH$_2$—), 5.29 (1H, s, 4-H), 6.53 (1H, d, J=7.5 Hz, 6-H), 6.85 (1H, s, 1-H), 7.15-7.25 (2H, m, 7-H, 8-H), 7.27 (2H, d, J=6.9 Hz, 2"-H, 6"-H), 7.32 (1H, m, 9-H), 7.51 (2H, d, J=6.9 Hz, 3"-H, 5"-H), 7.69 (1H, d, J=7.2 Hz, 4'-H), 7.78 (1H, d, J=7.8 Hz, 5'-H), 8.31 (1H, s, 6'-H), 8.57 (1H, s, 2'-H). $^{13}$C NMR (100 MHz, CDCl$_3$) δ: 21.43, 33.65, 57.00, 69.98, 89.06, 99.54, 114.33, 122.80, 123.64, 127.77, 128.28, 131.76, 134.75, 135.17, 135.66, 136.86, 139.89, 143.48, 143.82, 144.12, 150.80, 151.40. HRMS (ESI-TOF$^+$): m/z [M+H]$^+$ calcd for C$_{30}$H$_{30}$N$_5$O: 476.2871; found: 476.2870.

TBI-339, 5-(4-Methylphenyl)-3-cyclopropylimino-2-(2-methoxy-3-pyridyl)amino-3,5-dihydrophenazine:

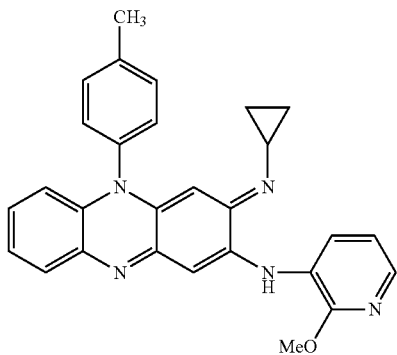

$^1$H NMR (300 MHz, CDCl$_3$) δ: 0.80-0.86 (4H, —CH$_2$—CH$_2$—), 2.55 (3H, s, —CH$_3$), 2.73 (1H, m, —CH$_2$—CH—CH$_2$—), 4.01 (3H, s, —OCH$_3$), 5.59 (1H, s, 4-H), 6.46 (1H, d, J=7.8 Hz, 6-H), 6.94 (1H, m, 9-H), 7.12 (1H, s, 1-H), 7.16-7.21 (2H, m, 7-H, 8-H), 7.20 (2H, d, J=7.5 Hz, 2"-H, 6"-H), 7.49 (2H, d, J=7.5 Hz, 3"-H, 5"-H), 7.67 (1H, d, J=7.2 Hz, 4'-H), 7.80 (1H, d, J=7.2 Hz, 5'-H), 7.85 (1H, d, J=7.2 Hz, 6'-H). $^{13}$C NMR (100 MHz, CDCl$_3$) δ: 9.91, 21.42, 32.77, 53.67, 89.26, 100.11, 114.16, 116.81, 122.55, 124.93, 127.50, 127.97, 128.52, 131.86, 132.23, 134.91, 135.75, 138.69, 139.60, 142.62, 151.49, 152.90, 155.40. HRMS (ESI-TOF$^+$): m/z [M+H]$^+$ calcd for C$_{28}$H$_{26}$N$_5$O: 448.3371; found: 448.3370.

TBI-340, 5-(4-Methylphenyl)-3-cyclopropylimino-2-(6-methyl-3-pyridyl)amino-3,5-dihydrophenazine:

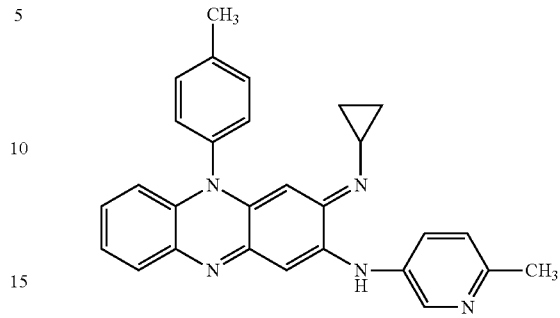

$^1$H NMR (300 MHz, CDCl$_3$) δ: 0.79-0.86 (4H, m, —CH$_2$—CH$_2$—), 2.54 (6H, s, —CH$_3$, -py-CH$_3$), 3.73 (1H, m, —CH$_2$—CH—CH$_2$—), 5.60 (1H, s, 4-H), 6.47 (1H, d, J=7.5 Hz, 6-H), 6.69 (1H, s, 1-H), 7.07-7.16 (3H, m, 7-H, 8-H, 9-H), 7.22 (2H, d, 7.8 Hz, 2"-H, 6"-H), 7.50 (2H, d, J=7.8 Hz, 3"-H, 5"-H), 7.65 (1H, d, J=5.1 Hz, 4'-H), 7.67 (1H, d, J=5.1 Hz, 5'-H), 8.41 (1H, s, 2'-H). $^{13}$C NMR (100 MHz, CDCl$_3$) δ: 9.76, 21.42, 23.81, 32.72, 89.40, 98.86, 114.22, 122.63, 123.16, 127.6, 128.01, 128.48, 129.53, 131.86, 132.05, 134.00, 134.95, 135.77, 139.65, 143.80, 144.14, 151.22. HRMS (ESI-TOF$^+$): m/z [M+H]$^+$ calcd for C$_{78}$H$_{26}$N$_5$: 432.2232; found: 432.2235.

TBI-341, 5-(4-Methylphenyl)-3-cyclopropylimino-2-(2-methyl-3-pyridyl)amino-3,5-dihydrophenazine:

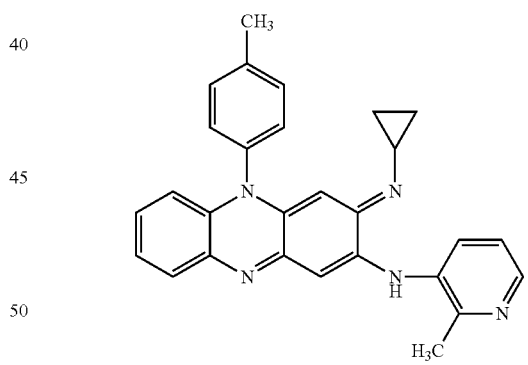

$^1$H NMR (300 MHz, CDCl$_3$) δ: 0.78-0.89 (4H, m, —CH$_2$—CH$_2$—), 2.54 (6H, s, —CH$_3$, py-CH$_3$), 2.77 (1H, m, —CH$_2$—CH—CH$_2$—), 5.61 (1H, s, 4-H), 6.48 (1H, d, J=7.8 Hz, 6-H), 6.53 (1H, s, 1-H), 7.11-7.19 (3H, m, 7-H, 8-H, 9-H), 7.25 (2H, d, J=8.1 Hz, 2"-H, 6"-H), 7.51 (2H, d, J=8.1 Hz, 3"-H, 5"-H), 7.66 (1H, d, J=7.2 Hz, 4'-H), 7.79 (1H, d, J=8.1 Hz, 5'-H), 8.29 (1H, d, J=4.2 Hz, 6'-H). $^{13}$C NMR (100 MHz, CDCl$_3$) δ: 9.97, 20.90, 21.43, 32.69, 89.32, 98.89, 114.21, 121.67, 122.62, 127.46, 127.97, 128.48, 129.55, 131.87, 132.08, 134.63, 134.98, 135.72, 139.65, 143.98, 144.30, 151.23, 152.41. HRMS (ESI-TOF$^+$): m/z [M+H]$^+$ calcd for C$_{28}$H$_{26}$N$_5$: 432.2641; found: 432.2639.

TBI-342, 5-(4-Methylphenyl)-3-cyclopropylimino-2-(5-methyl-3-pyridyl)amino-3,5-dihydrophenazine:

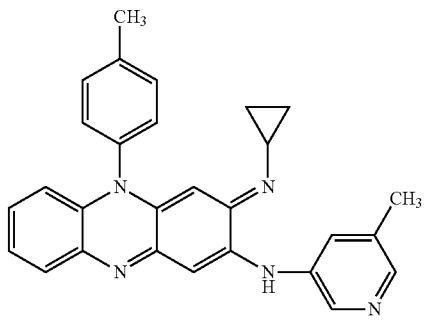 [SMILES: Cc1ccc(-n2c3c/c(=N\C4CC4)c(Nc4cncc(C)c4)cc-3nc3ccccc32)cc1]

$^1$H NMR (300 MHz, CDCl$_3$) δ: 0.78-0.86 (4H, m, —CH$_2$—CH$_2$—), 2.27 (3H, s, —CH$_3$), 2.53 (3H, s, py-CH$_3$), 2.72 (1H, m, —CH$_2$—CH—CH$_2$—), 5.59 (1H, s, 4-H), 6.47 (1H, d, J=7.2 Hz, 6-H), 6.79 (1H, s, 1-H), 7.10-7.17 (2H, m, 7-H, 8-H), 7.22 (2H, d, J=7.5 Hz, 2"-H, 6"-H), 7.49 (2H, d, J=7.5 Hz, 3"-H, 5"-H), 7.56 (1H, s, 4'-H), 7.67 (1H, d, J=7.8 Hz, 9-H), 8.16 (1H, s, 6'-H), 8.35 (1H, s, 2'-H). $^{13}$C NMR (100 MHz, CDCl$_3$) 9.82, 18.45, 21.43, 32.74, 89.42, 99.34, 114.23, 122, 65, 127.58, 129.01, 128.47, 131.88, 133.48, 134.97, 135.74, 136.34, 139.67, 141.15, 143.48, 144.92, 151.27, 152.68. HRMS (ESI-TOF$^+$): m/z [M+H]$^+$ calcd for C$_{28}$H$_{26}$N$_5$: 432.2639; found: 432.2637.

TBI-343, 5-(3,4-Dichlorophenyl)-3-cyclopropylimino-2-(3-pyridyl)amino-3,5-dihydrophenazine:

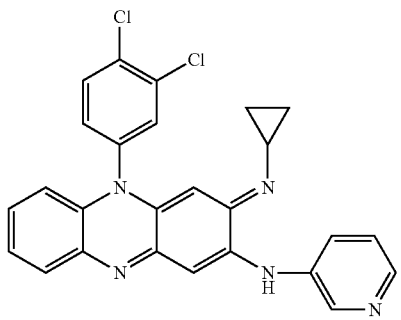

$^1$H NMR (300 MHz, CDCl$_3$) δ: 0.85-0.96 (4H, m, —CH$_2$—CH$_2$—), 2.77 (1H, m, —CH$_2$—CH—CH$_2$—), 5.55 (1H, s, 4-H), 6.42 (1H, d, J=7.5 Hz, 6-H), 6.76 (1H, s, 1-H), 7.13-7.20 (2H, m, 7-H, 8-H), 7.28-7.31 (2H, m, 5"-H, 6"-H), 7.51 (1H, s, 2"-H), 7.65 (1H, d, J=7.8 Hz, 4'-H), 7.75 (1H, d, J=7.8 Hz, 5'-H), 7.81 (1H, d, J=8.4 Hz, 9-H), 8.33 (1H, d, J=4.5 Hz, 6'-H), 8.54 (1H, s, 2'-H). $^{13}$C NMR (100 MHz, CDCl$_3$) δ: 10.23, 33.10, 89.59, 99.42, 113.63, 123.19, 123.65, 127.82, 128.21, 128.37, 128.70, 131.33, 133.19, 134.39, 135.39, 135.63, 136.56, 136.77, 143.48, 144.10, 144.50, 151.76, 152.01. HRMS (ESI-TOF$^+$): m/z [M+H]$^+$ calcd for C$_{26}$H$_{20}$Cl$_2$N$_5$: 473.1143; found: 473.1147.

TBI-344, 5-(4-Methylphenyl)-3-cyclobutylimino-2-(2-methoxy-3-pyridyl)amino-3,5-dihydrophenazine:

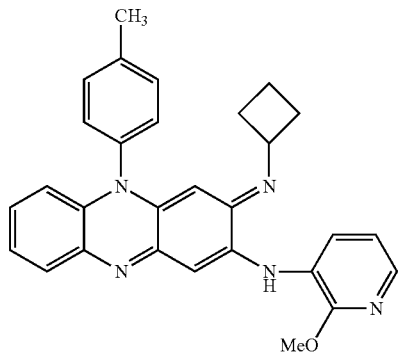

$^1$H NMR (300 MHz, CDCl$_3$) δ: 1.65-1.80 (2H, m, —CH$_2$—CH$_2$—CH$_2$—), 2.01-2.22 (4H, m, —CH$_2$—CH$_2$—CH$_2$—), 2.55 (3H, s, —CH$_3$), 3.85 (1H, m, —CH$_2$—CH—CH$_2$—), 4.04 (3H, s, —OCH$_3$), 5.15 (1H, s, 4-H), 6.54 (1H, d, J=7.5 Hz, 6-H), 6.91 (1H, m, 9-H), 6.93 (1H, s, 1-H), 7.14-7.16 (2H, m, 7-H, 8-H), 7.20 (2H, d, J=8.1 Hz, 2"-H, 6"-H), 7.51 (2H, d, J=8.1 Hz, 3"-H, 5"-H), 7.72 (1H, d, J=7.2 Hz, 4'-H), 7.82 (1H, d, J=7.2 Hz, 5'-H), 7.85 (1H, s, 6'-H). $^{13}$C NMR (100 MHz, CDCl$_3$) δ: 16.01, 21.43, 31.78, 53.70, 54.57, 90.69, 100.52, 114.40, 116.84, 122.93, 124.76, 125.26, 127.77, 128.19, 128.38, 131.76, 134.69, 134.77, 135.87, 138.99, 139.82, 142.70, 150.91, 151.68, 155.57. HRMS (ESI-TOF$^+$): m/z [M+H]$^+$ calcd for C$_{29}$H$_{28}$N$_5$O: 462.4060; found: 462.4058.

TBI-345, 5-(4-Methylphenyl)-3-cyclobutylimino-2-(3-pyridyl)amino-3,5-dihydrophenazine:

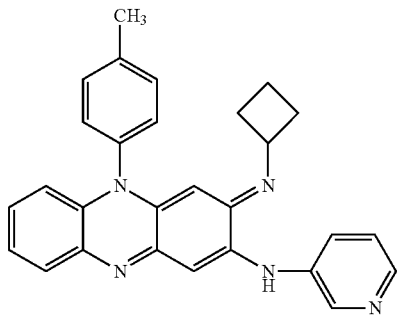

$^1$H NMR (300 MHz, CDCl$_3$) δ: 1.65-2.12 (6H, m, —CH$_2$—CH$_2$—CH$_2$—), 2.56 (3H, s, —CH$_3$), 3.87 (1H, m, —CH$_2$—CH—CH$_2$—), 5.17 (1H, s, 4-H), 6.55 (1H, d, J=7.2 Hz, 6-H), 6.88 (1H, s, 1-H), 7.11-7.18 (2H, m, 7-H, 8-H), 7.21 (2H, d, J=8.1 Hz, 2"-H, 6"-H), 7.31 (1H, m, 9-H), 7.52 (2H, d, J=8.1 Hz, 3"-H, 5"-H), 7.71 (1H, d, J=6.9 Hz, 4'-H), 7.79 (1H, d, J=7.8 Hz, 5'-H), 8.32 (1H, d, J=6.9 Hz, 6'-H), 8.61 (1H, s, 2'-H). $^{13}$C NMR (100 MHz, CDCl$_3$) δ: 16.01, 21.34, 31.72, 54.51, 90.52, 99.76, 114.50, 123.07, 123.67, 127.96, 128.31, 131.79, 134.79, 135.89, 136.83, 139.93, 143.98, 144.30, 151.43. HRMS (ESI-TOF$^+$): m/z [M+H]$^+$ calcd for C$_{28}$H$_{26}$N$_5$: 432.2232; found: 432.2235.

TBI-346, 5-(4-Methylphenyl)-3-cyclobutylimino-2-(6-methyl-3-pyridyl)amino-3,5-dihydrophenazine:

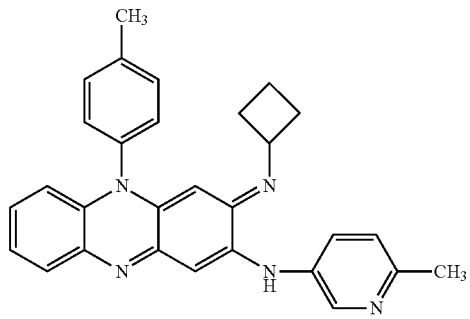 [SMILES: Cc1ccc(-n2c3c/c(=N\C4CCC4)c(Nc4ccc(C)nc4)cc-3nc3ccccc32)cc1]

$^1$H NMR (300 MHz, CDCl$_3$) δ: 1.65-1.79 (2H, m, —CH$_2$—CH$_2$—CH$_2$—), 2.00-2.18 (4H, m, —CH$_2$—CH$_2$—CH$_2$—), 2.56 (6H, s, —CH$_3$, -py-CH$_3$), 3.86 (1H, m, —CH$_2$—CH—CH$_2$—), 5.14 (1H, s, 4-H), 6.53 (1H, d, J=6.9 Hz, 6-H), 6.70 (1H, s, 1-H), 7.14-7.17 (3H, m, 7-H, 8-H, 9-H), 7.20 (2H, d, J=7.8 Hz, 2"-H, 6"-H), 7.51 (2H, d, J=7.8 Hz, 3"-H, 5"-H), 7.65 (1H, s, 4'-H), 7.79 (1H, d, s, 5'-H), 8.47 (1H, s, 2'-H). $^{13}$C NMR (100 MHz, CDCl$_3$) δ: 16.01, 21.42, 23.81, 31.889, 54.73, 90.51, 98.94, 114.36, 122.82, 123.188, 127.58, 128.13, 129.45, 131.75, 134.50, 134.71, 135.75, 139.76, 143.75, 144.24, 150.84, 151.46. HRMS (ESI-TOF$^+$): m/z [M+H]$^+$ calcd for C$_{29}$H$_{28}$N$_5$: 446.2436; found: 446.2435.

TBI-347, 5-(4-Methylphenyl)-3-cyclobutylimino-2-(2-methyl-3-pyridyl)amino-3,5-dihydrophenazine:

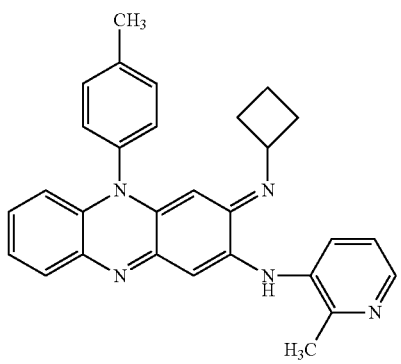

$^1$H NMR (300 MHz, CDCl$_3$) δ: 1.68-1.81 (2H, m, —CH$_2$—CH$_2$—CH$_2$—), 2.04-2.22 (4H, m, —CH$_2$—CH$_2$—CH$_2$—), 2.56 (6H, s, —CH$_3$, py-CH$_3$), 3.89 (1H, m, —CH$_2$—CH—CH$_2$—), 5.22 (1H, s, 4-H), 6.55 (1H, s, 1-H), 6.50 (1H, d, J=7.8 Hz, 6-H), 7.16-7.20 (3H, m, 7-H, 8-H, 9-H), 7.22 (2H, d, J=8.1 Hz, 2"-H, 6"-H), 7.53 (2H, d, J=8.1 Hz, 3"-H, 5"-H), 7.73 (1H, d, J=7.8 Hz, 4'-H), 7.88 (1H, d, J=7.8 Hz, 5'-H), 8.30 (1H, d, J=6.9 Hz, 6'-H). $^{13}$C NMR (100 MHz, CDCl$_3$) δ: 16.01, 20.99, 21.43, 24.03, 31.44, 53.98, 90.45, 99.57, 114.68, 121.77, 123.43, 128.00, 128.21, 128.43, 130.29, 131.79, 134.65, 134.79, 136.14, 137.36, 140.08, 143.97, 144.72, 150.15, 151.41, 152.96. HRMS (ESI-TOF$^+$): m/z [M+H]$^+$ calcd for C$_{29}$H$_{28}$N$_5$: 446.2588; found: 446.2587.

TBI-348, 5-(4-Methylphenyl)-3-cyclobutylimino-2-(5-methyl-3-pyridyl)amino-3,5-dihydrophenazine:

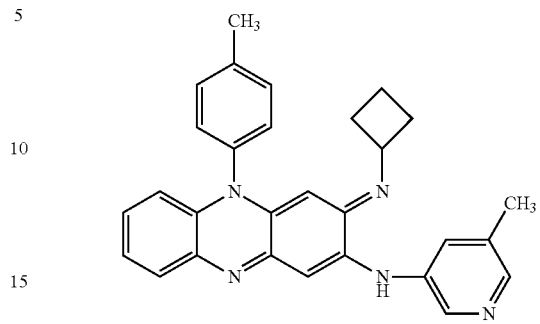

$^1$H NMR (300 MHz, CDCl$_3$) δ: 1.64-1.80 (2H, m, —CH$_2$—CH$_2$—CH$_2$—), 2.04-2.18 (4H, m, —CH$_2$—CH$_2$—CH$_2$—), 2.37 (3H, s, —CH$_3$), 2.56 (3H, s, py-CH$_3$), 3.87 (1H, m, —CH$_2$—CH—CH$_2$—), 5.22 (1H, s, 4-H), 6.62 (1H, d, J=8.1 Hz, 6-H), 6.93 (1H, s, 1-H), 7.16-7.19 (2H, m, 7-H, 8-H), 7.22 (2H, d, J=8.1 Hz, 2"-H, 6"-H), 7.52 (2H, d, J=8.1 Hz, 3"-H, 5"-H), 7.60 (1H, s, 4'-H), 7.77 (1H, d, J=7.8 Hz, 9-H), 8.18 (1H, s, 6'-H), 8.43 (1H, s, 2'-H). $^{13}$C NMR (100 MHz, CDCl$_3$) δ: 19.61, 21.43, 32.36, 89.56, 99.71, 114.41, 122.94, 123.67, 127.89, 128.34, 131.89, 134.75, 135.01, 135.93, 136.75, 137.44, 139.84, 143.26, 144.00, 144.31, 150.87, 152.88. HRMS (ESI-TOF$^+$): m/z [M+H]$^+$ calcd for C$_{29}$H$_{28}$N$_5$: 446.2586; found: 446.2589.

TBI-349, 5-(4-Methylphenyl)-3-cyclopropylimino-2-(3-pyridyl)amino-3,5-dihydrophenazine:

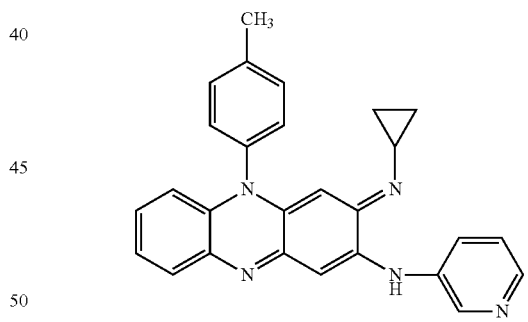

$^1$H NMR (300 MHz, CDCl$_3$) δ: 0.80-0.86 (6H, m, —CH$_2$—CH—CH$_2$—), 2.54 (3H, s, —CH$_3$), 2.71 (1H, m, —CH$_2$—CH—CH$_2$—), 5.64 (1H, s, 4-H), 6.53 (1H, d, J=7.2 Hz, 6-H), 6.84 (1H, s, 1-H), 7.16-7.21 (2H, m, 7-H, 8-H), 7.24 (2H, d, J=8.1 Hz, 2"-H, 6"-H), 7.30 (1H, m, 9-H), 7.51 (2H, d, J=8.1 Hz, 3"-H, 5"-H), 7.70 (1H, d, J=6.3 Hz, 4'-H), 7.77 (1H, d, J=7.5 Hz, 5'-H), 8.32 (1H, d, J=3.6 Hz, 6'-H), 8.56 (1H, s, 2'-H). $^{13}$C NMR (100 MHz, CDCl$_3$) δ: 9.61, 21.43, 32.36, 89.56, 99.71, 114.41, 122.94, 123.67, 127.89, 128.34, 131.89, 134.75, 135.01, 135.93, 136.75, 137.44, 139.84, 143.26, 144.00, 144.31, 150.87, 152.88. HRMS (ESI-TOF$^+$): m/z [M+H]$^+$ calcd for C$_{27}$H$_{24}$N$_5$: 418.2233; found: 418.2231.

TBI-350, 5-(3,4-Dichlorophenyl)-3-cyclohexylimino-2-(3-pyridyl)amino-3,5-dihydrophenazine:

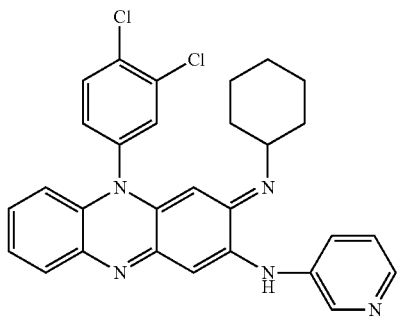

$^1$H NMR (300 MHz, CDCl$_3$) δ: 1.24-2.04 (10H, m, —CH$_2$—CH$_2$—CH$_2$—CH$_2$—CH$_2$—), 3.14 (1H, m, —CH$_2$—CH—CH$_2$—), 5.28 (1H, s, 4-H), 6.47 (1H, d, J=8.4 Hz, 6-H), 6.76 (1H, s, 1-H), 7.12-7.31 (4H, m, 7-H, 8-H, 5''-H, 6''-H), 7.50 (1H, s, 2''-H), 7.76 (1H, d, J=8.1 Hz, 4'-H), 7.75 (1H, d, J=7.8 Hz, 5'-H), 7.81 (1H, d, J=8.4 Hz, 9-H), 8.33 (1H, d, J=4.8 Hz, 6'-H), 8.57 (1H, d, J=2.1 Hz, 2'-H). $^{13}$C NMR (100 MHz, CDCl$_3$) δ: 24.54, 25.81, 33.67, 57.94, 89.47, 99.45, 113.63, 123.20, 123.63, 127.82, 127.93, 128.44, 128.56, 131.08, 131.27, 132.99, 134.27, 134.46, 135.29, 135.56, 136.75, 143.70, 143.96, 144.33, 150.31, 151.00. HRMS (ESI-TOF$^+$): m/z [M+H]$^+$ calcd for C$_{29}$H$_{26}$O$_7$N$_5$: 514.1720; found: 514.1719.

TBI-351, 5-(3,4-Dichlorophenyl)-3-(4-tetrahydropyranyl)imino-2-(3-pyridyl)amino-3,5-dihydrophenazine:

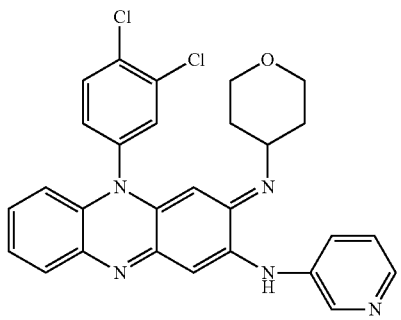

$^1$H NMR (300 MHz, CDCl$_3$) δ: 1.52 (4H, m, —CH$_2$—CH—CH$_2$—), 3.42 (3H, m, —CH$_2$—CH—CH$_2$—), 3.97 (2H, m, —CH$_2$—CH—CH$_2$—), 5.27 (1H, s, 4-H), 6.49 (1H, d, J=7.8 Hz, 6-H), 6.84 (1H, s, 1-H), 7.14-7.33 (4H, m, 7-H, 8-H, 5''-H, 6''-H), 7.50 (1H, s, 2''-H), 7.70 (1H, d, J=7.2 Hz, 4'-H), 7.75 (1H, d, J=7.2 Hz, 5'-H), 7.81 (1H, d, J=8.4 Hz, 9-H), 8.34 (1H, d, J=4.5 Hz, 6'-H), 8.59 (1H, s, 2'-H). $^{13}$C NMR (100 MHz, CDCl$_3$) δ: 33.41, 54.31, 66.02, 89.02, 99.64, 113.77, 123.44, 123.68, 128.04, 128.14, 128.45, 128.57, 130.93, 131.18, 133.07, 134.47, 135.38, 135.57, 136.55, 136.65, 143.61, 144.04, 144.56, 150.67, 150.90. HRMS (ESI-TOF$^+$): m/z [M+H]$^+$ calcd for C$_{28}$H$_{24}$Cl$_2$N$_5$O: 516.1373; found: 516.1370.

TBI-352, 5-(3,4-Dichlorophenyl)-3-(4-methoxycyclohexyl)imino-2-(3-pyridyl)amino-3,5-dihydrophenazine:

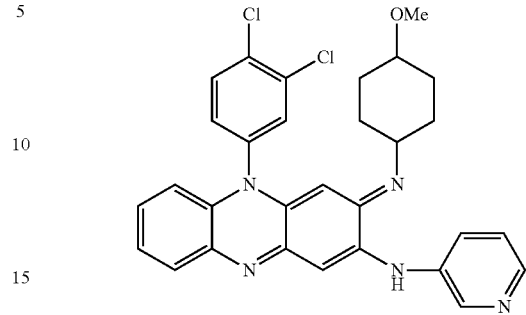

$^1$H NMR (300 MHz, CDCl$_3$) δ: 1.20-1.46 (4H, m, —CH$_2$—CH—CH$_2$—), 1.49-2.06 (4H, m, —CH$_2$—O—CH$_2$—), 3.14-3.20 (2H, m, —CH$_2$—CH—CH$_2$—, —CH$_2$—CH—CH$_2$—), 3.36 (3H, s, —OCH$_3$), 5.27 (1H, s, 4-H), 6.48 (1H, d, J=7.8 Hz, 6-H), 6.81 (1H, s, 1-H), 7.13-7.31 (4H, m, 7-H, 8-H, 5''-H, 6''-H), 7.49 (1H, s, 2''-H), 7.68 (1H, d, J=7.2 Hz, 4'-H), 7.75 (1H, s, 5'-H), 7.81 (1H, d, J=6.6 Hz, 9-H), 8.33 (1H, d, J=4.8 Hz, 6'-H), 8.57 (1H, s, $^{13}$C NMR (100 MHz, CDCl$_3$) δ: 29.75, 29.88, 31.16, 55.85, 57.30, 78.42, 89.21, 99.57, 113.73, 123.31, 123.66, 127.97, 128.43, 131.16, 133.09, 134.54, 135.38, 135.56, 136.63, 143.57, 143.98, 144.42, 150.92. HRMS (ESI-TOF$^+$): m/z [M+H]$^+$ calcd for C$_{30}$H$_{28}$Cl$_2$N$_3$O: 544.1173; found: 544.1172.

TBI-353, 5-(3,4-Dichlorophenyl)-3-(1-methylethyl)imino-2-(6-ethyl-3-pyridyl)amino-3,5-dihydrophenazine:

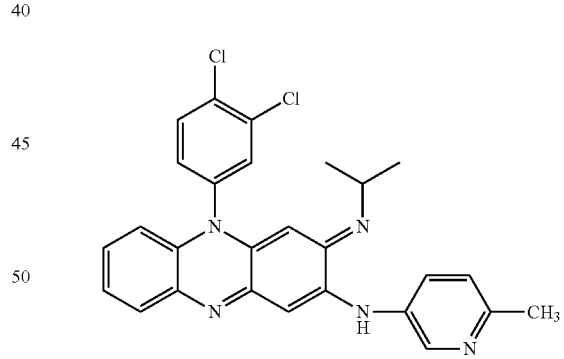

$^1$H NMR (300 MHz, CDCl$_3$) δ: 1.12 (6H, d, J=7.5 Hz, (CH$_3$)$_2$—CH—), 2.55 (3H, s, —CH$_3$), 3.51 (1H, m, (CH$_3$)$_2$—CH—), 5.29 (1H, s, 4-H), 6.44 (1H, d, 17.5 Hz, 6-H), 6.69 (1H, s, 1-H), 7.11-7.23 (5H, m, 7-H, 8-H, 9-H, 5''-H, 6''-H), 7.49 (1H, s, 2''-H), 7.66 (1H, d, J=3.0 Hz, 4'-H), 7.82 (1H, d, J=3.0 Hz, 5'-H), 8.45 (1H, d, J=2.4 Hz, 2'-H). $^{13}$C NMR (100 MHz, CDCl$_3$) δ: 23.53, 23.82, 49.48, 89.16, 98.86, 113.63, 123.17, 128.33, 128.57, 129.55, 131.06, 131.23, 133.09, 134.33, 134.52, 135.35, 136.82, 143.82, 144.45, 150.22, 150.96, 153.47. HRMS (ESI-TOF$^+$): m/z [M+H]$^+$ calcd for C$_{27}$H$_{24}$Cl$_2$N$_5$: 488.1523; found: 488.1524.

TBI-354, 5-(3,4-Dichlorophenyl)-3-cyclohexylimino-2-(6-methyl-3-pyridyl)amino-3,5-dihydrophenazine:

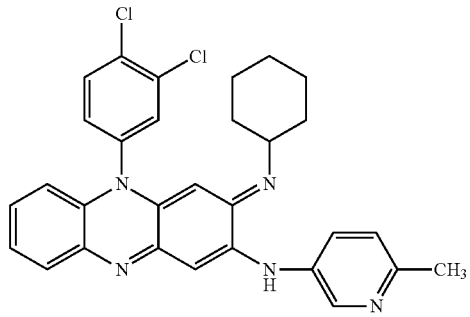 [SMILES: Cc1ccc(Nc2cc3nc4ccccc4n(-c4ccc(Cl)c(Cl)c4)c-3c/c2=N\C2CCCCC2)cn1]

¹H NMR (300 MHz, CDCl₃) δ: 1.23-1.76 (10H, m, —CH₂—CH₂—CH₂—CH₂—CH₂—), 2.56 (3H, s, —CH₃), 3.13 (1H, m, —CH₂—CH—CH₂—), 5.28 (1H, s, 4-H), 6.47 (1H, d, J=8.7 Hz, 6-H), 6.69 (1H, s, 1-H), 7.13-7.23 (5H, m, 7-H, 8-H, 9-H, 5''-H, 6''-H), 7.49 (1H, s, 2''-H), 7.66 (1H, d, J=6.3 Hz, 4'-H), 7.82 (1H, d, J=2.7 Hz, 5'-H), 8.45 (1H, d, J=2.4 Hz, 2'-H). ¹³C NMR (100 MHz, CDCl₃) δ: 23.82, 24.60, 25.81, 33.68, 57.99, 89.47, 98.85, 113.61, 123.17, 127.61, 128.34, 128.58, 129.48, 131.00, 131.29, 132.97, 133.98, 134.22, 134.41, 135.26, 135.58, 136.82, 136.82, 143.78, 144.45, 150.38, 151.02, 153.43. HRMS (ESI-TOF⁺): m/z [M+H]⁺ calcd for C₃₀H₂₈Cl₂N₅: 528.1736; found: 528.1735.

TBI-355, 5-(3,4-Dichlorophenyl)-3-(4-methoxycyclohexyl)imino-2-(6-methyl-3-pyridyl)amino-3,5-dihydrophenazine:

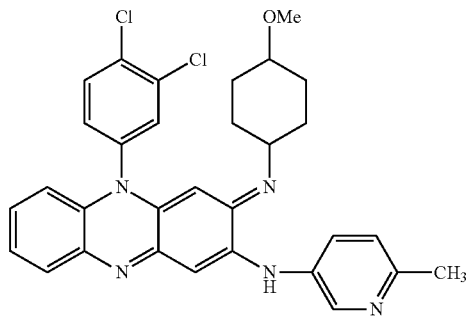 [SMILES: COC1CCC(/N=c2\cc3n(-c4ccc(Cl)c(Cl)c4)c4ccccc4nc-3cc2Nc2ccc(C)nc2)CC1]

¹H NMR (300 MHz, CDCl₃) δ: 1.20-1.50 (4H, m, —CH₂—CH—CH₂—), 1.70-2.06 (4H, m, —CH₂—CH—CH₂—), 2.55 (3H, s, py-CH₃), 3.10-3.23 (2H, m, —CH₂—CH—CH₂—, —CH₂—CH—CH₂), 3.34 (3H, s, —OCH₃), 5.27 (1H, s, 4-H), 6.48 (1H, d, J=7.2 Hz, 6-H), 6.69 (1H, s, 1-H), 7.13-7.21 (5H, 7-H, 8-H, 9-H, 5''-H, 6''-H), 7.48 (1H, s, 2''-H), 7.67 (1H, d, J=6.9 Hz, 4'-H), 7.82 (1H, d, J=2.7 Hz, 5'-H), 8.43 (1H, s, 2'-H). ¹³C NMR (100 MHz, CDCl₃) δ: 23.83, 29.78, 29.92, 31.19, 55.84, 57.33, 89.20, 98.96, 113.70, 123.19, 127.74, 128.39, 128.44, 129.51, 130.96, 132.99, 133.90, 134.49, 135.34, 135.57, 136.65, 143.80, 144.34, 150.85, 150.98, 153.53. HRMS (ESI-TOF⁺): m/z [M+H]⁺ calcd for C₃₁H₃₀Cl₂N₅O: 558.1885; found: 558.1884.

TBI-356, 5-(4-Methylphenyl)-3-(1-methylethyl)imino-2-(6-methoxy-3-pyridyl)amino-3,5-dihydrophenazine:

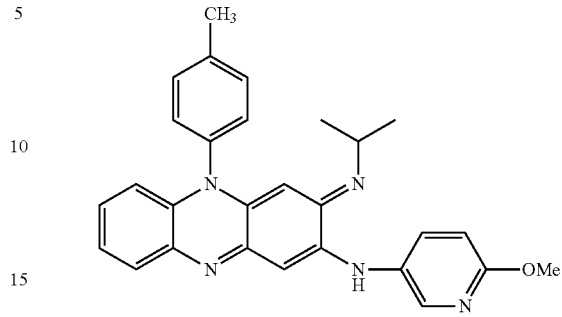

¹H NMR (300 MHz, CDCl₃) δ: 1.07 (6H, d, J=6.0 Hz, —CH—(CH₃)₂), 2.52 (3H, s, —CH₃), 3.34 (1H, m, —CH—(CH₃)₂), 3.39 (3H, s, —OCH₃), 5.30 (1H, s, 4-H), 6.46 (1H, s, 6-H), 6.48 (1H, s, 1-H), 6.75 (1H, d, J=8.4 Hz, 9-H), 7.04-7.12 (2H, m, 7-H, 8-H), 7.17 (2H, d, J=8.1 Hz, 2''-H, 6''-H), 7.47 (2H, J=8.1 Hz, 3''-H, 5''-H), 7.62 (1H, s, 4'-H), 7.65 (1H, s, 5'-H), 8.13 (1H, s, 2'-H). ¹³C NMR (100 MHz, CDCl₃) δ: 21.43, 23.55, 49.25, 53.61, 88.98, 98.03, 110.96, 114.20, 122.56, 127.16, 127.93, 128.43, 130.36, 131.78, 135.08, 135.67, 139.63, 142.40, 145.95, 150.74, 151.02, 161.13. HRMS (ESI-TOF⁺): m/z [M+H]⁺ calcd for C₂₈H₂₈N₅O: 450.2332; found: 450.2330.

TBI-357, 5-(4-Methylphenyl)-3-cyclohexylimino-2-(6-methoxy-3-pyridyl)amino-3,5-dihydrophenazine:

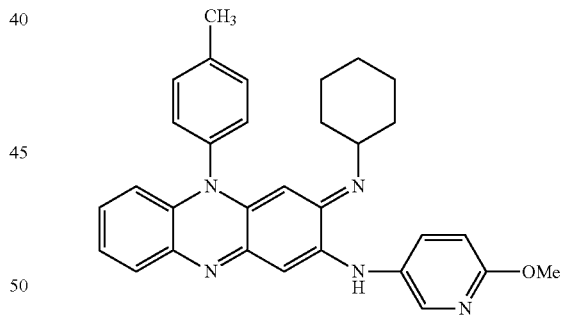

¹H NMR (300 MHz, CDCl₃) δ: 1.09-1.95 (10H, m, —CH₂—CH₂—CH₂—CH₂—CH₂—), 2.53 (3H, s, —CH₃), 3.06 (1H, m, —CH2-CH—CH₂), 3.95 (3H, s, —OCH₃), 5.27 (1H, s, 4-H), 6.49 (1H, s, 1-H), 6.52 (1H, d, J=9.3 Hz, 6-H), 6.76 (1H, d, J=8.7 Hz, 9-H), 7.06-7.13 (2H, m, 8-H), 7.18 (2H, d, J=7.8 Hz, 2''-H, 6''-H), 7.49 (2H, J=7.8 Hz, 3''-H, 5''-H), 7.62-7.66 (2H, m, 4'-H, 5'-H), 8.13 (1H, d, J=2.1 Hz, 2'-H). ¹³C NMR 100 MHz, CDCl₃) δ: 21.35, 24.70, 25.89, 33.62, 53.60, 57.87, 89.30, 98.01, 110.94, 114.17, 122.54, 127.15, 127.93, 128.43, 130.39, 131.67, 135.00, 135.71, 139.59, 142.33, 145.94, 150.89, 151.06. HRMS (ESI-TOF⁺): m/z [M+H]⁺ calcd for C₃₁H₃₂N₅O: 490.4490; found: 490.4489.

TBI-358, 5-(4-Methylphenyl)-3-(4-methoxycyclohexyl)imino-2-(6-methoxy-3-pyrid)amino-3,5-dihydrophenazine:

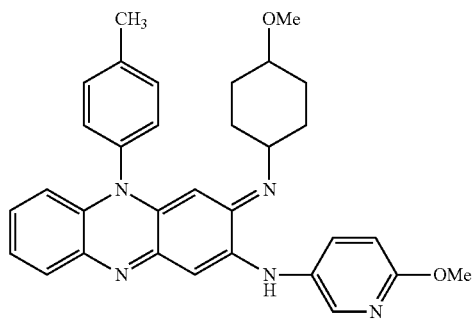 [SMILES: COc1ccc(Nc2cc3nc4ccccc4n(-c4ccc(C)cc4)c-3c/c2=N\C2CCC(OC)CC2)cn1]

$^1$H NMR (300 MHz, CDCl$_3$) δ: 1.09-1.45 (4H, m, —CH$_2$—CH—CH$_2$—), 1.68-1.72 (2H, m, —CH$_2$—CH—CH$_2$—), 2.02-2.07 (2H, m, —CH$_2$—CH—CH$_2$—), 2.53 (3H, s, —CH$_3$), 3.03-3.21 (2H, m, —CH$_2$—CH—CH$_2$—, —CH$_2$—CH—CH$_2$—), 3.35 (3H, s, py-OCH$_3$), 3.95 (3H, s, —OCH$_3$), 5.28 (1H, s, 4-H), 6.50 (1H, s, 1-H), 6.53 (1H, s, 6-H), 6.77 (1H, d, J=8.7 Hz, 9-H), 7.07-7.14 (2H, m, 7-H, 8-H), 7.18 (2H, d, J=8.1 Hz, 2''-H, 6''-H), 7.48 (2H, J=8.1 Hz, 3''-H, 5''-H), 7.62-7.66 (2H, 4'-H, 5'-H), 8.13 (1H, d, J=2.1 Hz, 2'-H). $^{13}$C NMR (100 MHz, CDCl$_3$) δ: 21.43, 30.01, 31.17, 53.61, 55.84, 57.28, 78.66, 89.03, 98.13, 110.97, 114.26, 122.64, 127.28, 127.99, 128.33, 130.26, 131.70, 134.91, 135.70, 135.70, 139.81, 142.37, 145.81, 150.90, 151.47, 161.16. HRMS (ESI-TOF$^+$): m/z [M+H]$^+$ calcd for C$_{32}$H$_{34}$N$_5$O$_2$: 520.2752; found: 520.2751.

TBI-359, 5-(3,4-Dichlorophenyl)-3-(1-methylethyl)imino-2-(2-methoxy-3-pyridyl)amino-3,5-dihydrophenazine:

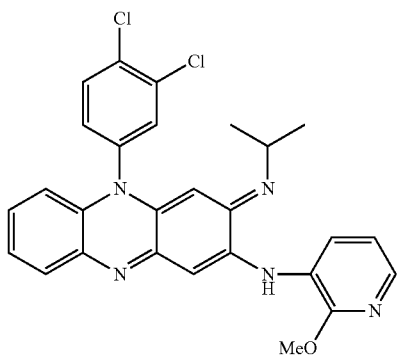

$^1$H NMR (300 MHz, CDCl$_3$) δ: 1.13 (6H, d, J=6.3 Hz, —CH—(CH$_3$)$_2$), 3.50 (1H, m, —CH—(CH$_3$)$_2$), 4.03 (3H, s, —OCH$_3$), 5.29 (1H, s, 4-H), 6.43 (1H, d, J=6.3 Hz, 6-H), 6.89 (1H, s, 1-H), 6.93 (1H, m, 9-H), 7.10-7.23 (3H, m, 7-H, 8-H, 5''-H), 7.49 (1H, d, J=2.4 Hz, 2''-H), 7.68 (1H, m, 6''-H), 7.80-7.84 (3H, m, 4'-H, 5'-H, 6'-H). $^{13}$C NMR (100 MHz, CDCl$_3$) δ: 23.57, 49.49, 53.74, 89.33, 100.12, 113.62, 116.80, 123.10, 124.79, 125.02, 127.68, 128.33, 131.26, 134.28, 134.47, 135.32, 135.55, 136.84, 138.96, 142.95, 150.40, 151.24, 155.51. HRMS (ESI-TOF$^+$) m/z [M+H]$^+$ calcd for C$_{27}$H$_{24}$Cl$_2$N$_5$O: 504.1853; found: 504.1852.

TBI-360, 5-(4-Methylphenyl)-3-(4-tetrahydropyranyl)imino-2-(6-methoxy-3-pyridyl)amino-3,5-dihydrophenazine

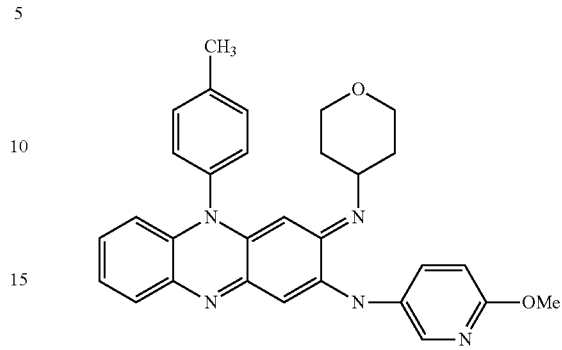

$^1$H NMR (CDCl$_3$) δ: 1.60-1.67 (4H, —CH$_2$—CH—CH$_2$—), 2.54 (3H, s, —CH$_3$), 3.34-3.42 (3H, m, —CH$_2$—CH—CH$_2$—), 3.95 (3H, s, —OCH$_3$), 3.98 (2H, m, —CH$_2$—CH—CH$_2$—), 5.26 (1H, s, 4-H), 6.52 (1H, s, 1-H), 6.55 (1H, m, 6-H), 6.78 (1H, m, 9-H), 7.11-7.17 (2H, m, 7-H, 8-H), 7.20 (2H, d, J=7.8 Hz, 2''-H, 6''-H), 7.50 (2H, J=7.8 Hz, 3''-H, 5''-H), 7.62-7.68 (2H, m, 4'-H, 5'-H), 8.14 (1H, m, 2'-H). $^{13}$C NMR (CDCl$_3$) δ: 21.37, 33.42, 53.63, 54.34, 66.22, 88.88, 98.20, 111.03, 114.30, 122.77, 127.37, 128.07, 128.37, 130.18, 131.59, 131.73, 134.97, 135.21, 135.72, 139.78, 142.48, 145.87, 150.76, 151.47. HRMS (ESI-TOF$^+$): m/z [M+H]$^+$ calcd for C$_{30}$H$_{30}$N$_5$O$_2$: 492.2514; found: 492.2513.

TBI-361, 5-(3,4-Dichlorophenyl)-3-(4-tetrahydropyranyl)imino-2-(2-methoxy-3-pyridyl)amino-3,5-dihydrophenazine:

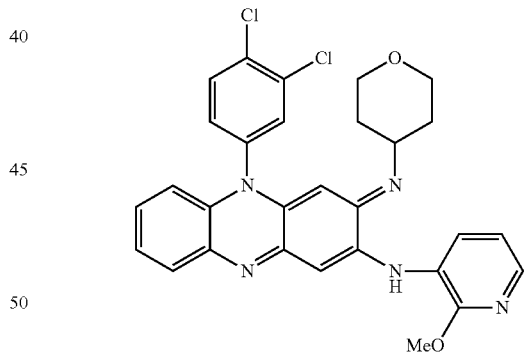

$^1$H NMR (300 MHz, CDCl$_3$) δ: 1.61-1.72 (4H, m, —CH$_2$—CH—CH$_2$—), 3.48-3.52 (3H, m, —CH$_2$—CH—CH$_2$—), 4.04 (5H, m, —CH$_2$—CH—CH$_2$—, —OCH$_3$), 5.26 (1H, s, 4-H), 6.47 (1H, d, J=7.8 Hz, 6-H), 6.90-6.94 (1H, m, 9-H), 6.95 (1H, s, 1-H), 7.13-7.23 (3H, m, 7-H, 8-H, 5''-H), 7.49 (1H, s, 2''-H), 7.70 (1H, d, J=7.2 Hz, 6''-H), 7.81-7.85 (3H, m, 4'-H, 5'-H, 6'-H). $^{13}$C NMR (100 MHz, CDCl$_3$) δ: 33.31, 53.28, 53.78, 65.50, 89.06, 100.32, 113.72, 116.83, 123.33, 124.38, 127.89, 128.44, 128.50, 131.03, 131.21, 134.41, 134.67, 135.36, 135.57, 136.69, 138.82, 142.63, 150.94, 155.31. HRMS (ESI-TOF$^+$): m/z [M+H]$^+$ calcd for C$_{29}$H$_{26}$Cl$_2$N$_5$O$_2$: 546.1875; found: 546.1874.

TBI-362, 5-(3,4-Dichlorophenyl)-3-(4-methoxycyclohexyl)imino-2-(2-methoxy-3-pyridyl)amino-3,5-dihydrophenazine:

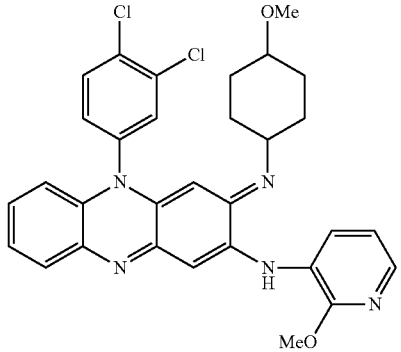

¹H NMR (300 MHz, CDCl₃) δ: 1.23-1.51 (4H, m, —CH₂—CH—CH₂—), 1.73-2.10 (4H, m, —CH₂—CH—CH₂—), 3.15-3.29 (2H, m, —CH₂—CH—CH₂—, —CH₂—CH—CH₂—), 3.37 (3H, s, —OCH₃), 3.78 (3H, s, —OCH₃), 5.27 (1H, s, 4-H), 6.48 (1H, d, J=8.4 Hz, 6-H), 6.90-6.93 (2H, m, 9-H, 1-H), 7.12-7.24 (3H, m, 7-H, 8-H, 5''-H), 7.49 (1H, d, J=2.1 Hz, 2''-H), 7.70 (1H, d, J=7.2 Hz, 6''-H), 7.79-7.84 (3H, m, 4'-H, 5'-H, 6'-H). ¹³C NMR (100 MHz, CDCl₃) δ: 29.25, 29.37, 30.73, 53.72, 55.81, 56.81, 89.34, 100.23, 113.67, 116.82, 123.19, 124.66, 124.78, 127.80, 128.49, 131.14, 131.21, 134.39, 134.48, 135.33, 135.56, 136.65, 138.83, 142.73, 151.06, 151.12, 155.36. HRMS (ESI-TOF⁺): m/z [M+H]⁺ calcd for $C_{31}H_{30}Cl_2N_5O_2$: 574.2129; found: 574.2128.

TBI-363, 5-(2,4-Dichlorophenyl)-3-(1-methylethyl)imino-2-(3-pyridyl)amino-3,5-dihydrophenazine:

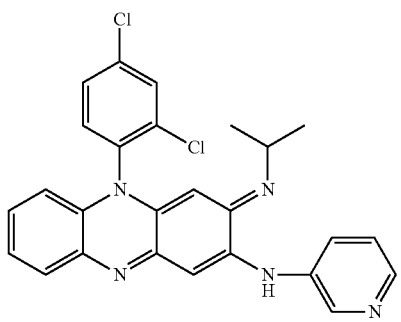

¹H NMR (300 MHz, CDCl₃) δ: 1.24 (6H, d, J=6.9 Hz, —CH—(CH₃)₂), 3.50 (1H, m, —CH—(CH₃)₂), 5.20 (1H, s, 4-H), 6.36 (1H, d, J=7.5 Hz, 6-H), 6.83 (1H, s, 1-H), 7.13-7.22 (2H, m, 7-H, 8-H), 7.28-7.36 (2H, m, 5''-H, 6''-H), 7.61 (1H, d, J=8.1 Hz, 4'-H), 7.70 (1H, d, J=8.4 Hz, 5'-H), 7.77 (1H, s, 9-H), 7.79 (1H, s, 2''-H), 8.33 (1H, d, J=3.6 Hz, 6'-H), 8.95 (1H, s, 2'-H). ¹³C NMR (100 MHz, CDCl₃) δ: 23.37, 23.58, 49.50, 88.82, 99.66, 113.19, 123.32, 123.67, 128.11, 128.52, 130.02, 131.74, 131.93, 133.29, 133.46, 134.71, 135.61, 136.72, 143.72, 144.03, 144.36, 150.45, 151.00. HRMS (ESI-TOF⁺): m/z [M+H]⁺ calcd for $C_{26}H_{22}Cl_2N_5$: 474.1259; found: 474.1257.

TBI-364, 5-(4-Trifluoromethoxyphenyl)-3-cyclopropylimino-2-(2-methoxy-3-pyridyl)amino-3,5-dihydrophenazine:

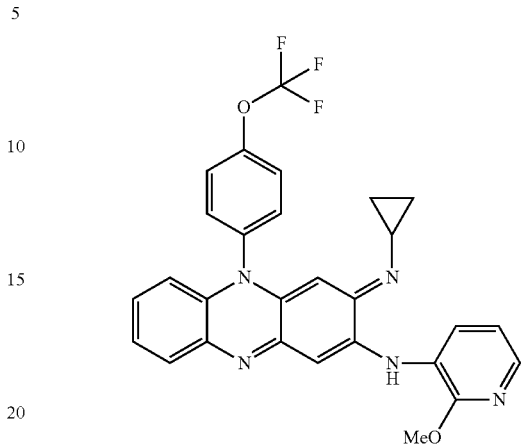

¹H NMR (300 MHz, CDCl₃) δ: 0.82-0.89 (4H, m, —CH₂—CH₂—), 2.71 (1H, m, —CH₂—CH—CH₂—), 4.08 (3H, s, —OCH₃), 5.49 (1H, s, 4-H), 6.41 (1H, d, J=7.8 Hz, 6-H), 6.87 (1H, s, 1-H), 6.90-6.92 (1H, m, 9-H), 7.09-7.18 (2H, m, 7-H, 8-H), 7.43 (2H, d, J=8.1 Hz, 2''-H, 6''-H), 7.58 (2H, d, J=8.1 Hz, 3''-H, 5''-H), 7.68 (1H, d, J=7.2 Hz, 4''-H), 7.79-7.83 (2H, m, 5'-H, 6'-H). ¹³C NMR (100 MHz, CDCl₃) δ: 10.02, 32.85, 53.69, 89.69, 100.07, 113.17, 116.82, 119.11, 121.69, 122.96, 123.63, 124.69, 125.11, 127.66, 128.20, 130.91, 131.70, 134.68, 135.72, 135.91, 138.92, 142.65, 149.66, 151.42, 152.63, 155.46. HRMS (ESI-TOF⁺): m/z [M+H]⁺ calcd for $C_{28}H_{23}F_3N_5O_2$: 518.3705; found: 518.3702.

TBI-365, 5-(4-Trifluoromethoxyphenyl)-3-cyclohexylimino-2-(2-methoxy-3-pyridyl)amino-3,5-dihydrophenazine:

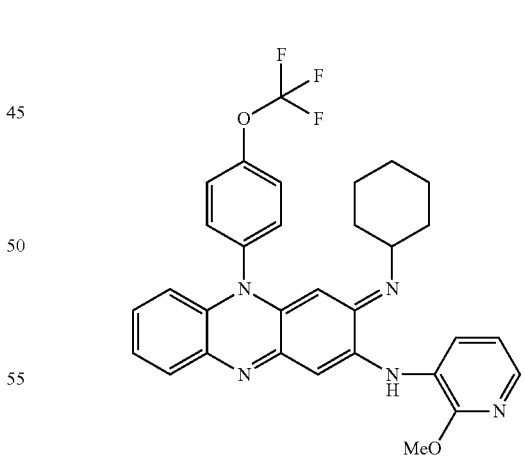

¹H NMR (300 MHz, CDCl₃) δ: 1.11-1.77 (10H, m, —CH₂—CH₂—CH₂—CH₂—CH₂—), 3.07 (1H, m, —CH₂—CH—CH₂—), 4.02 (3H, s, —OCH₃), 5.18 (1H, s, 4-H), 6.47 (1H, d, J=7.2 Hz, 6-H), 6.88 (1H, s, 1-H), 6.90-6.92 (1H, m, 9-H), 7.11-7.19 (2H, m, 7-H, 8-H), 7.41 (2H, d, J=8.1 Hz, 2''-H, 6''-H), 7.58 (2H, d, J=8.1 Hz, 3''-H, 5''-H), 7.70 (1H, d, J=8.1 Hz, 4'-H), 7.79-7.84 (2H, 5'-H, 6'-H). ¹³C NMR (100 MHz, CDCl₃) δ: 24.35, 25.92, 33.54, 53.70, 57.69, 89.54, 100.09, 113.68, 116.79, 122.91, 123.80, 124.62, 124.90, 127.65, 128.26, 130.83, 131.50, 134.80, 135.61, 136.06, 138.71, 142.86, 150.63, 151.32, 155.40. HRMS (ESI-TOF$^+$): m/z calcd for C$_{31}$H$_{29}$F$_3$N$_5$O$_2$: 560.3973; found: 560.3972.

TBI-366, 5-(3,4-Dichlorophenyl)-3-cyclopropylimino-2-(2-methoxy-3-pyridyl)amino-3,5-dihydrophenazine:

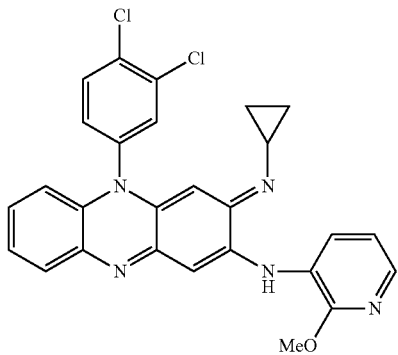

$^1$H NMR (300 MHz, CDCl$_3$) δ: 0.86-0.96 (4H, m, —CH$_2$—CH$_2$—), 2.80 (1H, m, —CH$_2$—CH—CH$_2$—), 4.00 (3H, s, —OCH$_3$), 5.54 (1H, s, 4-H), 6.41 (1H, d, J=8.7 Hz, 6-H), 6.86 (1H, s, 1-H), 6.91 (1H, m, 9-H), 7.10-7.28 (3H, m, 7-H, 8-H, 5"-H), 7.51 (1H, d=2.1 Hz, 2"-H), 7.65 (1H, m, 6"-H), 7.80-7.83 (3H, m, 4'-H, 5'-H, 6'-H). $^{13}$C NMR (100 MHz, CDCl$_3$) δ: 33.07, 53.70, 89.75, 100.04, 113.57, 116.80, 123.10, 124.65, 125.15, 127.66, 128.23, 128.76, 131.38, 133.17, 134.31, 135.35, 135.65, 136.83, 138.97, 142.67, 151.42, 152.23, 155.44. HRMS (ESI-TOF$^+$): m/z [M+H]$^+$ calcd for C$_{27}$H$_{22}$Cl$_2$N$_5$O: 502.1317; found: 502.1316.

TBI-367, 5-(2,4-Dichlorophenyl)-3-cyclopropylimino-2-(3-pyridyl)amino-3,5-dihydrophenazine:

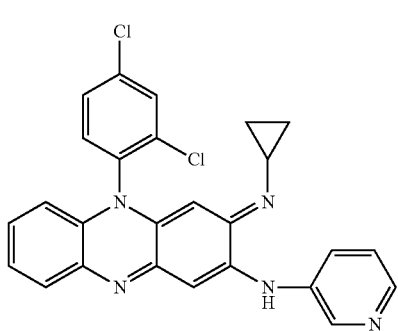

$^1$H NMR (300 MHz, CDCl$_3$) δ: 0.84-0.94 (4H, m, —CH$_2$—CH$_2$—), 2.77 (1H, m, —CH$_2$—CH—CH$_2$—), 5.46 (1H, s, 4-H), 6.33 (1H, d, J=7.5 Hz, 6-H), 6.78 (1H, s, 1-H), 6.78-7.16 (2H, m, 7-H, 8-H), 7.27-7.31 (2H, m, 5"-H, 6"-H), 7.37 (1H, d, J=8.1 Hz, 4'-H), 7.60 (1H, d, J=8.4 Hz, 5'-H), 7.68 (1H, s, 9-H), 7.79 (1H, s, 2"-H), 8.33 (1H, d, J=3.6 Hz, 6'-H), 8.54 (1H, s, 2'-H). $^{13}$C NMR (100 MHz, CDCl$_3$) δ: 10.13, 33.05, 89.21, 99.57, 113.13, 123.26, 123.68, 127.97, 128.28, 130.04, 130.43, 131.89, 132.06, 133.34, 134.71, 135.70, 136.57, 143.52, 144.13, 144.48, 151.29, 152.26. HRMS (ESI-TOF$^+$): m/z [M+H]$^+$ calcd for C$_{26}$H$_{20}$Cl$_2$N$_5$: 472.1149; found: 472.1146.

TBI-368, 5-(2,4-Dichlorophenyl)-3-cyclohexylimino-2-(3-pyridyl)amino-3,5-dihydrophenazine:

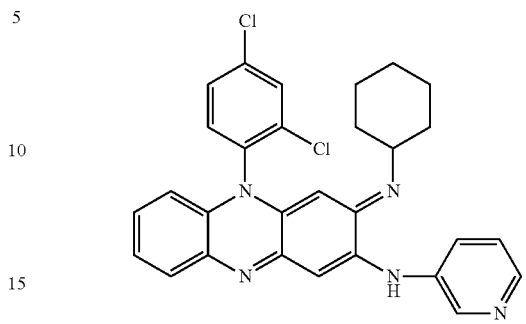

$^1$H NMR (300 MHz, CDCl$_3$) δ: 1.18-1.77 (10H, m, —CH$_2$—CH$_2$—CH$_2$—CH$_2$—CH$_2$—), 3.12 (1H, m, —CH$_2$—CH—CH$_2$—), 5.16 (1H, s, 4-H), 6.38 (1H, d, J=7.5 Hz, 6-H), 6.82 (1H, s, 1-H), 7.13-7.22 (2H, m, 7-H, 8-H), 7.27-7.31 (2H, m, 5"-H, 6"-H), 7.59 (1H, d, J=8.1 Hz, 4'-H), 7.62 (1H, d, J=8.4 Hz, 5'-H), 7.68 (1H, s, 9-H), 7.79 (1H, s, 2"-H), 8.33 (1H, d, J=3.6 Hz, 6'-H), 8.56 (1H, s, 2'-H). $^{13}$C NMR (100 MHz, CDCl$_3$) δ: 24.57, 25.82, 33.49, 33.68, 57.95, 89.09, 99.59, 113.15, 123.25, 123.64, 127.97, 128.49, 129.92, 130.32, 131.82, 122.35, 134.72, 135.60, 136.58, 136.74, 143.74, 143.98, 144.32, 150.50, 151.12. HRMS (ESI-TOF$^+$): m/z [M+H]$^+$ calcd for C$_{29}$H$_{26}$Cl$_2$N$_5$: 514.1608; found: 514.1606.

TBI-369, 5-(2,4-Dichlorophenyl)-3-(1-methylethyl)imino-2-(2-methoxy-3-pyridyl)amino-3,5-dihydrophenazine:

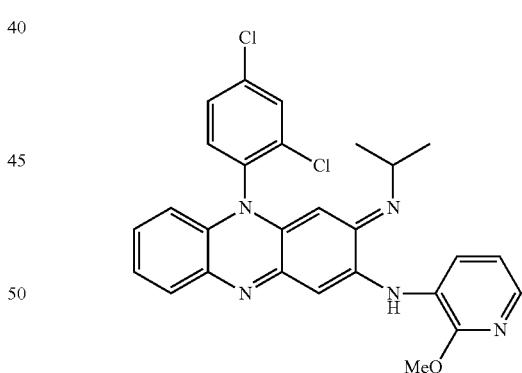

$^1$H NMR (300 MHz, CDCl$_3$) δ: 1.16 (6H, d, J=6.9 Hz, —CH—(CH$_3$)$_2$), 3.49 (1H, m, —CH—(CH$_3$)$_2$), 3.79 (3H, s, —OCH$_3$), 5.19 (1H, s, 4-H), 6.35 (1H, d, J=7.8 Hz, 6-H), 6.89-6.93 (2H, m, 1-H, 9-H), 7.11-7.21 (2H, m, 7-H, 8-H), 7.35 (1H, d, J=8.4 Hz), 7.58-7.61 (1H, m), 7.68-7.61 (1H, m), 7.79-7.85 (3H, m). $^{13}$C NMR (100 MHz, CDCl$_3$) δ: 23.40, 23.62, 49.51, 53.71, 89.01, 100.17, 113.10, 116.79, 123.16, 124.76, 125.14, 127.81, 128.36, 129.98, 130.42, 131.83, 131.91, 134.79, 135.58, 136.55, 128.94, 142.99, 150.65, 151.35, 155.54. HRMS (ESI-TOF$^+$): m/z [M+H]$^+$ calcd for C$_{27}$H$_{24}$Cl$_2$N$_5$O: 504.1353; found: 504.1351.

TBI-370, 5-(2,4-Dichlorophenyl)-3-cyclopropylimino-2-(2-methoxy-3-pyridyl)amino-3,5-dihydrophenazine:

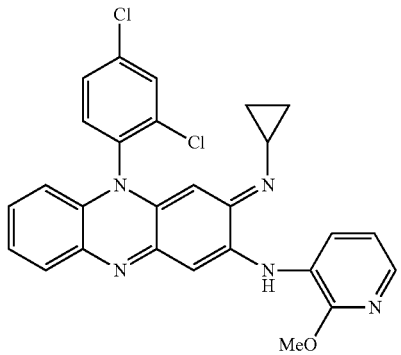 [SMILES: COc1ncccc1Nc1cc2nc3ccccc3n(-c3ccc(Cl)cc3Cl)c-2c/c1=N\C1CC1]

$^1$H NMR (300 MHz, CDCl$_3$) δ: 0.86-0.94 (4H, m, —CH$_2$—CH$_2$—), 2.78 (1H, m, —CH$_2$—CH—CH$_2$), 3.81 (3H, s, —OCH$_3$), 5.45 (1H, s, 4-H), 6.32 (1H, J=7.8 Hz, 6-H), 6.87-6.92 (2H, m, 1-H, 9-H), 7.11-7.20 (2H, m, 7-H, 8-H), 7.35 (1H, d, J=8.4 Hz), 7.36-7.89 (1H, m), 7.66-7.69 (1H, m), 7.78-7.83 (3H, m). $^{13}$C NMR (100 MHz, CDCl$_3$) δ: 10.18, 10.27, 33.06, 53.70, 89.38, 100.11, 113, 07, 116.82, 123.16, 124.67, 125.30, 127.80, 130.02, 130.53, 132.01, 133.25, 133.41. 134.41, 135.71, 136.49, 138.99, 142.76, 151.57, 152.47, 155.50. HRMS (ESI-TOF$^+$): m/z [M+H]$^+$ calcd for C$_{27}$H$_{22}$Cl$_2$N$_5$O: 502.1223; found: 502.1220.

TBI-371, 5-(2,4-Dichlorophenyl)-3-(4-methoxycyclohexyl)imino-2-(2-methoxy-3-pyridyl)amino-3,5-dihydrophenazine:

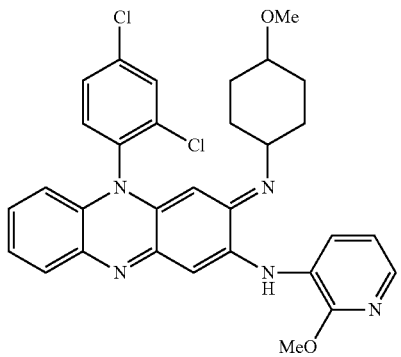 [SMILES: COc1ncccc1Nc1cc2nc3ccccc3n(-c3ccc(Cl)cc3Cl)c-2c/c1=N\C1CCC(OC)CC1]

$^1$H NMR (300 MHz, CDCl$_3$) δ: 1.24-2.07 (8H, m, —CH$_2$—CH$_2$—, —CH$_2$—CH$_2$—), 3.16-3.34 (2H, m, —CH—CH$_2$—CH$_2$—CH—), 3.37 (3H, s, —OCH3), 4.00 (3H, m, —OCH3), 5.17 (1H, s, 4-H), 6.37 (1H, d, J=7.8 Hz, 6-H), 6.89-6.93 (2H, m, 1-H, 9-H), 7.13-7.22 (2H, m, 7-H, 8-H), 7.33 (1H, d, J=8.4 Hz), 7.57-7.61 (1H, m), 7.69-7.72 (1H, m), 7.78-7.85 (3H, m). $^{13}$C NMR (100 MHz, CDCl$_3$) δ: 29.37, 30.53, 30.79, 53.17, 55.82, 56.87, 78.22, 89.00, 100.31, 113.19, 116.84, 123.25, 124.83, 127.94, 128.42, 129.94, 130.37, 131.76, 131.84, 133.26, 134.67, 125.62, 136.71, 138.86, 142.82, 151.29. HRMS (ESI-TOF$^+$): m/z [M+H]$^+$ calcd for C$_{31}$H$_{30}$Cl$_2$N$_5$O$_2$: 574.1935; found: 574.1793.

TBI-372, 5-(4-Trifluoromethoxyphenyl)-3-(1,3-dimethoxyisopropyl)imino-2-methoxy-3-pyridyl)amino-3,5-dihydrophenazine:

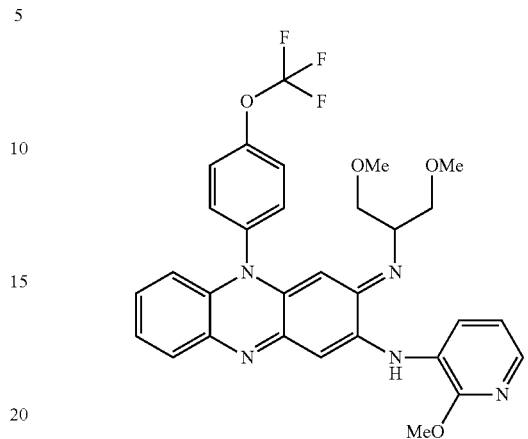

$^1$H NMR (300 MHz, CDCl$_3$) δ: 3.26 (6H, s, —OCH$_3$, —OCH$_3$), 3.34-3.39 (2H, m, —CH—CH$_2$—), 3.52-3.57 (2H, m, —CH—CH$_2$—), 3.68-3.72 (1H, m, —CH$_2$—CH—CH$_2$—), 4.01 (3H, s, —OCH$_3$), 5.49 (1H, s, 4-H), 6.52 (1H, d, J=7.2 Hz, 6-H), 6.89-6.96 (2H, m, 1-H, 9-H), 7.12-7.20 (4H, m, 7-H, 8-H, 2"-H, 6"-H), 7.48 (2H, d, J=7.8 Hz, 3"-H, 5"-H), 7.79-7.86 (2H, m, 4'-H, 5'-H), 8.43 (1H, s, 6'-H). $^{13}$C NMR (100 MHz, CDCl$_3$) δ: 53.65, 58.55, 59.00, 74.42, 90.24, 100.20, 113.86, 123.09, 123.52, 124.76, 124.94, 126.80, 127.82, 128.36, 130.81, 131.48, 135.64, 135.83, 138.90, 142.72, 149.74, 150.95, 153.46, 155.42. HRMS (ESI-TOF$^+$): m/z [M+H]$^+$ calcd for C$_{30}$H$_{29}$F$_3$N$_5$O$_4$: 580.2252; found: 580.2249.

TBI-373, 5-(4-Methylphenyl)-3-(1,3-dimethoxyisopropyl)imino-2-(2-methoxy-3-pyridyl)amino-3,5-dihydrophenazine:

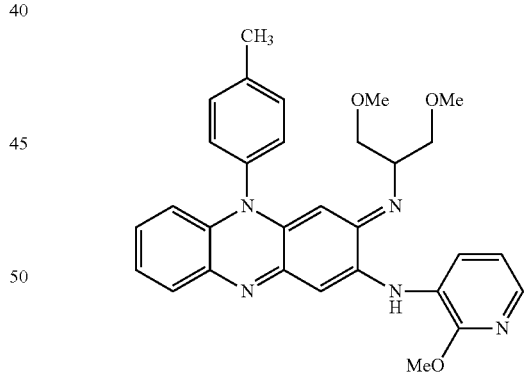

$^1$H NMR (300 MHz, CDCl$_3$) δ: 2.50 (3H, s, —CH$_3$), 3.24 (6H, s, —OCH$_3$, —OCH$_3$), 3.54 (3H, s, —OCH$_3$), 3.33-3.38 (2H, m, —CH—CH$_2$—), 3.50-3.55 (2H, m, —CH—CH$_2$—), 3.67-3.72 (1H, m, —CH$_2$—CH—CH$_2$—), 5.48 (1H, s, 4-H), 6.50 (1H, d, J=7.8 Hz, 6-H), 6.73 (1H, s, 1-H), 7.13-7.16 (3H, m, 7-H, 8-H, 9-H), 7.23 (2H, d, J=7.8 Hz, 2"-H, 6"-H), 7.47 (2H, d, J=7.8 Hz, 3"-H, 5"-H), 7.67-7.68 (1H, m, 6'-H), 7.80 (2H, m, 4'-H, 5'-H). $^{13}$C NMR (100 MHz, CDCl$_3$) δ: 21.36, 23.82, 58.21, 58.98, 74.28, 89.71, 98.99, 114.39, 122.79, 123.15, 127.59, 128.15, 128.38, 129.56, 131.79, 134.03, 134.84, 135.13, 135.68, 139.81, 143.89, 144.32, 150.69, 153.33, 153.46. HRMS (ESI-TOF$^+$): m/z [M+H]$^+$ calcd for C$_{30}$H$_{32}$N$_5$O$_3$: 510.2511; found: 510.2510.

TBI-374, 5-(4-Methylphenyl)-3-(1,3-dimethoxyisopropyl)imino-2-(6-methyl-3-pyridyl)amino-3,5-dihydrophenazine:

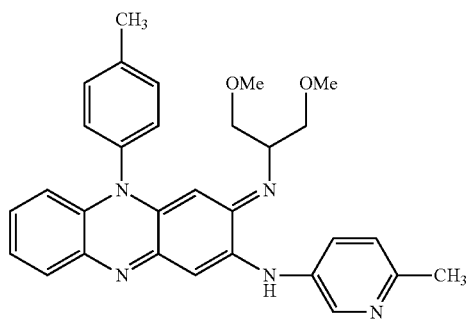 [SMILES: COCC(COC)/N=c1\cc2n(-c3ccc(C)cc3)c3ccccc3nc-2cc1Nc1ccc(C)nc1]

¹H NMR (300 MHz, CDCl₃) δ: 2.28 (3H, s, —CH₃), 3.01 (3H, s, —CH₃), 3.30 (6H, s, —OCH₃, —OCH₃), 3.36-3.44 (2H, m, —CH—CH₂—), 3.55-3.57 (2H, m, —CH—CH₂—), 3.72-3.76 (1H, m, —CH₂—CH—CH₂—), 5.49 (1H, s, 4-H), 6.49 (1H, d, J=8.4 Hz, 6-H), 6.73 (1H, s, 1-H), 7.14-7.17 (3H, m, 7-H, 8-H, 9-H), 7.23 (2H, d, 7.8 Hz, 2"-H, 6"-H), 7.47 (2H, d, J=7.8 Hz, 3"-H, 5"-H), 7.67-7.68 (1H, m, 2'-H), 7.80 (2H, m, 4'-H, 5"-H). ¹³C NMR (100 MHz, CDCl₃) δ: 21.26, 23.72, 58.31, 58.98, 74.28, 89.71, 99.99, 114.75, 123.22, 127.86, 128.42, 128.58, 131.58, 134.03, 134.84, 135.32, 135.68, 139.81, 143.23, 144.32, 150.69, 153.33, 153.46. HRMS (ESI-TOF⁺): m/z [M+H]⁺ calcd for C₃₀H₃₂N₅O₂: 494.2555; found: 494.2553.

TBI-375, 5-(3,4-Dichlorophenyl)-3-(1,3-dimethoxyisopropyl)imino-2-(2-methoxy-3-pyridyl)amino-3,5-dihydrophenazine:

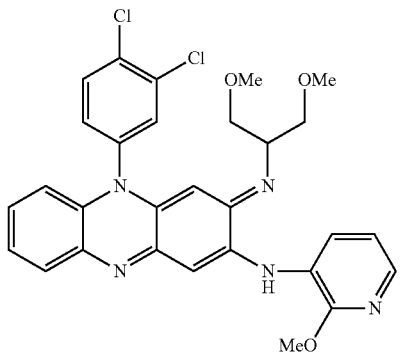

¹H NMR (300 MHz, CDCl₃) δ: 3.28 (3H, s, —OCH₃), 3.30 (6H, s, —OCH₃, —OCH₃), 3.36-3.44 (2H, m, —CH—CH₂—), 3.55-3.57 (2H, m, —CH—CH₂—), 3.72-3.76 (1H, m, —CH₂—CH—CH₂—), 5.49 (1H, s, 4-H), 6.49 (1H, d, J=8.4 Hz, 6-H), 6.89-6.93 (2H, m, 1-H, 9-H), 7.15-7.22 (3H, m, 7-H, 8-H, 5"-H), 7.49 (1H, d, J=2.4 Hz, 2"-H), 7.70 (1H, m, 6"-H), 7.78-7.84 (3H, m, 4'-H, 5'-H, 6'-H). ¹³C NMR (100 MHz, CDCl₃) δ: 53.67, 58.82, 59.10, 59.19, 74.48, 74.73, 90.59, 100.23, 113.75, 116.81, 123.22, 124.72, 125.00, 127.86, 128.42, 128.58, 131.58, 133.04, 135.32, 138.70, 138.94, 142.73, 150.95, 153.41, 155.44. HRMS (ESI-TOF⁺): m/z [M+H]⁺ calcd for C₂₉H₂₈Cl₂N₅O₃: 564.1578; found: 564.1577.

TBI-157, 5-(4-Trifluoromethoxyphenyl)-3-(1-methylethyl)imino-2-(3-pyridyl)amino-3,5-dihydrophenazine:

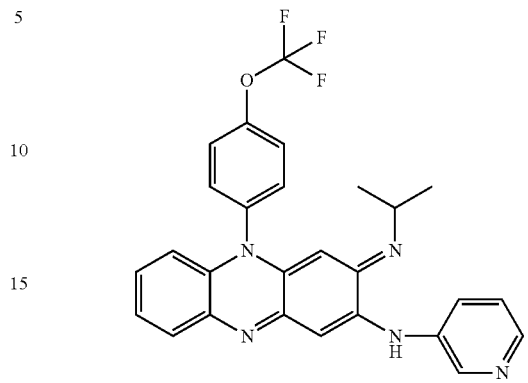

¹H NMR (300 MHz, CDCl₃) δ: 1.08-1.20 (d, J=6.6 Hz, 6H), 3.38-3.45 (m, J=6.3 Hz, 1H), 5.23 (s, 1H), 6.45 (m, 2H), 6.83 (s, 1H), 7.12-7.18 (m, 2H), 7.40-7.42 (m, 2H), 7.57-7.60 (m, 2H), 7.78 (1H, m), 8.33-8.35 (2H, m), 8.58 (1H, s). ¹³C NMR (100 MHz, CDCl₃) δ: 23.48, 49.44, 89.12, 99.41, 113.78, 123.06, 123.63, 127.79, 127.95, 128.37, 130.79, 131.45, 134.94, 135.60, 135.90, 136.77, 143.68, 143.98, 144.32, 149.73, 150.35, 150.95. HRMS (ESI-TOF⁺): m/z [M+H]⁺ calcd for C₂₇H₂₃F₃N₅O: 490.1870; found: 490.1869.

TBI-158, 5-(4-Trifluoromethoxyphenyl)-3-(N-isobutyl-4-piperidyl)imino-2-(3-pyridyl)amino-3,5-dihydrophenazine:

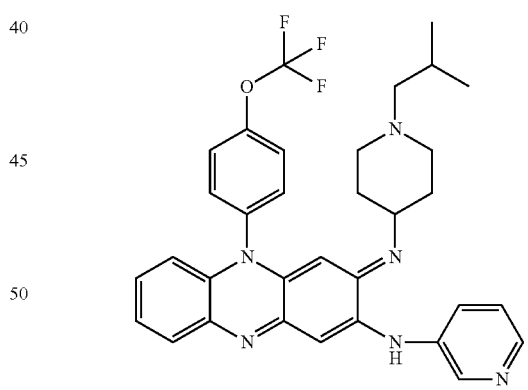

¹H NMR (300 MHz, CDCl₃) δ: 0.87-0.93 (d, J=6.0 Hz, 6H), 1.47-1.86 (m, 5H), 2.04 (brs, 4H), 2.78 (m, 2H), 3.07 (m, 1H), 5.19 (s, 1H), 6.52 (m, 1H), 6.85 (s, 1H), 7.19 (m, 2H), 7.26-7.32 (m, 1H), 7.40-7.43 (m, 2H), 7.59-7.62 (m, 2H), 7.70-7.72 (m, 1H), 7.76-7.79 (m, 1H), 8.33-8.34 (m, 1H), 8.59 (brs, 1H). ¹³C NMR (100 MHz, CDCl₃) δ: 20.97, 25.68, 32.28, 45.59, 52.49, 56.37, 67.04, 89.28, 99.45, 113.82, 123.15, 123.67, 123.90, 127.91, 128.46, 131.27, 134.95, 135.96, 136.70, 143.57, 143.96, 144.37, 149.75, 150.94. HRMS (ESI-TOF⁺): m/z [M+H]⁺ calcd for C₃₃H₃₄F₃N₆O: 587.2854; found: 587.2856.

TBI-159, 5-(4-Trifluoromethoxyphenyl)-3-(N-methyl-4-piperidyl)imino-2-(3-pyridyl)amino-3,5-dihydrophenazine:

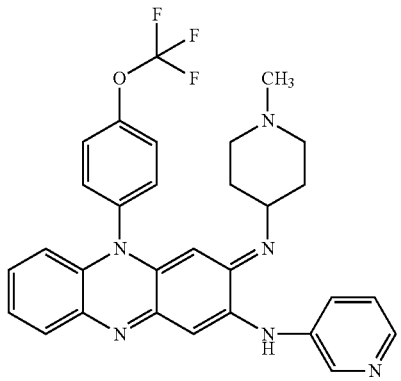 [SMILES: CN1CCC(/N=c2\cc3n(-c4ccc(OC(F)(F)F)cc4)c4ccccc4nc-3cc2Nc2cccnc2)CC1]

$^1$H NMR (300 MHz, CDCl$_3$) δ: 1.62-1.74 (m, 4H), 1.89-1.95 (m, 2H), 2.26 (s, 3H), 2.77-2.80 (m, 2H), 3.06 (m, 1H), 5.17 (s, 1H), 6.50-6.52 (d, J=7.2 Hz, 1H), 6.84 (s, 1H), 7.14-7.19 (m, 2H), 7.30-7.32 (m, 1H) 7.40-7.43 (d, J=8.4 Hz, 2H), 7.59-7.62 (d, J=8.4 Hz, 2H), 7.70-7.73 (m, 1H), 7.76-7.79 (m, 1H), 8.33-8.35 (m, 1H), 8.60 (brs, 1H). $^{13}$C NMR (100 MHz, CDCl$_3$) δ: 32.79, 46.39, 53.40, 54.19, 89.19, 99.43, 113.80, 123.17, 123.64, 123.93, 127.90, 128.02, 128.46, 130.75, 131.28, 134.98, 135.63, 136.00, 136.65, 143.60, 144.41, 149.72, 150.83, 151.10. HRMS (ESI-TOF$^+$): m/z [M+H]$^+$ calcd for C$_{30}$H$_{28}$F$_3$N$_6$O: 545.2368; found: 545.2370.

TBI-160, 5-(4-Trifluoromethoxyphenyl)-3-(2-morpholinoethyl)imino-2-pyridyl)amino-3,5-dihydrophenazine:

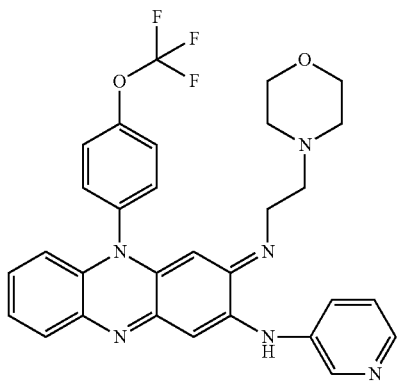 [SMILES: FC(F)(F)Oc1ccc(-n2c3c/c(=N\CCN4CCOCC4)c(Nc4cccnc4)cc-3nc3ccccc32)cc1]

$^1$H NMR (300 MHz, CDCl$_3$) δ: 2.47-2.50 (t, J=4.5 Hz, 4H), 2.70-2.75 (t, J=6.6 Hz, 2H), 3.35-3.39 (t, J=6.6 Hz, 2H), 3.68-3.71 (t, J=4.5 Hz, 4H), 5.36 (s, 1H), 6.57-6.59 (d, J=7.8 Hz, 1H), 7.00 (s, 1H), 7.27-7.35 (m, 3H), 7.43-7.46 (m, 2H), 7.61-7.64 (m, 1H), 7.79-7.84 (m, 2H), 8.36-8.38 (m, 1H), 8.64-8.65 (m, 1H). $^{13}$C NMR (100 MHz, CDCl$_3$) δ: 46.23, 53.72, 58.51, 66.66, 88.95, 100.75, 114.44, 123.68, 123.82, 124.26, 128.75, 128.89, 130.35, 130.82, 135.04, 135.30, 136.26, 136.67, 143.12, 144.03, 144.59, 149.60, 150.05, 153.02. HRMS (ESI-TOF$^+$): m/z [M+H]$^+$ calcd for C$_{30}$H$_{28}$F$_3$N$_6$O$_2$: 561.2633; found: 561.2630.

TBI-161, 5-(4-Trifluoromethoxyphenyl)-3-(4-tetrahydropyranyl)imino-2-(3-pyridyl)amino-3,5-dihydrophenazine:

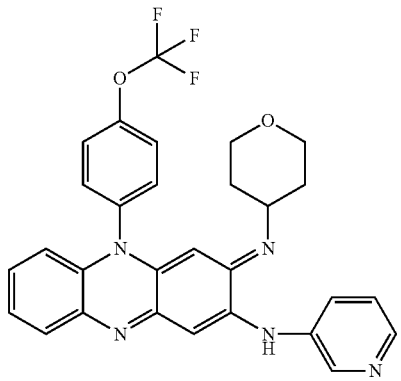 [SMILES: FC(F)(F)Oc1ccc(-n2c3c/c(=N\C4CCOCC4)c(Nc4cccnc4)cc-3nc3ccccc32)cc1]

$^1$H NMR (300 MHz, CDCl$_3$) δ: 1.57-1.69 (5H, m), 3.28-3.39 (3H, m), 3.95-4.00 (1H, m), 5.18 (1H, s), 6.50-6.53 (1H, m), 6.86 (1H, s), 7.15-7.20 (2H, m), 7.29-7.33 (1H, m), 7.40-7.43 (2H, m), 7.59-7.62 (2H, m), 7.71-7.79 (2H, m), 8.34-8.36 (1H, m), 8.59-8.60 (1H, m). $^{13}$C NMR (100 MHz, CDCl$_3$) δ: 33.41, 54.72, 66.21, 88.98, 99.57, 113.87, 123.69, 123.67, 123.90, 128.01, 128.09, 128.51, 130.72, 131.21, 135.09, 135.63, 135.93, 136.60, 143.59, 144.00, 149.76, 150.67, 151.12. HRMS (ESI-TOF$^+$): m/z [M+H]$^+$ calcd for C$_{29}$H$_{25}$F$_3$NO$_2$: 532.1976; found: 532.1978.

TBI-162, 5-(4-Trifluoromethoxyphenyl)-3-(4-methoxycyclohexyl)imino-2-(3-pyridyl)amino-3,5-dihydrophenazine:

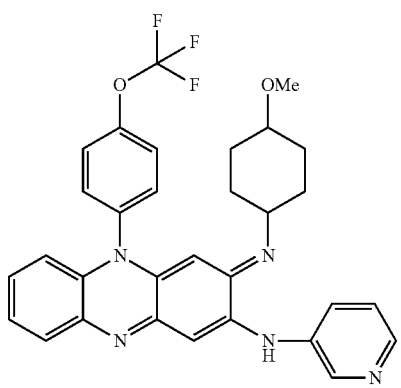 [SMILES: COC1CCC(/N=c2\cc3n(-c4ccc(OC(F)(F)F)cc4)c4ccccc4nc-3cc2Nc2cccnc2)CC1]

$^1$H NMR (300 MHz, CDCl$_3$) δ: 1.09-1.20 (2H, m), 1.37-1.44 (2H, 1.67-1.71 (2H, m), 2.08 (2H, m), 3.07 (1H, m), 3.16 (1H, m), 3.36 (3H, s), 5.20 (1H, s), 6.49 (2H, m), 6.84 (1H, s), 7.12-7.18 (2H, m), 7.40-7.43 (2H, m), 7.58-7.61 (2H, m), 7.79 (1H, m), 8.33-8.35 (2H, m), 8.58 (1H, s). HRMS (ESI-TOF$^+$): m/z [M+H]$^+$ calcd for C$_{31}$H$_{29}$F$_3$N$_5$O$_2$: 560.2257; found: 560.2259.

TBI-163, 5-(4-Trifluoromethoxyphenyl)-3-(N-cyclopentyl-4-piperidyl)imino-2-(3-pyridyl)amino-3,5-dihydrophenazine:

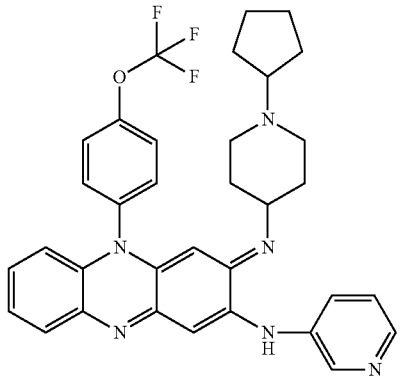 [SMILES: FC(F)(F)Oc1ccc(-n2c3c/c(=N\C4CCN(C5CCCC5)CC4)c(Nc4cccnc4)cc-3nc3ccccc32)cc1]

¹H NMR (300 MHz, CDCl₃) δ: 1.43-1.58 (4H, m), 1.68 (6H, m), 1.86 (2H, m), 2.01 (2H, m), 2.46-2.51 (1H, m), 2.93-2.97 (2H, m), 3.11 (1H, m), 5.30 (1H, s), 6.50-6.52 (1H, d), 6.85 (1H, s), 7.15-7.23 (2H, m), 7.27-7.33 (1H, m), 7.41-7.43 (2H, d), 7.59-7.62 (2H, d), 7.70-7.78 (2H, m), 8.33-8.35 (1H, d), 8.57-8.58 (1H, m). HRMS (ESI-TOF⁺): m/z [M+H]⁺ calcd for $C_{34}H_{34}F_3N_6O$: 599.2705; found: 599.2702.

TBI-164, 5-(4-Trifluoromethoxyphenyl)-3-(1-methylethyl)imino-2-(2-methoxy-3-pyridyl)amino-3,5-dihydrophenazine:

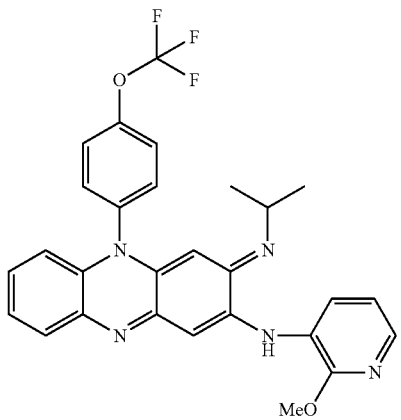 [SMILES: COc1ncccc1Nc1cc2nc3ccccc3n(-c3ccc(OC(F)(F)F)cc3)c-2c/c1=N\C(C)C]

¹H NMR (300 MHz, CDCl₃) δ: 1.08-1.11 (6H, d, J=6.6 Hz), 3.38-3.47 (1H, J=6.3 Hz), 4.03 (3H, s), 5.22 (1H, s), 6.42-6.45 (1H, m), 6.89-6.93 (2H, m), 7.10-7.23 (2H, m), 7.39-7.42 (2H, m), 7.57-7.59 (2H, m), 7.68-7.71 (1H, m), 7.80-7.85 (2H, m), 8.92 (1H, brs). ¹³C NMR (100 MHz, CDCl₃) δ: 23.47, 49.23, 53.70, 89.30, 100.08, 113.71, 116.77, 122.93, 123.61, 124.81, 124.92, 127.64, 128.25, 130.84, 131.54, 134.84, 135.60, 135.96, 138.85, 142.89, 149.68, 150.60, 151.23, 155.48. HRMS (ESI-TOF⁺): m/z [M+H]⁺ calcd for $C_{28}H_{25}F_3N_5O_2$: 520.1921; found: 520.1909.

TBI-165, 5-(4-Trifluoromethoxyphenyl)-3-(N-isobutyl-4-piperidyl)imino-2-(2-methoxy-3-pyridyl)amino-3,5-dihydrophenazine:

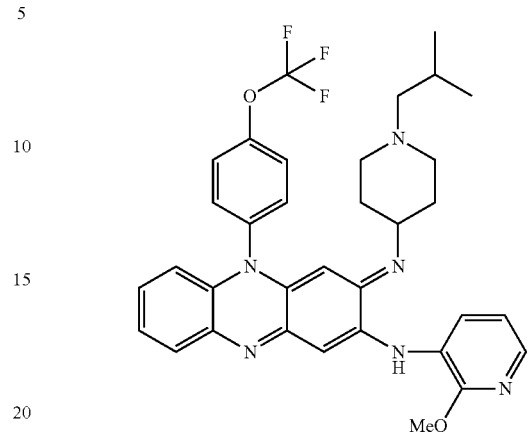

¹H NMR (300 MHz, CDCl₃) δ: 0.83-0.91 (6H, d, J=6.3 Hz), 1.63-1.80 (5H, m), 1.94 (2H, m), 2.05-2.07 (2H, m), 2.75-2.79 (2H, m), 3.11 (1H, brs), 4.03 (3H, s), 5.18 (1H, s), 6.47-6.49 (1H, m), 6.89-6.93 (2H, m), 7.10-7.23 (2H, m), 7.39-7.42 (2H, m), 7.57-7.59 (2H, m), 7.68-7.71 (1H, m), 7.80-7.85 (2H, m), 8.92 (1H, brs). ¹³C NMR (100 MHz, CDCl₃) δ: 21.06, 25.68, 32.78, 52.21, 53.71, 55.65, 67.32, 89.32, 100.14, 113.74, 116.80, 119.15, 123.02, 124.40, 124.88, 127.72, 128.33, 130.80, 131.44, 134.92, 135.64, 136.02, 138.69, 142.71, 149.68, 151.01, 151.21, 155.33. HRMS (ESI-TOF⁺): m/z [M+H]⁺ calcd for $C_{34}H_{36}F_3N_6O_2$: 617.3442; found: 617.3443.

TBI-166, 5-(4-Trifluoromethoxyphenyl)-(4-methoxycyclohexyl)imino-2-(2-methoxy-3-pyridyl)amino-3,5-dihydrophenazine:

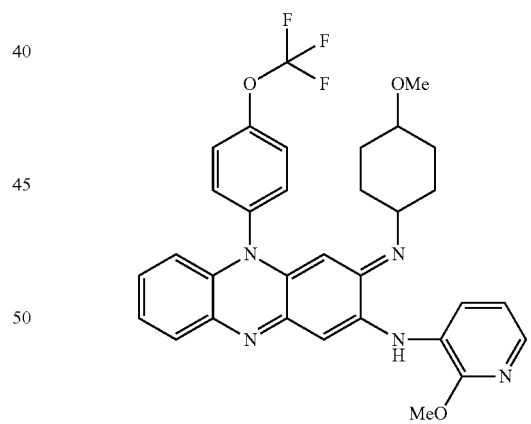

¹H NMR (300 MHz, CDCl₃) δ: 1.14-1.25 (2H, m), 1.38-1.49 (2H, m), 1.68-1.72 (2H, m), 2.04-2.08 (2H, m), 3.06-3.13 (1H, m), 3.19-3.26 (1H, m), 3.35 (3H, m), 4.02 (3H, s), 5.19 (1H, s), 6.47-6.49 (1H, m), 6.89-6.93 (2H, m), 7.12-7.21 (2H, m), 7.39-7.42 (2H, m), 7.57-7.59 (2H, m), 7.69-7.71 (1H, m), 7.80-7.85 (2H, m), 8.92 (1H, brs). ¹³C NMR (100 MHz, CDCl₃) δ: 29.44, 30.78, 53.71, 55.74, 56.95, 78.28, 89.29, 100.20, 113.78, 116.82, 123.02, 123.67, 124.65, 124.82, 127.77, 128.31, 130.76, 131.47, 134.88, 135.63, 135.87, 138.78, 142.73, 149.73, 151.14, 151.23, 155.36. HRMS (ESI-TOF⁺): m/z [M+H]⁺ calcd for $C_{32}H_{31}F_3N_5O_3$: 590.2978; found: 590.2977.

TBI-167, 5-(4-Trifluoromethoxyphenyl)-3-(4-tetrahydropyranyl)imino-2-(2-methoxy-3-pyridyl)amino-3,5-dihydrophenazine:

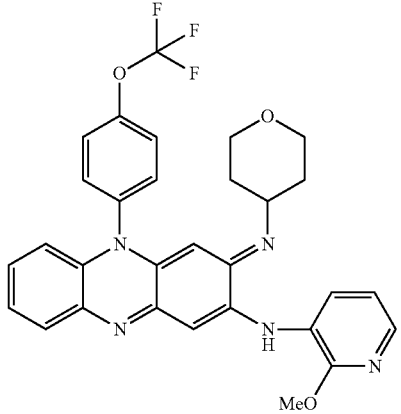 [SMILES: COc1ncccc1Nc1cc2nc3ccccc3n(-c3ccc(OC(F)(F)F)cc3)c-2c/c1=N\C1CCOCC1]

¹H NMR (300 MHz, CDCl₃) δ: 1.65-1.67 (4H, m), 3.35-3.48 (4H, 3.97-4.02 (1H, m), 4.03 (3H, s), 5.18 (1H, s), 6.48-6.51 (1H, m), 6.90-6.93 (2H, m), 7.16-7.21 (2H, m), 7.40-7.43 (2H, m), 7.59-7.62 (2H, m), 7.72-7.74 (1H, m), 7.81-7.86 (2H, m), 9.03 (1H, brs). ¹³C NMR (100 MHz, CDCl₃) δ: 33.23, 53.76, 53.82, 65.79, 89.05, 100.27, 113.82, 116.82, 123.17, 123.84, 124.48, 124.79, 127.86, 128.40, 130.76, 131.33, 135.06, 135.65, 135.95, 138.83, 142.66, 149.72, 150.96, 151.22, 155.34. HRMS (ESI-TOF⁺): m/z [M+H]⁺ calcd for $C_{30}H_{27}F_3N_5O_3$: 562.2109; found: 562.2107.

TBI-168, 5-(4-Trifluoromethoxyphenyl)-3-(N-methyl-4-piperidyl)imino-2-(2-methoxy-3-pyridyl)amino-3,5-dihydrophenazine:

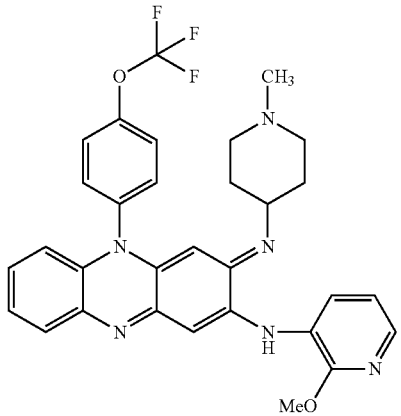 [SMILES: COc1ncccc1Nc1cc2nc3ccccc3n(-c3ccc(OC(F)(F)F)cc3)c-2c/c1=N\C1CCN(C)CC1]

¹H NMR (300 MHz, CDCl₃) δ: 1.68-1.69 (4H, m), 2.07 (2H, brs), 2.30 (3H, s), 2.77-2.81 (2H, m), 3.15 (1H, s), 4.03 (3H, s), 5.17 (1H, s), 6.47-6.50 (1H, m), 6.89-6.95 (2H, m), 7.13-7.22 (2H, m), 7.39-7.42 (2H, m), 7.58-7.61 (2H, m), 7.70-7.73 (1H, m), 7.80-7.85 (2H, m), 9.06 (1H, brs). HRMS (ESI-TOF⁺): m/z [M+H]⁺ calcd for $C_{31}H_{30}F_3N_6O_2$: 575.2443; found: 575.2446.

TBI-169, 5-(4-Trifluoromethoxyphenyl)-3-(2-morpholinoethyl)imino-2-(2-methoxy-3-pyridyl)amino-3,5-dihydrophenazine:

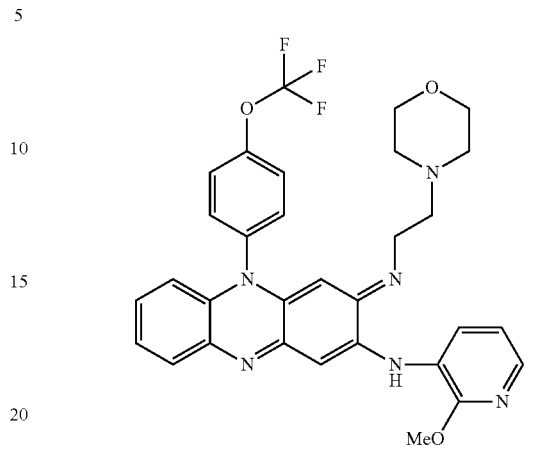

¹H NMR (300 MHz, CDCl₃) δ: 2.24-2.32 (4H, m), 2.46-2.54 (2H, m), 2.72-2.77 (2H, m), 3.31-3.36 (2H, m), 3.69-3.72 (2H, m), 4.03 (3H, s), 5.23 (1H, s), 6.49 (2H, m), 6.84 (1H, s), 7.12-7.18 (2H, m), 7.39-7.42 (2H, m), 7.56-7.59 (2H, m), 7.75 (1H, m), 7.81-7.86 (2H, m). HRMS (ESI-TOF⁺): m/z [M+H]⁺ calcd for $C_{31}H_{30}F_3N_6O_3$: 591.2479; found: 591.2481.

TBI-1001, 5-(4-Fluorophenyl)-3-(4-methoxycyclohexyl)imino-2-(6-methyl-3-pyridyl)amino-3,5-dihydrophenazine:

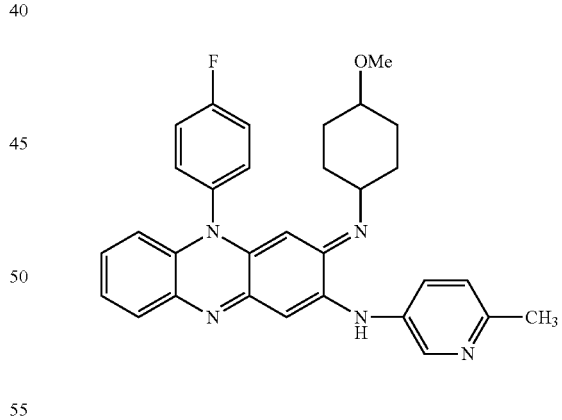

¹H NMR (300 MHz, CDCl₃) δ: 8.44 (1H, d, J=2.1 Hz), 7.69 (2H, m), 7.42 (2H, t, J=8.4 Hz), 7.32 (2H, dd, J=8.7, 4.5 Hz), 7.16 (3H, m), 6.72 (1H, s), 6.48 (1H, dd, J=7.5 Hz, 1.8 Hz), 5.25 (1H, s), 3.36 (3H, s), 3.08 (1H, m), 3.07 (1H, m), 2.56 (3H, s), 2.06 (2H, m), 1.70 (2H, m), 1.43 (2H, m), 1.13 (2H, m). ¹³C NMR (100 MHz, CDCl₃) δ: 162.7, 153.4, 151.2, 150.9, 144.3, 143.7, 135.7, 135.1, 134.0, 133.4, 131.6, 130.8, 130.7, 129.4, 128.3, 127.7, 123.0, 118.4, 113.9, 98.9, 89.1, 78.5, 65.5, 55.8, 31.2, 30.0, 23.8. HRMS (ESI-TOF⁺): m/z [M+H]⁺ calcd for $C_{31}H_{31}FN_5O$: 508.2513; found: 508.2512.

TBI-1002, 5-(4-Fluorophenyl)-3-(4-methoxycyclohexyl)imino-2-(2-methoxy-3-pyridyl)amino-3,5-dihydrophenazine:

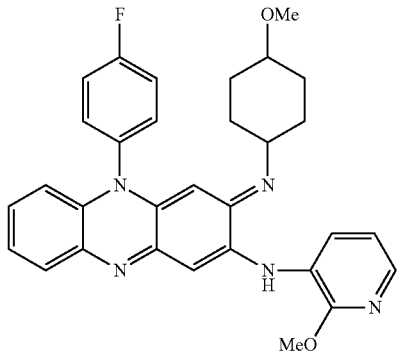 [SMILES: COc1ncccc1Nc1cc2nc3ccccc3n(-c3ccc(F)cc3)c-2c/c1=N\C1CCC(OC)CC1]

$^1$H NMR (300 MHz, CDCl$_3$) δ: 8.92 (1H, s), 7.85 (1H, d, J=7.5 Hz), 7.81 (1H, d, J=4.8 Hz), 7.70 (1H, dd, J=7.5 Hz, 1.2 Hz), 7.42 (2H, t, J=8.4 Hz), 7.32 (2H, dd, J=8.4 Hz, 4.8 Hz), 7.16 (2H, m), 6.94 (1H, s), 6.90 (1H, dd, J=7.5 Hz, 2.7 Hz), 6.48 (1H, dd, J=7.5 Hz, 1.5 Hz), 5.24 (1H, s), 4.03 (3H, s), 3.37 (3H, s), 3.25 (1H, m), 3.12 (1H, m), 2.08 (2H, m), 1.72 (2H, m), 1.43 (2H, m), 1.23 (2H, m). $^{13}$C NMR (100 MHz, CDCl$_3$) δ: 162.8, 155.4, 151.3, 151.2, 142.7, 138.7, 135.7, 135.1, 133.4, 131.8, 130.9, 130.8, 128.3, 127.7, 122.9, 118.4, 116.8, 113.9, 100.2, 89.2, 78.3, 57.0, 55.8, 53.7, 30.8, 29.5. HRMS (ESI-TOF$^+$): m/z [M+H]$^+$ calcd for C$_{31}$H$_{31}$FN$_5$O$_2$: 524.2462; found: 524.2457.

TBI-1003, 5-(4-Fluorophenyl)-3-(4-tetrahydropyranyl)imino-2-(2-methoxy-3-pyridyl)amino-3,5-dihydrophenazine:

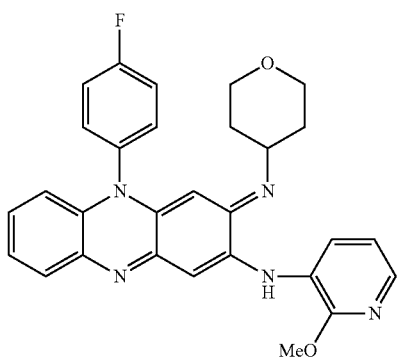

$^1$H NMR (300 MHz, CDCl$_3$) δ: 9.08 (1H, s), 7.85 (1H, dd, J=7.8, 1.5 Hz), 7.81 (1H, dd, J=5.1, 1.5 Hz), 7.72 (1H, dd, J=7.5, 1.8 Hz), 7.43 (2H, t, J=8.7 Hz), 7.33 (2H, dd, J=8.7, 4.8 Hz), 7.17 (2H, m), 6.97 (1H, s), 6.92 (1H, dd, J=7.8, 5.1 Hz), 6.48 (1H, dd, J=7.8, 1.2 Hz), 5.24 (1H, s), 4.04 (3H, s), 4.00 (2H, m), 3.50 (2H, m), 3.42 (1H, m), 1.69 (4H, m). $^{13}$C NMR (100 MHz, CDCl$_3$) δ: 162.8, 155.3, 151.2, 151.0, 142.6, 138.7, 135.7, 135.2, 133.4, 131.7, 130.8, 130.7, 128.3, 127.8, 124.9, 124.3, 123.0, 118.4, 116.8, 113.9, 100.3, 88.9, 65.6, 53.7, 53.3, 33.3. HRMS (ESI-TOF$^+$): m/z [M+H]$^+$ calcd for C$_{29}$H$_{27}$FN$_5$O$_2$: 496.2149; found: 496.2145.

TBI-1004, 5-(4-Fluorophenyl)-3-(1-methylethyl)imino-2-(2-methoxy-3-pyridyl)amino-3,5-dihydrophenazine:

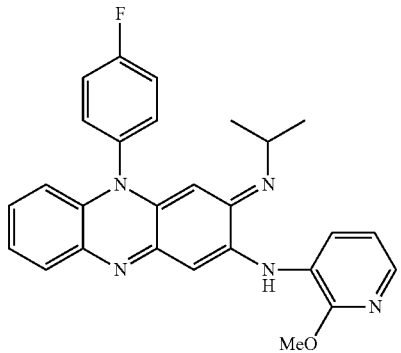 [SMILES: COc1ncccc1Nc1cc2nc3ccccc3n(-c3ccc(F)cc3)c-2c/c1=N\C(C)C]

$^1$H NMR (300 MHz, CDCl$_3$) δ: 7.83 (m, 2H), 7.70 (dd, J=7.5, 1.5 Hz, 1H), 7.42 (t, J=8.7 Hz, 2H), 7.34 (dd, J=8.7, 4.8 Hz, 2H), 7.16 (m, 2H), 6.91 (m, 2H), 6.47 (d, J=7.2 Hz, 1H), 5.28 (s, 1H), 4.03 (s, 3H), 3.45 (m, 1H), 1.11 (d, J=6.6 Hz, 6H). $^{13}$C NMR (100 MHz, CDCl$_3$) δ: 162.8 (d, J=248.9 Hz), 155.6, 151.1, 150.8, 142.9, 139.0, 135.7, 135.1, 133.5, 131.7, 130.9, 130.8, 128.2, 127.7, 125.3, 124.8, 123.0, 118.5 (d, J=23.1 Hz), 116.8, 113.9, 100.3, 89.3, 53.7, 49.3, 23.4. HRMS (ESI-TOF$^+$): m/z [M+H]$^+$ calcd for C$_{27}$H$_{25}$FN$_5$O: 454.2043; found: 454.2042.

TBI-1005, 5-(4-Fluorophenyl)-3-(N-methyl-4-piperidyl)imino-2-(2-methoxy-3-pyridyl)amino-3,5-dihydrophenazine:

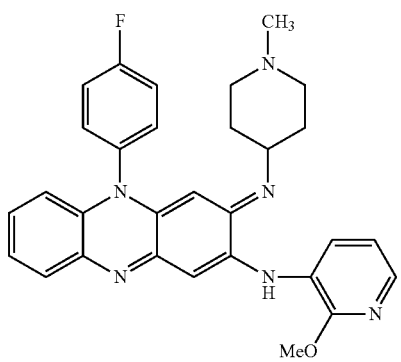 [SMILES: COc1ncccc1Nc1cc2nc3ccccc3n(-c3ccc(F)cc3)c-2c/c1=N\C1CCN(C)CC1]

$^1$H NMR (300 MHz, CDCl$_3$) δ: 9.12 (s, 1H), 7.85 (dd, J=7.8, 1.5 Hz, 1H), 7.80 (dd, J=4.8, 1.5 Hz, 1H), 7.71 (dd, J=7.2, 1.5 Hz, 1H), 7.43 (t, J=8.7 Hz, 2H), 7.33 (dd, J=8.7, 5.1 Hz, 2H), 7.16 (m, 2H), 6.97 (s, 1H), 6.92 (dd, J=7.8, 4.8 Hz, 1H), 6.48 (d, J=7.8 Hz, 1H), 5.24 (s, 1H), 4.04 (s, 3H), 3.21 (m, 1H), 2.75 (m, 2H), 2.31 (s, 3H), 2.14 (m, 2H), 1.70 (m, 4H). $^{13}$C NMR (100 MHz, CDCl$_3$) δ: 162.8 (d, J=250 Hz), 155.3, 151.1, 151.0, 142.6, 138.6, 135.6, 135.2, 133.4, 131.8, 130.9, 130.8, 128.3, 127.7, 125.0, 124.1, 123.0, 118.4 (d, J=23.1 Hz), 116.8, 113.9, 100.2, 89.0, 53.7, 53.4, 46.5, 32.6. HRMS (ESI-TOF$^+$): m/z [M+H]$^+$ calcd for C$_{30}$H$_{30}$FN$_6$O: 509.2465; found: 509.2466.

TBI-1008, 5-(4-Fluorophenyl)-3-(4-hydroxycyclohexyl)imino-2-(2-methoxy-3-pyridyl)amino-3,5-dihydrophenazine:

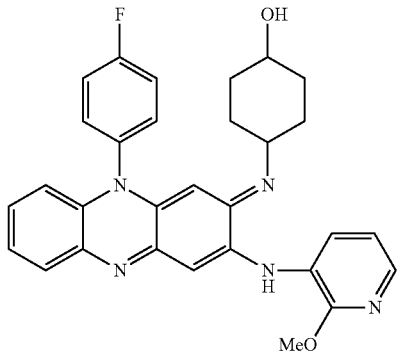 [SMILES: COc1ncccc1Nc1cc2nc3ccccc3n(-c3ccc(F)cc3)c-2c/c1=N\C1CCC(O)CC1]

$^1$H NMR (300 MHz, CDCl$_3$) δ: 7.84 d, J=7.8 Hz, 1H), 7.81 (d, J=5.1 Hz, 1H), 7.70 (dd, J=7.5, 1.5 Hz, 1H), 7.43 (t, J=8.7 Hz, 2H), 7.33 (dd, J=8.7, 5.1 Hz, 2H), 7.16 (m, 2H), 6.94 (s, 1H), 6.90 (dd, J=7.8, 5.1 Hz, 1H), 6.48 (d, J=7.5 Hz, 1H), 5.24 (s, 1H), 4.03 (s, 3H), 3.73 (m, 1H), 3.10 (m, 1H), 2.03 (m, 2H), 1.70 (m, 2H), 1.48 (m, 2H), 1.27 (m, 2H). $^{13}$C NMR (100 MHz, CDCl$_3$) δ: 162.8 (d, J=249.3 Hz), 155.4, 151.4, 151.1, 142.8, 138.8, 135.6, 135.1, 133.4, 131.8, 130.9, 130.8, 128.3, 127.7, 124.8, 124.7, 122.9, 118.4 (d, J=22.7 Hz), 116.8, 113.9, 100.2, 89.2, 69.8, 56.8, 53.7, 33.4, 30.9. HRMS (ESI-TOF$^+$): m/z [M+H]$^+$ calcd for C$_{30}$H$_{29}$FN$_5$O$_2$: 510.2305; found: 510.2304.

TBI-1009, 5-(4-Fluorophenyl)-3-cyclohexylimino-2-(2-methoxy-3-pyridyl)amino-3,5-dihydrophenazine:

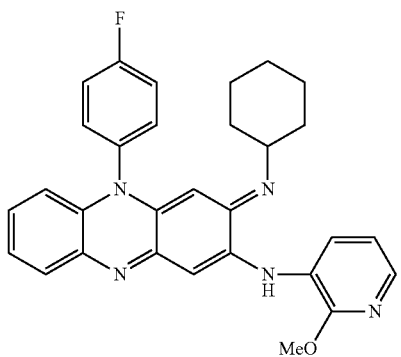

$^1$H NMR (300 MHz, CDCl$_3$) δ: 9.04 (s, 1H), 7.84 (d, J=7.5 Hz, 1H), 7.80 (d, J=4.8 Hz, 1H), 7.69 (d, J=7.5 Hz, 1H), 7.42 (t, J=8.4 Hz, 2H), 7.34 (dd, J=8.4, 4.8 Hz, 2H), 7.14 (m, 2H), 6.91 (m, 2H), 6.47 (d, J=8.1 Hz, 1H), 5.24 (s, 1H), 4.03 (s, 3H), 3.13 (m, 1H), 1.76 (m, 2H), 1.59 (m, 3H), 1.33 (m, 5H). $^{13}$C NMR (100 MHz, CDCl$_3$) δ: 162.8 (d, J=248.9 Hz), 155.4, 151.4, 150.6, 142.9, 138.6, 135.6, 135.0, 133.5, 131.9, 130.9, 130.8, 128.2, 127.6, 125.0, 124.5, 122.8, 118.3 (d, J=22.6 Hz), 116.8, 113.8, 100.1, 89.4, 57.4, 53.7, 33.5, 26.0, 24.3. HRMS (ESI-TOF$^+$): m/z [M+H]$^+$ calcd for C$_{30}$H$_{29}$FN$_5$O: 494.2356; found: 494.2358.

TBI-1010, 5-(4-Fluorophenyl)-3-cyclopropylimino-2-(2-methoxy-3-pyridyl)amino-3,5-dihydrophenazine:

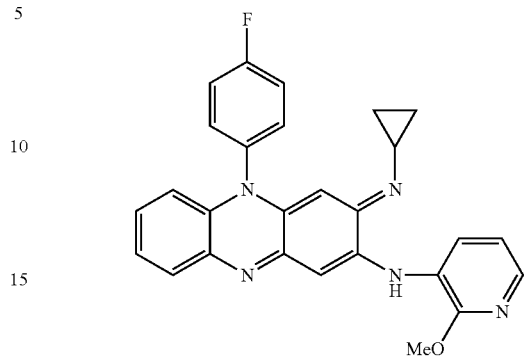

$^1$H NMR (300 MHz, CDCl$_3$) δ: 8.58 (s, 1H), 7.81 (m, 2H), 7.66 (d, J=7.2 Hz, 1H), 7.37 (m, 4H), 7.13 (m, 2H), 6.90 (m, 2H), 6.42 (d, J=7.8 Hz, 1H), 5.52 (s, 1H), 3.99 (s, 3H), 2.73 (m, 1H), 0.88 (d, J=4.8 Hz, 2H), 0.82 (s, 2H). $^{13}$C NMR (100 MHz, CDCl$_3$) δ: 162.8 (d, J=248.9 Hz), 155.4, 152.7, 151.5, 142.7, 138.9, 135.8, 134.9, 133.5, 132.0, 131.0, 130.9, 128.1, 127.6, 125.0, 124.8, 122.8, 118.5 (d, J=22.7 Hz), 116.8, 113.8, 100.1, 89.6, 53.7, 32.9, 10.0. HRMS (ESI-TOF$^+$): m/z [M+H]$^+$ calcd for C$_{27}$H$_{23}$FN$_5$O: 452.1887; found: 452.1885.

TBI-1012, 5-(4-Fluorophenyl)-3-(4-tetrahydropyranyl)imino-2-(2-methyl-3-pyridyl)amino-3,5-dihydrophenazine:

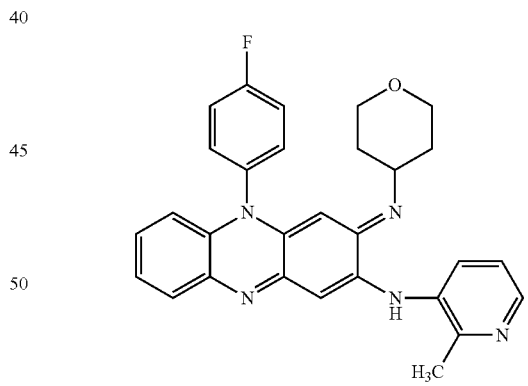

$^1$H NMR (300 MHz, CDCl$_3$) δ: 8.29 (d, J=4.5 Hz, 1H), 7.83 (d, J=8.1 Hz, 1H), 7.70 (d, J=7.8 Hz, 1H), 7.44 (t, J=8.1 Hz, 2H), 7.33 (dd, J=8.1, 4.8 Hz, 2H), 7.18 (m, 3H), 6.64 (s, 1H), 6.49 (d, J=7.2 Hz, 1H), 5.26 (s, 1H), 3.98 (m, 2H), 3.43 (m, 3H), 2.50 (s, 3H), 1.66 (m, 4H). $^{13}$C NMR (100 MHz, CDCl$_3$) δ: 162.8 (d, J=249.7 Hz), 152.1, 151.1, 150.7, 144.2, 144.0, 135.6, 135.3, 134.6, 133.4, 131.5, 130.8, 130.7, 129.0, 128.3, 127.8, 123.1, 121.7, 118.5 (d, J=22.7 Hz), 114.0, 99.0, 88.8, 65.9, 53.7, 33.3, 20.9. HRMS (ESI-TOF$^+$): m/z [M+H]$^+$ calcd for C$_{29}$H$_{27}$FN$_5$O: 480.2200; found: 480.2197.

TBI-1013, 5-(4-Fluorophenyl)-3-(4-methoxycyclohexyl)imino-2-(2-methyl-3-pyridyl)amino-3,5-dihydrophenazine:

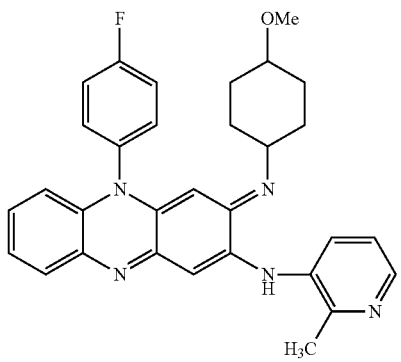 [SMILES: COC1CCC(/N=c2\cc3n(-c4ccc(F)cc4)c4ccccc4nc-3cc2Nc2cccnc2C)CC1]

$^1$H NMR (300 MHz, CDCl$_3$) δ: 8.27 (d, J=4.2 Hz, 1H), 7.81 (d, J=8.1 Hz, 1H), 7.68 (dd, J=7.5, 1.8 Hz, 1H), 7.42 (t, J=8.7 Hz, 2H), 7.33 (dd, J=8.7, 5.1 Hz, 2H), 7.16 (m, 3H), 6.60 (s, 1H), 6.49 (dd, J=7.2, 1.8 Hz, 1H), 5.26 (s, 1H), 3.36 (s, 3H), 3.22 (m, 1H), 3.11 (m, 1H), 2.54 (s, 3H), 2.06 (m, 2H), 1.72 (m, 2H), 1.42 (m, 2H), 1.21 (m, 2H). $^{13}$C NMR (100 MHz, CDCl$_3$) δ: 162.8 (d, J=249.7 Hz), 152.0, 151.1, 150.9, 144.1, 144.0, 135.6, 135.1, 134.7, 133.4, 133.3, 131.6, 130.8, 130.7, 128.9, 128.2, 127.7, 123.0, 121.7, 118.4 (d, J=22.7 Hz), 113.9, 98.9, 89.0, 57.0, 55.8, 31.0, 29.7, 20.9. HRMS (ESI-TOF$^+$): m/z [M+H]$^+$ calcd for C$_{31}$H$_{31}$FN$_5$O: 508.2513; found: 508.2516.

TBI-1015, 5-(4-Fluorophenyl)-3-(4-hydroxycyclohexyl)imino-2-(2-methyl-3-pyridyl)amino-3,5-dihydrophenazine:

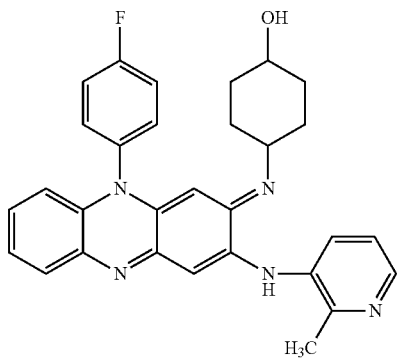

$^1$H NMR (300 MHz, CDCl$_3$) δ: 8.28 (d, J=4.8 Hz, 1H), 7.82 (d, J=8.1 Hz, 1H), 7.69 (d, J=7.5 Hz, 1H), 7.44 (t, J=8.1 Hz, 2H), 7.34 (dd, J=8.1, 4.5 Hz, 2H), 7.17 (m, 3H), 6.61 (s, 1H), 6.50 (d, J=7.8 Hz, 1H), 5.26 (s, 1H), 3.71 (m, 1H), 3.1 (m, 1H), 2.54 (s, 3H), 2.00 (m, 2H), 1.71 (m, 2H), 1.46 (m, 2H), 1.28 (m, 2H). $^{13}$C NMR (100 MHz, CDCl$_3$) δ: 162.8 (d, J=249.3 Hz), 152.1, 151.2, 150.9, 144.2, 144.0, 135.6, 135.2, 134.7, 133.4, 131.6, 130.8, 130.7, 129.1, 128.3, 127.7, 123.0, 121.7, 118.4 (d, J=22.7 Hz), 114.0, 98.9, 89.0, 69.8, 56.9, 33.5, 31.1, 20.9. HRMS (ESI-TOF$^+$): m/z [M+H]$^+$ calcd for C$_{30}$H$_{29}$FN$_5$O: 494.2356; found: 494.2357.

TBI-1014, 5-(4-Fluorophenyl)-3-cyclopropylimino-2-(2-methyl-3-pyridyl)amino-3,5-dihydrophenazine:

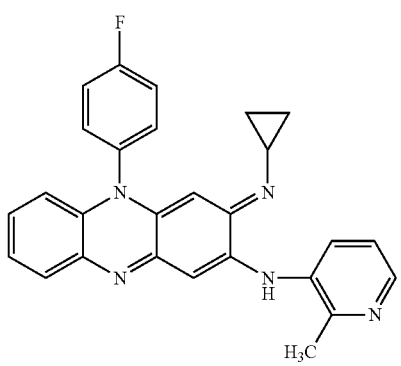 [SMILES: Cc1ncccc1Nc1cc2nc3ccccc3n(-c3ccc(F)cc3)c-2c/c1=N\C1CC1]

$^1$H NMR (300 MHz, CDCl$_3$) δ: 8.28 (d, J=7.5 Hz, 1H), 7.78 (d, J=8.1 Hz, 1H), 7.65 (d, J=7.2 Hz, 1H), 7.38 (m, 4H), 7.14 (m, 3H), 6.49 (s, 1H), 6.43 (d, J=8.1 Hz, 1H), 5.54 (s, 1H), 2.76 (m, 1H), 2.51 (s, 3H), 0.90 (m, 2H), 0.80 (m, 2H). $^{13}$C NMR (100 MHz, CDCl$_3$) δ: 162.8 (d, J=250.0 Hz), 152.6, 152.3, 151.2, 144.5, 144.1, 135.7, 135.0, 134.5, 133.5, 131.8, 131.0, 130.9, 129.8, 128.1, 127.6, 122.9, 121.7, 118.5 (d, J=22.6 Hz), 113.9, 98.9, 89.4, 32.8, 20.9, 10.1. HRMS (ESI-TOF$^+$): m/z [M+H]$^+$ calcd for C$_{27}$H$_{23}$FN$_5$: 436.1937; found: 436.1939.

TBI-1016, 5-(4-Fluorophenyl)-3-cyclobutylimino-2-(2-methoxy-3-pyridyl)amino-3,5-dihydrophenazine:

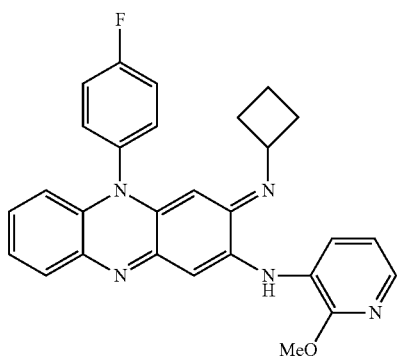 [SMILES: COc1ncccc1Nc1cc2nc3ccccc3n(-c3ccc(F)cc3)c-2c/c1=N\C1CCC1]

$^1$H NMR (300 MHz, CDCl$_3$) δ: 7.83 (m, 2H), 7.70 (d, J=7.5 Hz, 1H), 7.42 (t, J=8.1 Hz, 2H), 7.32 (dd, J=8.1, 4.5 Hz, 2H), 7.16 (m, 2H), 6.91 (m, 2H), 6.47 (d, J=7.5 Hz, 1H), 5.07 (s, 1H), 4.04 (s, 3H), 3.88 (m, 1H), 2.18 (m, 2H), 2.06 (m, 2H), 1.75 (m, 2H). $^{13}$C NMR (100 MHz, CDCl$_3$) δ: 162.8 (d, J=249.3 Hz), 155.4, 151.5, 151.2, 142.7, 138.8, 135.7, 134.6, 133.4, 131.7, 131.0, 130.9, 128.3, 127.7, 124.8, 123.0, 118.4 (d, J=22.7 Hz), 116.8, 113.9, 100.3, 90.8, 54.9, 53.7, 32.0, 16.0. HRMS (ESI-TOF$^+$): [M+H]$^+$ calcd for C$_{28}$H$_{25}$FN$_5$O: 466.2043; found: 466.2042.

TBI-1017, 5-(4-Fluorophenv-3-cyclobutylimino-2-(6-methyl-3-pyridyl)amino-3,5-dihydrophenazine:

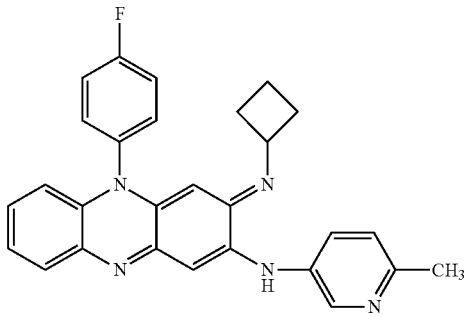 [SMILES: Cc1ccc(Nc2cc3nc4ccccc4n(-c4ccc(F)cc4)c-3c/c2=N\C2CCC2)cn1]

$^1$H NMR (300 MHz, CDCl$_3$) δ: 8.46 (s, 1H), 7.69 (m, 2H), 7.43 (t, J=8.4 Hz, 2H), 7.34 (dd, J=8.4, 5.1 Hz, 2H), 7.16 (m, 3H), 6.72 (s, 1H), 6.49 (d, J=8.4 Hz, 1H), 5.09 (s, 1H), 3.86 (m, 1H), 2.57 (s, 3H), 2.17 (m, 2H), 2.05 (m, 2H), 1.74 (m, 2H). $^{13}$C NMR (100 MHz, CDCl$_3$) δ: 162.8 (d, J=249.3 Hz), 153.5, 151.3, 150.9, 144.3, 143.8, 135.7, 134.7, 133.9, 133.5, 131.5, 130.9, 130.8, 129.5, 128.3, 127.7, 123.1 (d, J=16.5 Hz), 118.4 (d, J=22.7 Hz), 113.9, 98.9, 90.6, 54.8, 32.0, 23.8, 16.0. HRMS (ESI-TOF$^+$): m/z [M+H]$^+$ calcd for C$_{28}$H$_{25}$FN$_5$: 450.2094; found: 450.2092.

TBI-1018, 5-(4-Fluorophenyl)-3-cyclobutylimino-2-(2-methyl-3-pyridyl)amino-3,5-dihydrophenazine:

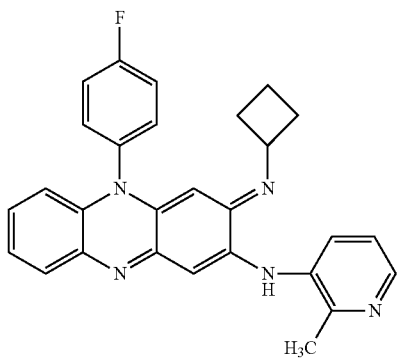 [SMILES: Cc1ncccc1Nc1cc2nc3ccccc3n(-c3ccc(F)cc3)c-2c/c1=N\C1CCC1]

$^1$H NMR (300 MHz, CDCl$_3$) δ: 8.30 (d, J=4.8 Hz, 1H), 7.80 (d, J=7.5 Hz, 1H), 7.68 (d, J=7.5 Hz, 1H), 7.44 (t, J=8.4 Hz, 2H), 7.34 (dd, J=8.4, 4.8 Hz, 2H), 7.17 (m, 3H), 6.55 (s, 1H), 6.49 (d, J=7.8 Hz, 1H), 5.10 (s, 1H), 3.91 (m, 1H), 2.57 (s, 3H), 2.18 (m, 2H), 2.04 (m, 2H), 1.78 (m, 2H). $^{13}$C NMR (100 MHz, CDCl$_3$) δ: 162.8 (d, J=248.9 Hz), 152.5, 151.2, 150.9, 144.4, 144.2, 135.7, 134.7, 134.6, 133.5, 131.5, 130.9, 130.8, 129.6, 128.2, 127.7, 123.0, 121.7, 118.4 (d, J=22.7 Hz), 114.0, 99.0, 90.5, 54.8, 32.0, 21.0, 16.0. HRMS (ESI-TOF$^+$): m/z [M+H]$^+$ calcd for C$_{28}$H$_{25}$FN$_5$: 450.2094; found: 450.2096.

TBI-1019, 5-(3-Trifluoro ethoxyphenyl)-3-(1-methylethyl)imino-2-(3-pyridyl)amino-3,5-dihydrophenazine:

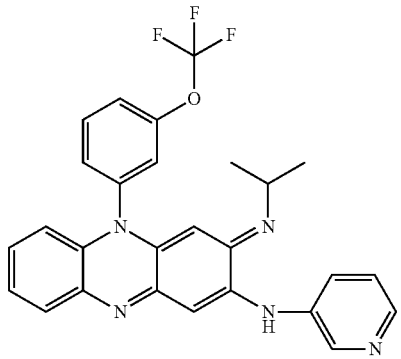 [SMILES: CC(C)/N=c1\cc2n(-c3cccc(OC(F)(F)F)c3)c3ccccc3nc-2cc1Nc1cccnc1]

$^1$H NMR (300 MHz, CDCl$_3$) δ: 8.59 (d, J=2.1 Hz, 1H), 8.34 (d, J=4.5 Hz, 1H), 7.8 (t, J=8.4 Hz, 2H), 7.70 (d, J=7.2 Hz, 1H), 7.53 (d, J=8.7 Hz, 1H), 7.30 (m, 3H), 7.17 (m, 2H), 6.83 (s, 1H), 6.46 (d, J=8.1 Hz, 1H), 5.25 (s, 1H), 3.43 (m, 1H), 1.10 (d, J=7.8 Hz, 3H), 1.07 (d, J=7.8 Hz, 3H). $^{13}$C NMR (100 MHz, CDCl$_3$) δ: 151.2, 151.0, 150.3, 144.3, 144.0, 143.7, 138.9, 136.8, 135.6, 134.7, 132.7, 131.2, 128.4, 128.0, 127.8, 127.6, 123.6, 123.1, 122.4, 122.0, 118.0 (q, J=249.3 Hz), 113.7, 99.4, 89.1, 49.5, 23.7, 23.2. HRMS (ESI-TOF$^+$): m/z [M+H]$^+$ calcd for C$_{27}$H$_{23}$F$_3$N$_5$O: 490.1855; found: 490.1855.

TBI-1020, 5-(3-Trifluoromethoxyphenyl)-3-(4-tetrahydropyranyl)imino-2-(3-pyridyl)amino-3,5-dihydrophenazine:

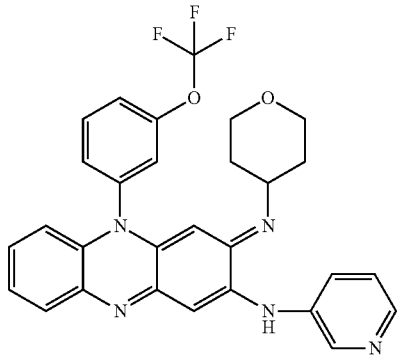 [SMILES: FC(F)(F)Oc1cccc(-n2c3c/c(=N\C4CCOCC4)c(Nc4cccnc4)cc-3nc3ccccc32)c1]

$^1$H NMR (300 MHz, CDCl$_3$) δ: 8.61 (s, 1H), 8.36 (d, J=4.5 Hz, 1H), 7.80 (m, 2H), 7.73 (d, J=7.8 Hz, 1H), 7.56 (d, J=7.8 Hz, 1H), 7.30 (m, 3H), 7.20 (m, 2H), 6.87 (s, 1H), 6.50 (d, J=7.5 Hz, 1H), 5.22 (s, 1H), 3.97 (m, 2H), 3.34 (m, 3H), 1.65 (m, 4H). $^{13}$C NMR (100 MHz, CDCl$_3$) δ: 151.1, 150.7, 144.5, 144.0, 143.6, 138.8, 136.6, 135.6, 134.8, 132.7, 131.0, 128.5, 128.1, 128.0, 127.6, 123.7, 123.3, 122.6, 122.1, 119.0 (q, J=249.3 Hz), 113.8, 99.6, 89.0, 66.2, 54.7, 33.6, 33.2. HRMS (ESI-TOF$^+$): m/z [M+H]$^+$ calcd for C$_{29}$H$_{25}$F$_3$N$_5$O$_2$: 532.1960; found: 532.1958.

TBI-1021, 5-(3-Trifluoromethoxyphenyl)-3-cyclopropylimino-2-(3-pyridyl)amino-3,5-dihydrophenazine:

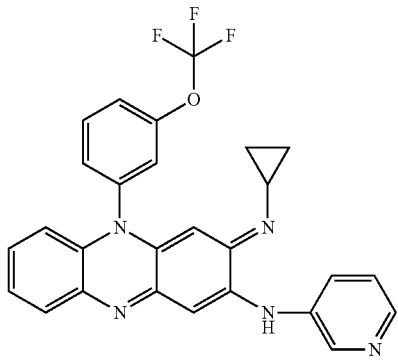 [SMILES: FC(F)(F)Oc1cccc(-n2c3c/c(=N\C4CC4)c(Nc4cccnc4)cc-3nc3ccccc32)c1]

¹H NMR (300 MHz, CDCl₃) δ: 8.59 (d, J=2.7 Hz, 1H), 8.48 (s, 1H), 8.31 (d, J=4.5 Hz, 1H), 7.95 (t, J=8.1 Hz, 1H), 7.84 (d, J=8.1 Hz, 1H), 7.75 (m, 2H), 7.64 (d, J=7.4 Hz, 2H), 7.44 (dd, J=8.1, 4.5 Hz, 1H), 7.21 (m, 2H), 6.61 (s, 1H), 6.42 (d, J=7.8 Hz, 1H), 5.44 (s, 1H), 2.65 (m, 1H), 0.83 (d, J=6.3 Hz, 2H), 0.76 (s, 2H). ¹³C NMR (100 MHz, CDCl₃) δ: 152.0, 150.4, 150.1, 144.1, 144.0, 143.4, 138.4, 136.6, 135.3, 134.2, 133.4, 131.2, 128.5, 128.4, 128.1, 127.8, 123.9, 122.7, 122.3, 119.0 (q, J=249.3 Hz), 113.7, 98.8, 88.7, 32.6, 9.6. HRMS (ESI-TOF⁺): m/z [M+H]⁺ calcd for $C_{27}H_{21}F_3N_5O$: 488.1698; found: 488.1697.

TBI-1022, 5-(3-Trifluoromethoxyphenyl)-3-cyclohexylimino-2-(3-pyridyl)amino-3,5-dihydrophenazine:

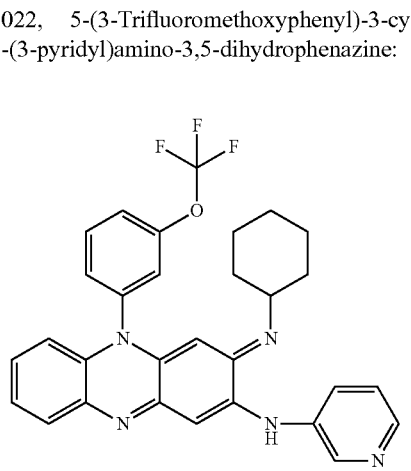

¹H NMR (300 MHz, CDCl₃) δ: 8.58 (d, J=2.6 Hz, 1H), 8.33 (dd, J=4.8, 1.2 Hz, 1H), 7.80 (m, 2H), 7.69 (dd, J=7.8, 1.8 Hz, 1H), 7.54 (d, J=7.2 Hz, 1H), 7.30 (m, 4H), 7.17 (m, 2H), 6.79 (s, 1H), 6.48 (dd, J=7.2, 2.1 Hz, 1H), 5.23 (s, 1H), 3.06 (m, 1H), 1.73 (m, 2H), 1.58 (m, 3H), 1.38 (m, 2H), 1.20 (m, 3H). ¹³C NMR (100 MHz, CDCl₃) δ: 151.1, 151.0, 150.4, 144.3, 143.9, 143.7, 138.9, 136.8, 135.6, 134.6, 132.6, 131.2, 128.4, 127.9, 127.8, 127.6, 123.6, 123.1, 122.4, 122.1, 120.0 (q, J=249.3 Hz), 113.7, 99.4, 89.4, 58.1, 33.8, 33.4, 25.8, 24.7, 24.6. HRMS (ESI-TOF⁺): m/z [M+H]⁺ calcd for $C_{30}H_{27}F_3N_5O$: 530.2168; found: 530.2170.

TBI-1023, 5-(4-Fluorophenyl)-3-cyclohexylimino-2-(2-methyl-3-pyridyl)amino-3,5-dihydrophenazine:

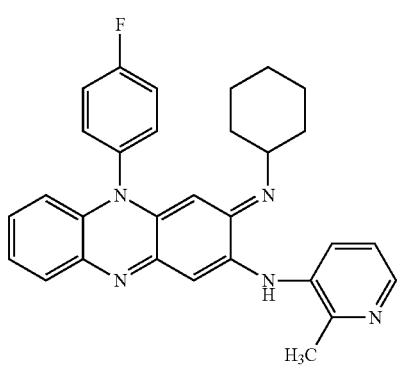

¹H NMR (300 MHz, CDCl₃) 8.26 (dd, J=4.5, 1.2 Hz, 1H), 7.82 (dd, J=8.4, 1.2 Hz, 1H), 7.67 (dd, J=7.5, 2.0 Hz, 1H), 7.43 (t, J=8.4 Hz, 2H), 7.34 (dd, J=8.7, 5.1 Hz, 2H), 7.15 (m, 3H), 6.61 (s, 1H), 6.48 (dd, J=7.8, 1.5 Hz, 1H), 5.26 (s, 1H), 3.13 (m, 1H), 2.55 (s, 3H), 1.74 (m, 2H), 1.62 (m, 3H), 1.39 (m, 2H), 1.26 (m, 3H). ¹³C NMR (100 MHz, CDCl₃) δ: 162.8 (d, J=248.9 Hz), 152.0, 151.1, 150.5, 144.0, 135.6, 135.1, 134.8, 133.5, 131.7, 130.9, 130.8, 128.8, 128.2, 127.6, 122.9, 121.7, 118.4 (d, J=22.7 Hz), 113.9, 98.8, 89.2, 57.4, 33.6, 25.9, 24.4, 20.9. HRMS (ESI-TOF⁺): m/z [M+H]⁺ calcd for $C_{30}H_{29}FN_5$: 478.2407; found: 478.2408.

TBI-1024, 5-(3-Trifluoromethoxyphenyl)-3-(4-methoxycyclohexyl)imino-2-(3-pyridyl)amino-3,5-dihydrophenazine:

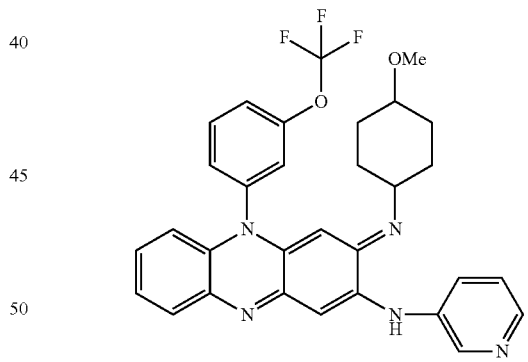

¹H NMR (300 MHz, CDCl₃) δ: 8.58 (d, J=2.4 Hz, 1H), 8.34 (d, 14.8 Hz, 1H), 7.80 (t, J=8.1 Hz, 2H), 7.72 (dd, J=7.2, 2.1 Hz, 1H), 7.53 (dd, J=8.4, 0.6 Hz, 1H), 7.31 (m, 2H), 7.27 (m, 1H), 7.19 (m, 2H), 6.84 (s, 1H), 6.50 (dd, J=7.5, 1.8 Hz, 1H), 5.20 (s, 1H), 3.36 (s, 3H), 3.18 (m, 1H), 3.05 (m, 1H), 2.07 (m, 2H), 1.66 (m, 2H), 1.44 (m, 2H), 1.16 (m, 2H). ¹³C NMR (100 MHz, CDCl₃) δ: 151.2, 151.1, 150.8, 144.4, 144.0, 143.6, 138.7, 136.7, 135.6, 134.8, 132.7, 131.1, 128.5, 128.0, 127.5, 123.7, 123.2, 122.5, 121.9, 119.0 (q, J=249.3 Hz), 113.8, 99.5, 89.2, 57.5, 55.8, 31.4, 30.9, 30.1, 29.9. HRMS (ESI-TOF⁺): m/z [M+H]⁺ calcd for $C_{31}H_{29}F_3N_5O_2$: 560.2273; found: 560.2274.

TBI-1025, 5-(4-Fluorophenyl)-3-(1-methylethyl)imino-2-(5-methyl-3-pyridyl)amino-3,5-dihydrophenazine:

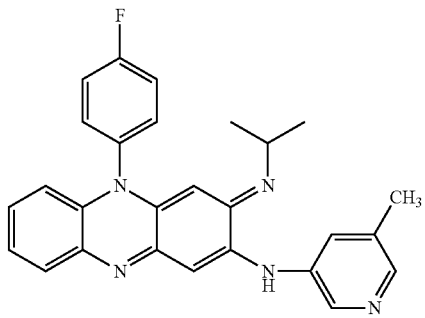 [SMILES: Cc1cncc(Nc2cc3nc4ccccc4n(-c4ccc(F)cc4)c-3c/c2=N\C(C)C)c1]

¹H NMR (300 MHz, CDCl₃) δ: 8.40 (s, 1H), 8.17 (s, 1H), 7.69 (d, 17.5 Hz, 1H), 7.58 (s, 1H), 7.42 (t, J=8.4 Hz, 2H), 7.34 (m, 2H), 7.16 (m, 2H), 6.83 (s, 1H), 6.46 (d, J=7.8 Hz, 1H), 5.27 (s, 1H), 3.45 (m, 1H), 2.38 (s, 3H), 1.10 (s, 3H), 1.08 (s, 3H). ¹³C NMR (100 MHz, CDCl₃) δ: 162.8 (d, J=249.3 Hz), 151.0, 150.4, 144.9, 143.7, 141.1, 136.4, 135.6, 135.1, 133.5, 131.7, 130.9, 130.8, 128.4, 128.2, 127.7, 122.9, 118.5 (d, J=22.7 Hz), 113.9, 99.3, 89.1, 49.4, 23.5, 18.4. HRMS (ESI-TOF⁺): m/z [M+H]⁺ calcd for C₇₇H₂₅FN₅: 438.2094; found: 438.2095.

TBI-1027, 5-(3-Trifluoromethoxyphenyl)-3-cyclobutyl-imino-2-(3-pyridyl)amino-3,5-dihydrophenazine:

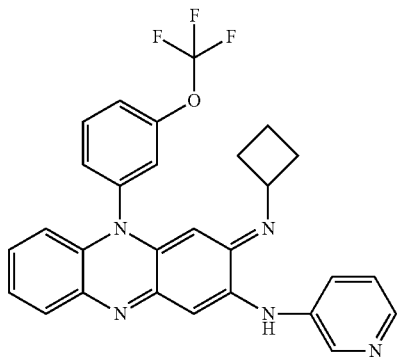 [SMILES: FC(F)(F)Oc1cccc(-n2c3c/c(=N\C4CCC4)c(Nc4cccnc4)cc-3nc3ccccc32)c1]

¹H NMR (300 MHz, CDCl₃) δ: 8.60 (d, J=2.4 Hz, 1H), 8.34 (d, J=4.8 Hz, 1H), 7.80 (m, 2H), 7.71 (d, J=7.2 Hz, 1H), 7.54 (d, J=8.4 Hz, 1H), 7.31 (m, 3H), 7.18 (m, 2H), 6.83 (s, 1H), 6.48 (d, J=8.1 Hz, 1H), 5.07 (s, 1H), 3.87 (m, 1H), 2.14 (m, 2H), 2.04 (m, 2H), 1.72 (m, 2H). ¹³C NMR (100 MHz, CDCl₃) δ: 151.1, 150.9, 144.4, 144.0, 143.6, 138.8, 136.6, 135.6, 134.3, 132.6, 131.1, 128.4, 128.1, 128.0, 127.6, 123.7, 123.2, 122.4, 122.0, 119.0 (q, J=249.3 Hz), 113.8, 99.5, 90.6, 54.9, 32.0, 31.8, 16.0. HRMS (ESI-TOF⁺): m/z [M+H]⁺ calcd for C₂₈H₂₃F₃N₅O: 502.1855; found: 502.1858.

TBI-1026, 5-(4-Fluorophenyl)-3-(4-methoxycyclohexyl)imino-2-(5-ethyl-3-pyridyl)amino-3,5-dihydrophenazine:

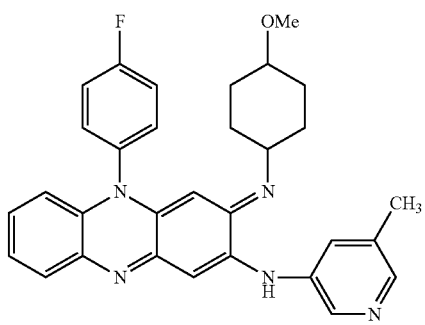

¹H NMR (300 MHz, CDCl₃) δ: 8.39 (d, J=2.4 Hz, 1H), 8.17 (s, 1H), 7.70 (dd, J=7.5, 1.5 Hz, 1H), 7.58 (s, 1H), 7.42 (t, J=8.4 Hz, 2H), 7.33 (dd, J=8.7, 5.1 Hz, 2H), 7.17 (m, 2H), 6.83 (s, 1H), 6.50 (dd, J=7.5, 1.8 Hz, 1H), 5.25 (s, 1H), 3.36 (s, 3H), 3.20 (m, 1H), 3.08 (m, 1H), 2.38 (s, 3H), 2.07 (m, 2H), 1.68 (m, 2H), 1.42 (m, 2H), 1.18 (m, 2H). ¹³C NMR (100 MHz, CDCl₃) δ: 162.8 (d, J=249.4 Hz), 151.1, 150.9, 144.9, 143.6, 141.1, 136.3, 135.6, 135.1, 133.5, 133.3, 131.6, 130.8, 130.7, 128.3, 128.2, 127.8, 123.0, 118.4 (d, 22.7 Hz), 114.0, 99.4, 89.1, 78.4, 57.4, 55.8, 31.1, 29.9, 18.5. HRMS (ESI-TOF⁺): m/z [M+H]⁺ calcd for C₃₁H₃₁FN₅O: 508.2513; found: 508.2516.

TBI-1028, 5-(4-Fluorophenyl)-3-(4-tetrahydropyranyl)imino-2-(5-methyl-3-pyridyl)amino-3,5-dihydrophenazine:

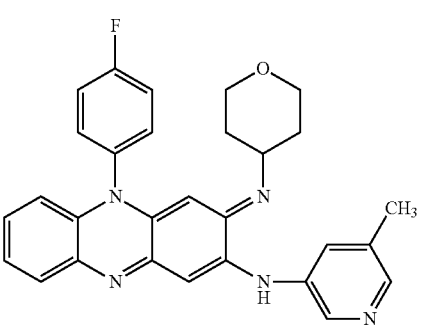 [SMILES: Cc1cncc(Nc2cc3nc4ccccc4n(-c4ccc(F)cc4)c-3c/c2=N\C2CCOCC2)c1]

¹H NMR (300 MHz, CDCl₃) δ: 8.30 (d, J=2.1 Hz, 1H), 8.07 (s, 1H), 7.60 (dd, J=7.2, 1.8 Hz, 1H), 7.46 (s, 1H), 7.32 (t, J=8.4 Hz, 2H), 7.23 (dd, J=8.7, 5.1 Hz, 2H), 7.07 (m, 2H), 6.75 (s, 1H), 6.38 (dd, J=7.5, 1.5 Hz, 1H), 5.14 (s, 1H), 3.86 (m, 2H), 3.29 (m, 3H), 2.27 (s, 3H), 1.54 (m, 4H). ¹³C NMR (100 MHz, CDCl₃) δ: 162.8 (d, 249.7 Hz), 151.1, 150.8, 145.1, 143.7, 141.1, 136.3, 135.6, 135.2, 133.6, 133.4, 131.5, 130.8, 130.7, 128.5, 128.3, 127.9, 123.1, 118.4 (d, J=22.7 Hz), 114.0, 99.5, 88.9, 66.1, 54.3, 33.4, 18.4. HRMS (ESI-TOF⁺): m/z [M+H]⁺ calcd for C₂₉H₂₇FN₅O: 480.2200; found: 480.2201.

TBI-1029, 5-(4-Fluorophenyl)-3-cyclohexylimino-2-(5-methyl-3-pyridyl)amino-3,5-dihydrophenazine:

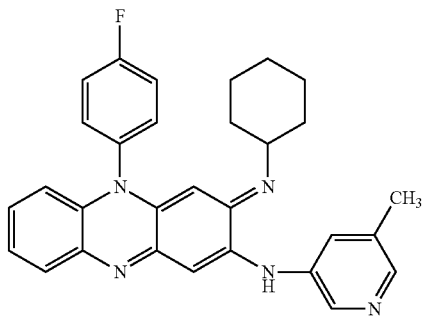 [SMILES: Cc1cncc(Nc2cc3nc4ccccc4n(-c4ccc(F)cc4)c-3c/c2=N\C2CCCCC2)c1]

$^1$H NMR (300 MHz, CDCl$_3$) 8.39 (s, 1H), 8.16 (s, 1H), 7.69 (d, J=7.2 Hz, 1H), 7.58 (s, 1H), 7.43 (t, J=7.5 Hz, 2H), 7.34 (m, 2 Ft), 7.16 (m, 2H), 6.82 (s, 1H), 6.48 (d, J=7.8 Hz, 1H), 5.25 (s, 1H), 3.08 (m, 1H), 2.38 (s, 3H), 1.75 (m, 2H), 1.60 (m, 3H), 1.38 (m, 2H), 1.22 (m, 3H). $^{13}$C NMR (100 MHz, CDCl$_3$) δ: 162.8 (d, J=249.4 Hz), 151.1, 150.5, 144.9, 143.8, 141.1, 136.5, 135.7, 135.0, 133.5, 131.7, 130.9, 130.8, 128.3, 128.2, 127.6, 122.9, 118.4 (d, J=22.9 Hz), 113.9, 99.3, 89.3, 57.9, 33.6, 25.8, 24.6, 18.5. HRMS (ESI-TOF$^+$): m/z [M+H]$^+$ calcd for C$_{30}$H$_{29}$FN$_5$: 478.2407; found: 478.2405.

TBI-1030, 5-(4-Fluorophenyl)-3-cyclopropylimino-2-(5-methyl-3-pyridyl)amino-3,5-dihydrophenazine:

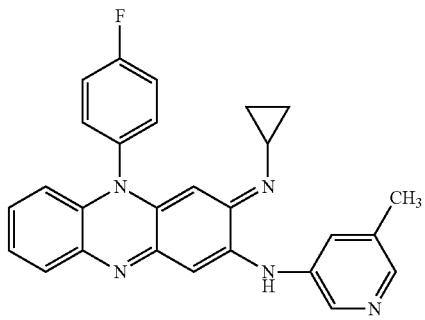 [SMILES: Cc1cncc(Nc2cc3nc4ccccc4n(-c4ccc(F)cc4)c-3c/c2=N\C2CC2)c1]

$^1$H NMR (300 MHz, CDCl$_3$) δ: 8.35 (d, J=1.5 Hz, 1H), 8.16 (s, 1H), 7.67 (dd, J=7.2, 1.5 Hz, 1H), 7.55 (s, 1H), 7.38 (m, 4H), 7.15 (m, 2H), 6.78 (s, 1H), 6.44 (d, J=7.3 Hz, 1H), 5.53 (s, 1H), 2.74 (m, 1H), 2.37 (s, 3H), 0.87 (m, 2H), 0.81 (m, 2H). $^{13}$C NMR (100 MHz, CDCl$_3$) δ: 162.8 (d, J=248.9 Hz), 152.4, 151.3, 145.0, 143.5, 141.2, 136.2, 135.7, 134.9, 133.5, 131.9, 131.0, 130.9, 128.5, 128.1, 127.6, 122.9, 118.5 (d, J=22.4 Hz), 113.8, 99.3, 89.4, 32.8, 18.4, 9.9. HRMS (ESI-TOF$^+$): m/z [M+H]$^+$ calcd for C$_{27}$H$_{23}$FN$_5$: 436.1937; found: 436.1940.

TBI-1031, 5-(4-Fluorophenyl)-3-cyclobutylimino-2-(5-ethyl-3-pyridyl)amino-3,5-dihydrophenazine:

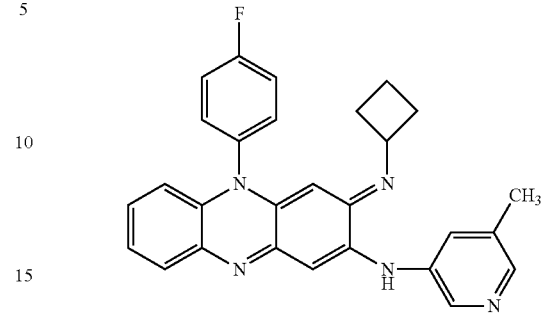

$^1$H NMR (300 MHz, CDCl$_3$) δ: 8.41 (d, J=2.1 Hz, 1H), 8.18 (s, 1H), 7.72 (dd, J=7.8, 1.2 Hz, 1H), 7.58 (s, 1H), 7.43 (t, J=8.4 Hz, 2H), 7.33 (dd, J=8.7, 5.1 Hz, 2H), 7.17 (m, 2H), 6.83 (s, 1H), 6.49 (dd, J=7.5, 1.5 Hz, 1H), 5.08 (s, 1H), 3.86 (m, 1H), 2.38 (s, 3H), 2.16 (m, 2H), 2.04 (m, 2H), 1.75 (m, 2H). $^{13}$C NMR (100 MHz, CDCl$_3$): 162.8 (d, J=248.9 Hz), 151.2, 151.0, 145.1, 143.7, 141.2, 136.3, 135.7, 134.7, 133.5, 131.6, 130.9, 130.8, 128.5, 128.3, 127.8, 123.1, 118.4 (d, J=22.9 Hz), 114.0, 99.4, 90.6, 54.8, 32.0, 18.5, 16.0. HRMS (ESI-TOF$^+$): m/z [M+H]$^+$ calcd for C$_{28}$H$_{25}$FN$_5$: 450.2094; found: 450.2092.

TBI-1032, 5-(3-Trifluoromethoxyphenyl)-3-(1-methylethyl)imino-2-(2-methyl-3-pyridyl)amino-3,5-dihydrophenazine:

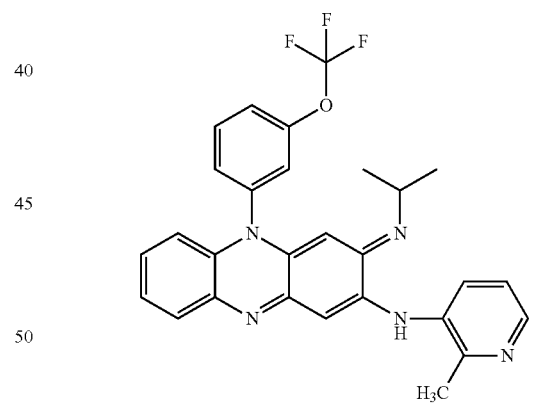

$^1$H NMR (300 MHz, CDCl$_3$) δ: 8.28 (dd, J=5.4, 1.8 Hz, 1H), 7.80 (t, J=8.1 Hz, 2H), 7.68 (dd, J=7.5, 1.8 Hz, 1H), 7.53 (d, J=8.1 Hz, 1H), 7.30 (d, J=7.8 Hz, 1H), 7.28 (m, 1H), 7.17 (m, 3H), 6.57 (s, 1H), 6.46 (dd, J=7.8, 1.5 Hz, 1H), 5.26 (s, 1H), 3.45 (m, 1H), 2.55 (s, 3H), 1.10 (d, J=6.6 Hz, 3H), 1.07 (d, J=6.3 Hz, 3H). $^{13}$C NMR (100 MHz, CDCl$_3$) δ: 152.4, 151.2, 151.0, 150.3, 144.3, 144.2, 139.0, 135.5, 134.7, 132.7, 131.2, 129.3, 128.3, 127.7, 127.6, 123.1, 122.4, 122.0, 121.7, 119.0 (q, J=249.3 Hz), 113.7, 98.8, 89.1, 49.4, 23.7, 23.2, 20.9. HRMS (ESI-TOF$^+$): m/z [M+H]$^+$ calcd for C$_{28}$H$_{25}$F$_3$N$_5$O: 504.2011; found: 504.2009.

TBI-1033, 5-(3-Trifluoromethoxyphenyl)-3-(4-methoxycyclohexyl)imino-2-(2-methyl-3-pyridyl)amino-3,5-dihydrophenazine:

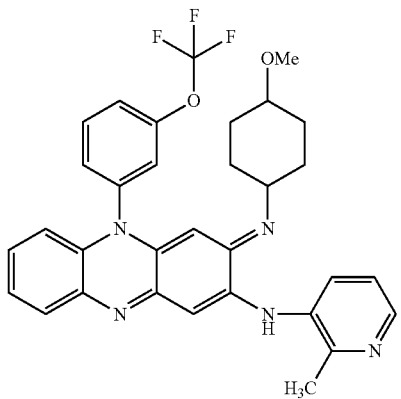 [SMILES: COC1CCC(/N=c2\cc3n(-c4cccc(OC(F)(F)F)c4)c4ccccc4nc-3cc2Nc2cccnc2C)CC1]

$^1$H NMR (300 MHz, CDCl$_3$) δ: 8.28 (dd, J=5.4, 1.8 Hz, 1H), 7.80 (t, J=8.1 Hz, 2H), 7.68 (dd, J=7.2, 2.1 Hz, 1H), 7.53 (d, J=8.1 Hz, 1H), 7.33 (d, J=7.8 Hz, 1H), 7.26 (m, 1H), 7.18 (m, 3H), 6.59 (s, 1H), 6.50 (dd, J=7.8, 1.5 Hz, 1H), 5.21 (s, 1H), 3.36 (s, 3H), 3.20 (m, 1H), 3.08 (m, 1H), 2.54 (s, 3H), 2.06 (m, 2H), 1.70 (m, 2H), 1.40 (m, 2H), 1.19 (m, 2H). $^{13}$C NMR (100 MHz, CDCl$_3$) δ: 152.2, 151.2, 151.1, 150.9, 144.3, 144.0, 138.8, 135.5, 134.7, 134.6, 132.7, 131.1, 129.2, 128.3, 127.8, 127.5, 123.2, 122.5, 121.9, 121.7, 119.0 (q, J=249.3 Hz), 113.7, 98.9, 89.1, 78.4, 57.2, 55.8, 31.3, 30.8, 29.8, 29.7, 20.9. HRMS (ESI-TOF$^+$): m/z [M+H]$^+$ calcd for C$_{32}$H$_{31}$F$_3$N$_5$O$_2$: 574.2430; found: 574.2430.

TBI-1034, 5-(3-Trifluoromethoxyphenyl)-3-cyclohexylimino-2-(2-methyl-3-pyridyl)amino-3,5-dihydrophenazine:

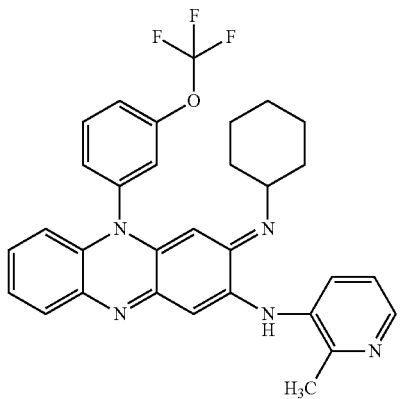 [SMILES: Cc1ncccc1Nc1cc2nc3ccccc3n(-c3cccc(OC(F)(F)F)c3)c-2c/c1=N\C1CCOCC1]

$^1$H NMR (300 MHz, CDCl$_3$) δ: 8.28 (dd, J=5.4, 1.8 Hz, 1H), 7.80 (t, J=8.1 Hz, 2H), 7.68 (dd, J=7.2, 1.8 Hz, 1H), 7.53 (d, J=8.7 Hz, 1H), 7.33 (d, J=9.0 Hz, 1H), 7.29 (m, 1H), 7.16 (m, 3H), 6.59 (s, 1H), 6.48 (dd, J=7.5, 1.8 Hz, 1H), 5.23 (s, 1H), 3.09 (m, 1H), 2.55 (s, 3H), 1.73 (m, 2H), 1.58 (m, 3H), 1.36 (m, 2H), 1.22 (m, 3H). $^{13}$C NMR (100 MHz, CDCl$_3$) δ: 152.1, 151.1, 151.0, 150.0, 144.1, 138.9, 135.5, 134.7, 134.6, 132.6, 131.1, 128.9, 128.3, 127.6, 123.0, 122.4, 122.1, 121.6, 119.0 (q, J=249.3 Hz), 113.6, 98.8, 89.3, 57.7, 33.8, 33.4, 25.8, 24.4, 20.9. HRMS (ESI-TOF$^+$): m/z [M+H]$^+$ calcd for C$_{31}$H$_{29}$F$_3$N$_5$O: 544.2324; found: 544.2324.

TBI-1035, 5-(3-Trifluoromethoxyphenyl) 3-(4-tetrahydropyranyl)imino-2-(2-methyl-3-pyridyl)amino-3,5-dihydrophenazine:

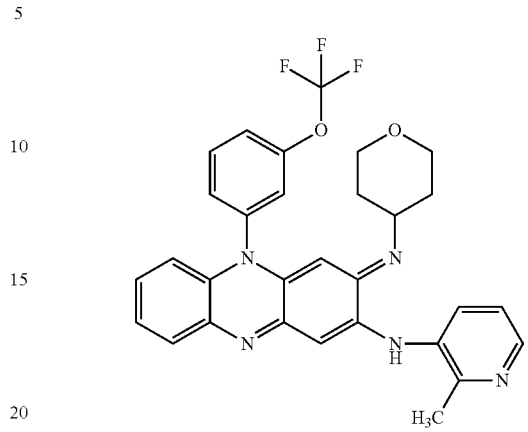

$^1$H NMR (300 MHz, CDCl$_3$) δ: 8.30 (dd, J=4.8, 1.2 Hz, 1H), 7.82 (t, J=7.5 Hz, 2H), 7.71 (dd, J=7.5, 1.8 Hz, 1H), 7.56 (d, J=8.1 Hz, 1H), 7.33 (d, J=7.8 Hz, 1H), 7.29 (m, 1H), 7.19 (m, 3H), 6.62 (s, 1H), 6.50 (dd, J=7.8, 1.5 Hz, 1H), 5.23 (s, 1H), 3.96 (m, 2H), 3.42 (m, 3H), 2.56 (s, 3H), 1.64 (m, 4H). $^{13}$C NMR (100 MHz, CDCl$_3$) δ: 152.2, 151.0, 150.7, 144.3, 144.0, 138.8, 135.6, 134.8, 134.5, 132.7, 131.0, 129.2, 128.4, 127.9, 127.6, 123.3, 122.6, 122.1, 121.7, 119.0 (q, J=249.3 Hz), 113.8, 99.0, 88.9, 66.0, 54.1, 33.5, 33.1, 20.9. HRMS (ESI-TOF$^+$): m/z [M+H]$^+$ calcd for C$_{30}$H$_{27}$F$_3$N$_5$O$_2$: 546.2117; found: 546.2119.

TBI-1038, 5-(3-Trifluoromethoxyphenyl ethylethyl)imino-2-(2-methoxy-3-pyridyl)amino-3,5-dihydrophenazine:

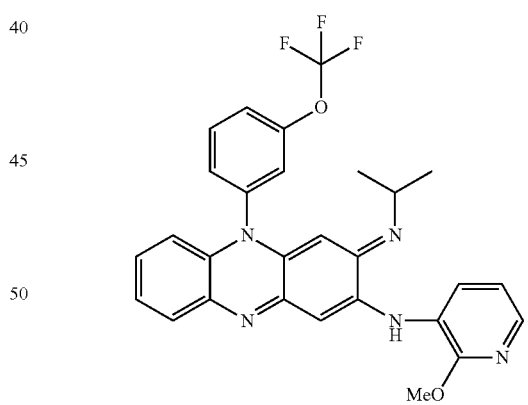

$^1$H NMR (300 MHz, CDCl$_3$) δ: 7.82 (m, 3H), 7.70 (dd, J=7.8, 1.8 Hz, 1H), 7.52 (d, J=8.7 Hz, 1H), 7.32 (d, J=7.8 Hz, 1H), 7.28 (brs, 1H), 7.16 (m, 2H), 6.90 (m, 2H), 6.45 (dd, J=7.2, 1.8 Hz, 1H), 5.24 (s, 1H), 4.04 (s, 3H), 3.42 (m, 1H), 1.11 (d, J=6.3 Hz, 3H), 1.08 (d, J=6.3 Hz, 3H). $^{13}$C NMR (100 MHz, CDCl$_3$) δ: 155.5, 151.2, 151.1, 150.6, 142.9, 138.9, 135.5, 134.6, 132.6, 131.3, 128.3, 127.7, 127.6, 125.0, 124.8, 123.0, 122.3, 122.0, 120.0 (q, J=249.3 Hz), 116.8, 113.6, 100.1, 89.3, 53.7, 49.4, 23.7, 23.2. HRMS (ESI-TOF$^+$): [M+H]$^+$ calcd for C$_{28}$H$_{25}$F$_3$N$_5$O$_2$: 520.1960; found: 520.1959.

TBI-1039, 5-(3-Trifluoromethoxyphenyl)-3-(4-methoxycyclohexyl)imino-2-(2-methoxy-3-pyridyl)amino-3,5-dihydrophenazine:

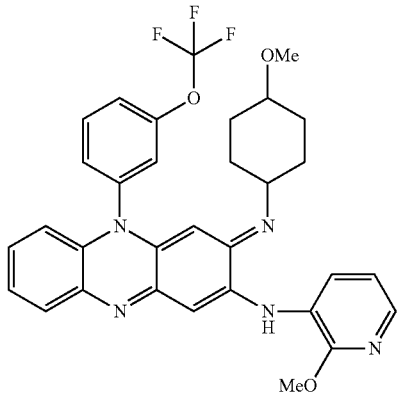 [SMILES: COc1ncccc1Nc1cc2nc3ccccc3n(-c3cccc(OC(F)(F)F)c3)c-2c/c1=N\C1CCC(OC)CC1]

$^1$H NMR (300 MHz, CDCl$_3$) δ: 8.90 (brs, 1H), 7.82 (m, 3H), 7.71 (dd, J=6.9, 2.1 Hz, 1H), 7.53 (d, J=7.8 Hz, 1H), 7.33 (d, J=7.8 Hz, 1H), 7.26 (brs, 1H), 7.17 (m, 2H), 6.92 (m, 2H), 6.49 (dd, J=7.5, 1.5 Hz, 1H), 5.20 (s, 1H), 4.03 (s, 3H), 3.36 (s, 3H), 3.22 (m, 1H), 3.08 (m. 1H), 2.05 (m, 2H), 1.70 (m, 2H), 1.44 (m, 2H), 1.18 (m, 2H). $^{13}$C NMR (100 MHz, CDCl$_3$) δ: 155.4, 151.2, 151.1, 142.8, 138.8, 135.6, 134.7, 132.6, 131.2, 128.3, 127.8, 127.6, 124.8, 123.1, 122.4, 122.0, 119.0 (q, J=249.3 Hz), 116.8, 113.7, 100.2, 89.3, 78.4, 57.1, 55.8, 53.7, 31.1, 30.6, 29.7, 29.5. HRMS (ESI-TOF$^+$): m/z [M+H]$^+$ calcd for C$_{32}$H$_{31}$F$_3$N$_5$O$_3$: 590.2379; found: 590.2378.

TBI-1040, 5-(3-Trifluoromethoxyphenyl)-3-cyclohexylimino-2-(2-methoxy-3-pyridyl)amino-3,5-dihydrophenazine:

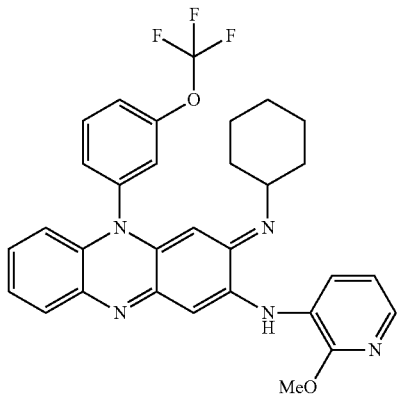 [SMILES: COc1ncccc1Nc1cc2nc3ccccc3n(-c3cccc(OC(F)(F)F)c3)c-2c/c1=N\C1CCCCC1]

$^1$H NMR (300 MHz, CDCl$_3$) δ: 9.00 (brs, 1H), 7.80 (m, 3H), 7.69 (dd, J=7.5, 1.8 Hz, 1H), 7.53 (d, J=8.7 Hz, 1H), 7.33 (d, J=7.8 Hz, 1H), 7.28 (brs, 1H), 7.16 (m, 2H), 6.92 (m, 2H), 6.46 (dd, J=7.8, 1.5 Hz, 1H), 5.22 (s, 1H), 4.03 (s, 3H), 3.09 (m, 1H), 1.74 (m, 2H), 1.58 (m, 3H), 1.37 (m, 2H), 1.22 (m, 3H). $^{13}$C NMR (100 MHz, CDCl$_3$) δ: 155.4, 151.3, 151.1, 150.5, 142.9, 138.9, 138.7, 135.6, 134.6, 132.6, 131.3, 128.3, 127.7, 124.9, 124.6, 123.0, 122.3, 122.2, 120.0 (q, J=249.3 Hz), 116.8, 113.6, 100.1, 89.5, 57.6, 53.7, 33.7, 33.3, 25.9, 24.3. HRMS (ESI-TOF$^+$): m/z [M+H]$^+$ calcd for C$_{31}$H$_{29}$F$_3$N$_5$O$_2$: 560.2273; found: 560.2272.

TBI-1041, 5-(3-Trifluoromethoxyphenyl)-3-(4-tetrahydropyranyl)imino-2-(2-methoxy-3-pyridyl)amino-3,5-dihydrophenazine:

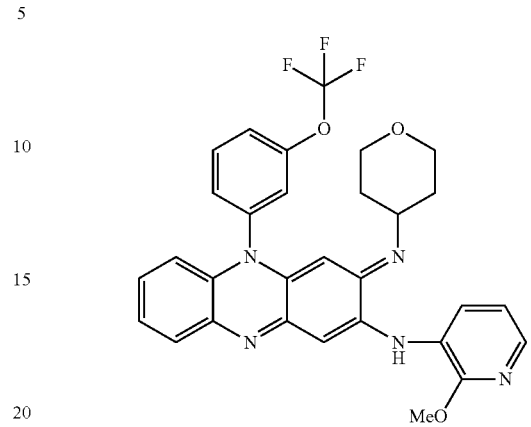

$^1$H NMR (300 MHz, CDCl$_3$) δ: 7.82 (m, 3H), 7.72 (d, J=7.2 Hz, 1H), 7.55 (d, J=8.1 Hz, 1H), 7.33 (d, J=8.1 Hz, 1H), 7.29 (brs, 1H), 7.18 (m, 2H), 6.93 (m, 2H), 6.48 (d, J=7.8 Hz, 1H), 5.21 (s, 1H), 4.04 (s, 3H), 3.99 (m, 2H), 3.41 (m, 3H), 1.66 (m, 4H). $^{13}$C NMR (100 MHz, CDCl$_3$) δ: 155.3, 151.1, 150.9, 142.6, 138.8, 135.6, 134.8, 132.7, 131.1, 128.4, 127.9, 127.6, 124.7, 124.5, 123.2, 122.5, 122.1, 119.0 (q, J=249.3 Hz), 116.8, 113.7, 100.3, 89.0, 65.7, 53.7, 33.4, 33.0. HRMS (ESI-TOF$^+$): m/z [M+H]$^+$ calcd for C$_{30}$H$_{27}$F$_3$N$_5$O$_3$: 562.2066; found: 562.2065.

TBI-1042, 5-(4-Fluorophenyl)-3-(4-tetrahydrothiopyranyl)imino-2-(2-methoxy-3-pyridyl)amino-3,5-dihydrophenazine:

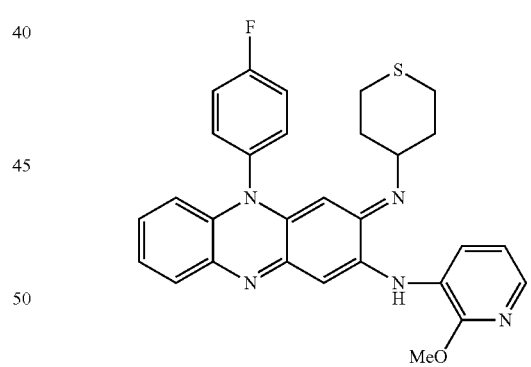

$^1$H NMR (300 MHz, CDCl$_3$) δ: 9.11 (1H, s), 7.85 (1H, dd, J=7.5, 1.5 Hz), 7.81 (1H, dd, J=5.1, 1.5 Hz), 7.72 (1H, dd, J=7.5, 1.8 Hz), 7.43 (2H, t, J=8.7 Hz), 7.33 (2H, dd, J=9.0, 5.1 Hz), 7.17 (2H, m), 6.98 (1H, s), 6.92 (1H, dd, J=7.8, 5.1 Hz), 6.49 (1H, dd, J=7.8, 1.2 Hz), 5.19 (1H, s), 4.06 (3H, s), 3.28 (1H, m), 2.95 (2H, m), 2.48 (2H, m), 1.86 (4H, m). $^{13}$C NMR (100 MHz, CDCl$_3$) δ: 162.8 (d, J=249.4 Hz), 155.3, 151.0, 150.8, 142.6, 138.7, 135.7, 135.3, 133.4, 131.7, 130.8, 130.7, 128.3, 127.8, 124.9, 124.2, 123.1, 118.5 (d, J=22.7 Hz), 116.8, 114.0, 100.3, 88.9, 55.1, 53.8, 34.0, 25.7. HRMS (ESI-TOF$^+$): m/z [M+H]$^+$ calcd for C$_{29}$H$_{27}$FN$_5$OS: 512.1920; found: 512.1917.

TBI-1043, 5-(4-Fluorophenyl)-3-(4-tetrahydrothiopyranyl)imino-2-(2-methyl-3-pyridyl)amino-3,5-dihydrophenazine:

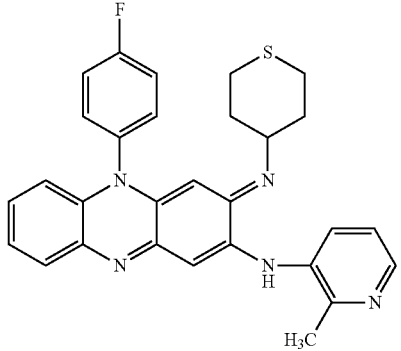 [SMILES: Cc1ncccc1Nc1cc2nc3ccccc3n(-c3ccc(F)cc3)c-2c/c1=N\C1CCSCC1]

¹H NMR (300 MHz, CDCl₃) δ: 8.29 (1H, d, J=4.5), 7.83 (1H, d, J=8.1 Hz), 7.70 (1H, d, J=7.5 Hz), 7.44 (2H, t, J=8.4 Hz), 7.34 (2H, dd, J=8.4, 4.8 Hz), 7.18 (3H, m), 6.63 (1H, s), 6.50 (1H, d, J=7.5 Hz), 5.21 (1H, s), 3.23 (1H, m), 2.83 (2H, m), 2.56 (3H, s), 2.50 (2H, 2H, m), 1.81 (2H, m), ¹³C NMR (100 MHz, CDCl₃) δ: 162.8 (d, J=249.4 Hz), 152.1, 150.8, 150.7, 144.3, 144.0, 135.7, 135.3, 134.6, 133.4, 131.5, 130.8, 130.7, 129.0, 128.3, 127.8, 123.1, 121.7, 118.5 (d, J=22.7 Hz), 114.0, 99.0, 88.8, 55.7, 34.2, 26.3, 20.9.

TBI-1044, 5-(2-Trifluoromethoxyphenyl)-3-(4-methoxycyclohexyl)imino-2-(2-methoxy-3-pyridyl)amino-3,5-dihydrophenazine:

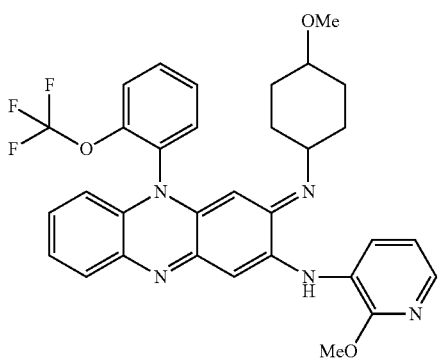 [SMILES: COc1ncccc1Nc1cc2nc3ccccc3n(-c3ccccc3OC(F)(F)F)c-2c/c1=N\C1CCC(OC)CC1]

¹H NMR (300 MHz, CDCl₃) δ: 8.90 (1H, brs), 7.85 (1H, d, J=7.8 Hz), 7.81 (1H, dd, J=4.8, 0.9 Hz), 7.71 (2H, m), 7.62 (2H, m), 7.42 (1H, d, J=7.5 Hz), 7.17 (2H, m), 6.92 (2H, 6.45 (1H, d, f=7.5 Hz), 5.20 (1H, s), 4.03 (3H, s), 3.36 (3H, s), 3.23 (1H, m), 3.08 (1H, 2.05 (2H, m), 1.70 (2H, m), 1.44 (2H, m), 1.18 (2H, m). ¹³C NMR (100 MHz, CDCl₃) O: 155.4, 152.1, 151.5, 146.2, 142.7, 138.8, 135.6, 134.0, 131.6, 131.3, 130.9, 128.7, 128.3, 127.8, 124.8, 121.5, 116.8, 113.5, 100.3, 89.2, 78.4, 57.2, 55.8, 53.7, 31.0, 30.6, 29.7, 29.6.

TBI-1045, 5-(2-Trifluoromethoxyphenyl)-3-(4-tetrahydropyranyl)imino-2-(2-methoxy-3-pyridyl)amino-3,5-dihydrophenazine

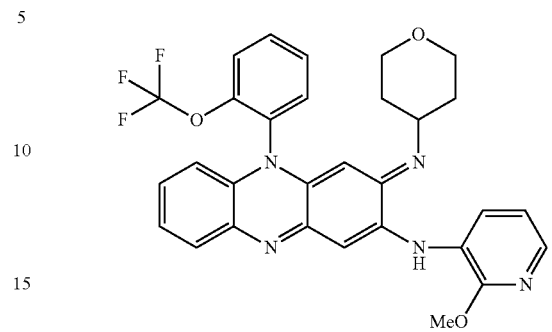

¹H NMR (300 MHz, CDCl₃) δ: 9.04 (1H, s), 7.86 (1H, dd, J=7.8, 1.5 Hz), 7.82 (1H, dd, J=5.1, 1.5 Hz), 7.73 (2H, m), 7.64 (2H, m), 7.43 (1H, dd, J=7.8, 1.2 Hz), 7.19 (2H, m), 6.98 (1H, s), 6.93 (1H, dd, J=7.8, 5.1 Hz), 6.44 (1H, d, J=7.5 Hz), 5.21 (1H, s), 4.04 (3H, s), 4.00 (2H, m), 3.47 (3H, m), 1.65 (4H, m), ¹³C NMR (100 MHz, CDCl₃) δ: 155.3, 151.3, 151.0, 146.2, 142.6, 138.8, 135.6, 134.2, 131.6, 131.3, 130.8, 128.8, 128.4, 127.9, 124.8, 124.5, 123.2, 121.6, 116.8, 113.5, 100.4, 88.9, 65.7, 65.6, 53.8, 53.5, 33.4, 33.1.

TBI-1046, 5-(2-Trifluoromethoxyphenyl)-3-(1-methylethyl)imino-2-(2-methoxy-3-pyridyl)amino-3,5-dihydrophenazine:

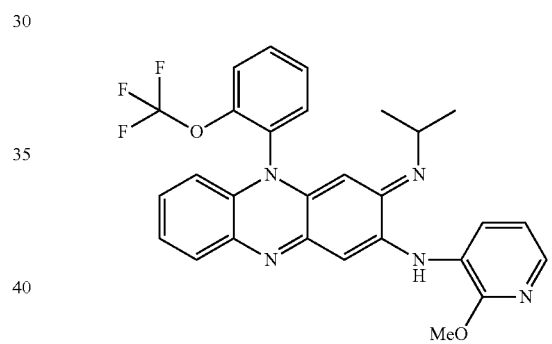

¹H NMR (300 MHz, CDCl₃) δ: 8.88 (brs, 1H), 7.83 (m, 2H), 7.69 (m, 4H), 7.43 (d, J=6.9 Hz, 1H), 7.16 (m, 2H), 6.92 (m, 2H), 6.40 (d, J=7.2 Hz, 1H), 5.24 (s, 1H), 4.04 (s, 3H), 3.45 (m, 1H), 1.11 (d, J=6.3 Hz, 3H), 1.10 (d, J=6.3 Hz, 3H). ¹³C NMR (100 MHz, CDCl₃) δ: 155.5, 151.3, 150.7, 146.3, 142.9, 138.8, 135.5, 134.0, 131.5, 131.4, 131.0, 128.9, 128.8, 128.2, 127.7, 125.0, 124.8, 123.0, 121.7, 116.8, 113.4, 100.2, 89.2, 53.7, 49.4, 23.6, 23.3.

TBI-1047, 5-(2-Trifluoromethoxyphenyl)-3-cyclohexylimino-2-(2-methoxy-3-pyridyl)amino-3,5-dihydrophenazine:

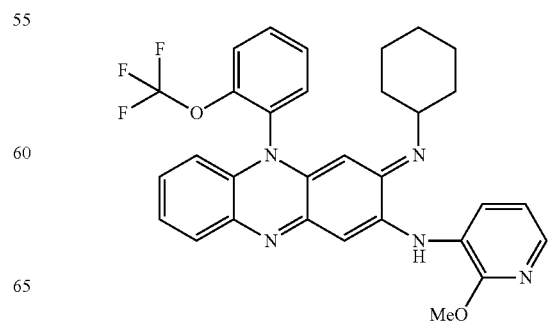

¹H NMR (300 MHz, CDCl₃) δ: 9.00 (brs, 1H), 7.85 (dd, J=8.1, 1.5 Hz, 1H), 7.80 (dd, J=4.2, 1.5 Hz, 1H), 7.67 (m, 4H), 7.43 (dd, J=7.8, 1.2 Hz, 1H), 7.16 (m, 2H), 6.93 (m, 2H), 6.43 (dd, J=7.5, 1.5 Hz, 1H), 5.21 (s, 1H), 4.03 (s, 3H), 3.10 (m, 1H), 1.76 (m, 2H), 1.58 (m, 3H), 1.41 (m, 2H), 1.22 (m, 3H). ¹³C NMR (100 MHz, CDCl₃) δ: 155.4, 151.4, 150.7, 146.3, 142.8, 138.7, 135.6, 133.9, 131.4, 131.0, 128.9, 128.7, 128.2, 127.7, 124.9, 124.7, 123.0, 121.5, 116.8, 113.4, 100.2, 89.4, 57.6, 53.7, 33.6, 33.3, 25.9, 24.3.

TBI-1048, 5-(4-Fluorophenyl)-3-(1,3-dimethoxyisopropyl)imino-2-(2-methoxy-3-pyridyl)amino-3,5-dihydrophenazine:

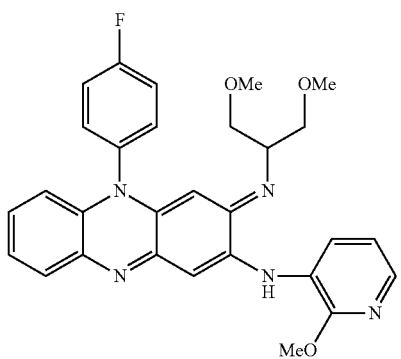 [SMILES: COCC(COC)/N=c1\cc2n(-c3ccc(F)cc3)c3ccccc3nc-2cc1Nc1cccnc1OC]

¹H NMR (300 MHz, CDCl₃) δ: 8.90 (brs, 1H), 7.83 (m, 2H), 7.72 (d, J=6.6 Hz, 1H), 7.36 (oz, 4H), 7.17 (m, 2H), 6.92 (m, 2H), 6.48 (d, J=7.5 Hz, 1H), 5.47 (s, 1H), 4.02 (s, 3H), 3.70 (m, 1H), 3.55 (m, 2H), 3.39 (m, 2H), 3.28 (s, 6H). ¹³C NMR (100 MHz, CDCl₃) δ: 162.9 (d, J=250.0 Hz), 155.4, 153.5, 151.0, 142.7, 138.9, 135.7, 135.0, 133.4, 131.8, 130.9, 128.3, 127.8, 125.0, 123.0, 118.4 (d, J=23.1 Hz), 116.8, 114.0, 100.2, 90.2, 74.4, 59.1, 58.7, 53.7

TBI-1049, 5-(4-Fluorophenyl)-3-(2,3-dimethoxy-1-propyl)imino-2-(2-methoxy-3-pyridyl)amino-3,5-dihydrophenazine:

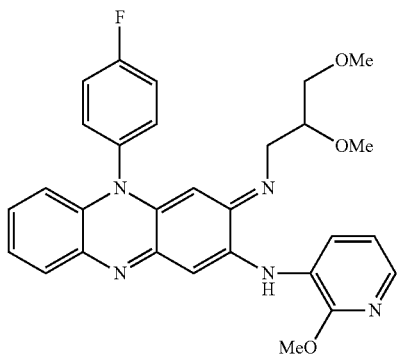 [SMILES: COCC(C/N=c1\cc2n(-c3ccc(F)cc3)c3ccccc3nc-2cc1Nc1cccnc1OC)OC]

¹H NMR (300 MHz, CDCl₃) δ: 9.34 (brs, 1H), 8.78 (s, 1H), 8.13 (m, 2H), 7.89 (d, J=7.2 Hz, 1H), 7.63 (m, 4H), 7.46 (m, 2H), 6.99 (m, 2H), 6.83 (s, 1H), 6.14 (s, 1H), 3.96 (s, 3H), 3.59 (m, 2H), 3.49 (m, 1H), 3.37 (m, 3H), 3.34 (s, 3H). ¹³C NMR (100 MHz, CDCl₃) δ: 163.6 (d, J=250.0 Hz), 157.8, 153.2, 144.1, 141.0, 138.7, 135.2, 134.4, 131.8, 130.3, 129.9, 129.6, 129.5, 127.3, 122.0, 118.9 (d, J=23.1 Hz), 117.3, 116.3, 107.0, 90.4, 78.2, 71.4, 59.5, 57.8, 53.7, 45.4.

TBI-1050, 5-(4-Chlorophenyl)-3-(1-ethylethyl)imino-2-(3-nitro-2-pyridyl)amino-3,5-dihydrophenazine:

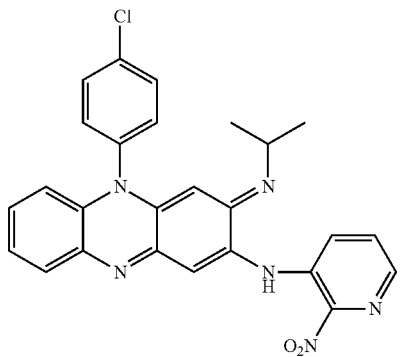 [SMILES: CC(C)/N=c1\cc2n(-c3ccc(Cl)cc3)c3ccccc3nc-2cc1Nc1cccnc1[N+](=O)[O-]]

¹H NMR (300 MHz, CDCl₃) δ: 12.24 (s, 1H), 8.72 (s, 1H), 8.66 (d, J=3.0 Hz, 1H), 8.56 (dd, J=8.4, 1.8 Hz, 1 Hz), 7.45 (m, 3H), 7.32 (m, 2H), 7.17 (m, 1H), 6.95 (dd, J=8.1, 4.5 Hz, 1H), 6.42 (m, 1H), 5.29 (s, 1H), 3.47 (m, 1H), 1.15 (dd, J=6.3 Hz, 6H). ¹³C NMR (100 MHz, CDCl₃) δ: 154.3, 151.9, 150.5, 148.7, 140.4, 135.8, 135.7, 135.6, 135.2, 135.1, 132.2, 131.8, 130.8, 130.4, 129.0, 128.8, 122.9, 114.8, 113.8, 111.5, 89.1, 49.5, 23.5.

TBI-90B, 5-(4-Fluorophenyl)-3-(4-tetrahydrothiopyranyl)imino-2-(6-methyl-3-pyridyl)amino-3,5-dihydrophenazine:

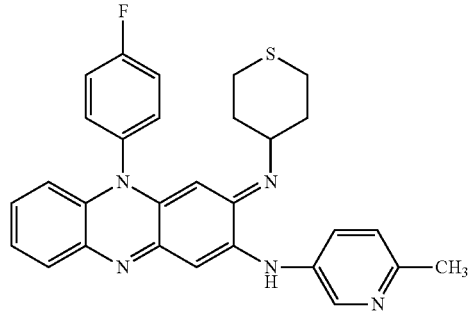 [SMILES: Cc1ccc(Nc2cc3nc4ccccc4n(-c4ccc(F)cc4)c-3c/c2=N\C2CCOCC2)cn1]

¹H NMR (300 MHz, CDCl₃) δ: 8.55 (1H, s), 8.17 (1H, d, J=4.8 Hz), 8.03 (2H, m), 7.76 (5H, m), 7.40 (1H, d, J=8.4 Hz), 7.20 (1H, s), 7.07 (1H, d, J=4.8 Hz), 6.22 (1H, s), 3.03 (1H, m), 2.66 (4H, m), 2.53 (3H, s), 2.18 (2H, m), 1.60 (2H, m).

TBI-900, 5-(4-Fluorophenyl)-3-(4-tetrahydropyranyl)imino-2-(6-methyl-3-pyridyl)amino-3,5-dihydrophenazine:

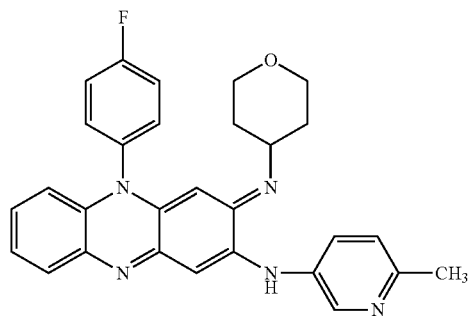

¹H NMR (300 MHz, CDCl₃) δ: 8.46 (1H, d, J=2.4 Hz), 7.69 (1H, d, J=7.8 Hz), 7.67 (1H, dd, J=7.8, 2.4 Hz), 7.43 (2H, dd, J=8.4, 8.1 Hz), 7.31 (2H, dd, J=8.4, 5.1 Hz), 7.17 (3H, m), 6.74 (1H, s), 6.49 (1H, d, J=7.5 Hz), 5.24 (1H, s), 3.97 (2H, m), 3.40 (3H, m), 2.58 (3H, s), 1.66 (4H, m). $^{13}$C NMR (100 MHz, CDCl$_3$) δ: 162.8 (d, J=250 Hz), 153.5, 151.1, 150.7, 144.3, 143.8, 135.7, 135.2, 133.9, 133.4, 131.5, 130.8, 130.7, 130.1, 129.5, 128.3, 127.7, 123.1 (d, J=12 Hz), 118.4 (d, J=23 Hz), 114.0, 99.0, 88.8, 66.1, 54.3, 33.4, 23.8. HRMS (ESI-TOF$^+$): m/z [M+H]$^+$ calcd for C$_{29}$H$_{27}$FN$_5$O: 480.2199; found: 480.2206.

TBI-901, 5-(4-Fluorophenyl)-3-(N-methyl-4-piperidyl)imino-2-(6-methyl-3-pyridyl)amino-3,5-dihydrophenazine:

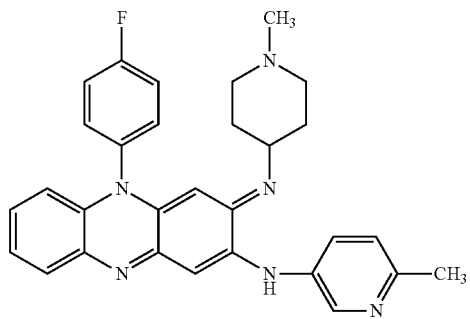 [SMILES: Cc1ccc(Nc2cc3nc4ccccc4n(-c4ccc(F)cc4)c-3c/c2=N\C2CCN(C)CC2)cn1]

$^1$H NMR (300 MHz, CDCl$_3$) δ: 8.47 (1H, d, J=2.4 Hz), 7.74 (1H, d, J=7.8 Hz), 7.68 (1H, dd, J=7.8, 2.4 Hz), 7.46 (2H, dd, J=8.4, 8.1 Hz), 7.35 (2H, dd, J=8.4, 5.1 Hz), 7.23 (3H, m), 6.79 (1H, s), 6.56 (1H, d, J=7.8 Hz), 5.27 (1H, s), 3.18 (1H, m), 2.87 (2H, m), 2.57 (3H, s), (3H, s), 1.74 (2H, m), 1.28 (4H, m). $^{13}$C NMR (100 MHz, CDCl$_3$) δ: 162.9 (d, J=250 Hz), 153.6, 152.5, 151.0, 144.2, 143.8, 135.7, 135.1, 134.0, 133.4, 131.5, 130.7, 130.6, 129.5, 129.3, 128.4, 127.7, 123.2 (d, J=23 Hz), 118.4 (d, J=23 Hz), 114.1, 99.4, 88.7, 60.51, 51.8, 45.3, 31.9, 23.5. HRMS (ESI-TOF$^+$): [M+H]$^+$ calcd for C$_{30}$H$_{30}$FN$_6$: 493.2516; found: 493.2512.

TBI-902, 5-(4-Fluorophenyl)-3-(N-methyl-3-piperidylmethyl)imino-2-(6-methyl-3-pyridyl)amino-3,5-dihydrophenazine:

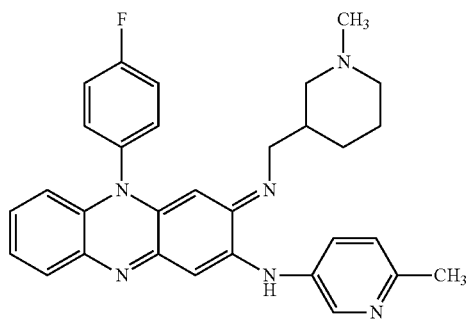 [SMILES: Cc1ccc(Nc2cc3nc4ccccc4n(-c4ccc(F)cc4)c-3c/c2=N\CC2CCCN(C)C2)cn1]

$^1$H NMR (300 MHz, CDCl$_3$) δ: 8.45 (1H, d, J=2.4 Hz), 7.70 (1H, d, J=7.5 Hz), 7.67 (1H, dd, J=7.5, 2.7 Hz), 7.42 (2H, dd, J=8.7, 8.1 Hz), 7.33 (2H, dd, J=8.4, 4.8 Hz), 7.16 (3H, m), 6.73 (1H, s), 6.47 (1H, d, J=7.8 Hz), 5.22 (1H, s), 3.00 (2H, m), 2.91 (1H, d, J=10.5 Hz), 2.79 (1H, d, J=10.5 Hz), 2.56 (3H, s), 2.26 (3H, s), 1.86 (2H, t, J=9.6 Hz), 1.66 (4H, m), 1.26 (1H, m). $^{13}$C NMR (100 MHz, CDCl$_3$) δ: 162.8 (d, J=250 Hz), 153.5, 151.6, 149.8, 143.9, 143.6, 135.8, 135.1, 133.8, 133.0, 131.0, 130.7, 130.4, 130.3, 129.9, 128.6, 128.3, 123.4 (d, J=12 Hz), 118.8 (d, J=23 Hz), 114.1, 98.9, 89.0, 60.9, 56.3, 54.1, 46.7, 38.1, 28.6, 23.8, HRMS (ESI-TOF$^+$): m/z [M+H]$^+$ calcd for C$_{31}$H$_{32}$FN$_6$: 507.2672; found: 507.2668.

TBI-904, 5-(4-Fluorophenyl)-3-(N-isobutyl-4-piperidyl)imino-2-(6-methyl-3-pyridyl)amino-3,5-dihydrophenazine:

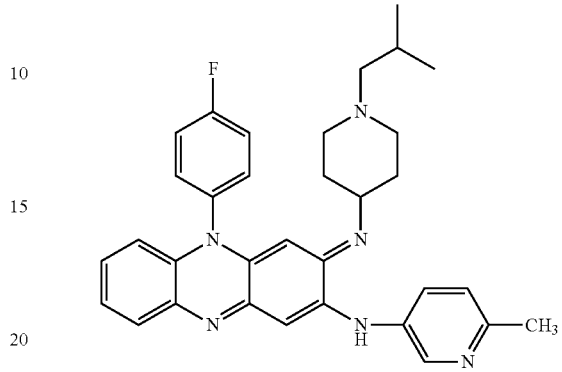

$^1$H NMR (300 MHz, CDCl$_3$) δ: 8.45 (1H, d, J=2.4 Hz), 7.70 (1H, d, J=7.5 Hz), 7.68 (1H, dd, J=7.5, 2.7 Hz), 7.44 (2H, dd, J=8.7, 8.1 Hz), 7.35 (2H, dd, J=8.4, 4.8 Hz), 7.17 (3H, m), 6.74 (1H, s), 6.48 (1H, d, J=7.8 Hz), 5.25 (1H, s), 3.12 (1H, m), 2.78 (2H, m), 2.57 (3H, s), 2.07 (2H, m), 1.90 (2H, m), 1.70 (4H, m), 1.46 (1H, m), 0.90 (6H, d, J=6.0 Hz). $^{13}$C NMR (100 MHz, CDCl$_3$) δ: 162.2 (d, J=250 Hz), 153.4, 151.0, 149.8, 144.4, 143.7, 135.7, 135.1, 134.1, 133.5, 131.6, 130.9, 129.4, 128.8, 128.3, 127.6, 123.1 (d, J=24 Hz), 118.4 (d, J=23 Hz), 113.9, 98.9, 89.1, 67.1, 56.1, 52.5, 32.8, 25.7, 23.8, 21.0. HRMS (ESI-TOF$^+$): m/z [M+H]$^+$ calcd for C$_{33}$H$_{36}$FN$_6$: 535.2985; found: 535.2982.

TBI-905, 5-(4-Fluorophenyl)-3-cyclohexylimino-2-(6-methyl-3-pyridyl)amino-3,5-dihydrophenazine:

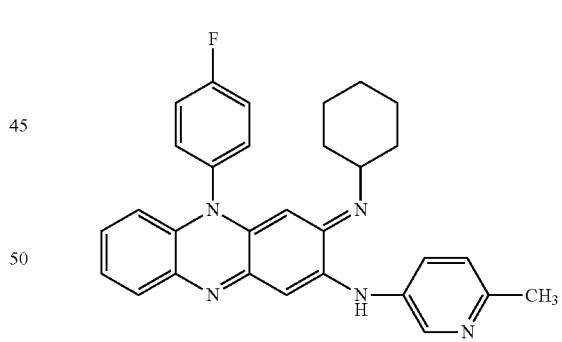

$^1$H NMR (300 MHz, CDCl$_3$) δ: 8.45 (1H, d, J=2.4 Hz), 7.70 (1H, d, J=7.5 Hz), 7.67 (1H, dd, J=7.5, 2.7 Hz), 7.43 (2H, dd, J=8.7, 8.1 Hz), 7.35 (2H, dd, J=8.4, 4.8 Hz), 7.13 (3H, m), 6.72 (1H, s), 6.48 (1H, d, J=7.8 Hz), 5.26 (1H, s), 3.07 (1H, m), 2.57 (3H, s), 1.74 (2H, d, J=10.0 Hz), 1.61 (2H, d, J=10.0 Hz), 1.38 (3H, m), 1.23 (3H, m). $^{13}$C NMR (100 MHz, CDCl$_3$) δ: 162.2 (d, J=250 Hz), 153.3, 151.1, 150.6, 144.4, 143.7, 135.7, 135.0, 134.1, 133.5, 131.6, 130.9, 130.8, 129.4, 128.2, 127.5, 123.1 (d, J=32 Hz), 118.3 (d, J=23 Hz), 113.8, 98.9, 89.3, 58.0, 33.6, 25.8, 24.7, 23.8. HRMS (ESI-TOF$^+$): [M+H]$^+$ calcd for C$_{30}$H$_{29}$FN$_5$: 478.2407; found: 478.2405.

TBI-906, 5-(4-Fluorophenyl)-3-(1',4'-trans-4-hydroxycyclohexyl)imino-2-(6-methyl-3-pyridyl)amino-3,5-dihydrophenazine:

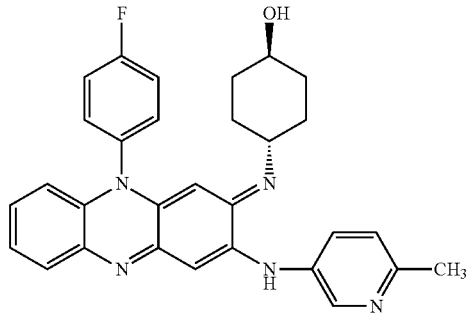 [SMILES: Cc1ccc(Nc2cc3nc4ccccc4n(-c4ccc(F)cc4)c-3c/c2=N\[C@H]2CC[C@H](O)CC2)cn1]

¹H NMR (300 MHz, CDCl₃) δ: 8.44 (1H, d, J=2.4 Hz), 7.70 (1H, d, J=7.5 Hz), 7.68 (1H, dd, J=7.5, 2.7 Hz), 7.43 (2H, dd, J=8.7, 8.1 Hz), 7.34 (2H, dd, J=8.4, 4.8 Hz), 7.16 (3H, m), 6.73 (1H, s), 6.49 (1H, d, J=7.8 Hz), 5.24 (1H, s), 3.66 (1H, m), 3.07 (1H, m), 2.56 (3H, s), 2.00 (2H, d, J=9.6 Hz), 1.68 (2H, d, J=9.6 Hz), 1.45 (2H, m), 1.24 (2H, m). ¹³C NMR (100 MHz, CDCl₃) δ: 162.2 (d, J=250 Hz), 153.4, 151.3, 150.8, 144.3, 143.6, 135.6, 135.1, 134.0, 133.4, 131.5, 130.8, 130.7, 129.5, 128.2, 127.7, 123.1 (d, J=23 Hz), 118.4 (d, J=23 Hz), 113.9, 98.9, 89.0, 69.9, 57.2, 33.8, 30.7, 23.8. HRMS (ESI-TOF⁺): m/z [M+H]⁺ calcd for C₃₀H₂FN₅O: 494.2356; found: 494.2352.

TBI-907, 5-(4-Fluorophenyl)-3-(1',4'-trans-4-methoxycyclohexyl)imino-2-(6-methyl-3-pyridyl)amino-3,5-dihydrophenazine:

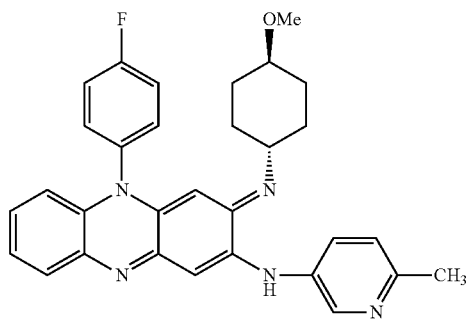 [SMILES: CO[C@H]1CC[C@H](/N=c2\cc3n(-c4ccc(F)cc4)c4ccccc4nc-3cc2Nc2ccc(C)nc2)CC1]

¹H NMR (300 MHz, CDCl₃) 8.44 (1H, d, J=2.4 Hz), 7.70 (1H, d, J=7.5 Hz), 7.68 (1H, dd, J=7.5, 2.7 Hz), 7.54 (2H, dd, J=8.7, 8.1 Hz), 7.43 (2H, dd, J=8.4, 4.8 Hz), 7.16 (3H, m), 6.73 (1H, s), 6.51 (1H, d, J=7.8 Hz), 5.25 (1H, s), 3.36 (3H, s), 3.16 (1H, m), 3.09 (1H, m), 2.56 (3H, s), 2.07 (2H, d, J=10.1 Hz), 1.71 (2H, d, J=10.1 Hz), 1.45 (2H, m), 1.17 (2H, m). ¹³C NMR (100 MHz, CDCl₃) δ: 162.2 (d, J=250 Hz), 153.4, 151.3, 150.8, 144.2, 143.7, 135.4, 135.1, 134.0, 133.2, 131.5, 130.8, 130.7, 128.8, 128.3, 127.3, 123.7 (d, J=23 Hz), 118.4 (d, J=23 Hz), 113.9, 98.9, 89.1, 78.4, 63.7, 55.8, 30.5, 30.0, 23.8. HRMS (ESI-TOF⁺): m/z [M+H]⁺ calcd for C₃₁H₃₁FN₅O: 508.2513; found: 508.2513.

TBI-908, 5-(4-Fluorophenyl)-3-cyclopropylimino-2-(6-methyl-3-pyridyl)amino-3,5-dihydrophenazine:

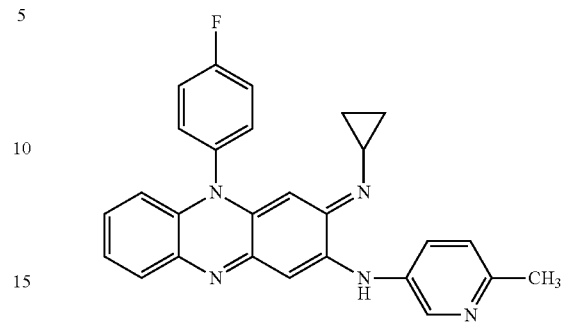

¹H NMR (300 MHz, CDCl₃) δ: 8.41 (1H, d, J=2.4 Hz), 7.65 (2H, dd, J=8.7, 8.1 Hz), 7.39 (2H, dd, J=8.4, 4.8 Hz), 7.36 (2H, m), 7.15 (3H, m), 6.66 (1H, s), 6.43 (1H, d, J=7.8 Hz), 5.54 (1H, s), 2.73 (1H, m), 2.56 (3H, s), 0.89 (2H, m), 0.81 (2H, m). ¹³C NMR (100 MHz, CDCl₃) δ: 162.2 (d, J=250 Hz), 153.4, 151.3, 150.8, 144.2, 143.7, 135.4, 135.1, 134.0, 133.2, 131.5, 130.8, 130.7, 128.8, 128.3, 127.3, 123.7 (d, J=23 Hz), 118.4 (d, J=23 Hz), 113.9, 98.9, 89.1, 32.8, 23.8, 9.9. HRMS (ESI-TOF⁺): m/z [M+H]⁺ calcd for C₂₇H₂₃FN₅: 436.1937; found: 436.1932.

TBI-910, 5-(4-Fluorophenyl)-3-(1-methylethyl)imino-2-(6-acetamino-3-pyridyl)amino-3,5-dihydrophenazine

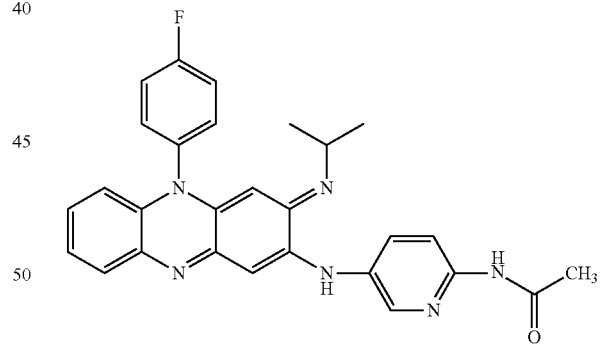

¹H NMR (300 MHz, CDCl₃) δ: 8.29 (1H, d, J=2.4 Hz), 8.22 (1H, d, J=8.7 Hz), 7.75 (1H, dd, J=8.7, 2.4 Hz), 7.68 (1H, d, J=7.2 Hz), 7.42 (2H, dd, J=9.0, 8.1 Hz), 7.34 (2H, dd, J=8.4, 4.8 Hz), 7.15 (2H, m), 6.70 (1H, s), 6.46 (1H, d, J=7.8 Hz), 5.27 (1H, s), 3.45 (1H, m), 2.23 (3H, s), 1.09 (6H, d, J=6.0 Hz). ¹³C NMR (100 MHz, CDCl₃) δ: 168.2, 162.8 (d, J=250 Hz), 150.9, 150.4, 147.1, 144.4, 142.1, 135.7, 135.1, 133.5, 133.2, 132.1, 131.7, 128.2, 127.6, 122.9, 118.5 (d, J=22 Hz), 114.0 (d, J=7.5 Hz), 98.8, 89.0, 49.4, 24.7, 23.5. HRMS (ESI-TOF⁺): [M+H]⁺ calcd for C₂₈H₂₆FN₆O: 481.2152; found: 481.2148.

TBI-911, 5-(4-Fluorophenyl)-3-(4-tetrahydropyranyl)imino-2-(6-acetamino-3-pyridyl)amino-3,5-dihydrophenazine:

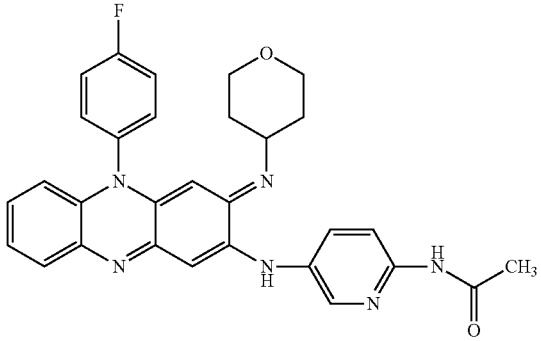 [SMILES: CC(=O)Nc1ccc(Nc2cc3nc4ccccc4n(-c4ccc(F)cc4)c-3c/c2=N\C2CCOCC2)cn1]

¹H NMR (300 MHz, CDCl₃) δ: 8.29 (1H, d, J=2.4 Hz), 8.23 (1H, d, J=8.7 Hz), 7.75 (1H, dd, J=8.7, 2.4 Hz), 7.70 (1H, d, J=7.2 Hz), 7.42 (2H, t, J=8.4 Hz), 7.33 (2H, dd, J=8.4, 4.8 Hz), 7.17 (2H, m), 6.73 (1H, s), 6.49 (1H, d, J=7.8 Hz), 5.24 (1H, s), 3.97 (2H, m), 3.45 (3H, m), 2.23 (3H, s), 1.65 (4H, m). ¹³C NMR (100 MHz, CDCl₃) δ: 168.3, 162.8 (d, J=250 Hz), 151.1, 150.6, 147.4, 144.3, 142.2, 135.7, 135.3, 133.4, 132.9, 132.1, 131.5, 130.8, 130.7, 128.4, 127.8, 123.1, 118.4 (d, J=23 Hz), 114.0 (d, J=7.5 Hz), 99.0, 88.8, 66.1, 54.3, 33.4, 24.6. HRMS (ESI-TOF⁺): m/z [M+H]⁺ calcd for $C_{30}H_{28}FN_6O_2$: 523.2258; found: 523.2252.

TBI-912, 5-(4-Fluorophenyl)-3-(N-methyl-4-piperidyl)imino-2-(6-acetamino-3-pyridyl)amino-3,5-dihydrophenazine:

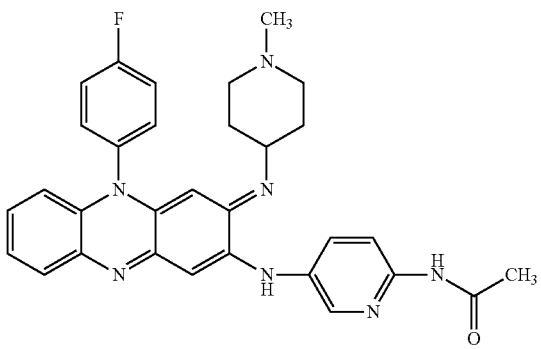 [SMILES: CC(=O)Nc1ccc(Nc2cc3nc4ccccc4n(-c4ccc(F)cc4)c-3c/c2=N\C2CCN(C)CC2)cn1]

¹H NMR (300 MHz, CDCl₃) δ: 8.29 (1H, d, J=2.4 Hz), 8.23 (1H, d=8.4 Hz), 7.75 (1H, dd, J=8.7, 2.4 Hz), 7.72 (1H, d, J=7.2 Hz), 7.44 (2H, dd, J=8.4, 8.1 Hz), 7.33 (2H, dd, J=8.7, 4.8 Hz), 7.20 (2H, m), 6.74 (1H, s), 6.52 (1H, d, J=7.2 Hz), 5.26 (1H, s), 3.18 (1H, m), 2.87 (2H, m), 2.36 (3H, s), 2.23 (3H, s), 1.74 (2H, m), 1.28 (4H, m). ¹³C NMR (100 MHz, CDCl₃) δ: 168.3, 162.9 (d, J=250 Hz), 151.4, 150.7, 147.4, 144.2, 142.4, 135.9, 135.2, 133.4, 132.9, 132.1, 131.4, 130.7, 130.6, 128.5, 128.0, 123.5, 118.5 (d, J=23 Hz), 114.1 (d, J=7.5 Hz), 99.2, 89.0, 60.51, 53.5, 45.9, 31.9, 24.7. HRMS (ESI-TOF⁺): [M+H]⁺ calcd for $C_{31}H_{31}FN_7O$: 536.2574; found: 536.2576.

TBI-913, 5-(4-Fluorophenyl)-3-(N-isobutyl-4-piperidyl)imino-2-(6-acetamino-3-pyridyl)amino-3,5-dihydrophenazine:

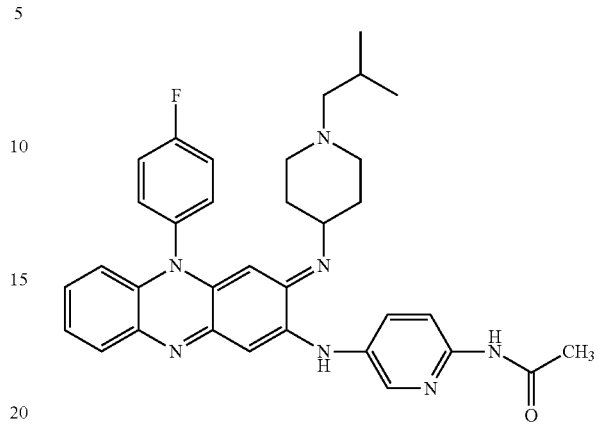

¹H NMR (300 MHz, CDCl₃) δ: 8.29 (1H, d, J=2.4 Hz), 8.22 (1H, d, J=8.4 Hz), 7.75 (1H, dd, J=8.7, 2.4 Hz), 7.72 (1H, d, J=7.2 Hz), 7.48 (2H, dd, J=8.4, 8.1 Hz), 7.33 (2H, dd, J=8.7, 4.8 Hz), 6.99 (2H, m), 6.78 (1H, s), 6.55 (1H, d, J=7.2 Hz), 5.31 (1H, s), 3.17 (1H, m), 2.81 (2H, m), 2.22 (3H, s), 1.96 (2H, m), 1.90 (2H, m), 1.73 (4H, m), 1.49 (1H, m), 0.89 (6H, d, J=6.0 Hz). ¹³C NMR (100 MHz, CDCl₃) δ: 168.5, 163.0 (d, J=250 Hz), 151.3, 150.7, 147.5, 144.0, 142.3, 135.8, 135.2, 133.2, 132.8, 132.3, 131.2, 130.6, 130.4, 128.7, 128.0, 123.6, 118.5 (d, J=23 Hz), 114.2 (d, J=7.5 Hz), 99.3, 89.2, 66.7, 52.5, 45.4, 32.0, 25.6, 24.6, 20.9. HRMS (ESI-TOF⁺): m/z [M+H]⁺ calcd for $C_{34}H_{37}FN_7O$: 578.3044; found: 578.3041.

TBI-915, 5-(4-Fluorophenyl)-3-(1',4'-trans-4-methoxycyclohexyl)imino-2-(6-acetamino-3-pyridyl)amino-3,5-dihydrophenazine:

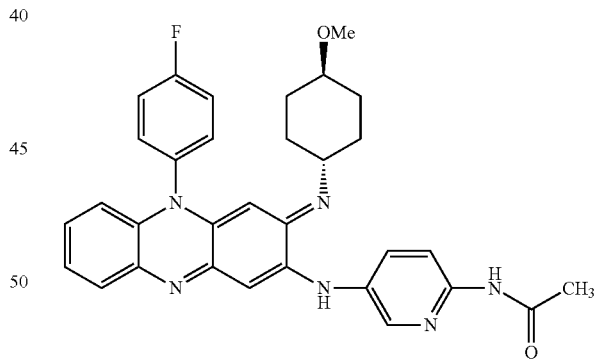

¹H NMR (300 MHz, CDCl₃) δ: 8.27 (1H, d, J=2.4 Hz), 8.23 (1H, d, J=8.4 Hz), 7.74 (1H, dd, J=8.7, 2.4 Hz), 7.72 (1H, d, J=7.5 Hz), 7.43 (2H, dd-J=8.7, 8.1 Hz), 7.33 (2H, dd, J=8.7, 4.8 Hz), 7.20 (2H, m), 6.74 (1H, s), 6.53 (1H, d, J=7.5 Hz), 5.28 (1H, s), 3.36 (3H, s), 3.19 (1H, 3.09 (1H, m), 2.23 (3H, s), 2.07 (2H, d, J=10.1 Hz), 1.71 (2H, d, J=10.1 Hz), 1.45 (2H, m), 1.17 (2H, m). ¹³C NMR (100 MHz, CDCl₃) δ: 168.4, 163.0 (d, J=250 Hz), 151.5, 150.6, 147.4, 144.1, 142.1, 135.7, 135.2, 133.2, 132.8, 132.3, 131.2, 130.6, 130.4, 128.8, 127.9, 123.4, 118.5 (d, J=23 Hz), 114.2 (d, J=7.5 Hz), 99.9, 89.2, 78.2, 56.2, 55.8, 30.7, 30.0, 24.6. HRMS (ESI-TOF⁺): m/z [M+H]⁺ calcd for $C_{32}H_{32}FN_6O_2$: 551.2571; found: 551.2571.

TBI-916, 5-(4-Fluorophenyl)-3-cyclohexylimino-2-(6-acetamino-3-pyridyl)amino-3,5-dihydrophenazine:

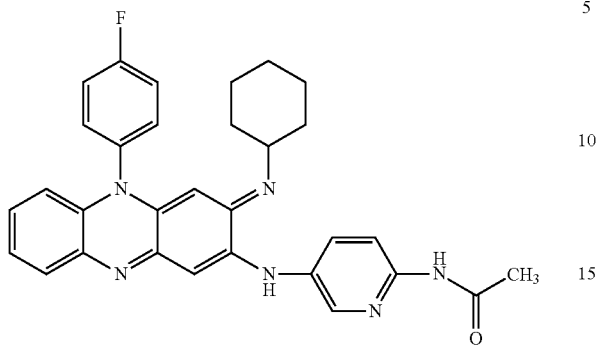

$^1$H NMR (300 MHz, CDCl$_3$) δ: 8.28 (1H, d, J=2.4 Hz), 8.21 (1H, d, J=9.0 Hz), 7.74 (1H, dd, J=9.0, 2.4 Hz), 7.68 (1H, d, J=7.5 Hz), 7.43 (2H, dd, J=8.7, 8.1 Hz), 7.33 (2H, dd, J=8.7, 4.8 Hz), 7.15 (2H, m), 6.70 (1H, s), 6.48 (1H, d, J=7.5 Hz), 5.25 (1H, s), 3.06 (1H, m), 2.23 (3H, s), 1.74 (2H, d, J=10.0 Hz), 1.61 (2H, d, J=10.0 Hz), 1.37 (3 m), 1.21 (3H, m). $^{13}$C NMR (100 MHz, CDCl$_3$) δ: 168.4, 163.0 (d, J=250 Hz), 151.5, 150.6, 147.4, 144.1, 142.1, 135.7, 135.2, 133.2, 132.8, 132.3, 131.2, 130.6, 130.4, 128.8, 127.9, 123.4, 118.5 (d, J=23 Hz), 114.2 (d, J=7.5 Hz), 99.9, 89.2, 58.0, 33.6, 25.8, 24.7, 24.6. HRMS (ESI-TOF$^+$): m/z [M+H]$^+$ calcd for C$_{31}$H$_{30}$FN$_6$O: 521.2465; found: 521.2465.

TBI-917, 5-(4-Fluorophenyl)-3-(1',4'-trans-4-hydroxycyclohexyl)imino-2-(6-acetamino-3-pyridyl)amino-3,5-dihydrophenazine:

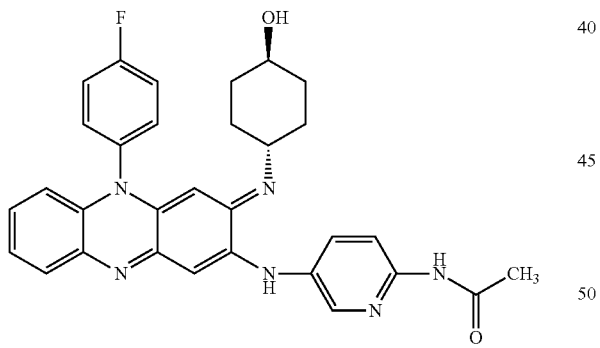

$^1$H NMR (300 MHz, CDCl$_3$) δ: 8.28 (1H, d, J=2.4 Hz), 8.22 (1H, d, J=9.0 Hz), 7.74 (1H, dd, J=9.0, 2.4 Hz), 7.69 (1H, d, J=7.5 Hz), 7.43 (2H, dd, J=8.7, 8.1 Hz), 7.33 (2H, dd, J=8.7, 4.8 Hz), 7.16 (2H, m), 6.70 (1H, s), 6.49 (1H, d, J=7.5 Hz), 5.24 (1H, s), 3.69 (1H, 3.07 (1H, m), 2.23 (3H, s), 2.01 (2H, d, J=9.6 Hz), 1.68 (2H, d, J=9.6 Hz), 1.46 (2H, m), 1.25 (2H, m). $^{13}$C NMR (100 MHz, CDCl$_3$) δ: 168.2, 162.8 (d, J=250 Hz), 151.2, 150.8, 147.2, 144.3, 142.2, 135.7, 135.1, 133.4, 133.0, 132.0, 131.6, 130.8, 130.7, 128.3, 127.7, 123.0, 118.4 (d, J=23 Hz), 114.0 (d, J=7.5 Hz), 98.9, 89.0, 70.0, 57.2, 33.7, 31.2, 24.7. HRMS (ESI-TOF$^+$): m/z [M+H]$^+$ calcd for C$_{31}$H$_{30}$FN$_6$O$_2$: 537.2414; found: 537.2419.

TBI-920, 5-(4-Fluorophenyl)-3-cyclohexylimino-2-(3-pyridyl)amino-3,5-dihydrophenazine:

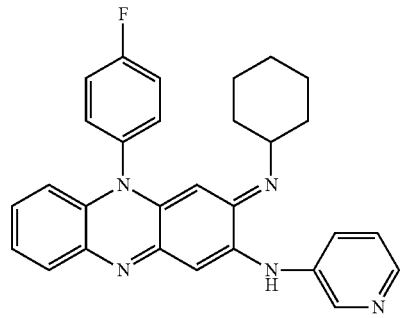

$^1$H NMR (300 MHz, CDCl$_3$) δ: 8.58 (1H, d, J=2.4 Hz), 832 (1H, dd, J=4.8, 1.2 Hz), 7.77 (1H, dd, J=8.4, 1.2 Hz), 7.69 (1H, d, J=7.5 Hz), 7.43 (2H, m), 7.35 (2H, m), 7.31 (1H, m), 7.30 (1H, m), 7.16 (2H, m), 6.84 (1H, s), 6.49 (1H, d, J=7.5 Hz), 5.26 (1H, s), 3.09 (1H, m), 1.74 (2H, m), 1.61 (3H, m), 1.38 (2H, m), 1.15 (3H, m). $^{13}$C NMR (100 MHz, CDCl$_3$) δ: 162.8 (d, J=250 Hz), 151.0, 150.5, 144.2, 143.9, 143.7, 136.9, 135.7, 135.1, 133.5, 131.7, 130.9, 130.8, 128.3, 127.8, 127.7, 123.6, 122.9, 118.4 (d, J=23 Hz), 113.9 (d, J=7.5 Hz), 99.4, 89.3, 57.9, 33.7, 25.7, 24.7. HRMS (ESI-TOF$^+$): m/z [M+H]$^+$ calcd for C$_{29}$H$_{27}$FN$_5$: 464.2250; found: 464.2252.

TBI-921, 5-(4-Fluorophenyl)-3-(1',4'-trans-4-hydroxycyclohexyl)imino-2-(3-pyridyl)amino-3,5-dihydrophenazine:

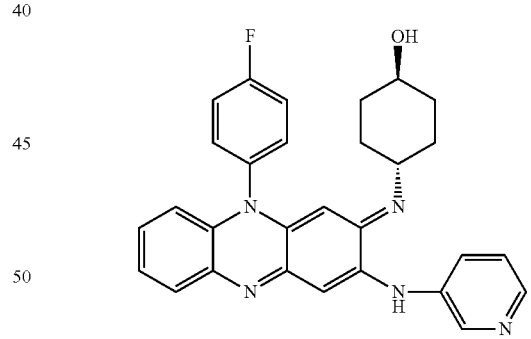

$^1$H NMR (300 MHz, CDCl$_3$) δ: 8.57 (1H, d, J=2.4 Hz), 8.33 (1H, dd, J=4.8, 1.2 Hz), 7.79 (1H, dd, J=8.4, 1.2 Hz), 7.71 (1H, d, J=7.5 Hz), 7.43 (2H, m), 7.36 (2H, m), 7.31 (1H, m), 7.17 (2H, m), 6.85 (1H, s), 6.50 (1H, d, J=7.5 Hz), 5.25 (1H, s), 3.70 (1H, m), 3.08 (1H, m), 2.00 (2H, m), 1.68 (2H, m), 1.43 (2H, m), 1.25 (2H, m). $^{13}$C NMR (100 MHz, CDCl$_3$) δ: 162.8 (d, J=250 Hz), 151.2, 150.8, 144.3, 143.9, 143.5, 136.8, 135.6, 135.2, 133.4, 131.7, 130.8, 130.7, 128.4, 127.9, 123.7, 123.1, 118.4 (d, J=23 Hz), 114.0 (d, J=7.5 Hz), 99.5, 89.0, 70.0, 57.2, 33.7, 31.2. HRMS (ESI-TOF$^+$): m/z [M+H]$^+$ calcd for C$_{29}$H$_{27}$FN$_5$O: 480.2200; found: 480.2199.

TBI-922, 5-(4-Fluorophenyl)-3-cyclopropylimino-2-(3-pyridyl)amino-3,5-dihydrophenazine:

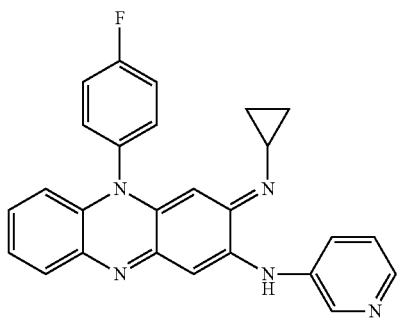 [SMILES: Fc1ccc(-n2c3c/c(=N\C4CC4)c(Nc4cccnc4)cc-3nc3ccccc32)cc1]

$^1$H NMR (300 MHz, CDCl$_3$) δ: 8.54 (1H, d, J=2.4 Hz), 8.31 (1H, dd, J=4.8, 1.2 Hz), 7.74 (1H, dd, J=8.4, 1.2 Hz), 7.66 (1H, d, J=7.5 Hz), 7.44 (3H, m), 7.28 (2H, dd, J=8.4, 4.8 Hz), 7.13 (2H, m), 6.78 (1H, s), 6.42 (1H, d, J=7.5 Hz), 5.53 (1H, s), 2.73 (1H, m), 0.88 (2H, m), 0.80 (2H, m). $^{13}$C NMR (100 MHz, CDCl$_3$) δ: 162.8 (d, J=250 Hz), 152.4, 151.2, 144.3, 143.9, 143.4, 136.6, 135.7, 134.9, 133.4, 131.9, 130.9, 130.8, 128.2, 127.8, 123.6, 122.9, 118.5 (d, J=23 Hz), 113.9 (d, J=7.5 Hz), 99.4, 89.4, 32.8, 9.9. HRMS (ESI-TOF$^+$): m/z [M+H]$^+$ calcd for C$_{26}$H$_{21}$FN$_5$: 422.1781; found: 422.1780.

TBI-923, 5-(4-Fluorophenyl)-3-cyclobutylimino-2-(3-pyridyl)amino-3,5-dihydrophenazine:

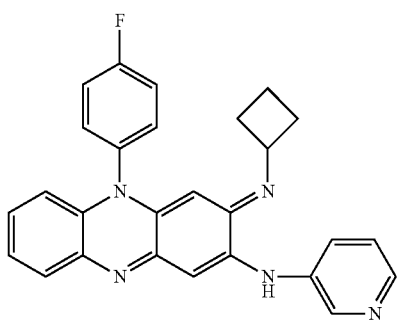 [SMILES: Fc1ccc(-n2c3c/c(=N\C4CCC4)c(Nc4cccnc4)cc-3nc3ccccc32)cc1]

$^1$H NMR (300 MHz, CDCl$_3$) δ: 8.60 (1H, d, J=2.4 Hz), 8.33 (1H, dd, J=4.8, 1.2 Hz), 7.77 (1H, dd, J=8.4, 1.2 Hz), 7.70 (1H, d, J=7.5 Hz), 7.43 (3H, m), 7.31 (2H, dd, J=8.4, 4.8 Hz), 7.17 (2H, m), 6.83 (1H, s), 6.49 (1H, d, J=7.5 Hz), 5.09 (1H, s), 3.89 (1H, m), 2.17 (2H, m), 2.04 (2H, m), 1.69 (2H, m). $^{13}$C NMR (100 MHz, CDCl$_3$) δ: 162.8 (d, J=250 Hz), 151.2, 150.9, 144.3, 143.9, 143.5, 136.7, 135.7, 134.7, 133.4, 131.6, 130.9, 130.8, 128.3, 127.8, 123.6, 123.1, 118.4 (d, J=23 Hz), 113.9 (d, J=7.5 Hz), 99.5, 90.5, 54.8, 31.9, 16.0. HRMS (ESI-TOF$^+$): m/z [M+H]$^+$ calcd for C$_{17}$H$_{23}$FN$_5$: 436.1937; found: 436.1936.

TBI-930, 5-(4-Fluorophenyl)-3-(1-methylethyl)imino-2-(6-ethoxy-3-pyridyl)amino-3,5-dihydrophenazine:

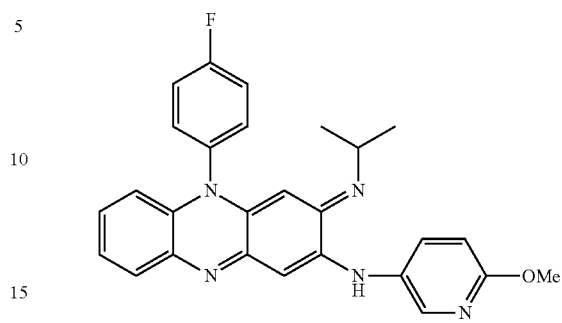

$^1$H NMR (300 MHz, CDCl$_3$) δ: 8.15 (1H, d, J=2.4 Hz), 7.64 (2H, m), 7.42 (2H, m), 7.34 (2H, m), 7.13 (2H, m), 6.78 (1H, d, J=8.7 Hz), 6.50 (1H, s), 6.46 (1H, d, J=7.8 Hz), 5.27 (1H, s), 3.96 (3H, s), 3.46 (1H, m), 1.09 (6H, d, J=6.3 Hz). $^{13}$C NMR (100 MHz, CDCl$_3$) δ: 162.7 (d, J=250 Hz), 161.2, 150.9, 150.5, 145.8, 142.4, 135.6, 135.2, 135.0, 133.5, 131.5, 130.9, 130.8, 130.1, 128.0, 127.3, 122.8, 118.4 (d, J=23 Hz), 113.8, 111.0, 98.0, 89.0, 53.6, 49.3, 22.7.

TBI-931, 5-(4-Fluorophenyl)-3-cyclopropyimino-2-(6-methoxy-3-pyridyl)amino-3,5-dihydrophenazine:

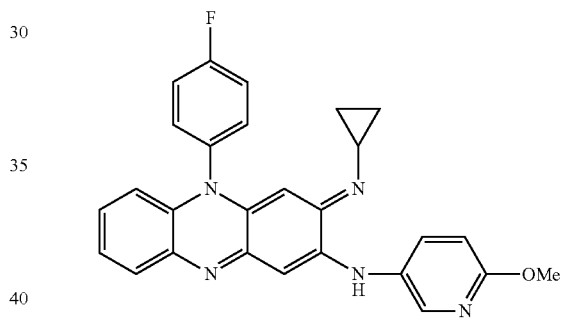

$^1$H NMR (300 MHz, CDCl$_3$) 8.10 (1H, d, J=2.4 Hz), 7.62 (2H, m), 7.44 (2H, m), 7.36 (2H, m), 7.12 (2H, m), 6.79 (1H, d, J=8.7 Hz), 6.43 (1H, s), 6.42 (1H, d, J=7.8 Hz), 5.53 (1H, s), 3.95 (3H, s), 2.73 (1H, m), 0.87 (2H, m), 0.79 (2H, m). $^{13}$C NMR (100 MHz, CDCl$_3$) δ: 162.7 (d, J=250 Hz), 161.3, 152.6, 151.2, 145.8, 142.7, 135.8, 135.3, 134.9, 133.6, 131.7, 130.9, 130.8, 130.0, 128.0, 127.3, 122.8, 118.4 (d, J=23 Hz), 113.8, 111.1, 98.1, 89.4, 53.6, 32.8, 9.8.

TBI-932, 5-(4-Fluorophenyl)-3-cyclohexylimino-2-(6-methoxy-3-pyridyl)amino-3,5-dihydrophenazine:

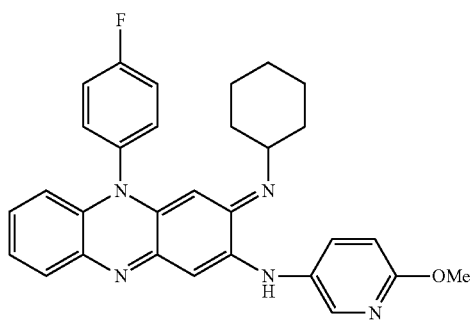 [SMILES: COc1ccc(Nc2cc3nc4ccccc4n(-c4ccc(F)cc4)c-3c/c2=N\C2CCCCC2)cn1]

¹H NMR (300 MHz, CDCl₃) δ: 8.15 (1H, d, J=2.4 Hz), 7.63 (2H, m), 7.42 (2H, m), 7.32 (2H, m), 7.13 (2 m), 6.78 (1H, d, J=8.7 Hz), 6.49 (1H, s), 6.47 (1H, d, J=7.8 Hz), 5.24 (1H, s), 3.95 (3H, s), 3.07 (1H, m), 1.73 (2H, m), 1.61 (3H, m), 1.33 (2H, m), 1.21 (3H, m). ¹³C NMR (100 MHz, CDCl₃) δ: 162.7 (d, J=250 Hz), 161.2, 151.1, 150.6, 145.9, 142.4, 135.6, 135.0, 134.9, 133.6, 131.5, 130.9, 130.8, 130.2, 128.1, 127.2, 122.8, 118.4 (d, J=23 Hz), 113.8, 111.0, 98.0, 89.3, 58.0, 53.6, 33.6, 25.8, 24.7.

TBI-933, 5-(4-Fluorophenyl)-3-(1',4'-trans-4-methoxycyclohexyl)imino-2-(6-methoxy-3-pyridyl)amino-3,5-dihydrophenazine:

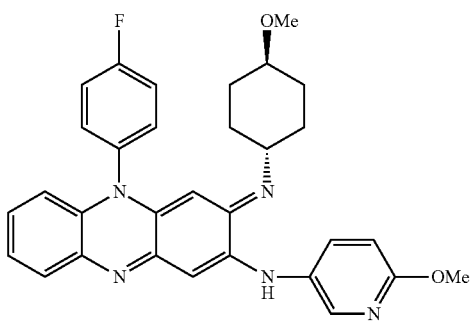 [SMILES: COc1ccc(Nc2cc3nc4ccccc4n(-c4ccc(F)cc4)c-3c/c2=N\[C@H]2CC[C@H](OC)CC2)cn1]

¹H NMR (300 MHz, CDCl₃) δ: 8.14 (1H, d, J=2.4 Hz), 7.68 (2H, m), 7.41 (2H, m), 7.32 (2H, m), 7.15 (2H, m), 6.78 (1H, d, J=8.7 Hz), 6.50 (1H, s), 6.48 (1H, d, J=7.8 Hz), 5.24 (1H, s), 3.96 (3H, s), 3.36 (3H, s), 3.19 (1H, m), 3.08 (1H, m), 2.08 (2H, m), 1.70 (2H, m), 1.40 (2H, m), 1.20 (2H, m). ¹³C NMR (100 MHz, CDCl₃) δ: 162.7 (d, J=250 Hz), 161.2, 151.3, 150.9, 145.9, 142.5, 135.7, 135.1, 134.9, 133.5, 131.5, 130.8, 130.7, 130.2, 128.2, 127.4, 122.9, 118.4 (d, J=23 Hz), 113.9, 111.0, 98.1, 89.0, 57.4, 55.8, 53.6, 31.2, 30.0.

TBI-934, 5-(4-Fluorophenyl)-3-cyclobutylimino-2-(6-methoxy-3-pyridyl)amino-3,5-dihydrophenazine:

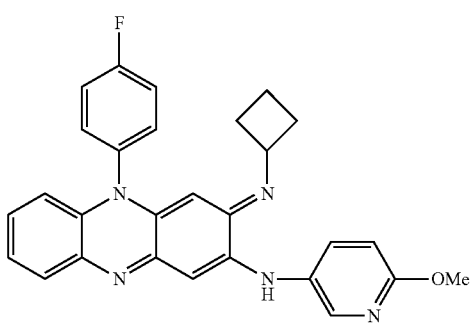 [SMILES: COc1ccc(Nc2cc3nc4ccccc4n(-c4ccc(F)cc4)c-3c/c2=N\C2CCC2)cn1]

¹H NMR (300 MHz, CDCl₃) δ: 8.13 (1H, d, J=2.4 Hz), 7.63 (2H, m), 7.43 (2H, m), 7.30 (2H, m), 7.12 (2H, m), 6.77 (1H, d, J=8.7 Hz), 6.48 (1H, s), 6.46 (1H, d, J=7.8 Hz), 5.06 (1H, s), 3.93 (3H, s), 3.87 (1H, m), 2.15 (2H, m), 2.03 (2H, m), 1.73 (2H, m). ¹³C NMR (100 MHz, CDCl₃) δ: 162.7 (d, J=250 Hz), 161.1, 151.2, 150.6, 145.5, 142.2, 135.5, 134.9, 134.4, 133.4, 131.2, 130.8, 130.7, 130.0, 128.0, 127.3, 122.8, 118.2 (d, J=23 Hz), 113.8, 110.9, 98.0, 90.4, 54.7, 53.4, 31.8, 15.9.

TBI-935, 5-(4-Fluorophenyl)-3-(4-tetrahydropyranyl)imino-2-(6-methoxy-3-pyridyl)amino-3,5-dihydrophenazine:

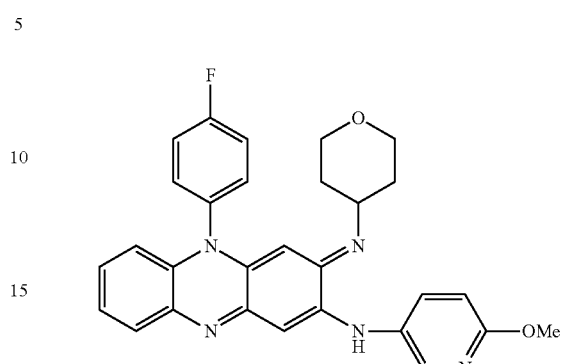

¹H NMR (300 MHz, CDCl₃) δ: 8.15 (1H, d, J=2.4 Hz), 7.65 (2H, m), 7.43 (2H, m), 7.34 (2H, m), 7.16 (2H, m), 6.79 (1H, d, J=8.7 Hz), 6.53 (1H, s), 6.48 (1H, d, J=7.5 Hz), 5.24 (1H, s), 3.99 (2H, m), 3.96 (3H, s), 3.40 (3H, m), 1.65 (4H, m). ¹³C NMR (100 MHz, CDCl₃) δ: 162.7 (d, J=250 Hz), 161.3, 151.2, 150.7, 145.9, 142.5, 135.7, 135.1, 134.4, 133.5, 131.4, 130.8, 130.7, 130.0, 128.2, 127.4, 123.0, 118.2 (d, J=23 Hz), 114.0, 111.1, 98.2, 88.8, 66.1, 54.4, 53.4, 33.4.

TBI-940, 5-(4-Fluorophenyl)-3-cyclopropylimino-2-(4-methyl-3-pyridyl)amino-3,5-dihydrophenazine:

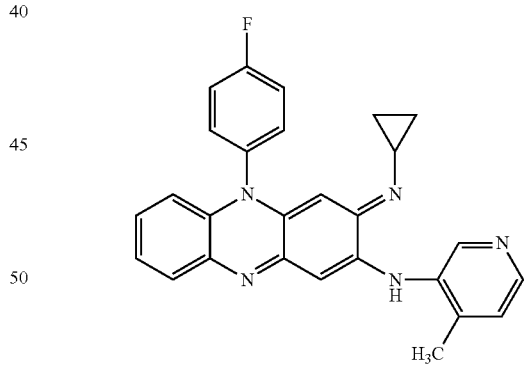

¹H NMR (300 MHz, CDCl₃) δ: 8.53 (1H, s), 8.26 (1H, d, J=4.8 Hz), 7.55 (1H, d, J=7.5 Hz), 7.35 (2H, t, J=8.4 Hz), 7.29 (2H, m), 7.10 (2H, d, J=4.8 Hz), 7.05 (2H, m), 6.36 (1H, d, J=7.5 Hz), 6.16 (1H, s), 5.47 (1H, s), 2.69 (1H, m), 2.19 (3H, s), 0.83 (2H, m), 0.78 (2H, m). ¹³C NMR (100 MHz, CDCl₃) δ: 162.7 (d, J=250 Hz), 152.3, 151.2, 146.7, 146.4, 145.2, 142.5, 135.7, 135.3, 134.9, 133.6, 131.8, 130.9, 130.8, 128.1, 127.4, 122.8, 118.5 (d, J=23 Hz), 113.8, 98.8, 89.3, 32.8, 17.4, 10.0.

TBI-950, 5-(4-Trifluoromethoxyphenyl)-3-(4-tetrahydro-pyranyl)imino-2-(6-methyl-3-pyridyl)amino-3,5-dihydrophenazine:

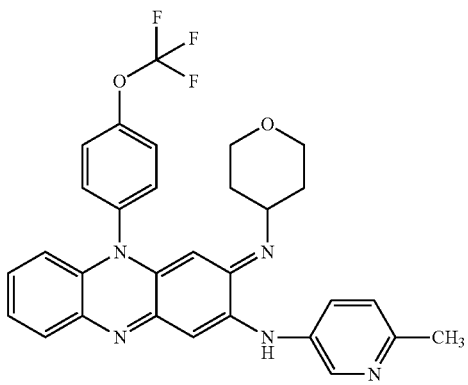 [SMILES: Cc1ccc(Nc2cc3nc4ccccc4n(-c4ccc(OC(F)(F)F)cc4)c-3c/c2=N\C2CCOCC2)cn1]

$^1$H NMR (300 MHz, CDCl$_3$) δ: 8.47 (1H, s), 7.70 (3H, m), 7.60 (2H, d, J=8.7 Hz), 7.41 (2H, d, J=8.7 Hz), 7.19 (2H, m), 6.74 (1H, s), 6.51 (1H, d, J=8.1 Hz), 5.17 (1H, s), 3.97 (2H, m), 3.36 (3H, m), 1.63 (4H, m).

TBI-951, 5-(4-Trifluoromethoxyphenyl)-3-(1-methyl-ethyl)imino-2-(pyrimidin-2-yl)amino-3,5-dihydrophenazine:

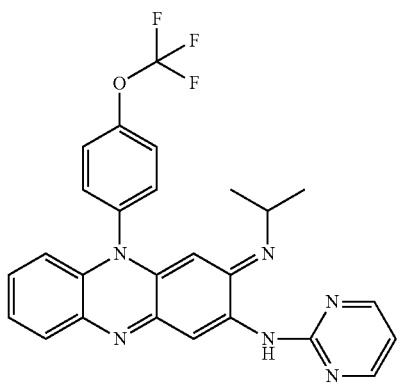 [SMILES: CC(C)/N=c1\cc2n(-c3ccc(OC(F)(F)F)cc3)c3ccccc3nc-2cc1Nc1ncccn1]

$^1$H NMR (300 MHz, CDCl$_3$) 9.55 (br. s), 8.36 (2H, d, J=4.8 Hz), 8.30 (1H, s), 7.58 (1H, d, J=7.5 Hz), 7.40 (2H, d, J=7.8 Hz), 7.23 (2H, d, J=7.8 Hz), 6.99 (2H, m), 6.64 (1H, s), 6.24 (1H, d, J=7.5 Hz), 5.03 (1H, s), 3.24 (1H, m), 1.06 (6H, d, J=6.0 Hz).

TBI-952, 5-(4-Trifluoromethoxyphenyl)-3-(1-methyl-ethyl)imino-2-(2-pyridyl)amino-3,5-dihydrophenazine:

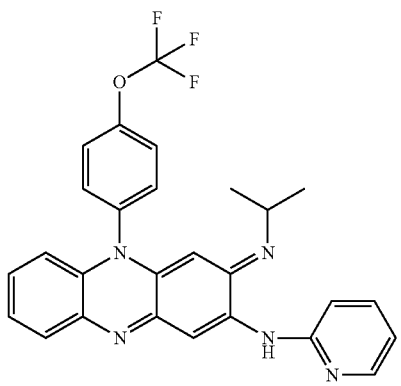 [SMILES: CC(C)/N=c1\cc2n(-c3ccc(OC(F)(F)F)cc3)c3ccccc3nc-2cc1Nc1ccccn1]

$^1$H NMR (300 MHz, CDCl$_3$) δ: 9.31 (1H, br. s), 8.38 (1H, d, 13.9 Hz), 8.28 (1H, s), 7.76 (1H, d, J=7.5 Hz), 7.58 (2H, d, J=7.8 Hz), 7.42 (2H, d, J=7.8 Hz), 7.16 (2H, m), 6.98 (1H, d, J=8.4 Hz), 6.85 (1H, m), 6.44 (1H, d, J=7.5 Hz), 5.21 (1H, s), 3.44 (1H, m), 1.07 (6H, d, J=6.0 Hz).

TBI-953, 5-(4-Trifluoromethoxyphenyl)-3-(1-methyl-ethyl)imino-2-(pyrazin-2-yl)amino-3,5-dihydrophenazine:

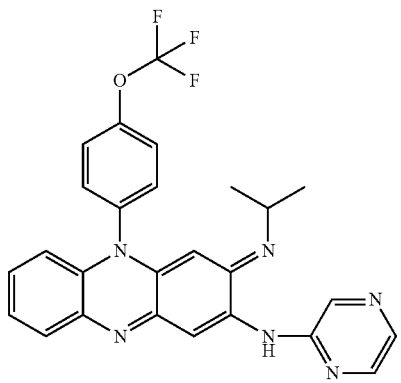 [SMILES: CC(C)/N=c1\cc2n(-c3ccc(OC(F)(F)F)cc3)c3ccccc3nc-2cc1Nc1cnccn1]

$^1$H NMR (300 MHz, CDCl$_3$) δ: 8.44 (1H, br. s), 8.31 (1H, s), 8.28 (1H, d, J=2.4 Hz), 8.05 (1H, d, J=2.4 Hz), 7.78 (1H, d, J=9.3 Hz), 7.59 (2H, d, J=7.8 Hz), 7.42 (2H, d, J=7.8 Hz), 7.19 (2H, 6.45 (1H, d, J=9.3 Hz), 5.30 (1H, s), 5.22 (1H, s), 3.43 (1H, m), 1.10 (6H, d, J=6.0 Hz).

TBI-954, 5-(4-Trifluoromethoxyphenyl)-3-(1-methyl-ethyl)imino-2-(3-nitro-2-pyridyl)amino-3,5-dihydrophenazine:

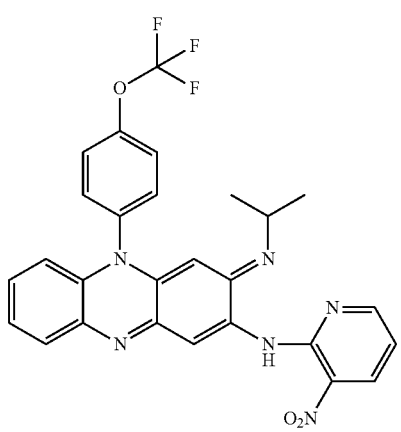 [SMILES: CC(C)/N=c1\cc2n(-c3ccc(OC(F)(F)F)cc3)c3ccccc3nc-2cc1Nc1ncccc1[N+](=O)[O-]]

$^1$H NMR (300 MHz, CDCl$_3$) δ: 12.24 (1H, br. s), 8.73 (1H, s), 8.66 (1H, d, J=4.5 Hz), 8.56 (1H, d, J=8.1 Hz), 7.78 (1H, d=9.3 Hz), 7.59 (2H, d, J=8.4 Hz), 7.42 (2H, d, J=8.4 Hz), 7.19 (2H, m), 6.95 (1 dd, J=8.1, 4.5 Hz), 6.44 (1H, d, J=9.3 Hz), 5.23 (1H, s), 3.45 (1H, m), 1.14 (6H, d, J=6.0 Hz).

TBI-960, 5-(4-Chlorophenyl)-3-(4-tetrahydropyranyl)imino-2-(pyrimidin-5-yl)amino-3,5-dihydrophenazine:

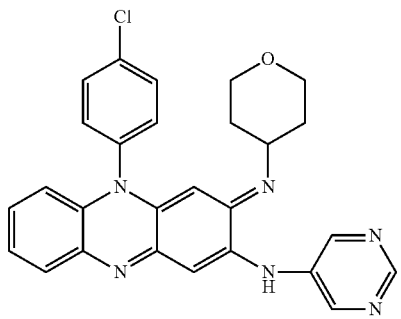

$^1$H NMR (300 MHz, CDCl$_3$) δ: 9.67 (1H, br. s), 9.00 (2H, s), 8.67 (1H, s), 7.71 (1H, d, J=7.5 Hz), 7.70 (2H, d, J=7.5 Hz), 7.27 (2H, d, J=7.5 Hz), 7.14 (2H, m), 6.47 (1H, d, J=7.5 Hz), 5.19 (1H, s), 3.96 (2H, m), 3.35 (3H, m), 1.61 (4H, m).

TBI-961, 5-(4-Chlorophenyl)-3-cyclohexylimino-2-(pyrimidin-5-yl)amino-3,5-dihydrophenazine:

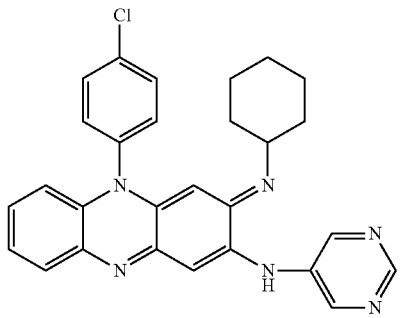

¹H NMR (300 MHz, CDCl₃) δ: 9.68 (1H, br. s), 9.01 (2H, s), 8.67 (1H, s), 7.73 (1H, d, J=7.5 Hz), 7.69 (2H, d, J=7.5 Hz), 7.27 (2H, d, J=7.5 Hz), 7.11 (2H, m), 6.43 (1H, d, J=7.5 Hz), 5.19 (1H, s), 3.05 (1H, m), 1.73 (2H, m), 1.57 (3H, m), 1.33 (2H, m), 1.19 (3H, m).

TBI-980, 5-(3-Chlorophenyl)-3-(4-tetrahydropyranyl)imino-2-(pyrimidin-5-yl)amino-3,5-dihydrophenazine:

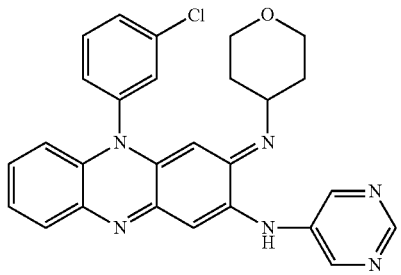 [SMILES: Clc1cccc(-n2c3c/c(=N\C4CCOCC4)c(Nc4cncnc4)cc-3nc3ccccc32)c1]

¹H NMR (300 MHz, CDCl₃) δ: 9.67 (1 br. s), 9.00 (2H, s), 8.67 (1H, s), 7.70 (3H, m), 7.36 (1H, s), 7.24 (1H, m), 7.15 (2H, m), 6.49 (1H, d/=7.5 Hz), 6.39 (1H, s), 5.19 (1H, s), 3.96 (2H, m), 3.35 (3H, m), 1.61 (4H, m).

TBI-80A, 5-(3-Chlorophenyl)-3-(4-tetrahydropyranyl)imino-2-(6-methyl-3-pyridyl)amino-3,5-dihydrophenazine:

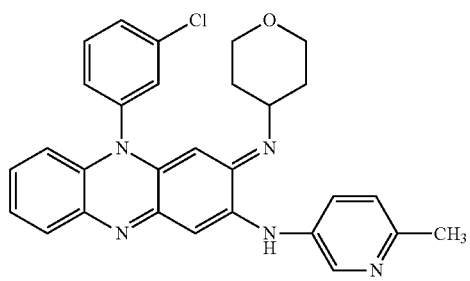 [SMILES: Cc1ccc(Nc2cc3nc4ccccc4n(-c4cccc(Cl)c4)c-3c/c2=N\C2CCOCC2)cn1]

¹H NMR (300 MHz, CDCl₃) δ: 8.47 (1H, s), 7.68 (4H, m), 7.38 (1H, s), 7.27 (1H, m), 7.18 (3H, m), 6.74 (1H, s), 6.53 (1H, d, J=7.5 Hz), 5.26 (1H, s), 3.98 (2H, m), 3.40 (2H, m), 2.84 (1H, m), 2.57 (3H, s), 1.67 (4H, m). ¹³C NMR (100 MHz, CDCl₃) δ: 153.8, 153.7, 151.2, 150.7, 144.3, 143.9, 138.6, 136.8, 135.7, 134.7, 133.9, 132.3, 131.0, 130.2, 129.6, 129.3, 128.4, 127.8, 127.2, 123.2, 114.0, 99.0, 89.1, 66.9, 54.5, 34.3, 23.8.

TBI-80B, 5-(3-Chlorophenyl)-3-cyclohexylimino-2-(6-methyl-3-pyridyl)amino-3,5-dihydrophenazine:

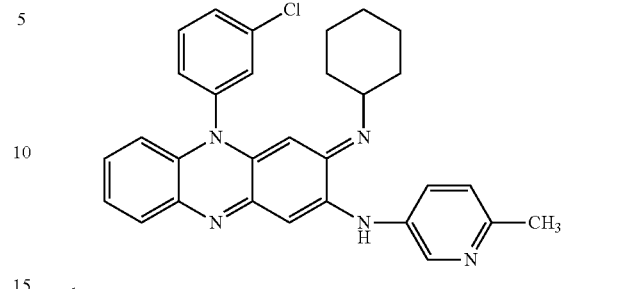

¹H NMR (300 MHz, CDCl₃) δ: 8.45 (1H, s), 7.67 (4H, m), 7.38 (1H, s), 7.28 (1H, m), 7.16 (3H, m), 6.71 (1H, s), 6.50 (1H, d, J=7.5 Hz), 5.25 (1H, s), 3.08 (1H, m), 1.76 (2H, m), 1.61 (3H, m), 1.35 (2H, m), 1.23 (3H, m). ¹³C NMR (100 MHz, CDCl₃) δ: 153.8, 153.3, 151.0, 150.6, 144.4, 143.7, 138.7, 136.7, 135.6, 134.5, 134.0, 132.2, 131.2, 130.2, 129.4, 128.2, 127.6, 127.3, 123.2, 123.0, 113.8, 98.8, 89.5, 58.1, 33.6, 25.8, 24.7, 23.8.

TBI-80C, 5-(3-Chlorophenyl)-3-(1,3-dimethoxyisopropyl)imino-2-(6-methyl-3-pyridyl)amino-3,5-dihydrophenazine:

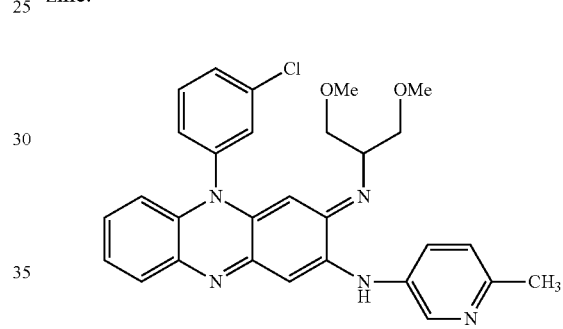

¹H NMR (300 MHz, CDCl₃) δ: 8.44 (1H, s), 7.67 (4H, m), 7.37 (1H, s), 7.28 (1H, m), 7.16 (3H, m), 6.74 (1H, s), 6.49 (1H, d, J=7.5 Hz), 5.47 (1H, s), 3.73 (1H, s), 3.52 (2H, m), 3.44 (2H, m), 3.36 (3H, s), 3.28 (3H, s), 2.56 (3H, s). ¹³C NMR (100 MHz, CDCl₃) δ: 153.5, 153.3, 151.0, 150.7, 144.4, 143.7, 138.7, 136.7, 135.6, 134.5, 134.0, 132.2, 131.2, 130.2, 129.4, 128.2, 127.6, 127.3, 123.2, 123.1, 114.0, 99.0, 90.1, 74.6, 74.3, 59.1, 59.0, 58.4, 23.8.

TBI-810, 5-(3-Chlorophenyl)-3-(1-methylethyl)imino-2-(3-pyridyl)amino-3,5-dihydrophenazine:

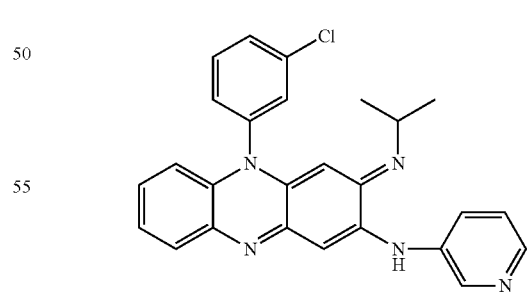

¹H NMR (300 MHz, CDCl₃) δ: 8.55 (1H, s), 8.33 (1H, d, J=4.8 Hz), 7.76 (1H, d, J=7.5 Hz), 7.66 (3H, m), 7.40 (1H, s), 7.29 (2H, m), 7.15 (2H, m), 6.78 (1H, s), 6.44 (1H, d, J=7.5 Hz), 5.55 (1H, s), 3.45 (1H, m), 1.09 (6H, d, J=6.0 Hz). ¹³C NMR (100 MHz, CDCl₃) δ: 152.3, 151.2, 144.4, 144.0, 143.4, 138.7, 136.8, 136.6, 135.6, 134.5, 132.4, 131.5, 130.1, 129.4, 128.2, 128.1, 127.8, 127.4, 123.6, 123.0, 113.8, 99.4, 89.6, 49.4, 23.6.

TBI-811, 5-(3-Chlorophenyl)-3-(1',4'-trans-4-hydroxycyclohexyl)imino-2-(3-pyridyl)amino-3,5-dihydrophenazine:

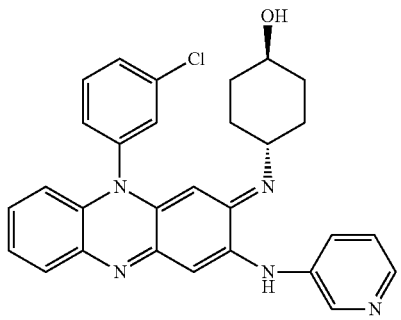 [SMILES: O[C@H]1CC[C@H](/N=c2\cc3n(-c4cccc(Cl)c4)c4ccccc4nc-3cc2Nc2cccnc2)CC1]

$^1$H NMR (300 MHz, CDCl$_3$) δ: 8.49 (1H, s), 8.25 (1H, d, J=3.7 Hz), 8.03 (1H, s), 7.72 (1H, d, J=7.5 Hz), 7.62 (3H, m), 7.31 (1H, s), 7.25 (2H, m), 7.12 (2H, m), 6.77 (1H, s), 6.46 (1H, d, J=7.5 Hz), 5.18 (1H, s), 3.71 (1H, m), 3.05 (1H, m), 1.96 (2H, m), 1.69 (2H, m), 1.47 (2H, m), 1.25 (2H, m). $^{13}$C NMR (100 MHz, CDCl$_3$) 151.2, 150.7, 144.1, 143.7, 143.4, 138.5, 136.7, 135.5, 134.7, 132.2, 131.1, 130.1, 129.2, 128.3, 128.0, 127.1, 125.0, 123.7, 123.2, 119.2, 113.9, 99.5, 89.2, 70.1, 57.3, 33.7, 31.2

TBI-812, 5-(3-Chlorophenyl)-3-cyclopropylimino-2-(3-pyridyl)amino-3,5-dihydrophenazine:

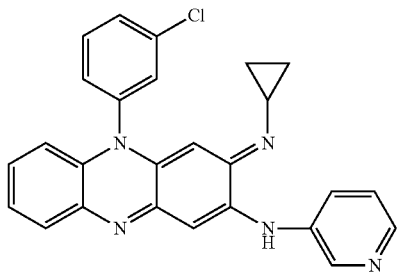 [SMILES: Clc1cccc(-n2c3c/c(=N\C4CC4)c(Nc4cccnc4)cc-3nc3ccccc32)c1]

$^1$H NMR (300 MHz, CDCl$_3$) δ: 8.55 (1H, d, J=1.7 Hz), 8.33 (1H, d, J=4.0 Hz), 8.03 (1H, s), 7.76 (1H, d, J=8.5 Hz), 7.65 (3H, m), 7.39 (1H, s), 7.28 (2H, m), 7.15 (2H, m), 6.78 (1H, s), 6.44 (1H, d, J=7.5 Hz), 5.55 (1H, s), 2.75 (1H, m), 0.89 (2H, m), 0.82 (2H, m). $^{13}$C NMR (100 MHz, CDCl$_3$) 152.3, 151.2, 144.4, 144.0, 143.4, 138.7, 136.8, 136.6, 135.6, 134.5, 132.4, 131.5, 130.1, 129.4, 128.3, 128.1, 127.8, 127.4, 123.6, 123.0, 113.8, 99.4, 89.6, 32.9, 10.0.

TBI-814, 5-(3-Chlorophenyl)-3-cyclobutylimino-2-(3-pyridyl)amino-3,5-dihydrophenazine:

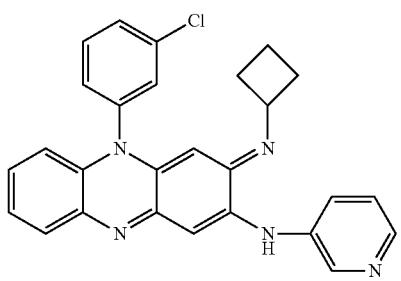 [SMILES: Clc1cccc(-n2c3c/c(=N\C4CCC4)c(Nc4cccnc4)cc-3nc3ccccc32)c1]

$^1$H NMR (300 MHz, CDCl$_3$) δ: 8.59 (1H, d, J=2.4 Hz), 8.33 (1H, d, J=4.8 Hz), 8.03 (1H, s), 7.78 (1H, d, J=8.4 Hz), 7.65 (3H, m), 7.38 (1H, s), 7.29 (2H, m), 7.17 (2H, m), 6.83 (1H, s), 6.51 (1H, d, J=8.4 Hz), 5.09 (1H, s), 3.89 (1H, m), 2.17 (2H, m), 2.04 (2H, m), 1.71 (2H, m). $^{13}$C NMR (100 MHz, CDCl$_3$) δ: 151.0, 150.4, 144.4, 143.5, 143.1, 138.3, 136.6, 136.6, 135.5, 134.1, 132.2, 130.8, 130.1, 129.0, 128.2, 128.0, 127.9, 127.0, 123.6, 123.2, 113.9, 99.5, 90.5, 54.4, 31.6, 15.9.

TBI-820, 5-(3-Chlorophenyl)-3-cyclohexylimino-2-(2-methoxy-3-pyridyl)amino-3,5-dihydrophenazine:

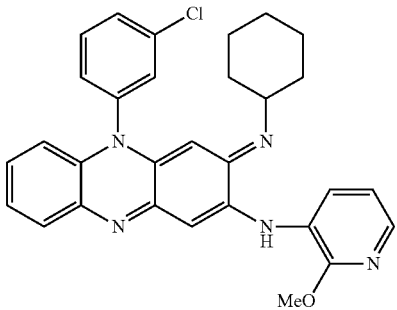

$^1$H NMR (300 MHz, CDCl$_3$) δ: 7.81 (5H, m), 7.55 (2H, m), 7.11 (3H, m), 6.81 (1H, m), 6.55 (2H, m), 5.12 (1H, s), 3.94 (3H, s), 2.98 (1H, m), 1.68 (2H, m), 1.53 (3H, m), 1.28 (2H, m), 1.10 (3H, m). $^{13}$C NMR (100 MHz, CDCl$_3$) δ: 150.3, 150.1, 141.5, 138.5, 138.2, 135.3, 135.1, 134.2, 132.9, 131.0, 130.0, 129.0, 128.2, 128.0, 127.9, 127.8, 124.1, 124.0, 122.8, 117.4, 113.9, 100.1, 88.7, 56.9, 53.6, 33.0, 25.4, 23.8.

TBI-821, 5-(3-Chlorophenyl)-3-(1-methylethyl)imino-2-(2-methoxy-3-pyridyl)amino-3,5-dihydrophenazine:

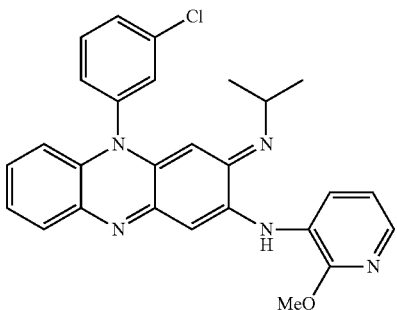

$^1$H NMR (300 MHz, CDCl$_3$) δ: 7.84 (2H, m), 7.74 (1H, m), 7.64 (2H, m), 7.37 (1H, s), 7.17 (3H, m), 6.90 (2H, m), 6.49 (1H, m), 5.48 (1H, s), 2.38 (3H, s), 1.09 (6H, d, J=6.0 Hz). $^{13}$C NMR (100 MHz, CDCl$_3$) δ: 161.0, 155.4, 153.5, 150.9, 142.7, 142.2, 138.9, 138.6, 136.7, 134.6, 132.3, 130.1, 129.3, 128.3, 127.8, 127.2, 127.1, 124.7, 124.4, 116.8, 113.9, 96.9, 90.4, 53.7, 49.4, 23.5.

TBI-822, 5-(3-Chlorophenyl)-3-(4-tetrahydropyranyl)imino-2-(2-methoxy-3-pyridyl)amino-3,5-dihydrophenazine:

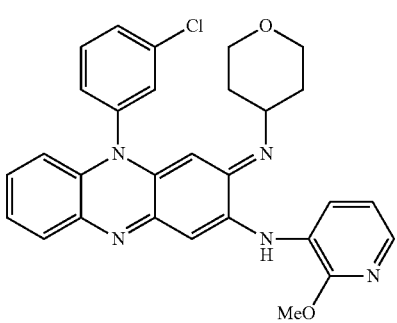

$^1$H NMR (300 MHz, CDCl$_3$) δ: 7.84 (2H, m), 7.74 (1H, m), 7.64 (2H, m), 7.38 (1H, s), 7.17 (3H, m), 6.90 (2H, m), 6.53 (1H, m), 5.27 (1H, s), 4.03 (3H, s), 3.96 (2H, m), 3.43 (2H, m), 2.85 (1H, m), 1.75 (4H, m). $^{13}$C NMR (100 MHz, CDCl$_3$) δ: 161.0, 155.4, 153.5, 150.9, 142.7, 142.2, 138.9, 138.6, 136.7, 134.6, 132.3, 130.1, 129.3, 128.3, 127.8, 127.2, 127.1, 124.7, 124.4, 116.7, 113.9, 100.4, 89.1, 66.9, 53.8, 53.5, 34.2.

TBI-823, 5-(3-Chlorophenyl)-3-cyclopropylimino-2-(2-methoxy-3-pyridyl)amino-3,5-dihydrophenazine:

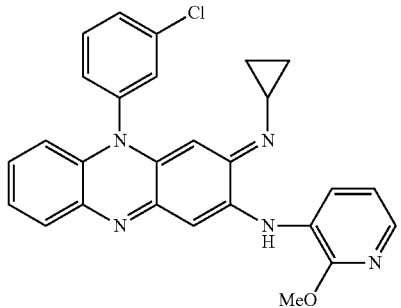 [SMILES: COc1ncccc1Nc1cc2nc3ccccc3n(-c3cccc(Cl)c3)c-2c/c1=N\C1CC1]

$^1$H NMR (300 MHz, CDCl$_3$) δ: 7.80 (2H, m), 7.74 (1H, m), 7.66 (2H, m), 7.38 (1H, s), 7.17 (3H, m), 6.90 (2H, m), 6.44 (1H, m), 5.54 (1H, s), 4.04 (3H, s), 2.72 (1H, m), 0.84 (4H, m), $^{13}$C NMR (100 MHz, CDCl$_3$) δ: 161.0, 155.4, 153.5, 150.9, 142.7, 142.2, 138.9, 138.6, 136.7, 134.6, 132.3, 130.1, 129.3, 128.3, 127.8, 127.2, 127.1, 124.7, 124.4, 116.8, 113.9, 100.2, 89.8, 53.7, 32.9, 10.1.

TBI-824, 5-(3-Chlorophenyl)-3-cyclobutylimino-2-(2-methoxy-3-pyridyl)amino-3,5-dihydrophenazine:

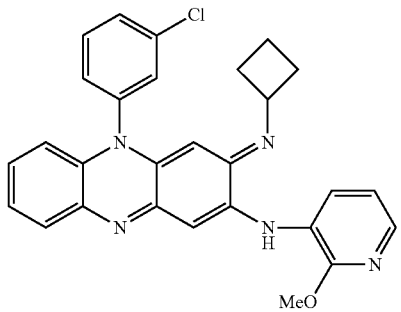 [SMILES: COc1ncccc1Nc1cc2nc3ccccc3n(-c3cccc(Cl)c3)c-2c/c1=N\C1CCC1]

$^1$H NMR (300 MHz, CDCl$_3$) δ: 7.84 (2H, m), 7.69 (3H, m), 7.38 (1H, s), 7.17 (3H, m), 6.93 (2H, m), 6.50 (1H, m), 5.08 (1H, s), 4.04 (3H, s), 3.93 (1H, m), 2.20 (2H, m), 2.07 (2H, m), 1.75 (2H, m). $^{13}$C NMR (100 MHz, CDCl$_3$) δ: 161.0, 155.4, 153.5, 150.9, 142.7, 142.2, 138.9, 138.6, 136.7, 134.6, 132.3, 130.1, 129.3, 128.3, 127.8, 127.2, 127.1, 124.7, 124.4, 116.8, 113.9, 100.2, 90.4, 54.8, 53.7, 31.9, 16.0.

TBI-825, 5-(3-Chlorophenyl)-3-(1,3-dimethoxyisopropyl)imino-2-(2-methoxy-3-pyridyl)amino-3,5-dihydrophenazine:

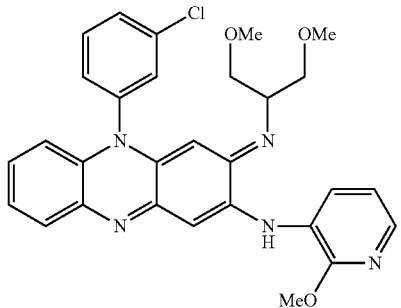 [SMILES: COCC(COC)/N=c1\cc2n(-c3cccc(Cl)c3)c3ccccc3nc-2cc1Nc1cccnc1OC]

$^1$H NMR (300 MHz, CDCl$_3$) δ: 7.86 (2H, m), 7.64 (3H, m), 7.37 (1H, s), 7.18 (3H, m), 6.91 (2H, m), 6.49 (1H, m), 5.48 (1H, s), 4.02 (3H, s), 3.72 (1H, s), 3.57 (2H, m), 3.41 (2H, m), 3.30 (3H, s), 3.29 (3H, s). $^{13}$C NMR (100 MHz, CDCl$_3$) δ: 161.0, 155.4, 153.5, 150.9, 142.7, 142.2, 138.9, 138.6, 136.7, 134.6, 132.3, 130.1, 129.3, 128.3, 127.8, 127.2, 127.1, 124.7, 124.4, 116.8, 113.9, 96.9, 90.4, 74.6, 74.3, 59.2, 59.1, 58.6, 53.6.

TBI-826, 5-(3-Chlorophenyl)-3-(2,3-dimethoxy-1-propyl)imino-2-(2-methoxy-3-pyridyl)amino-3,5-dihydrophenazine:

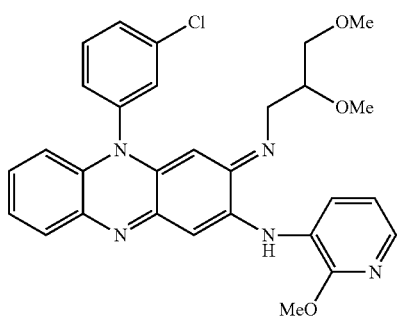 [SMILES: COCC(C/N=c1\cc2n(-c3cccc(Cl)c3)c3ccccc3nc-2cc1Nc1cccnc1OC)OC]

$^1$H NMR (300 MHz, CDCl$_3$) δ: 7.83 (2H, m), 7.73 (1H, d, J=7.5 Hz), 7.68 (2H, m), 7.36 (1H, s), 7.19 (2H, m), 6.98 (1H, s), 6.93 (1H, dd, J=7.5, 5.1 Hz), 6.47 (1H, d, J=7.5 Hz), 5.28 (1H, s), 4.03 (3H, s), 3.68 (2H, m), 3.57 (1H, m), 3.48 (3H, s), 3.39 (3H, s), 3.25 (2H, m). $^{13}$C NMR (100 MHz, CDCl$_3$) δ: 161.0, 155.4, 153.5, 150.9, 142.7, 142.2, 138.9, 138.6, 136.7, 134.6, 132.3, 130.1, 129.3, 128.3, 127.8, 127.2, 127.1, 124.7, 124.4, 116.9, 114.1, 100.2, 89.3, 81.1, 73.3, 59.3, 57.9, 53.7, 50.3.

TBI-830, 5-(4-Trifluoromethoxyphenyl)-3-(4-tetrahydropyranyl)imino-2-(pyrimidin-2-yl)amino-3,5-dihydrophenazine:

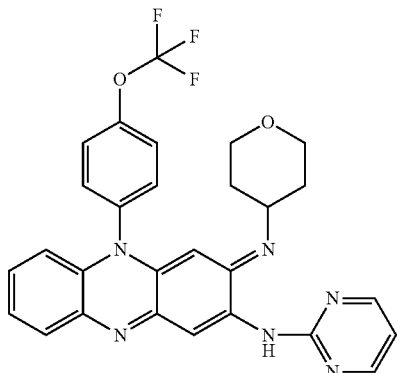

$^1$H NMR (300 MHz, CDCl$_3$) δ: 9.66 (1H, br. s), 8.55 (2H, d, J=4.8 Hz), 8.52 (1H, s), 7.78 (1H, d, J=7.8 Hz), 7.60 (2H, d, J=7.8 Hz), 7.42 (2H, d, J=7.8 Hz), 7.20 (2H, m), 6.83 (1H, t, J=4.8 Hz), 6.49 (1H, d, J=7.8 Hz), 5.16 (1H, s), 3.97 (2H, m), 3.35 (3H, m), 1.65 (4H, m).

TBI-860, 5-(4-Chlorophenyl)-3-(4-tetrahydropyranyl)imino-2-(pyrimidin-2-yl)amino-3,5-dihydrophenazine:

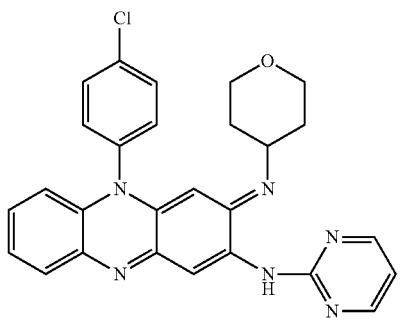

$^1$H NMR (300 MHz, CDCl$_3$) δ: 9.69 (1H, br. s), 8.55 (2H, d, J=4.8 Hz), 8.53 (1H, s), 7.79 (1H, d, J=7.8 Hz), 7.72 (2H, d, J=8.1 Hz), 7.31 (2H, d, J=8.1 Hz), 7.20 (2H, m), 6.83 (1H, t, J=4.8 Hz), 8.47 (1H, d, J=7.5 Hz), 5.24 (1H, s), 3.98 (2H, m), 3.41 (3H, 1.62 (4H, m).

TBI-870, 5-(2-Chlorophenyl)-3-(4-tetrahydropyranyl)imino-2-(2-methoxy)-3-pyridyl)amino-3,5-dihydrophenazine:

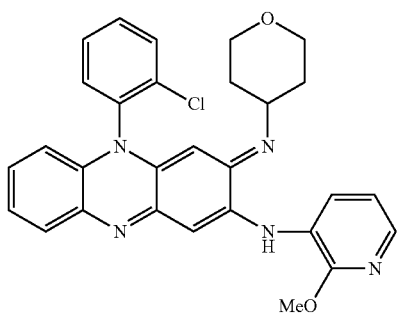 [SMILES: COc1ncccc1Nc1cc2nc3ccccc3n(-c3ccccc3Cl)c-2c/c1=N\C1CCOCC1]

$^1$H NMR (300 MHz, CDCl$_3$) δ: 9.05 (1H, br. s), 7.87 (1H, d, J=8.1 Hz), 7.79 (3H, m), 7.63 (2H, dd, J=6.0, 3.0 Hz), 7.40 (1H, dd, J=6.0, 3.0 Hz), 7.20 (2H, m), 7.00 (1H, s), 6.93 (1H, m), 6.42 (1H, d, J=8.1 Hz), 5.16 (1H, s), 4.05 (3H, s), 4.00 (2H, m), 3.48 (3H, m), 1.68 (4H, m).

TBI-871, 5-(4-Chlorophenyl)-3-(1,3-dimethoxyisopropyl)imino-2-(2-methoxy-3-pyridyl)amino-3,5-dihydrophenazine:

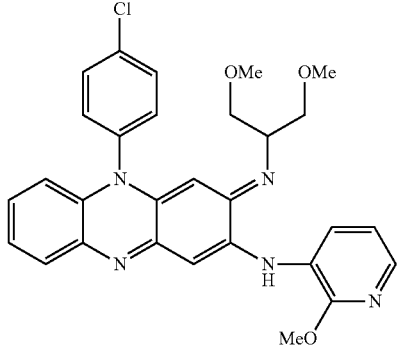

$^1$H NMR (300 MHz, CDCl$_3$) δ: 7.83 (2H, m), 7.72 (3H, m), 7.31 (2H, d, J=8.1 Hz), 7.16 (2H, m), 7.00 (1H, s), 6.92 (1H, dd, J=7.8, 4.8 Hz), 6.47 (1H, d, J=7.5 Hz), 5.49 (1H, s), 4.02 (3H, s), 3.72 (1H, m), 3.57 (2H, m), 3.39 (2H, m), 3.26 (6H, s). $^{13}$C NMR (100 MHz, CDCl$_3$) δ: 155.5, 153.5, 150.9, 142.7, 139.0, 135.9, 135.8, 134.7, 131.6, 131.5, 130.4, 128.7, 128.5, 128.4, 127.8, 125.0, 124.7, 123.1, 114.0, 101.7, 89.7, 74.4, 59.1, 58.7, 53.7.

TBI-872, 5-(4-Chlorophenyl)-3-(2,3-dimethoxy-1-propyl)imino-2-(2-methoxy-3-pyridyl)amino-3,5-dihydrophenazine

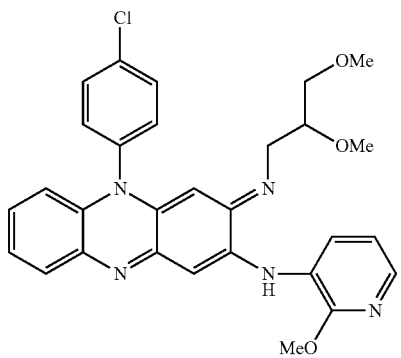

$^1$H NMR (300 MHz, CDCl$_3$) δ: 7.85 (2H, m), 7.71 (3H, m), 7.30 (2H, d, J=8.1 Hz), 7.15 (2H, m), 6.99 (1H, s), 6.93 (1H, dd, J=7.8, 4.8 Hz), 6.46 (1H, d, J=7.5 Hz), 5.29 (1H, s), 4.03 (3H, s), 3.68 (2H, m), 3.57 (1H, dd, J=9.9, 5.4 Hz), 3.49 (3H, s), 3.40 (3H, s), 3.28 (2H, m). $^{13}$C NMR (100 MHz, CDCl$_3$) δ: 155.2, 153.2, 150.9, 142.4, 138.7, 135.9, 135.8, 134.8, 131.8, 131.7, 130.2, 129.6, 129.3, 128.3, 127.9, 124.7, 124.4, 123.2, 114.1, 100.2, 89.2, 81.0, 73.3, 59.3, 57.9, 53.7, 50.4.

TBI-880, 5-(4-Chlorophenyl)-3-(4-tetrahydropyranyl)imino-2-(5-bromo-3-pyridyl)amino-3,5-dihydrophenazine:

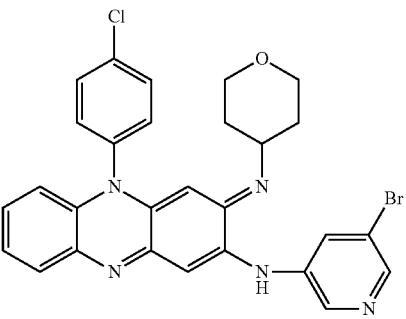 [SMILES: Clc1ccc(-n2c3c/c(=N\C4CCOCC4)c(Nc4cncc(Br)c4)cc-3nc3ccccc32)cc1]

$^1$H NMR (300 MHz, CDCl$_3$) δ: 8.52 (1H, d, J=1.8 Hz), 8.37 (1H, d, J=1.5 Hz), 7.91 (1H, s), 7.74 (1H, dd, J=7.8, 1.5 Hz), 7.73 (2H, d, J=8.4 Hz), 7.30 (2H, d, J=8.4 Hz), 7.18 (2H, m), 6.90 (1H, s), 6.50 (1H, dd, J=7.8, 1.5 Hz), 5.25 (1H, s), 3.97 (2H, m), 3.41 (3H, m), 1.63 (4H, m).

TBI-881, 5-(4-Chlorophenyl)-3-(1',4'-trans-4-methoxycyclohexyl)imino-2-(5-bromo-3-pyridyl)amino-3,5-dihydrophenazine:

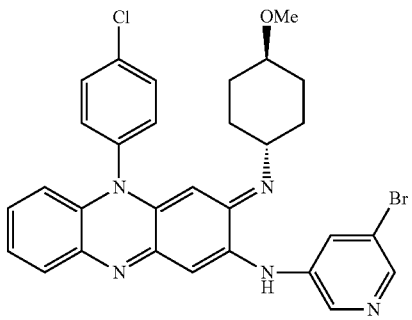 [SMILES: CO[C@H]1CC[C@H](/N=c2\cc3n(-c4ccc(Cl)cc4)c4ccccc4nc-3cc2Nc2cncc(Br)c2)CC1]

$^1$H NMR (300 MHz, CDCl$_3$) 8.50 (1H, d, J=1.8 Hz), 8.36 (1H, d, J=1.5 Hz), 7.90 (1H, s), 7.72 (1H, dd, J=7.8, 1.5 Hz), 7.71 (2H, d, J=7.8 Hz), 7.30 (2H, d, J=7.8 Hz), 7.18 (2H, m), 6.87 (1H, s), 6.50 (1H, dd, J=7.8, 1.5 Hz), 5.27 (1H, s), 3.37 (3H, s), 3.20 (1H, m), 3.10 (1H, m), 2.07 (2H, m), 1.70 (2H, 1.42 (2H, m), 1.22 (2H, m).

TBI-882, 5-(4-Chlorophenyl)-3-cyclopropylimino-2-(5-bromo-3-pyridyl)amino-3,5-dihydrophenazine:

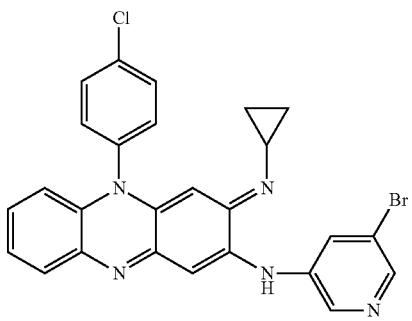 [SMILES: Clc1ccc(-n2c3c/c(=N\C4CC4)c(Nc4cncc(Br)c4)cc-3nc3ccccc32)cc1]

$^1$H NMR (300 MHz, CDCl$_3$) δ: 8.55 (1H, s), 8.47 (1H, s), 7.88 (1H, s), 7.72 (2H, d, J=8.1 Hz), 7.70 (1H, d, J=7.5 Hz), 7.33 (2H, d, J=8.1 Hz), 7.17 (2H, m), 6.82 (1H, s), 6.44 (1H, d, J=7.5 Hz), 5.54 (1H, s), 2.74 (1H, m), 0.91 (2H, m), 0.81 (2H, m). $^{13}$C NMR (100 MHz, CDCl$_3$) δ: 150.9, 150.5, 144.8, 142.5, 141.5, 137.8, 135.9, 135.8, 134.8, 131.8, 131.7, 130.5, 129.5, 128.4, 128.2, 123.1, 120.6, 113.9, 99.8, 89.5, 32.9, 10.1.

TBI-883, 5-(4-Chlorophenyl)-3-cyclobutylimino-2-(5-bromo-3-pyridyl)amino-3,5-dihydrophenazine:

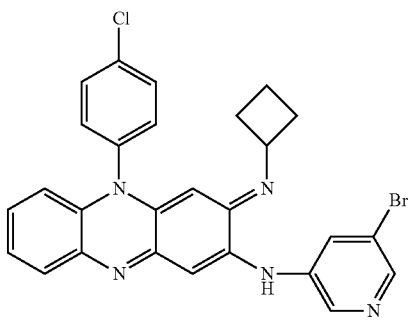 [SMILES: Clc1ccc(-n2c3c/c(=N\C4CCC4)c(Nc4cncc(Br)c4)cc-3nc3ccccc32)cc1]

$^1$H NMR (300 MHz, CDCl$_3$) δ: 8.52 (1H, s), 8.36 (1H, s), 7.90 (1H, s), 7.73 (2H, d, J=8.1 Hz), 7.72 (1H, d, J=7.5 Hz), 7.30 (2H, d, J=8.1 Hz), 7.20 (2H, m), 6.88 (1H, s), 6.50 (1H, d, J=7.5 Hz), 5.11 (1H, s), 3.89 (1H, m), 2.18 (2H, m), 2.05 (2H, m), 1.76 (2H, m). $^{13}$C NMR (100 MHz, CDCl$_3$) δ: 151.0, 150.6, 144.7, 142.7, 141.5, 138.1, 135.9, 135.8, 134.6, 131.8, 131.7, 130.3, 129.4, 128.5, 128.2, 123.4, 120.6, 114.1, 100.5, 90.5, 54.6, 31.9, 16.0.

TBI-890, 5-(2-Chlorophenyl)-3-(1-methylethyl)imino-2-(3-pyridyl)amino-3,5-dihydrophenazine:

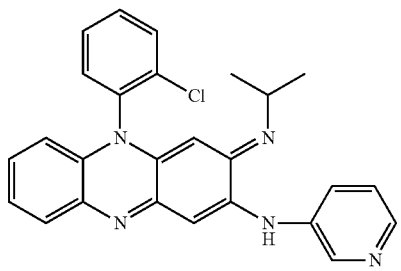 [SMILES: CC(C)/N=c1\cc2n(-c3ccccc3Cl)c3ccccc3nc-2cc1Nc1cccnc1]

$^1$H NMR (300 MHz, CDCl$_3$) δ: 8.58 (1H, d, J=2.3 Hz), 8.32 (1H, d, 14.8 Hz), 8.10 (1H, s), 7.78 (2H, m), 7.72 (1H, d, J=7.5 Hz), 7.62 (2H, m), 7.40 (1H, m), 7.29 (1H, m), 7.15 (2H, m), 6.85 (1H, s), 6.42 (1H, d, J=7.5 Hz), 5.16 (1H, s), 3.46 (1H, m), 1.08 (6H, d, J=6.0 Hz). $^{13}$C NMR (100 MHz, CDCl$_3$) δ: 151.0, 150.7, 144.1, 143.8, 143.6, 136.8, 135.6, 134.6, 133.5, 133.4, 131.8, 131.2, 130.7, 130.5, 129.4, 128.4, 128.0, 127.9, 123.6, 123.1, 113.4, 99.7, 89.1, 49.5, 23.7.

TBI-891, 5-(2-Chlorophenyl)-3-cyclohexylimino-2-(3-pyridyl)amino-3,5-dihydrophenazine:

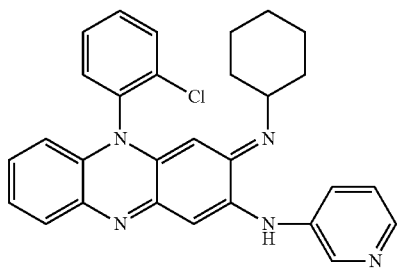 [SMILES: Clc1ccccc1-n1c2c/c(=N\C3CCCCC3)c(Nc3cccnc3)cc-2nc2ccccc21]

$^1$H NMR (300 MHz, CDCl$_3$) δ: 8.58 (1H, d, J=2.3 Hz), 8.32 (1H, d, J=4.7 Hz), 7.78 (2H, m), 7.72 (1H, dd, J=7.8, 2.5 Hz), 7.62 (2H, m), 7.40 (1H, m), 7.29 (1H, m), 7.18 (2 m), 6.85 (1H, s), 6.42 (1H, dd, J=7.8, 2.5 Hz), 5.16 (1H, s), 3.06 (1H, m), 1.71 (2H, m), 1.61 (3H, m), 1.43 (2H, m), 1.22 (3H, m). $^{13}$C NMR (100 MHz, CDCl$_3$) δ: 151.0, 150.7, 144.1, 143.8, 143.6, 136.8, 135.6, 134.6, 133.5, 133.4, 131.7, 131.2, 130.7, 130.5, 129.4, 128.4, 128.0, 127.9, 123.6, 123.1, 113.4, 99.7, 89.1, 57.9, 33.7, 25.7, 24.7.

TBI-892, 5-(2-Chlorophenyl)-3-cyclopropylimino-2-(3-pyridyl)amino-3,5-dihydrophenazine:

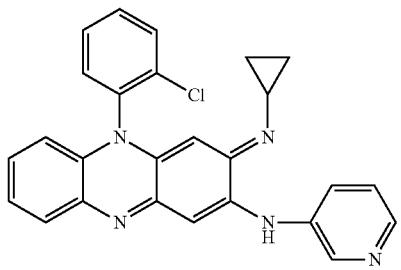 [SMILES: Clc1ccccc1-n1c2c/c(=N\C3CC3)c(Nc3cccnc3)cc-2nc2ccccc21]

¹H NMR (300 MHz, CDCl₃) δ: 8.56 (1H, d, J=2.3 Hz), 8.31 (1H, d, J=4.7 Hz), 7.79 (2H, m), 7.74 (1H, dd, J=7.8, 2.5 Hz), 7.61 (2H, m), 7.42 (1H, m), 7.30 (1H, m), 7.18 (2H, m), 6.85 (1H, s), 6.42 (1H, dd, J=7.8, 2.5 Hz), 5.16 (1H, s), 2.74 (1H, m), 0.83 (2 m), 0.78 (2H, m).

TBI-678, 5-(4-Trifluoromethylphenyl)-3-(1-methylethyl)imino-2-(3-pyridyl)amino-3,5-dihydrophenazine:

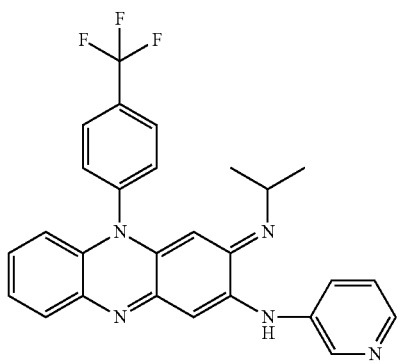 [SMILES: CC(C)/N=c1\cc2n(-c3ccc(C(F)(F)F)cc3)c3ccccc3nc-2cc1Nc1cccnc1]

¹H NMR (300 MHz, CDCl₃) δ: 8.64 (brs, 1H), 8.61 (d, J=2.4 Hz, 1H), 8.34~8.32 (dd, J=4.5, 1.2 Hz, 1H), 8.20 (d, J=8.4 Hz, 2H), 7.89~7.88 (m, 1H), 7.84 (d, J=8.4 Hz, 2H), 7.66~7.63 (m, 1H), 7.47~7.43 (dd, J=8.1, 4.5 Hz, 1H), 7.24~7.21 (m, 2H), 6.67 (s, 1H), 6.43~6.40 (m, 1H), 5.15 (s, 1H), 3.39~3.31 (m, 1H), 1.04 (d, J=6.0 Hz, 6H). ¹³C NMR (100 MHz, CDCl₃) δ: 150.9, 150.2, 144.4, 144.0, 143.7, 140.8, 136.7, 135.6, 134.6, 131.2, 129.9, 128.6, 128.5, 128.4, 128.0, 127.8, 123.6, 123.2, 113.7, 99.4, 89.1, 49.4, 23.5. HRMS (ESI-TOF⁺): m/z [M+H]⁺ calcd for C₂₇H₂₃F₃N₅: 474.19055; found: 474.1906.

TBI-679, 5-(4-Fluorophenyl)-3-(1-methylethyl)imino-2-(3-pyridyl)amino-3,5-dihydrophenazine:

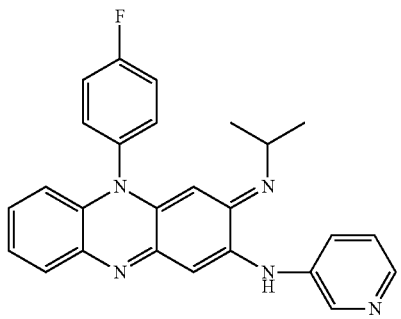

¹H NMR (300 MHz, DMSO-d₆) δ: 8.61 (d, J=2.1 Hz, 1H), 8.32 (d, J=4.5 Hz, 1H), 7.88~7.85 (m, 1H), 7.65~7.63 (m, 5H), 7.47~7.43 (dd, J=8.1, 4.2 Hz, 1H), 7.25 (br, 2H), 6.70 (s, 1H), 6.51 (br, 1H), 5.23 (s, 1H), 3.42~3.38 (m, 1H), 1.07 (d, J=6.3 Hz, 6H). ¹³C NMR (100 MHz, CDCl₃) δ: 162.9 (d, J=250.0 Hz), 150.9, 150.4, 144.3, 144.0, 143.7, 136.8, 135.6, 135.2, 133.5, 131.7, 130.9, 130.8, 128.3, 127.9, 127.7, 123.6, 123.0, 118.5 (d, J=22.7 Hz), 113.9, 99.4, 89.1, 49.4, 23.5. HRMS (ESI-TOF⁺): m/z [M+H]⁺ calcd for C₂₁H₂₃FN₅: 424.1937; found: 424.1938.

TBI-680, 5-(4-Fluorophenyl)-3-(2-morpholinoethyl)imino-2-(3-pyridyl)amino-3,5-dihydrophenazine:

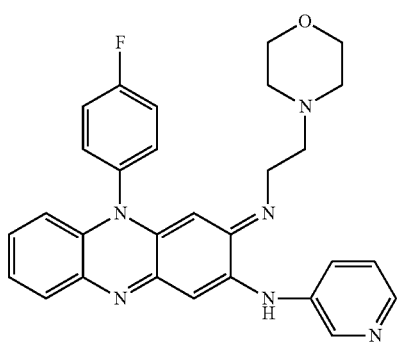 [SMILES: Fc1ccc(-n2c3c/c(=N\CCN4CCOCC4)c(Nc4cccnc4)cc-3nc3ccccc32)cc1]

¹H NMR (300 MHz, CDCl₃) δ: 8.58 (s, 1H), 8.34 (d, J=4.5 Hz, 1H), 7.78~7.71 (m, 2H), 7.45~7.40 (m, 2H), 7.35~7.31 (m, 3H), 7.21~7.14 (m, 2H), 6.86 (s, 1H), 6.48 (d, J=7.5, 1H), 5.27 (s, 1H), 3.71 (t, J=4.5 Hz, 4H), 3.34 (t, J=7.5 Hz, 2H), 2.71 (t, J=7.5 Hz, 2H), 2.48 (br, 4H). ¹³C NMR (100 MHz, CDCl₃) δ: 162.9 (d, J=250.0 Hz) 152.8, 150.7, 144.5, 144.0, 143.4, 136.7, 135.7, 135.2, 133.3, 131.6, 130.7, 130.7, 128.5, 128.0, 123.7, 123.2, 118.7 (d, J=22.6 Hz), 114.1, 99.5, 89.0, 66.9, 59.9, 54.1, 47.9. HRMS (ESI-TOF⁺): m/z [M+H]⁺ calcd for C₂₉H₂₈FN₆O: 495.2308; found: 495.2307.

TBI-681, 5-(4-Fluorophenyl)-3-(4-tetrahydropyranyl)imino-2-(3-pyridyl)amino-3,5-dihydrophenazine:

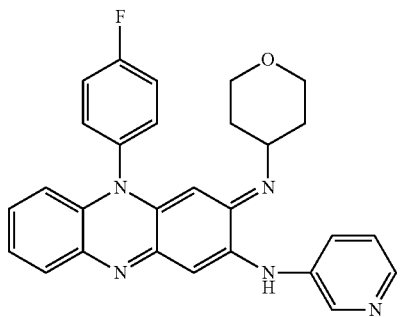

¹H NMR (300 MHz, DMSO-d₆) δ: 8.66 (brs, 1H), 8.62 (d, J=2.4 Hz, 1H), 8.34~8.32 (dd, J=4.8, J=1.2, 1H), 7.90~7.86 (m, 1H), 7.68~7.62 (m, 5H), 7.48~7.44 (m, 1H), 7.28~7.20 (m, 2H), 6.68 (s, 1H), 6.52~6.49 (m, 1H), 5.19 (s, 1H), 3.90~3.86 (m, 2H), 3.30~3.24 (m, 3H), 1.58~1.48 (m, 4H). ¹³C NMR (100 MHz, CDCl₃) δ: 162.9 (d, J=250.0 Hz) 151.1, 150.7, 144.5. 144.0, 143.6, 136.6, 135.7, 135.3, 133.4, 131.6, 130.8, 130.7, 128.4, 128.0, 127.9, 123.7, 123.1, 118.5 (d, J=22.7 Hz), 114.0, 99.6, 88.9, 66.1, 54.3, 33.4. HRMS (ESI-TOF⁺): m/z [M+H]⁺ calcd for C₂₈H₂₅FN₅O: 466.2043; found: 466.2042.

TBI-682, 5-(4-Fluorophenyl)-3-(N-ethyl-4-piperidyl)imino-2-(3-pyridyl)amino-3,5-dihydrophenazine:

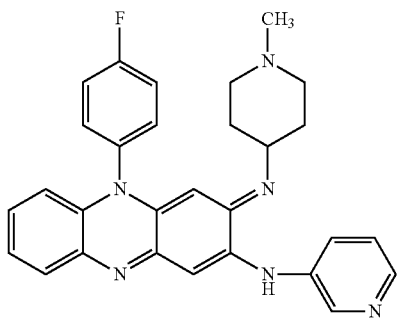

¹H NMR (300 MHz, CDCl₃) δ: 8.60 (br, 1H), 8.34 (d, J=4.5 Hz, 1H), 7.78 (d, J=8.7 Hz, 1H), 7.71 (d, J=7.5 Hz, 1H), 7.47~7.42 (m, 2H), 7.37~7.27 (m, 3H), 7.22~7.13 (m, 2H), 6.86 (s, 1H), 6.50 (d, J=7.5 Hz, 1H), 5.21 (s, 1H), 3.15~3.11 (m, 1H), 2.81~2.77 (m, 2H), 2.30 (s, 3H), 2.05 (br, 2H), 1.68 (br, 4H). ¹³C NMR (100 MHz, CDCl₃) δ: 162.8 (d, J=249.3 Hz), 151.0, 150.8, 144.4, 144.0, 143.5, 136.7, 135.7, 135.2, 133.4, 131.6, 130.8, 130.7, 128.4, 128.0, 127.9, 123.6, 123.1, 118.4 (d, J=22.6 Hz), 114.0, 99.5, 89.0, 54.0, 46.4, 32.7. HRMS (ESI-TOF⁺): m/z [M+H]⁺ calcd for $C_{29}H_{28}FN_6$: 479.2359; found: 479.2358.

TBI-683, 5-(4-Fluorophenyl)-3-(N-isobutyl-4-piperidyl)imino-2-(3-pyridyl)amino-3,5-dihydrophenazine:

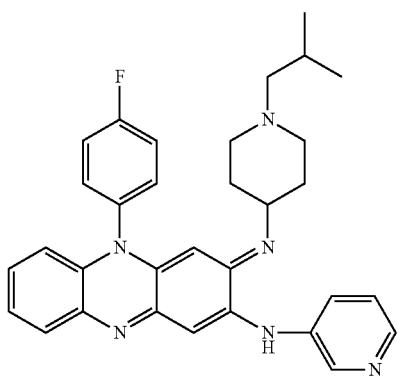

¹H NMR (300 MHz, CDCl₃) δ: 8.58 (d, J=1.8 Hz, 1H), 8.34 (d, J=3.9 Hz, 1H), 7.78 (d, J=7.8 Hz, 1H), 7.70 (d, J=7.5 Hz, 1H), 7.46~7.41 (m, 2H), 7.36~7.26 (m, 3H), 7.21~7.12 (m, 2H), 6.85 (s, 1H), 6.49 (d, J=7.5 Hz, 1H), 5.25 (s, 1H), 3.13~3.11 (m, 1H), 2.80~2.77 (m, 2H), 2.06 (d, J=7.2 Hz, 2H), 1.96~1.81 (m, 2H), 1.81~1.62 (m, 5H), 0.90 (d, J=6.6 Hz, 6H). ¹³C NMR (100 MHz, CDCl₃) δ: 162.8 (d, J=248.9 Hz), 151.0, 150.9, 144.3, 143.9, 143.6, 136.8, 135.7, 135.1, 133.4, 131.7, 130.9, 130.8, 128.4, 127.8, 123.6, 123.0, 118.4 (d, J=22.7 Hz), 114.0, 99.5, 89.1, 67.1, 56.0, 52.5, 32.8, 25.7, 21.0. HRMS (ESI-TOF⁺): m/z [M+H]⁺ calcd for $C_{32}H_{34}FN_6$: 521.2828; found: 521.2819.

TBI-684, 5-(4-Fluorophenyl)-3-(N-cyclopentyl-4-piperidyl)imino-2-(3-pyridyl)amino-3,5-dihydrophenazine:

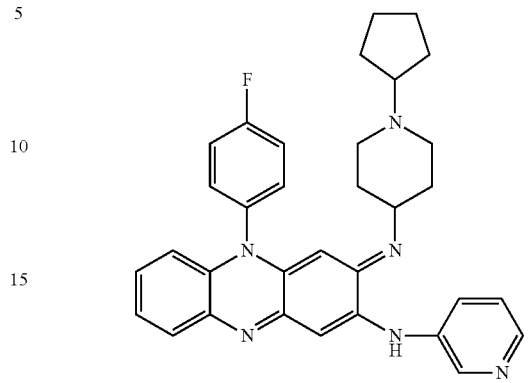

¹H NMR (300 MHz, CDCl₃) δ: 8.58 (d, J=2.7 Hz, 1H), 8.35~8.33 (dd, J=4.8, 1.2 Hz, 1H), 7.79~7.76 (m, 1H), 7.72~7.69 (m, 1H), 7.47~7.41 (m, 2H), 7.36~7.28 (m, 3H), 7.21~7.12 (m, 2H), 6.50~6.47 (m, 1H), 6.85 (s, 1H), 5.25 (s, 1H), 3.15 (m, 1H), 2.95~2.91 (m, 2H), 2.49~2.44 (m, 1H), 2.05 (br, 2H), 1.87 (br, 2H), 1.67 (br, 6H), 1.58~1.54 (m, 2H), 1.41 (br, 2H). ¹³C NMR (100 MHz, CDCl₃) δ: 162.8 (d, J=248.9 Hz), 150.9, 144.3, 143.9, 143.6, 136.8, 135.7, 135.2, 133.4, 131.7, 130.9, 130.8, 128.4, 127.8, 123.6, 123.0, 118.4 (d, J=22.7 Hz), 113.9, 99.5, 89.0, 67.7, 55.5, 50.9, 32.8, 30.7, 24.2. HRMS (ESI-TOF⁺): m/z [M+H]⁺ calcd for $C_{33}H_{34}FN_6$: 533.28289; found: 533.2827.

TBI-685, 5-(4-Fluorophenyl)-3-(4-methoxycyclohexyl)imino-2-(3-pyridyl)amino-3,5-dihydrophenazine:

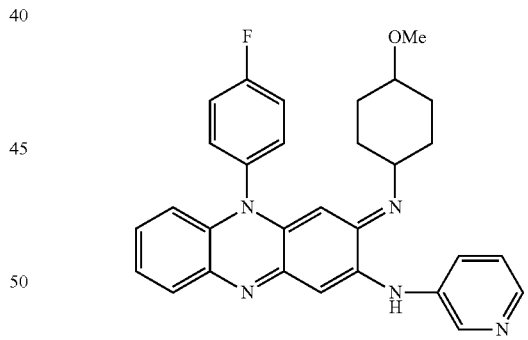

¹H NMR (300 MHz, CDCl₃) δ: 8.58 (d, J=2.4, 1H), 8.33 (d, J=3.9 Hz, 1H), 7.80~7.45 (m, 2H), 7.42~7.39 (m, 2H), 7.35~7.28 (m, 1H), 7.21~7.13 (m, 4H), 6.85 (s, 1H), 6.51~6.48 (m, 1H), 5.25 (s, 1H), 3.37 (s, 3H), 3.23~3.15 (m, 1H), 3.12~3.06 (m, 1H), 2.10~2.05 (m, 2H), 1.72~1.68 (m, 2H), 1.49~1.37 (m, 2H), 1.26~1.12 (m, 2H). ¹³C NMR (100 MHz, CDCl₃) δ: 162.8 (d, J=250.1 Hz), 151.2, 150.9, 144.3, 143.9, 143.6, 136.7, 135.6, 135.1, 133.3, 131.7, 130.8, 130.7, 128.4, 127.9, 123.6, 123.0, 118.4 (d, J=22.7 Hz), 114.0, 99.5, 89.1, 78.4, 57.4, 55.8, 31.1, 30.0. HRMS (ESI-TOF⁺): m/z [M+H]⁺ calcd for $C_{30}H_{29}FN_5O$: 494.23561; found: 494.2355

207

TBI-686, 5-(4-Trifluoromethylphenyl)-3-(4-tetrahydropyranyl)imino-2-(3-pyridyl)amino-3,5-dihydrophenazine:

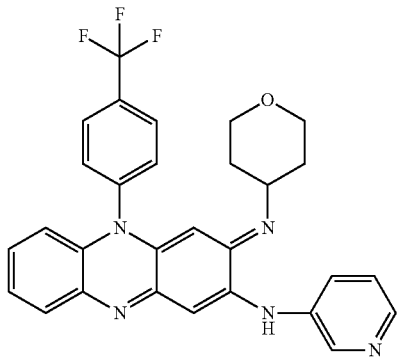 [SMILES: FC(F)(F)c1ccc(-n2c3c/c(=N\C4CCOCC4)c(Nc4cccnc4)cc-3nc3ccccc32)cc1]

$^1$H NMR (300 MHz, CDCl$_3$) δ: 8.61 (d, J=2.4 Hz, 1H), 8.36 (d, J=4.2 Hz, 1H), 8.04 (d, J=8.4 Hz, 2H), 7.79~7.72 (m, 2H), 7.53 (d, J=8.4 Hz, 2H), 7.34~7.29 (dd, J=8.1, 4.5 Hz, 1H), 7.25~7.14 (m, 2H), 6.87 (s, 1H), 6.46 (d, J=8.1 Hz, 1H), 5.16 (s, 1H), 3.99~3.94 (m, 2H), 3.41~3.28 (m, 3H), 1.73~1.57 (m, 4H), $^{13}$C NMR (100 MHz, CDCl$_3$) δ: 151.0, 150.6, 144.6, 144.0, 143.6, 140.8, 136.5, 135.6, 134.8, 130.9, 129.8, 128.6, 128.1, 128.0, 123.7, 123.4, 113.8, 99.6, 89.0, 66.1, 54.5, 33.4. HRMS (ESI-TOF$^+$): m/z [M+H]$^+$ calcd for C$_{29}$H$_{25}$F$_3$N$_5$O: 516.20112; found: 516.2011.

TBI-687, 5-(4-Trifluoromethylphenyl)-3-(N-isobutyl-4-piperidyl)imino-2-(3-pyridyl)amino-3,5-dihydrophenazine:

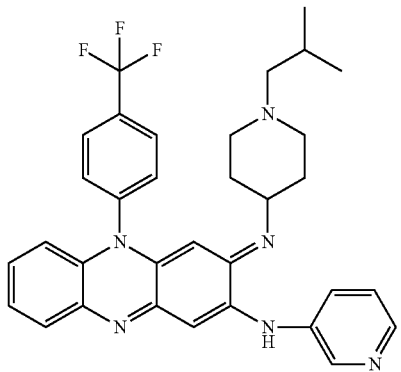 [SMILES: CC(C)CN1CCC(/N=c2\cc3n(-c4ccc(C(F)(F)F)cc4)c4ccccc4nc-3cc2Nc2cccnc2)CC1]

$^1$H NMR (300 MHz, CDCl$_3$) δ: 8.59 (d, J=2.4 Hz, 1H), 8.34 (d, J=3.9 Hz, 1H), 8.03 (d, J=8.7 Hz, 2H), 7.77 (d, J=8.7 Hz, 1H), 7.72 (d, J=7.5 Hz, 1H), 7.52 (d, J=8.4 Hz, 2H), 7.33~7.29 (dd, J=8.4, 4.5 Hz, 1H), 7.23~7.13 (m, 2H), 6.85 (s, 1H), 6.45 (d, J=7.5 Hz, 1H), 5.15 (s, 1H), 3.09~3.05 (m, 1H), 2.80~2.76 (m, 2H), 2.06 (d, J=7.2 Hz, 2H), 1.93~1.86 (m, 2H), 1.81~1.54 (m, 5H), 0.89 (d, J=6.6 Hz, 6H). $^{13}$C NMR (100 MHz, CDCl$_3$) δ: 150.9, 144.4, 144.0, 143.6, 140.9, 136.7, 135.6, 134.7, 131.0, 129.9, 128.6, 128.5, 128.0, 127.9, 123.7, 123.3, 113.7, 99.5, 89.3, 67.0, 56.1, 52.3, 32.7, 25.7, 21.0. HRMS (ESI-TOF$^+$): m/z [M+H]$^+$ calcd for C$_{33}$H$_{34}$F$_3$N$_6$: 571.2797; found: 571.2799.

208

TBI-688, 5-(4-Trifluoromethylphenyl)-3-(4-methoxycyclohexyl)imino-2-(3-pyridyl)amino-3,5-dihydrophenazine:

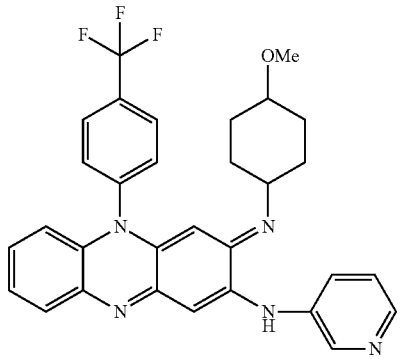 [SMILES: COC1CCC(/N=c2\cc3n(-c4ccc(C(F)(F)F)cc4)c4ccccc4nc-3cc2Nc2cccnc2)CC1]

$^1$H NMR (300 MHz, CDCl$_3$) δ: 8.58 (d, J=2.7 Hz, 1H), 8.34 (d, J=4.8 Hz, 1H), 8.02 (d, J=8.1 Hz, 2H), 7.78 (d, J=8.4 Hz, 1H), 7.73~7.70 (dd, J=7.5, 1.2 Hz, 1H), 7.52 (d, J=8.1 Hz, 2H), 7.33~7.28 (dd, J=8.4, 4.8 Hz, 1H), 7.23~7.13 (m, 2H), 6.85 (s, 1H), 6.43 (d, J=7.5 Hz, 1H), 5.18 (s, 1H), 3.22~3.15 (m, 1H), 3.09~3.03 (m, 1H), 2.07~2.04 (m, 2H), 1.70~1.66 (m, 2H), 1.47~1.35 (m, 2H), 1.21~1.09 (m, 2H). $^{13}$C NMR (100 MHz, CDCl$_3$) δ: 151.0, 150.9, 144.5, 144.0, 143.6, 140.8, 136.7, 135.6, 134.7, 131.1, 129.8, 128.57, 128.53, 128.51, 128.0, 127.9, 123.7, 123.3, 113.8, 99.6, 89.2, 78.4, 57.3, 55.8, 31.1, 29.8. HRMS (ESI-TOF$^+$): m/z calcd for C$_{31}$H$_{29}$F$_3$N$_5$O: 544.2324; found: 544.2328.

TBI-689, 5-(4-Trifluoromethylphenyl)-3-(N-methyl-4-piperidyl)imino-2-(3-pyridyl)amino-3,5-dihydrophenazine:

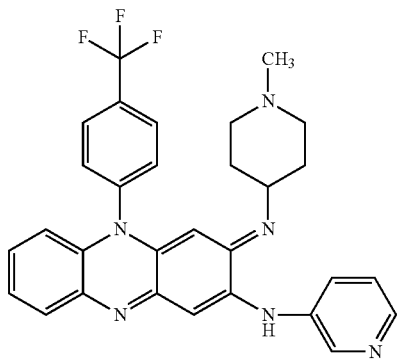 [SMILES: CN1CCC(/N=c2\cc3n(-c4ccc(C(F)(F)F)cc4)c4ccccc4nc-3cc2Nc2cccnc2)CC1]

$^1$H NMR (300 MHz, CDCl$_3$) δ: 8.60 (d, J=2.7 Hz, 1H), 8.36~8.34 (m, 1H), 8.04 (d, J=8.4 Hz, 2H), 7.78 (d, J=8.4 Hz, 1H), 7.74~7.71 (dd, J=7.5, 1.5 Hz, 1H), 7.53 (d, J=8.4 Hz, 2H), 7.33~7.29 (dd, J=8.4, 4.8 Hz, 1H), 7.24~7.14 (m, 2H), 6.85 (s, 1H), 6.46 (d, J=8.1 Hz, 1H), 5.14 (s, 1H), 3.06~3.04 (m, 1H), 2.80~2.76 (m, 2H), 2.26 (s, 3H), 1.97~1.93 (m, 2H), 1.73~1.62 (m, 4H). $^{13}$C NMR (100 MHz, CDCl$_3$) δ: 151.0, 150.8, 144.5, 144.1, 143.6, 140.9, 136.6, 135.6, 134.7, 131.2, 129.9, 128.6, 128.5, 128.4, 128.0, 127.8, 123.6, 123.2, 113.7, 99.5, 89.3, 58.4, 55.4, 54.1, 46.4, 32.8, 18.5. HRMS (ESI-TOF$^+$): m/z [M+H]$^+$ calcd for C$_{30}$H$_{28}$F$_3$N$_6$: 529.2327; found: 529.2326.

TBI-690, 5-(4-Trifluoromethylphenyl)-3-(2-morpholino-ethyl)imino-2-(3-pyridyl)amino-3,5-dihydrophenazine:

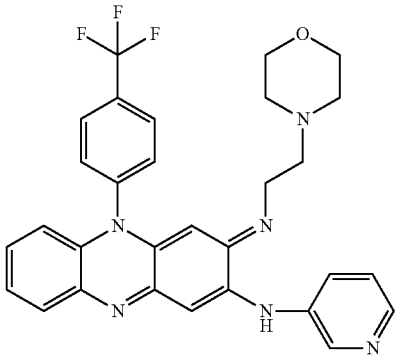 [SMILES: FC(F)(F)c1ccc(-n2c3c/c(=N\CCN4CCOCC4)c(Nc4cccnc4)cc-3nc3ccccc32)cc1]

$^1$H NMR (300 MHz, CDCl$_3$) δ: 8.59 (d, J=2.4 Hz, 1H), 8.35 (d, J=4.5 Hz, 1H), 2.47 (t, J=4.5 Hz, 4H), 8.03 (d, J=8.4 Hz, 2H), 7.79~7.73 (m, 2H) 7.52 (d, J=8.4 Hz, 2H), 2.70 (t, J=7.5 Hz, 2H), 7.34~7.29 (dd, J=8.1, 4.5 Hz, 1H), 7.27~7.14 (m, 2H), 6.87 (s, 1H), 6.40 (d, J=8.1 Hz, 1H), 5.23 (s, 1H), 3.70 (t, J=4.8 Hz, 4H), 3.34 (t, J=7.5 Hz, 2H). $^{13}$C NMR (100 MHz, CDCl$_3$) δ: 152.7, 150.7, 144.6, 144.0, 143.4, 140.7, 136.6, 135.7, 134.7, 131.0, 129.8, 128.8, 128.6, 128.1, 123.7, 123.5, 113.9, 99.6, 89.0, 66.9, 59.7, 54.1, 48.0. HR-MS/TOF: [M+H$^+$]: 545.2280. HRMS (ESI-TOF$^+$): m/z [M+H]$^+$ calcd for C$_{30}$H$_{28}$F$_3$N$_6$O: 545.2276; found: 545.2280.

TBI-691, 5-(4-Trifluoromethylphenyl)-3-(N-cyclopentyl-4-piperidyl)imino-2-(3-pyridyl)amino-3,5-dihydrophenazine:

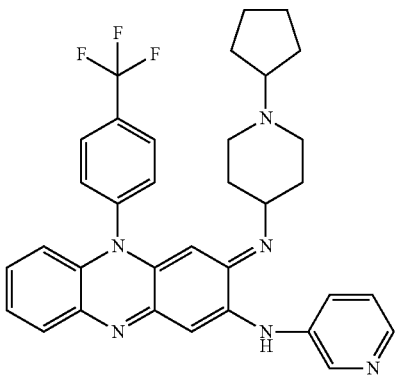 [SMILES: FC(F)(F)c1ccc(-n2c3c/c(=N\C4CCN(C5CCCC5)CC4)c(Nc4cccnc4)cc-3nc3ccccc32)cc1]

$^1$H NMR (300 MHz, CDCl$_3$) δ: 8.59 (br, 1H), 8.35 (d, J=3.9 Hz, 1H) 8.04 (d, J=8.1 Hz, 2H), 7.77 (d, J=8.1 Hz, 1H), 7.73 (d, J=7.8 Hz, 1H), 7.53 (d, J=8.1 Hz, 2H), 7.34~7.29 (m, 1H), 7.24~7.14 (m, 2H), 6.86 (s, 1H), 6.46 (d, J=8.1 Hz, 1H) 5.15 (s, 1H), 3.09 (br, 1H), 2.96~2.92 (br, 2H), 2.47 (br, 1H), 2.00 (br, 2H), 1.85 (br, 2H), 1.67~1.57 (br, 8H), 1.42 (br, 2H). $^{13}$C NMR (100 MHz, CDCl$_3$) δ: 150.9, 144.5, 144.0, 143.6, 140.8, 136.6, 135.6, 134.7, 131.0, 129.9, 128.5, 128.0, 123.7, 123.3, 113.7, 99.5, 89.3, 67.6, 50.7, 32.6, 30.5, 24.2. HRMS (ESI-TOF$^+$): m/z [M+H]$^+$ calcd for C$_{34}$H$_{34}$F$_3$N$_6$: 583.2797; found: 583.2797.

TBI-692, 5-(4-Fluorophenyl)-3-(1-methylethyl)imino-2-(6-methyl-3-pyridyl)amino-3,5-dihydrophenazine:

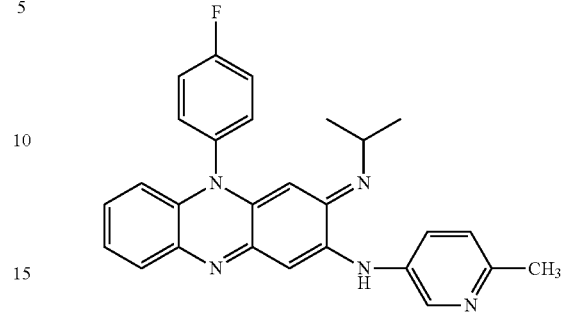

$^1$H NMR (300 MHz, CDCl$_3$) δ: 8.45 (d, J=2.4 Hz, 1H), 7.70~7.67 (m, 2H), 7.45~7.39 (m, 2H), 7.35~7.31 (m, 2H), 7.19~7.10 (m, 3H), 6.71 (s, 1H), 6.47~6.44 (dd, J=8.1, 1.5 Hz, 1H), 5.27 (s, 1H), 3.50~3.41 (m, 1H), 2.56 (s, 3H), 1.10 (d, J=6.3 Hz, 6H). $^{13}$C NMR (100 MHz, CDCl$_3$) δ: 162.8 (d, J=248.5 Hz), 153.3, 151.0, 150.5, 144.4, 143.7, 135.6, 135.1, 134.1, 133.5, 131.7, 130.9, 130.8, 129.4, 128.2, 127.5, 123.1, 122.9, 118.4 (d, J=22.7 Hz), 113.9, 98.8, 89.0, 49.4, 23.8, 23.5. HRMS (ESI-TOF$^+$): m/z [M+H]$^+$ calcd for C$_{27}$H$_{25}$FN$_5$: 438.2088; found: 438.2090.

TBI-693, 5-(4-Fluorophenyl)-3-(1-methylethyl)imino-2-(2-methyl-3-pyridyl)amino-3,5-dihydrophenazine:

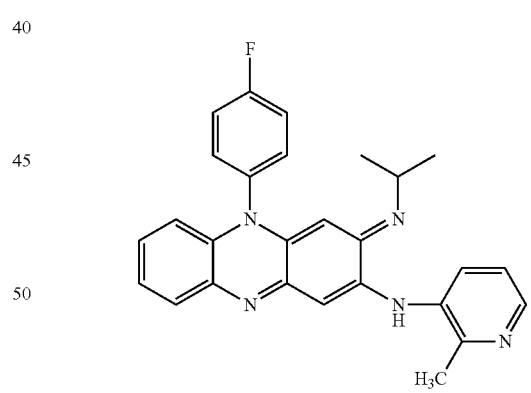

$^1$H NMR (300 MHz, CDCl$_3$) δ: 8.28 (d, 4.2 Hz, 1H), 7.81 (d, J=8.1 Hz, 1H), 7.67 (d, 7.2 Hz, 1H), 7.45~7.40 (m, 2H), 7.36~7.31 (m, 2H), 7.20~7.10 (m, 3H), 6.58 (s, 1H), 6.46 (d. J=7.8 Hz, 1H), 5.27 (s, 1H), 3.51~3.43 (m, 1H), 2.55 (s, 3H), 1.10 (d, J=6.3 Hz, 6H). $^{13}$C NMR (100 MHz, CDCl$_3$) δ: 162.8 (d, J=248.9 Hz), 152.2, 151.0, 150.4, 144.2, 135.6, 135.1, 134.8, 133.5, 131.7, 130.9, 130.8, 129.1, 128.2, 127.5, 122.9, 121.6, 118.5 (d, J=23.1 Hz), 113.9, 98.8, 89.0, 49.3, 23.6, 20.9. HRMS (ESI-TOF$^+$): m/z [M+H]$^+$ calcd for C$_{27}$H$_{25}$FN$_3$: 438.2088; found: 438.2094.

TBI-694, 5-(4-Trifluoromethylphenyl)-3-(1-ethylethyl)imino-2-(6-methyl-3-pyridyl)amino-3,5-dihydrophenazine:

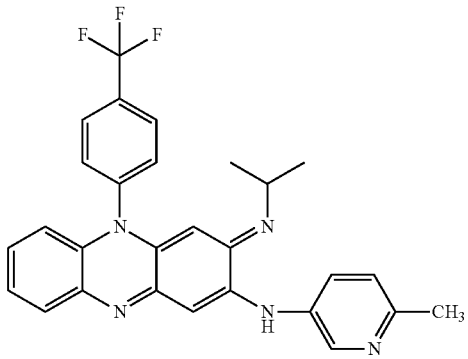 [SMILES: Cc1ccc(Nc2cc3nc4ccccc4n(-c4ccc(C(F)(F)F)cc4)c-3c/c2=N\C(C)C)cn1]

$^1$H NMR (300 MHz, CDCl$_3$) δ: 8.46 (d, J=2.4 Hz, 1H), 8.02 (d, J=7.8 Hz, 2H), 7.69 (d, J=7.8, 2 Hz, 2H), 7.52 (d, J=8.1 Hz, 2H), 7.21~7.09 (m, 3H), 6.72 (s, 1H), 6.38 (d, J=8.4 Hz, 1H), 5.22 (s, 1H), 3.45~3.41 (m, 1H), 2.56 (s, 3H), 1.09 (d, J=6.0 Hz, 6H). $^{13}$C NMR (100 MHz, CDCl$_3$) δ: 153.5, 151.0, 150.3, 144.5, 143.8, 140.9, 135.6, 134.6, 131.1, 129.9, 129.5, 128.6, 128.3, 127.6, 123.2, 123.1, 113.6, 98.8, 89.1, 49.4, 23.8, 23.5. HRMS (ESI-TOF$^+$): m/z [M+H]$^+$ calcd for C$_{28}$H$_{25}$F$_3$N$_5$: 488.2062; found: 488.2063.

TBI-695, 5-(4-Trifluoromethylphenyl)-3-(4-methoxycyclohexyl)imino-2-(6-methyl-3-pyridyl)amino-3,5-dihydrophenazine:

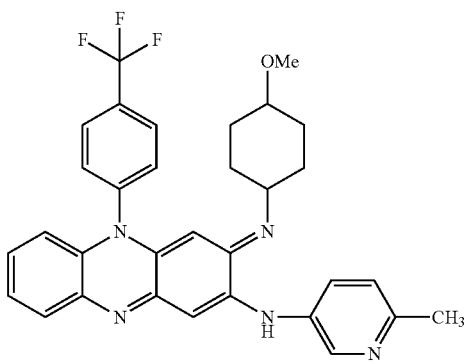 [SMILES: COC1CCC(/N=c2\cc3n(-c4ccc(C(F)(F)F)cc4)c4ccccc4nc-3cc2Nc2ccc(C)nc2)CC1]

$^1$H NMR (300 MHz, CDCl$_3$) δ: 8.44 (d, J=2.1 Hz, 1H), 8.02 (d, J=8.1 Hz, 2H), 7.71~7.69 (m, 2H), 7.52 (d, J=8.1 Hz, 2H), 7.22~7.12 (m, 3H), 6.72 (s, 1H), 6.42 (d, J=8.1 Hz, 1H), 5.17 (s, 1H), 3.35 (s, 3H), 3.22~3.02 (m, 2H), 2.56 (s, 3H), 2.07~2.04 (m, 2H), 1.69~1.66 (m, 2H), 1.46~1.08 (m, 4H). $^{13}$C NMR (100 MHz, CDCl$_3$) δ: 153.5, 151.0, 150.8, 144.3, 143.8, 140.8, 135.6, 134.6, 133.9, 131.0, 129.8, 129.5, 128.5, 128.4, 127.7, 123.2, 113.7, 98.9, 89.2, 78.4, 57.3, 55.8, 31.1, 30.6, 30.0, 29.8, 23.8. HRMS (ESI-TOF$^+$): [M+H]$^+$ calcd for C$_{32}$H$_{31}$F$_3$N$_5$O: 558.5469; found: 558.2471.

TBI-696, 5-(4-Trifluoromethylphenyl)-3-(4-tetrahydropyranyl)imino-2-(6-methyl-3-pyridyl)amino-3,5-dihydrophenazine:

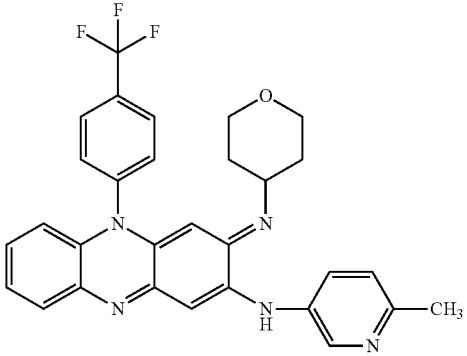

$^1$H NMR (300 MHz, CDCl$_3$) δ: 8.47 (d, J=2.1 Hz, 1H), 8.03 (d, J=8.4 Hz, 2H), 7.73~7.66 (m, 2H), 7.52 (d, J=8.4 Hz, 2H), 7.24~7.13 (m, 3H), 6.74 (s, 1H), 6.45 (d, J=8.1 Hz, 1H), 5.15 (s, 1H), 3.99~3.95 (m, 2H), 3.39~3.29 (m, 3H), 2.57 (s, 3H), 1.69~1.57 (m, 4H). $^{13}$C NMR (100 MHz, CDCl$_3$) δ: 153.7, 151.1, 150.7, 144.4, 143.9, 140.9, 135.6, 134.7, 133.8, 130.9, 129.8, 129.6, 128.5, 127.8, 123.3, 123.2, 113.7, 99.0, 89.0, 66.5, 66.1, 54.6, 33.4, 32.5, 23.9. HRMS (ESI-TOF$^+$): m/z [M+H]$^+$ calcd for C$_{30}$H$_{27}$F$_3$N$_5$O: 530.21677; found: 530.2167.

TBI-697, 5-(4-Trifluoromethylphenyl)-3-(N-methyl-4-piperidyl)imino-2-(6-methyl-3-pyridyl)amino-3,5-dihydrophenazine:

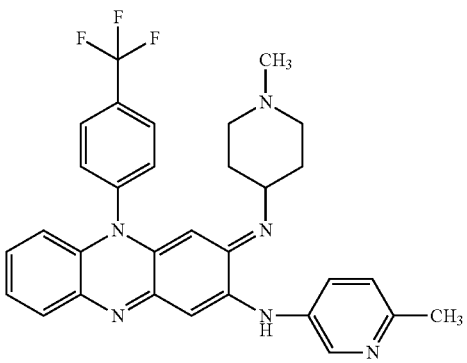 [SMILES: Cc1ccc(Nc2cc3nc4ccccc4n(-c4ccc(C(F)(F)F)cc4)c-3c/c2=N\C2CCN(C)CC2)cn1]

$^1$H NMR (300 MHz, CDCl$_3$) δ: 8.47 (d, J=2.7 Hz, 1H), 8.03 (d, J=8.4 Hz, 2H), 7.71~7.65 (m, 2H), 7.52 (d, J=8.4 Hz, 2H), 7.22~7.12 (m, 3H), 6.72 (s, 1H), 6.45 (d, J=7.5 Hz, 1H), 5.12 (s, 1H), 3.05 (br, 1H), 2.80~2.76 (m, 2H), 2.56 (s, 3H), 2.26 (s, 3H), 1.94 (br, 2H), 1.73~1.62 (m, 4H). $^{13}$C NMR (100 MHz, CDCl$_3$) δ: 153.6, 151.1, 150.8, 144.4, 143.9, 140.9, 135.6, 134.6, 133.9, 130.9, 129.9, 129.6, 128.5, 127.7, 123.2, 113.7, 98.9, 89.2, 55.2, 54.0, 46.3, 32.7, 23.8. HRMS (ESI-TOF$^+$): m/z [M+H]$^+$ calcd for C$_{31}$H$_{30}$F$_3$N$_6$: 543.2484; found: 543.2484.

TBI-698, 5-(4-Trifluoromethylphenyl)-3-(2-morpholinoethyl)imino-2-(6-meth-3-pyridyl)amino-3,5-dihydrophenazine:

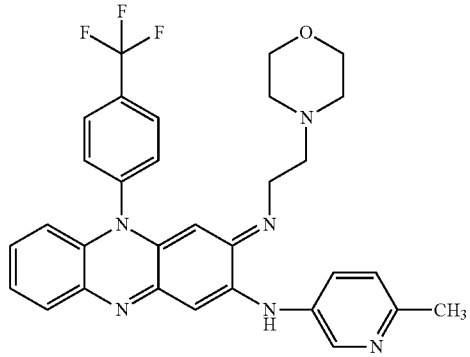 [SMILES: Cc1ccc(Nc2cc3nc4ccccc4n(-c4ccc(C(F)(F)F)cc4)c-3c/c2=N\CCN2CCOCC2)cn1]

¹H NMR (300 MHz, CDCl₃) δ: 8.46 (br, 1H), 8.03 (d, J=8.4 Hz, 2H), 7.70~7.67 (m, 2H), 7.52 (d, J=8.1 Hz, 2H), 7.20~7.17 (m, 3H), 6.75 (s, 1H), 6.41 (br, 1H), 5.22 (s, 1H), 3.70 (t, 4.5 Hz, 4H), 3.34 (t, J=7.2 Hz, 2H), 2.70 (t, J=7.2 Hz, 2H), 2.57 (s, 3H), 2.47 (t, J=4.5 Hz, 4H). ¹³C NMR (100 MHz, CDCl₃) δ: 153.7, 152.8, 150.6, 143.9, 140.7, 135.6, 134.7, 133.8, 130.9, 129.7, 128.7, 127.9, 123.3, 113.9, 98.9, 89.0, 66.9, 59.7, 54.1, 47.9, 23.9. HRMS (ESI-TOF⁺): m/z [M+H]⁺ calcd for $C_{31}H_{30}F_3N_6O$: 559.2433; found: 559.2433.

TBI-699, 5-(4-Trifluoromethylphenyl)-3-(1-methylethyl)imino-2-(2-methoxy-3-pyridyl)amino-3,5-dihydrophenazine:

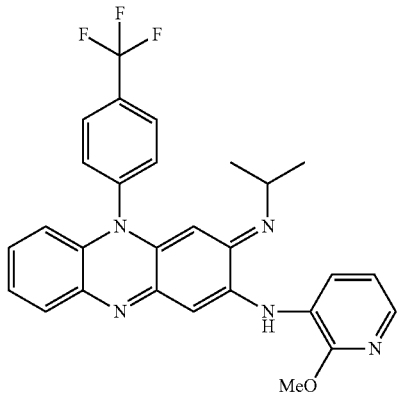 [SMILES: COc1ncccc1Nc1cc2nc3ccccc3n(-c3ccc(C(F)(F)F)cc3)c-2c/c1=N\C(C)C]

¹H NMR (300 MHz, CDCl₃) δ: 8.92 (br, 1H), 8.02 (d, J=8.1 Hz, 2H), 7.86~7.81 (m, 2H), 7.70 (d, J=8.4 Hz, 1H), 7.52 (d, J=8.4 Hz, 2H), 7.21~7.09 (m, 2H), 6.94~6.90 (m, 2H), 6.37 (d, J=8.1 Hz, 1H), 5.22 (s, 1H), 4.04 (s, 3H), 3.47~3.38 (m, 1H), 1.09 (d, J=6.3 Hz, 6H). ¹³C NMR (100 MHz, CDCl₃) δ: 155.5, 151.2, 150.5, 142.9, 140.9, 138.9, 131.3, 129.9, 128.6, 128.3, 127.7, 125.0, 124.8, 123.0, 116.8, 113.6, 100.1, 89.3, 53.7, 49.4, 23.5. HRMS (ESI-TOF⁺): m/z [M+H]⁺ calcd for $C_{28}H_{25}F_3N_5O$: 504.2011; found: 504.2013.

TBI-700, 5-(4-Trifluoromethylphenyl)-3-(4-methoxycyclohexyl)imino-2-(2-methoxy-3-pyridyl)amino-3,5-dihydrophenazine:

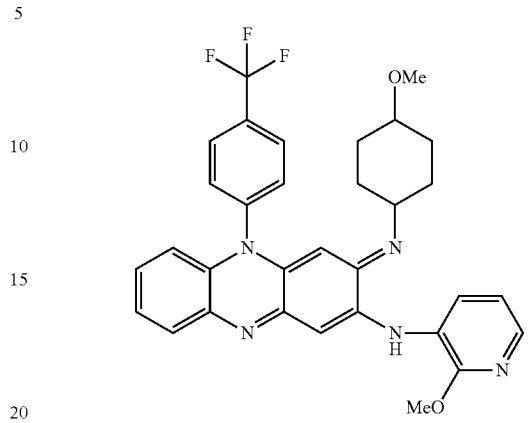

¹H NMR (300 MHz, CDCl₃) δ: 8.95 (br, 1H), 8.02 (d, J=8.1 Hz, 2H), 7.86~7.81 (m, 2H), 7.73~7.70 (dd, J=7.5, 1.5 Hz, 1H), 7.52 (d, J=7.8 Hz, 2H), 7.22~7.11 (m, 2H), 7.06~6.90 (m, 2H), 6.41 (d, J=8.1 Hz, 1H), 5.18 (s, 1H), 4.03 (s, 3H), 3.35 (s, 3H), 3.28~3.20 (m, 1H), 3.13~3.06 (m, 1H), 2.07~2.03 (m, 2H), 1.72~1.68 (m, 2H), 1.49~1.36 (m, 2H), 1.25~1.15 (m, 2H). ¹³C NMR (100 MHz, CDCl₃) δ: 155.4, 151.1, 142.8, 140.8, 138.8, 135.6, 134.6, 131.2, 129.9, 128.5, 128.4, 127.8, 124.8, 124.7, 123.1, 116.8, 113.7, 100.2, 89.3, 78.2, 56.8, 55.7, 53.7, 30.7, 29.3. HRMS (ESI-TOF⁺): m/z [M+H]⁺ calcd for $C_{32}H_{31}F_3N_5O_2$: 574.2429; found: 574.2432.

TBI-701, 5-(4-Trifluoromethylphenyl)-3-(4-tetrahydropyranyl)imino-2-(2-methoxy-3-pyridyl)amino-3,5-dihydrophenazine:

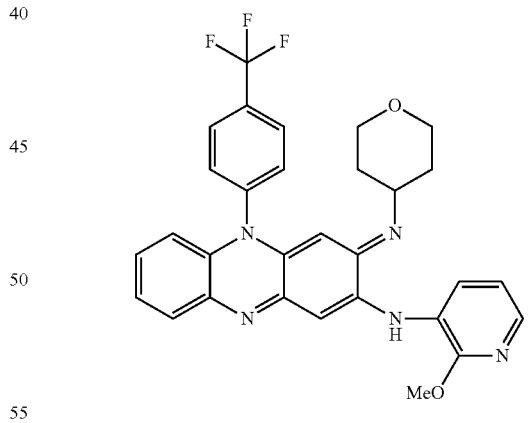

¹H NMR (300 MHz, CDCl₃) δ: 9.04 (brs, 1H), 8.03 (d, J=8.4 Hz, 2H), 7.87~7.82 (m, 2H), 7.75~7.72 (dd, J=8.1, 1.5 Hz, 1H), 7.43 (d, J=8.4 Hz, 2H), 7.24~7.13 (m, 2H), 6.98 (s, 1H), 6.95~6.91 (dd, J=7.5, 4.8 Hz, 1H), 6.43 (d, J=7.8 Hz, 1H), 5.16 (s, 1H), 4.04 (s, 3H), 4.02~3.95 (m, 2H), 3.49~3.37 (m, 3H), 1.66~1.59 (m, 4H). ¹³C NMR (100 MHz, CDCl₃) δ: 155.3, 151.1, 150.9, 142.7, 140.8, 138.9, 135.6, 134.8, 131.6, 129.9, 128.5, 128.4, 127.9, 124.8, 124.5, 123.3, 116.8, 113.7, 100.3, 89.1, 65.6, 53.8, 53.6, 33.3. HRMS (ESI-TOF⁺): [M+H]⁺ calcd for $C_{30}H_{27}F_3N_5O_2$: 546.2116; found: 546.2126.

TBI-702, 5-(4-Trifluoromethylphenyl)-3-(N-isobutyl-4-piperidyl)imino-2-methoxy-3-pyridyl)amino-3,5-dihydrophenazine:

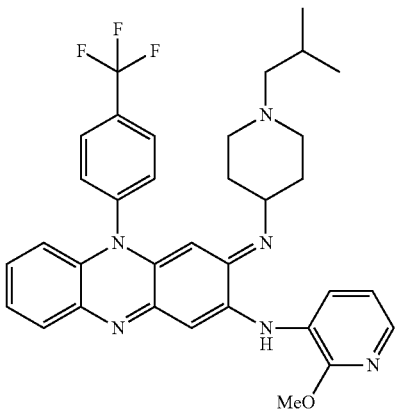 [SMILES: COc1ncccc1Nc1cc2nc3ccccc3n(-c3ccc(C(F)(F)F)cc3)c-2c/c1=N\C1CCN(CC(C)C)CC1]

¹H NMR (300 MHz, CDCl₃) δ: 9.03 (brs, 1H), 8.02 (d, J=8.1 Hz, 2H), 7.86~7.81 (m, 2H), 7.72 (d, J=7.2 Hz, 1H), 7.52 (d, J=8.1 Hz, 2H), 7.22~7.12 (m, 2H), 6.95~6.90 (m, 2H), 6.43 (d, J=8.1 Hz, 1H), 5.16 (s, 1H), 4.04 (s, 3H), 3.11 (br, 1H), 2.74 (br, 2H), 2.07~1.96 (m, 4H), 1.80~1.63 (m, 5H), 0.90 (d, J=6.6 Hz, 6H). ¹³C NMR (100 MHz, CDCl₃) δ: 155.3, 150.9, 142.7, 140.9, 138.7, 135.6, 134.7, 131.1, 129.9, 128.5, 128.4, 127.8, 124.8, 124.4, 123.2, 116.8, 113.7, 100.2, 89.3, 67.3, 55.4, 53.7, 52.0, 32.7, 25.6, 21.1. HRMS (ESI-TOF⁺): m/z [M+H]⁺ calcd for C₃₄H₃₆F₃N₆O: 601.2902; found: 601.2908.

TBI-703, 5-(4-Trifluoromethylphenyl)-3-(N-methyl-4-piperidyl)imino-2-(2-methoxy-3-pyridyl)amino-3,5-dihydrophenazine:

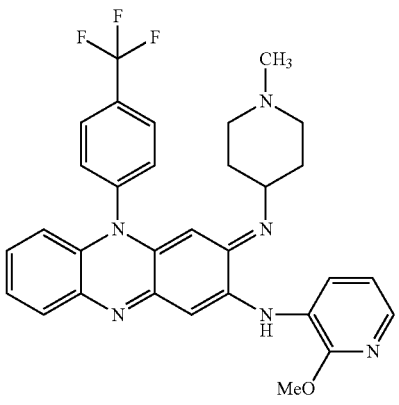

¹H NMR (300 MHz, CDCl₃) δ: 9.08 (brs, 1H), 8.03 (d, J=8.4 Hz, 2H), 7.86~7.80 (m, 2H), 7.74~7.71 (m, 1H), 7.52 (d, J=8.4 Hz, 2H), 7.23~7.12 (m, 2H), 6.96 (s, 1H), 6.49~6.90 (dd, J=7.8, 4.8 Hz, 1H) 6.42 (d, J=7.5 Hz, 1H), 5.16 (s, 1H), 4.03 (s, 3H), 3.15 (br, 1H), 2.79~2.75 (m, 2H), 2.30 (s, 3H), 2.07 (br, 2H), 1.68~1.67 (m, 4H). ¹³C NMR (100 MHz, CDCl₃) δ: 155.3, 151.0, 150.9, 142.6, 140.8, 138.7, 135.6, 134.7, 131.1, 129.9, 128.5, 128.4, 127.8, 124.8, 124.3, 123.2, 116.8, 113.7, 100.2, 89.2, 53.7, 53.4, 46.4, 32.5. HRMS (ESI-TOF⁺): m/z [M+H]⁺ calcd for C₃₁H₃₀F₃N₆O: 559.2433; found: 559.2437.

TBI-704, 5-(4-Trifluoromethylphenyl)-3-(2-morpholinoethyl)imino-2-(2-methoxy-3-pyridyl)amino-3,5-dihydrophenazine:

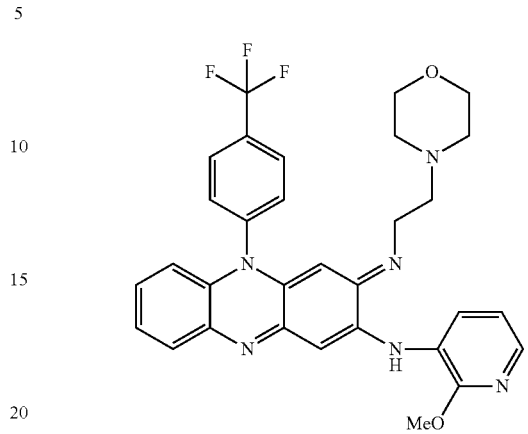

¹H NMR (300 MHz, CDCl₃) δ: 8.82 (brs, 1H), 8.02 (d, J=8.1 Hz, 2H), 7.87~7.82 (m, 2H), 7.74 (d, J=7.8 Hz, 1H), 7.52 (d, J=8.1 Hz, 2H), 7.24~7.13 (m, 2H), 6.97 (s, 1H), 6.95~6.91 (dd, J=7.2, 4.8 Hz, 1H), 6.39 (d, J=7.8 Hz, 1H), 5.21 (s, 1H), 4.04 (s, 3H), 3.70 (t, J=4.5 Hz, 4H), 3.34 (t, J=6.6 Hz, 2H), 2.74 (t, J=6.6 Hz, 2H), 2.53 (t, J=4.2 Hz, 4H). ¹³C NMR (100 MHz, CDCl₃) δ: 155.3, 152.8, 150.9, 142.5, 140.8, 139.0, 135.6, 134.6, 131.1, 129.8, 128.7, 128.7, 128.4, 127.9, 124.8, 124.6, 123.3, 116.8, 113.8, 100.1, 89.2, 67.0, 59.7, 54.2, 53.7, 48.5. HRMS (ESI-TOF⁺): m/z [M+H]⁺ calcd for C₃₁H₃₀F₃N₆O₂: 575.2382; found: 575.2385.

TBI-705, 5-(4-Trifluoromethylphenyl)-3-(1-methylethyl)imino-2-(2-methyl-3-pyridyl)amino-3,5-dihydrophenazine:

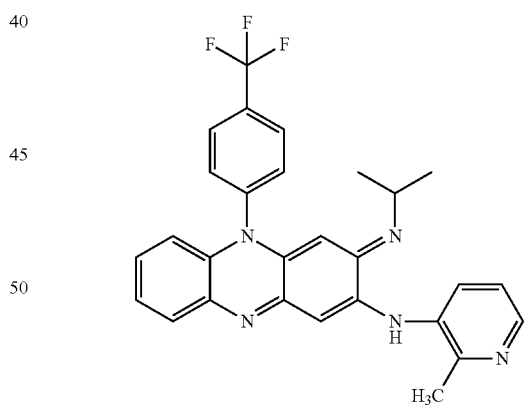

¹H NMR (300 MHz, CDCl₃) δ: 8.29 (d, J=3.6 Hz, 1H), 8.02 (d, J=8.1 Hz, 2H), 7.81 (d, J=7.2 Hz, 2H), 7.70~7.67 (m, 1H), 7.52 (d, J=8.4 Hz, 2H), 7.21~7.10 (m, 3H), 6.58 (s, 1H), 6.39~6.37 (m, 1H), 5.23 (s, 1H), 3.49~3.41 (m, 1H), 2.56 (s, 3H), 1.09 (d, J=6.0 Hz, 6H). ¹³C NMR (100 MHz, CDCl₃) δ: 152.3, 151.0, 150.2, 144.3, 144.2, 140.9, 135.5, 134.7, 131.1, 129.9, 129.3, 128.5, 128.3, 127.6, 123.1, 121.7, 113.7, 98.8, 89.1, 49.3, 23.6, 20.9. HRMS (ESI-TOF⁺): m/z [M+H]⁺ calcd for C₂₈H₂₅F₃N₅: 488.2062; found: 488.2060.

TBI-706, 5-(4-Trifluoromethylphenyl)-3-(4-methoxycyclohexyl)imino-2-(2-methyl-3-pyridyl)amino-3,5-dihydrophenazine:

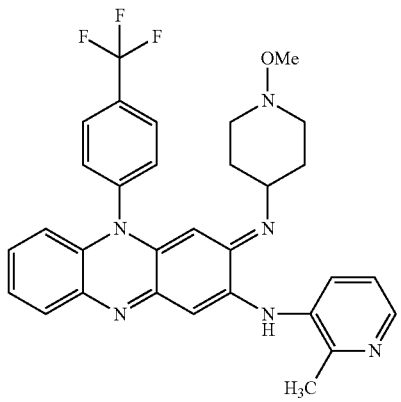

¹H NMR (300 MHz, CDCl₃) δ: 8.29 (d, J=4.2 Hz, 1H), 8.02 (d, J=8.1 Hz, 2H), 7.82 (d, J=7.8 Hz, 2H), 7.70 (d, J=7.8 Hz, 1H), 7.52 (d, J=8.4 Hz, 2H), 7.22~7.12 (m, 3H), 6.60 (s, 1H), 6.42 (d, J=7.8 Hz, 1H), 5.17 (s, 1H), 3.35 (s, 3H), 3.24~3.06 (m, 2H), 2.54 (s, 3H), 2.06~2.03 (m, 2H), 1.72~1.68 (m, 2H), 1.47~1.13 (m, 4H). ¹³C NMR (100 MHz, CDCl₃) δ: 152.2, 150.9, 150.8, 144.2, 144.0, 140.8, 135.6, 134.7, 134.6, 131.0, 129.8, 129.1, 128.5, 128.4, 127.8, 123.2, 121.7, 113.7, 99.0, 89.1, 78.2, 56.9, 55.8, 31.0, 29.9, 29.5, 20.9. HRMS (ESI-TOF⁺): m/z [M+H]⁺ calcd for C₃₂H₃₁F₃N₅O: 558.5480; found: 558.2479.

TBI-707, 5-(4-Trifluoromethylphenyl)-3-(4-tetrahydropyranyl)imino-2-(2-methyl-3-pyridyl)amino-3,5-dihydrophenazine:

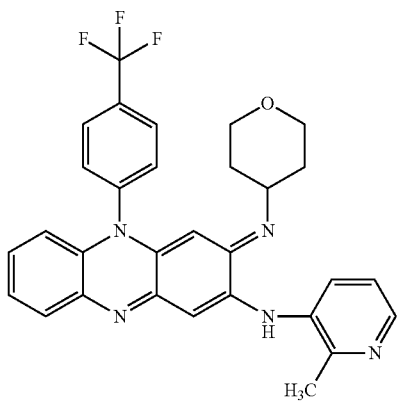

¹H NMR (300 MHz, CDCl₃) δ: 8.30 (d, J=4.2 Hz, 1H), 8.04 (d, J=8.4 Hz, 2H), 7.82 (d, J=8.1 Hz, 1H), 7.71 (d, J=7.2 Hz, 1H), 7.53 (d, J=8.4 Hz, 2H), 7.24~7.14 (m, 3H), 6.63 (s, 1H), 6.45 (d, J=7.8 Hz, 1H), 5.18 (s, 1H), 4.00~3.94 (m, 2H), 3.46~3.34 (m, 3H), 2.55 (s, 3H), 1.67~1.63 (m, 4H). ¹³C NMR (100 MHz, CDCl₃) δ: 152.4, 151.2, 150.9, 144.6, 144.3, 141.0, 135.8, 135.0, 134.7, 131.1, 130.1, 129.4, 128.8, 128.7, 128.1, 123.6, 121.9, 114.0, 99.3, 89.2, 66.1, 54.2, 33.6, 21.2. HRMS (ESI-TOF⁺): m/z [M+H]⁺ calcd for C₃₀H₂₇F₃N₅O: 530.2167; found: 530.2165.

TBI-708, 5-(4-Trifluoromethylphenyl)-3-cyclohexylimino-2-(2-methyl-3-pyridyl)amino-3,5-dihydrophenazine:

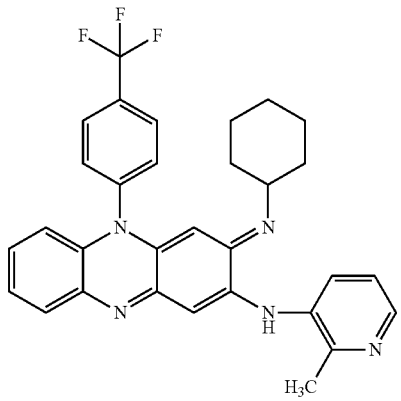 [SMILES: Cc1ncccc1Nc1cc2nc3ccccc3n(-c3ccc(C(F)(F)F)cc3)c-2c/c1=N\C1CCCCC1]

¹H NMR (300 MHz, CDCl₃) δ: 8.28~8.27 (m, 1H), 8.03 (d, J=8.1 Hz, 2H), 7.83~7.80 (m, 1H), 7.70~7.67 (dd, J=7.5, 1.2 Hz, 1H), 7.53 (d, J=8.4 Hz, 2H), 7.21~7.10 (m, 3H), 6.60 (s, 1H), 6.45~6.42 (dd, J=7.8, 1.2 Hz, 1H), 5.17 (s, 1H), 3.11~3.04 (m, 1H), 2.55 (s, 3H), 1.75~1.71 (m, 2H), 1.60~1.57 (m, 3H), 1.43~1.11 (m, 5H). ¹³C NMR (100 MHz, CDCl₃) δ: 152.1, 151.0, 150.4, 144.2, 140.9, 135.6, 134.7, 134.6, 131.0, 129.9, 129.0, 128.5, 128.3, 127.6, 123.1, 121.7, 113.6, 98.8, 89.4, 57.6, 33.6, 25.8, 24.4, 20.9. HRMS (ESI-TOF⁺): m/z [M+H]⁺ calcd for C₃₁H₂₉F₃N₅: 528.2375; found: 528.2374.

TBI-709, 5-(4-Trifluoromethylphenyl)-3-(4-hydroxycyclohexyl)imino-2-(2-methyl-3-pyridyl)amino-3,5-dihydrophenazine:

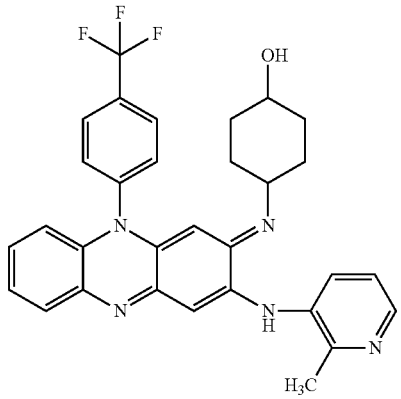 [SMILES: Cc1ncccc1Nc1cc2nc3ccccc3n(-c3ccc(C(F)(F)F)cc3)c-2c/c1=N\C1CCC(O)CC1]

¹H NMR (300 MHz, CDCl₃) δ: 8.28 (d, J=3.6, 1H), 8.04 (d, J=8.4, 2H), 7.84 (d, J=7.2, 1H), 7.72~7.69 (dd, J=8.1, J=1.5, 1H), 7.53 (d, J=8.1, 2H), 7.21~7.12 (m, 3H), 6.60 (s, 1H), 6.44 (d, J=7.8, 1H), 5.17 (s, 1H), 3.74~3.66 (m, 1H), 3.10~3.04 (m, 1H), 2.53 (s, 3H), 2.05~1.97 (m, 2H), 1.70~1.67 (m, 2H), 1.50~1.39 (m, 2H), 1.28~1.17 (m, 2H). ¹³C NMR (100 MHz, CDCl₃) δ: 152.2, 151.0, 150.8, 144.3, 144.1, 140.8, 135.6, 134.7, 134.6, 131.0, 129.8, 129.2, 128.5, 128.4, 127.8, 123.2, 121.7, 113.7, 98.9, 89.1, 69.8, 56.8, 33.4, 31.1, 20.9. HRMS (ESI-TOF⁺): m/z [M+H]⁺ calcd for C₃₁H₂₉F₃N₅O: 544.2324; found: 544.2324.

TBI-710, 5-(4-Trifluoromethylphenyl)-3-cyclohexylimino-2-(2-methoxy-3-pyridyl)amino-3,5-dihydrophenazine:

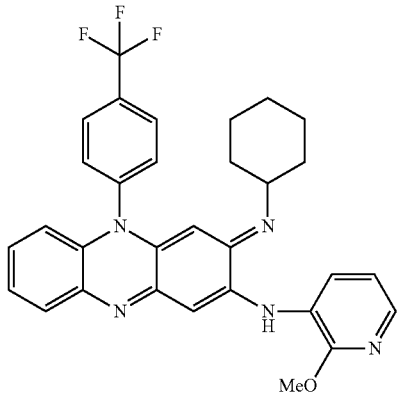 [SMILES: COc1ncccc1Nc1cc2nc3ccccc3n(-c3ccc(C(F)(F)F)cc3)c-2c/c1=N\C1CCCCC1]

$^1$H NMR (300 MHz, CDCl$_3$) δ: 8.02 (d, J=8.1 Hz, 2H), 7.85~7.80 (m, 2H), 7.72~7.69 (dd, J=7.2, 1.2 Hz, 1H), 7.52 (d, J=8.4 Hz, 2H), 7.21~7.10 (m, 2H), 6.93~6.90 (m, 2H), 6.43~6.41 (m, 1H), 5.16 (s, 1H), 4.03 (s, 3H), 3.10~3.04 (m, 1H), 1.78~1.74 (m, 2H), 1.60~1.56 (m, 3H), 1.46~1.15 (m, 5H). $^{13}$C NMR (100 MHz, CDCl$_3$) δ: 155.4, 151.3, 150.5, 142.8, 140.9, 138.7, 135.6, 134.5, 131.2, 129.9, 128.5, 128.4, 128.3, 127.7, 124.9, 124.6, 123.0, 116.8, 113.6, 100.1, 89.6, 67.1, 57.5, 53.7, 33.5, 25.9, 24.2. HRMS (ESI-TOF$^+$): m/z [M+H]$^+$ calcd for C$_{31}$H$_{29}$F$_3$N$_5$O: 544.2324; found: 544.2327.

TBI-711, 5-(4-Trifluoromethylphenyl)-3-(1-methylethyl)imino-2-(6-acetamino-3-pyridyl)amino-3,5-dihydrophenazine:

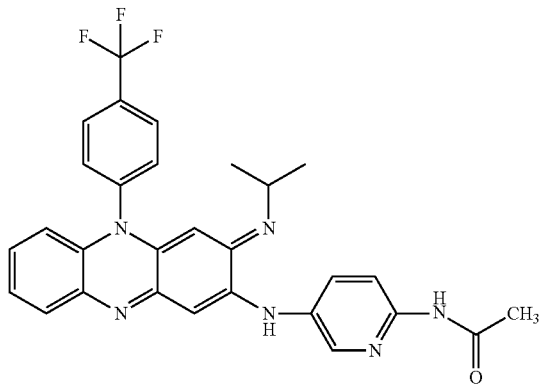 [SMILES: CC(=O)Nc1ccc(Nc2cc3nc4ccccc4n(-c4ccc(C(F)(F)F)cc4)c-3c/c2=N\C(C)C)cn1]

$^1$H NMR (300 MHz, DMSO-d$_6$) δ: 8.37 (brs, 1H), 8.27 (d, J=1.8 Hz, 1H), 8.24 (s, 1H), 8.03 (d, J=8.4 Hz, 2H), 7.78~7.74 (dd, J=8.7, 1.8 Hz, 1H), 7.71 (d, J=7.2 Hz, 1H), 7.52 (d, J=8.4 Hz, 2H), 7.24~7.12 (m, 2H), 6.72 (s, 1H), 6.40 (d, J=8.1 Hz, 1H), 5.24 (s, 1H), 3.48~3.39 (m, 1H), 2.23 (s, 3H), 1.10 (d, J=6.3 Hz, 6H). $^{13}$C NMR (100 MHz, CDCl$_3$) δ: 168.4, 150.7, 150.4, 147.4, 144.4, 141.2, 140.8, 135.7, 134.7, 133.0, 132.4, 131.0, 129.8, 128.6, 128.5, 128.4, 127.8, 123.4, 114.2, 113.8, 99.1, 89.1, 49.3, 24.6, 23.4. HRMS (ESI-TOF$^+$): m/z [M+H]$^+$ calcd for C$_{29}$H$_{26}$F$_3$N$_6$O: 531.2120; found: 531.2122.

TBI-712, 5-(4-Trifluoromethylphenyl)-3-(4-tetrahydropyranyl)imino-2-(6-acetamino-3-pyridyl)amino-3,5-dihydrophenazine:

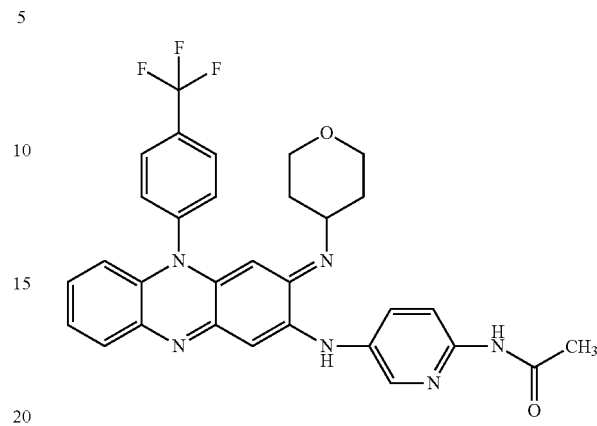

$^1$H NMR (300 MHz, DMSO-d$_6$) δ: 8.29 (d, J=2.7 Hz, 1H), 8.25 (d, J=9.3 Hz, 1H), 8.17 (brs, 1H), 8.03 (d, J=8.4 Hz, 2H), 7.77~7.70 (m, 2H), 7.52 (d, J=8.4 Hz, 2H), 7.24~7.13 (m, 2H), 6.72 (s, 1H), 6.45 (d, J=7.8 Hz, 1H), 5.15 (s, 1H), 3.98~3.93 (m, 2H), 3.40~3.27 (m, 3H), 2.23 (s, 3H), 1.71~1.57 (m, 4H). $^{13}$C NMR (100 MHz, CDCl$_3$) δ: 168.3, 151.0, 150.6, 147.4, 144.4, 142.2, 140.8, 135.6, 134.8, 132.8, 132.2, 130.8, 129.8, 128.6, 128.5, 127.8, 123.3, 114.1, 113.7, 98.9, 89.0, 66.1, 54.6, 33.4, 24.6. HRMS (ESI-TOF$^+$): m/z [M+H]$^+$ calcd for C$_{31}$H$_{28}$F$_3$N$_6$O$_2$: 573.2225; found: 573.2227.

TBI-713, 5-(4-Trifluoromethylphenyl)-3-cyclohexylimino-2-(6-acetamino-3-pyridyl)amino-3,5-dihydrophenazine:

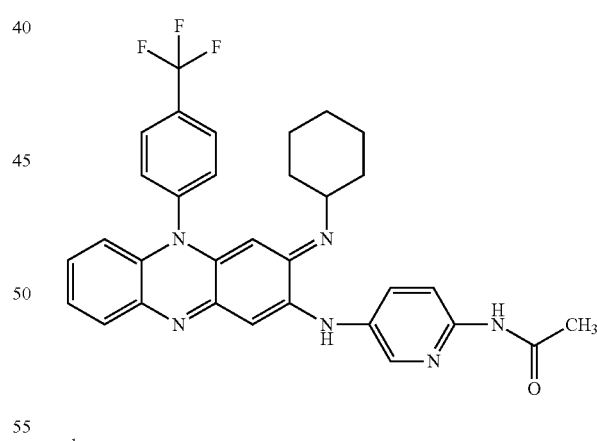

$^1$H NMR (300 MHz, DMSO-d$_6$) δ: 8.28 (d, J=2.4 Hz, 1H), 8.23 (d, J=8.7 Hz, 1H), 8.02 (d, J=8.1 Hz, 3H), 7.76~7.72 (dd, J=9.0, 2.4 Hz, 1H), 7.71~7.68 (m, 1H), 7.52 (d, J=8.1 Hz, 2H), 7.21~7.11 (m, 2H), 6.69 (s, 1H), 6.44 (d, J=7.8 Hz, 1H), 5.15 (s, 1H), 3.06~2.99 (m, 1H), 2.23 (s, 3H), 1.75~1.71 (m, 2H), 1.61~1.57 (m, 3H), 1.42~1.07 (m, 5H). $^{13}$C NMR (100 MHz, CDCl$_3$) δ: 168.2, 150.9, 150.4, 147.2, 144.5, 142.1, 140.9, 135.6, 134.6, 133.0, 132.1, 131.0, 129.9, 128.5, 128.4, 128.3, 127.6, 123.1, 114.1, 113.6, 98.8, 89.4, 58.1, 33.6, 25.8, 24.7, 24.6. HRMS (ESI-TOF$^+$): m/z [M+H]$^+$ calcd for C$_{32}$H$_{30}$F$_3$N$_6$O: 571.2433; found: 571.2437.

TBI-714, 5-(4-Trifluoromethylphenyl)-3-(4-hydroxycyclohexyl)imino-2-(6-acetamino-3-pyridyl)amino-3,5-dihydrophenazine:

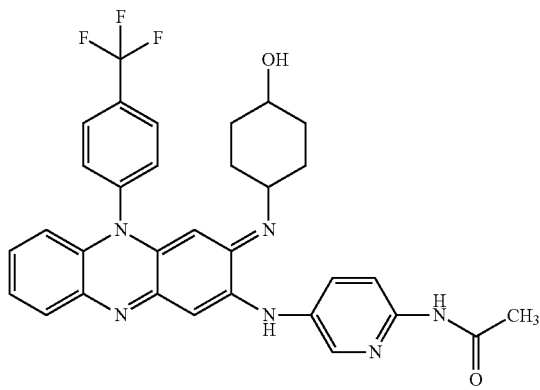 [SMILES: CC(=O)Nc1ccc(Nc2cc3nc4ccccc4n(-c4ccc(C(F)(F)F)cc4)c-3c/c2=N\C2CCC(O)CC2)cn1]

¹H NMR (300 MHz, DMSO-d₆) δ: 8.27 (d, J=2.4 Hz, 1H), 8.23 (d, J=8.7 Hz, 1H), 8.13 (brs, 1H), 8.02 (d, J=8.4 Hz, 2H), 7.75 (d, J=2.4 Hz, 1H), 7.71~7.68 (m, 1H), 7.52 (d, J=7.8 Hz, 2H), 7.22~7.11 (m, 2H), 6.69 (s, 1H), 6.43 (d, J=7.2, 1H), 5.15 (s, 1H), 3.70~3.63 (m, 1H), 3.06~2.99 (m, 1H), 2.22 (s, 3H), 2.03~1.95 (m, 2H), 1.67~1.63 (m, 2H), 1.50~1.39 (m, 2H), 1.25~1.13 (m, 2H). ¹³C NMR (100 MHz, CDCl₃) δ: 168.2, 151.0, 150.8, 147.3, 144.3, 142.2, 140.9, 135.6, 134.7, 132.9, 132.1, 131.0, 129.9, 128.5, 127.8, 125.0, 123.3, 114.1, 113.7, 98.9, 89.1, 69.9, 57.1, 33.6, 32.2, 31.2, 26.4, 24.7. HRMS (ESI-TOF⁺): m/z [M+H]⁺ calcd for $C_{32}H_{30}F_3N_6O_2$: 587.2382; found: 587.2379.

TBI-715, 5-(4-Trifluoromethylphenyl)-3-(4-methoxycyclohexyl)imino-2-(6-acetamino-3-pyridyl)amino-3,5-dihydrophenazine:

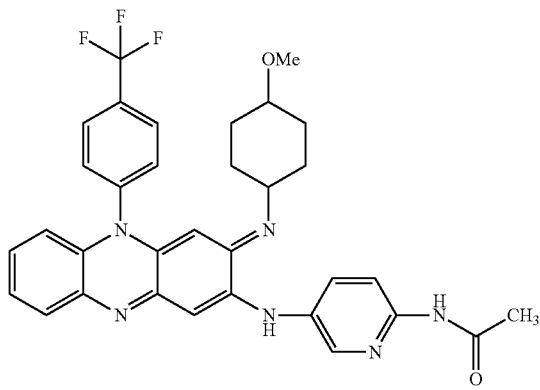 [SMILES: COC1CCC(/N=c2\cc3n(-c4ccc(C(F)(F)F)cc4)c4ccccc4nc-3cc2Nc2ccc(NC(C)=O)nc2)CC1]

¹H NMR (300 MHz, DMSO-d₆) δ: 8.57 (brs, 1H), 8.28~8.26 (m, 2H), 8.03 (d, J=8.4, 2 H), 7.78~7.72 (m, 2H), 7.52 (d, J=8.4 Hz, 2H), 7.23~7.14 (m, 2H), 6.73 (s, 1H), 6.45 (d, J=8.1 Hz, 1H), 5.20 (s, 1H), 3.35 (s, 3H), 3.21~3.15 (m, 1H), 3.09~3.02 (m, 1H), 2.23 (s, 3H), 2.10~2.05 (m, 2H), 1.71~1.67 (m, 2H), 1.49~1.38 (m, 2H), 1.19~1.08 (m, 2H). ¹³C NMR (100 MHz, CDCl₃) δ: 168.5, 151.1, 150.5, 147.5, 144.2, 141.7, 140.7, 135.8, 134.7, 132.9, 132.5, 130.8, 129.7, 128.5, 128.0, 123.5, 114.3, 113.9, 99.2, 89.1, 78.3, 57.1, 55.8, 30.9, 29.8, 24.6. HRMS (ESI-TOF⁺): m/z [M+H]⁺ calcd for $C_{33}H_{32}F_3N_6O_2$: 601.2539; found: 601.2538.

TBI-716, 5-(4-Trifluoromethylphenyl)-3-cyclopropylimino-2-(6-methyl-3-pyridyl)amino-3,5-dihydrophenazine:

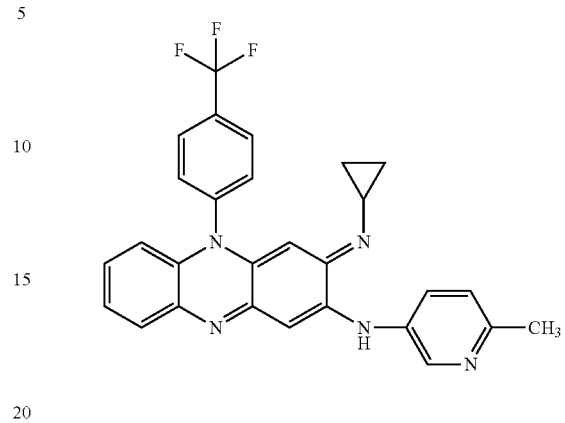

¹H NMR (300 MHz, CDCl₃) δ: 8.41 (br, 1H), 8.02 (d, J=8.1 Hz, 2H), 7.67~7.64 (m, 2H), 7.54 (d, J=8.1 Hz, 2H), 7.19~7.09 (m, 3H), 6.66 (s, 1H), 6.35 (d, J=7.8 Hz, 1H), 5.49 (s, 1H), 2.71 (br, 1H), 2.56 (s, 3H), 0.90~0.87 (m, 2H), 0.82 (br, 2H). ¹³C NMR (100 MHz, CDCl₃) δ: 153.6, 152.3, 151.1, 144.2, 143.9, 140.9, 135.7, 134.4, 133.8, 131.2, 129.9, 129.8, 128.6, 128.3, 127.6, 123.2, 113.7, 98.8, 89.5, 32.9, 23.8, 10.0. HRMS (ESI-TOF⁺): m/z [M+H]⁺ calcd for $C_{28}H_{23}F_3N_5$: 486.1905; found: 486.1907.

TBI-717, 5-(4-Trifluoromethylphenyl)-3-cyclohexylimino-2-(6-methyl-3-pyridyl)amino-3,5-dihydrophenazine:

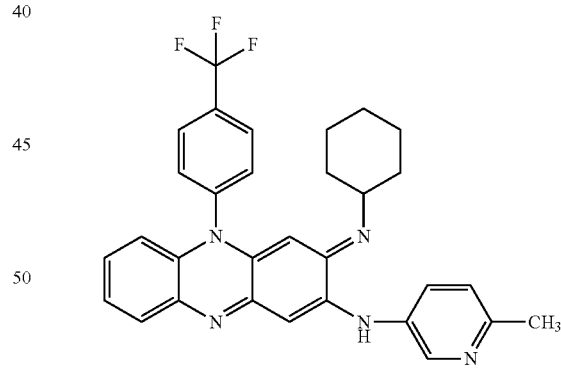

¹H NMR (300 MHz, CDCl₃) δ: 8.45 (d, J=2.4 Hz, 1H), 8.02 (d, J=8.1 Hz, 2H), 7.70~7.66 (m, 2H), 7.54 (d, J=8.4 Hz, 2H), 7.21~7.11 (m, 3H), 6.71 (s, 1H), 6.45~6.42 (dd, J=7.8, 1.2 Hz, 1H), 5.15 (s, 1H), 3.06~2.99 (m, 1H), 2.56 (s, 3H), 1.75~1.71 (m, 2H), 1.61~1.57 (m, 3H), 1.43~1.11 (m, 5H). ¹³C NMR (100 MHz, CDCl₃) δ: 153.4, 151.0, 150.5, 144.5, 143.8, 140.9, 135.6, 134.5, 134.0, 131.0, 129.9, 129.5, 128.5, 128.3, 127.6, 123.2, 123.1, 113.6, 98.8, 89.5, 58.1, 33.6, 25.8, 24.6, 23.8. HRMS (ESI-TOF⁺): m/z [M+H]⁺ calcd for $C_{31}H_{29}F_3N_5$: 528.2375; found: 528.2378.

TBI-718, 5-(4-Trifluoromethylphenyl)-3-cyclopropylimino-2-(2-methoxy-3-pyridyl)amino-3,5-dihydrophenazine:

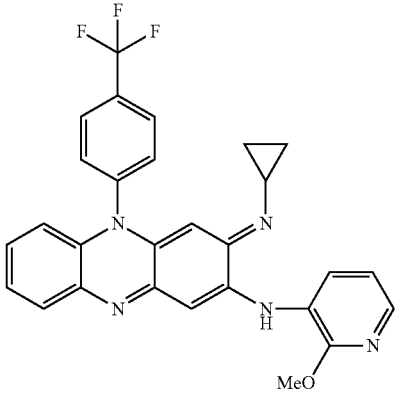 [SMILES: COc1ncccc1Nc1cc2nc3ccccc3n(-c3ccc(C(F)(F)F)cc3)c-2c/c1=N\C1CC1]

$^1$H NMR (300 MHz, CDCl$_3$) 8.58 (brs, 1H), 8.02 (d, J=8.1 Hz, 2H), 7.84~7.82 (m, 2H), 7.70~7.67 (m, 1H), 7.54 (d, J=8.1 Hz, 2H), 7.20~7.09 (m, 2H), 6.93~6.89 (m, 2H), 6.35 (d, J=7.2 Hz, 1H), 5.49 (s, 1H), 4.01 (s, 3H), 2.71 (br, 1H), 0.91~0.83 (m, 4H). $^{13}$C NMR (100 MHz, CDCl$_3$) δ: 155.5, 152.4, 151.4, 142.7, 140.9, 139.0, 135.7, 134.4, 131.4, 130.0, 128.6. 128.6, 128.2, 127.6, 125.1, 124.7, 123.0, 116.8, 113.6, 100.0, 89.7, 53.7, 32.9, 10.2. HRMS (ESI-TOF$^+$): m/z [M+H]$^+$ calcd for C$_{28}$H$_{23}$F$_3$N$_5$O: 502.1854; found: 502.1854.

TBI-719, 5-(4-Trifluoromethylphenyl)-3-(4-hydroxycyclohexyl)imino-2-(2-methoxy-3-pyridyl)amino-3,5-dihydrophenazine:

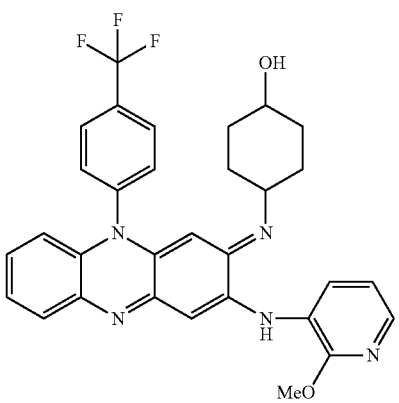 [SMILES: COc1ncccc1Nc1cc2nc3ccccc3n(-c3ccc(C(F)(F)F)cc3)c-2c/c1=N\C1CCC(O)CC1]

$^1$H NMR (300 MHz, CDCl$_3$) δ: 8.03 (d, J=8.3 Hz, 2H), 7.86~7.81 (m, 2H), 7.73~7.70 (dd, J=7.2, J=1.5 Hz, 1H), 7.53 (d, J=8.4 Hz, 2H), 7.26 (s, 2H), 7.23~7.12 (m, 2H), 6.94 (s, 1H), 6.92~6.90 (m, 1H), 6.44~6.41 (m, 1H), 5.16 (s, 1H), 4.03 (s, 3H), 3.76~3.69 (m, 1H), 3.10~3.03 (m, 1H), 2.05~1.98 (m, 2H), 1.70~1.66 (m, 2H), 1.53~1.41 (m, 2H), 1.29~1.16 (m, 1H). $^{13}$C NMR (100 MHz, CDCl$_3$) δ: 155.4, 151.2, 151.0, 142.8, 140.8, 138.9, 135.6, 134.6, 131.1, 129.9, 128.6, 128.5, 128.4, 127.8, 124.8, 123.2, 116.8, 113.7, 100.2, 89.3, 69.8, 56.8, 53.7, 33.2, 30.8. HRMS (ESI-TOF$^+$): m/z [M+H]$^+$ calcd for C$_{31}$H$_{29}$F$_3$N$_5$O$_2$: 560.2273; found: 560.2271.

TBI-720, 5-(2-Trifluoromethylphenyl)-3-(1-methylethyl)imino-2-(3-pyridyl)amino-3,5-dihydrophenazine:

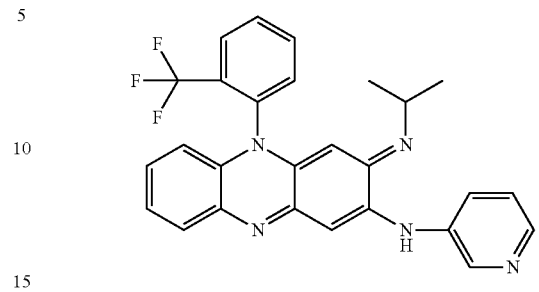

$^1$H NMR (300 MHz, CDCl$_3$) δ: 8.59 (d, J=2.6, 1H), 8.33 (d, J=4.6, 1H), 8.05 (d, J=7.7 Hz, 1H), 7.94 (t, J=7.7 Hz, 1H), 7.81 (m, 2H), 7.70 (dd, J=7.7 Hz, 1.3, 1H), 7.41 (d, J=7.8 Hz, 1H), 7.35~7.2 (m, 2H), 7.23~7.02 (m, 2H), 6.83 (s, 1H), 6.28 (d, J=7.8 Hz, 1H), 5.07 (s, 1H), 3.39 (dt, J=12.6, 6.2 Hz, 1H), 1.20~0.82 (m, 6H). $^{13}$C NMR (100 MHz, CDCl$_3$) δ: 150.9, 150.4, 144.3, 144.0, 143.5, 136.8, 135.5, 135.4, 135.2, 134.9, 131.8, 131.6, 130.5, 129.0, 128.9, 128.2, 128.0, 127.6, 123.6, 123.0, 114.2, 99.5, 90.1, 49.4, 23.6, 23.3. HRMS (ESI-TOF$^+$): m/z [M+H]$^+$ calcd for C$_{27}$H$_{23}$F$_3$N$_5$: 474.1905; found: 474.1906.

TBI-721, 5-(4-Trifluoromethylphenyl)-3-(1-methylethyl)imino-2-(5-methyl-3-pyridyl)amino-3,5-dihydrophenazine:

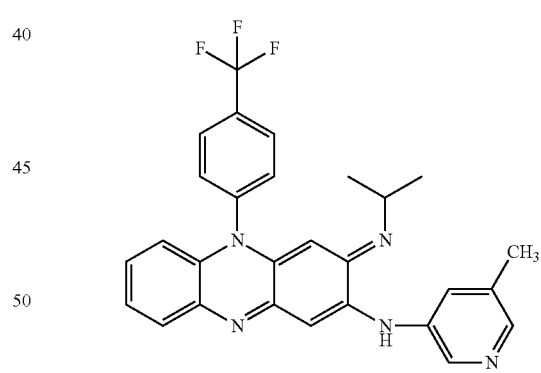

$^1$H NMR (300 MHz, CDCl$_3$) δ: 8.41 (d, J=2.1 Hz, 1H), 8.18 (s, 1H), 8.02 (d, J=8.3 Hz, 2H), 7.70 (dd, J=7.7, 1.3 Hz, 1H), 7.58 (s, 1H), 7.52 (d, J=8.2 Hz, 2H), 7.16 (dt, J=15.5, 6.7 Hz, 2H), 6.83 (s, 1H), 6.38 (d, J=8.7 Hz, 1H), 5.22 (s, 1H), 3.43 (dt, J=12.6, 6.2 Hz, 1H), 2.38 (s, 3H), 1.08 (d, J=6.2 Hz, 6H). $^{13}$C NMR (100 MHz, CDCl$_3$) δ: 151.0, 150.2, 145.0, 143.8, 141.2, 140.9, 136.3, 135.5, 134.6, 133.5, 131.2, 129.8, 128.5, 128.3, 127.7, 123.1, 113.7, 99.3, 89.1, 49.4, 23.5, 18.5. HRMS (ESI-TOF$^+$): m/z [M+H]$^+$ calcd for C$_{28}$H$_{25}$F$_3$N$_5$: 488.2062; found: 488.2060.

TBI-722, 5-(4-Trifluoromethylphenyl)-3-cyclohexylimino-2-(5-methyl-3-pyridyl)amino-3,5-dihydrophenazine:

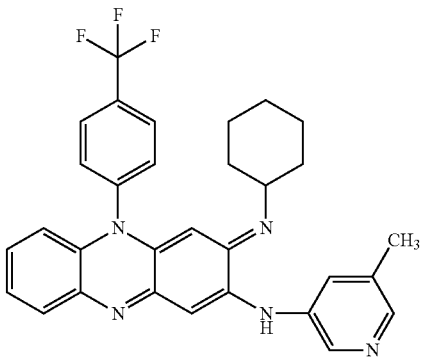

¹H NMR (300 MHz, CDCl₃) δ: 8.40 (d, J=2.0 Hz, 1H), 8.18 (s, 1H), 8.03 (d, J=8.2 Hz, 2H), 7.71 (dd, J=7.6, 1.4 Hz, 1H), 7.57 (s, 1H), 7.52 (d, J=8.1 Hz, 2H), 7.24-7.02 (m, 2H), 6.82 (s, 1H), 6.44 (d, J=7.2 Hz, 1H), 5.16 (s, 1H), 3.15~2.86 (m, 1H), 2.38 (s, 3H), 1.75~1.71 (m, 2H), 1.58 (br, 3H), 1.25 (ddt, J=43.9, 22.5, 11.3 Hz, 5H). ¹³C NMR (100 MHz, CDCl₃) δ: 151.1, 150.4, 145.0, 143.8, 141.1, 140.9, 136.3, 135.6, 134.6, 133.5, 131.1, 129.9, 128.5, 128.4, 128.3, 127.7, 123.1, 113.6, 99.3, 89.5, 58.1, 33.6, 25.8, 24.6, 18.5. HRMS (ESI-TOF⁺): m/z [M+H]⁺ calcd for $C_{31}H_{29}F_3N_5$: 528.2375; found: 528.2372.

TBI-723, 5-(4-Trifluoromethylphenyl)-3-(4-tetrahydropyranyl)imino-2-(5-methyl-3-pyridyl)amino-3,5-dihydrophenazine:

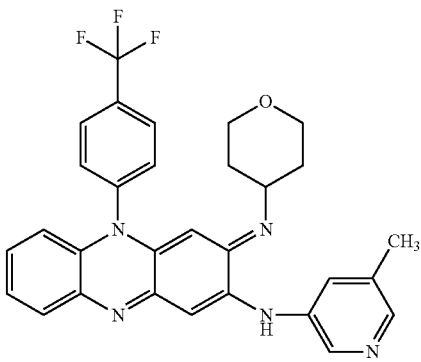 [SMILES: Cc1cncc(Nc2cc3nc4ccccc4n(-c4ccc(C(F)(F)F)cc4)c-3c/c2=N\C2CCOCC2)c1]

¹H NMR (300 MHz, CDCl₃) δ: 8.42 (s, 1H), 8.20 (s, 1H), 8.04 (d, J=7.9 Hz, 2H), 7.74 (d, J=7.5 Hz, 1H), 7.58 (s, 1H), 7.53 (d, J=7.8 Hz, 2H), 7.25~7.13 (m, 2H), 6.86 (s, 1H), 6.46 (d, J=7.9 Hz, 1H), 5.16 (s, 1H), 3.68~3.94 (m, 2H), 3.40~3.33 (m, 3H), 2.39 (s, 3H), 1.82~1.31 (m, 4H). ¹³C NMR (100 MHz, CDCl₃) δ: 151.0, 150.7, 145.3, 143.7, 141.2, 140.8, 136.2, 135.6, 134.8, 133.6, 131.0, 129.8, 128.7, 128.6, 128.0, 123.4, 113.8, 99.5, 89.0, 66.1, 54.5, 33.4, 18.5. HRMS (ESI-TOF⁺): m/z [M+H]⁺ calcd for $C_{30}H_{27}F_3N_5O$: 530.2167; found: 530.2166.

TBI-724, 5-(4-Trifluoromethylphenyl)-3-(4-methoxycyclohexyl)imino-2-(5-meth-3-pyridyl)amino-3,5-dihydrophenazine:

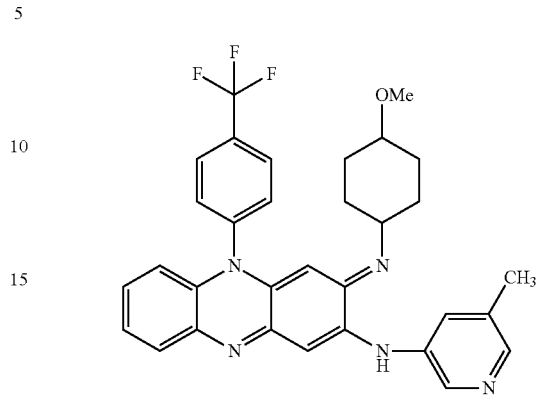

¹H NMR (300 MHz, CDCl₃) δ: 8.39 (s, 1H), 8.18 (s, 1H), 8.02 (d, 8.2 Hz, 2H), 7.71 (d, J=7.5 Hz, 1H), 7.58 (s, 1H), 7.52 (d, J=8.1 Hz, 2H), 7.26 (s, 1H), 7.25~7.02 (m, 2H), 6.83 (s, 1H), 6.43 (d, J=7.9 Hz, 1H), 5.18 (s, 1H), 3.35 (s, 3H), 3.28~3.12 (m, 1H), 3.12~2.90 (m, 1H), 2.38 (s, 3H), 2.22~1.86 (m, 2H), 1.69~1.65 (m, 2H), 1.47~1.36 (m, 2H), 1.21~1.09 (m, 2H). ¹³C NMR (100 MHz, CDCl₃) δ: 150.9, 145.1, 143.7, 141.2, 140.8, 136.3, 135.6, 134.6, 133.5, 131.1, 129.8, 128.5, 128.4, 127.9, 123.2, 113.7, 99.4, 89.2, 78.4, 57.2, 55.8, 31.1, 29.7, 18.5. HRMS (ESI-TOF⁺): m/z [M+H]⁺ calcd for $C_{32}H_{31}F_3N_5O$: 558.2480; found: 558.2480.

TBI-725, 5-(4-Trifluoromethylphenyl)-3-cyclopropylimino-2-(5-methyl-3-pyridyl)amino-3,5-dihydrophenazine:

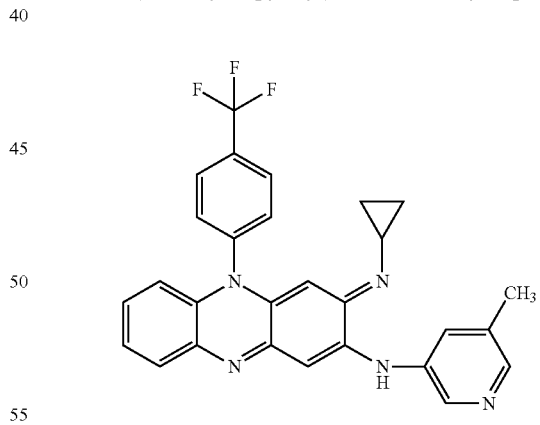

¹H NMR (300 MHz, CDCl₃) δ: 8.36 (s, 1H), 8.18 (s, 1H), 8.02 (d, J=8.1 Hz, 2H), 7.68 (d, J=7.5 Hz, 1H), 7.55~7.53 (m, 3H), 7.23~6.99 (m, 2H), 6.78 (s, 1H), 6.36 (d, J=7.8 Hz, 1H), 5.49 (s, 1H), 2.88~2.52 (m, 1H), 2.37 (s, 3H), 1.03~0.60 (m, 4H). ¹³C NMR (100 MHz, CDCl₃) δ: 152.1, 151.2, 145.2, 143.6, 141.2, 140.9, 136.2, 135.7, 134.4, 133.5, 131.3, 129.9, 128.6, 128.6, 128.3, 127.7, 123.1, 113.6, 99.3, 89.5, 32.9, 18.5, 10.1. HRMS (ESI-TOF⁺): m/z [M+H]⁺ calcd for $C_{28}H_{13}F_3N_5$: 486.1905; found: 486.1907.

TBI-726, 5-(4-Trifluoromethylphenyl)-3-cyclobutyl-imino-2-(5-methyl-3-pyridyl)amino-3,5-dihydrophenazine:

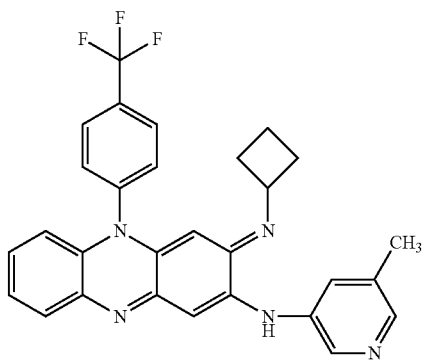 [SMILES: Cc1cncc(Nc2cc3nc4ccccc4n(-c4ccc(C(F)(F)F)cc4)c-3c/c2=N\C2CCC2)c1]

¹H NMR (300 MHz, CDCl₃) δ: 8.38 (s, 1H), 8.16 (s, 1H), 8.00 (d, J=7.7 Hz, 2H), 7.69 (d, J=7.5, 1H), 7.63~7.35 (m, 3H), 7.22~6.99 (m, 2H), 6.81 (s, 1H), 6.39 (d, J=7.9 Hz, 1H), 4.99 (s, 1H), 4.03~3.59 (m, 1H), 2.36 (s, 3H), 2.23~1.88 (m, 4H), 1.70 (dt, J=17.6, 7.7 Hz, 2H). ¹³C NMR (100 MHz, CDCl₃) δ: 151.0, 150.9, 145.1, 143.7, 141.2, 140.8, 136.2, 135.6, 134.2, 133.5, 131.0, 129.9, 128.5, 128.4, 127.8, 123.3, 113.7, 99.4, 90.6, 54.8, 31.9, 18.4, 16.0. HRMS (ESI-TOF⁺): m/z [M+H]⁺ calcd for $C_{29}H_{25}F_3N_5$: 500.2062; found: 500.2061.

TBI-727, 5-(4-Trifluoromethylphenyl)-3-(4-hydroxycyclohexyl)imino-2-(5-methyl-3-pyridyl)amino-3,5-dihydrophenazine:

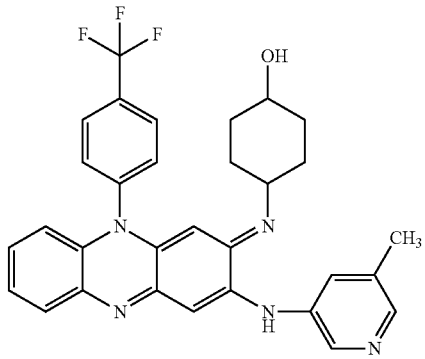 [SMILES: Cc1cncc(Nc2cc3nc4ccccc4n(-c4ccc(C(F)(F)F)cc4)c-3c/c2=N\C2CCC(O)CC2)c1]

¹H NMR (300 MHz, CDCl₃) δ: 8.39 (d, J=2.1 Hz, 1H), 8.18 (s, 1H), 8.03 (d, J=8.3 Hz, 2H), 7.72 (d, J=6.5 Hz, 1H), 7.64~7.39 (m, 3H), 7.25~7.00 (m, 2H), 6.83 (s, 1H), 6.44 (d, J=7.1 Hz, 1H), 5.16 (s, 1H), 3.87~3.50 (m, 1H), 3.20~2.80 (m, 1H), 2.38 (s, 3H), 1.99 (d, J=11.7 Hz, 2H), 1.66 (d, J=13.9 Hz, 2H), 1.57~1.33 (m, 2H), 1.25~1.14 (m, 2H). ¹³C NMR (100 MHz, CDCl₃) δ: 151.0, 150.9, 145.1, 143.7, 141.1, 140.8, 136.2, 135.6, 134.6, 133.6, 131.0, 129.8, 128.5, 128.4, 127.9, 123.2, 113.7, 99.4, 89.2, 69.9, 57.1, 33.6, 31.2, 18.5. HRMS (ESI-TOF⁺): m/z [M+H]⁺ calcd for $C_{31}H_{29}F_3N_5O$: 544.23242; found: 544.2321.

TBI-728, 5-(4-Trifluoromethylphenyl)-3-cyclobutyl-imino-2-(2-methoxy-3-pyridyl)amino-3,5-dihydrophenazine:

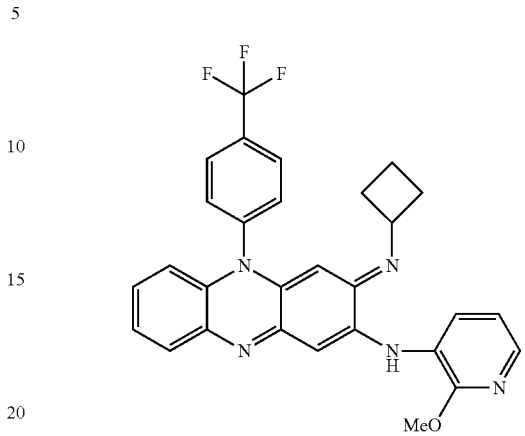

¹H NMR (300 MHz, CDCl₃) δ: 8.79 (s, 1H), 8.02 (d, J=8.2 Hz, 2H), 7.85~7.81 (m, 2H), 7.73~7.70 (dd, J=7.8, 1.5 Hz, 1H), 7.52 (d, J=8.2 Hz, 2H), 7.24~7.04 (m, 2H), 6.93~6.89 (m, 2H), 6.41 (d, J=8.1 Hz, 1H), 5.01 (s, 1H), 4.05 (s, 3H), 3.98~3.70 (m, 1H), 2.3~1.91 (m, 4H), 1.91~1.47 (m, 2H). ¹³C NMR (100 MHz, CDCl₃) δ: 155.4, 151.3, 151.1, 142.8, 140.9, 139.0, 135.6, 134.1, 131.1, 123.0, 128.5, 128.4, 127.8, 124.9, 124.7, 123.2, 116.8, 113.7, 100.3, 90.8, 54.9, 53.7, 32.0, 16.1. HRMS (ESI-TOF⁺): [M+H]⁺ calcd for $C_{29}H_{25}F_3N_5O$: 516.2013; found: 516.2011.

TBI-729, 5-(4-Trifluoromethylphenyl)-3-cyclopropy-limino-2-ethyl-3-pyridyl)amino-3,5-dihydrophenazine:

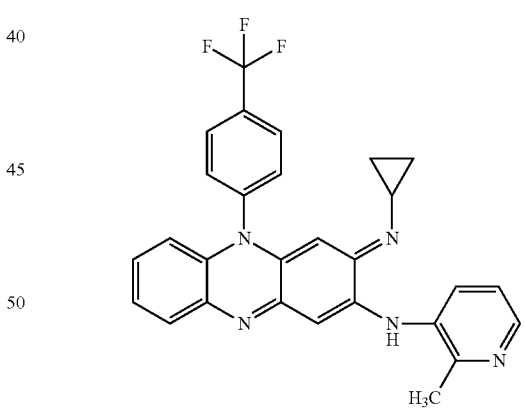

¹H NMR (300 MHz, CDCl₃) δ: 8.29 (d, J=4.7 Hz, 1H), 8.02 (d, J=8.3 Hz, 2H), 7.77 (d, J=8.0 Hz, 1H), 7.66 (d, J=8.5 Hz, 1H), 7.54 (d, J=8.1 Hz, 2H), 7.20~7.11 (m, 3H), 6.49 (s, 1H), 6.35 (d, J=7.7 Hz, 1H), 5.50 (s, 1H), 2.76~2.72 (m, 1H), 2.51 (s, 3H), 1.04~0.85 (m, 2H), 0.85~0.65 (m, 2H). ¹³C NMR (100 MHz, CDCl₃) δ: 152.6, 152.0, 151.2, 144.6, 144.1, 140.9, 135.6, 134.4, 131.3, 129.9, 129.8, 128.6, 128.2, 127.6, 123.1, 121.7, 113.6, 98.8, 89.4, 32.9, 20.9, 10.2. HRMS (ESI-TOF⁺): m/z [M+H]⁺ calcd for $C_{28}H_{23}F_3N_5$: 486.1905; found: 486.1906.

TBI-730, 5-(3-Trifluoromethylphenyl)-3-(1-methylethyl)imino-2-(3-pyridyl)amino-3,5-dihydrophenazine:

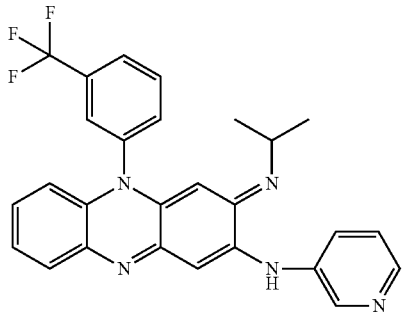 [SMILES: CC(C)/N=c1\cc2n(-c3cccc(C(F)(F)F)c3)c3ccccc3nc-2cc1Nc1cccnc1]

¹H NMR (300 MHz, CDCl₃) δ: 8.59 (d, J=2.4 Hz, 1H), 8.34 (d, J=3.8 Hz, 1H), 8.04~7.84 (m, 2H), 7.78 (d, J=8.2 Hz, 1H), 7.70 (m, 2H), 7.60 (d, J=7.3 Hz, 1H), 7.30 (dd, J=8.2, 4.7 Hz, 1H), 7.25~7.06 (m, 2H), 6.84 (s, 1H), 6.42 (d, J=7.1 Hz, 1H), 5.20 (s, 1H), 3.40 (dt, J=12.3, 6.2 Hz, 1H), 1.08 (t, J=6.8 Hz, 6H). ¹³C NMR (100 MHz, CDCl₃) δ: 150.9, 150.3, 144.3, 144.0, 143.7, 138.3, 136.8, 135.6, 134.8, 132.8, 132.1, 131.2, 128.5, 128.0, 127.8, 126.6, 126.5, 123.6, 123.2, 113.6, 99.5, 89.5, 49.5, 23.6, 23.2. HRMS (ESI-TOF⁺): m/z [M+H]⁺ calcd for $C_{27}H_{23}F_3N_5$: 474.1903; found: 474.1905.

TBI-731, 5-(4-Trifluoromethylphenyl)-3-(1-ethylethyl)imino-2-(6-methoxy-3-pyridyl)amino-3,5-dihydrophenazine:

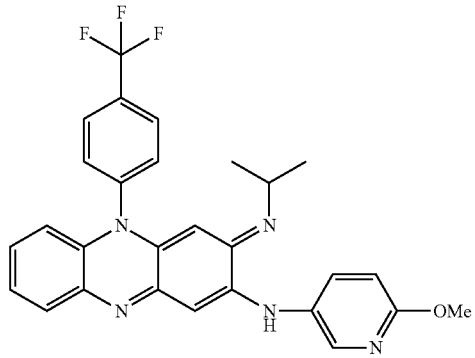 [SMILES: COc1ccc(Nc2cc3nc4ccccc4n(-c4ccc(C(F)(F)F)cc4)c-3c/c2=N\C(C)C)cn1]

¹H NMR (300 MHz, CDCl₃) δ: 8.15 (d, J=2.6 Hz, 1H), 8.02 (d, J=8.3 Hz, 2H), 7.75~7.57 (m, 2H), 7.51 (d, J=8.2 Hz, 2H), 7.14 (m, 2H), 6.79 (d, J=8.8 Hz, 1H), 6.49 (s, 1H), 6.37 (d, 18.1 Hz, 1H), 5.21 (s, 1H), 3.96 (s, 3H), 3.57~3.30 (m, 1H), 1.09 (d, J=6.2 Hz, 6H). ¹³C NMR (100 MHz, CDCl₃) δ: 161.3, 150.9, 150.3, 146.0, 142.5, 141.0, 135.6, 135.1, 134.5, 131.0, 130.1, 129.9, 128.5, 128.2, 127.3, 123.1, 113.6, 111.0, 98.1, 89.1, 53.6, 49.4, 23.5. HRMS (ESI-TOF⁺): m/z [M+H]⁺ calcd for $C_{28}H_{25}F_3N_5O$: 504.1012; found: 504.2011.

TBI-732, 5-(4-Trifluoromethylphenyl)-3-cyclohexylimino-2-(6-ethoxy-3-pyridyl)amino-3,5-dihydrophenazine:

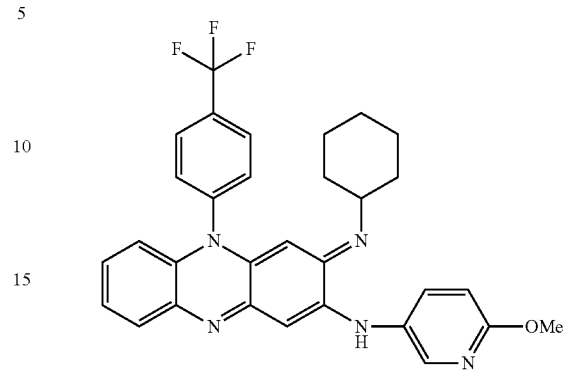

¹H NMR (300 MHz, CDCl₃) δ: 8.15 (s, 1H), 8.02 (d, J=8.0 Hz, 2H), 7.65 (m, 3H), 7.52 (d, J=8.0 Hz, 2H), 7.24~6.99 (m, 2H), 6.78 (d, J=8.7 Hz, 1H), 6.49 (s, 1H), 6.43 (d, J=8.2 Hz, 1H), 5.15 (s, 1H), 3.95 (s, 3H), 3.03 (m, 1H), 1.73 (d, J=11.0 Hz, 2H), 1.59 (d, J=11.5 Hz, 3H), 1.47~0.86 (m, 5H). ¹³C NMR (100 MHz, CDCl₃) δ: 161.2, 151.0, 150.5, 146.0, 142.5, 141.0, 135.6, 135.1, 134.5, 131.0, 130.1, 129.9, 128.5, 128.2, 127.3, 123.0, 113.6, 111.0, 98.0, 89.4, 58.1, 53.6, 33.6, 25.8, 24.6. HRMS (ESI-TOF⁺): m/z [M+H]⁺ calcd for $C_{31}H_{29}F_3N_5O$: 544.2322; found: 544.2324.

TBI-733, 5-(4-Trifluoromethylphenyl)-3-(4-tetrahydropyranyl)imino-2-(6-methoxy-3-pyridyl)amino-3,5-dihydrophenazine:

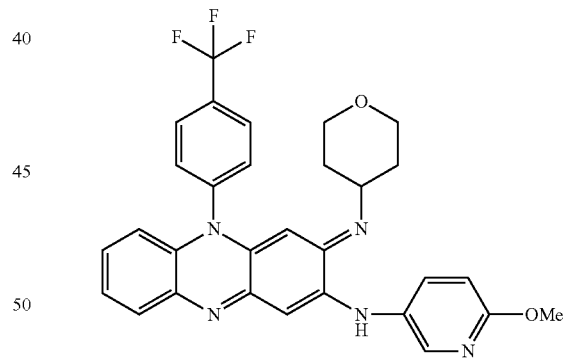

¹H NMR (300 MHz, CDCl₃) δ: 8.16 (d, J=2.3 Hz, 1H), 8.03 (d, J=8.2 Hz, 2H), 7.69 (dd, J=7.8, 1.4 Hz, 1H), 7.63 (dd, J=8.8, 2.7 Hz, 1H), 7.52 (d, J=8.2 Hz, 2H), 7.24~7.05 (m, 2H), 6.80 (d, J=8.8 Hz, 1H), 6.52 (s, 1H), 6.44 (dd, J=8.0, 1.1 Hz, 1H), 5.14 (s, 1H), 4.10~3.80 (m, 5H), 3.51~3.15 (m, 3H), 1.81~1.43 (m, 4H). ¹³C NMR (100 MHz, CDCl₃) δ: 161.4, 151.1, 150.7, 145.9, 142.6, 140.9, 135.6, 135.2, 134.7, 130.7, 129.9, 129.8, 128.5, 128.4, 128.3, 127.6, 123.3, 113.7, 111.1, 98.2, 89.0, 66.1, 54.6, 53.6, 33.4. HRMS (ESI-TOF⁺): m/z [M+H]⁺ calcd for $C_{30}H_{27}F_1N_5O_1$: 546.2114; found: 546.2117.

TBI-734, 5-(4-Trifluoromethylphenyl)-3-cyclobutyl-imino-2-(2-methyl-3-pyridyl)amino-3,5-dihydrophenazine:

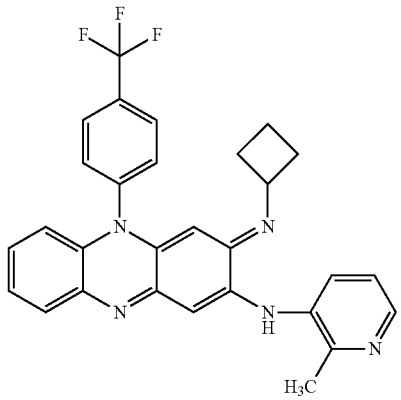 [SMILES: Cc1ncccc1Nc1cc2nc3ccccc3n(-c3ccc(C(F)(F)F)cc3)c-2c/c1=N\C1CCC1]

¹H NMR (300 MHz, CDCl₃) δ: 8.31 (d, J=4.5 Hz, 1H), 8.04 (d, J=8.0 Hz, 2H), 7.80 (d, J=8.0 Hz, 1H), 7.70 (d, J=7.7 Hz, 1H), 7.52 (d, J=7.9 Hz, 2H), 7.16 (m, 3H), 6.54 (s, 1H), 6.42 (d, J=7.9 Hz, 1H), 5.04 (s, 1H), 3.89 (p, J=7.8 Hz, 1H), 2.57 (s, 3H), 2.14 (m, 2H), 2.01 (m, 2H), 1.90~1.56 (m, 2H). ¹³C NMR (100 MHz, CDCl₃) δ: 152.7, 151.0, 150.8, 144.6, 144.3, 140.9, 135.6, 134.5, 134.2, 130.9, 129.9, 129.8, 128.5, 128.4, 127.7, 123.3, 121.7, 113.7, 99.0, 90.6, 54.8, 32.0, 21.0, 16.0. HRMS (ESI-TOF⁺): m/z [M+H]⁺ calcd for C₂₉H₂₅F₃N₅: 500.2063; found: 500.2062.

TBI-735, 5-(4-Trifluoromethylphenyl)-3-(4-methoxycyclohexyl)imino-2-(6-methoxy-3-pyridyl)amino-3,5-dihydrophenazine:

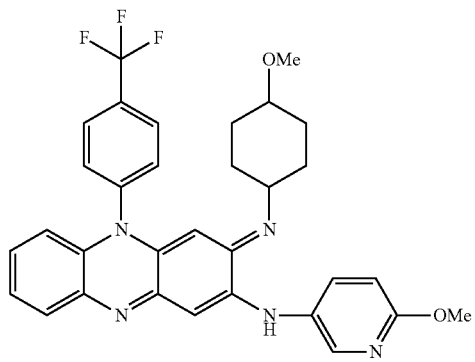 [SMILES: COc1ccc(Nc2cc3nc4ccccc4n(-c4ccc(C(F)(F)F)cc4)c-3c/c2=N\C2CCC(OC)CC2)cn1]

¹H NMR (300 MHz, CDCl₃) δ: 8.14 (d, J=2.3 Hz, 1H), 8.02 (d, J=8.3 Hz, 2H), 7.68 (dd, J=7.8, 1.4 Hz, 1H), 7.63 (dd, J=8.8, 2.8 Hz, 1H), 7.51 (d, J=8.1 Hz, 2H), 7.23~7.04 (m, 2H), 6.79 (d, J=8.8 Hz, 1H), 6.50 (s, 1H), 6.41 (dd, J=8.0, 1.1 Hz, 1H), 5.17 (s, 1H), 3.96 (s, 3H), 3.35 (s, 3H), 3.27~3.12 (m, 1H), 3.05 (dq, J=10.8, 5.9 Hz, 1H), 2.05 (m, 2H), 1.68 (m, 2H), 1.55~1.31 (m, 2H), 1.14 (m, 2H). ¹³C NMR (100 MHz, CDCl₃) δ: 161.3, 151.1, 150.8, 145.9, 142.5, 140.9, 135.6, 135.1, 134.6, 130.9, 130.0, 129.8, 128.5, 128.3, 127.5, 123.1, 113.7, 111.1, 98.7, 89.1, 78.5, 57.3, 55.7, 53.6, 31.1, 29.8.

TBI-736, 5-(4-Trifluoromethylphenyl)-3-cyclopropylimino-2-(6-methoxy-3-pyridyl)amino-3,5-dihydrophenazine:

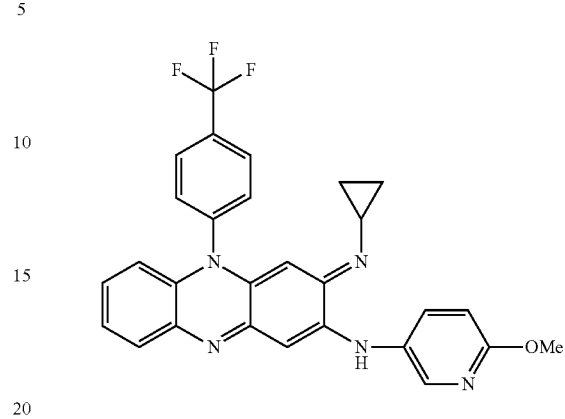

¹H NMR (300 MHz, CDCl₃) δ: 8.10 (brs, 1H), 8.01 (d, J=8.2 Hz, 2H), 7.62 (m, 2H), 7.53 (d, J=8.1 Hz, 2H), 7.12 (m, 2H), 6.77 (d, J=8.7 Hz, 1H), 6.43 (s, 1H), 6.34 (d, J=8.1 Hz, 1H), 5.48 (s, 1H), 3.95 (s, 3H), 2.84~2.57 (m, 1H), 0.88 (m, 2H), 0.80 (m, 2H). ¹³C NMR (100 MHz, CDCl₃) δ: 161.4, 152.4, 151.2, 145.8, 142.7, 141.0, 135.7, 135.4, 134.4, 131.1, 129.9, 128.6, 128.2, 127.4, 123.1, 113.6, 111.1, 98.1, 89.4, 53.6, 32.9, 9.9.

TBI-737, 5-(4-Trifluoromethylphenyl)-3-cyclobutyl-imino-2-(6-methoxy-3-pyridyl)amino-3,5-dihydrophenazine:

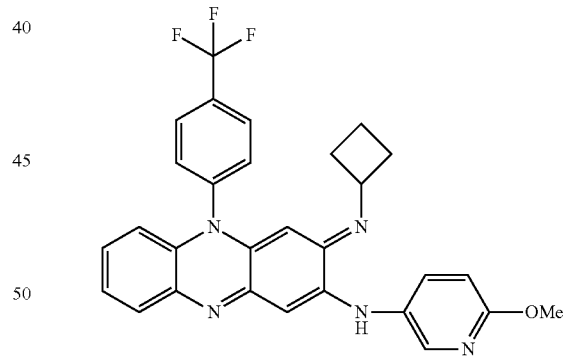

¹H NMR (300 MHz, CDCl₃) δ: 8.15 (d, J=2.5 Hz, 1H), 8.02 (d, J=8.3 Hz, 2H), 7.68 (d, J=7.7 Hz, 1H), 7.63 (dd, J=8.8, 2.7 Hz, 1H), 7.51 (d, J=8.1 Hz, 2H), 7.15 (m, 2H), 6.79 (d, J=8.7 Hz, 1H), 6.49 (s, 1H), 6.41 (d, J=8.1 Hz, 1H), 5.01 (s, 1H), 3.96 (s, 3H), 3.87 (p, J=7.6 Hz, 1H), 2.28~1.90 (m, 4H), 1.90~1.60 (m, 2H). ¹³C NMR (100 MHz, CDCl₃) δ: 161.4, 151.2, 150.9, 145.9, 142.6, 141.0, 135.7, 135.2, 134.1, 132.2, 131.8, 130.8, 129.9, 128.5, 128.3, 127.5, 123.2, 113.7, 111.1, 98.2, 90.6, 54.9, 53.6, 32.0, 16.0. HRMS (ESI-TOF⁺): m/z [M+H]⁺ calcd for C₂₉H₂₅F₃N₅O: 516.2009; found: 516.2011.

233

TBI-738, 5-(4-Trifluoromethylphenyl)-3-cyclobutyl-imino-2-(6-methyl-3-pyridyl)amino-3,5-dihydrophenazine:

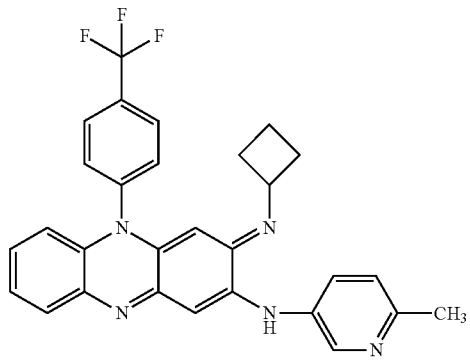 [SMILES: Cc1ccc(Nc2cc3nc4ccccc4n(-c4ccc(C(F)(F)F)cc4)c-3c/c2=N\C2CCC2)cn1]

$^1$H NMR (300 MHz, CDCl$_3$) δ: 8.46 (brs, 1H), 8.03 (d, J=7.8 Hz, 2H), 7.71~7.66 (m, 2H), 7.51 (d, J=8.1 Hz, 2H), 7.22~7.11 (m, 3H), 6.72 (s, 1H), 6.42 (d, J=8.1 Hz, 1H), 5.02 (s, 1H), 3.89~3.84 (m, 1H), 2.56 (s, 3H), 2.15~2.00 (m, 4H), 1.80~1.68 (m, 2H). $^{13}$C NMR (100 MHz, CDCl$_3$) δ: 153.6, 151.1, 150.9, 144.3, 143.9, 140.8, 135.7, 134.2, 133.9, 132.2, 131.9, 130.9, 129.9, 129.6, 128.5, 127.8, 123.2, 113.7, 98.9, 90.6, 54.8, 31.9, 23.8, 16.0.

TBI-739, 5-(2-Trifluoromethylphenyl)-3-(4-methoxycyclohexyl)imino-2-pyridyl)amino-3,5-dihydrophenazine:

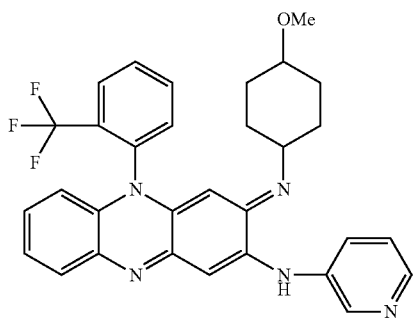 [SMILES: COC1CCC(/N=c2\cc3n(-c4ccccc4C(F)(F)F)c4ccccc4nc-3cc2Nc2cccnc2)CC1]

$^1$H NMR (300 MHz, CDCl$_3$) δ: 8.57 (d, J=2.5 Hz, 1H), 8.35~8.33 (dd, J=4.8, 1.2 Hz, 1H), 8.04 (d, J=7.6 Hz, 1H), 7.94 (t, J=7.3 Hz, 1H), 7.84~7.78 (m, 2H), 7.71 (dd, J=7.6, 1.6 Hz, 1H), 7.41 (d, J=7.7 Hz, 1H), 7.32~7.28 (dd, J=8.4, 4.8 Hz, 2H), 7.24~7.05 (m, 2H), 6.84 (s, 1H), 6.34 (d, J=8.7 Hz, 1H), 5.02 (s, 1H), 3.36 (s, 3H), 3.28~3.08 (m, 1H), 3.08~2.83 (m, 1H), 2.06 (d, J=10.2 Hz, 2H), 1.66 (brs, 2H), 1.55~1.23 (m, 2H), 1.23~0.94 (m, 2H). $^{13}$C NMR (100 MHz, CDCl$_3$) δ: 151.2, 150.8, 144.3, 144.0, 143.5, 136.7, 135.5, 135.3, 135.1, 134.9, 131.7, 131.5, 130.6, 129.8, 129.6, 128.9, 128.9, 128.3, 127.9, 127.8, 123.6, 123.1, 114.2, 99.6, 90.2, 78.5, 57.6, 55.9, 31.3, 30.9, 30.0. HRMS (ESI-TOF$^+$): m/z [M+H]$^+$ calcd for C$_{31}$H$_{29}$F$_3$N$_5$O: 544.2320; found: 544.2324.

234

TBI-740, 5-(3-Trifluoromethylphenyl)-3-(4-methoxycyclohexyl)imino-2-(3-pyridyl)amino-3,5-dihydrophenazine:

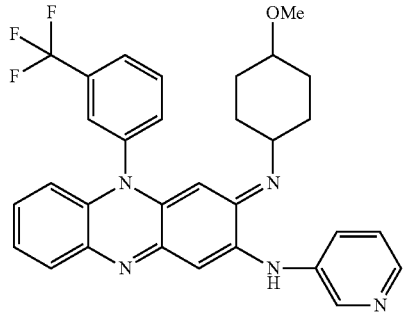 [SMILES: COC1CCC(/N=c2\cc3n(-c4cccc(C(F)(F)F)c4)c4ccccc4nc-3cc2Nc2cccnc2)CC1]

$^1$H NMR (300 MHz, CDCl$_3$) 8.58 (s, 1H), 8.34 (d, J=4.5 Hz, 1H), 7.95~7.87 (q, J=8.3 Hz, 2H), 7.79 (d, J=8.3 Hz, 1H), 7.72 (d, J=7.4 Hz, 1H), 7.67 (s, 1H), 7.60 (d, J=7.2 Hz, 1H), 7.41~7.28 (m, 2H), 7.25~7.08 (m, 2H), 6.84 (s, 1H), 6.48 (d, J=7.7 Hz, 1H), 5.14 (s, 1H), 3.35 (s, 3H), 3.28~3.09 (m, 1H), 3.09~2.86 (m, 1H), 2.07 (d, J=12.3 Hz, 2H), 1.72~1.61 (m, 2H), 1.57~1.25 (m, 2H), 1.25~0.94 (m, 2H). $^{13}$C NMR (125 MHz, CDCl$_3$) δ: 151.1, 150.9, 144.4, 144.0, 143.6, 138.2, 136.7, 135.6, 134.8, 134.3, 134.0, 132.7, 132.1, 131.1, 128.5, 128.0, 126.6, 126.3, 123.6, 123.3, 113.7, 99.6, 89.3, 78.5, 57.6, 55.8, 31.5, 30.9, 30.1, 29.8. HRMS (ESI-TOF$^+$): m/z [M+H]$^+$ calcd for C$_{31}$H$_{29}$F$_3$N$_5$O: 544.2325; found: 544.2324.

TBI-741, 5-(4-Chlorophenyl)-3-(1-methylethyl)imino-2-(2-methoxy-3-pyridyl)amino-7-fluoro-3,5-dihydrophenazine

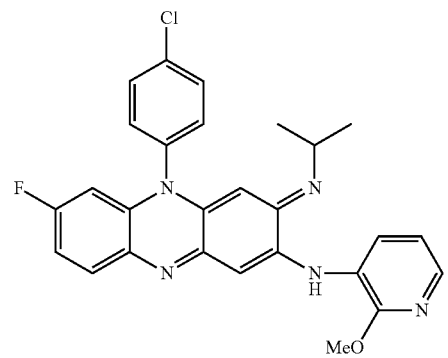 [SMILES: COc1ncccc1Nc1cc2nc3ccc(F)cc3n(-c3ccc(Cl)cc3)c-2c/c1=N\C(C)C]

$^1$H NMR (300 MHz, CDCl$_3$) δ: 8.89 (brs, 1H), 7.84~7.81 (m, 2H), 7.72 (d, J=8.4 Hz, 2H), 7.66~7.61 (dd, J=8.7, 6.0 Hz, 1H), 7.29 (d, i=8.4 Hz, 2H), 6.93~6.84 (m, 3H), 6.14~6.10 (dd, J=10.8, 2.7 Hz, 1H), 5.30 (s, 1H), 4.04 (s, 3H), 3.51~3.42 (m, 1H), 1.11 (d, J=6.3 Hz, 6H). HRMS (ESI-TOF$^+$): m/z [M+H]$^+$ calcd for C$_{27}$H$_{24}$ClFN$_5$O: 488.1654; found: 488.1653.

TBI-744, 5-(4-Trifluoromethylphenyl)-2,3-dimethoxy-1-propyl)imino-2-(2-methoxy-3-pyridyl)amino-3,5-dihydrophenazine:

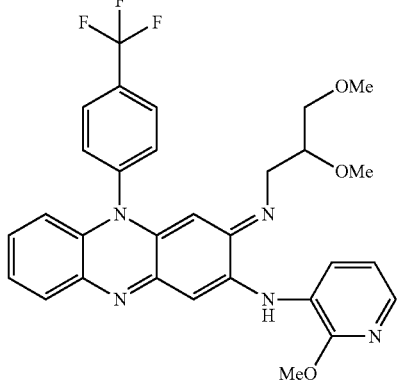

¹H NMR (300 MHz, CDCl₃) δ: 8.91 (s, 1H), 8.01 (d, J=8.1, 2 H), 7.87~7.82 (m, 2H), 7.74 (d, J=7.5, 1H), 7.51 (d, J=8.1, 2 H), 7.26~7.15 (m, 2H), 6.99 (s, 1H), 6.99~6.91 (dd, J=7.2, J=4.5, 1H), 6.38 (d, J=7.8, 1H), 5.23 (s, 1H), 4.03 (s, 3H), 3.68~3.64 (m, 2H), 3.58~3.55 (m, 1H), 3.46 (s, 3H), 3.38 (s, 3H), 3.28~3.24 (m, 2H). ¹³C NMR (125 MHz, CDCl₃) 155.3, 153.2, 150.9, 142.5, 140.7, 138.8, 135.6, 134.6, 131.1, 129.7, 128.8, 128.4, 128.0, 124.8, 124.5, 123.4, 116.9, 113.9, 100.1, 89.3, 81.0, 73.2, 59.3, 57.9, 53.7, 50.5.

TBI-422, 5-(4-Chlorophenyl)-3-cyclohexylimino-2-(3-pyridyl)amino-3,5-dihydrophenazine:

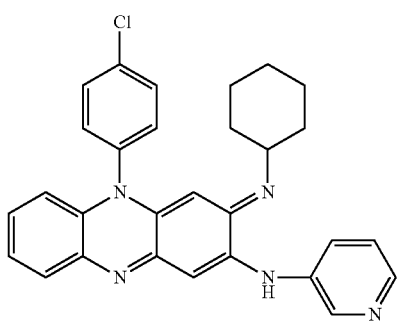

mp: 194-196° C. ¹H NMR (300 MHz, CDCl₃) δ: 8.58 (d, J=2.7 Hz, 1H), 8.33 (d=4.5 Hz, 1H), 7.80-7.76 (m, 1H, 7.73-7.67 (m, 3H), 7.32-7.26 (m, 3H), 7.19-7.13 (m, 2H), 6.83 (d, J=1.2 Hz, 1H), 6.49-6.46 (m, 1H), 5.26 (s, 1H), 3.10 (m, 1H), 1.76-1.73 (m, 2H), 1.64-1.59 (m, 3H), 1.40-1.37 (m, 2H), 1.26-1.22 (m, 3H). ¹³C NMR (100 MHz, CDCl₃) δ: 151.0, 150.4, 144.2, 143.9, 143.7, 136.8, 136.0, 135.7, 135.6, 134.8, 131.6, 131.5, 130.4, 128.3, 127.8, 127.7, 123.6, 123.0, 113.8, 99.4, 89.3, 57.8, 33.6, 25.8, 24.6, HRMS (ESI-TOF⁺): m/z [M+H]⁺ calcd for C₂₉H₂₇ClN₅: 480.1955; found: 480.1953.

TBI-427, 5-(4-Chlorophenyl)-3-(N-methyl-4-piperidyl)imino-2-(3-pyridyl)amino-3,5-dihydrophenazine:

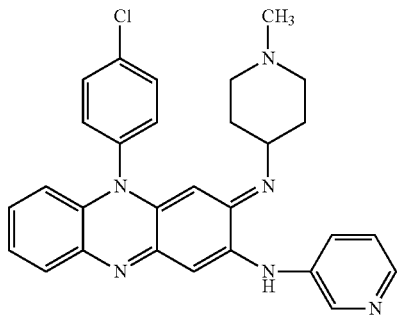 [SMILES: CN1CCC(/N=c2\cc3n(-c4ccc(Cl)cc4)c4ccccc4nc-3cc2Nc2cccnc2)CC1]

mp: 198-200° C. ¹H NMR (300 MHz, CDCl₃) δ: 8.60 (d, J=2.4 Hz, 1H), 8.35 (d, J=5.1 Hz, 1H), 7.80-7.77 (m, 1H), 7.74-7.70 (m, 3H), 7.33-7.29 (m, 3H), 7.22-7.13 (m, 2H), 6.85 (s, 1H), 6.49 (d, J=7.5 Hz, 1H), 5.25 (s, 1H), 3.15-3.13 (m, 1H), 2.81-2.77 (m, 2H), 2.30 (s, 3H), 2.04 (m, 2H), 1.68 (m, 4H). ¹³C NMR (100 MHz, CDCl₃) δ: 151.0, 144.4, 144.0, 143.6, 136.7, 136.0, 135.8, 134.9, 131.7, 130.3, 128.4, 127.9, 123.7, 123.2, 114.0, 99.5, 89.1, 53.9, 46.4, 32.7. HRMS (ESI-TOF⁺): m/z [M+H]⁺ calcd for C₂₉H₂₈ClN₆: 495.2058; found: 495.2057.

TBI-428, 5-(4-Chlorophenyl)-3-(N-methyl-4-piperidylmethyl)imino-2-(3-pyridyl)amino-3,5-dihydrophenazine:

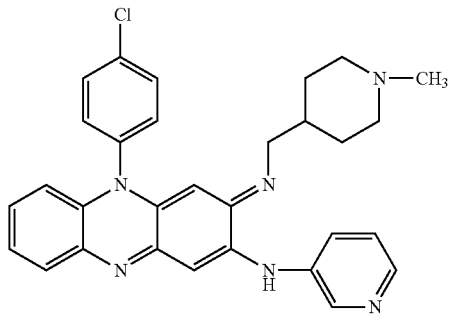 [SMILES: CN1CCC(C/N=c2\cc3n(-c4ccc(Cl)cc4)c4ccccc4nc-3cc2Nc2cccnc2)CC1]

mp: 188-190° C., ¹H NMR (300 MHz, CDCl₃) δ: 8.58 (d, J=2.4 Hz, 1H), 8.35 (dd, J=4.5 Hz, 1.2 Hz, 1H), 7.79-7.76 (m, 1H), 7.73-7.70 (m, 3H), 7.33-7.28 (m, 3H), 7.22-7.12 (m, 2H), 6.83 (s 1H), 6.46 (d, J=7.8 Hz, 1H), 5.27 (s, 1H), 3.05 (d, J=11.4 Hz, 2H), 2.87 (d, J=11.4 Hz, 2H), 2.28 (s, 3H), 1.98-1.90 (m, 2H), 1.76-1.63 (m, 3H), 1.43-1.34 (m, 2H). ¹³C NMR (100 MHz, CDCl₃) δ: 152.2, 150.9, 144.4, 144.1, 143.6, 136.7, 135.9, 135.8, 135.6, 134.8, 131.8, 131.5, 130.2, 128.4, 128.2, 127.9, 125.0, 123.7, 123.1, 114.0, 99.3, 89.0, 55.9, 50.7, 46.5, 37.1, 30.8. HRMS (ESI-TOF⁺): m/z [M+H]⁺ calcd for C₃₀H₃₀ClN₆: 509.2215; found: 509.2219.

TBI-433, 5-(4-Chlorophenyl)-3-(2-morpholinoethyl)imino-2-(3-pyridyl)amino-3,5-dihydrophenazine:

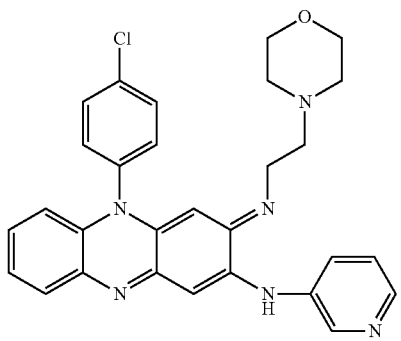 [SMILES: Clc1ccc(-n2c3c/c(=N\CCN4CCOCC4)c(Nc4cccnc4)cc-3nc3ccccc32)cc1]

mp: 116-118° C. $^1$H NMR (300 MHz, CDCl$_3$) δ: 8.60 (s, 1H), 8.35 (d, J=3.6 Hz, 1H), 7.80-7.77 (m, 1H), 7.74-7.71 (m, 3H), 7.33-7.29 (m, 3H), 7.23-7.21 (m, 2H), 6.89 (s, 1H), 6.51 (m, 1H), 5.30 (s, 1H), 3.74-3.71 (m, 4H), 3.36 (t, J=7.2 Hz, 2H), 2.71 (t, J=7.2 Hz, 2H), 2.50-2.47 (m, 4H). $^{13}$C NMR (100 MHz, CDCl$_3$) δ: 152.8, 144.5, 144.0, 143.4, 136.6, 135.8, 135.0, 131.9, 131.2, 130.2, 128.5, 128.1, 123.7, 114.2, 99.6, 89.0, 66.9, 59.8, 54.1, 47.8, HRMS (ESI-TOF$^+$): m/z [M+H]$^+$ calcd for C$_{29}$H$_{28}$ClN$_6$O: 511.2013; found: 511.2014.

TBI-434, 5-(4-Chlorophenyl)-3-(4-tetrahydropyranyl)imino-2-(3-pyridyl)amino-3,5-dihydrophenazine:

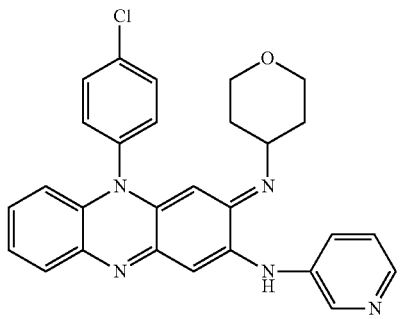

mp: 215-217° C. $^1$H NMR (300 MHz, CDCl$_3$) δ: 8.61 (d, J=1.8 Hz, 1H), 8.36 (d, J=3.9 Hz, 1H), 7.80-7.77 (m, 1H), 7.74-7.72 (m, 3H), 7.34-7.29 (m, 3H), 7.24-7.14 (m, 2H), 6.87 (s, 1H), 6.50 (d, J=7.1 Hz, 1H), 5.26 (s, 1H), 4.01-3.97 (m, 2H), 3.49-3.37 (m, 3H), 1.73-1.65 (m, 4H). $^{13}$C NMR (100 MHz, CDCl$_3$) δ: 151.1, 150.7, 144.5, 144.0, 143.6, 136.6, 135.9, 135.8, 135.7, 135.0, 131.7, 131.3, 130.3, 128.5, 128.1, 128.0, 123.7, 123.2, 114.0, 99.6, 88.9, 66.1, 54.3, 33.4, HRMS (ESI-TOF$^+$): m/z [M+H]$^+$ calcd for C$_{28}$H$_{25}$ClN$_5$O: 482.1742; found: 482.1741.

TBI-435, 5-(4-Chlorophenyl)-3-(N-isobutyl-4-piperidyl)imino-2-(3-pyridyl)amino-3,5-dihydrophenazine:

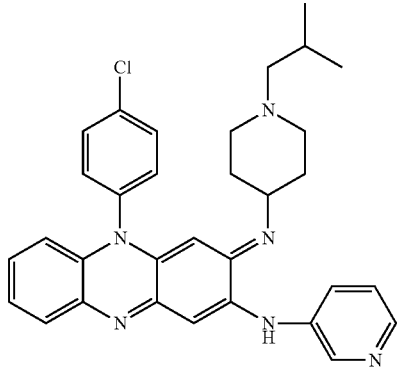

mp: 209-210° C. $^1$H NMR (300 MHz, CDCl$_3$) δ: 8.59 (m, 1H), 8.34 (d, J=4.8 Hz, 1H), 7.80-7.76 (m, 1H), 7.73-7.71 (m, 3H), 7.32-7.29 (m, 3H), 7.19-7.12 (m, 2H), 6.85 (s, 1H), 6.48 (d, J=7.8 Hz, 1H), 5.26 (s, 1H), 3.14 (m, 1H), 2.80-2.77 (m, 2H), 2.09-2.05 (m, 2H), 1.96-1.93 (m, 2H), 1.82-1.63 (m, 5H), 0.90 (d, J=6.6 Hz, 6H). $^{13}$C NMR (100 MHz, CDCl$_3$) 150.8, 144.3, 143.9, 143.6, 136.8, 136.0, 135.6, 134.9, 131.6, 130.4, 128.4, 127.8, 123.6, 123.1, 113.9, 99.5, 89.2, 67.1, 55.9, 52.4, 32.9, 25.7, 21.0. HRMS (ESI-TOF$^+$): m/z [M+H]$^+$ calcd for C$_{32}$H$_{34}$ClN$_6$: 537.2533; found: 537.2546.

TBI-436, 5-(4-Chlorophenyl)-3-(4-methoxycyclohexyl)imino-2-(3-pyridyl)amino-3,5-dihydrophenazine:

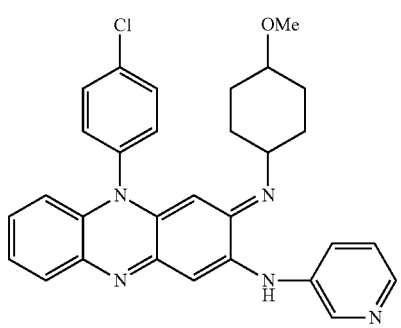

mp: 228-230° C. $^1$H NMR (300 MHz, CDCl$_3$) δ: 8.58 (d, J=2.4 Hz, 1H), 8.34 (d, J=3.6 Hz, 1H), 7.80-7.77 (m, 1H), 7.72-7.69 (m, 3H), 7.32-7.28 (m, 3H), 7.22-7.13 (m, 2H), 6.84 (s, 1H), 6.50-6.47 (m, 1H), 5.27 (s, 1H), 3.37 (s, 3H), 3.24-3.08 (m, 2H), 2.10-2.06 (m, 2H), 1.72-1.69 (m, 2H), 1.48-1.38 (m, 2H), 1.26-1.15 (m, 2H). $^{13}$C NMR (100 MHz, CDCl$_3$) δ: 151.1, 144.4, 144.0, 143.6, 136.7, 135.9, 135.6, 134.9, 131.6, 130.3, 128.4, 127.9, 123.6, 123.1, 113.9, 99.5, 89.1, 78.5, 57.3, 55.8, 31.1, 29.9, HRMS (ESI-TOF$^+$): m/z [M+H]$^+$ calcd for C$_{30}$H$_{29}$ClN$_5$O: 510.2060; found: 510.2069.

TBI-437, 5-(4-Chlorophenyl)-3-(N-cyclopentyl-4-piperidyl)imino-2-(3-pyridyl)amino-3,5-dihydrophenazine:

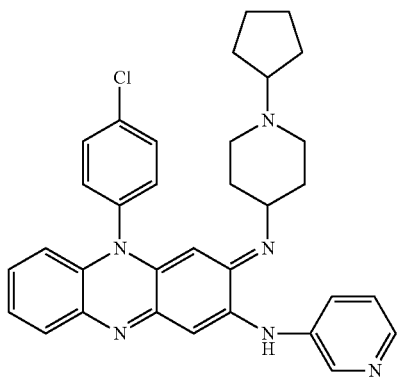

mp: 170-172° C. $^1$H NMR (300 MHz, CDCl$_3$) δ: 8.58 (d, J=2.4 Hz, 1H), 8.35 (d, J=4.2 Hz, 1H), 7.79-7.76 (m, 1H), 7.74-7.71 (m, 3H), 7.33-7.29 (m, 3H), 7.23-7.14 (m, 2H), 6.86 (s, 1H), 6.50 (d, J=7.8 Hz, 1H), 5.26 (s, 1H), 3.20 (m, 1H), 2.97 (m, 2H), 2.52 (m, 1H), 2.05 (m, 2H), 1.90 (m, 2H), 1.71 (m, 4H), 1.55 (m, 6H). $^{13}$C NMR (100 MHz, CDCl$_3$) δ: 150.9, 144.4, 144.0, 143.6, 136.7, 136.0, 134.9, 131.7, 130.4, 128.4, 127.9, 123.7, 123.1, 113.9, 99.5, 89.1, 67.7, 55.4, 50.8, 32.8, 30.7, 24.2. HRMS (ESI-TOF$^+$): m/z [M+H]$^+$ calcd for C$_{33}$H$_{34}$ClN$_6$: 549.2527; found: 549.2527.

TBI-438, 5-(4-Chlorophenyl)-3-(1-methylethyl)imino-2-(2-methoxy-3-pyridyl)amino-3,5-dihydrophenazine:

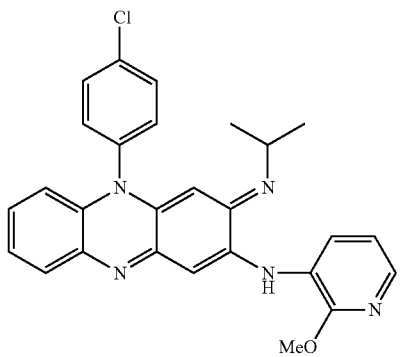

$^1$H NMR (300 MHz, CDCl$_3$) δ: 8.94 (brs, 1H), 7.86-7.81 (m, 2H), 7.72-7.67 (m, 3H), 7.30 (d, J=8.4 Hz, 2H), 7.19-7.09 (m, 2H), 6.93-6.89 (m, 2H), 6.44 (dd, J=7.5 Hz, 1.5 Hz, 1H), 5.28 (s, 1H), 4.04 (s, 3H), 3.51-3.42 (m, 1H), 1.11 (d, J=6.3 Hz, 6H). $^{13}$C NMR (125 MHz, CDCl$_3$) δ: 155.5, 151.3, 150.6, 143.0, 138.9, 136.1, 135.7, 134.8, 131.7, 130.5, 128.2, 127.6, 124.9, 122.9, 116.8, 113.8, 100.1, 89.3, 53.7, 49.4, 23.6.

TBI-439, 5-(4-Chlorophenyl)-3-(2-morpholinoethyl)imino-2-(2-methoxy-3-pyridyl)amino-3,5-dihydrophenazine:

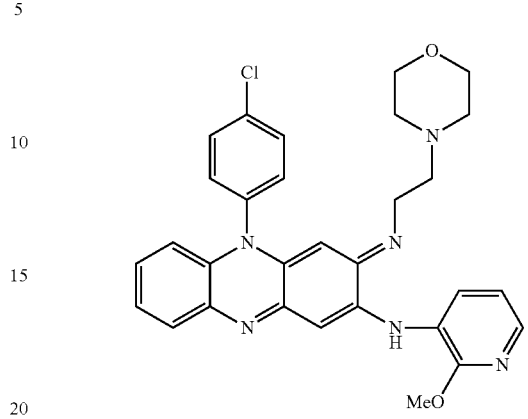

$^1$H NMR (300 MHz, CDCl$_3$) δ: 8.83 (brs, 1H), 7.87-7.82 (m, 2H), 7.74-7.69 (m, 3H), 7.30 (d, J=8.4 Hz, 2H), 7.21-7.13 (m, 2H), 6.97 (s, 1H), 6.93 (dd, J=7.8 Hz, 4.5 Hz, 1H), 6.47 (dd, J=7.5 Hz, 1.5 Hz, 1H), 5.26 (s, 1H), 4.04 (s, 3H), 3.73 (t, 14.5 Hz, 4H), 3.36 (t, J=6.9 Hz, 2H), 2.75 (t, J=7.2 Hz, 2H), 2.54 (t, J=4.5 Hz, 4H). $^{13}$C NMR (125 MHz, CDCl$_3$) δ: 155.3, 152.9, 151.0, 142.6, 138.9, 136.0, 135.8, 135.7, 134.9, 131.8, 131.5, 130.3, 128.4, 127.9, 124.8, 123.2, 116.8, 114.0, 100.2, 89.2, 67.0, 59.8, 54.3, 53.7, 48.5.

TBI-440, 5-(4-Chlorophenyl)-3-(N-methyl-4-piperidyl)imino-2-(2-methoxy-3-pyridyl)amino-3,5-dihydrophenazine:

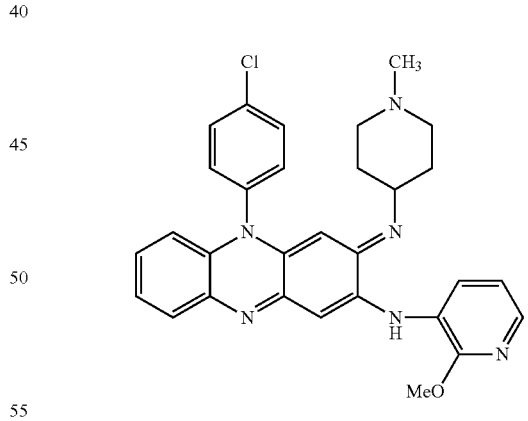

$^1$H NMR (300 MHz, CDCl$_3$) δ: 9.13 (brs, 1H), 7.86-7.79 (m, 2H), 7.73-7.70 (m, 3H), 7.30 (d, J=8.4 Hz, 2H), 7.21-7.11 (m, 2H), 6.96 (s, 1H), 6.92 (dd, J=8.1 Hz, 5.4 Hz, 1H), 6.46 (dd, J=8.1 Hz, 1.5 Hz, 1H), 5.25 (s, 1H), 4.04 (s, 3H), 3.23 (m, 1H), 2.78-2.75 (m, 2H), 2.31 (s, 3H), 2.16 (m, 2H), 1.71-1.66 (m, 4H). $^{13}$C NMR (125 MHz, CDCl$_3$) 155.3, 151.2, 150.9, 142.6, 138.6, 136.0, 135.7, 135.6, 134.9, 131.7, 131.5, 130.4, 128.3, 127.7, 125.0, 124.1, 123.0, 116.8, 113.9, 100.2, 89.1, 53.7, 53.4, 46.6, 32.7.

241

TBI-441, 5-(4-Chlorophenyl)-3-(1-methylethyl)imino-2-(6-ethyl-3-pyridyl)amino-3,5-dihydrophenazine:

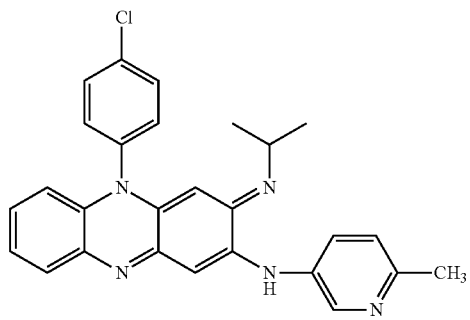

$^1$H NMR (300 MHz, CDCl$_3$) δ: 8.45 (s, 1H), 7.71-7.66 (m, 3H), 7.29 (d, J=8.4 Hz, 2H), 7.25 (m, 1H), 7.19-7.09 (m, 3H), 6.70 (s, 1H), 6.44 (d, J=7.5 Hz, 1H), 5.28 (s, 1H), 3.51-3.42 (m, 1H), 2.55 (s, 3H), 1.10 (d, J=6.3 Hz, 6H). $^{13}$C NMR (125 MHz, CDCl$_3$) δ: 153.4, 151.0, 150.4, 144.5, 143.9, 136.1, 135.7, 135.6, 134.8, 134.1, 131.7, 131.5, 130.4, 129.5, 128.3, 127.5, 123.2, 122.9, 113.8, 98.9, 89.1, 49.4, 23.8, 23.6.

TBI-442, 5-(4-Chlorophenyl)-3-(N-isobutyl-4-piperidyl)imino-2-(2-methoxy-3-pyridyl)amino-3,5-dihydrophenazine:

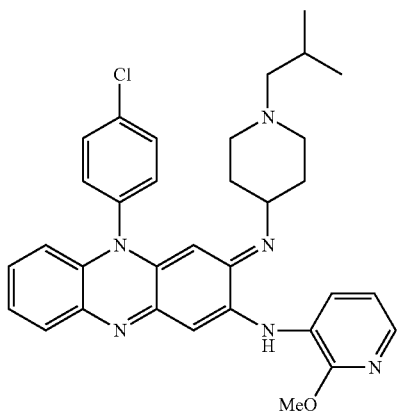

$^1$H NMR (300 MHz, CDCl$_3$) δ: 9.06 (brs, 1H), 7.86-7.79 (m, 2H), 7.73-7.69 (m, 3H), 7.30 (d, J=8.4 Hz, 2H), 7.20-7.11 (m, 2H), 6.95 (s, 1H), 6.91 (dd, J=7.8 Hz, 5.1 Hz, 1H), 6.46 (dd, J=7.8 Hz, 1.8 Hz, 1H), 5.25 (s, 1H), 4.04 (s, 3H), 3.21-3.17 (m, 1H), 2.79-2.75 (m, 2H), 2.11-2.05 (m, 4H), 1.84-1.64 (m, 5H), 0.91 (d, J=6.3 Hz, 6H). $^{13}$C NMR (125 MHz, CDCl$_3$) δ: 155.3, 151.2, 150.9, 142.7, 138.6, 136.1, 135.7, 134.9, 131.6, 131.5, 130.4, 128.3, 127.7, 125.0, 124.3, 123.0, 116.8, 113.8, 100.2, 89.2, 71.1, 67.4, 55.1, 53.7, 52.0, 32.8, 25.7, 21.1.

242

TBI-443, 5-(4-chlorophenyl)-3-(4-tetrahydropyranyl)imino-2-(2-methoxy-3-pyridyl)amino-3,5-dihydrophenazine:

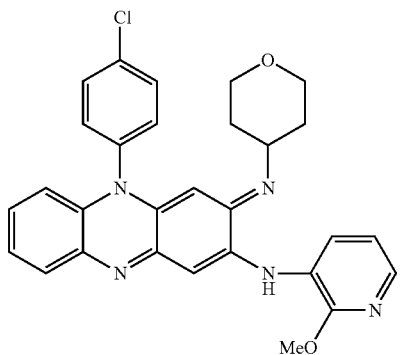

$^1$H NMR (300 MHz, CDCl$_3$) δ: 9.09 (brs, 1H), 7.86-7.81 (m, 2H), 7.73-7.70 (m, 3H), 7.30 (d, J=8.4 Hz, 2H), 7.22-7.12 (m, 2H), 6.97 (s, 1H), 6.92 (dd, J=7.8 Hz, 5.4 Hz, 1H), 6.46 (dd, J=7.8 Hz, 1.2 Hz, 1H), 5.25 (s, 1H), 4.04 (s, 3H), 4.02-3.99 (m, 2H), 3.55-3.42 (m, 3H), 1.75-1.57 (m, 4H). $^{13}$C NMR (125 MHz, CDCl$_3$) δ: 155.3, 151.1, 151.0, 142.6, 138.7, 136.0, 135.8, 135.0, 131.7, 131.4, 130.4, 128.3, 127.8, 124.9, 124.3, 123.1, 116.8, 113.9, 100.3, 89.0, 65.5, 53.7, 53.3, 33.3.

TBI-444, 5-(4-Chlorophenyl)-3-(4-methoxycyclohexyl)imino-2-(2-methoxy-3-pyridyl)amino-3,5-dihydrophenazine:

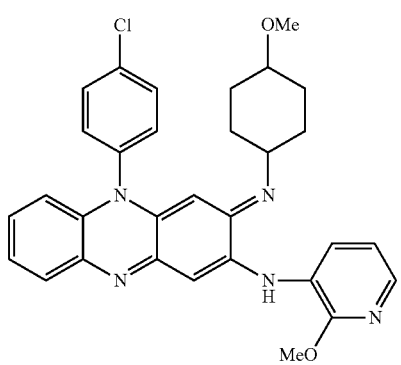 [SMILES: COc1ncccc1Nc1cc2nc3ccccc3n(-c3ccc(Cl)cc3)c-2c/c1=N\C1CCC(OC)CC1]

$^1$H NMR (300 MHz, CDCl$_3$) δ: 8.97 (brs, 1H), 7.86-7.80 (m, 2H), 7.71-7.69 (m, 3H), 7.29 (d, J=8.4 Hz, 2H), 7.20-7.11 (m, 2H), 6.94 (s, 1H), 6.92 (dd, J=7.5 Hz, 4.8 Hz, 1H), 6.47 (d, J=7.5 Hz, 1H), 5.30 (s, 1H), 4.03 (s, 3H), 3.37 (s, 3H), 3.28-3.22 (m, 1H), 3.17-3.14 (m, 1H), 2.10-2.07 (m, 2H), 1.74-1.71 (m, 2H), 1.49-1.39 (m, 2H), 1.31-1.20 (m, 2H). $^{13}$C NMR (125 MHz, CDCl$_3$) δ: 151.2, 142.8, 138.8, 135.7, 131.6, 130.4, 128.3, 127.7, 124.9, 124.7, 123.0, 116.8, 113.9, 100.3, 89.3, 56.8, 55.8, 53.7, 30.7, 29.4.

TBI-445, 5-(4-Chlorophenyl)-3-(2-morpholinoethyl)imino-2-(6-methyl-3-pyridyl)amino-3,5-dihydrophenazine:

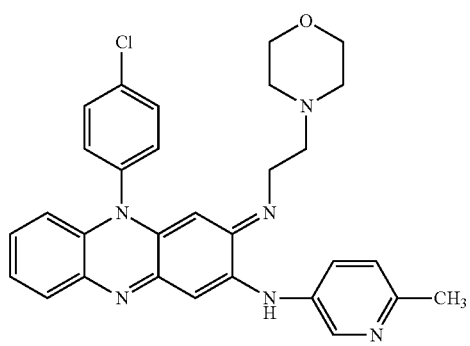 [SMILES: Cc1ccc(Nc2cc3nc4ccccc4n(-c4ccc(Cl)cc4)c-3c/c2=N\CCN2CCOCC2)cn1]

$^1$H NMR (300 MHz, CDCl$_3$) δ: 8.45 (s, 1H), 7.73-7.66 (m, 3H), 7.30 (d, J=8.1 Hz, 2H), 7.25 (m, 1H), 7.19-7.16 (m, 3H), 6.74 (s, 1H), 6.47 (d, J=6.9 Hz, 1H), 5.28 (s, 1H), 3.72 (t, J=4.5 Hz, 4H), 3.36 (t, J=7.2 Hz, 2H), 2.71 (t, J=7.5 Hz, 2H), 2.57 (s, 3H), 2.48 (t, J=4.2 Hz, 4H). $^{13}$C NMR (125 MHz, CDCl$_3$) δ: 152.9, 150.7, 143.8, 136.0, 134.9, 133.9, 131.9, 130.3, 129.5, 128.4, 127.8, 123.2, 114.1, 99.0, 89.0, 67.0, 59.8, 54.1, 47.9, 23.9.

TBI-446, 5-(4-Chlorophenyl)-3-(N-methyl-4-piperidyl)imino-2-(6-methyl-3-pyridyl)amino-3,5-dihydrophenazine:

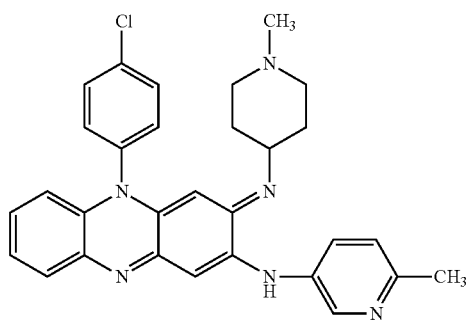 [SMILES: Cc1ccc(Nc2cc3nc4ccccc4n(-c4ccc(Cl)cc4)c-3c/c2=N\C2CCN(C)CC2)cn1]

$^1$H NMR (300 MHz, CDCl$_3$) δ: 8.45 (d, J=2.7 Hz, 1H), 7.73-7.66 (m, 3H), 7.30 (d, J=8.4 Hz, 2H), 7.25 (m, 1H), 7.21-7.12 (m, 3H), 6.73 (s, 1H), 6.48 (d, J=7.8 Hz, 1H), 5.24 (s, 1H), 3.14-3.13 (m, 1H), 2.81-2.77 (m, 2H), 2.56 (s, 3H), 2.30 (s, 3H), 2.05 (m, 2H), 1.68 (m, 4H). $^{13}$C NMR (125 MHz, CDCl$_3$) δ: 153.5, 151.1, 144.4, 143.8, 136.0, 135.8, 134.9, 134.0, 131.6, 131.3, 130.4, 129.6, 128.4, 127.7, 123.2, 114.0, 99.0, 89.1, 53.9, 46.4, 32.7, 23.8.

TBI-447, 5-(4-Chlorophenyl)-3-(N-isobutyl-4-piperidyl)imino-2-(6-methyl-3-pyridyl)amino-3,5-dihydrophenazine:

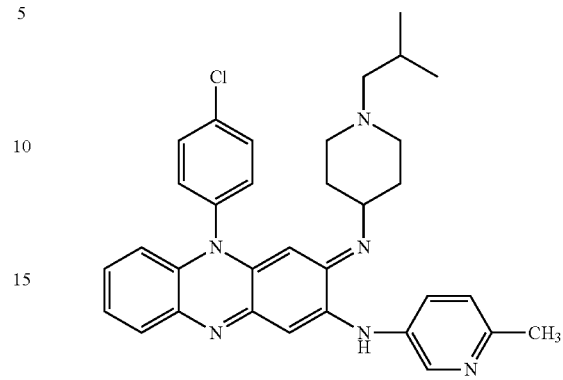

$^1$H NMR (300 MHz, CDCl$_3$) δ: 8.45 (d, J=2.1 Hz, 1H), 7.73-7.66 (m, 3H), 7.30 (d, J=8.4 Hz, 2H), 7.25 (m, 1H), 7.20-7.11 (m, 3H), 6.72 (s, 1H), 6.47 (d, J=7.5 Hz, 1H), 5.25 (s, 1H), 3.14-3.11 (m, 1H), 2.80-2.77 (m, 2H), 2.56 (s, 3H), 2.08-2.05 (m, 2H), 1.98-1.92 (m, 2H), 1.81-1.62 (m, 5H), 0.90 (d, J=6.9 Hz, 6H). $^{13}$C NMR (125 MHz, CDCl$_3$) δ: 153.4, 151.0, 150.9, 144.4, 143.8, 136.1, 135.7, 134.8, 134.1, 131.6, 131.4, 130.4, 129.4, 128.3, 127.6, 123.2, 123.0, 113.9, 98.9, 89.2, 67.1, 56.0, 52.4, 32.9, 25.7, 23.8, 21.0.

TBI-448, 5-(4-Chlorophenyl)-3-(1-methylethyl)imino-2-(2-methyl-3-pyridyl)amino-3,5-dihydrophenazine:

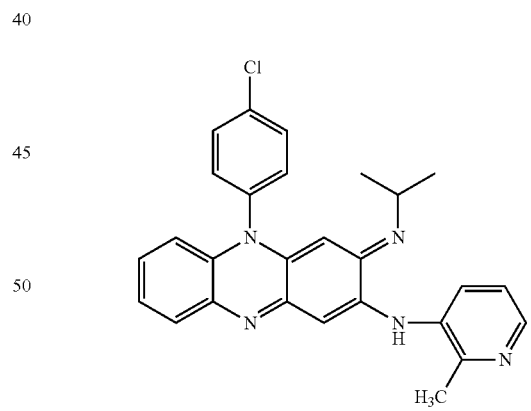

$^1$H NMR (300 MHz, CDCl$_3$) δ: 8.28 (d, J=3.6 Hz, 1H), 7.81 (d, J=7.2 Hz, 1H), 7.73-7.66 (m, 3H), 7.31 (d, J=8.4 Hz, 2H), 7.20-7.10 (m, 3H), 6.58 (s, 1H), 6.45 (d, J=7.2 Hz, 1H), 5.29 (s, 1H), 3.53-3.45 (m, 1H), 2.55 (s, 3H), 1.11 (d, J=6.3 Hz, 6H). $^{13}$C NMR (100 MHz, CDCl$_3$) δ: 152.3, 151.0, 150.3, 144.2, 136.1, 135.7, 135.6, 134.9, 134.7, 131.7, 131.4, 130.4, 129.2, 128.2, 127.6, 123.0, 121.6, 113.8, 98.8, 89.0, 67.1, 49.3, 23.6, 20.9.

TBI-449, 5-(4-Chlorophenyl)-3-(4-tetrahydropyranyl)imino-2-(6-methyl-3-pyridyl)amino-3,5-dihydrophenazine:

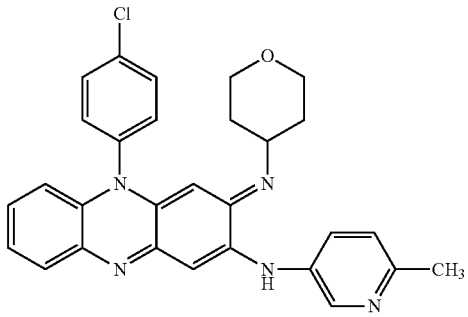 [SMILES: Cc1ccc(Nc2cc3nc4ccccc4n(-c4ccc(Cl)cc4)c-3c/c2=N\C2CCOCC2)cn1]

¹H NMR (300 MHz, CDCl₃) δ: 8.46 (d, J=2.4 Hz, 1H), 7.73-7.66 (m, 3H), 7.30 (d, J=8.4 Hz, 2H), 7.25 (m, 1H), 7.20-7.14 (m, 3H), 6.74 (s, 1H), 6.48 (dd, J=7.8 Hz, 1.5 Hz, 1H), 5.25 (s, 1H), 4.02-3.95 (m, 2H), 3.48-3.37 (m, 3H), 2.57 (s, 3H), 1.69-1.62 (m, 4H). ¹³C NMR (100 MHz, CDCl₃) δ: 153.6, 151.1, 150.7, 144.4, 143.8, 136.0, 135.8, 135.7, 135.0, 134.0, 131.6, 131.3, 130.3, 129.6, 128.4, 127.7, 123.2, 123.1, 113.9, 99.0, 89.0, 66.1, 54.3, 33.4, 23.8.

TBI-450, 5-(4-Chlorophenyl)-3-(4-methoxycyclohexyl)imino-2-(6-methyl-3-pyridyl)amino-3,5-dihydrophenazine:

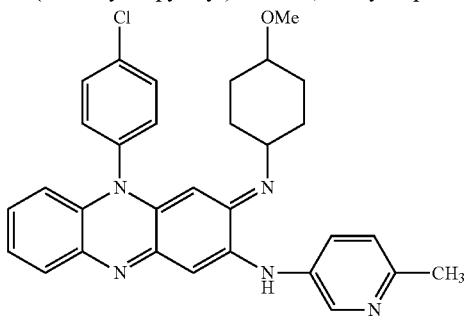

¹H NMR (300 MHz, CDCl₃) δ: 8.44 (d, J=2.4 Hz, 1H), 7.72-7.67 (m, 3H), 7.29 (d, J=8.7 Hz, 2H), 7.25 (m, 1H), 7.20-7.11 (m, 3H), 6.72 (s, 1H), 6.48 (d, J=7.5 Hz, 1H), 5.26 (s, 1H), 3.71 (s, 3H), 3.37-3.15 (m, 1H), 3.14-3.07 (m, 1H), 2.56 (s, 3H), 2.10-2.06 (m, 2H), 1.72-1.69 (m, 2H), 1.49-1.38 (m, 2H), 1.25-1.14 (m, 2H). ¹³C NMR (100 MHz, CDCl₃) δ: 153.4, 151.1, 150.9, 144.3, 143.8, 135.9, 135.8, 135.6, 134.8, 134.0, 131.6, 131.4, 130.3, 129.4, 128.3, 127.7, 123.2, 123.0, 113.9, 98.9, 89.1, 78.5, 67.1, 57.3, 55.8, 31.2, 29.9, 23.8.

TBI-451, 5-(4-Chlorophenyl)-3-cyclohexylimino-2-(2-ethoxy-3-pyridyl)amino-3,5-dihydrophenazine:

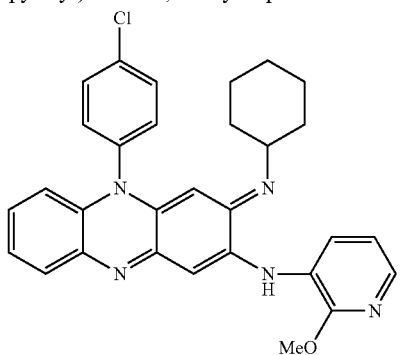

¹H NMR (300 MHz, CDCl₃) δ: 7.86-7.79 (m, 2H), 7.72-7.67 (m, 3H), 7.30 (d, J=8.4 Hz, 2H), 7.19-7.09 (m, 2H), 6.92-6.89 (m, 2H), 6.46 (dd, J=7.8 Hz, 1.8 Hz, 1H), 5.25 (s, 1H), 4.03 (s, 3H), 3.18-3.12 (m, 1H), 1.79-1.77 (m, 2H), 1.59 (m, 3H), 1.48-1.22 (m, 5H). ¹³C NMR (100 MHz, CDCl₃) δ: 155.4, 151.4, 150.6, 142.9, 138.6, 136.1, 135.6, 134.7, 131.6, 130.5, 128.2, 127.6, 125.0, 124.5, 122.8, 116.8, 113.8, 100.1, 89.5, 57.3, 53.7, 33.5, 26.0, 24.2.

TBI-452, 5-(4-Chlorophenyl-3-(4-tetrahydropyranyl)imino-2-(2-methyl-3-pyridyl)amino-3,5-dihydrophenazine:

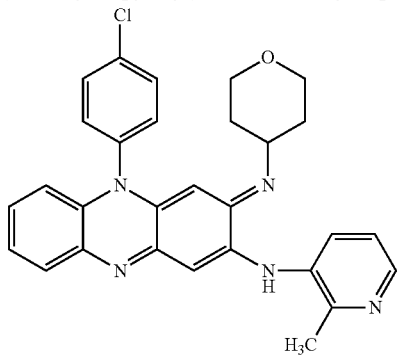

¹H NMR (300 MHz, CDCl₃) δ: 8.30-8.28 (m, 1H), 7.83 (d, J=8.1 Hz, 1H), 7.74-7.69 (m, 3H), 7.30 (d, J=8.7 Hz, 2H), 7.22-7.12 (m, 3H), 6.64 (s, 1H), 6.49 (dd, J=7.8 Hz, 1.2 Hz, 1H), 5.27 (s, 1H), 4.02-3.95 (m, 2H), 3.53-3.40 (m, 3H), 2.56 (s, 3H), 1.73-1.60 (m, 4H). ¹³C NMR (100 MHz, CDCl₃) δ: 152.1, 151.0, 150.7, 144.3, 144.0, 136.0, 135.8, 135.6, 135.0, 134.6, 131.7, 131.3, 130.3, 129.0, 128.3, 127.8, 123.2, 121.7, 114.0, 99.0, 88.8, 65.8, 53.7, 33.4, 21.0.

TBI-453, 5-(4-Chlorophenyl)-3-(4-methoxycyclohexyl)imino-2-(2-methyl-3-pyridyl)amino-3,5-dihydrophenazine:

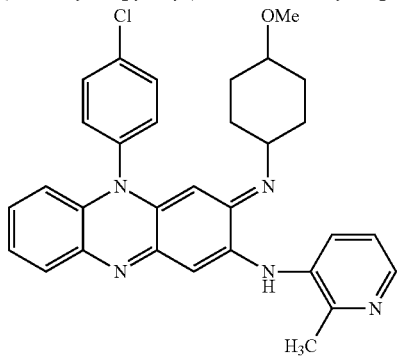

¹H NMR (300 MHz, CDCl₃) δ: 8.28 (dd, J=5.1 Hz, 1.5 Hz, 1H), 7.82 (dd, J=8.4 Hz, 1.5 Hz, 1H), 7.72-7.67 (m, 3H), 7.29 (d, J=8.4 Hz, 2H), 7.21-7.11 (m, 3H), 6.60 (s, 1H), 6.48 (dd, J=7.8 Hz, 1.2 Hz, 1H), 5.28 (s, 1H), 3.36 (s, 3H), 3.26-3.11 (m, 2H), 2.54 (s, 3H), 2.10-2.04 (m, 2H), 1.74-1.71 (m, 2H), 1.48-1.36 (m, 2H), 1.30-1.19 (m, 2H).

TBI-454, 5-(3-Methylthiophenyl)-3-(1-methylethyl)imino-2-(3-pyridyl)amino-3,5-dihydrophenazine:

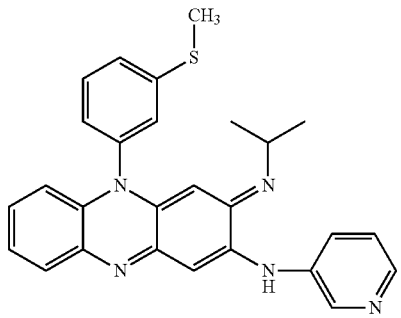 [SMILES: CSc1cccc(-n2c3c/c(=N\C(C)C)c(Nc4cccnc4)cc-3nc3ccccc32)c1]

¹H NMR (300 MHz, CDCl₃) δ: 8.59 (brs, 1H), 8.33 (d, J=4.8 Hz, 1H), 7.80-7.77 (m, 1H), 7.70-7.68 (m, 1H), 7.65-7.60 (m, 1H), 7.50-7.48 (m, 1H), 7.32-7.29 (m, 1H), 7.20-7.08 (m, 4H), 6.84 (s, 1H), 6.54-6.51 (m, 1H), 5.32 (s, 1H), 3.51-3.43 (m, 1H), 2.52 (s, 3H), 1.11-1.08 (m, 6H).

TBI-455, 5-(3-Methylsulfinylphenyl)-3-(1-methylethyl)imino-2-(3-pyridyl)amino-3,5-dihydrophenazine:

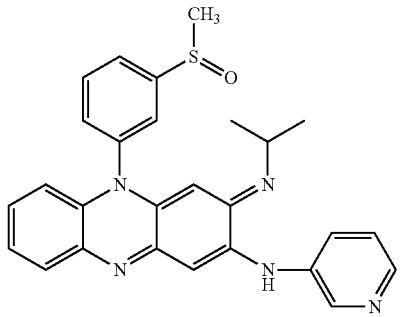 [SMILES: CC(C)/N=c1\cc2n(-c3cccc(S(C)=O)c3)c3ccccc3nc-2cc1Nc1cccnc1]

¹H NMR (300 MHz, CDCl₃) δ: 8.60 (brs, 1H), 8.34 (d, J=4.8 Hz, 1H), 7.97-7.94 (m, 2H), 7.79 (d, J=8.7 Hz, 1H), 7.72-7.64 (m, 2H), 7.54-7.52 (m, 1H), 7.33-7.28 (m, 1H), 7.22-7.17 (m, 2H), 6.84 (s, 1H), 6.41 (t, J=7.2 Hz, 1H), 5.21-5.19 (m, 1H), 3.42-3.38 (m, 1H), 2.83 (s, 3H), 1.10-1.05 (m, 6H).

TBI-456, 5-(4-Methylthiophenyl)-3-(1-methylethyl)imino-2-(3-pyridyl)amino-3,5-dihydrophenazine:

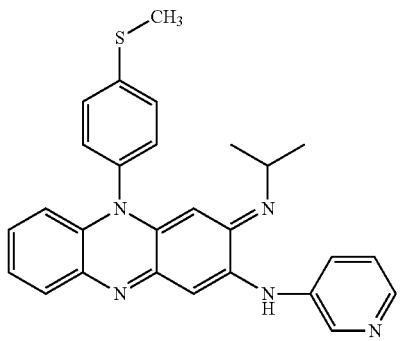 [SMILES: CSc1ccc(-n2c3c/c(=N\C(C)C)c(Nc4cccnc4)cc-3nc3ccccc32)cc1]

¹H NMR (300 MHz, CDCl₃) δ: 8.59 (d, J=2.4 Hz, 1H), 8.32 (dd, J=4.8 Hz, 1.5 Hz, 1H), 7.80-7.76 (m, 1H), 7.68 (dd, J=8.1 Hz, 2.1 Hz, 1H), 7.54 (d, J=8.4 Hz, 1H), 7.31-7.23 (m, 4H), 7.19-7.09 (m, 2H), 6.84 (s, 1H), 6.51 (dd, J=7.8 Hz, 1.2 Hz, 1H), 5.36 (s, 1H), 3.50-3.44 (m, 1H), 2.62 (s, 3H), 1.10 (d, J=6.3 Hz, 6H).

TBI-457, 5-(4-Methylsulfinylphenyl)-3-(1-methylethyl)imino-2-(3-pyridyl)amino-3,5-dihydrophenazine:

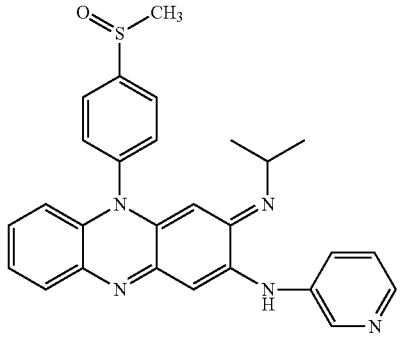 [SMILES: CC(C)/N=c1\cc2n(-c3ccc(S(C)=O)cc3)c3ccccc3nc-2cc1Nc1cccnc1]

¹H NMR (300 MHz, CDCl₃) δ: 8.59 (s, 1H), δ 8.34 (d, J=4.8 Hz, 1H), 8.09-7.97 (m, 2H), 7.79-7.77 (m, 1H), 7.72-7.70 (m, 1H), 7.56 (m, 2H), 7.32-7.28 (m, 1H), 7.22-7.11 (m, 2H), 6.84 (s, 1H), 6.41 (d, J=7.8 Hz, 1H), 5.23 (s, 1H), 3.46-3.38 (m, 1H), 2.90 (s, 3H), 1.08 (d, J=6.0 Hz, 6H).

TBI-458, 5-(4-Chlorophenyl)-3-(4-tetrahydrothiopyranyl)imino-2-pyridyl)amino-3,5-dihydrophenazine:

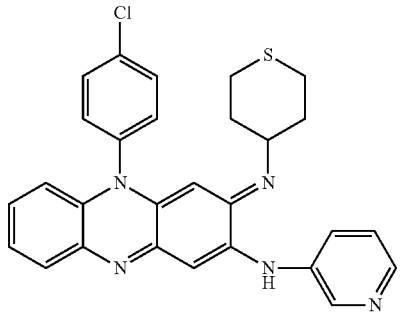

¹H NMR (300 MHz, CDCl₃) δ: 8.60 (d, J=2.7 Hz, 1H), 8.35 (d, J=4.2 Hz, 1H), 7.79-7.71 (m, 3H), 7.34-7.29 (m, 2H), 7.23-7.14 (m, 2H), 6.86 (s, 1H), 6.50 (d, J=8.1 Hz, 1H), 5.20 (s, 1H), 3.21-3.16 (m, 1H), 2.82-2.78 (m, 2H), 2.59-2.50 (m, 2H), 1.94-1.74 (m, 4H). ¹³C NMR (100 MHz, CDCl₃) δ: 150.7, 150.6, 144.5, 144.0, 143.6, 136.6, 135.9, 135.6, 135.0, 131.7, 131.3, 130.3, 128.5, 128.1, 128.0, 123.7, 123.2, 114.0, 99.6, 88.8, 56.3, 34.3, 26.6.

TBI-914, 7-Fluoro-5-(4-chlorophenyl)-3-(1-methylethyl)imino-2-(6-methyl-3-pyridyl)amino-3,5-dihydrophenazine:

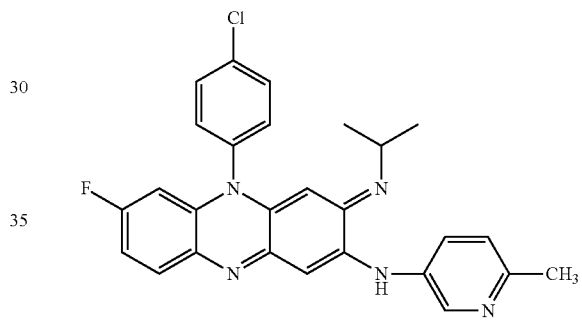

¹H NMR (300 MHz, CDCl₃) δ: 8.45 (1H, d, J=2.1 Hz), 7.72 (2H, d, J=8.1 Hz), 7.67 (1H, d, J=8.7, 2.1 Hz), 7.62 (1H, m), 7.29 (2H, d, J=8.1 Hz), 7.16 (1H, d, J=8.7 Hz), 6.87 (1H, m), 6.67 (1H, s), 6.13 (1H, m), 5.30 (1H, s), 3.47 (1H, m), 2.56 (3H, s), 1.10 (6H, d, J=6.6 Hz). ¹³C NMR (100 MHz, CDCl₃) δ: 161.4 (d, J=246 Hz), 153.4, 150.3, 144.2, 143.8, 136.0, 135.7, 134.4, 134.0, 132.4, 132.3, 131.9, 130.2, 129.7, 129.6, 129.4, 123.2, 110.6 (d, J=23 Hz), 100.7 (d, J=28 Hz), 98.8, 89.7, 58.4, 23.8, 23.5. HRMS (ESI-TOF⁺): m/z [M+H]⁺ calcd for $C_{27}H_{24}ClFN_5$: 472.1699; found: 472.1677.

TBI-918, 7-Fluoro-5-(4-chlorophenyl)-3-cyclohexylimino-2-(6-methyl-3-pyridyl)amino-3,5-dihydrophenazine:

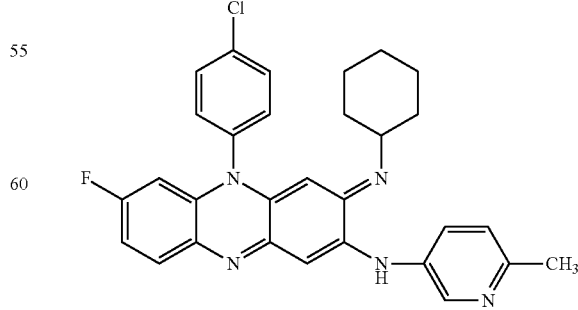

¹H NMR (300 MHz, CDCl₃) δ: 8.44 (1H, d, J=2.4 Hz), 7.72 (2H, d, J=8.4 Hz), 7.66 (1H, d, J=8.1, 2.4 Hz), 7.62 (1H, dd, J=8.7, 6.0 Hz), 7.29 (2H, d, J=8.4 Hz), 7.16 (1H, d, J=8.1 Hz), 6.87 (1H, ddd, J=11.1, 8.7, 2.7 Hz), 6.67 (1H, s), 6.15 (1H, dd, J=11.1, 2.7 Hz), 5.27 (1H, s), 3.09 (1H, m), 2.56 (3H, s), 1.74 (2H, m), 1.59 (3H, m), 1.39 (2H, m), 1.20 (3H, m). $^{13}$C NMR (100 MHz, CDCl$_3$. δ: 161.6 (d, J=246 Hz), 153.4, 150.4, 144.3, 143.8, 136.0, 135.7, 134.3, 134.0, 132.4, 132.3, 131.8, 130.2, 129.9, 129.8, 129.4, 123.2, 110.4 (d, J=23 Hz), 100.6 (d, J=29 Hz), 98.8, 90.0, 60.0, 33.7, 25.8, 24.6, 23.8. HRMS (ESI-TOF$^+$): m/z [M+H]$^+$ calcd for $C_{30}H_{28}ClFN$: 512.2012; found: 512.2028.

TBI-919, 7-Fluoro-5-(4-chlorophenyl)-3-(4-tetrahydropyranyl)imino-2-(6-methyl-3-pyridyl)amino)-3,5-dihydrophenazine:

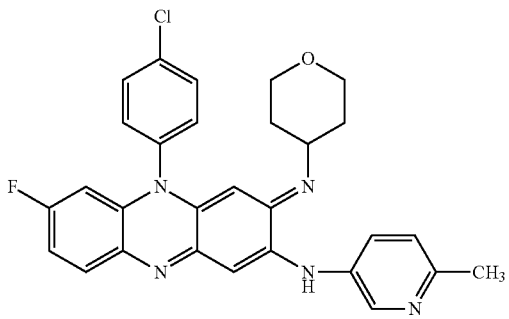 [SMILES: Cc1ccc(Nc2cc3nc4ccc(F)cc4n(-c4ccc(Cl)cc4)c-3c/c2=N\C2CCOCC2)cn1]

$^1$H NMR (300 MHz, CDCl$_3$. δ: 8.53 (1H, d, J=2.7 Hz), 7.72 (2H, d, J=8.4 Hz), 7.66 (1H, d, J=8.4, 2.7 Hz), 7.63 (1H, dd, J=9.0, 5.7 Hz), 7.30 (2H, d, J=8.4 Hz), 7.16 (1H, d, J=8.4 Hz), 6.87 (1H, ddd, J=11.2, 9.0, 2.4 Hz), 6.67 (1H, s), 6.16 (1H, dd, J=11.2, 2.4 Hz), 5.26 (1H, s), 3.95 (2H, m), 3.36 (3H, m), 2.56 (3H, s), 1.63 (4H, m). $^{13}$C NMR (100 MHz, CDCl$_3$. δ: 162.3 (d, J=250 Hz), 153.3, 150.2, 144.1, 143.6, 136.2, 135.5, 134.1, 133.8, 132.3, 132.2, 131.6, 130.0, 129.8, 129.6, 129.3, 123.1, 110.3 (d, J=22 Hz), 100.4 (d, J=28 Hz), 98.7, 90.1, 66.2, 54.7, 33.4, 23.8. HRMS (ESI-TOF$^+$): m/z [M+H]$^+$ calcd for $C_{29}H_{26}ClFN_5O$: 514.1804; found: 514.1798.

TBI-925, 7-Fluoro-5-(4-chlorophenyl)-3-(4-methoxycyclohexyl)imino-2-(6-methyl-3-pyridyl)amino)-3,5-dihydrophenazine:

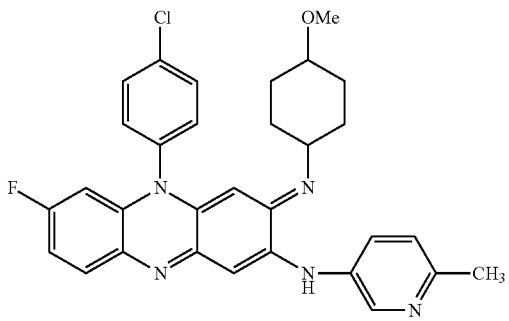 [SMILES: COC1CCC(/N=c2\cc3n(-c4ccc(Cl)cc4)c4cc(F)ccc4nc-3cc2Nc2ccc(C)nc2)CC1]

$^1$H NMR (300 MHz, CDCl$_3$. δ: 8.44 (1H, br. s), 7.72 (2H, d, J=8.7 Hz), 7.65 (2H, m), 7.28 (2H, d, J=8.4 Hz), 7.16 (1H, d, J=8.7 Hz), 6.88 (1H, m), 6.67 (1H, s), 6.16 (1H, m), 5.28 (1H, s), 3.37 (3H, s), 3.20 (1H, m), 3.10 (1H, m), 2.56 (3H, s), 2.07 (2 m), 1.69 (2H, m), 1.43 (2H, m), 1.19 (2H, m). $^{13}$C NMR (100 MHz, CDCl$_3$. δ: 161.7 (d, J=247 Hz), 153.5, 151.0, 150.2, 144.1, 143.8, 136.2, 135.6, 134.4, 133.9, 132.4, 132.3, 131.8, 130.1, 129.8, 129.4, 123.2, 110.6 (d, J=24 Hz), 100.7 (d, J=29 Hz), 98.9, 89.8, 78.4, 57.3, 55.8, 31.2, 29.9, 23.8. HRMS (ESI-TOF$^+$): m/z [M+H]$^+$ calcd for $C_{31}H_{30}ClFN_5O$: 542.2117; found: 542.2097.

TBI-924, 7-Fluoro-5-(4-chlorophenyl)-3-(4-methoxycyclohexyl)imino-2-methoxy-3-pyridyl)amino-3,5-dihydrophenazine:

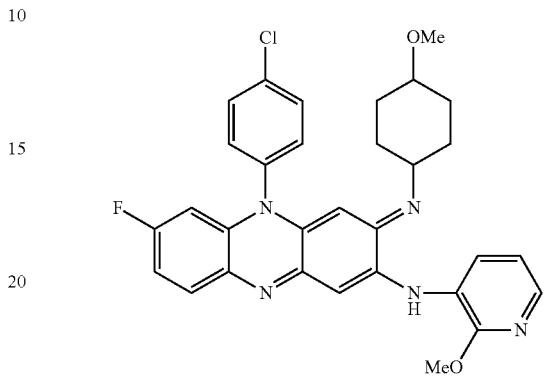

$^1$H NMR (300 MHz, CDCl$_3$. δ: 8.91 (1H, br. s), 7.81 (2H, m), 7.71 (2H, d, J=7.8 Hz), 7.64 (1H, m), 7.28 (2H, d, J=7.8 Hz), 6.85 (3H, m), 6.16 (1H, m), 5.28 (1H, s), 4.03 (3H, s), 3.37 (3H, s), 3.25 (1H, m), 3.14 (1H, m), 2.07 (2H, m), 1.71 (2H, m), 1.44 (2H, m), 1.24 (2H, m). $^{13}$C NMR (100 MHz, CDCl$_3$. δ: 161.7 (d, J=246 Hz), 155.3, 151.1, 150.4, 142.5, 138.8, 136.1, 135.5, 134.3, 132.6, 132.5, 131.8, 130.1, 129.8, 124.8, 124.5, 116.8, 110.5 (d, J=23 Hz), 100.7 (d, J=28 Hz), 100.2, 89.9, 78.2, 56.8, 55.8, 53.7, 30.7, 29.3. HRMS (ESI-TOF$^+$): m/z [M+H]$^+$ calcd for $C_{31}H_{30}ClFN_5O_2$: 558.2067; found: 558.2043.

TBI-926, 7-Fluoro-5-(4-chlorophenyl)-3-(1-methylethyl)imino-2-(2-methoxy-3-pyridyl)amino)-3,5-dihydrophenazine:

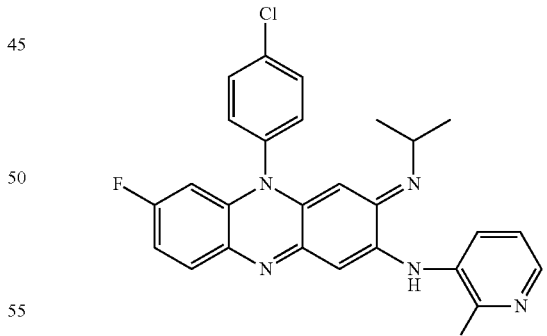

$^1$H NMR (300 MHz, CDCl$_3$. δ: 8.89 (1H, br. s), 7.81 (2H, m), 7.71 (2H, d, J=7.8 Hz), 7.63 (1H, m), 7.29 (2H, d, J=7.8 Hz), 6.89 (3H, m), 6.11 (1H, 5.30 (1H, s), 4.03 (3H, s), 3.46 (1H, m), 1.10 (6H, d, J=6.3 Hz). $^{13}$C NMR (100 MHz, CDCl$_3$. δ: 161.7 (d, J=246 Hz), 155.5, 150.5, 150.4, 142.7, 138.9, 136.0, 135.7, 134.3, 132.6, 132.3, 131.9, 130.2, 129.8, 124.9, 124.6, 116.8, 110.4 (d, J=23 Hz), 100.6 (d, J=28 Hz), 99.8, 89.9, 53.7, 49.5, 23.6. HRMS (ESI-TOF$^+$): m/z [M+H]$^+$ calcd for $C_{27}H_{24}ClFN_5O$: 488.1648; found: 488.1629.

TBI-927, 7-Fluoro-5-(4-chlorophenyl)-3-cyclohexylimino-2-(2-methoxy-3-pyridyl)amino-3,5-dihydrophenazine:

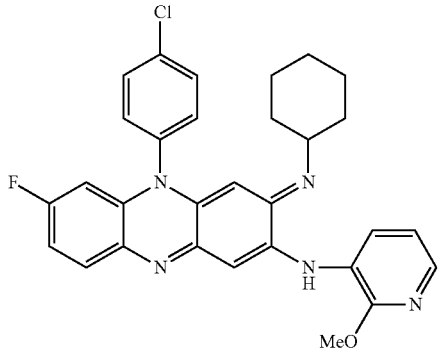 [SMILES: COc1ncccc1Nc1cc2nc3ccc(F)cc3n(-c3ccc(Cl)cc3)c-2c/c1=N\C1CCCCC1]

$^1$H NMR (300 MHz, CDCl$_3$. δ: 8.88 (1H, br. s), 7.81 (2H, m), 7.72 (2H, d, J=8.1 Hz), 7.63 (1H, dd, J=8.4, 6.3 Hz), 7.29 (2H, d, J=8.1 Hz), 6.87 (3H, m), 6.14 (1H, dd, J=10.2, 2.1 Hz), 5.27 (1H, s), 4.03 (3H, s), 3.15 (1H, m), 1.78 (2H, m), 1.58 (3H, m), 1.38 (2H, m), 1.28 (3H, m). $^{13}$C NMR (100 MHz, CDCl$_3$. δ: 161.7 (d=246 Hz), 155.3, 150.6, 150.4, 142.6, 138.6, 135.9, 135.7, 134.2, 132.6, 132.3, 131.8, 130.2, 129.6, 124.9, 124.3, 116.8, 110.3 (d, J=23 Hz), 100.6 (d, J=29 Hz), 100.1, 90.1, 57.3, 53.7, 33.5, 25.9, 24.1. HRMS (ESI-TOF$^+$): m/z [M+H]$^+$ calcd for C$_{30}$H$_{28}$ClFN$_5$O: 528.1961; found: 528.1952.

TBI-928, 7-Fluoro-5-(4-chlorophenyl)-3-(4-tetrahydropyranyl)imino-2-(2-methoxy-3-pyridyl)amino-3,5-dihydrophenazine:

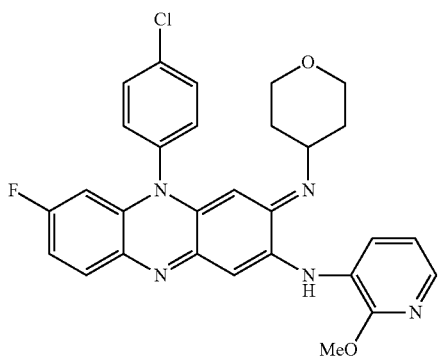 [SMILES: COc1ncccc1Nc1cc2nc3ccc(F)cc3n(-c3ccc(Cl)cc3)c-2c/c1=N\C1CCOCC1]

$^1$H NMR (300 MHz, CDCl$_3$. δ: 9.04 (1H, br. s), 7.83 (2H, m), 7.73 (2H, d, J=8.7 Hz), 7.66 (1H, dd, J=8.4, 6.0 Hz), 7.29 (2H, d, J=8.7 Hz), 6.88 (3H, m), 6.14 (1H, dd, J=9.9, 2.1 Hz), 5.27 (1H, s), 4.04 (3H, s), 4.01 (2H, m), 3.50 (3H, m), 1.64 (4H, m). $^{13}$C NMR (100 MHz, CDCl$_3$. δ: 161.7 (d, J=246 Hz), 155.3, 151.0, 150.2, 142.4, 138.8, 136.2, 135.6, 134.5, 132.5, 132.3, 131.9, 130.1, 129.9, 124.8, 124.3, 116.8, 110.7 (d, J=23 Hz), 100.6 (d, J=28 Hz), 100.3, 89.6, 65.5, 53.8, 53.3, 33.3. HRMS (ESI-TOF$^+$): m/z [M+H]$^+$ calcd for C$_{29}$H$_{26}$ClFN$_5$O$_2$: 530.1754; found: 530.1746.

TBI-938, 8-Fluoro-5-(4-chlorophenyl)-3-(4-methoxycyclohexyl)imino-2-(6-methyl-3-pyridyl)amino-3,5-dihydrophenazine:

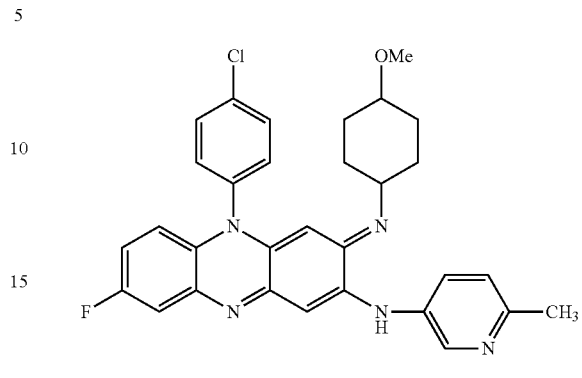

$^1$H NMR (300 MHz, CDCl$_3$. δ: 8.44 (1H, br. s), 7.68 (3H, m), 7.35 (1H, br. d, J=8.1 Hz), 7.27 (2H, m), 7.16 (1H, d, J=8.1 Hz), 6.84 (1H, m), 6.67 (1H, s), 6.42 (1H, dd, J=9.0, 4.5 Hz), 5.23 (1H, s), 3.36 (3H, s), 3.20 (1H, m), 3.09 (1H, m), 2.56 (3H, s), 2.06 (2H, m), 1.69 (2H, m), 1.43 (2H, m), 1.23 (2H, m). $^{13}$C NMR (100 MHz, CDCl$_3$. δ: 158.5 (d, J=240 Hz), 153.7, 151.9, 151.0, 145.0, 143.9, 136.4 (d, J=14 Hz), 135.8 (d, J=16 Hz), 134.6, 133.8, 132.0, 131.7, 130.8, 130.2, 129.7, 128.0, 123.2, 115.9 (d, J=22 Hz), 113.4 (d, J=22 Hz), 98.5, 88.8, 78.4, 57.3, 55.8, 31.1, 29.9, 23.8. HRMS (ESI-TOF$^+$): m/z [M+H]$^+$ calcd for C$_{31}$H$_{30}$ClFN$_5$O: 542.2117; found: 542.2079.

TBI-943, 8-Fluoro-5-(4-chlorophenyl)-3-(1-methylethyl)imino-2-(6-methyl-3-pyridyl)amino-3,5-dihydrophenazine:

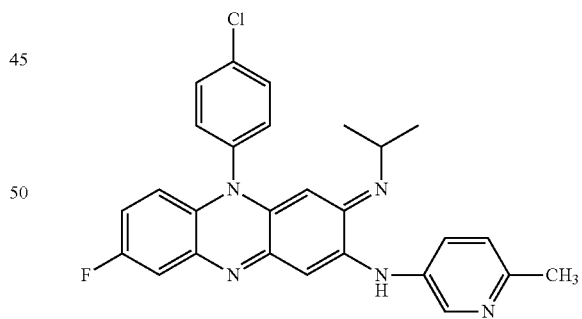

$^1$H NMR (300 MHz, CDCl$_3$. δ: 8.46 (1H, br. s), 7.70 (3H, m), 7.33 (3H, m), 7.17 (1H, d, J=7.8 Hz), 6.84 (1H, m), 6.67 (1H, s), 6.39 (1H, m), 5.27 (1H, s), 3.48 (1H, m), 2.56 (3H, s), 1.10 (6H, d, J=6.0 Hz). $^{13}$C NMR (100 MHz, CDCl$_3$. δ: 158.5 (d 241 Hz), 153.6, 152.0, 150.2, 145.1, 143.9, 136.3 (d, J=12 Hz), 135.8 (d, J=14 Hz), 134.6, 133.9, 132.0, 131.8, 130.5, 130.3, 129.7, 128.0, 123.2, 114.7 (d, J=23 Hz), 113.3 (d, J=22 Hz), 98.4, 88.8, 49.4, 23.8, 23.5. HRMS (ESI-TOF$^+$): m/z [M+H]$^+$ calcd for C$_{27}$H$_{24}$ClFN$_5$: 472.1699; found: 472.1680.

TBI-929, 8-Fluoro-5-(4-chlorophenyl)-3-(1-methylethyl)imino-2-(2-methoxy-3-pyridyl)amino-3,5-dihydrophenazine:

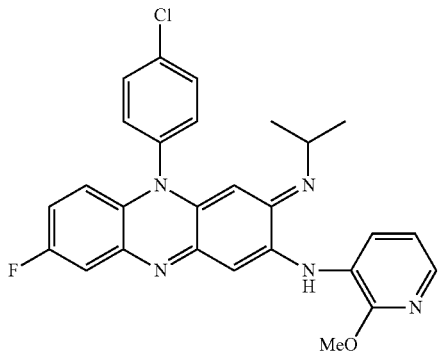 [SMILES: COc1ncccc1Nc1cc2nc3cc(F)ccc3n(-c3ccc(Cl)cc3)c-2c/c1=N\C(C)C]

$^1$H NMR (300 MHz, CDCl$_3$. δ: 8.99 (1H, br. s), 7.84 (2H, m), 7.72 (2H, d, J=7.8 Hz), 7.37 (1H, dd, J=9.3, 2.1 Hz), 7.30 (2H, d, J=7.8 Hz), 6.96 (1H, dd, J=8.4, 6.0 Hz), 6.88 (1H, s), 6.84 (1H, m), 6.38 (1H, dd, J=9.0, 4.5 Hz), 5.27 (1H, s), 4.05 (3H, s), 3.47 (1H, m), 1.12 (6H, d, J=6.0 Hz). $^{13}$C NMR (100 MHz, CDCl$_3$. δ: 158.5 (d, J=240 Hz), 155.5, 152.3, 150.4, 143.5, 139.1, 136.2 (d, J=12 Hz), 135.8 (d, J=17 Hz), 134.5, 131.8, 130.4, 128.2, 125.2, 124.6, 116.8, 114.7 (d, J=25 Hz), 114.6, 114.5, 113.3 (d, J=23 Hz), 99.6, 89.0, 53.7, 49.4, 23.5. HRMS (ESI-TOF$^+$): m/z [M+H]$^+$ calcd for C$_{27}$H$_{24}$ClFN$_5$O: 488.1648; found: 488.1629.

TBI-936, 8-Fluoro-5-(4-chlorophenyl)-3-(4-methoxycyclohexyl)imino-2-(2-methoxy-3-pyridyl)amino-3,5-dihydrophenazine:

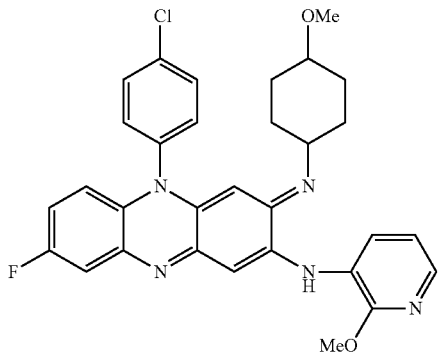 [SMILES: COc1ncccc1Nc1cc2nc3cc(F)ccc3n(-c3ccc(Cl)cc3)c-2c/c1=N\C1CCC(OC)CC1]

$^1$H NMR (300 MHz, CDCl$_3$. δ: 8.98 (1H, br. s), 7.82 (2H, m), 7.69 (2H, d, J=7.8 Hz), 7.37 (1H, dd, J=9.0, 2.1 Hz), 7.27 (2H, d, J=7.8 Hz), 6.88 (3H, m), 6.39 (1H, dd, J=8.7, 5.1 Hz), 5.23 (1H, s), 4.05 (3H, s), 3.36 (3H, s), 3.24 (1H, m), 3.13 (1H, m), 2.07 (2H, m), 1.71 (2H, m), 1.43 (2H, m), 1.24 (2H, m). $^{13}$C NMR (100 MHz, CDCl$_3$. δ: 158.5 (d, J=240 Hz), 155.4, 152.2, 151.0, 143.3, 139.1, 136.4 (d, J=12 Hz), 135.8 (d, J=12 Hz), 134.6, 131.7, 130.3, 128.2, 124.9, 124.6, 116.8, 114.9 (d, J=24 Hz), 114.7, 114.6, 113.4 (d, 23 Hz), 99.8, 89.0, 78.2, 56.8, 55.8, 53.8, 30.7, 29.4. HRMS (ESI-TOF$^+$): m/z [M+H]$^+$ calcd for C$_{31}$H$_{30}$ClFN$_5$O$_2$: 558.2067; found: 558.2044.

TBI-937, 8-Fluoro-5-(4-chlorophenyl)-3-(4-tetrahydropyranyl)imino-2-(2-methoxy-3-pyridyl)amino-3,5-dihydrophenazine:

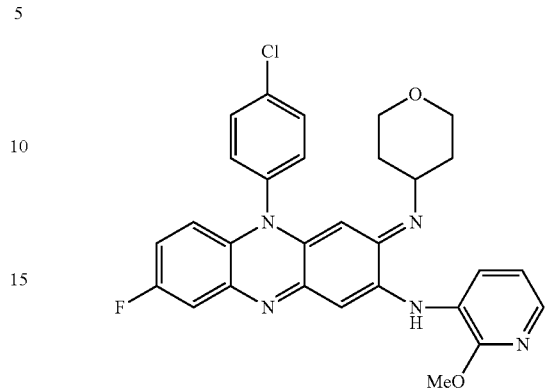

$^1$H NMR (300 MHz, CDCl$_3$. δ: 9.13 (1H, br. s), 7.85 (2H, m), 7.72 (2H, d, J=8.1 Hz), 7.39 (1H, dd, J=8.7, 2.1 Hz), 7.29 (2H, d, J=8.1 Hz), 6.89 (3H, m), 6.42 (1H, m), 5.24 (1H, s), 4.04 (3H, s), 3.97 (2H, m), 3.49 (3H, m), 1.69 (4H, m). $^{13}$C NMR (100 MHz, CDCl$_3$. δ: 158.5 (d, J=241 Hz), 155.4, 152.0, 150.9, 143.2, 139.1, 135.8 (d, J=11 Hz), 134.8 (d, J=12 Hz), 133.8, 131.8, 130.3, 128.0, 124.6, 124.4, 116.8, 115.2 (d, J=23 Hz), 114.9, 114.7, 113.4 (d, J=22 Hz), 99.9, 88.7, 65.5, 53.8, 53.3, 33.2. HRMS (ESI-TOF$^+$): m/z [M+H]$^+$ calcd for C$_{29}$H$_{26}$ClFN$_5$O$_7$: 530.1754; found: 530.1728.

TBI-939, 7-Methoxy-5-(4-chlorophenyl)-3-(1-methylethyl)imino-2-(2-methoxy-3-pyridyl)amino-3,5-dihydrophenazine:

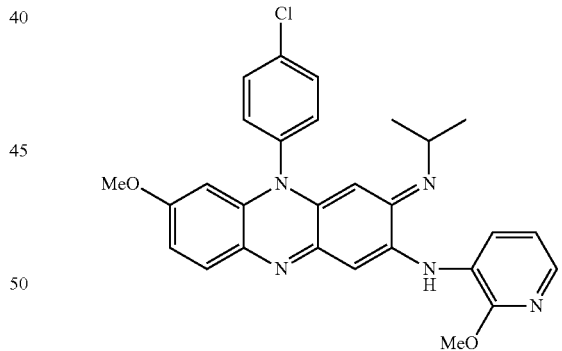

$^1$H NMR (300 MHz, CDCl$_3$) δ: 8.86 (1H, br. s), 7.83 (1H, dd, J=7.8, 1.5 Hz), 7.79 (1H, dd, J=5.1, 1.5 Hz), 7.70 (2H, J=8.7 Hz), 7.62 (1H, d, J=8.7 Hz), 7.29 (2H, d, J=8.7 Hz), 6.90 (2H, m), 6.77 (1H, dd, J=8.7, 2.4 Hz), 5.91 (1H, d, J=2.4 Hz), 5.26 (1H, s), 3.94 (3H, s), 3.70 (3H, s), 3.44 (1H, m), 1.10 (6H, d, J=6.3 Hz). $^{13}$C NMR (100 MHz, CDCl$_3$) δ: 159.4, 155.3, 150.6, 148.9, 141.9, 138.4, 136.0, 135.7, 134.6, 132.8, 131.7, 130.6, 130.4, 129.4, 125.1, 124.4, 116.8, 109.3, 100.4, 98.9, 89.6, 55.5, 53.7, 49.3, 23.6. HRMS (ESI-TOF$^+$): m/z [M+H]$^+$ calcd for C$_{28}$H$_{27}$ClN$_5$O$_2$: 500.1848; found: 500.1832.

TBI-941, 7-Methoxy-5-(4-chlorophenyl)-3-(4-methoxycyclohexyl)imino-2-(2-methoxy-3-pyridyl)amino-3,5-dihydrophenazine:

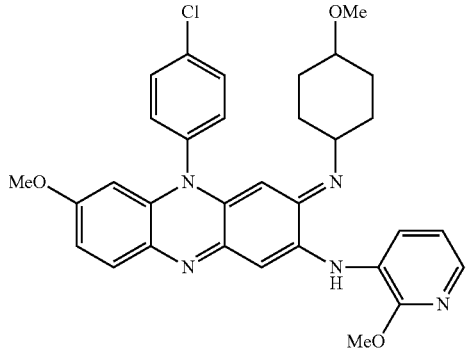 [SMILES: COc1ccc2nc3cc(Nc4cccnc4OC)/c(=N/C4CCC(OC)CC4)cc-3n(-c3ccc(Cl)cc3)c2c1]

$^1$H NMR (300 MHz, CDCl$_3$. δ: 8.89 (1H, br. s), 7.82 (1H, dd, J=8.4, 1.8 Hz), 7.77 (1H, 7.68 (2H, d, J=8.7 Hz), 7.62 (1H, d, J=8.7 Hz), 7.28 (2H, d, J=8.7 Hz), 6.90 (2H, m), 6.78 (1H, dd, J=8.7, 2.1 Hz), 5.92 (1H, d, J=2.1 Hz), 5.23 (1H, s), 4.02 (3H, s), 3.69 (3H, s), 3.36 (3H, s), 3.24 (1H, m), 3.12 (1 m), 2.04 (2H, m), 1.69 (2H, m), 1.42 (2H, m), 1.23 (2H, m). $^{13}$C NMR (100 MHz, CDCl$_3$. δ: 159.5, 155.2, 151.3, 148.7, 141.7, 138.3, 135.9, 135.8, 134.6, 132.7, 131.6, 130.6, 130.3, 129.5, 125.1, 124.1, 116.8, 109.5, 100.5, 98.8, 89.5, 78.3, 56.7, 55.8, 55.5, 53.7, 30.7, 29.4. HRMS (ESI-TOF$^+$): m/z [M+H]$^+$ calcd for C$_{32}$H$_{33}$ClN$_5$O$_3$: 570.2266; found: 570.2241.

TBI-942, 7-Methoxy-5-(4-chlorophenyl)-3-(4-tetrahydropyranyl)imino-2-(2-methoxy-3-pyridyl)amino-3,5-dihydrophenazine:

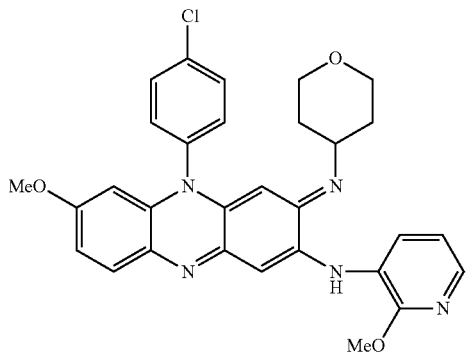 [SMILES: COc1ccc2nc3cc(Nc4cccnc4OC)/c(=N/C4CCOCC4)cc-3n(-c3ccc(Cl)cc3)c2c1]

$^1$H NMR (300 MHz, CDCl$_3$) δ: 9.02 (1H, br. s), 7.82 (1H, dd, J=7.8, 1.8 Hz), 7.79 (1H, dd, J=4.8, 1.8 Hz), 7.70 (2H, d, J=8.4 Hz), 7.65 (1H, d, J=8.4 Hz), 7.29 (2H, d, J=8.4 Hz), 6.95 (1H, s), 6.90 (1H, dd, J=7.8, 4.8 Hz), 6.80 (1H, dd, J=8.4, 2.4 Hz), 5.93 (1H, d, J=2.4 Hz), 5.23 (1H, s), 4.04 (3H, s), 4.01 (2H, m), 3.71 (3H, s), 3.48 (3H, m), 1.63 (4H, m). $^{13}$C NMR (100 MHz, CDCl$_3$) δ: 159.5, 155.1, 151.1, 148.6, 141.6, 138.3, 135.9, 135.8, 134.8, 132.6, 131.7, 130.7, 130.3, 129.6, 125.1, 123.8, 116.8, 109.7, 100.6, 98.9, 89.3, 65.6, 55.5, 53.7, 53.2, 33.3. HRMS (ESI-TOF$^+$): m/z [M+H]$^+$ calcd for C$_{30}$H$_{29}$ClN$_5$O$_3$: 542.1953; found: 542.1934.

TBI-894, 7-Methoxy-5-(4-chlorophenyl)-3-cyclopropylimino-2-(2-methoxy-3-pyridyl)amino-3,5-dihydrophenazine:

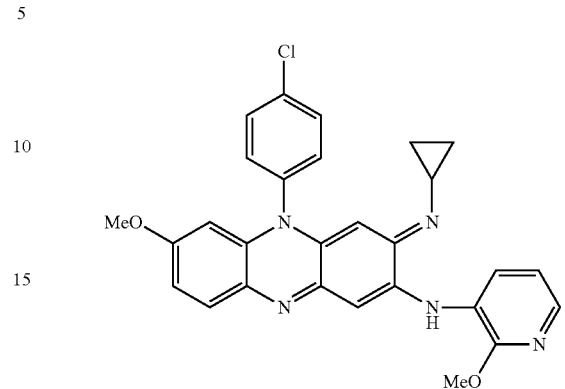

$^1$H NMR (300 MHz, CDCl$_3$) δ: 9.00 (1H, br. s), 7.78 (2H, m), 7.68 (2H, d, J=8.1 Hz), 7.60 (1H, d, J=8.7 Hz), 7.30 (2H, d, J=8.1 Hz), 6.87 (1H, dd, J=7.8, 5.1 Hz), 6.84 (1H, s), 6.74 (1H, dd, J=8.7, 2.1 Hz), 5.88 (1H, d, J=2.1 Hz), 5.52 (1H, s), 3.99 (3H, s), 3.68 (3H, s), 2.71 (1H, m), 0.87 (2H, m), 0.80 (2H, m). $^{13}$C NMR (100 MHz, CDCl$_3$) δ: 159.5, 155.3, 152.7, 149.1, 141.6, 138.4, 136.0, 135.6, 134.4, 132.9, 131.8, 130.7, 130.5, 129.4, 125.0, 124.5, 116.8, 109.2, 100.4, 98.9, 90.0, 55.5, 53.7, 53.2, 32.8, 9.9. HRMS (ESI-TOF$^+$): m/z [M+H]$^+$ calcd for C$_{28}$H$_{24}$ClN$_5$O$_2$: 498.1691; found: 498.1667.

TBI-895, 7-Methoxy-5-(4-chlorophenyl)-3-cyclobutylimino-2-(2-methoxy-3-pyridyl)amino-3,5-dihydrophenazine:

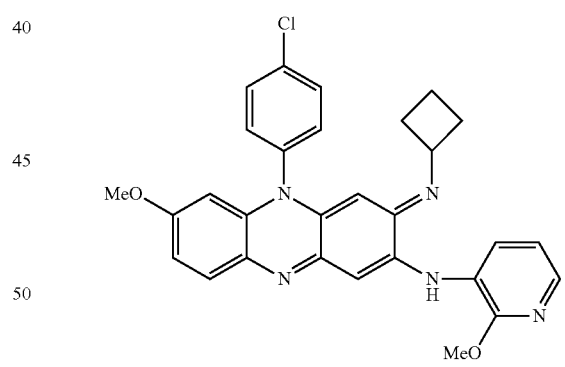

$^1$H NMR (300 MHz, CDCl$_3$) δ: 8.92 (1H, br. s), 7.82 (1H, dd, J=7.2, 1.5 Hz), 7.79 (1H, dd, J=5.4, 1.5 Hz), 7.70 (2H, d, J=8.4 Hz), 7.63 (1H, d, J=8.7 Hz), 7.29 (2H, d, J=8.4 Hz), 6.90 (2H, m), 6.78 (1H, dd, J=8.7, 2.4 Hz), 5.92 (1H, d, J=2.4 Hz), 5.07 (1H, s), 4.04 (3H, s), 3.88 (1H, m), 3.70 (3H, s), 2.17 (2H, m), 2.06 (2H, m), 1.75 (2H, m). $^{13}$C NMR (100 MHz, CDCl$_3$) δ: 159.5, 155.2, 151.5, 148.7, 141.7, 138.4, 136.0, 135.7, 134.2, 132.6, 131.7, 130.7, 130.4, 129.5, 125.0, 124.2, 116.8, 109.6, 100.6, 98.8, 91.1, 55.5, 54.8, 53.7, 32.0, 16.0. HRMS (ESI-TOF$^+$): m/z [M+H]$^+$ calcd for C$_{29}$H$_{26}$ClN$_5$O$_2$: 512.1848; found: 512.1816.

TBI-944, 5-(3,4-Dichlorophenyl)-3-cyclopropylimino-2-(6-methyl-3-pyridyl)amino-3,5-dihydrophenazine:

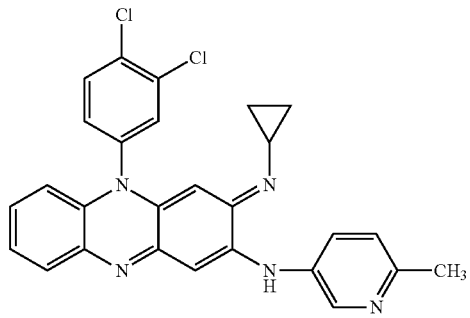 [SMILES: Cc1ccc(Nc2cc3nc4ccccc4n(-c4ccc(Cl)c(Cl)c4)c-3c/c2=N\C2CC2)cn1]

$^1$H NMR (300 MHz, CDCl$_3$) δ: 8.41 (1H, br. s), 7.82 (1H, d, J=8.7 Hz), 7.65 (2H, m), 7.52 (1H, d, J=1.8 Hz), 7.27 (1H, m), 7.15 (3H, m), 6.64 (1H, s), 6.42 (1H, d, J=7.5 Hz), 5.55 (1H, s), 2.79 (1H, m), 2.56 (3H, s), 0.94 (2H, m), 0.86 (2H, m). $^{13}$C NMR (100 MHz, CDCl$_3$) δ: 153.6, 152.1, 151.2, 144.2, 143.9, 136.8, 135.6, 135.4, 134.3, 133.8, 133.2, 131.3, 131.2, 129.7, 128.7, 128.3, 127.6, 123.2, 123.1, 113.6, 98.8, 89.6, 33.1, 23.8, 10.2. HRMS (ESI-TOF$^+$): m/z [M+H]$^+$ calcd for C$_{27}$H$_{22}$Cl$_2$N$_5$: 486.1247; found: 486.1228.

TBI-948, 5-(3,4-Dichlorophenyl)-3-cyclobutylimino-2-(6-methyl-3-pyridyl)amino-3,5-dihydrophenazine:

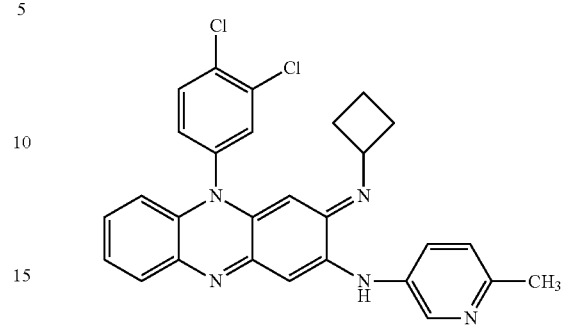

$^1$H NMR (300 MHz, CDCl$_3$) δ: 8.47 (1H, br. s), 7.82 (1H, d, J=8.7 Hz), 7.67 (2H, m), 7.50 (1H, br. s), 7.24 (1H, m), 7.15 (3H, m), 6.70 (1H, s), 6.48 (1H, br. d, J=7.5 Hz), 5.11 (1H, s), 3.94 (1H, m), 2.56 (3H, s), 2.21 (2H, m), 2.05 (2H, m), 1.79 (2H, m). $^{13}$C NMR (100 MHz, CDCl$_3$) δ: 153.6, 151.0, 150.9, 144.4, 143.8, 136.8, 135.6, 135.3, 134.3, 134.1, 133.9, 133.0, 131.2, 130.9, 129.6, 128.6, 128.4, 127.4, 123.3, 123.2, 113.7, 98.9, 90.6, 54.8, 32.0, 23.8, 16.1. HRMS (ESI-TOF$^+$): m/z [M+H]$^+$ calcd for C$_{28}$H$_{74}$Cl$_2$N$_5$: 500.1317; found: 500.1335.

TBI-945, 5-(3,4-Dichlorophenyl)-3-(4-tetrahydropyranyl)imino-2-(6-methyl-3-pyridyl)amino-3,5-dihydrophenazine:

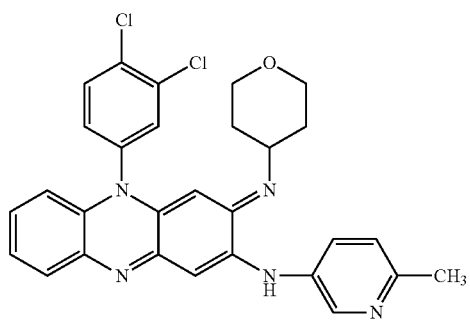 [SMILES: Cc1ccc(Nc2cc3nc4ccccc4n(-c4ccc(Cl)c(Cl)c4)c-3c/c2=N\C2CCOCC2)cn1]

$^1$H NMR (300 MHz, CDCl$_3$) δ: 8.53 (1H, d, J=2.1 Hz), 7.98 (1H, dd, J=7.8, 1.8 Hz), 7.83 (1H, d, J=8.1 Hz), 7.69 (1H, dd, J=8.4, 2.7 Hz), 7.50 (1H, d, J=2.7 Hz), 7.43 (2H, m), 7.21 (2H, m), 7.14 (1H, s), 6.82 (1H, dd, J=7.8, 1.8 Hz), 5.70 (1H, s), 3.99 (2H, m), 3.45 (3H, s), 2.57 (3H, s), 1.67 (4H, m). $^{13}$C NMR (100 MHz, CDCl$_3$) δ: 154.2, 153.7, 144.4, 143.9, 136.7, 135.5, 135.3, 134.6, 133.8, 133.2, 131.3, 131.2, 129.7, 128.7, 128.3, 127.6, 123.3, 123.2, 115.1, 99.0, 89.3, 66.1, 54.3, 33.4, 23.9. HRMS (ESI-TOF$^+$): m/z [M+H]$^+$ calcd for C$_{29}$H$_{26}$Cl$_2$N$_5$O: 530.1509; found: 530.1511.

TBI-946, 5-(3,4-Dichlorophenyl)-3-cyclobutylimino-2-(2-methoxy-3-pyridyl)amino-3,5-dihydrophenazine:

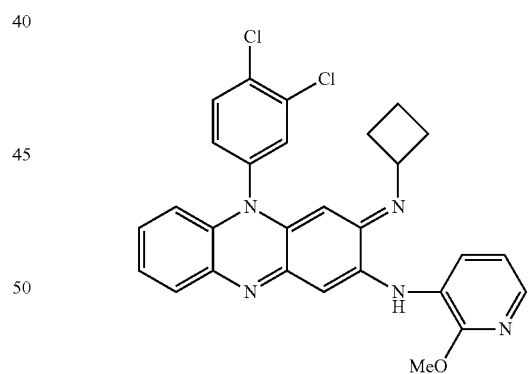

$^1$H NMR (300 MHz, CDCl$_3$) δ: 8.79 (1H, br. s), 7.84 (3H, 7.69 (1H, d, J=7.5 Hz), 7.50 (1H, d, J=2.1 Hz), 7.23 (1H, m), 7.17 (2H, m), 6.91 (2H, m), 6.47 (1H, d, J=7.5 Hz), 5.11 (1H, s), 4.05 (3H, s), 3.95 (1H, m), 2.22 (2H, m), 2.08 (2H, m), 1.81 (2H, m). $^{13}$C NMR (100 MHz, CDCl$_3$) δ: 155.4, 151.2, 151.1, 142.8, 139.0, 136.7, 135.6, 135.3, 134.3, 134.0, 133.0, 131.3, 131.1, 128.6, 128.4, 127.8, 124.9, 124.7, 123.2, 116.8, 113.7, 100.3, 90.8, 54.8, 53.7, 32.0, 16.1. HRMS (ESI-TOF$^+$): m/z [M+H]$^+$ calcd for C$_{28}$H$_{24}$Cl$_2$N$_5$O: 516.1352; found: 516.1322.

TBI-947, 5-(2,4-Dichlorophenyl)-3-(4-tetrahydropyranyl)imino-2-(2-methoxy-3-pyridyl)amino-3,5-dihydrophenazine:

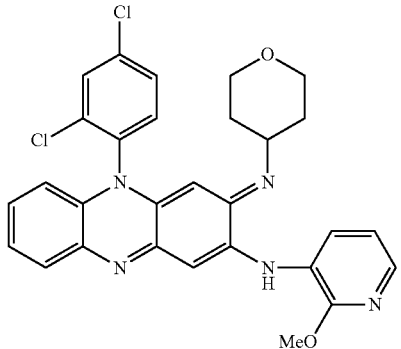

$^1$H NMR (300 MHz, CDCl$_3$) δ: 8.56 (1H, br. s), 7.81 (3H, m), 7.68 (1H, d, J=7.8 Hz), 7.50 (1H, m), 7.37 (1H, d, J=8.1 Hz), 7.18 (2H, m), 6.91 (2H, m), 6.32 (1H, d, J=7.8 Hz), 5.17 (1H, s), 4.01 (3H, s), 3.96 (2 N, m), 3.49 (3H, m), 1.68 (4H, m). $^{13}$C NMR (100 MHz, CDCl$_3$) δ: 155.3, 151.2, 151.1, 142.8, 139.1, 136.7, 135.6, 135.3, 134.2, 134.0, 133.0, 131.3, 131.0, 128.6, 128.4, 127.7, 124.9, 124.7, 123.2, 116.8, 113.7, 100.1, 89.3, 65.5, 53.6, 33.1. HRMS (ESI-TOF$^+$): m/z [M+H]$^+$ calcd for C$_{29}$H$_{26}$Cl$_2$N$_5$O$_2$: 546.1358; found: 546.1374.

TBI-893, 5-(2,4-Dichlorophenyl)-3-cyclobutylimino-2-(2-methoxy-3-pyridyl)amino-3,5-dihydrophenazine:

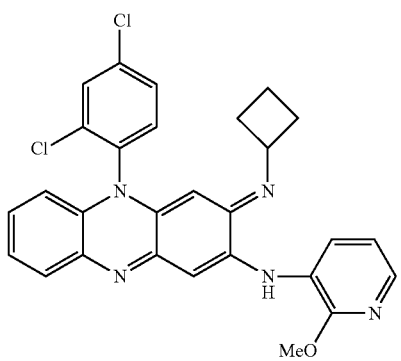

$^1$H NMR (300 MHz, CDCl$_3$) δ: 7.86 (1H, m), 7.82 (3H, m), 7.72 (1H, d, J=7.8 Hz), 7.60 (1H, dd, J=8.4, 2.1 Hz), 7.34 (1H, d, J=8.4 Hz), 7.19 (2H, m), 6.91 (2H, m), 6.38 (1H, d, J=7.8 Hz), 5.01 (1H, s), 4.05 (3H, s), 3.95 (1H, m), 2.20 (2H, m), 2.13 (2H, m), 1.78 (2H, m). $^{13}$C NMR (100 MHz, CDCl$_3$) δ: 155.5, 151.5, 151.3, 142.8, 139.0, 136.7, 135.7, 134.8, 133.3, 132.9, 131.9, 131.8, 130.3, 129.9, 128.4, 127.9, 125.1, 124.7, 123.3, 116.8, 113.2, 100.3, 90.5, 54.9, 53.7, 32.0, 16.1. HRMS (ESI-TOF$^+$): m/z [M+H]$^+$ calcd for C$_{28}$H$_{24}$Cl$_2$N$_5$O: 516.1352; found: 516.1328.

TBI-949, 7-Fluoro-5-(3,4-dichlorophenyl)-3-(4-tetrahydropyranyl)imino-2-(6-methyl-3-pyridyl)amino-3,5-dihydrophenazine:

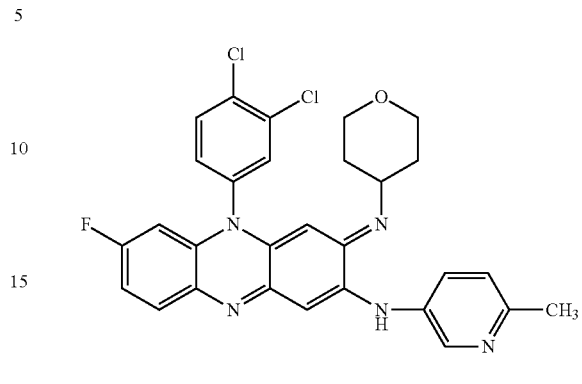

$^1$H NMR (300 MHz, CDCl$_3$) δ: 8.46 (1H, d, J=2.1 Hz), 7.85 (1H, d, J=8.1 Hz), 7.65 (2H, m), 7.49 (1H, d, J=2.4 Hz), 7.24 (1H, dd, J=8.1, 2.4 Hz), 7.17 (1H, d, J=8.7 Hz), 6.91 (1H, m), 6.69 (1H, s), 6.18 (1H, dd, J=10.2, 3.0 Hz), 5.29 (1H, s), 3.99 (2H, 3.44 (3H, m), 2.57 (3H, s), 1.66 (4H, m). $^{13}$C NMR (100 MHz, CDCl$_3$) δ: 163.0 (d, J=246 Hz), 153.8, 150.8, 150.0, 144.2, 143.9, 136.3, 135.6, 134.8, 134.2, 133.8, 133.2, 132.3, 131.8 (d, J=11 Hz), 131.0, 130.0 (d, J=12 Hz), 129.7, 128.2, 123.3, 111.0 (d, J=23 Hz), 100.6 (d, J=28 Hz), 99.0, 89.7, 66.5, 54.4, 33.4, 23.9. HRMS (ESI-TOF$^+$): m/z [M+H]$^+$ calcd for C$_{29}$H$_{25}$Cl$_2$FN$_5$O: 548.1288; found: 548.1339.

TBI-896, 7-Fluoro-5-(3,4-dichlorophenyl)-3-(1-methylethyl)imino-2-(6-methyl-3-pyridyl)amino-3,5-dihydrophenazine:

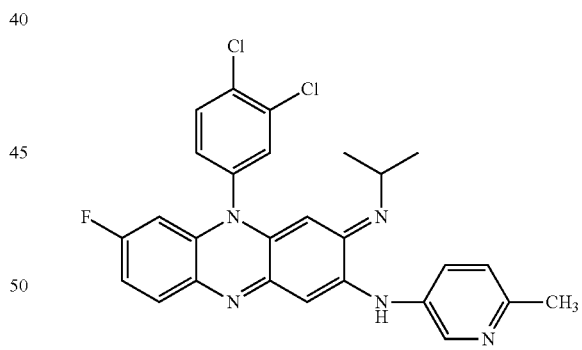

$^1$H NMR (300 MHz, CDCl$_3$) δ: 8.46 (1H, d, J=2.1 Hz), 7.84 (1H, d, J=8.7 Hz), 7.66 (2H, m), 7.49 (1H, d, J=2.4 Hz), 7.24 (1H, dd, J=8.7, 2.4 Hz), 7.16 (1H, d, J=8.1 Hz), 6.90 (1H, m), 6.66 (1H, s), 6.13 (1H, br. d, J=9.9 Hz), 5.32 (1H, s), 3.52 (1H, m), 2.56 (3H, s), 1.13 (6H, d, J=6.6 Hz). $^{13}$C NMR (100 MHz, CDCl$_3$) δ: 162.8 (d, J=246 Hz), 153.5, 150.6, 150.1, 144.2, 143.8, 136.4, 135.6, 134.7, 134.1, 133.9, 133.3, 132.2, 131.9 (d, J=12 Hz), 131.0, 130.0 (d, J=12 Hz), 129.6, 128.3, 123.2, 110.7 (d, J=23 Hz), 100.6 (d, J=28 Hz), 98.8, 89.8, 49.6, 23.8, 23.6. HRMS (ESI-TOF$^+$): m/z [M+H]$^+$ calcd for C$_{27}$H$_{22}$Cl$_2$FN$_5$: 506.1309; found: 506.1276.

261

TBI-897, 7-Fluoro-5-(3,4-dichlorophenyl)-3-(4-methoxy-cyclohexyl)imino-2-(6-methyl-3-pyridyl)amino-3,5-dihydrophenazine:

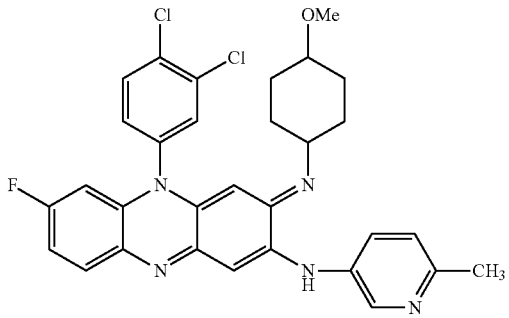 [SMILES: COC1CCC(/N=c2\cc3n(-c4ccc(Cl)c(Cl)c4)c4cc(F)ccc4nc-3cc2Nc2ccc(C)nc2)CC1]

$^1$H NMR (300 MHz, CDCl$_3$) δ: 8.44 (1H, d, J=2.1 Hz), 7.84 (1H, d, J=7.8 Hz), 7.64 (2H, m), 7.48 (1H, d, J=2.4 Hz), 7.24 (1H, dd, J=7.8, 2.4 Hz), 7.16 (1H, d, J=7.5 Hz), 6.90 (1H, m), 6.66 (1H, s), 6.13 (1H, br. d, J=10.5 Hz), 5.30 (1H, s), 3.37 (3H, s), 3.18 (2H, m), 2.56 (3H, s), 2.09 (2H, m), 1.71 (2H, m), 1.45 (2H, m), 1.23 (2H, m). $^{13}$C NMR (100 MHz, CDCl$_3$) δ: 162.8 (d, J=246 Hz), 153.6, 150.8, 150.1, 144.1, 143.8, 136.2, 135.6, 134.8, 134.0, 133.9, 133.2, 132.2, 132.0 (d, J=12 Hz), 131.0, 130.0 (d, J=12 Hz), 129.5, 128.2, 123.2, 110.8 (d, J=24 Hz), 100.6 (d, J=29 Hz), 98.9, 89.9, 78.4, 57.4, 55.8, 31.2, 29.8, 23.8. HRMS (ESI-TOF$^+$): m/z [M+H]$^+$ calcd for C$_{31}$H$_{29}$Cl$_2$FN$_5$O: 576.1626; found: 576.1629.

TBI-899, 7-Fluoro-5-(3,4-dichlorophenyl)-3-(1-methyl-ethyl)imino-2-(2-methoxy-3-pyridyl)amino-3,5-dihydrophenazine:

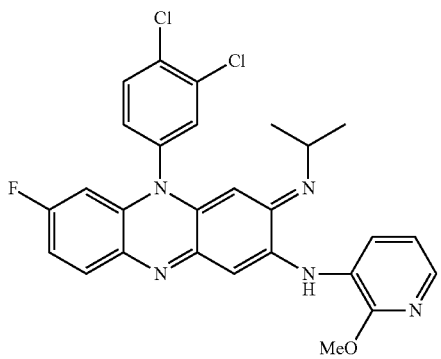

$^1$H NMR (300 MHz, CDCl$_3$) δ: 8.52 (1H, br. s), 7.81 (3H, m), 7.62 (1H, m), 7.49 (1H, br. s), 7.25 (1H, br. d, J=7.8 Hz), 6.91 (2H, m), 6.83 (1H, s), 6.10 (1H, br. d, J=10.5 Hz), 5.31 (1H, s), 4.03 (3H, s), 3.51 (1H, m), 1.13 (6H, d, J=6.3 Hz). $^{13}$C NMR (100 MHz, CDCl$_3$) δ: 161.7 (d, J=247 Hz), 155.5, 151.0, 150.3, 142.7, 139.0, 136.4, 135.6, 134.7, 134.0, 133.3, 132.2 (d, J=12 Hz), 131.0, 129.8 (d, J=11 Hz), 128.4, 125.0, 124.7, 116.8, 110.7 (d, J=24 Hz), 100.6 (d, J=29 Hz), 100.0, 90.0, 53.7, 49.5, 23.6. HRMS (ESI-TOF$^+$): m/z [M+H]$^+$ calcd for C$_{27}$H$_{23}$Cl$_2$FN$_5$O: 522.1258; found: 522.1227.

262

TBI-884, 7-Fluoro-5-(3,4-dichlorophenyl)-3-(4-tetrahydropyranyl)imino-2-(2-methoxy-3-pyridyl)amino-3,5-dihydrophenazine:

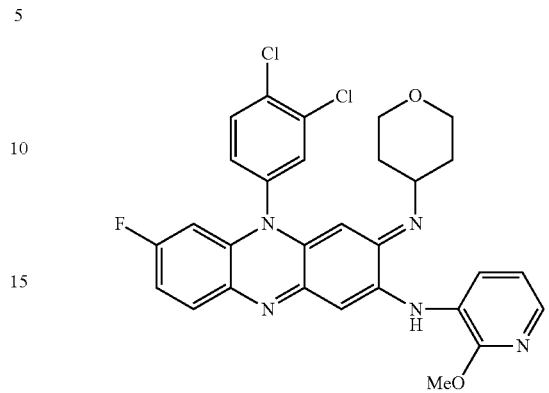

$^1$H NMR (300 MHz, CDCl$_3$) δ: 8.60 (1H, br. s), 7.84 (3H, m), 7.67 (1H, m), 7.50 (1H, br. s), 7.24 (1H, br. d, J=7.8 Hz), 6.93 (2H, m), 6.92 (1H, s), 6.17 (1H, br. d, J=9.6 Hz), 5.30 (1H, s), 4.05 (3H, s), 4.02 (2H, m), 3.50 (3H, m), 1.76 (4H, m). $^{13}$C NMR (100 MHz, CDCl$_3$) δ: 161.8 (d, J=247 Hz), 155.3, 150.8, 150.2, 142.4, 138.9, 136.3, 135.6, 134.8, 134.2, 133.3, 132.3, 132.2 (d, J=12 Hz), 131.0, 130.0 (d, J=10 Hz), 128.2, 124.7, 124.3, 116.8, 110.9 (d, J=23 Hz), 100.6 (d, J=28 Hz), 100.3, 89.7, 65.5, 53.8, 53.3, 33.3. HRMS (ESI-TOF$^+$): m/z [M+H]$^+$ calcd for C$_{29}$H$_{25}$Cl$_2$FN$_5$O$_2$: 564.1364; found: 564.1376.

TBI-885, 7-Fluoro-5-(3,4-dichlorophenyl)-3-cyclopropy-limino-2-(2-methoxy-3-pyridyl)amino-3,5-dihydrophenazine:

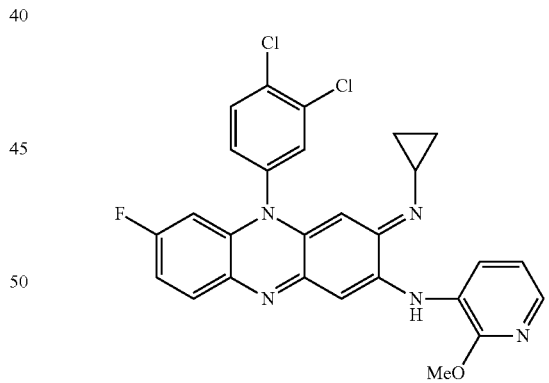

$^1$H NMR (300 MHz, CDCl$_3$) δ: 8.53 (1H, br. s), 7.81 (3H, m), 7.61 (1H, 7.51 (1H, br. s), 7.24 (1H, br. d, J=7.5 Hz), 6.90 (2H, m), 6.81 (1H, s), 6.10 (1H, br. d, J=10.2 Hz), 5.56 (1H, s), 4.01 (3H, s), 2.79 (1H, m), 0.96 (2H, m), 0.88 (2H, m). $^{13}$C NMR (100 MHz, CDCl$_3$) δ: 161.7 (d, J=248 Hz), 155.4, 152.0, 150.7, 142.5, 139.0, 136.4, 135.6, 134.7, 133.8, 133.4, 132.3 (d, J=12 Hz), 131.2, 129.7 (d, J=10 Hz), 128.5, 125.1, 124.6, 116.8, 110.5 (d, J=23 Hz), 100.5 (d, J=28 Hz), 100.0, 90.4, 53.7, 33.2, 10.4. HRMS (ESI-TOF$^+$): m/z [M+H]$^+$ calcd for C$_{27}$H$_{21}$Cl$_2$FN$_5$O: 520.1102; found: 520.1078.

TBI-886, 7-Fluoro-5-(3,4-dichlorophenyl)-3-cyclobutylimino-2-(2-methoxy-3-pyridyl)amino-3,5-dihydrophenazine:

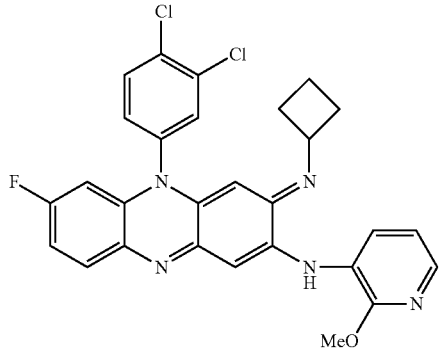 [SMILES: COc1ncccc1Nc1cc2nc3ccc(F)cc3n(-c3ccc(Cl)c(Cl)c3)c-2c/c1=N\C1CCC1]

$^1$H-NMR (300 MHz, CDCl$_3$) δ: 7.83 (3H, m), 7.65 (1H, m), 7.49 (1H, br. s), 7.23 (1H, br. d, J=7.5 Hz), 6.90 (2H, m), 6.87 (1H, s), 6.15 (1H, br. d, J=8.7 Hz), 5.13 (1H, s), 4.05 (3H, s), 3.95 (1H, m), 2.22 (2H, m), 2.11 (2H, m), 1.79 (2H, m). $^{13}$C NMR (100 MHz, CDCl$_3$) δ: 161.6 (d, J=248 Hz), 155.5, 151.1, 150.4, 142.6, 139.0, 136.3, 135.5, 134.7, 133.6, 133.2, 132.1 (d, J=12 Hz), 131.1, 130.0 (d, J=10 Hz), 128.4, 124.9, 124.6, 116.8, 110.8 (d, J=23 Hz), 100.6 (d, J=28 Hz), 100.2, 91.5, 54.9, 53.8, 32.0, 16.1. HRMS (ESI-TOF$^+$): m/z [M+H]$^+$ calcd for C$_{28}$H$_{73}$Cl$_2$FN$_5$O: 534.1258; found: 534.1225.

TBI-887, 8-Fluoro-5-(3,4-dichlorophenyl)-3-(1-methylethyl)imino-2-(6-methyl-3-pyridyl)amino-3,5-dihydrophenazine:

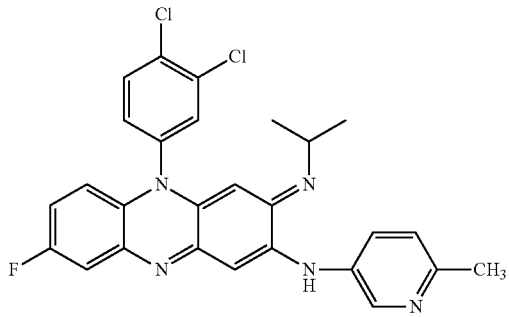 [SMILES: Cc1ccc(Nc2cc3nc4cc(F)ccc4n(-c4ccc(Cl)c(Cl)c4)c-3c/c2=N\C(C)C)cn1]

$^1$H NMR (300 MHz, CDCl$_3$) δ: 8.46 (1H, br. s), 7.82 (1H, d, J=8.7 Hz), 7.66 (1H, dd, J=8.1, 2.1 Hz), 7.49 (1H, d, J=2.1 Hz), 7.35 (1H, dd, J=9.0, 2.1 Hz), 7.24 (1H, dd, J=8.7, 2.1 Hz), 7.18 (1H, d, J=8.1 Hz), 6.87 (1H, m), 6.65 (1H, s), 6.38 (1H, dd, J=9.0, 4.5 Hz), 5.28 (1H, s), 3.50 (1H, m), 2.57 (3H, s), 1.13 (6H, d, J=6.3 Hz). $^{13}$C NMR (100 MHz, CDCl$_3$) δ: 158.7 (d, J=241 Hz), 153.8, 152.0, 150.1, 145.1, 143.9, 136.7, 136.4 (d, J=12 Hz), 135.5, 134.4 (d, J=10 Hz), 134.1, 133.8, 133.2, 131.2, 129.8, 128.5, 127.7, 123.2, 114.8 (d, J=23 Hz), 114.5, 113.5 (d, J=22 Hz), 98.5, 88.9, 49.5, 23.8, 23.6. HRMS (ESI-TOF$^+$): m/z [M+H]$^+$ calcd for C$_{27}$H$_{23}$Cl$_2$FN$_5$: 506.1309; found: 506.1276.

TBI-888, 8-Fluoro-5-(3,4-dichlorophenyl)-3-cyclopropylimino-2-(6-ethyl-3-pyridinyl)amino-3,5-dihydrophenazine:

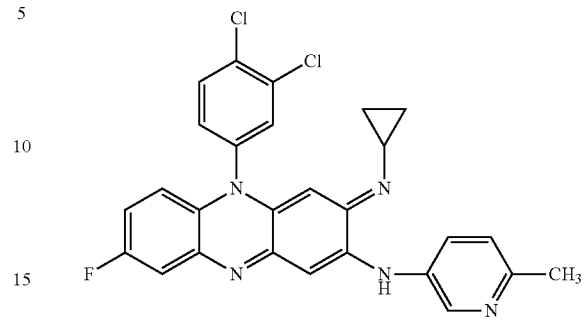

$^1$H NMR (300 MHz, CDCl$_3$) δ: 8.42 (1H, br. s), 7.82 (1H, d, J=8.7 Hz), 7.64 (1H, dd, J=8.1, 2.4 Hz), 7.50 (1H, d, J=1.8 Hz), 7.33 (1H, dd, J=9.0, 2.4 Hz), 7.25 (1H, dd, J=8.7, 1.8 Hz), 7.16 (1H, d, J=8.1 Hz), 6.85 (1H, m), 6.60 (1H, s), 6.35 (1H, dd, J=9.3, 5.1 Hz), 5.53 (1H, s), 2.80 (1H, m), 2.56 (3H, s), 0.96 (2H, m), 0.87 (2H, m). $^{13}$C NMR (100 MHz, CDCl$_3$) δ: 158.7 (d, J=240 Hz), 153.9, 152.2, 151.9, 144.9, 144.0, 136.8, 136.5 (d, J=12 Hz), 135.5, 134.5 (d, J=10 Hz), 134.1, 133.6, 133.3, 131.3, 129.9, 128.6, 127.8, 123.3, 114.6 (d, J=23 Hz), 114.5, 113.5 (d, J=22 Hz), 98.4, 89.3, 33.2, 23.8, 10.3. HRMS (ESI-TOF$^+$): m/z [M+H]$^+$ calcd for C$_{27}$H$_{21}$Cl$_2$FN$_5$: 504.1153; found: 504.1122.

TBI-873, 8-Fluoro-5-(3,4-dichlorophenyl)-3-(4-tetrahydropyranyl)imino-2-(6-methyl-3-pyridyl)amino-3,5-dihydrophenazine:

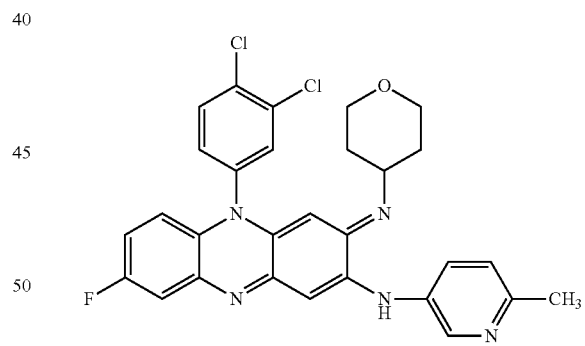

$^1$H NMR (300 MHz, CDCl$_3$) δ: 8.46 (1H, br. s), 7.83 (1H, d, J=8.1 Hz), 7.66 (1H, dd, J=8.4, 2.4 Hz), 7.50 (1H, br. s), 7.37 (1H, d, J=8.1 Hz), 7.24 (1H, m), 7.17 (1H, d, J=8.4 Hz), 6.89 (1H, m), 6.68 (1H, s), 6.43 (1H, m), 5.25 (1H, s), 3.97 (2H, m), 3.44 (3H, m), 2.56 (3H, s), 1.67 (4H, m). $^{13}$C NMR (100 MHz, CDCl$_3$) δ: 158.7 (d, J=240 Hz), 154.0, 151.7, 150.8, 144.9, 144.0, 136.7, 136.5 (d, J=12 Hz), 135.5, 134.5 (d, J=10 Hz), 134.3, 133.6, 133.2, 131.1, 129.9, 128.4, 127.4, 123.3, 114.8 (d, J=25 Hz), 114.6, 113.6 (d, J=22 Hz), 98.7, 88.8, 66.0, 54.3, 33.4, 23.9. HRMS (ESI-TOF$^+$): m/z [M+H]$^+$ calcd for C$_{29}$H$_{25}$Cl$_2$FN$_5$O: 548.1288; found: 548.1312.

TBI-878, 8-Fluoro-5-(3,4-dichlorophenyl)-3-(4-methoxy-cyclohexyl)imino-2-(6-methyl-3-pyridinyl)amino-3,5-dihydrophenazine:

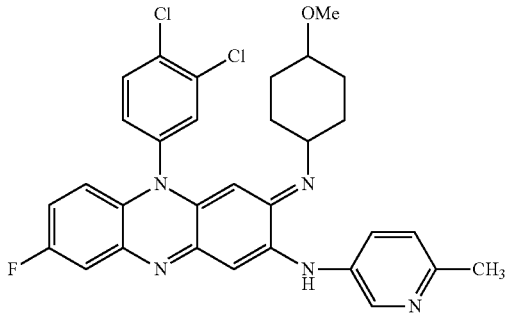 [SMILES: COC1CCC(/N=c2\cc3n(-c4ccc(Cl)c(Cl)c4)c4ccc(F)cc4nc-3cc2Nc2ccc(C)nc2)CC1]

$^1$H NMR (300 MHz, CDCl$_3$) δ: 8.45 (1H, br. s), 7.82 (1H, d, J=8.1 Hz), 7.65 (1H, dd, J=8.4, 2.4 Hz), 7.49 (1H, br. s), 7.36 (1H, d, J=8.1 Hz), 7.25 (1H, m), 7.18 (1H, d, J=8.4 Hz), 6.90 (1H, m), 6.69 (1H, s), 6.44 (1H, m), 5.49 (1H, s), 3.37 (3H, s), 3.25 (1H, m), 3.13 (1H, m), 2.57 (3H, s), 2.05 (2H, m), 1.68 (2H, m), 1.43 (2H, m), 1.23 (2H, m). $^{13}$C NMR (100 MHz, CDCl$_3$) 158.7 (d, J=241 Hz), 154.0, 151.6, 150.7, 144.9, 144.0, 136.7, 136.4 (d, J=11 Hz), 135.5, 134.6 (d, J=11 Hz), 134.3, 133.6, 133.2, 131.1, 129.9, 128.4, 127.4, 123.3, 114.9 (d, J=25 Hz), 114.6, 113.7 (d, J=22 Hz), 98.9, 89.1, 78.4, 57.3, 55.8, 31.2, 29.7, 23.8. HRMS (ESI-TOF$^+$): m/z [M+H]$^+$ calcd for C$_{31}$H$_{29}$Cl$_2$FN$_5$O: 576.1626; found: 576.1629.

TBI-859, 8-Fluoro-5-(4-chlorophenyl)-3-cyclopropylimino-2-(2-methoxy-3-pyridyl)amino-3,5-dihydrophenazine:

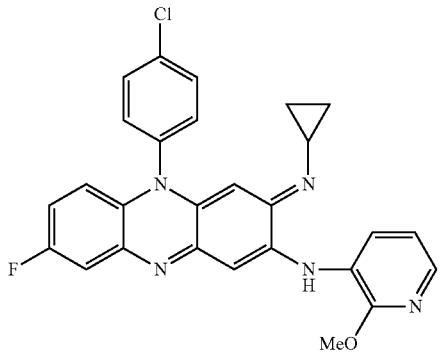 [SMILES: COc1ncccc1Nc1cc2nc3cc(F)ccc3n(-c3ccc(Cl)cc3)c-2c/c1=N\C1CC1]

$^1$H NMR 300 MHz, CDCl$_3$) δ: 8.62 (1H, br. s), 7.81 (2H, m), 7.70 (2H, d, J=7.8 Hz), 7.35 (1H, dd, J=9.3, 2.1 Hz), 7.31 (2H, d, J=7.8 Hz), 6.91 (1H, dd, J=8.4, 6.0 Hz), 6.83 (1H, s), 6.82 (1H, m), 6.34 (1H, dd, J=9.0, 4.5 Hz), 5.52 (1H, s), 4.01 (3H, s), 2.75 (1H, m), 0.91 (2H, m), 0.85 (2H, m). $^{13}$C NMR (100 MHz, CDCl$_3$) δ: 158.6 (d, J=240 Hz), 155.5, 152.4, 152.3, 143.3, 139.3, 135.9 (d, J=12 Hz), 135.8 (d, J=17 Hz), 134.4, 131.8, 130.5, 128.4, 125.4, 124.5, 116.8, 114.8 (d, J=25 Hz), 114.6, 114.5, 113.3 (d, J=23 Hz), 99.6, 89.4, 53.7, 33.0, 10.2. HRMS (ESI-TOF+): m/z [M+H]$^+$ calcd for C$_{27}$H$_{22}$ClFN$_5$O: 486.1491; found: 486.1518.

TBI-874, 8-Fluoro-5-(3,4-dichlorophenyl)-3-(1-methylethyl)imino-2-(2-methoxy-3-pyridyl)amino-3,5-dihydrophenazine:

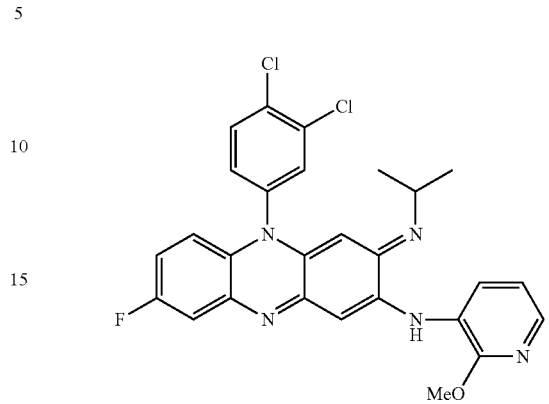

$^1$H NMR (300 MHz, CDCl$_3$) δ: 8.52 (1H, br. s), 7.81 (3H, m), 7.62 (1H, m), 7.49 (1H, br. s), 7.25 (1H, br. d, J=7.8 Hz), 6.91 (2H, m), 6.83 (1H, s), 6.10 (1H, br. d, J=10.5 Hz), 5.31 (1H, s), 4.03 (3H, s), 3.51 (1H, m), 1.13 (6H, d, J=6.3 Hz). $^{13}$C NMR (100 MHz, CDCl$_3$): 158.8 (d, J=233 Hz), 155.7, 151.5, 150.3, 143.4, 139.5, 136.7, 136.5 (d, J=11 Hz), 135.5, 134.5, 134.3, 133.2, 131.1, 128.5, 127.8, 125.9, 124.1, 116.8, 114.9 (d, J=24 Hz), 114.5 (d, J=10 Hz), 113.8 (d, J=22 Hz), 99.9, 89.1, 53.7, 49.5, 23.4. HRMS (ESI-TOF$^+$): m/z [M+H]$^+$ calcd for C$_{27}$H$_{23}$Cl$_2$FN$_5$O: 522.1258; found: 522.1231.

TBI-875, 8-Fluoro-5-(3,4-dichlorophenyl)-3-cyclopropylimino-2-(2-methoxy-3-pyridyl)amino-3,5-dihydrophenazine:

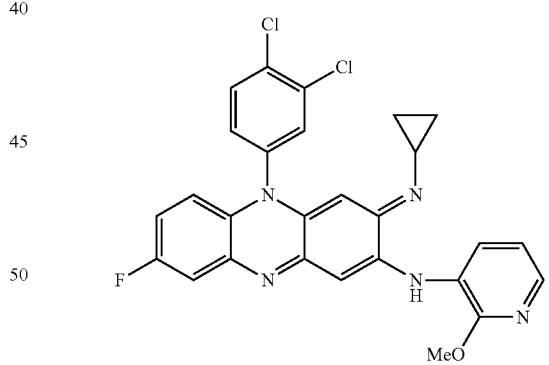

$^1$H NMR (300 MHz, CDCl$_3$) δ: 7.83 (3H, m), 7.51 (1H, d, J=1.8 Hz), 7.36 (1H, dd, J=9.0, 2.1 Hz), 7.24 (1H, m), 6.88 (2H, m), 6.82 (1H, s), 6.37 (1H, dd, J=9.0, 4.5 Hz), 5.25 (1H, s), 4.02 (3H, s), 2.79 (1H, m), 0.96 (2H, m), 0.87 (2H, m). $^{13}$C NMR (100 MHz, CDCl$_3$) δ: 158.6 (d, J=240 Hz), 155.5, 152.5, 152.0, 143.4, 139.3, 136.8, 136.5 (d, J=11 Hz), 135.5, 134.4, 134.1, 133.3, 131.3, 128.7, 128.0, 125.5, 124.4, 116.8, 114.7 (d, J=24 Hz), 114.4 (d, J=10 Hz), 113.5 (d, J=23 Hz), 99.4, 89.6, 53.7, 33.2, 10.5. HRMS (ESI-TOF$^+$): m/z [M+H]$^+$ calcd for C$_{27}$H$_{21}$Cl$_2$FN$_5$O: 520.1102; found: 520.1071.

TBI-877, 8-Fluoro-5-(3,4-dichlorophenyl)-3-(4-tetrahydropyranyl)imino-2-(2-methoxy-3-pyridyl)amino-3,5-dihydrophenazine:

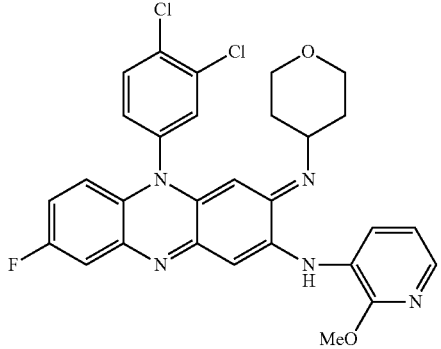 [SMILES: COc1ncccc1Nc1cc2nc3cc(F)ccc3n(-c3ccc(Cl)c(Cl)c3)c-2c/c1=N\C1CCOCC1]

$^1$H NMR (300 MHz, CDCl$_3$) δ: 7.82 (3H, m), 7.49 (1H, br. s), 7.37 (1H, dd, J=8.7, 2.4 Hz), 7.23 (1H, m), 6.92 (2H, m), 6.91 (1H, s), 6.41 (1H, dd, J=8.4, 5.1 Hz), 5.26 (1H, s), 4.03 (3H, s), 4.01 (2H, m), 3.51 (3H, m), 1.71 (4H, m). $^{13}$C NMR (100 MHz, CDCl$_3$) δ: 158.8 (d, J=242 Hz), 155.5, 152.5, 143.2, 142.7, 139.3, 136.6, 136.3 (d, J=11 Hz), 135.5, 134.7, 134.4, 133.2, 131.3, 128.6, 128.2, 127.6, 124.5, 116.8, 115.1 (d, J=24 Hz), 114.5 (d, J=10 Hz), 113.6 (d, J=23 Hz), 100.1, 88.8, 65.5, 55.3, 53.8, 33.2. HRMS (ESI-TOF$^+$): m/z [M+H]$^+$ calcd for C$_{29}$H$_{25}$Cl$_2$FN$_5$O$_2$: 564.1364; found: 564.1323.

TBI-879, 8-Fluoro-5-(3,4-dichlorophenyl)-3-(4-methoxycyclohexyl)imino-2-(2-methoxy-3-pyridyl)amino-3,5-dihydrophenazine:

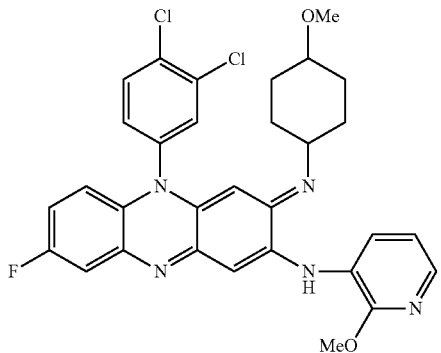 [SMILES: COc1ncccc1Nc1cc2nc3cc(F)ccc3n(-c3ccc(Cl)c(Cl)c3)c-2c/c1=N\C1CCC(OC)CC1]

$^1$H NMR (300 MHz, CDCl$_3$) δ: 7.83 (3H, m), 7.50 (1H, d, J=1.8 Hz), 7.39 (1H, dd, J=9.0, 2.4 Hz), 7.24 (1H, m), 6.93 (2H, m), 6.91 (1H, s), 6.44 (1H, dd, J=8.7, 4.5 Hz), 5.26 (1H, s), 4.04 (3H, s), 3.37 (3H, s), 3.27 (1H, m), 3.17 (1H, m), 2.08 (2H, m), 1.69 (2H, m), 1.44 (2H, m), 1.26 (2H, m). $^{13}$C NMR (100 MHz, CDCl$_3$): 158.7 (d, J=240 Hz), 155.5, 152.2, 150.9, 143.3, 139.2, 136.6, 136.4 (d, J=12 Hz), 135.5, 134.6, 134.3, 133.2, 131.2, 128.4, 127.8, 125.0, 124.5, 116.8, 115.0 (d, J=24 Hz), 114.5 (d, J=10 Hz), 113.6 (d, J=22 Hz), 99.8, 89.1, 78.2, 56.9, 55.8, 53.8, 30.6, 29.3. HRMS (ESI-TOF$^+$): m/z [M+H]$^+$ calcd for C$_{31}$H$_{29}$Cl$_2$FN$_5$O$_2$: 592.1677; found: 592.1662.

TBI-889, 8-Fluoro-5-(4-trifluoromethoxyphenyl)-3-(1-methylethyl)imino-2-(2-methoxy-3-pyridyl)amino-3,5-dihydrophenazine:

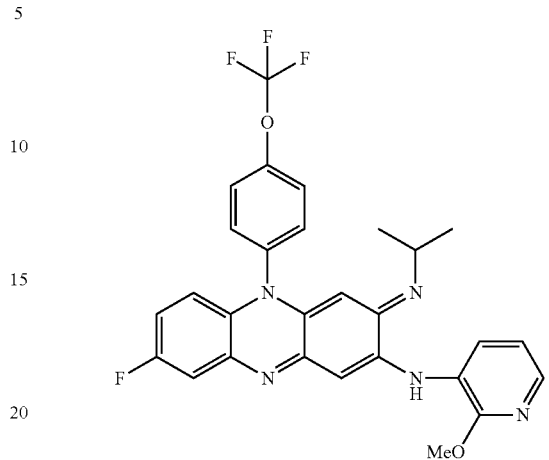

$^1$H NMR (300 MHz, CDCl$_3$) δ: 7.83 (2H, m), 7.58 (2H, d, J=8.1 Hz), 7.39 (3H, m), 6.90 (2H, m), 6.88 (1H, s), 6.37 (1H, dd, J=8.7, 5.1 Hz), 5.20 (1H, s), 4.04 (3H, s), 3.43 (1H, m), 1.11 (6H, d, J=6.3 Hz). $^{13}$C NMR (100 MHz, CDCl$_3$) δ: 158.6 (d, J=240 Hz), 155.6, 152.3, 150.4, 149.8, 143.9, 139.2, 136.3 (d, J=10 Hz), 135.8, 134.6, 130.8, 129.4, 128.2, 125.3, 124.6, 123.7, 116.8, 114.8 (d, J=24 Hz), 114.5 (d, J=9 Hz), 113.4 (d, J=22 Hz), 99.6, 89.1, 53.8, 49.5, 23.5. HRMS (ESI-TOF$^+$): m/z [M+H]$^+$ calcd for C$_{28}$H$_{24}$F$_4$N$_5$O$_2$: 538.1861; found: 538.1880.

TBI-876, 8-Fluoro-5-(4-trifluoromethoxyphenyl)-3-cyclopropylimino-2-(2-methoxy-3-pyridyl)amino-3,5-dihydrophenazine:

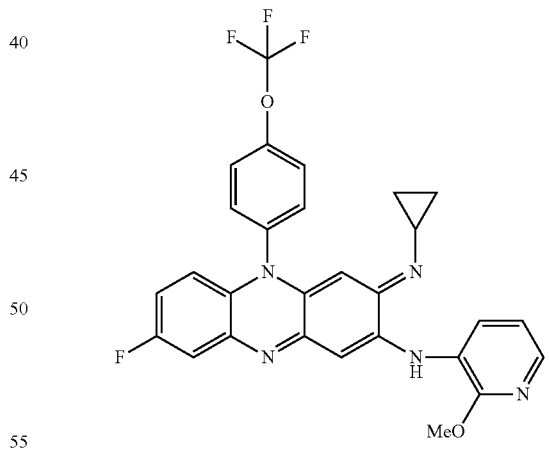

$^1$H NMR (300 MHz, CDCl$_3$) δ: 8.62 (1H, br. s), 7.83 (2H, m), 7.58 (2H, d, J=8.1 Hz), 7.42 (2H, d, J=8.1 Hz), 7.35 (1H, dd, J=9.3, 2.1 Hz), 6.91 (2H, m), 6.84 (1H, s), 6.35 (1H, dd, J=8.1, 5.1 Hz), 5.48 (1H, s), 4.01 (3H, s), 2.71 (1H, m), 0.89 (2H, m), 0.83 (2H, m). $^{13}$C NMR (100 MHz, CDCl$_3$) δ: 158.6 (d, J=240 Hz), 155.5, 152.5, 152.4, 149.7, 143.3, 139.3, 136.5 (d, J=11 Hz), 135.8, 134.5, 130.9, 128.4, 125.4, 124.5, 123.7, 121.7, 116.8, 114.7 (d, J=24 Hz), 114.5 (d, J=9 Hz), 113.4 (d, J=22 Hz), 99.6, 89.4, 53.7, 33.0, 10.2. HRMS (ESI-TOF$^+$): m/z [M+H]$^+$ calcd for C$_{28}$H$_{22}$F$_4$N$_5$O$_2$: 536.1704; found: 536.1735.

TBI-861, 8-Fluoro-5-(4-trifluoromethoxyphenyl)-3-(4-methoxycyclohexyl)imino-2-(2-methoxy-3-pyridyl)amino-3,5-dihydrophenazine:

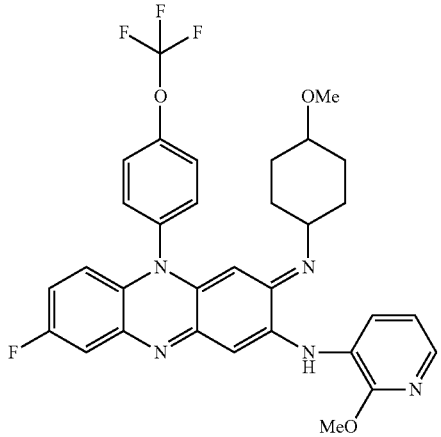 [SMILES: COc1ncccc1Nc1cc2nc3cc(F)ccc3n(-c3ccc(OC(F)(F)F)cc3)c-2c/c1=N\C1CCC(OC)CC1]

$^1$H NMR (300 MHz, CDCl$_3$) δ: 7.85 (2H, m), 7.59 (2H, d, J=7.8 Hz), 7.40 (2H, d, J=7.8 Hz), 7.35 (1H, dd, J=9.3, 2.1 Hz), 6.93 (2H, m), 6.88 (1H, s), 6.42 (1H, m), 5.17 (1H, s), 4.02 (3H, s), 3.35 (3H, s), 3.23 (1H, m), 3.10 (1H, m), 2.06 (2H, m), 1.68 (2H, m), 1.43 (2H, m), 1.23 (2H, m). $^{13}$C NMR (100 MHz, CDCl$_3$) δ: 158.6 (d, J=240 Hz), 155.5, 152.2, 151.1, 149.8, 143.3, 139.2, 136.4 (d, J=11 Hz), 135.8, 134.7, 130.7, 128.1, 125.0, 124.6, 123.8, 121.7, 116.9, 114.9 (d, J=26 Hz), 114.6 (d, J=9 Hz), 113.5 (d, J=22 Hz), 99.8, 89.0, 78.2, 57.0, 55.9, 53.7, 30.7, 29.4. HRMS (ESI-TOF$^+$): m/z [M+H]$^+$ calcd for C$_{32}$H$_{30}$F$_4$N$_5$O$_3$: 608.2207; found: 608.2181.

TBI-862, 8-Fluoro-5-(4-trifluoromethoxyphenyl)-3-cyclohexylimino-2-(2-methoxy-3-pyridyl)amino-3,5-dihydrophenazine:

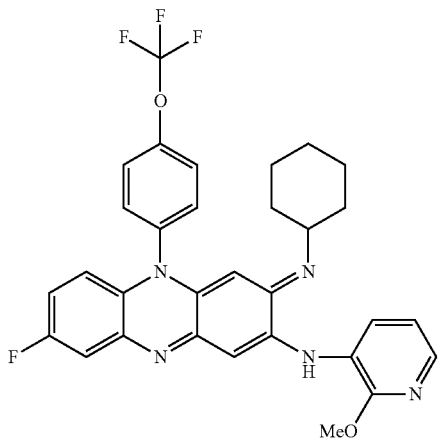 [SMILES: COc1ncccc1Nc1cc2nc3cc(F)ccc3n(-c3ccc(OC(F)(F)F)cc3)c-2c/c1=N\C1CCCCC1]

$^1$H NMR (300 MHz, CDCl$_3$) δ: 7.83 (2H, m), 7.59 (2H, d, J=7.8 Hz), 7.40 (3H, m), 6.92 (2H, m), 6.87 (1H, s), 6.42 (1H, m), 5.17 (1H, s), 4.03 (3H, s), 3.08 (1H, m), 1.76 (2H, m), 1.58 (3H, m), 1.41 (2H, m), 1.25 (3H, m). $^{13}$C NMR (100 MHz, CDCl$_3$) δ: 158.6 (d, J=240 Hz), 155.5, 152.4, 150.5, 149.7, 143.4, 139.1, 136.2 (d, J=11 Hz), 135.9, 134.6, 130.8, 128.1, 125.0, 124.7, 123.9, 121.7, 116.8, 114.9 (d, J=24 Hz), 114.5 (d, J=9 Hz), 113.5 (d, J=22 Hz), 99.7, 89.3, 57.7, 53.7, 33.5, 25.9, 24.3. HRMS (ESI-TOF$^+$): m/z [M+H]$^+$ calcd for C$_{31}$H$_{28}$F$_4$N$_5$O$_2$: 578.2174; found: 578.2114.

TBI-863, 8-Fluoro-5-(4-trifluoromethoxyphenyl)-3-(1-methylethyl)imino-2-(6-methyl-3-pyridyl)amino-3,5-dihydrophenazine:

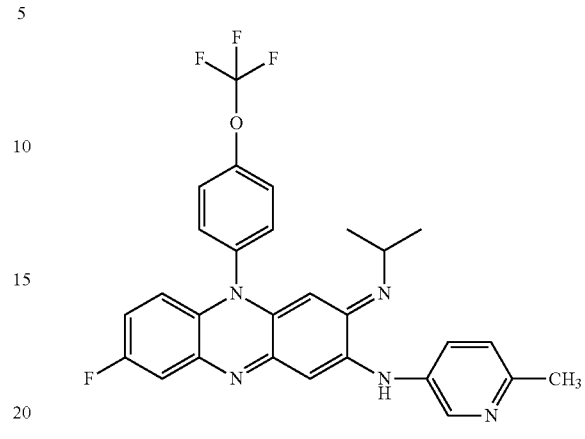

$^1$H NMR (300 MHz, CDCl$_3$) δ: 8.46 (1H, d, J=2.1 Hz), 7.67 (1H, dd, J=8.1, 2.4 Hz), 7.59 (2H, d, J=8.1 Hz), 7.40 (2H, d, J=8.1 Hz), 7.37 (1H, m), 7.17 (1H, d, J=8.1 Hz), 6.85 (1H, m), 6.68 (1H, s), 6.40 (1H, m), 5.21 (1H, s), 3.44 (1H, m), 2.56 (3H, s), 1.10 (6H, d, J=6.3 Hz). $^{13}$C NMR (100 MHz, CDCl$_3$) δ: 158.6 (d, J=241 Hz), 153.7, 152.0, 150.3, 149.8, 145.1, 143.9, 136.5 (d, J=11 Hz), 135.8, 134.7, 133.8, 130.7, 129.7, 127.9, 123.7, 123.2, 119.1, 114.7 (d, J=24 Hz), 114.6 (d, J=9 Hz), 113.4 (d, J=22 Hz), 98.4, 88.9, 49.5, 23.8, 23.4. HRMS (ESI-TOF$^+$): m/z [M+H]$^+$ calcd for C$_{78}$H$_{24}$F$_4$N$_5$O: 522.1911; found: 522.1898.

TBI-864, 8-Fluoro-5-(4-trifluoromethoxyphenyl)-3-cyclopropylimino-2-(6-methyl-3-pyridyl)amino-3,5-dihydrophenazine:

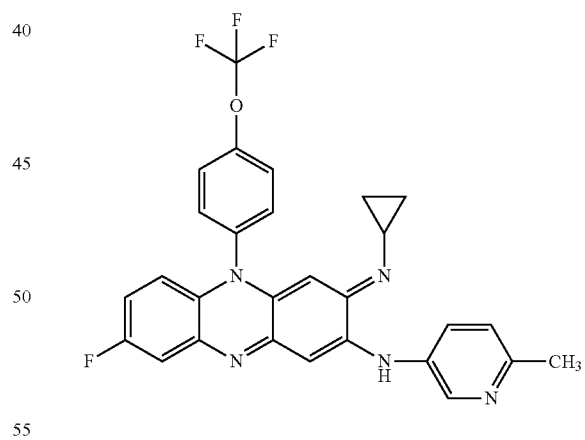

$^1$H NMR (300 MHz, CDCl$_3$) δ: 8.42 (1H, br. s), 7.63 (1H, dd, J=8.1, 2.4 Hz), 7.58 (2H, d, J=8.1 Hz), 7.42 (2H, d, J=8.1 Hz), 7.34 (1H, m), 7.16 (1H, d, J=8.1 Hz), 6.85 (1H, m), 6.62 (1H, s), 6.35 (1H, dd, J=9.3, 5.4 Hz), 5.48 (1H, s), 2.71 (1H, m), 2.56 (3H, s), 0.88 (2H, m), 0.83 (2H, m). $^{13}$C NMR (100 MHz, CDCl$_3$) δ: 158.6 (d, J=242 Hz), 153.9, 152.2, 149.7, 144.9, 144.0, 143.8, 136.5 (d, J=10 Hz), 135.8, 134.5, 133.6, 130.8, 129.9, 128.2, 123.7, 123.3, 119.1, 114.7 (d, J=23 Hz), 114.6 (d, J=10 Hz), 113.4 (d, J=23 Hz), 98.4, 89.2, 33.0, 23.9, 11.4. HRMS (ESI-TOF$^+$): m/z [M+H]$^+$ calcd for C$_{28}$H$_{22}$F$_4$N$_5$O: 520.1755; found: 520.1743.

TBI-865, 8-Fluoro-5-(4-trifluoromethoxyphenyl)-3-cyclohexylimino-2-(6-methyl-3-pyridyl)amino-3,5-dihydrophenazine:

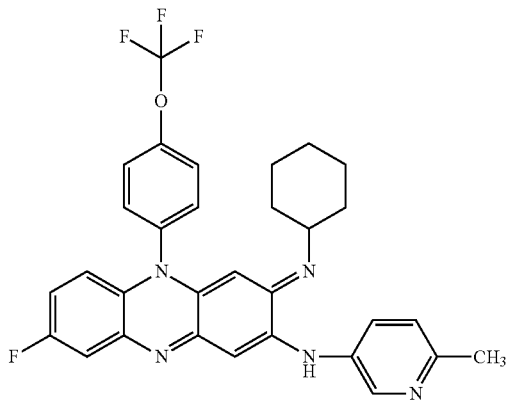 [SMILES: Cc1ccc(Nc2cc3nc4cc(F)ccc4n(-c4ccc(OC(F)(F)F)cc4)c-3c/c2=N\C2CCCCC2)cn1]

$^1$H NMR (300 MHz, CDCl$_3$) δ: 8.45 (1H, br. s), 7.66 (1H, dd, J=8.1, 2.1 Hz), 7.59 (2H, d, J=8.1 Hz), 7.40 (2H, d, J=8.1 Hz), 7.36 (1H, m), 7.17 (1H, d, J=8.1 Hz), 6.87 (1H, m), 6.67 (1H, s), 6.43 (1H, m), 5.17 (1H, s), 3.04 (1H, m), 2.56 (3H, s), 1.73 (2H, m), 1.58 (3H, m), 1.37 (2H, m), 1.16 (3H, m). $^{13}$C NMR (100 MHz, CDCl$_3$) δ: 159.8 (d, J=239 Hz), 153.7, 152.1, 150.4, 149.7, 145.1, 143.9, 136.5 (d, J=10 Hz), 135.9, 134.7, 133.9, 130.8, 129.7, 127.9, 123.9, 123.2, 119.1, 114.9 (d, J=23 Hz), 114.6 (d, J=10 Hz), 113.4 (d, J=23 Hz), 98.4, 89.2, 58.2, 33.6, 25.8, 24.7, 23.8. HRMS (ESI-TOF$^+$): m/z [M+H]$^+$ calcd for C$_{31}$H$_{28}$F$_4$N$_5$O: 562.2224; found: 562.2182.

TBI-866, 8-Fluoro-5-(4-trifluoromethoxyphenyl)-3-(4-methoxycyclohexyl)imino-2-(6-methyl-3-pyridyl)amino-3,5-dihydrophenazine:

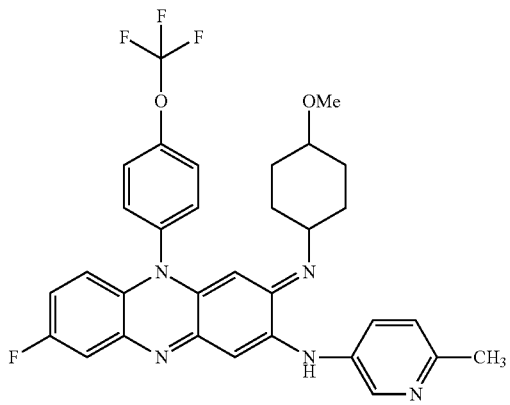 [SMILES: COC1CCC(/N=c2\cc3n(-c4ccc(OC(F)(F)F)cc4)c4ccc(F)cc4nc-3cc2Nc2ccc(C)nc2)CC1]

$^1$H NMR (300 MHz, CDCl$_3$) δ: 8.45 (1H, br. s), 7.67 (1H, br. d, J=7.8 Hz), 7.59 (2H, d, J=8.1 Hz), 7.40 (2H, d, J=8.1 Hz), 7.37 (1H, m), 7.18 (1H, d, J=7.8 Hz), 6.88 (1H, m), 6.68 (1H, s), 6.44 (1H, m), 5.18 (1H, s), 3.36 (3H, s), 3.19 (1H, m), 3.07 (1H, m), 2.57 (3H, s), 2.07 (2H, m), 1.68 (2H, m), 1.43 (2H, m), 1.17 (2H, m). $^{13}$C NMR (100 MHz, CDCl$_3$) δ: 158.6 (d, J=239 Hz), 153.8, 151.9, 151.0, 149.8, 144.9, 143.9, 136.5 (d, J=10 Hz), 135.8, 134.5, 133.8, 130.8, 129.7, 127.9, 123.8, 123.3, 119.1, 114.9 (d, J=24 Hz), 114.6 (d, J=10 Hz), 113.5 (d, J=21 Hz), 98.5, 88.9, 78.4, 57.4, 55.8, 31.1, 29.9, 23.8. HRMS (ESI-TOF$^+$): m/z [M+H]$^+$ calcd for C$_{32}$H$_{30}$F$_4$N$_5$O$_7$: 592.2271; found: 592.2247.

TBI-898, 7-Methoxy-5-(4-chlorophenyl)-3 ethylethyl)imino-2-(6-methyl-3-pyridyl)amino-3,5-dihydrophenazine:

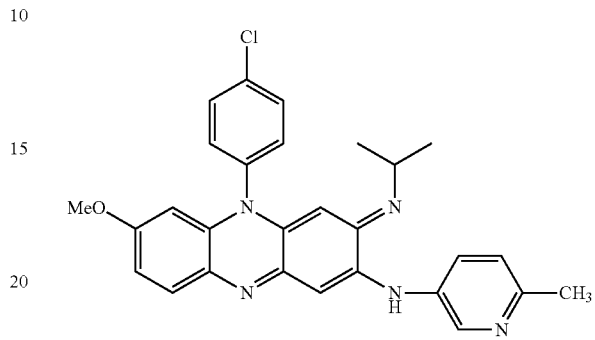

$^1$H NMR (300 MHz, CDCl$_3$) 8.44 (1H, d, J=1.5 Hz), 7.70 (2H, d, J=7.8 Hz), 7.67 (1H, m), 7.61 (1H, d, J=9.0 Hz), 7.29 (2H, d, J=7.8 Hz), 7.14 (1H, d, J=8.4 Hz), 6.77 (1H, dd, J=9.0, 2.1 Hz), 6.70 (1H, s), 5.91 (1H, d, J=2.1 Hz), 5.26 (1H, s), 3.70 (3H, s), 3.45 (1H, m), 2.55 (3H, s), 1.09 (6H, d, J=6.3 Hz). $^{13}$C NMR (100 MHz, CDCl$_3$) δ: 159.3, 152.9, 150.4, 148.7, 143.5, 143.4, 136.1, 135.7, 134.7, 134.3, 132.6, 131.7, 130.6, 130.3, 129.5, 129.1, 123.1, 109.4, 99.1, 98.9, 89.4, 55.5, 49.3, 23.8, 23.6. HRMS (ESI-TOF$^+$): m/z [M+H]$^+$ calcd for C$_{28}$H$_{27}$ClN$_5$O: 484.1899; found: 484.1890.

TBI-867, 7-Methoxy-5-(4-chlorophenyl)-3-(4-methoxycyclohexyl)imino-2-(6-methyl-3-pyridyl-amino)-3,5-dihydrophenazine:

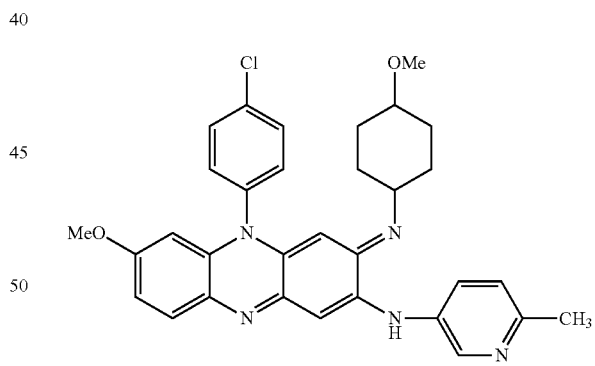

$^1$H NMR (300 MHz, CDCl$_3$) δ: 8.43 (1H, br. s), 7.70 (2H, d, J=8.1 Hz), 7.67 (1H, m), 7.61 (1H, d, J=9.0 Hz), 7.29 (2H, d, J=8.1 Hz), 7.14 (1H, d, J=8.4 Hz), 6.78 (1H, dd, J=9.0, 1.8 Hz), 6.71 (1H, s), 5.94 (1H, d, J=1.8 Hz), 5.24 (1H, s), 3.71 (3H, s), 3.36 (3H, s), 3.18 (1H, m), 3.09 (1H, m), 2.55 (3H, s), 2.07 (2H, m), 1.70 (2H, m), 1.42 (2H, m), 1.17 (2H, m). $^{13}$C NMR (100 MHz, CDCl$_3$) δ: 159.4, 153.0, 151.2, 148.5, 143.5, 143.3, 136.0, 135.9, 134.7, 134.2, 132.5, 131.6, 130.7, 130.2, 129.5, 129.1, 123.1, 109.6, 99.2, 98.8, 89.4, 78.5, 57.2, 55.8, 55.5, 31.2, 29.9, 23.8. HRMS (ESI-TOF$^+$): m/z [M+H]$^+$ calcd for C$_{32}$H$_{33}$ClN$_5$O$_2$: 554.2277; found: 554.2269.

TBI-868, 7-Methoxy-5-(4-chlorophenyl)-3-cyclopropylimino-2-(6-methyl-3-pyridyl)amino-3,5-dihydrophenazine:

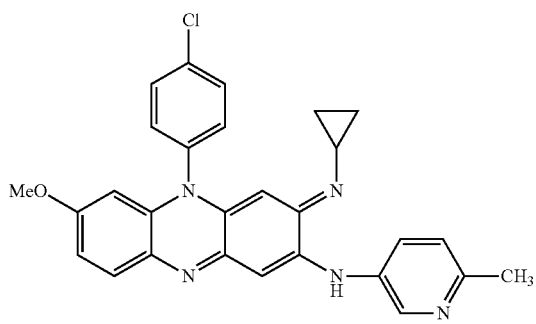 [SMILES: COc1ccc2nc3cc(Nc4ccc(C)nc4)/c(=N/C4CC4)cc-3n(-c3ccc(Cl)cc3)c2c1]

$^1$H NMR (300 MHz, CDCl$_3$) δ: 8.40 (1H, d, J=2.1 Hz), 7.70 (2H, d, J=8.7 Hz), 7.64 (1H, dd, J=8.7, 2.1 Hz), 7.61 (1H, d, J=9.0 Hz), 7.31 (2H, d, J=8.7 Hz), 7.14 (1H, d, J=8.7 Hz), 6.76 (1H, dd, J=9.0, 2.4 Hz), 6.65 (1H, s), 5.90 (1H, d, J=2.4 Hz), 5.53 (1H, s), 3.70 (3H, s), 2.72 (1H, m), 2.54 (3H, s), 0.87 (2H, m), 0.79 (2H, m). $^{13}$C NMR (100 MHz, CDCl$_3$) δ: 159.4, 153.1, 152.6, 148.9, 143.6, 143.2, 136.1, 135.7, 134.5, 134.2, 132.8, 131.8, 130.7, 130.4. 129.4, 129.3, 123.1, 109.3, 99.1, 98.9, 89.8, 55.5, 32.8, 23.8, 9.8. HRMS (ESI-TOF$^+$): m/z [M+H]$^+$ calcd for C$_{28}$H$_{25}$ClN$_5$O: 482.1660; found: 482.1667.

TBI-869, 7-Methoxy-5-(4-chlorophenyl)-3-cyclohexylimino-2-(6-methyl-3-pyridyl)amino-3,5-dihydrophenazine:

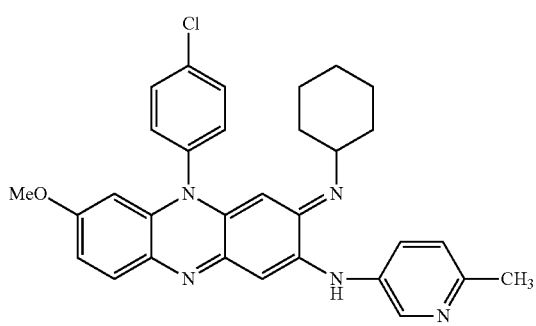 [SMILES: COc1ccc2nc3cc(Nc4ccc(C)nc4)/c(=N/C4CCCCC4)cc-3n(-c3ccc(Cl)cc3)c2c1]

$^1$H NMR (300 MHz, CDCl$_3$) δ: 8.44 (1H, br. s), 7.70 (2H, d, J=8.4 Hz), 7.64 (1H, m), 7.61 (1H, m), 7.31 (2H, d, J=8.7 Hz), 7.14 (1H, d, J=7.8 Hz), 6.81 (1H, m), 6.74 (1H, s), 5.96 (1H, br. s), 5.26 (1H, s), 3.70 (3H, s), 3.05 (1H, m), 2.53 (3H, s), 1.72 (2H, m), 1.60 (3H, m), 1.34 (2H, m), 1.16 (3H, m). $^{13}$C NMR (100 MHz, CDCl$_3$) δ: 160.2, 153.1, 152.7, 150.7, 143.6, 143.1, 135.9, 135.8, 134.7, 134.3, 132.4, 131.6, 130.6, 130.2, 129.5, 129.4, 123.1, 109.7, 99.2, 98.7, 89.7, 57.7, 55.6, 33.4, 25.7, 24.7, 23.8. HRMS (ESI-TOF$^+$): m/z [M+H]$^+$ calcd for C$_{31}$H$_{31}$ClN$_5$O: 524.2174; found: 524.2155.

TBI-858, 7-Fluoro-5-(4-trifluoromethoxyphenyl)-3-(1-methylethyl)imino-2-(2-methoxy-3-pyridyl)amino-3,5-dihydrophenazine:

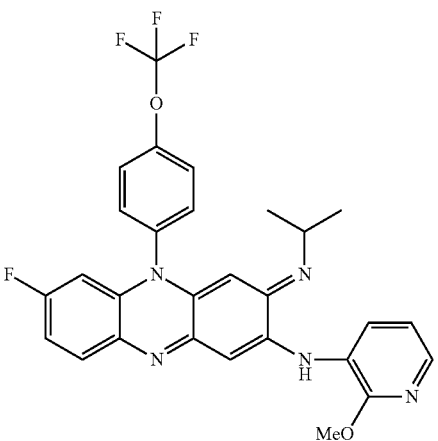 [SMILES: COc1ncccc1Nc1cc2nc3ccc(F)cc3n(-c3ccc(OC(F)(F)F)cc3)c-2c/c1=N\C(C)C]

$^1$H NMR (300 MHz, CDCl$_3$) δ: 8.88 (1H, br. s), 7.82 (2H, m), 7.64 (1H, m), 7.59 (2H, d, J=8.7 Hz), 7.40 (2H, d, J=8.7 Hz), 6.91 (2H, m), 6.87 (1H, s), 6.12 (1H, m), 5.24 (1H, s), 4.03 (3H, s), 3.42 (1H, m), 1.09 (6H, d, J=6.3 Hz). $^{13}$C NMR (100 MHz, CDCl$_3$) δ: 161.2 (d, J=246 Hz), 155.5, 150.5, 150.4, 149.9, 142.7, 138.9, 135.5, 134.4, 132.5 (d, J=11.5 Hz), 132.3, 130.7, 129.8 (d, J=9.9 Hz), 124.9, 124.8, 123.8, 116.8, 110.4 (d, J=23.4 Hz), 100.6 (d, J=28.6 Hz), 100.0, 90.0, 53.7, 49.5, 23.5. HRMS (ESI-TOF$^+$): m/z [M+H]$^+$ calcd for C$_{28}$H$_{24}$F$_4$N$_5$O$_2$: 538.1861; found: 538.1833.

TBI-857, 7-Fluoro-5-(4-trifluoromethoxyphenyl)-3-cyclopropylimino-2-(2-methoxy-3-pyridyl-amino-3,5-dihydrophenazine:

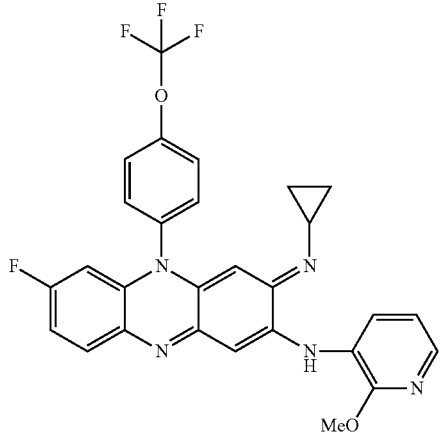 [SMILES: COc1ncccc1Nc1cc2nc3ccc(F)cc3n(-c3ccc(OC(F)(F)F)cc3)c-2c/c1=N\C1CC1]

$^1$H NMR (300 MHz, CDCl$_3$) δ: 8.54 (1H, br. s), 7.80 (2H, m), 7.62 (1H, dd, J=8.7, 6.0 Hz), 7.59 (2H, d=8.1 Hz), 7.42 (2H, d, J=8.1 Hz), 6.90 (2H, in), 6.83 (1H, s), 6.09 (1H, dd, J=7.2, 2.4 Hz), 5.52 (1H, s), 4.01 (3H, s), 2.71 (1H, m), 0.90 (2H, m), 0.84 (2H, m). $^{13}$C NMR (100 MHz, CDCl$_3$) δ: 161.2 (d, J=246 Hz), 155.4, 152.4, 150.7, 149.9, 142.5, 139.0, 135.5, 134.2, 132.6 (d, J=11.1 Hz), 132.4, 130.7, 129.6 (d, J=9.6 Hz), 125.0, 124.7, 123.8, 116.8, 110.4 (d, J=23.5 Hz), 100.6 (d, J=28.6 Hz), 100.0, 90.4, 53.7, 33.0, 10.2. HRMS (ESI-TOF$^+$): m/z [M+H]$^+$ calcd for C$_{28}$H$_{22}$F$_4$N$_5$O$_2$: 536.1704; found: 536.1679.

TBI-856, 7-Fluoro-5-(4-trifluoromethoxyphenyl)-3-cyclohexylimino-2-(2-methoxy-3-pyridyl)amino-3,5-dihydrophenazine:

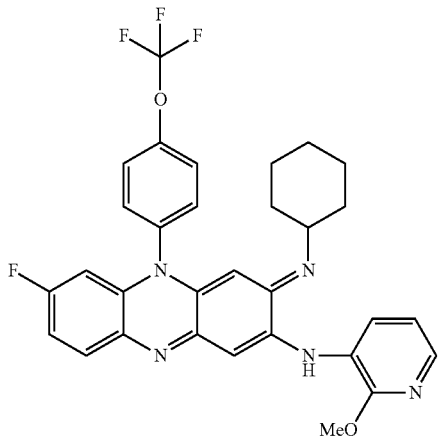 [SMILES: COc1ncccc1Nc1cc2nc3ccc(F)cc3n(-c3ccc(OC(F)(F)F)cc3)c-2c/c1=N\C1CCCCC1]

$^1$H NMR (300 MHz, CDCl$_3$) δ: 8.94 (1H, br. s), 7.81 (2H, m), 7.63 (1H, dd, J=9.3, 6.3 Hz), 7.60 (2H, d, J=8.7 Hz), 7.40 (2H, d, J=8.7 Hz), 6.90 (2H, m), 6.87 (1H, s), 6.16 (1H, dd, J=10.2, 2.4 Hz), 5.20 (1H, s), 4.03 (3H, s), 3.08 (1H, m), 1.75 (2H, m), 1.58 (3H, m), 1.40 (3H, m), 1.21 (2H, m). $^{13}$C NMR (100 MHz, CDCl$_3$) δ: 161.7 (d, J=247 Hz), 155.4, 150.6, 150.5, 149.8, 142.6, 138.7, 135.6, 134.3, 132.4 (d, J=11.5 Hz), 132.3, 130.7, 129.7 (d, J=9.9 Hz), 124.9, 124.5, 123.9, 116.8, 110.4 (d, J=23.4 Hz), 100.5 (d, J=28.6 Hz), 100.0, 90.2, 57.8, 53.7, 33.6, 25.9, 24.3. HRMS (ESI-TOF$^+$): m/z [M+H]$^+$ calcd for C$_{31}$H$_{28}$F$_4$N$_5$O$_2$: 578.2174; found: 578.2161.

TBI-855, 7-Fluoro-5-(4-trifluoromethoxyphenyl)-3-(4-tetrahydropyranyl)imino)-2-(2-methoxy-3-pyridyl)amino-3,5-dihydrophenazine:

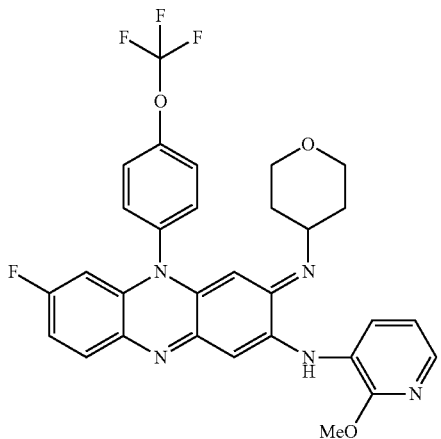 [SMILES: COc1ncccc1Nc1cc2nc3ccc(F)cc3n(-c3ccc(OC(F)(F)F)cc3)c-2c/c1=N\C1CCOCC1]

$^1$H NMR (300 MHz, CDCl$_3$) δ: 8.93 (1H, br. s), 7.83 (2H, m), 7.71 (1H, dd, J=9.3, 6.3 Hz), 7.61 (2H, d, J=8.7 Hz), 7.41 (2H, d, J=8.7 Hz), 6.96 (2H, m), 6.93 (1H, s), 6.18 (1H, s), 5.21 (1H, s), 4.04 (3H, s), 4.01 (2H, m), 3.41 (3H, m), 1.65 (4H, m). $^{13}$C NMR (100 MHz, CDCl$_3$) δ: 161.9 (d, J=246 Hz), 155.4, 151.1, 150.1, 150.0, 142.5, 139.0, 135.5, 134.6, 132.4 (d, J=11.1 Hz), 132.2, 130.5, 130.1 (d, J=9.6 Hz), 125.2, 124.7, 123.7, 116.8, 110.8 (d, J=23.5 Hz), 100.7 (d, J=28.6 Hz), 97.5, 89.7, 65.7, 53.9, 53.8, 33.3. HRMS (ESI-TOF$^+$): m/z [M+H]$^+$ calcd for C$_{30}$H$_{26}$F$_4$N$_5$O$_3$: 580.1966; found: 580.1930.

TBI-854, 7-Fluoro-5-(4-trifluoromethoxyphenyl)-3-(1-methylethyl)imino-2-(6-methyl-3-pyridyl)amino-3,5-dihydrophenazine:

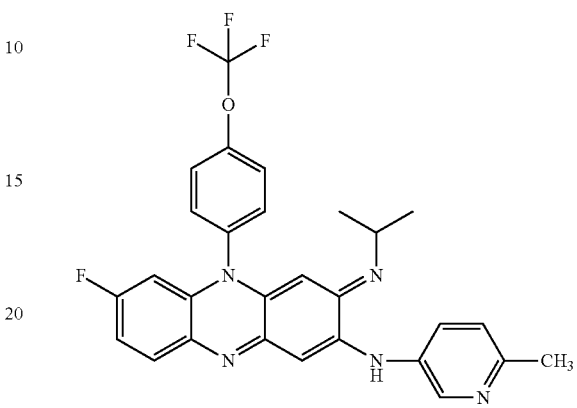

$^1$H NMR (300 MHz, CDCl$_3$) δ: 8.45 (1H, d, J=2.4 Hz), 7.65 (2H, m), 7.59 (2H, d, J=8.7 Hz), 7.40 (2H, d, J=8.7 Hz), 7.16 (1H, d, J=8.1 Hz), 6.88 (1H, m), 6.67 (1H, s), 6.13 (1H, dd, J=10.2, 2.1 Hz), 5.24 (1H, s), 3.43 (1H, m), 2.56 (3H, s), 1.09 (6H, d, J=6.3 Hz). $^{13}$C NMR (100 MHz, CDCl$_3$) δ: 161.6 (d, J=246 Hz), 153.5, 150.3, 150.2, 149.9, 144.2, 143.8, 135.5, 134.4, 134.0, 132.4, 132.3 (d, J=11.1 Hz), 130.6, 129.7 (d, J=9.5 Hz), 129.5, 123.7, 123.2, 110.5 (d, J=23.3 Hz), 100.6 (d, J=28.6 Hz), 98.7, 89.8, 49.5, 23.8, 23.5. HRMS (ESI-TOF$^+$): m/z [M+H]$^+$ calcd for C$_{28}$H$_{24}$F$_4$N$_5$O: 522.1911; found: 522.1872.

TBI-853, 7-Fluoro-5-(4-trifluoromethoxyphenyl)-3-cyclohexylimino-2-(6-methyl-3-pyridyl)amino-3,5-dihydrophenazine:

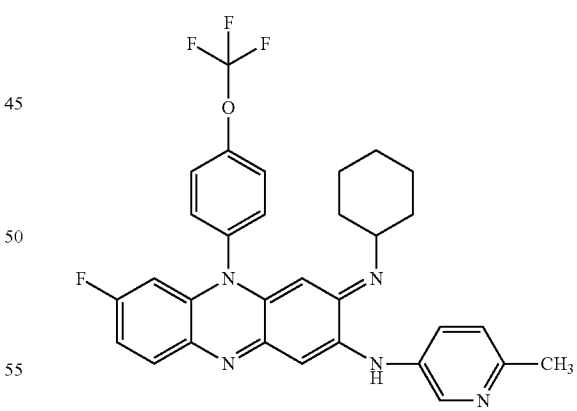

$^1$H NMR (300 MHz, CDCl$_3$) δ: 8.45 (1H, d, J=2.7 Hz), 7.66 (2H, m), 7.60 (2H, d, J=8.7 Hz), 7.40 (2H, d, J=8.7 Hz), 7.16 (1H, d, J=8.4 Hz), 6.87 (1H, m), 6.66 (1H, s), 6.17 (1H, dd, J=11.2, 2.4 Hz), 5.21 (1H, s), 3.04 (1H, m), 2.56 (3H, s), 1.73 (2H, m), 1.58 (3H, m), 1.37 (2H, m), 1.18 (3H, m). $^{13}$C NMR (100 MHz, CDCl$_3$) δ: 161.6 (d, J=246 Hz), 153.5, 150.5, 150.4, 149.9, 144.3, 143.8, 135.7, 134.3, 134.0, 132.3, 132.2 (d, J=11.1 Hz), 130.6, 129.7 (d, J=9.5 Hz), 129.5, 124.0, 123.2, 110.5 (d, J=23.2 Hz), 100.6 (d, J=28.6 Hz), 98.7, 90.1, 58.3, 33.7, 25.8, 24.7, 23.8. HRMS (ESI-TOF⁺): m/z [M+H]⁺ calcd for $C_{31}H_{28}F_4N_5O$: 562.2224; found: 562.2196.

TBI-852, 7-Fluoro-5-(4-trifluoromethoxyphenyl)-3-(4-methoxycyclohexyl)imino-2-(6-methyl-3-pyridyl)amino-3,5-dihydrophenazine:

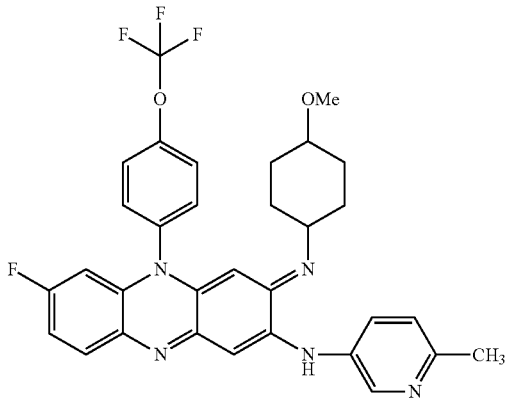 [SMILES: COC1CCC(/N=c2\cc3n(-c4ccc(OC(F)(F)F)cc4)c4cc(F)ccc4nc-3cc2Nc2ccc(C)nc2)CC1]

¹H NMR (300 MHz, CDCl₃) δ: 8.44 (1H, d, J=2.1 Hz), 7.65 (2H, m), 7.59 (2H, d, J=8.4 Hz), 7.39 (2H, d, J=8.4 Hz), 7.16 (1H, d, J=8.1 Hz), 6.89 (1H, m), 6.68 (1H, s), 6.17 (1H, dd, J=11.8, 2.1 Hz), 5.21 (1H, s), 3.35 (3H, s), 3.18 (1H, m), 3.06 (1H, m), 2.56 (3H, s), 2.06 (2H, m), 1.67 (2H, m), 1.38 (2H, m), 1.17 (2H, m). ¹³C NMR (100 MHz, CDCl₃) δ: 161.6 (d, J=246 Hz), 153.6, 151.0, 150.2, 150.0, 144.2, 143.8, 135.5, 134.4, 133.9, 132.3, 132.2 (d, J=11.1 Hz), 130.6, 129.8 (d, J=9.5 Hz), 129.5, 123.8, 123.2, 110.6 (d, J=23.2 Hz), 100.6 (d, J=28.6 Hz), 98.8, 89.8, 78.4, 57.5, 55.8, 31.2, 29.9, 23.8. HRMS (ESI-TOF⁺): m/z [M+H]⁺ calcd for $C_{32}H_{30}F_4N_5O_2$: 592.2271; found: 592.2255.

TBI-1051, 5-(4-Chlorophenyl)-3-(1-methylethyl)imino-2-(pyrimidin-2-yl)amino-3,5-dihydrophenazine:

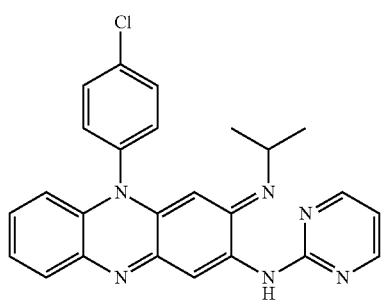 [SMILES: CC(C)/N=c1\cc2n(-c3ccc(Cl)cc3)c3ccccc3nc-2cc1Nc1ncccn1]

¹H NMR (300 MHz, CDCl₃) δ: 9.76 (1H, br s), 8.56 (2H, d, J=4.5 Hz), 8.49 (s, 1H), 7.77 (1H, d, J=6.9 Hz), 7.71 (2H, m), 7.32 (2H, m), 7.17 (2H, m), 6.83 (1H, m), 6.44 (1H, d, J=6.9 Hz), 5.28 (1H, s), 3.47 (1H, m), 1.10 (6H, d, J=6.0 Hz). ¹³C NMR (100 MHz, CDCl₃) δ: 159.3, 157.9, 151.8, 150.1, 140.2, 136.0, 135.7, 135.0, 132.0, 131.7, 130.5, 128.8, 128.3, 122.8, 113.7, 113.5, 108.4, 89.0, 49.4, 23.6. HRMS (ESI-TOF⁺): m/z [M+H]⁺ calcd for $C_{25}H_{22}ClN_6$: 441.1589; found: 441.1589.

TBI-1052, 5-(4-Fluorophenyl)-3-(1-methylethyl)imino-2-(3-nitro-2-pyridyl)amino-3,5-dihydrophenazine:

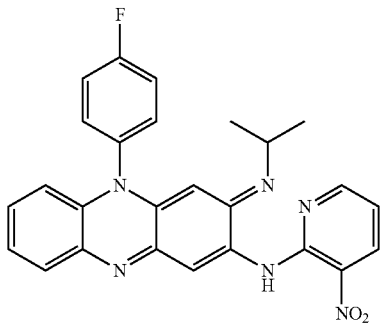 [SMILES: CC(C)/N=c1\cc2n(-c3ccc(F)cc3)c3ccccc3nc-2cc1Nc1ncccc1[N+](=O)[O-]]

¹H NMR (300 MHz, CDCl₃) δ: 12.23 (1H, br s), 8.73 (1H, s), 8.66 (1H, d, J=3.9 Hz), 8.56 (1H, d, J=8.1 Hz), 7.76 (1H, d, J=5.1 Hz), 7.43 (2H, m), 7.36 (2H, m), 7.17 (1H, m), 6.95 (1H, dd, J=7.8, 4.5 Hz), 6.44 (1H, m), 5.28 (1H, s), 3.48 (1H, m), 1.15 (6H, d, J=6.3 Hz). ¹³C NMR (100 MHz, CDCl₃) δ: 162.8 (d, J=247.7 Hz), 154.3, 151.9, 150.6, 148.8, 140.4, 135.6, 135.5, 135.1, 133.2, 132.4, 130.9, 130.8, 129.0, 128.8, 128.5, 122.9, 118.6 (d, J=23.1 Hz), 114.8, 113.8, 111.5, 89.1, 49.5, 23.5. HRMS (ESI-TOF⁺): [M+H]⁺ calcd for $C_{26}H_{22}FN_6O_2$: 469.1783; found: 469.1781.

TBI-1053, 5-(4-Fluorophenyl)-3-(1-methylethyl)imino-2-(pyrimidin-2-yl)amino-3,5-dihydrophenazine:

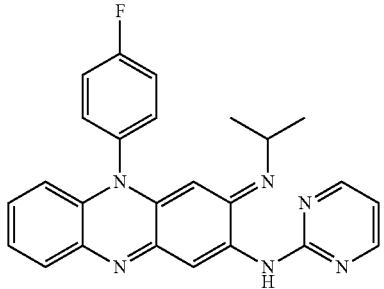

¹H NMR (300 MHz, CDCl₃) δ: 9.75 (1H, br s), 8.54 (2H, d, J=4.8 Hz), 8.48 (1H, s), 7.77 (1H, s), 7.42 (2H, m), 7.35 (2H, m), 7.16 (2H, s), 6.81 (1H, m), 6.45 (1H, s), 5.25 (1H, s), 3.44 (1H, m), 1.08 (6H, d, J=4.8 Hz). ¹³C NMR (100 MHz, CDCl₃) δ: 162.8 (d, J=248.9 Hz), 159.4, 157.8, 151.8, 150.2, 140.1, 135.3, 133.3, 132.2, 131.3, 130.9, 130.8, 130.2, 128.8, 128.3, 122.8, 118.5 (d, J=22.6 Hz), 113.8, 113.5, 108.4, 89.0, 49.4, 23.5. HRMS (ESI-TOF⁺): m/z [M+H]⁺ calcd for $C_{25}H_{22}FN_6$: 425.1884; found: 425.1892.

TBI-1054, 5-(4-Fluorophenyl)-3-(1-methylethyl)imino-2-(2-pyridyl)amino-3,5-dihydrophenazine:

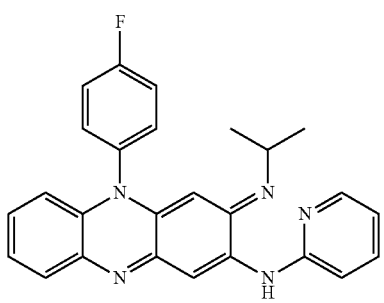 [SMILES: CC(C)/N=c1\cc2n(-c3ccc(F)cc3)c3ccccc3nc-2cc1Nc1ccccn1]

¹H NMR (300 MHz, CDCl₃) δ: 8.39 (1H, d, J=3.0 Hz), 8.28 (1H, s), 7.77 (1H, d, J=6.9 Hz), 7.58 (1H, m), 7.42 (2H, m), 7.36 (2H, m), 7.16 (2H, m), 6.99 (1H, d, J=8.1 Hz), 6.86 (1H, m), 6.46 (1H, d, J=7.8 Hz), 5.26 (1H, s), 3.45 (1H, m), 1.09 (6H, d, J=6.0 Hz). ¹³C NMR (100 MHz, CDCl₃) δ: 162.8 (d, J=249.2 Hz), 154.1, 151.8, 150.6, 148.2, 141.0, 137.1, 135.8, 135.1, 133.5, 132.0, 131.0, 130.9, 128.6, 127.8, 122.7, 118.4 (d, J=22.9 Hz), 116.3, 113.8, 112.8, 105.4, 89.0, 49.3, 23.6. HRMS (ESI-TOF⁺): m/z [M+H]⁺ calcd for C₂₆H₂₃FN₅: 424.1932; found: 424.1929.

TBI-1055, 5-(4-Fluorophenyl)-3-(1-methylethyl)imino-2-(pyrazin-2-yl)amino-3,5-dihydrophenazine:

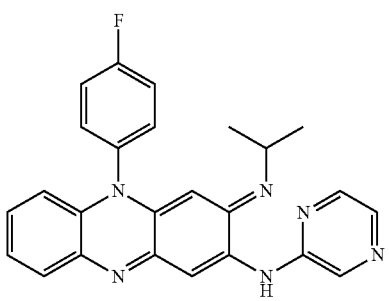 [SMILES: CC(C)/N=c1\cc2n(-c3ccc(F)cc3)c3ccccc3nc-2cc1Nc1cnccn1]

¹H NMR (300 MHz, CDCl₃) δ: 8.44 (1H, s), 8.29 (2H, m), 8.05 (1H, d, J=2.7 Hz), 7.78 (1H, dd, J=6.6, 2.7 Hz), 7.43 (2H, m), 7.35 (2H, m), 7.18 (2H, m), 6.45 (1H, dd, J=7.2, 2.1 Hz), 5.26 (1H, s), 3.45 (1H, m), 1.09 (6H, d, J=6.3 Hz). ¹³C NMR (100 MHz, CDCl₃) δ: 162.8 (d, J=249.3 Hz), 151.4, 151.1, 150.5, 141.6, 140.0, 136.3, 135.7, 135.5, 135.4, 133.3, 132.0, 130.9, 130.8, 128.8, 128.3, 128.2, 123.0, 118.5 (d, J=23.1 Hz), 113.9, 107.4, 88.9, 49.3, 23.5. HRMS (ESI-TOF⁺): m/z [M+H]⁺ calcd for C₂₅H₂₂FN₆: 425.1884; found: 425.1883.

TBI-1057, 5-(4-Fluorophenyl)-34 ethylethyl)imino-2-(3-cyano-2-pyridyl)amino-3,5-dihydrophenazine:

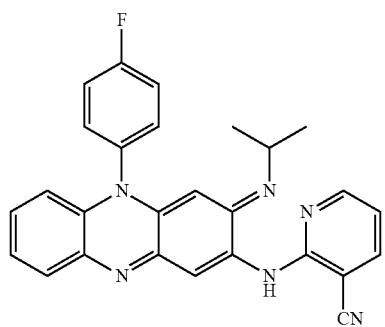 [SMILES: CC(C)/N=c1\cc2n(-c3ccc(F)cc3)c3ccccc3nc-2cc1Nc1ncccc1C#N]

¹H NMR (300 MHz, CDCl₃) δ: 10.29 (1H, br s), 8.59 (1H, s), 8.53 (1H, dd, J=4.8, 1.8 Hz), 7.80 (2H, m), 7.45 (2H, m), 7.38 (2H, m), 7.22 (2H, m), 6.82 (1H, dd, J=7.5, 5.1 Hz), 6.53 (1H, d, J=7.8 Hz), 5.31 (1H, s), 3.48 (1H, m), 1.16 (6H, d, J=6.3 Hz). ¹³C NMR (100 MHz, CDCl₃) δ: 162.9 (d, J=249.3 Hz), 156.7, 151.4, 150.8, 141.2, 140.5, 136.3, 135.8, 133.2, 131.4, 130.7, 130.6, 128.9, 128.3, 123.6, 118.5 (d, J=22.6 Hz), 116.5, 114.2, 108.3, 97.6, 88.4, 48.4, 23.1. HRMS (ESI-TOF⁺): m/z [M+H]⁺ calcd for C₂₇H₂₂FN₆: 448.1884; found: 449.1890.

TBI-1064, 8-Cyano-5-(4-fluorophenyl)-3-(1-methylethyl)imino-2-(2-methoxy-3-pyridyl)amino-3,5-dihydrophenazine:

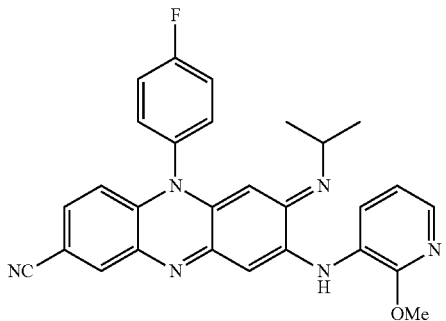 [SMILES: COc1ncccc1Nc1cc2nc3cc(C#N)ccc3n(-c3ccc(F)cc3)c-2c/c1=N\C(C)C]

¹H NMR (300 MHz, CDCl₃) δ: 7.90 (1H, s), 7.83 (1H, m), 7.44 (2H, m), 7.32 (4H, m), 6.94 (1H, m), 6.84 (1H, s), 6.45 (1H, d, J=8.4 Hz), 5.34 (1H, s), 4.03 (3H, s), 3.47 (1H, m), 1.11 (6H, d, J=2.4 Hz). ¹³C NMR (100 MHz, CDCl₃) δ: 163.0 (d, J=249.7 Hz), 155.7, 152.8, 150.2, 143.7, 139.7, 135.4, 135.0, 134.4, 132.6, 131.9, 130.7, 130.6, 130.0, 125.6, 124.3, 118.9, 118.8 (d, J=15.1 Hz), 116.8, 114.5, 105.5, 99.6, 91.2, 53.8, 49.8, 23.5, 21.1. HRMS (ESI-TOF⁺): m/z [M+H]⁺ calcd for C₂₉H₂₄FN₆O: 479.1990; found: 479.1980.

TBI-1065, 8-Cyano-5-(4-fluorophenyl)-3-(4-methyoxy-cyclohexyl)imino-2-(2-methoxy-3-pyridyl)amino-3,5-dihydrophenazine:

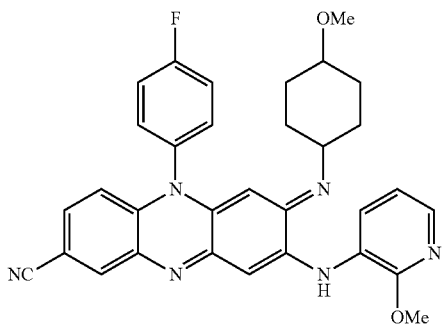 [SMILES: COc1ncccc1Nc1cc2nc3cc(C#N)ccc3n(-c3ccc(F)cc3)c-2c/c1=N\C1CCC(OC)CC1]

¹H NMR (300 MHz, CDCl₃) δ: 7.92 (1H, s), 7.86 (1H, d, 14.5 Hz), 7.82 (1H, d, J=8.1 Hz), 7.45 (2H, m), 7.33 (3H, m), 6.95 (1H, dd, J=7.2, 5.4 Hz), 6.87 (1H, s), 6.49 (1H, d, J=8.4 Hz), 5.33 (1H, s), 4.04 (3H, s), 3.37 (3H, s), 3.25 (1H, m), 3.15 (1H, m), 2.09 (2H, m), 1.70 (2H, m), 1.47 (2H, m), 1.24 (2H, m), ¹³C NMR (100 MHz, CDCl₃) δ: 163.0 (d, J=250.9 Hz), 155.5, 152.7, 150.9, 143.5, 139.5, 135.4, 134.8, 134.4, 132.5, 132.0, 130.6, 130.5, 130.1, 125.3, 124.2, 118.9, 118.7 (d, J=14.6 Hz), 116.9, 114.5, 105.6, 99.7, 91.1, 57.2, 55.8, 53.8, 30.7, 29.3. HRMS (ESI-TOF⁺): m/z [M+H]⁺ calcd for C₃₂H₃₀FN₆O₂: 549.2409; found: 549.2393.

TBI-1066, 8-Cyano-5-(4-fluorophenyl)-3-(4-tetrahydropyranyl)imino-2-(2-methoxy-3-pyridyl)amino-3,5-dihydrophenazine:

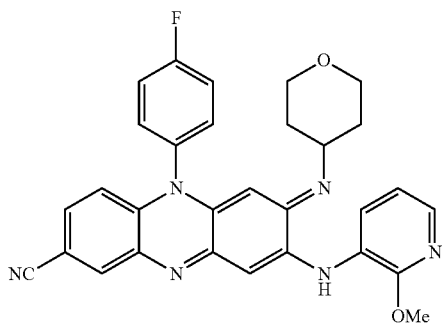 [SMILES: COc1ncccc1Nc1cc2nc3cc(C#N)ccc3n(-c3ccc(F)cc3)c-2c/c1=N\C1CCOCC1]

¹H NMR (300 MHz, CDCl₃) δ: 9.02 (1H, br s), 7.93 (1H, d, J=1.5 Hz), 7.84 (2H, m), 7.46 (2H, m), 7.34 (3H, m), 6.95 (1H, dd, J=7.5, 5.4 Hz), 6.90 (1H, s), 6.49 (1H, d, J=8.4 Hz), 5.31 (1H, s), 4.05 (3H, s), 3.99 (2H, m), 3.50 (3H, m), 1.66 (4H, m). ¹³C NMR (100 MHz, CDCl₃) δ: 177.4, 163.1 (d, J=250.9 Hz), 155.4, 152.5, 150.8, 143.4, 140.5, 139.5, 135.4, 134.7, 134.6, 133.7, 132.5, 132.1, 130.8, 130.6, 130.5, 130.2, 130.1, 130.0, 125.1, 125.0, 124.3, 118.8 (d, J=22.6 Hz), 116.9, 116.2, 114.6, 105.8, 101.1, 100.2, 99.9, 90.8, 65.5, 53.8, 53.7, 33.3.

TBI-1067, 8-Cyano-5-(4-fluorophenyl)-3-(1-methylethyl)imino-2-(6-methyl-3-pyridyl)amino-3,5-dihydrophenazine:

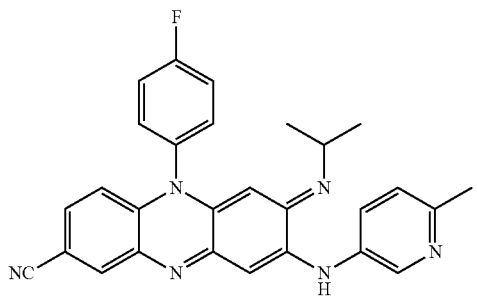 [SMILES: Cc1ccc(Nc2cc3nc4cc(C#N)ccc4n(-c4ccc(F)cc4)c-3c/c2=N\C(C)C)cn1]

¹H NMR (300 MHz, CDCl₃) δ: 8.46 (1H, d, J=2.4 Hz), 7.89 (1H, s), 7.66 (1H, dd, J=8.4, 2.7 Hz), 7.45 (2H, m), 7.31 (3H, m), 7.19 (1H, d, J=8.1 Hz), 6.64 (1H, s), 6.46 (1H, d, J=8.7 Hz), 5.34 (1H, s), 3.47 (1H, m), 2.59 (3H, s), 1.10 (6H, d, J=6.3 Hz). ¹³C NMR (100 MHz, CDCl₃) δ: 163.0 (d, J=250.1 Hz), 154.1, 152.5, 150.0, 145.3, 144.0, 135.4, 134.8, 134.5, 133.5, 132.6, 132.0, 130.6, 130.5, 130.0, 123.3, 118.8 (d, J=22.6 Hz), 118.7, 114.5, 105.6, 98.5, 91.0, 49.8, 23.9, 23.5. HRMS (ESI-TOF⁺): m/z [M+H]⁺ calcd for C₂₈H₂₄FN₆: 463.2041; found: 463.2053.

TBI-1068, 8-Cyano-5-(4-fluorophenyl)-3-(4-methyoxycyclohexyl)imino-2-(6-methyl-3-pyridyl)amino-3,5-dihydrophenazine:

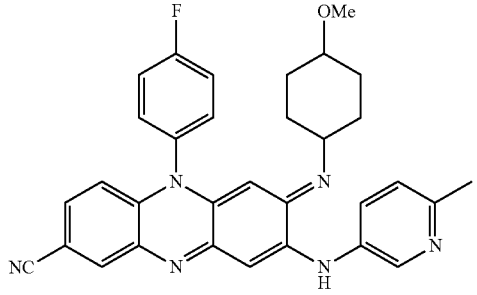 [SMILES: COC1CCC(/N=c2\cc3n(-c4ccc(F)cc4)c4ccc(C#N)cc4nc-3cc2Nc2ccc(C)nc2)CC1]

¹H NMR (300 MHz, CDCl₃) δ: 8.45 (1H, s), 7.90 (1H, s), 7.65 (1H, d, J=8.7 Hz), 7.44 (2H, m), 7.32 (3H, m), 7.19 (1H, d, J=8.1 Hz), 6.64 (1H, s), 6.49 (1H, d, J=8.4 Hz), 5.32 (1H, s), 3.36 (3H, s), 3.20 (1H, m), 3.10 (1H, m), 2.57 (3H, s), 2.08 (2H, m), 1.67 (2H, m), 1.45 (2H, m), 1.21 (2H, m). ¹³C NMR (100 MHz, CDCl₃) δ: 163.0 (d, J=251.3 Hz), 154.2, 152.4, 150.8, 145.2, 144.0, 135.4, 134.7, 134.5, 133.4, 132.5, 132.0, 130.6, 130.5, 130.0, 129.9, 123.3, 118.8 (d, J=22.6 Hz), 118.9, 114.6, 105.7, 98.6, 91.0, 78.3, 57.7, 55.8, 31.2, 29.8, 23.9. HRMS (ESI-TOF⁺): m/z [M+H]⁺ calcd for C₃₂H₃₀FN₆O: 533.2460; found: 533.2446.

TBI-1075, 5-(4-Chlorophenyl)-3-(1-methylethyl)imino-2-(3-cyano-2-pyridyl)amino-3,5-dihydrophenazine:

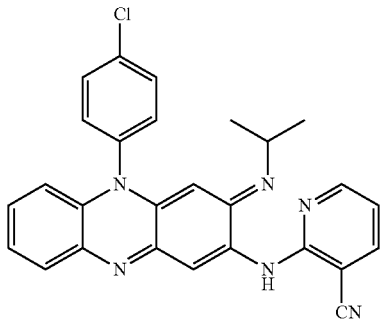 [SMILES: CC(C)/N=c1\cc2n(-c3ccc(Cl)cc3)c3ccccc3nc-2cc1Nc1ncccc1C#N]

¹H NMR (300 MHz, CDCl₃) δ: 10.29 (1H, br s), 8.58 (1H, s), 8.52 (1H, d, J=3.3 Hz), 7.81 (2H, m), 7.73 (2H, d, J=8.4 Hz), 7.33 (2H, d, J=8.4 Hz), 7.21 (2H, m), 6.82 (1H, dd, J=7.2, 4.8 Hz), 6.51 (1H, d, J=8.1 Hz), 5.32 (1H, s), 3.49 (1H, m), 1.16 (6H, d=6.0 Hz). ¹³C NMR (100 MHz, CDCl₃) δ: 156.5, 152.1, 151.3, 150.8, 141.2, 140.4, 136.2, 136.0, 135.7, 135.5, 131.7, 131.3, 130.2, 128.9, 128.3, 123.6, 116.4, 114.3, 114.2, 108.3, 97.5, 88.5, 48.5, 23.2. HRMS (ESI-TOF⁺): m/z [M+H]⁺ calcd for C₂₇H₂₂ClN₆: 465.1589; found: 465.1583.

TBI-1076, 5-(4-Chlorophenyl)-3-(1-methylethyl)imino-2-(2-pyridyl)amino-3,5-dihydrophenazine:

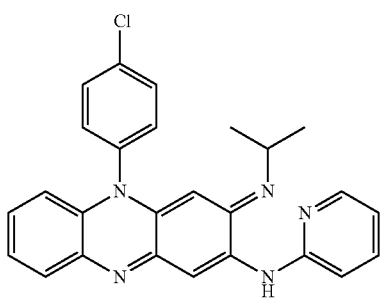 [SMILES: CC(C)/N=c1\cc2n(-c3ccc(Cl)cc3)c3ccccc3nc-2cc1Nc1ccccn1]

¹H NMR (300 MHz, CDCl₃) δ: 8.38 (1H, d, J=4.5 Hz), 82.7 (1H, s), 7.75 (1H, d, J=8.1 Hz), 7.70 (2H, d, J=8.7 Hz), 7.57 (1H, m), 7.31 (2H, d, J=8.7 Hz), 7.15 (2H, m), 6.98 (1H, d, J=8.7 Hz), 6.85 (1H, m), 6.43 (1H, d, J=7.5 Hz), 5.26 (1H, s), 3.45 (1H, m), 1.08 (6H, d, J=6.0 Hz). ¹³C NMR (100 MHz, CDCl₃) δ: 154.1, 151.7, 150.5, 148.2, 141.0, 137.1, 136.1, 135.7, 135.6, 134.8, 131.7, 131.6, 130.5, 128.6, 127.8, 122.8, 116.3, 113.7, 112.8, 105.4, 89.0, 49.3, 23.6. HRMS (ESI-TOF⁺): m/z [M+H]⁺ calcd for C₂₆H₂₃ClN₅: 440.1636; found: 440.1647.

TBI-1077, 5-(4-Chlorophenyl)-3-(1-ethylethyl)imino-2-(pyrazin-2-yl)amino-3,5-dihydrophenazine:

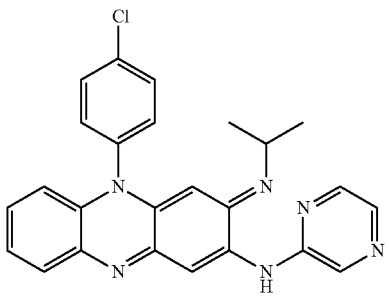

$^1$H NMR (300 MHz, CDCl$_3$) δ: 8.43 (1H, s), 8.29 (2H, m), 8.05 (1H, d, J=2.4 Hz), 7.77 (1H, d, J=6.9 Hz), 7.71 (2H, d, J=8.1 Hz), 7.31 (2H, d, J=8.1 Hz), 7.17 (2H, m), 6.45 (1H, d, J=7.8 Hz), 5.28 (1H, s), 3.47 (1H, m), 1.11 (6H, d, J=6.3 Hz). $^{13}$C NMR (100 MHz, CDCl$_3$) δ: 151.4, 151.0, 150.4, 141.6, 140.0, 136.4, 135.9, 135.8, 135.5, 135.1, 131.7, 130.4, 128.9, 128.4, 123.0, 113.8, 107.5, 88.9, 49.3, 23.6. HRMS (ESI-TOF$^+$): m/z [M+H]$^+$ calcd for C$_{25}$H$_{22}$ClN$_6$: 441.1589; found: 441.1567.

TBI-1078, 5-(4-Fluorophenyl)-3-(4-methoxycyclohexyl)imino-2-(2-pyridyl)amino-3,5-dihydrophenazine:

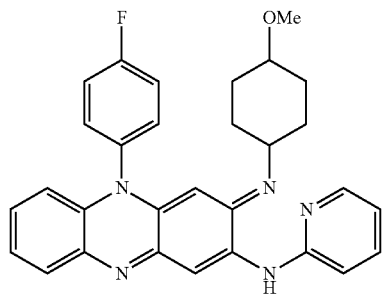 [SMILES: COC1CCC(/N=c2\cc3n(-c4ccc(F)cc4)c4ccccc4nc-3cc2Nc2ccccn2)CC1]

$^1$H NMR (300 MHz, CDCl$_3$) δ: 9.20 (1H, br s), 8.38 (1H, d, J=3.6 Hz), 8.26 (1H, s), 7.76 (1H, dd, J=7.2, 2.1 Hz), 7.57 (1H, m), 7.41 (2H, m), 7.34 (2H, m), 7.16 (2H, m), 6.97 (1H, d, J=8.4 Hz), 6.85 (1H, m), 6.48 (1H, dd, J=7.2, 1.8 Hz), 5.23 (1H, s), 3.36 (3H, s), 3.19 (1H, m), 3.07 (1H, m), 2.06 (2H, m), 1.68 (2H, m), 1.41 (2H, m), 1.21 (2H, m). $^{13}$C NMR (100 MHz, CDCl$_3$) δ: 162.8 (d, J=249.3 Hz), 154.0, 151.6, 151.4, 148.2, 140.9, 137.1, 135.8, 135.1, 133.4, 131.9, 130.9, 130.8, 128.6, 127.9, 122.8, 118.4 (d, J=23.0 Hz), 116.3, 113.8, 112.8, 105.4, 89.0, 78.5, 57.3, 55.8, 31.1, 29.9. HRMS (ESI-TOF$^+$): m/z [M+H]$^+$ calcd for C$_{30}$H$_{29}$FN$_5$O: 494.2351; found: 494.2345.

TBI-1079, 5-(4-Fluorophenyl)-3-(4-methoxycyclohexyl)imino-2-(pyrazin-2-yl)amino-3,5-dihydrophenazine:

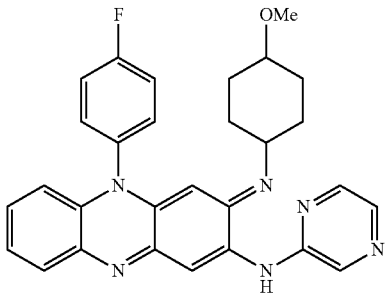 [SMILES: COC1CCC(/N=c2\cc3n(-c4ccc(F)cc4)c4ccccc4nc-3cc2Nc2cnccn2)CC1]

$^1$H NMR (300 MHz, CDCl$_3$) δ: 8.44 (1H, s), 8.29 (2H, s), 8.06 (1H, s), 7.78 (1H, d, J=7.8 Hz), 7.42 (2H, m), 7.35 (2H, m), 7.19 (2H, m), 6.49 (1H, d, J=7.8 Hz), 5.24 (1H, s), 3.37 (3H, s), 3.21 (1H, m), 3.08 (1H, m), 2.07 (2H, m), 1.69 (2H, m), 1.43 (2H, m), 1.22 (2H, m). $^{13}$C NMR (100 MHz, CDCl$_3$) δ: 162.8 (d, J=250.5 Hz), 151.2, 151.0, 141.6, 139.9, 136.3, 135.8, 135.3, 133.2, 131.9, 130.8, 130.7, 128.9, 128.5, 123.1, 118.4 (d, J=23.1 Hz), 113.9, 107.5, 88.9, 78.4, 57.2, 55.8, 31.1, 29.9. HRMS (ESI-TOF$^+$): m/z [M+H]$^+$ calcd for C$_{29}$H$_{28}$FN$_6$O: 495.2303; found: 495.2293.

TBI-1080, 5-(4-Fluorophenyl)-3-(4-methoxycyclohexyl)imino-2-(pyrimidin-2-yl)amino-3,5-dihydrophenazine:

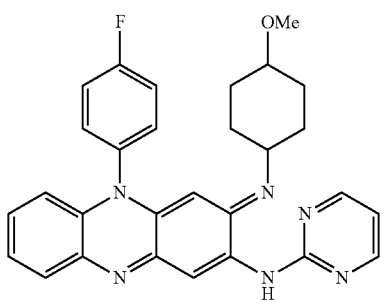 [SMILES: COC1CCC(/N=c2\cc3n(-c4ccc(F)cc4)c4ccccc4nc-3cc2Nc2ncccn2)CC1]

$^1$H NMR (300 MHz, CDCl$_3$) δ: 9.69 (1H, br s), 8.54 (2H, d, J=4.8 Hz), 8.49 (1H, s), 7.77 (1H, d, J=8.1 Hz), 7.41 (2H, m), 7.34 (2H, m), 7.17 (2H, m), 6.82 (1H, m), 7.47 (1H, d, J=8.1 Hz), 5.24 (1H, s), 3.37 (3H, s), 3.21 (1H, m), 3.08 (1H, m), 2.07 (2H, m), 1.69 (2H, m), 1.43 (2H, m), 1.22 (2H, m). $^{13}$C NMR (100 MHz, CDCl$_3$) δ: 162.8 (d, J=249.7 Hz), 159.3, 157.9, 151.7, 151.0, 140.1, 135.7, 135.3, 133.3, 132.1, 130.9, 130.8, 128.8, 128.4, 122.8, 118.4 (d, J=22.6 Hz), 113.8, 113.5, 108.5, 89.0, 78.5, 57.4, 55.8, 31.1, 29.9. HRMS (ESI-TOF$^+$): m/z [M+H]$^+$ calcd for C$_{29}$H$_{28}$FN$_6$O: 495.2303; found: 495.2306.

TBI-1082, 5-(4-Fluorophenyl)-3-(4-methoxycyclohexyl)imino-2-(3-cyano-2-pyridyl)amino-3,5-dihydrophenazine:

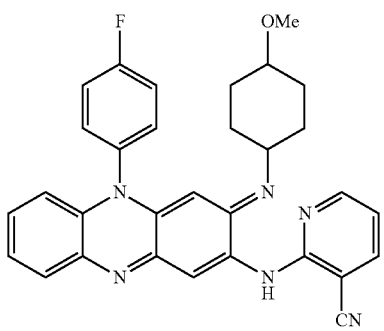 [SMILES: COC1CCC(/N=c2\cc3n(-c4ccc(F)cc4)c4ccccc4nc-3cc2Nc2ncccc2C#N)CC1]

$^1$H NMR (300 MHz, CDCl$_3$) δ: 10.33 (1H, br s), 8.59 (1H, s), 8.53 (1H, dd, J=4.5, 1.2 Hz), 7.80 (2H, dd, J=7.5, 1.8 Hz), 7.43 (2H, m), 7.36 (2H, m), 7.21 (2H, m), 6.84 (1H, dd, J=7.5, 4.8 Hz), 6.52 (1H, d, J=8.7 Hz), 5.27 (1H, s), 3.35 (3H, s), 3.26 (1H, m), 3.15 (1H, m), 2.07 (2H, m), 1.73 (2H, m), 1.47 (2H, m), 1.24 (2H, m). $^{13}$C NMR (100 MHz, CDCl$_3$) δ: 162.9 (d, J=250.2 Hz), 155.9, 152.1, 151.4, 151.1, 141.2, 139.9, 136.0, 135.6, 133.1, 131.7, 130.7, 130.6, 129.0, 128.5, 123.4, 118.5 (d, J=22.6 Hz), 116.2, 114.5, 114.1, 108.7, 96.8, 88.6, 77.9, 56.0, 55.8, 30.4, 29.2. HRMS (ESI-TOF$^+$): m/z [M+H]$^+$ calcd for C$_{31}$H$_{28}$FN$_6$O: 519.2303; found: 519.2338.

TBI-1083, 5-(4-Fluorophenyl)-3-(4-methoxycyclohexyl)imino-2-(3-nitro-2-pyridyl)amino-3,5-dihydrophenazine:

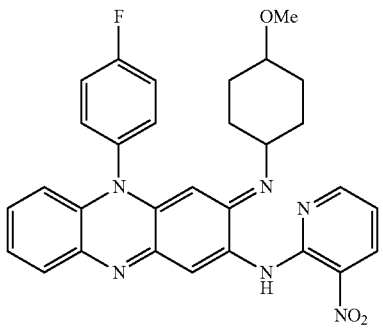 [SMILES: COC1CCC(/N=c2\cc3n(-c4ccc(F)cc4)c4ccccc4nc-3cc2Nc2ncccc2[N+](=O)[O-])CC1]

$^1$H NMR (300 MHz, CDCl$_3$) δ: 12.20 (1H, br s), 8.73 (1H, s), 8.66 (1H, m), 8.56 (1H, d, J=8.1 Hz), 7.77 (1H, m), 7.42 (2H, m), 7.35 (2H, m), 7.18 (2H, m), 6.95 (1H, dd, J=7.8, 4.5 Hz), 6.47 (1H, m), 5.25 (1H, s), 3.36 (3H, s), 3.27 (1H, m), 3.14 (1H, m), 2.11 (2H, m), 1.72 (2H, m), 1.54 (2H, m), 1.24 (2H, m). $^{13}$C NMR (100 MHz, CDCl$_3$) δ: 162.8 (d, J=249.3 Hz), 154.3, 151.8, 151.3, 148.7, 140.2, 135.7, 135.5, 135.2, 133.1, 132.4, 130.9, 130.8, 129.0, 128.9, 122.9, 118.5 (d, J=22.6 Hz), 114.8, 113.9, 111.6, 89.1, 78.2, 56.9, 55.8, 30.7, 29.4. HRMS (ESI-TOF$^+$): m/z [M+H]$^+$ calcd for C$_{30}$H$_{28}$FN$_6$O$_3$: 539.2201; found: 539.2204.

TBI-1084, 5-(4-Fluorophenyl)-3-(4-tetrahydropyranyl)imino-2-(pyrimidin-2-yl)amino-3,5-dihydrophenazine:

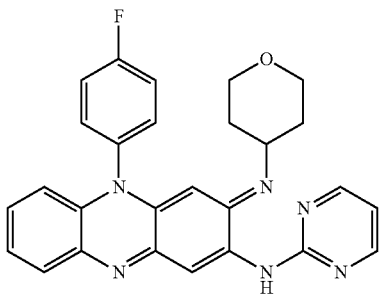 [SMILES: Fc1ccc(-n2c3c/c(=N\C4CCOCC4)c(Nc4ncccn4)cc-3nc3ccccc32)cc1]

$^1$H NMR (300 MHz, CDCl$_3$): 9.70 (1H, br s), 8.56 (2H, d, J=4.8 Hz), 8.53 (1H, s), 7.79 (1H, d, J=7.2 Hz), 7.44 (2H, m), 7.35 (2H, m), 7.19 (2H, m), 6.83 (1H, m), 6.48 (1H, d, J=7.2 Hz), 5.23 (1H, s), 3.98 (2H, m), 3.41 (3H, m), 1.64 (4H, m). $^{13}$C NMR (100 MHz, CDCl$_3$) δ: 162.8 (d, J=249.3 Hz), 159.3, 157.9, 151.5, 151.0, 140.1, 135.7, 135.4, 133.3, 132.0, 130.9, 130.8, 128.9, 128.4, 123.0, 118.5 (d, J=22.7 Hz), 113.9, 113.6, 108.5, 88.9, 66.0, 54.3, 33.3. HRMS (ESI-TOF$^+$): m/z [M+H]$^+$ calcd for C$_{27}$H$_{24}$FN$_6$O: 467.1990; found: 467.1980.

TBI-1085, 5-(4-Fluorophenyl)-3-(4-tetrahydropyranyl)imino-2-(pyrazin-2-yl)amino-3,5-dihydrophenazine:

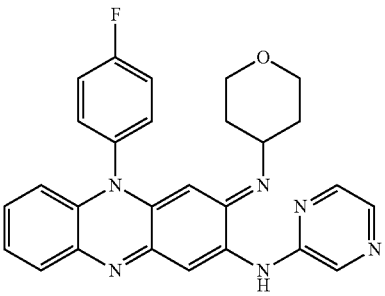 [SMILES: Fc1ccc(-n2c3c/c(=N\C4CCOCC4)c(Nc4cnccn4)cc-3nc3ccccc32)cc1]

$^1$H NMR (300 MHz, CDCl$_3$) δ: 9.50 (1H, br s), 8.47 (1H, s), 8.30 (2H, m), 8.06 (1H, d, J=2.4 Hz), 7.79 (1H, d, J=9.0 Hz), 7.44 (2H, m), 7.35 (2H, m), 7.20 (2H, m), 6.49 (1H, d, J=9.0 Hz), 5.23 (1H, s), 3.98 (2H, m), 3.41 (3H, m), 1.64 (4H, m). $^{13}$C NMR (100 MHz, CDCl$_3$) δ: 162.9 (d, J=249.7 Hz), 151.2, 150.9, 141.6, 139.9, 136.3, 135.7, 135.5, 133.2, 131.9, 130.8, 130.7, 129.0, 128.6, 123.2, 118.5 (d, J=22.6 Hz), 114.0, 107.6, 88.7, 66.1, 54.2, 33.4. HRMS (ESI-TOF$^+$): m/z [M+H]$^+$ calcd for C$_{27}$H$_{24}$FN$_6$O: 467.1990; found: 467.1979.

TBI-1086, 5-(4-Fluorophenyl)-3-(4-tetrahydropyranyl)imino-2-(3-cyano-2-pyridyl)amino-3,5-dihydrophenazine:

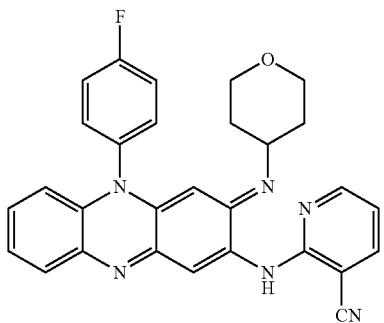 [SMILES: N#Cc1cccnc1Nc1cc2nc3ccccc3n(-c3ccc(F)cc3)c-2c/c1=N\C1CCOCC1]

$^1$H NMR (300 MHz, CDCl$_3$) δ: 10.38 (1H, br s), 8.63 (1H, s), 8.55 (1H, d, J=7.2 Hz), 7.82 (2H, m), 7.44 (2H, m), 7.36 (2H, m), 7.21 (2H, m), 6.88 (1H, m), 6.50 (1H, d, J=7.2 Hz), 5.25 (1H, s), 4.03 (2H, m), 3.47 (3H, m), 1.69 (4H, m). $^{13}$C NMR (100 MHz, CDCl$_3$) δ: 162.9 (d, J=249.7 Hz), 155.3, 152.1, 151.2, 151.1, 141.3, 139.6, 135.9, 135.7, 133.2, 131.9, 130.8, 130.7, 129.0, 128.7, 123.3, 118.6 (d, J=22.7 Hz), 115.9, 114.8, 114.1, 109.0, 96.5, 88.6, 66.5, 53.0, 33.1. HRMS (ESI-TOF$^+$): m/z [M+H]$^+$ calcd for C$_{29}$H$_{24}$FN$_6$O: 491.1990; found: 491.1981.

TBI-1087, 5-(4-Fluorophenyl)-3-(4-tetrahydropyranyl)imino-2-(2-pyridyl)amino-3,5-dihydrophenazine:

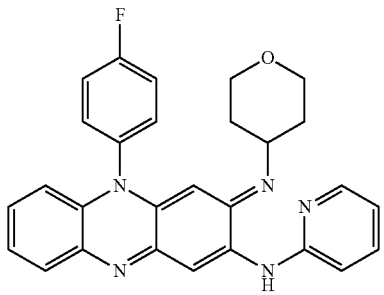 [SMILES: Fc1ccc(-n2c3c/c(=N\C4CCOCC4)c(Nc4ccccn4)cc-3nc3ccccc32)cc1]

$^1$H NMR (300 MHz, CDCl$_3$) δ: 9.25 (1H, br s), 8.39 (1H, d, J=3.3 Hz), 8.34 (1H, s), 7.78 (1H, dd, J=7.5, 1.8 Hz), 7.58 (1H, m), 7.43 (2H, m), 7.35 (2H, m), 7.18 (2H, m), 6.96 (1H, d, J=8.4 Hz), 6.86 (1H, m), 6.48 (1H, dd, J=7.5, 1.8 Hz), 5.23 (1H, s), 3.96 (2H, m), 3.38 (3H, m), 1.63 (4H, m). $^{13}$C NMR (100 MHz, CDCl$_3$) δ: 162.8 (d, J=249.3 Hz), 154.0, 151.5, 151.3, 148.2, 140.9, 137.2, 135.8, 135.3, 133.4, 131.8, 130.9, 130.8, 128.7, 128.0, 123.0, 118.4 (d, J=22.6 Hz), 116.4, 113.9, 112.9, 105.6, 88.8, 66.1, 54.1, 33.4. HRMS (ESI-TOF$^+$): m/z [M+H]$^+$ calcd for C$_{28}$H$_{25}$FN$_5$O: 466.2038; found: 466.2022.

TBI-1088, 5-(4-Fluorophenyl)-3-(4-tetrahydropyranyl)imino-2-(3-nitro-2-pyridyl)amino-3,5-dihydrophenazine:

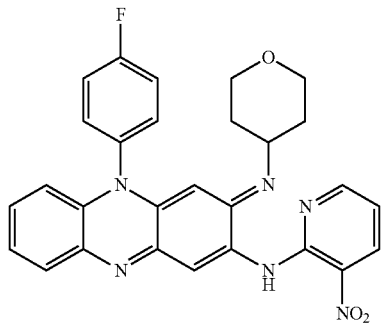 [SMILES: O=[N+]([O-])c1cccnc1Nc1cc2nc3ccccc3n(-c3ccc(F)cc3)c-2c/c1=N\C1CCOCC1]

$^1$H NMR (300 MHz, CDCl$_3$) δ: 12.20 (1H, s), 8.78 (1H, s), 8.67 (1H, m), 8.57 (1H, d, J=8.1 Hz), 7.79 (1H, m), 7.44 (2H, m), 7.37 (2H, m), 7.20 (2H, m), 6.97 (1H, m), 6.48 (1H, m), 5.25 (1H, s), 4.06 (2H, m), 3.50 (3H, m), 1.71 (4H, m). $^{13}$C NMR (100 MHz, CDCl$_3$) δ: 162.9 (d, J=249.3 Hz), 154.3, 151.7, 151.4, 148.7, 140.2, 135.7, 135.6, 135.2, 133.2, 132.3, 130.8, 130.7, 129.1, 129.0, 123.1, 118.6 (d, J=22.7 Hz), 115.0, 113.9, 111.7, 89.0, 65.5, 53.5, 33.2. HRMS (ESI-TOF$^+$): m/z [M+H]$^+$ calcd for C$_{28}$H$_{24}$FN$_6$O$_3$: 511.1888; found: 511.1884.

TBI-1090, 5-(4-Chlorophenyl)-3-(4-methoxycyclohexyl)imino-2-(pyrimidin-2-yl)amino-3,5-dihydrophenazine:

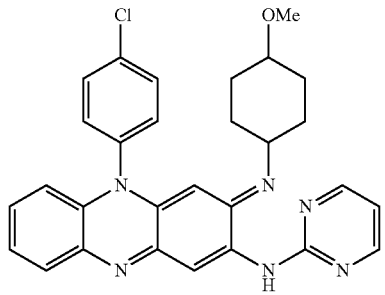 [SMILES: COC1CCC(/N=c2\cc3n(-c4ccc(Cl)cc4)c4ccccc4nc-3cc2Nc2ncccn2)CC1]

$^1$H NMR (300 MHz, CDCl$_3$) δ: 9.68 (1H, br s), 8.54 (2H, d, J=4.8 Hz), 8.48 (1H, s), 7.77 (1H, m), 7.69 (2H, d, J=8.4 Hz), 7.29 (2H, d, J=8.4 Hz), 7.16 (2H, m), 6.81 (1H, m), 6.45 (1H, m), 5.25 (1H, s), 3.36 (3H, s), 3.19 (1H, m), 3.09 (1H, m), 2.06 (2H, m), 1.64 (2H, m), 1.43 (2H, m), 1.18 (2H, m). $^{13}$C NMR (100 MHz, CDCl$_3$) δ: 159.3, 157.9, 151.7, 150.9, 140.1, 135.8, 135.7, 135.0, 131.9, 131.6, 130.4, 128.9, 128.4, 122.9, 113.8, 113.5, 108.5, 89.0, 78.5, 57.3, 55.8, 31.1, 29.8; HRMS (ESI-TOF$^+$): m/z [M+H]$^+$ calcd for C$_{29}$H$_{28}$ClN$_6$O: 511.2008; found: 511.1993.

TBI-091, 5-(4-Chlorophenyl)-3-(4-methoxycyclohexyl)imino-2-(pyrazin-2-yl)amino-3,5-dihydrophenazine:

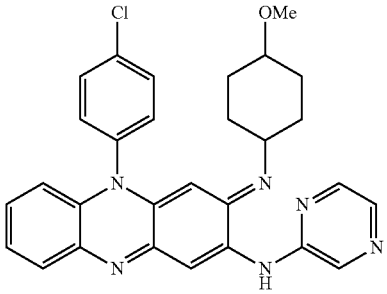 [SMILES: COC1CCC(/N=c2\cc3n(-c4ccc(Cl)cc4)c4ccccc4nc-3cc2Nc2cnccn2)CC1]

$^1$H NMR (300 MHz, CDCl$_3$) δ: 8.44 (1H, s), 8.29 (2H, s), 8.06 (1H, s), 7.79 (1H, dd, J=5.1, 3.3 Hz), 7.71 (2H, d, J=7.8 Hz), 7.30 (2H, d, J=7.8 Hz), 7.19 (2H, m), 6.48 (1H, dd, J=5.1, 3.3 Hz), 5.26 (1H, s), 3.37 (3H, s), 3.21 (1H, m), 3.11 (1H, m), 2.08 (2H, m), 1.68 (2H, m), 1.44 (2H, m), 1.22 (2H, m). $^{13}$C NMR (100 MHz, CDCl$_3$) δ: 151.3, 151.1, 150.9, 141.6, 139.9, 136.3, 135.9, 135.8, 135.6, 135.1, 131.8, 131.6, 130.3, 128.9, 128.5, 123.1, 113.9, 107.5, 88.9, 78.4, 57.1, 55.8, 31.1, 29.8. HRMS (ESI-TOF$^+$): m/z [M+H]$^+$ calcd for C$_{29}$H$_{28}$ClN$_6$O: 511.2008; found: 511.1977.

TBI-1092, 5-(4-Fluorophenyl)-3-(1-methylethyl)imino-2-(2-methoxy-6-methyl-3-pyridyl)amino-3,5-dihydrophenazine:

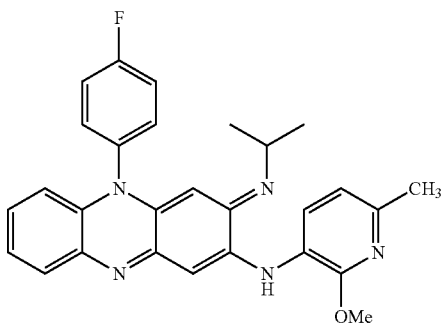 [SMILES: COc1nc(C)ccc1Nc1cc2nc3ccccc3n(-c3ccc(F)cc3)c-2c/c1=N\C(C)C]

$^1$H NMR (300 MHz, CDCl$_3$) δ: 7.70 (2H, m), 7.42 (2H, m), 7.34 (2H, m), 7.14 (2H, m), 6.81 (1H, s), 6.73 (1H, d, J=7.5 Hz), 6.44 (1H, d, J=7.5 Hz), 5.26 (1H, s), 4.00 (3H, s), 3.44 (1H, m), 2.44 (3H, s), 1.10 (6H, d, J=6.3 Hz). $^{13}$C NMR (100 MHz, CDCl$_3$) δ: 162.8 (d, J=249.3 Hz), 155.1, 151.3, 150.8, 148.6, 143.5, 135.7, 135.0, 133.6, 131.7, 130.9, 130.8, 128.1, 127.3, 126.7, 122.8, 121.6, 118.4 (d, J=22.7 Hz), 115.4, 113.8, 99.3, 89.2, 63.7, 53.5, 49.3, 23.6. HRMS (ESI-TOF$^+$): m/z [M+H]$^+$ calcd for C$_{28}$H$_{27}$FN$_5$O: 468.2194; found: 468.2188.

TBI-1220, 5-(4-Acetamidophenyl)-3-(1-methylethyl)imino-2-(2-methoxy-3-pyridyl)amino-3,5-dihydrophenazine:

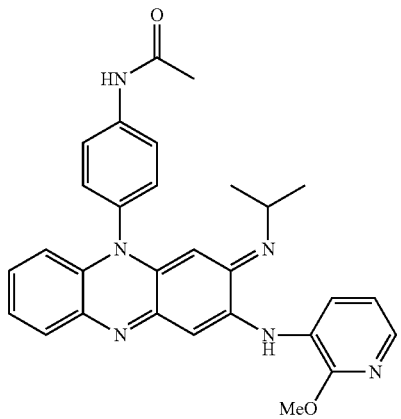 [SMILES: COc1ncccc1Nc1cc2nc3ccccc3n(-c3ccc(NC(C)=O)cc3)c-2c/c1=N\C(C)C]

$^1$H NMR (300 MHz, CDCl$_3$) δ: 7.90 (2H, d, J=7.8 Hz), 7.82 (2H, m), 7.69 (1H, d, J=6.0 Hz), 7.28 (2H, m), 7.13 (2H, m), 6.91 (2H, m), 6.48 (1H, d, J=7.8 Hz), 5.34 (1H, s), 4.03 (3H, s), 3.45 (1H, m), 2.29 (3H, s), 1.15 (6H, d, J=6.0 Hz). $^{13}$C NMR (100 MHz, CDCl$_3$) δ: 168.6, 155.5, 151.2, 150.7, 142.9, 139.1, 138.8, 135.6, 135.0, 132.9, 132.0, 129.5, 128.0, 127.6, 124.9, 124.8, 122.8, 121.8, 116.8, 114.1, 100.1, 89.2, 53.7, 49.2, 24.7, 23.5. HRMS (ESI-TOF+): m/z [M+H]+ calcd for $C_{29}H_{29}N_6O_2$: 492.2274; found: 492.2254.

TBI-1221, 5-(4-Acetamidophenyl)-3-cyclopropylimino-2-(2-methoxy-3-pyridyl)amino-3,5-dihydrophenazine:

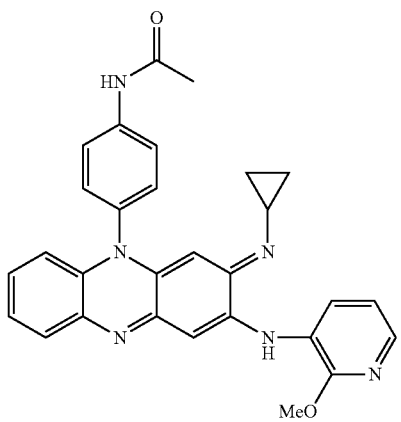 [SMILES: COc1ncccc1Nc1cc2nc3ccccc3n(-c3ccc(NC(C)=O)cc3)c-2c/c1=N\C1CC1]

$^1$H NMR (300 MHz, CDCl$_3$) δ: 7.89 (2H, d, J=8.4 Hz), 7.81 (3H, m), 7.66 (1H, d, J=5.8 Hz), 7.29 (2H, d, J=8.7 Hz), 7.12 (3H, m), 6.87 (1H, s), 6.45 (1H, d, J=7.8 Hz), 5.6 (1H, s), 4.00 (3H, s), 2.72 (1H, s), 2.26 (3H, s), 0.85 (4H, m). $^{13}$C NMR (100 MHz, CDCl$_3$) δ: 168.7, 155.6, 152.7, 151.1, 147.4, 142.5, 139.1, 135.9, 134.9, 132.8, 132.0, 129.4, 128.1, 127.8, 125.5, 124.6, 123.0, 121.9, 116.8, 114.2, 100.3, 89.7, 53.7, 32.5, 24.7. HRMS (ESI-TOF+): m/z [M+H]+ calcd for $C_{29}H_{27}N_6O_2$: 490.2117; found: 490.2088.

TBI-1222, 5-(4-Acetamidophenyl)-3-(4-methoxycyclohexyl)imino-2-(2-methoxy-3-pyridyl)amino-3,5-dihydrophenazine:

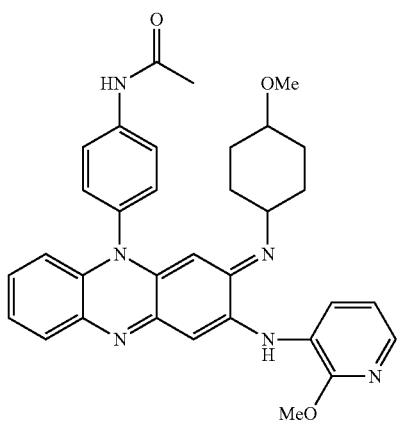 [SMILES: COc1ncccc1Nc1cc2nc3ccccc3n(-c3ccc(NC(C)=O)cc3)c-2c/c1=N\C1CCC(OC)CC1]

$^1$H NMR (300 MHz, CDCl$_3$) δ: 10.14 (1H, s), 9.04 (1H, s), 8.18 (2H, d, J=7.8 Hz), 8.09 (2H, m), 7.76 (1H, d, J=8.4 Hz), 7.60 (2H, m), 7.25 (2H, m), 7.08 (1H, d, J=8.4 Hz), 6.95 (1H, m), 6.65 (1H, s), 5.87 (1H, s), 3.90 (3H, s), 3.71 (1H, m), 3.29 (3H, s), 3.19 (1H, m), 2.33 (3H, s), 2.10 (2H, m), 1.60 (2H, m), 1.25 (2H, m), 1.09 (2H, m). $^{13}$C NMR (100 MHz, CDCl$_3$) δ: 169.6, 158.4, 151.5, 145.8, 144.6, 141.7, 141.5, 138.8, 135.5, 135.3, 131.3, 130.2, 130.0, 129.8, 127.5, 127.3, 122.1, 121.7, 117.5, 105.7, 89.7, 55.9, 54.3, 53.6, 29.9, 28.7, 24.7. HRMS (ESI-TOF+): m/z [M+H]+ calcd for $C_{33}H_{35}N_6O_3$: 562.2692; found: 562.2742.

TBI-1223, 5-(4-Acetamidophenyl)-3-cyclohexylimino-2-(2-methoxy-3-pyridyl)amino-3,5-dihydrophenazine:

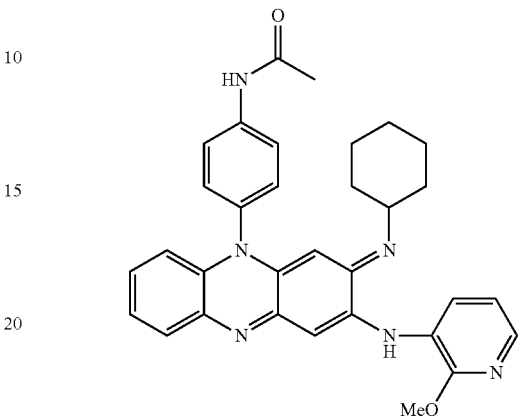

$^1$H NMR (300 MHz, CDCl$_3$) δ: 7.91 (2H, d, J=8.1 Hz), 7.81 (2H, m), 7.70 (1H, d, J=7.8 Hz), 7.27 (2H, m), 7.14 (2H, m), 6.91 (2H, m), 6.52 (1H, d, J=7.8 Hz), 5.35 (1H, s), 4.02 (3H, s), 3.15 (1H, m), 2.28 (3H, s), 1.47 (10H, m). $^{13}$C NMR (100 MHz, CDCl$_3$) δ: 168.6, 155.5, 151.0, 150.7, 142.8, 139.2, 138.8, 135.8, 135.0, 132.8, 131.9, 129.3, 128.1, 127.7, 124.9, 122.9, 121.7, 116.8, 114.2, 100.4, 89.4, 56.9, 53.7, 33.3, 25.9, 24.7, 24.2. HRMS (ESI-TOF+): m/z [M+H]+ calcd for $C_{32}H_{33}N_6O_2$: 532.2587; found: 532.2576.

TBI-1224, 5-(4-Acetamidophenyl)-3-(4-tetrahydropyranyl)imino-2-(6-methyl-3-pyridyl)amino-3,5-dihydrophenazine:

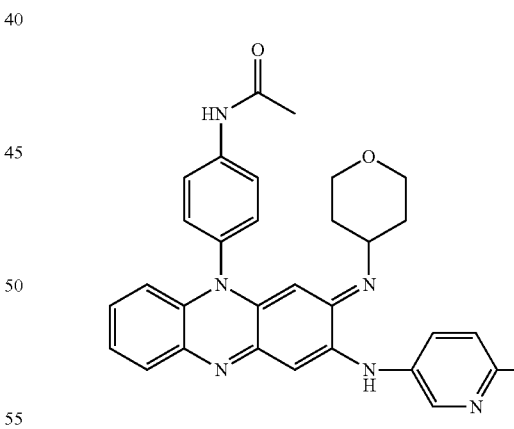

$^1$H NMR (300 MHz, CDCl$_3$) δ: 10.36 (1H, s), 9.70 (1H, s), 8.69 (1H, s), 8.29 (2H, d, J=8.1 Hz), 8.16 (1H, d, J=7.5 Hz), 7.85 (1H, m), 7.67 (2H, m), 7.38 (1H, s), 7.18 (2H, d, J=8.1 Hz), 5.93 (1H, s), 3.90 (2H, m), 3.49 (1H, m), 3.26 (2H, m), 2.62 (3H, s), 2.35 (3H, s), 2.11 (2H, m), 1.83 (2H, m). $^{13}$C NMR (100 MHz, CDCl$_3$) δ: 170.1, 151.1, 145.4, 142.3, 139.3, 135.3, 132.9, 132.3, 130.4, 130.0, 129.8, 127.8, 127.4, 124.6, 121.9, 117.2, 105.9, 90.3, 66.0, 52.0, 31.0, 24.7. HRMS (ESI-TOF+): m/z [M+H]+ calcd for $C_{31}H_{31}N_6O_2$: 518.2430; found: 518.2472.

TBI-1225, 5-(4-Acetamidophenyl)-3-(4-tetrahydropyranyl)imino-2-(2-methoxy-3-pyridyl)amino-3,5-dihydrophenazine:

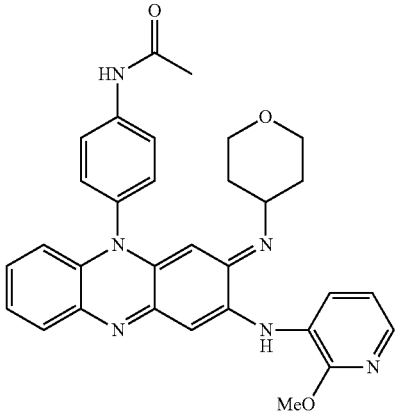 [SMILES: COc1ncccc1Nc1cc2nc3ccccc3n(-c3ccc(NC(C)=O)cc3)c-2c/c1=N\C1CCOCC1]

$^1$H NMR (300 MHz, CDCl$_3$) δ: 7.85 (4H, m), 7.71 (1H, d, J=7.2 Hz), 7.61 (1H, m), 7.30 (1H, s), 7.16 (2H, m), 6.98 (1H, s), 6.92 (1H, m), 6.52 (1H, d, J=7.2 Hz), 5.31 (1H, s), 4.04 (3H, s), 3.98 (1H, m), 3.49 (4H, m), 2.29 (3H, s), 1.65 (4H, m). $^{13}$C NMR (100 MHz, CDCl$_3$) δ: 168.9, 155.6, 151.5, 151.0, 142.8, 139.6, 139.0, 136.0, 135.5, 133.0, 128.5, 128.2, 125.0, 123.4, 122.0, 117.1, 114.6, 100.8, 89.2, 65.8, 54.0, 53.3, 33.4, 25.0. HRMS (ESI-TOF$^+$): [M+H]$^+$ calcd for C$_{31}$H$_{31}$N$_6$O$_3$: 534.2379; found: 534.2350.

TBI-1227, 5-(4-Acetamidophenyl)-3-(1,3-dimethoxyisopropyl)imino-2-(2-methoxy-3-pyridyl)amino-3,5-dihydrophenazine:

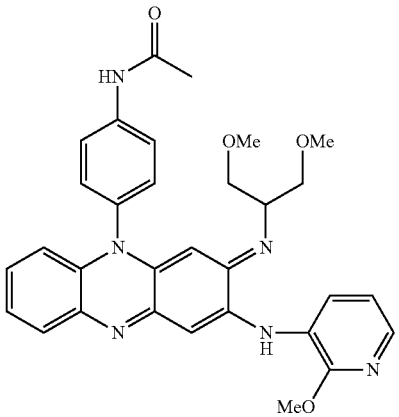 [SMILES: COCC(COC)/N=c1\cc2n(-c3ccc(NC(C)=O)cc3)c3ccccc3nc-2cc1Nc1cccnc1OC]

$^1$H NMR (300 MHz, CDCl$_3$) δ: 7.85 (4H, m), 7.72 (2H, d, J=6.9 Hz), 7.28 (1H, s), 7.17 (2H, m), 6.95 (1H, s), 6.90 (1H, m), 6.53 (1H, d, J=7.5 Hz), 5.53 (1H, s), 4.01 (3H, s), 3.72 (1H, m), 3.55 (2H, m), 3.39 (2H, m), 3.27 (6H, s), 2.27 (3H, s). $^{13}$C NMR (100 MHz, CDCl$_3$) δ: 168.6, 155.7, 153.5, 142.6, 139.5, 132.5, 131.7, 129.2, 128.3, 125.8, 124.6, 123.3, 121.8, 116.9, 114.5, 100.8, 90.1, 56.2, 58.3, 53.6, 24.7. HRMS (ESI-TOF$^+$): m/z [M+H]$^+$ calcd for C$_{31}$H$_{33}$N$_6$O$_4$: 552.2485; found: 552.2474.

TBI-1228, 5-(4-Acetamidophenyl)-3-(1-methylethyl)imino-2-(6-methyl-3-pyridyl)amino-3,5-dihydrophenazine:

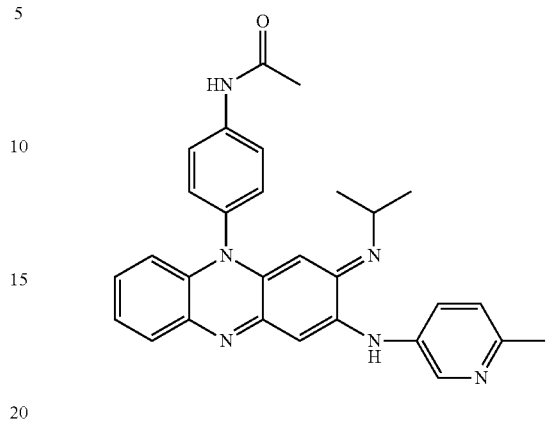

$^1$H NMR (300 MHz, CDCl$_3$) δ: 8.45 (1H, s), 7.90 (2H, d, J=8.1 Hz), 7.68 (2H, m), 7.28 (2H, m), 7.14 (3H, m), 6.73 (1H, s), 6.50 (1H, d, J=7.8 Hz), 5.34 (1H, s), 3.45 (1H, m), 2.56 (3H, s), 2.28 (3H, s), 1.08 (6H, m). $^{13}$C NMR (100 MHz, CDCl$_3$) δ: 168.8, 153.3, 150.6, 144.0, 143.7, 139.5, 135.9, 135.1, 134.2, 132.6, 131.6, 129.6, 129.2, 128.2, 127.9, 123.3, 121.7, 123.3, 121.7, 114.4, 89.1, 49.0, 24.7, 23.7, 23.3. HRMS (ESI-TOF$^+$): m/z [M+H]$^+$ calcd for C$_{29}$H$_{29}$N$_6$O: 476.2325; found: 476.237.

TBI-1229, 5-(4-Acetamidophenyl)-3-(4-methoxycyclohexyl)imino)-(6-methyl-3-pyridyl)amino-3,5-dihydrophenazine:

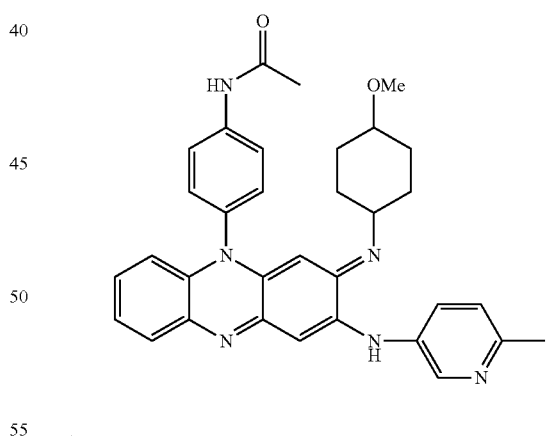

$^1$H NMR (300 MHz, CDCl$_3$) δ: 8.44 (1H, s), 7.88 (2H, d, J=8.1 Hz), 7.68 (2H, m), 7.28 (2H, m), 7.16 (3H, m), 6.72 (1H, s), 6.53 (1H, d, J=6.3 Hz), 5.30 (1H, s), 3.36 (3H, s), 3.19 (1H, m), 3.09 (1H, m), 2.56 (3H, s), 2.30 (3H, s), 2.06 (2H, m), 1.69 (2H, m), 1.41 (2H, m), 1.18 (2H, m). $^{13}$C NMR (100 MHz, CDCl$_3$) δ: 168.7, 153.3, 151.3, 150.8, 144.2, 143.7, 139.2, 135.6, 135.1, 134.1, 132.7, 131.7, 129.4, 128.1, 127.6, 123.3, 122.8, 121.7, 114.2, 98.9, 89.0, 57.3, 55.9, 31.2, 30.0, 24.8, 23.8. HRMS (ESI-TOF$^+$): m/z [M+H]$^+$ calcd for C$_{33}$H$_{35}$N$_6$O$_2$: 546.2743; found: 546.2793.

TBI-1230, 5-(4-Acetamidophenyl)-3-cyclopropylimino-2-(6-methyl-3-pyridyl)amino-3,5-dihydrophenazine:

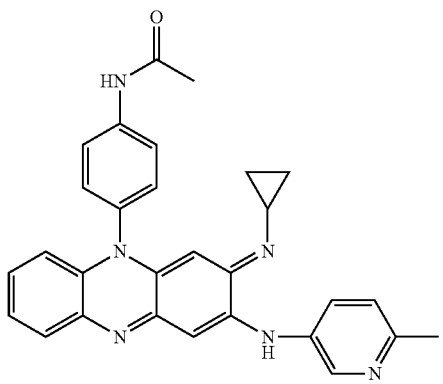 [SMILES: CC(=O)Nc1ccc(-n2c3c/c(=N\C4CC4)c(Nc4ccc(C)nc4)cc-3nc3ccccc32)cc1]

$^{1}$H NMR (300 MHz, CDCl$_3$) δ: 8.41 (1H, s), 7.90 (2H, s), 7.64 (2H, m), 7.28 (2H, s), 7.22 (3H, m), 6.67 (1H, s), 6.48 (1H, s), 5.60 (1H, s), 2.72 (1H, s), 2.55 (3H, s), 2.27 (3H, s), 0.84 (2H, m), 0.79 (2H, m). $^{13}$C NMR (100 MHz, CDCl$_3$) δ: 168.6, 153.4, 152.6, 151.1, 144.1, 143.7, 139.2, 135.8, 134.9, 134.0, 132.9, 131.9, 129.7, 129.5, 128.0, 127.6, 123.3, 122.9, 121.8, 116.9, 114.2, 99.0, 89.5, 32.7, 24.7, 23.8, 9.8. HRMS (ESI-TOF$^+$): m/z [M+H]$^+$ calcd for C$_{29}$H$_{27}$N$_6$O: 474.2168; found: 474.2176.

TBI-1231, 5-(4-Acetamidophenyl)-3-cyclohexylimino-2-(6-methyl-3-pyridyl)amino-3,5-dihydrophenazine:

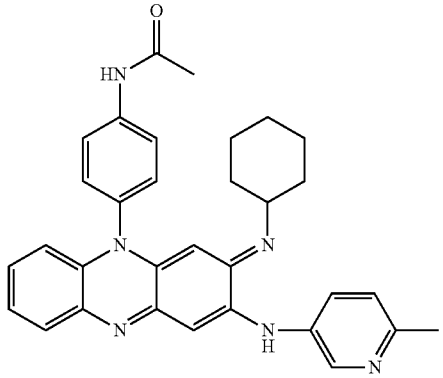 [SMILES: CC(=O)Nc1ccc(-n2c3c/c(=N\C4CCCCC4)c(Nc4ccc(C)nc4)cc-3nc3ccccc32)cc1]

$^{1}$H NMR (300 MHz, CDCl$_3$) 8.45 (1H, s), 7.91 (2H, d, J=8.1 Hz), 7.68 (2H, m), 7.28 (2H, m), 7.16 (3H, m), 6.73 (1H, s), 6.54 (1H, m), 5.35 (1H, s), 3.08 (1H, m), 2.56 (3H, s), 2.29 (3H, s), 1.44 (10H, m). $^{13}$C NMR (100 MHz, CDCl$_3$) δ: 168.8, 153.4, 150.7, 143.8, 139.6, 135.0, 134.3, 131.5, 129.8, 129.1, 128.2, 123.4, 121.7, 114.5, 89.3, 57.3, 33.2, 25.7, 24.6, 23.8. HRMS (ESI-TOF$^+$): m/z [M+H]$^+$ calcd for C$_{32}$H$_{33}$N$_6$O: 516.2638; found: 516.2612.

TBI-1236, 5-(4-Methoxycarbonylphenyl)-3-(1-methylethyl)imino-2-(2-methoxy-3-pyridyl)amino-3,5-dihydrophenazine:

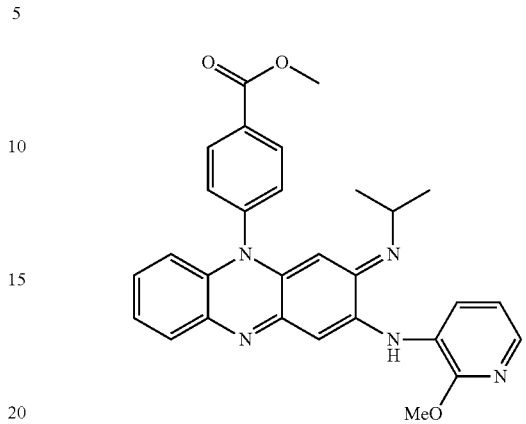

$^{1}$H NMR (300 MHz, CDCl$_3$) δ: 8.39 (2H, d, J=8.1 Hz), 7.82 (2H, m), 7.68 (2H, d, J=6.9 Hz), 7.45 (2H, d, J=8.4 Hz), 7.12 (2H, m), 6.92 (2H, s), 6.39 (1H, d, J=7.8 Hz), 5.24 (1H, s), 4.02 (6H, s), 3.41 (1H, m), 1.07 (6H, d, J=6.3 Hz). $^{13}$C-NMR (100 MHz, CDCl$_3$) δ: 166.0, 155.5, 151.2, 150.5, 142.9, 141.7, 138.8, 135.6, 134.5, 132.6, 131.4, 131.3, 129.3, 128.2, 127.6, 124.9, 124.8, 122.9, 116.8, 113.7, 100.1, 89.3, 53.7, 52.6, 49.4, 23.5. HRMS (ESI-TOF$^+$): m/z [M+H]$^+$ calcd for C$_{29}$H$_{28}$N$_5$O$_3$: 493.2114; found: 493.2113.

TBI-1237, 5-(4-Methoxycarbonylphenyl)-3-cyclopropylimino-2-(2-methoxy-3-pyridyl)amino-3,5-dihydrophenazine:

$^{1}$H NMR (300 MHz, CDCl$_3$) δ: 8.58 (1H, brs), 8.39 (2H, d, J=9.9 Hz), 7.82 (2H, d, J=7.8 Hz), 7.67 (1H, d, J=7.5 Hz), 7.47 (2H, d, J=6.9 Hz), 7.11 (2H, m), 6.90 (2H, m), 6.37 (1H, d, J=8.1 Hz), 5.50 (1H, s), 4.01 (6H, s), 2.68 (1H, m), 0.83 (4H, m). $^{13}$C NMR (100 MHz, CDCl$_3$) δ: 166.0, 155.4, 152.4, 151.4, 142.6, 141.7, 138.9, 135.7, 134.3, 132.7, 131.4, 129.4, 128.2, 127.6, 125.0, 124.7, 122.9, 116.8, 113.7, 100.0, 89.7, 53.7, 52.6, 32.9, 10.8. HRMS (ESI-TOF$^+$): [M+H]$^+$ calcd for C$_{29}$H$_{26}$N$_5$O$_3$: 491.1957; found: 491.1960.

TBI-1426, 5-(3,4-Difluorophenyl)-3-cyclopropylimino-2-(ethoxy-3-pyridyl)amino-3,5-dihydrophenazine:

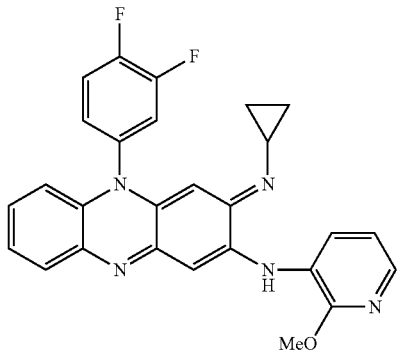 [SMILES: COc1ncccc1Nc1cc2nc3ccccc3n(-c3ccc(F)c(F)c3)c-2c/c1=N\C1CC1]

¹H NMR (300 MHz, CDCl₃) δ: 8.58 (1H, s), 7.82 (2H, m), 7.66 (1H, d, J=8.1 Hz), 7.52 (1H, m), 7.12 (3H, m), 6.09 (1H, m), 6.86 (1H, s), 6.42 (1H, d, J=8.4 Hz), 5.54 (1H, s), 4.01 (3H, s), 2.77 (1H, m), 0.93 (2H, d, J=6.0 Hz), 0.86 (2H, d, J=2.7 Hz). ¹³C NMR (100 MHz, CDCl₃) δ: 155.5, 153.1, 152.4, 151.5, 150.5, 149.6, 142.7, 139.0, 135.7, 133.7, 131.6, 128.2, 127.7, 125.1, 124.7, 123.1, 120.1, 118.9, 116.8, 113.5, 100.5, 89.6, 53.7, 33.0, 10.2. HRMS (ESI-TOF⁺): m/z [M+H]⁺ calcd for C₂₇H₂₂F₂N₅O: 470.1787; found: 470.1762.

TBI-1427, 5-(3,4-Difluorophenyl)-3-(4-methoxycyclohexyl)imino-2-(2-methoxy-3-pyridyl)amino-3,5-dihydrophenazine:

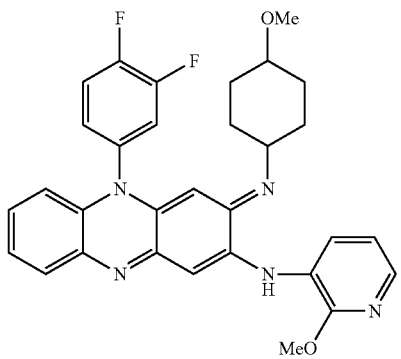 [SMILES: COc1ncccc1Nc1cc2nc3ccccc3n(-c3ccc(F)c(F)c3)c-2c/c1=N\C1CCC(OC)CC1]

¹H NMR (300 MHz, CDCl₃) δ: 8.94 (1H, brs), 7.82 (2H, m), 7.69 (1H, d, J=8.1 Hz), 7.53 (1H, m), (1H, m), 7.15 (3H, m), 6.92 (2H, m), 6.46 (1H, d, J=7.95 Hz), 5.26 (1H, s), 4.03 (3H, s), 3.36 (3H, s), 3.27 (1H, m), 3.16 (1H, 2.05 (2H, m), 1.73 (2H, m), 1.40 (2H, m), 1.26 (2H, m). ¹³C NMR (100 MHz, CDCl₃) δ: 155.4, 153.2, 152.2, 151.1, 149.7, 142.7, 138.8, 135.6, 134.7, 133.5, 131.3, 128.4, 127.8, 125.7, 124.7, 123.1, 119.9, 118.7, 116.8, 113.6, 100.2, 89.2, 78.2, 56.9, 55.8, 33.7, 30.8, 29.3. HRMS (ESI-TOF⁺): m/z [M+H]⁺ calcd for C₃₁H₃₀F₂N₅O₇: 542.2362; found: 542.2238.

TBI-1428, 5-(3,4-Difluorophenyl)-3-(4-tetrahydropyranyl)imino-2-(2-methoxy-3-pyridyl)amino-3,5-dihydrophenazine:

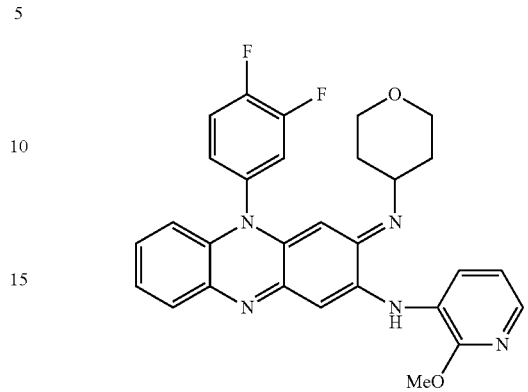

¹H NMR (300 MHz, CDCl₃) δ: 9.08 (1H, s), 7.83 (2H, d, J=7.5 Hz), 7.71 (1H, d, J=6.6 Hz), 7.55 (1H, m), 7.18 (4H, m), 6.91 (2H, m), 6.46 (1H, d, J=7.8 Hz), 5.25 (1H, s), 4.04 (5H, brs), 3.49 (3H, m), 1.68 (4H, brs). ¹³C NMR (100 MHz, CDCl₃) δ: 155.3, 153.2, 152.2, 151.0, 149.8, 142.6, 138.8, 135.6, 134.9, 133.6, 131.2, 128.4, 127.9, 125.7, 124.8, 124.4, 123.3, 120.0, 118.7, 116.8, 113.7, 100.3, 88.9, 65.5, 53.8, 53.3, 33.3. HRMS (ESI-TOF⁺): m/z [M+H]⁺ calcd for C₂₉H₂₆F₂N₅O₂: 514.2049; found: 514.2054.

TBI-1429, 5-(3,4-Difluorophenyl)-3-cyclopropylimino-2-(3-pyridyl)amino-3,5-dihydrophenazine:

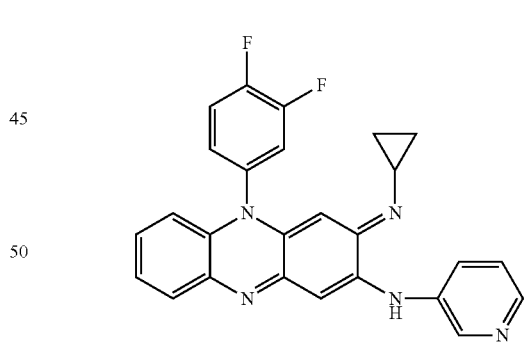

¹H NMR (300 MHz, CDCl₃) δ: 8.55 (1H, d, J=1.8 Hz), 8.33 (1H, d, J=4.2 Hz), 7.75 (1H, d, J=8.1 Hz), 7.66 (1H, d, J=6.3 Hz), 7.54 (1H, m), 7.30 (1H, m), 7.23 (1H, m), 7.15 (3H, m), 6.77 (1H, s), 6.43 (1H, d, J=7.8 Hz), 5.54 (1H, s), 2.78 (1H, m), 0.93 (2H, d, J=6.9 Hz), 0.84 (2H, brs). ¹³C NMR (100 MHz, CDCl₃) δ: 153.1, 152.1, 151.2, 150.6, 149.7, 144.5, 144.1, 143.5, 136.6, 135.6, 134.6, 133.6, 131.5, 128.3, 128.2, 127.8, 125.8, 123.6, 123.1, 120.0, 118.8, 113.6, 99.4, 89.5, 33.0, 10.1. HRMS (ESI-TOF⁺): m/z [M+H]⁺ calcd for C₂₆H₂₀F₂N₅: 440.1681; found: 440.1667.

TBI-1430, 5-(3,4-Difluorophenyl)-3-(4-methoxycyclohexyl)imino-2-(3-pyridyl)amino-3,5-dihydrophenazine:

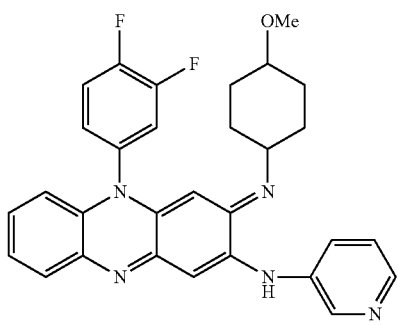 [SMILES: COC1CCC(/N=c2\cc3n(-c4ccc(F)c(F)c4)c4ccccc4nc-3cc2Nc2cccnc2)CC1]

$^1$H NMR (300 MHz, CDCl$_3$) δ: 8.57 (1H, s), 8.34 (1H, d, J=4.5 Hz), 7.77 (1H, d, J=7.8 Hz), 7.69 (1H, d, J=7.2 Hz), 7.53 (1H, m), 7.31 (1H, m), 7.20 (1H, m), 7.16 (3H, m), 6.82 (1H, s), 6.48 (1H, d, J=8.1 Hz), 5.27 (1H, s), 3.37 (3H, s), 3.2 (1H, m), 3.13 (1H, m), 2.10 (2H, m), 1.71 (2H, m), 1.42 (2H, m), 1.21 (2H, m). $^{13}$C NMR (100 MHz, CDCl$_3$) δ: 153.1, 152.2, 151.0, 150.8, 150.6, 149.7, 144.4, 144.0, 143.6, 136.6, 135.6, 134.7, 133.5, 131.2, 128.5, 127.9, 125.6, 123.6, 123.2, 119.9, 118.7, 113.7, 99.5, 89.1, 78.4, 57.4, 55.8, 31.2, 29.9. HRMS (ESI-TOF$^+$): m/z [M+H]$^+$ calcd for C$_{30}$H$_{28}$F$_2$N$_5$O: 512.2256; found: 512.2245.

TBI-1431, 5-(3,4-Difluorophenyl)-3,5-dihydro-1'-(2-methoxy-3-pyridyl)-2',2'-dimethyl-1'H-imidazo[4',5',2,3]phenazine:

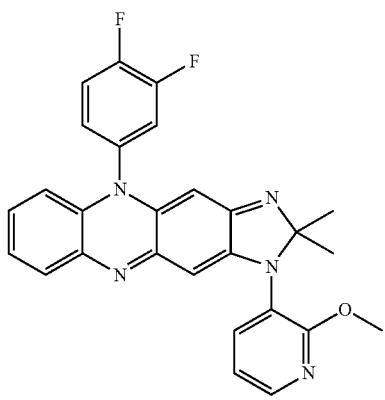 [SMILES: COc1ncccc1N1c2cc3c(cc2=NC1(C)C)N(c1ccc(F)c(F)c1)c1ccccc1N=3]

$^1$H NMR (300 MHz, CDCl$_3$) δ: 8.24 (1H, d, J=4.5 Hz), 7.54 (3H, m), 7.22 (1H, m), 7.12 (2H, d, J=8.4 Hz), 7.02 (2H, m), 6.42 (1H, d, J=8.4 Hz), 5.48 (1H, s), 5.40 (1H, s), 3.93 (3H, s), 1.26 (6H, s). $^{13}$C NMR (100 MHz, CDCl$_3$) δ: 160.8, 159.1, 153.1, 152.2, 150.5, 149.7, 149.2, 147.1, 139.1, 138.3, 135.9, 133.7, 131.0, 127.8, 126.8, 125.7, 123.4, 120.3, 119.8, 118.7, 117.0, 113.7, 96.1, 92.1, 91.5, 53.7, 27.0. HRMS (ESI-TOF$^+$): m/z [M+H]$^+$ calcd for C$_{27}$H$_{22}$F$_2$N$_5$O: 470.1787; found: 470.1817.

TBI-1432, 5-(3,4-Difluorophenyl)-3-(4-tetrahydropyranyl)imino-2-(3-pyridyl)amino-3,5-dihydrophenazine:

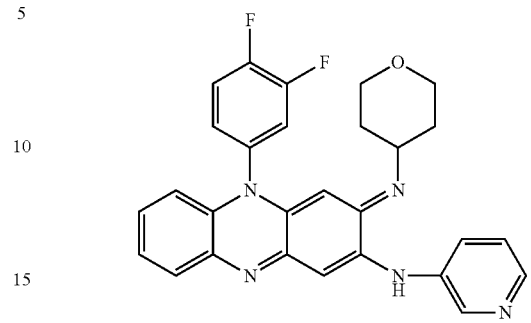

$^1$H NMR (300 MHz, CDCl$_3$) δ: 8.61 (1H, s), 8.36 (1H, d, J=4.2 Hz), 7.78 (1H, d, J=8.1 Hz), 7.72 (1H, d, J=8.9 Hz), 7.56 (1H, m), 7.33 (1H, m), 7.25 (1H, m), 7.22 (3H, m), 6.86 (1H, s), 6.49 (1H, d, J=7.5 Hz), 5.28 (1H, s), 4.00 (2H, d, J=5.4 Hz), 3.45 (3H, m), 1.66 (4H, m). $^{13}$C NMR (100 MHz, CDCl$_3$) δ: 155.1, 152.2, 150.9, 150.7, 149.7, 144.5, 144.0, 143.6, 136.6, 135.6, 134.9, 133.5, 131.1, 128.5, 128.1, 125.6, 123.7, 123.4, 119.9, 118.6, 113.7, 99.6, 88.8, 66.0, 54.3, 33.5, 33.3. HRMS (ESI-TOF$^+$): m/z [M+H]$^+$ calcd for C$_{28}$H$_{24}$F$_2$N$_5$O: 484.1943; found: 484.1962.

TBI-1433, 5-(3,4-Difluorophenyl)-3-(4-methoxycyclohexyl)imino-2-(pyrimidin-2-yl)amino-3,5-dihydrophenazine:

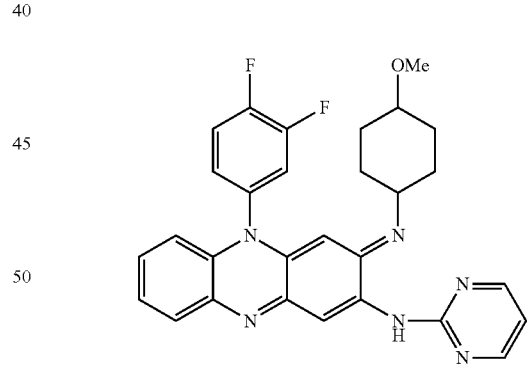

$^1$H NMR (300 MHz, CDCl$_3$) δ: 9.66 (1H, s), 8.54 (1H, d, J=5.1 Hz), 8.47 (1H, s), 7.75 (1H, m), 7.58 (2H, m), 7.15 (3H, m), 6.82 (1H, m), 6.45 (1H, d, J=6.0 Hz), 5.24 (1H, s), 3.34 (3H, s), 3.18 (1H, m), 3.11 (1H, m), 2.05 (2H, m), 1.65 (2H, m), 1.32 (2H, m), 1.20 (2H, m). $^{13}$C NMR (100 MHz, CDCl$_3$) δ: 159.3, 157.9, 153.1, 152.2, 151.7, 150.6, 149.7, 140.1, 135.6, 134.9, 133.4, 131.7, 131.3, 128.9, 128.4, 128.2, 125.7, 123.1, 119.9, 118.7, 113.6, 108.5, 89.0, 78.4, 57.4, 55.8, 31.1, 29.8. HRMS (ESI-TOF$^+$): m/z [M+H]$^+$ calcd for C$_{29}$H$_{27}$F$_2$N$_6$O: 513.2209; found: 513.2242.

TBI-1436, 5-(3,4-Difluorophenyl)-3-(1-methylethyl)imino-2-(2-pyridyl)amino-3,5-dihydrophenazine:

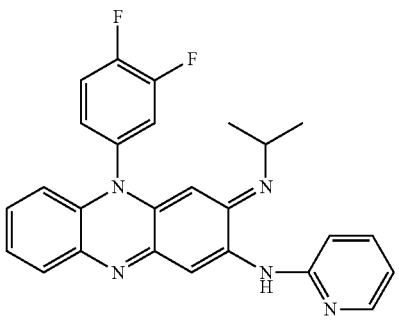 [SMILES: CC(C)/N=c1\cc2n(-c3ccc(F)c(F)c3)c3ccccc3nc-2cc1Nc1ccccn1]

$^1$H NMR (300 MHz, CDCl$_3$), δ: 8.38 (1H, d, J=3.6 Hz), 8.27 (1H, s), 7.75 (1H, d, J=6.9 Hz), 7.54 (2H, m), 7.25 (1H, m), 7.17 (3H, brs), 6.99 (1H, d, J=7.5 Hz), 6.85 (1H, s), 6.43 (1H, d, J=7.2 Hz), 5.20 (1H, s), 3.48 (1H, m), 1.10 (6H, brs). $^{13}$C NMR (100 MHz, CDCl$_3$) δ: 154.1, 153.1, 151.7, 150.3, 148.2, 141.0, 137.1, 135.7, 134.8, 133.7, 131.5, 128.7, 127.9, 125.8, 123.0, 119.9, 118.8, 116.3, 113.5, 112.9, 105.4, 89.0, 49.4, 23.7. HRMS (ESI-TOF$^+$): m/z [M+H]$^+$ calcd for C$_{26}$H$_{21}$F$_2$N$_6$: 442.1838; found: 442.1865.

TBI-1437, 5-(3,4-Difluorophenyl)-3-(1-methylethyl)imino-2-(pyrimidin-2-yl)amino-3,5-dihydrophenazine:

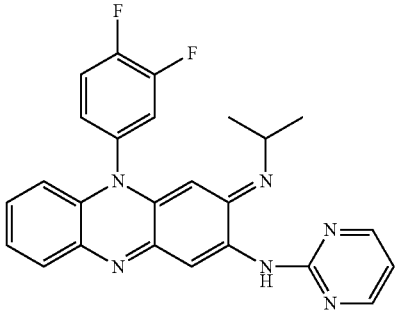 [SMILES: CC(C)/N=c1\cc2n(-c3ccc(F)c(F)c3)c3ccccc3nc-2cc1Nc1ncccn1]

$^1$H NMR (300 MHz, CDCl$_3$), δ: 8.55 (2H, d, J=4.8 Hz), 8.47 (1H, s), 7.76 (1H, d, J=6.3 Hz), 7.53 (1H, m), 7.21 (1H, m), 7.17 (3H, m), 6.82 (1H, t, J=4.8 Hz), 6.43 (1H, d, J=7.8 Hz), 5.27 (1H, s), 3.48 (1H, m), 1.10 (6H, brs). $^{13}$C NMR (100 MHz, CDCl$_3$) δ: 159.3, 157.7, 151.8, 150.0, 140.2, 135.6, 134.9, 133.6, 131.8, 128.9, 128.3, 125.8, 123.0, 120.0, 118.7, 113.5, 108.4, 89.2, 44.5, 23.5. HRMS (ESI-TOF$^+$): m/z [M+H]$^+$ calcd for C$_{25}$H$_{21}$F$_2$N$_6$: 443.1790; found: 443.1750.

TBI-1438, 5-(3,4-Difluorophenyl)-3-(1-methylethyl)imino-2-(3-cyano-2-pyridyl)amino-3,5-dihydrophenazine:

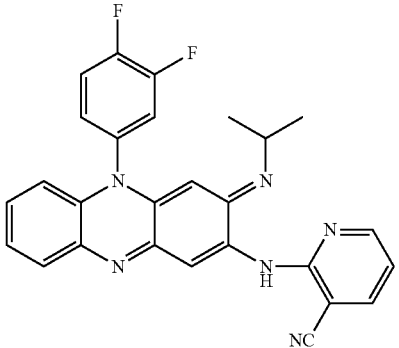 [SMILES: CC(C)/N=c1\cc2n(-c3ccc(F)c(F)c3)c3ccccc3nc-2cc1Nc1ncccc1C#N]

$^1$H NMR (300 MHz, CDCl$_3$), δ: 10.36 (1H, s), 8.57 (2H, m), 7.80 (2H, d, J=6.3 Hz), 7.57 (1H, m), 7.40 (1H, s), 7.22 (3H, m), 6.85 (1H, s), 6.48 (1H, d, J=6.9 Hz), 5.30 (1H, s), 3.52 (1H, m), 1.21 (6H, brs). $^{13}$C NMR (100 MHz, CDCl$_3$) δ: 155.9, 153.1, 152.8, 152.1, 151.1, 150.7, 142.5, 141.2, 140.0, 135.9, 135.3, 133.4, 131.3, 129.0, 128.5, 125.6, 123.5, 122.1, 120.0, 118.6, 116.1, 114.5, 113.8, 108.6, 97.0, 88.6, 48.9, 29.7, 23.4. HRMS (ESI-TOF$^+$): m/z [M+H]$^+$ calcd for C$_{27}$H$_{21}$F$_7$N$_6$: 467.1790; found: 467.1786.

TBI-1444, 5-(3,4-Difluorophenyl)-3-(4-methoxycyclohexyl)imino-2-(5-nitro-2-pyridyl)amino-3,5-dihydrophenazine:

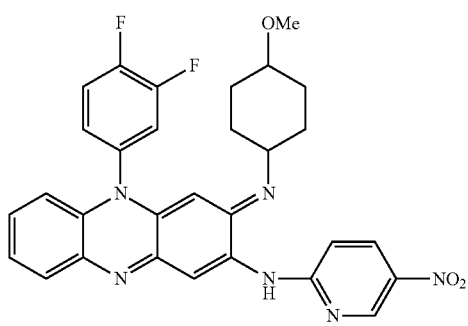

$^1$H NMR (300 MHz, DMSO-d$_6$), δ: 9.76 (1H, brs), 9.23 (1H, s), 8.48 (1H, s), 8.33 (1H, d, J=9.3 Hz), 7.89 (2H, m), 7.78 (1H, d, J=6.3 Hz), 7.52 (1H, m), 7.32 (3H, m), 6.65 (1H, d, J=8.4 Hz), 5.22 (1H, s), 3.31 (3H, s), 3.14 (1H, m), 3.11 (1H, m), 1.96 (2H, m), 1.66 (2H, 1.40 (2H, m), 1.13 (2H, m). $^{13}$C NMR (100 MHz, DMSO-d$_6$) δ: 159.3, 158.5, 151.4, 145.6, 144.9, 141.5, 137.1, 135.1, 134.1, 133.0, 132.2, 128.6, 126.4, 123.6, 120.3, 119.6, 118.7, 114.6, 109.3, 88.4, 77.5, 55.1, 47.6, 30.1, 29.4. HRMS (ESI-TOF$^+$): m/z [M+H]$^+$ calcd for C$_{30}$H$_{27}$F$_7$N$_6$O$_3$: 557.2107; found: 557.2133.

TBI-1445, 5-(3,4-Difluorophenyl)-3-(4-methoxycyclohexyl)imino-2-(pyrazin-2-yl)amino-3,5-dihydrophenazine:

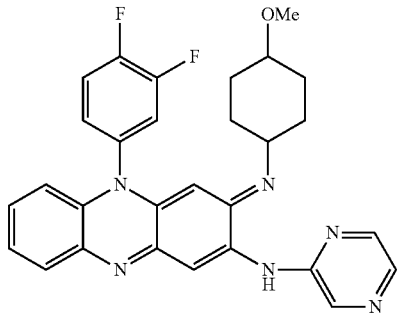 [SMILES: COC1CCC(/N=c2\cc3n(-c4ccc(F)c(F)c4)c4ccccc4nc-3cc2Nc2cnccn2)CC1]

$^1$H NMR (300 MHz, CDCl$_3$) δ: 8.43 (1H, s), 8.29 (2H, s), 8.06 (1H, d, J=2.4 Hz), 7.78 (1H, d, J=9.0 Hz), 7.55 (1H, m), 7.24 (1H, m), 7.21 (3H, m), 6.48 (1H, d, J=9.9 Hz), 5.25 (1H, s), 3.37 (3H, s), 3.22 (1H, m), 3.12 (1H, m), 2.09 (2H, m), 1.71 (2H, m), 1.47 (2H, m), 1.23 (2H, m). $^{13}$C NMR (100 MHz, CDCl$_3$) δ: 153.1, 151.3, 151.0, 150.9, 141.6, 139.9, 136.3, 135.7, 135.0, 133.4, 131.6, 129.0, 128.6, 125.6, 123.3, 120.0, 118.7, 113.7, 107.6, 88.9, 78.4, 57.3, 55.8, 31.2, 30.0, 29.8. HRMS (ESI-TOF$^+$): m/z [M+H]$^+$ calcd for C$_{29}$H$_{27}$F$_2$N$_6$O: 513.2209; found: 513.2178.

TBI-1446, 5-(3,4-Difluorophenyl)-3-(1-methylethyl)imino-2-(pyrazin-2-yl)amino-3,5-dihydrophenazine:

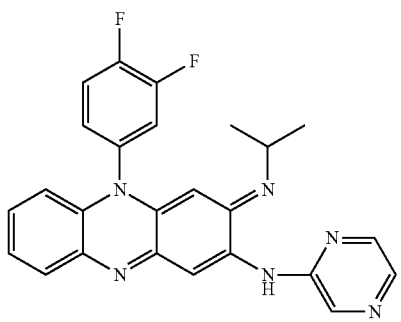 [SMILES: CC(C)/N=c1\cc2n(-c3ccc(F)c(F)c3)c3ccccc3nc-2cc1Nc1cnccn1]

$^1$H NMR (300 MHz, CDCl$_3$) δ: 8.43 (1H, s), 8.29 (2H, d, J=9.9 Hz), 8.06 (1H, s), 7.77 (1H, d, J=5.7 Hz), 7.55 (1H, m), 7.26 (1H, m), 7.17 (3H, m), 6.45 (1H, d, J=8.4 Hz), 5.27 (1H, s), 3.49 (1H, m), 1.12 (6H, m). $^{13}$C NMR (100 MHz, CDCl$_3$) δ: 153.2, 151.4, 151.0, 150.7, 150.3, 141.6, 140.0, 136.3, 135.6, 135.0, 133.5, 131.6, 129.0, 128.4, 125.7, 123.2, 120.0, 118.7, 113.6, 107.5, 88.9, 49.4, 23.7, 23.5. HRMS (ESI-TOF$^+$): m/z [M+H]$^+$ calcd for C$_{25}$H$_{21}$F$_2$N$_6$: 443.1790; found: 443.1776.

REFERENCES CITED

The content of each of the documents listed below is hereby incorporated by reference.

U.S. Patent Documents

U.S. Pat. No. 3,499,899

Non-Patent Publications

Barry, V. C., Belton, J. G., Conalty, M. L., Denneny, J. M., Edward, D. W., O'Sullivan, J. F., Twomey, D., Winder, F. A new series of phenazines (rimino-compounds) with high antituberculosis activity. *Nature* 179: 1013-1015 (1957).
Ma Z, Lienhardt C. Clin Chest Med. 30(4):755-68 (2009).
V. M. Reddy, G. Nadadhur, D. Daneluzzi, J. F. O'Sullivan, P. R. J. Gangadharam, *Antimicrobial Agents and Chemother.*, 40, 633-636 (1996).

What is claimed is:
1. A compound having a structure of:

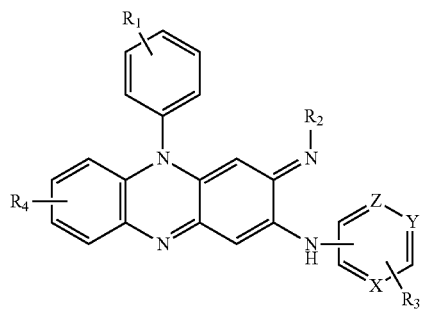

wherein R$_1$, R$_2$, R$_3$, R$_4$, X, Y, and Z are one of the following combinations of substituents:

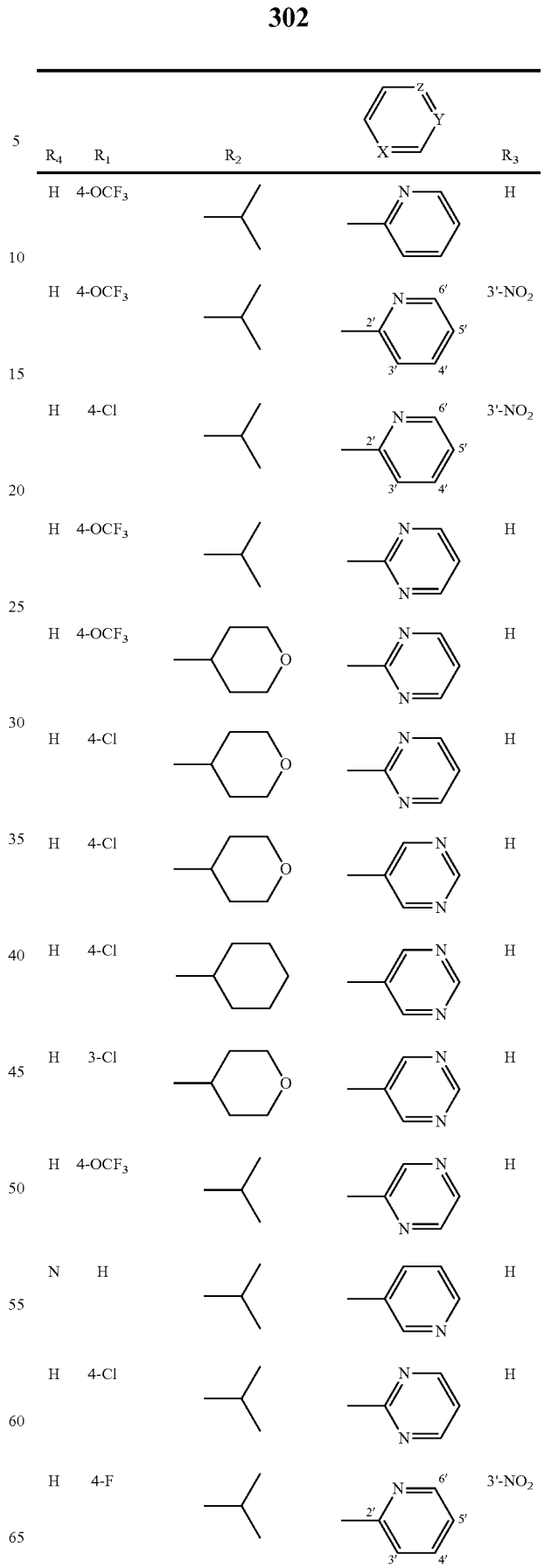

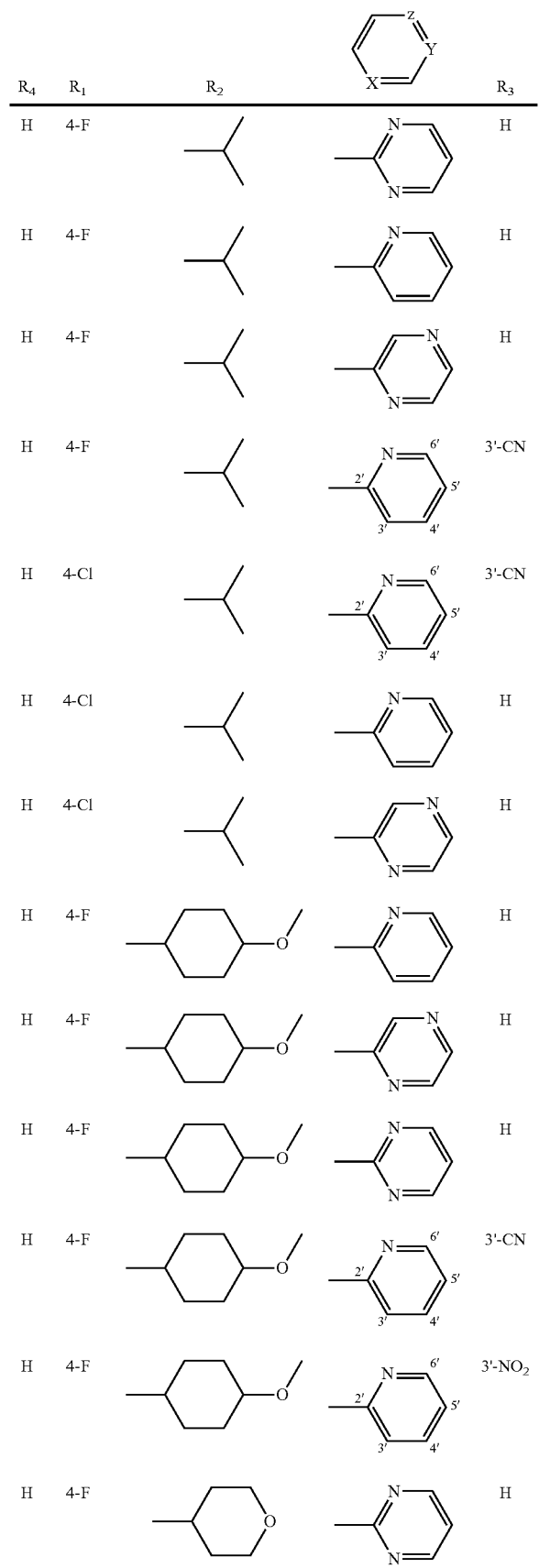
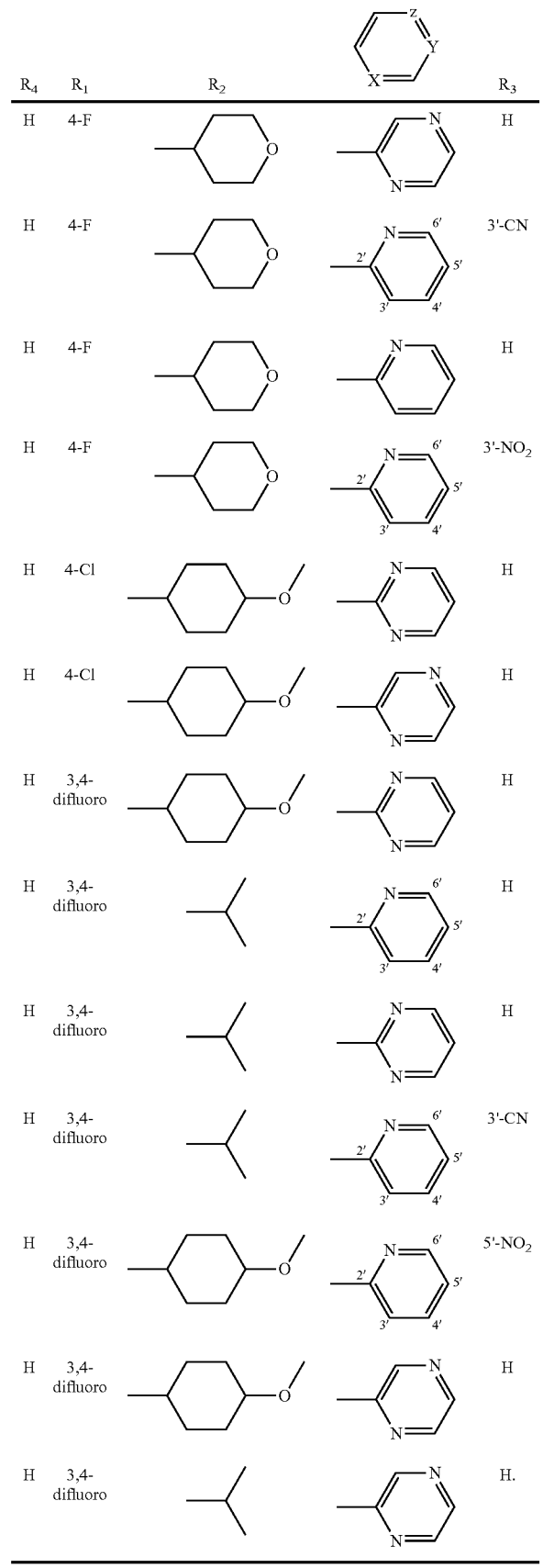

2. A pharmaceutical composition comprising a therapeutically effective amount of the compound of claim 1 and a pharmaceutically acceptable excipient, adjuvant, carrier, buffer or stabilizer.

3. A compound having a structure of:

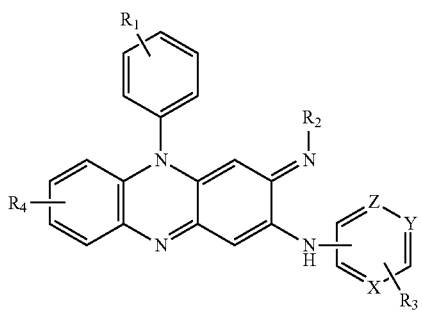

wherein $R_1$, $R_2$, $R_3$ and $R_4$ are one of the following combinations of substituents:

| $R_1$ | $R_2$ | $R_3$ | $R_4$ |
|---|---|---|---|
| H | isopropyl | H | H |
| H | 4-methylpiperidine (N-methyl) | H | H |
| H | propyl-morpholine | H | H |
| H | 4-methylpiperidine-N-isobutyl | H | H |
| H | tetrahydropyran-4-yl | H | H |
| H | 4-methoxycyclohexyl | H | H |
| H | 4-methylpiperidine-N-cyclopentyl | H | H |
| 4-CH$_3$ | isopropyl | H | H |
| 4-CH$_3$ | 4-methoxycyclohexyl | H | H |
| 4-CH$_3$ | propyl-morpholine | H | H |
| 4-CH$_3$ | tetrahydropyran-4-yl | H | H |
| 4-CH$_3$ | 4-methylpiperidine (N-methyl) | H | H |
| 4-CH$_3$ | 4-methylpiperidine-N-isobutyl | H | H |
| 4-CH$_3$ | 4-methylpiperidine-N-cyclopentyl | H | H |
| 4-Cl | isopropyl | H | H |
| 4-Cl | 4-methylpiperidine (N-methyl) | H | H |
| 4-Cl | 4-ethylpiperidine (N-methyl) | H | H |
| 4-Cl | propyl-morpholine | H | H |
| 4-Cl | tetrahydropyran-4-yl | H | H |
| 4-Cl | 4-methylpiperidine-N-isobutyl | H | H |
| 4-Cl | 4-methoxycyclohexyl | H | H |
| 4-Cl | 4-methylpiperidine-N-cyclopentyl | H | H |
| 4-Cl | cyclohexyl | H | H |
| 4-Cl | tetrahydrothiopyran-4-yl | H | H |

| R1 | R2 | R3 | R4 |
|---|---|---|---|
| 4-F |  | H | H |
| 4-F | 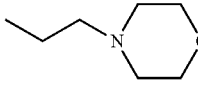 | H | H |
| 4-F | 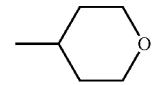 | H | H |
| 4-F | 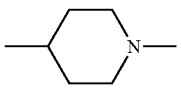 | H | H |
| 4-F | 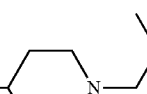 | H | H |
| 4-F | 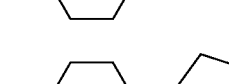 | H | H |
| 4-F | 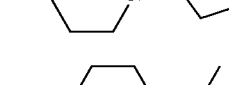 | H | H |
| 4-F | 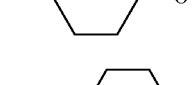 | H | H |
| 4-F | 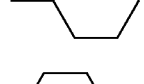 | H | H |
| 4-F | 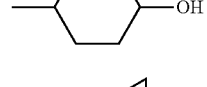 | H | H |
| 4-F |  | H | H |
| 4-CF$_3$ |  | H | H |
| 4-CF$_3$ | 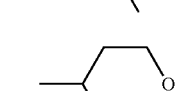 | H | H |
| 4-CF$_3$ | 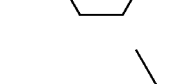 | H | H |
| 4-CF$_3$ | 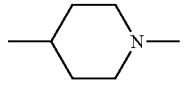 | H | H |
| 4-CF$_3$ | 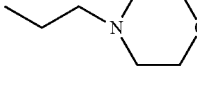 | H | H |
| 4-CF$_3$ | 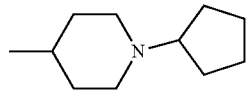 | H | H |
| 4-CF$_3$ |  | H | H |
| 4-OCF$_3$ | 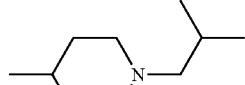 | H | H |
| 4-OCF$_3$ | 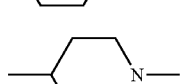 | H | H |
| 4-OCF$_3$ | 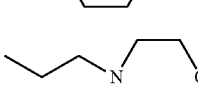 | H | H |
| 4-OCF$_3$ | 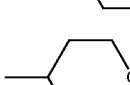 | H | H |
| 4-OCF$_3$ | 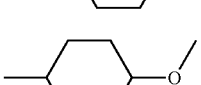 | H | H |
| 4-OCF$_3$ | 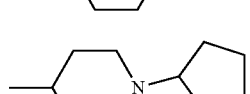 | H | H |
| 4-OCF$_3$ |  | H | H |
| H | 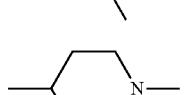 | 2'-MeO | H |
| H | 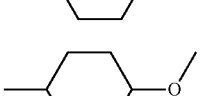 | 2'-MeO | H |
| H | 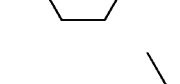 | 2'-MeO | H |
| H | 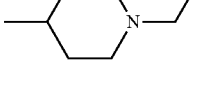 | 2'-MeO | H |
| H | | 2'-MeO | H |

309
-continued
| R₁ | R₂ | R₃ | R₄ |
|---|---|---|---|
| H | 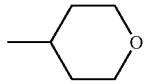 | 2'-MeO | H |
| H | 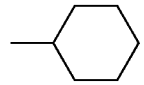 | 2'-MeO | H |
| H |  | 2'-MeO | H |
| H | 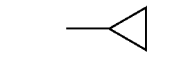 | 2'-MeO | H |
| H | 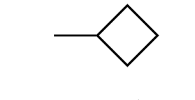 | 2'-MeO | H |
| H | 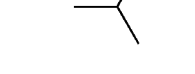 | 2'-Me | H |
| H | 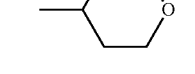 | 2'-Me | H |
| H | 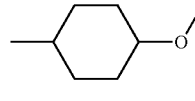 | 2'-Me | H |
| H | 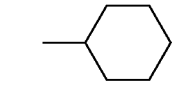 | 2'-Me | H |
| H |  | 2'-Me | H |
| H | ▢Me | 2'-Me | H |
| H |  | 6'-Me | H |
| H |  | 6'-Me | H |
| H | 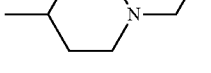 | 6'-Me | H |
| H | 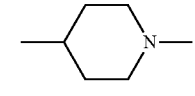 | 6'-Me | H |
| H |  | 6'-Me | H |
310
-continued
| R₁ | R₂ | R₃ | R₄ |
|---|---|---|---|
| H | 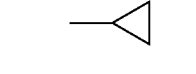 | 6'-Me | H |
| H |  | 6'-Me | H |
| H | 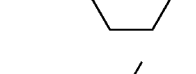 | 6'-Me | H |
| H | 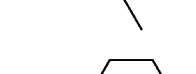 | 6'-Me | H |
| H | 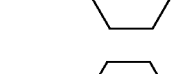 | 5'-Me | H |
| H | 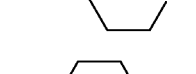 | 5'-Me | H |
| H | 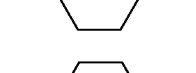 | 5'-Me | H |
| H | 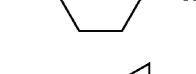 | 5'-Me | H |
| H | 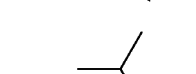 | 5'-Me | H |
| H | 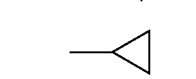 | 5'-Me | H |
| H | 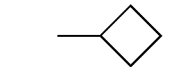 | 6'-MeO | H |
| H | 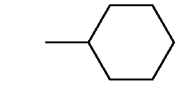 | 6'-MeO | H |
| H |  | 6'-MeO | H |
| H | 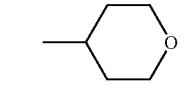 | 6'-MeO | H |
| H | 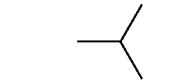 | 6'-MeO | H |
| H |  | 6'-MeO | H |
| H |  | 6'-MeO | H |
| 4-Br |  | H | H |

311
-continued
| R₁ | R₂ | R₃ | R₄ |
|---|---|---|---|
| 4-Br | 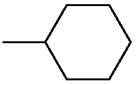 | H | H |
| 4-Br | 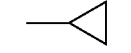 | H | H |
| 4-Br | 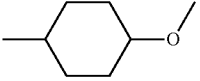 | H | H |
| 4-Br | 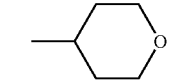 | H | H |
| 4-Br |  | H | H |
| 4-Br | 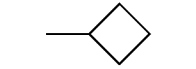 | H | H |
| 4-Br | 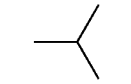 | 6'-Me | H |
| 4-Br | 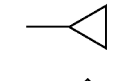 | 6'-Me | H |
| 4-Br | 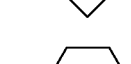 | 6'-Me | H |
| 4-Br | 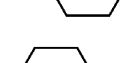 | 6'-Me | H |
| 4-Br | 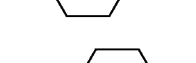 | 6'-Me | H |
| 4-Br | 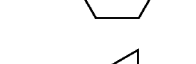 | 6'-Me | H |
| 4-Br | 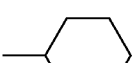 | 2'-Me | H |
| 4-Br | 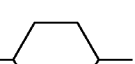 | 2'-Me | H |
| 4-Br |  | 2'-Me | H |
| 4-Br | 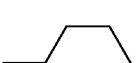 | 2'-MeO | H |
| 4-Br |  | 2'-MeO | H |
312
-continued
| R₁ | R₂ | R₃ | R₄ |
|---|---|---|---|
| 4-CH₃ | 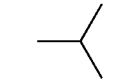 | 2'-MeO | H |
| 4-CH₃ |  | 2'-MeO | H |
| 4-CH₃ | 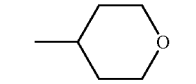 | 2'-MeO | H |
| 4-CH₃ | 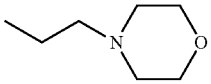 | 2'-MeO | H |
| 4-CH₃ | 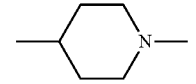 | 2'-MeO | H |
| 4-CH₃ | 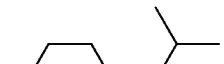 | 2'-MeO | H |
| 4-CH₃ | 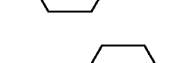 | 2'-Me | H |
| 4-CH₃ | 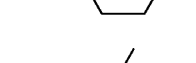 | 2'-Me | H |
| 4-CH₃ | 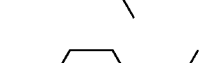 | 2'-Me | H |
| 4-CH₃ | 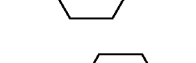 | 2'-Me | H |
| 4-CH₃ | 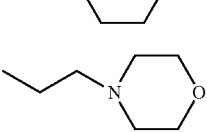 | 2'-Me | H |
| 4-CH₃ |  | 2'-Me | H |
| 4-CH₃ | 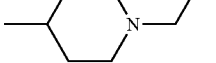 | 2'-Me | H |
| 4-CH₃ | | 6'-Me | H |
| 4-CH₃ | | 6'-Me | H |

313
-continued
| R₁ | R₂ | R₃ | R₄ |
|---|---|---|---|
| 4-CH₃ | 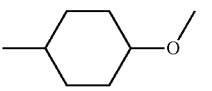 | 6'-Me | H |
| 4-CH₃ | 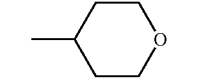 | 6'-Me | H |
| 4-CH₃ | 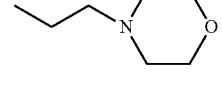 | 6'-Me | H |
| 4-CH₃ | 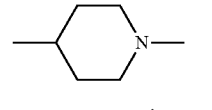 | 6'-Me | H |
| 4-CH₃ | 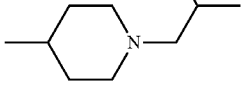 | 6'-Me | H |
| 4-F |  | 2'-Me | H |
| 4-F | 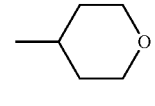 | 2'-Me | H |
| 4-F | 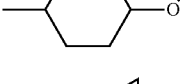 | 2'-Me | H |
| 4-F | 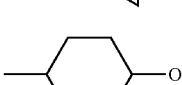 | 2'-Me | H |
| 4-F | 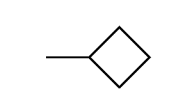 | 2'-Me | H |
| 4-F | 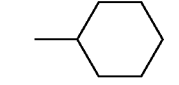 | 2'-Me | H |
| 4-F | 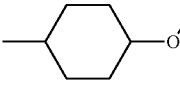 | 2'-Me | H |
| 4-F | 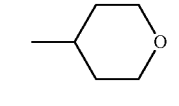 | 2'-MeO | H |
| 4-F | 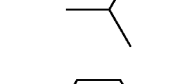 | 2'-MeO | H |
| 4-F | 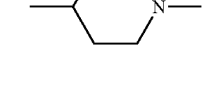 | 2'-MeO | H |
| 4-F | 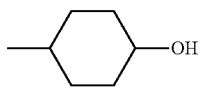 | 2'-MeO | H |
314
-continued
| R₁ | R₂ | R₃ | R₄ |
|---|---|---|---|
| 4-F | 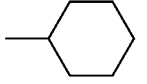 | 2'-MeO | H |
| 4-F | 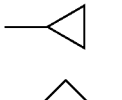 | 2'-MeO | H |
| 4-F | 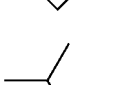 | 2'-MeO | H |
| 4-F | 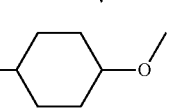 | 2'-MeO | H |
| 4-F | 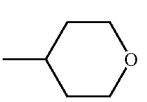 | 6'-Me | H |
| 4-F | 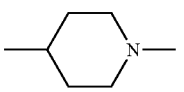 | 6'-Me | H |
| 4-F | 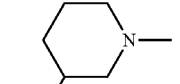 | 6'-Me | H |
| 4-F | 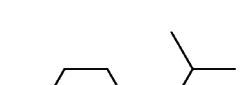 | 6'-Me | H |
| 4-F |  | 6'-Me | H |
| 4-F | 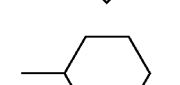 | 6'-Me | H |
| 4-F | 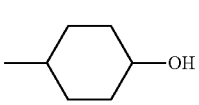 | 6'-Me | H |
| 4-F | 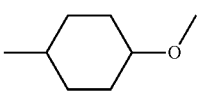 | 6'-Me | H |
| 4-F | 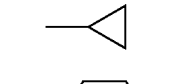 | 6'-Me | H |
| 4-F | 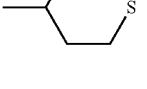 | 6'-Me | H |

315
-continued
| R₁ | R₂ | R₃ | R₄ |
|---|---|---|---|
| 4-F |  | 6'-NHAc | H |
| 4-F | 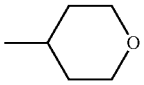 | 6'-NHAc | H |
| 4-F | 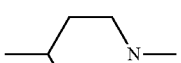 | 6'-NHAc | H |
| 4-F |  | 6'-NHAc | H |
| 4-F | 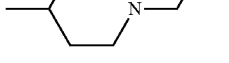 | 6'-NHAc | H |
| 4-F | 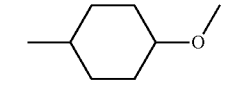 | 6'-NHAc | H |
| 4-F | 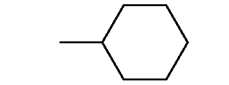 | 6'-NHAc | H |
| 4-Cl |  | 2'-MeO | H |
| 4-Cl | 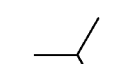 | 2'-MeO | H |
| 4-Cl | 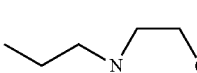 | 2'-MeO | H |
| 4-Cl | 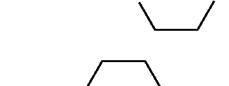 | 2'-MeO | H |
| 4-Cl | 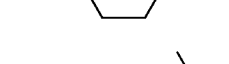 | 2'-MeO | H |
| 4-Cl | 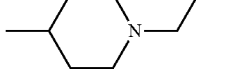 | 2'-MeO | H |
| 4-Cl | 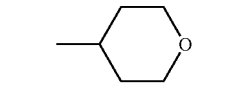 | 2'-MeO | H |
| 4-Cl |  | 6'-Me | H |
316
-continued
| R₁ | R₂ | R₃ | R₄ |
|---|---|---|---|
| 4-Cl | 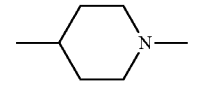 | 6'-Me | H |
| 4-Cl | 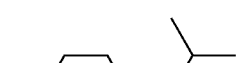 | 6'-Me | H |
| 4-Cl | 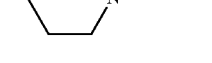 | 6'-Me | H |
| 4-Cl | 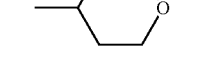 | 6'-Me | H |
| 4-Cl | 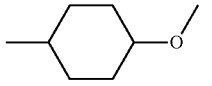 | 6'-Me | H |
| 4-Cl | 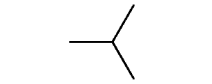 | 2'-Me | H |
| 4-Cl | 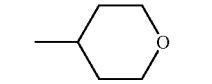 | 2'-Me | H |
| 4-Cl | 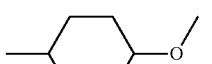 | 2'-Me | H |
| 4-CF₃ |  | 2'-MeO | H |
| 4-CF₃ | 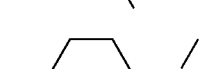 | 2'-MeO | H |
| 4-CF₃ | 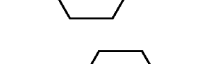 | 2'-MeO | H |
| 4-CF₃ |  | 2'-MeO | H |
| 4-CF₃ |  | 2'-MeO | H |
| 4-CF₃ |  | 2'-MeO | H |
| 4-CF₃ |  | 2'-MeO | H |

317
-continued
| R₁ | R₂ | R₃ | R₄ |
|---|---|---|---|
| 4-CF₃ |  | 2'-MeO | H |
| 4-CF₃ |  | 2'-MeO | H |
| 4-CF₃ | 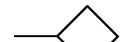 | 2'-MeO | H |
| 4-CF₃ |  | 6'-Me | H |
| 4-CF₃ |  | 6'-Me | H |
| 4-CF₃ | 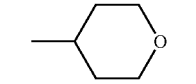 | 6'-Me | H |
| 4-CF₃ | 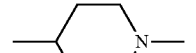 | 6'-Me | H |
| 4-CF₃ | 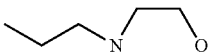 | 6'-Me | H |
| 4-CF₃ | 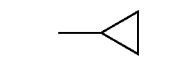 | 6'-Me | H |
| 4-CF₃ |  | 6'-Me | H |
| 4-CF₃ |  | 6'-Me | H |
| 4-OCF₃ | 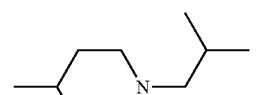 | 2'-MeO | H |
| 4-OCF₃ | 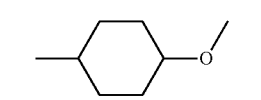 | 2'-MeO | H |
| 4-OCF₃ | 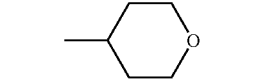 | 2'-MeO | H |
| 4-OCF₃ |  | 2'-MeO | H |
| 4-OCF₃ | 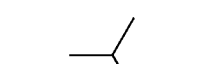 | 2'-MeO | H |
318
-continued
| R₁ | R₂ | R₃ | R₄ |
|---|---|---|---|
| 4-OCF₃ | 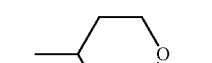 | 2'-MeO | H |
| 3,4-dichloro | 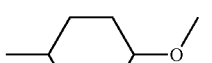 | 2'-MeO | H |
| 3,4-dichloro | 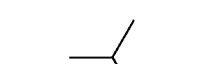 | 2'-MeO | H |
| 3,4-dichloro | 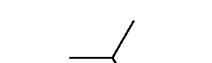 | 2'-MeO | H |
| 2,4-dichloro | 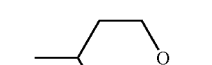 | H | H |
| 3-OCF₃ | 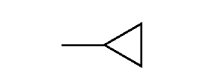 | H | H |
| 3-OCF₃ | 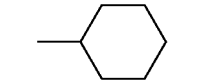 | H | H |
| 3-OCF₃ | 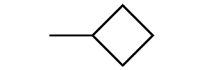 | H | H |
| 3-OCF₃ | 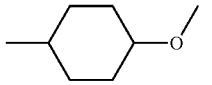 | H | H |
| 3-OCF₃ | 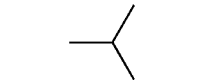 | H | H |
| 3-OCF₃ | 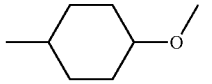 | H | H |
| 3-OCF₃ | | 2'-Me | H |
| 3-OCF₃ | | 2'-Me | H |
| 3-OCF₃ | | 2'-Me | H |
| 3-OCF₃ | | 2'-Me | H |
| 3-OCF₃ | | 2'-MeO | H |

| 319 -continued | | | |
|---|---|---|---|
| R₁ | R₂ | R₃ | R₄ |
| 3-OCF₃ |  | 2'-MeO | H |
| 3-OCF₃ | 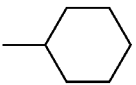 | 2'-MeO | H |
| 3-OCF₃ | 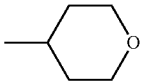 | 2'-MeO | H |
| 4-F |  | 5'-Me | H |
| 4-F |  | 5'-Me | H |
| 4-F | 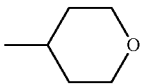 | 5'-Me | H |
| 4-F | 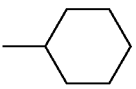 | 5'-Me | H |
| 4-F |  | 5'-Me | H |
| 4-F | 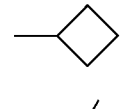 | 5'-Me | H |
| 4-F | 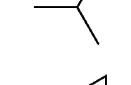 | 6'-MeO | H |
| 4-F | 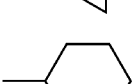 | 6'-MeO | H |
| 4-F |  | 6'-MeO | H |
| 4-F | 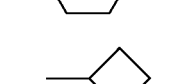 | 6'-MeO | H |
| 4-F | 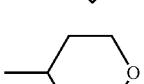 | 6'-MeO | H |
| 4-F | 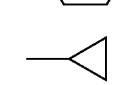 | 6'-MeO | H |
| 4-F |  | 4'-Me | H |
| 4-CF₃ |  | 2'-Me | H |
| 320 -continued | | | |
|---|---|---|---|
| R₁ | R₂ | R₃ | R₄ |
| 4-CF₃ |  | 2'-Me | H |
| 4-CF₃ | 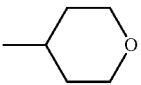 | 2'-Me | H |
| 4-CF₃ | 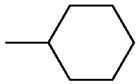 | 2'-Me | H |
| 4-CF₃ |  | 2'-Me | H |
| 4-CF₃ | 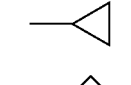 | 2'-Me | H |
| 4-CF₃ |  | 2'-Me | H |
| 4-CF₃ | 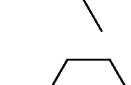 | 6'-NHAc | H |
| 4-CF₃ | 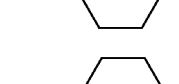 | 6'-NHAc | H |
| 4-CF₃ |  | 6'-NHAc | H |
| 4-CF₃ | 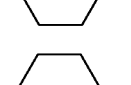 | 6'-NHAc | H |
| 4-CF₃ | 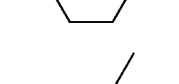 | 6'-NHAc | H |
| 4-CF₃ | 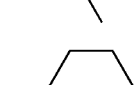 | 5'-Me | H |
| 4-CF₃ | 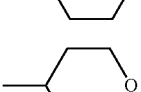 | 5'-Me | H |
| 4-CF₃ |  | 5'-Me | H |
| 4-CF₃ | 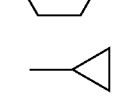 | 5'-Me | H |
| 4-CF₃ | 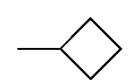 | 5'-Me | H |

321 -continued

| R₁ | R₂ | R₃ | R₄ |
|---|---|---|---|
| 4-CF₃ | cyclohexyl-OH | 5'-Me | H |
| 4-CF₃ | isopropyl | 6'-MeO | H |
| 4-CF₃ | cyclohexyl | 6'-MeO | H |
| 4-CF₃ | tetrahydropyranyl | 6'-MeO | H |
| 4-CF₃ | cyclohexyl-OMe | 6'-MeO | H |
| 4-CF₃ | cyclopropyl | 6'-MeO | H |
| 4-CF₃ | cyclobutyl | 6'-MeO | H |
| 2-Cl | cyclohexyl | H | H |
| 2-Cl | cyclopropyl | H | H |
| 2-Cl | tetrahydropyranyl | 2'-MeO | H |
| 3-Cl | cyclohexyl | 2'-MeO | H |
| 3-Cl | cyclohexyl-OH | H | H |
| 3-Cl | cyclopropyl | H | H |
| 3-Cl | cyclobutyl | H | H |
| 4-Cl | tetrahydropyranyl | 5'-Br | H |
| 4-Cl | cyclohexyl-OMe | 5'-Br | H |
| 2-CF₃ | isopropyl | H | H |

322 -continued

| R₁ | R₂ | R₃ | R₄ |
|---|---|---|---|
| 2-CF₃ | cyclohexyl-OMe | H | H |
| 3-CF₃ | isopropyl | H | H |
| 3-CH₃S | isopropyl | H | H |
| 3-CH₃SO | isopropyl | H | H |
| 4-CH₃S | isopropyl | H | H |
| 4-CH₃SO | isopropyl | H | H |
| 4-CH₃ | isopropyl | 5'-CH₃ | H |
| 4-CH₃ | tetrahydropyranyl | 5'-CH₃ | H |
| 4-CH₃ | cyclohexyl | 5'-CH₃ | H |
| 4-CH₃ | cyclohexyl-OMe | 5'-CH₃ | H |
| 4-CH₃ | cyclohexyl | 2'-MeO | H |
| 4-CH₃ | cyclohexyl-OH | 2'-MeO | H |
| 4-CH₃ | cyclohexyl | H | H |
| 4-CH₃ | cyclohexyl-OH | 6'-CH₃ | H |
| 3-CH₃S | cyclohexyl-OH | 2'-CH₃ | H |
| 3,4-dichloro | isopropyl | H | H |

323 -continued

| R₁ | R₂ | R₃ | R₄ |
|---|---|---|---|
| 4-CH₃ | 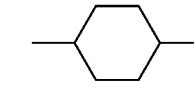 cyclohexyl-OH | 5'-CH₃ | H |
| 4-CH₃ | cyclohexyl-OH | H | H |
| 4-CH₃ | cyclopropyl | 2'-MeO | H |
| 4-CH₃ | cyclopropyl | 6'-CH₃ | H |
| 4-CH₃ | cyclopropyl | 2'-CH₃ | H |
| 4-CH₃ | cyclopropyl | 5'-CH₃ | H |
| 3,4-dichloro | cyclopropyl | H | H |
| 4-CH₃ | cyclobutyl | 2'-MeO | H |
| 4-CH₃ | cyclobutyl | H | H |
| 4-CH₃ | cyclobutyl | 6'-CH₃ | H |
| 4-CH₃ | cyclobutyl | 2'-CH₃ | H |
| 4-CH₃ | cyclobutyl | 5'-CH₃ | H |
| 4-CH₃ | cyclopropyl | H | H |
| 3,4-dichloro | cyclohexyl | H | H |
| 3,4-dichloro | tetrahydropyranyl | H | H |
| 3,4-dichloro | methoxycyclohexyl | H | H |
| 3,4-dichloro | isopropyl | 6'-CH₃ | H |
| 3,4-dichloro | cyclohexyl | 6'-CH₃ | H |

324 -continued

| R₁ | R₂ | R₃ | R₄ |
|---|---|---|---|
| 3,4-dichloro | methoxycyclohexyl | 6'-CH₃ | H |
| 4-CH₃ | isopropyl | 6'-MeO | H |
| 4-CH₃ | cyclohexyl | 6'-MeO | H |
| 4-CH₃ | methoxycyclohexyl | 6'-MeO | H |
| 4-CH₃ | tetrahydropyranyl | 6'-MeO | H |
| 4-OCF₃ | cyclopropyl | 2'-MeO | H |
| 4-OCF₃ | cyclohexyl | 2'-MeO | H |
| 3,4-dichloro | cyclopropyl | 2'-MeO | H |
| 2,4-dichloro | cyclopropyl | H | H |
| 2,4-dichloro | cyclohexyl | H | H |
| 2,4-dichloro | isopropyl | 2'-MeO | H |
| 2,4-dichloro | cyclopropyl | 2'-MeO | H |
| 2,4-dichloro | methoxycyclohexyl | 2'-MeO | H |
| 4-OCF₃ | CH(CH₂OMe)₂ | 2'-MeO | H |
| 4-CH₃ | CH(CH₂OMe)₂ | 2'-MeO | H |
| 4-CH₃ | CH(CH₂OMe)₂ | 6'-CH₃ | H |

US 8,716,292 B2
325
-continued
| R₁ | R₂ | R₃ | R₄ |
|---|---|---|---|
| 3,4-dichloro | 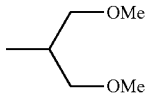 | 2'-MeO | H |
| 4-Br | 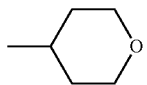 | 2'-MeO | H |
| 4-Br | 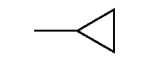 | 2'-MeO | H |
| 4-Br | 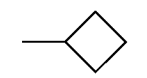 | 2'-MeO | H |
| 4-Br | 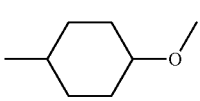 | 2'-MeO | H |
| 3-F | 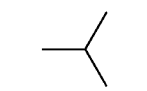 | H | H |
| 3-F | 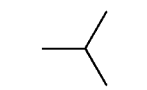 | 2'-MeO | H |
| 3-F | 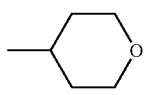 | 2'-MeO | H |
| 3,4-difluoro | 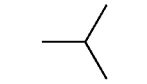 | H | H |
| 3,4-difluoro | 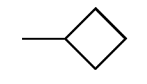 | H | H |
| 3,4-difluoro | 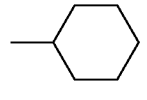 | H | H |
| 3,4-difluoro | 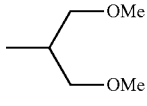 | H | H |
| 3,4-difluoro | 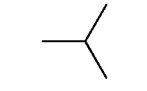 | 2'-MeO | H |
| 3,4-difluoro | 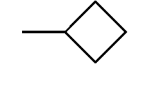 | 2'-MeO | H |
| 3,4-difluoro | 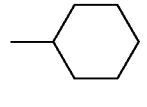 | 2'-MeO | H |
| 3,4-difluoro | 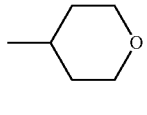 | 2'-MeO | H |
326
-continued
| R₁ | R₂ | R₃ | R₄ |
|---|---|---|---|
| 4-F | 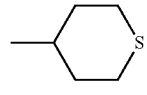 | 2'-MeO | H |
| 4-F | 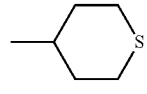 | 2'-CH₃ | H |
| 2-OCF₃ | 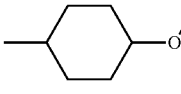 | 2'-MeO | H |
| 2-OCF₃ | 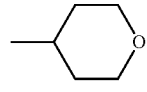 | 2'-MeO | H |
| 2-OCF₃ | 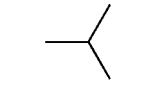 | 2'-MeO | H |
| 2-OCF₃ | 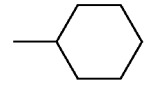 | 2'-MeO | H |
| 4-F | 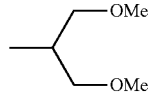 | 2'-MeO | H |
| 4-F | 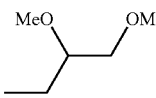 | 2'-MeO | H |
| 4-CF₃ | 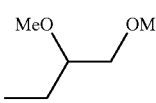 | 2'-MeO | H |
| 3-Cl | 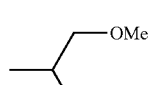 | 2'-MeO | H |
| 4-Cl | 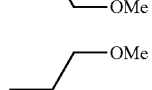 | 2'-MeO | H |
| 3-Cl | 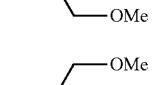 | 6'-CH₃ | H |
| 3-Cl | 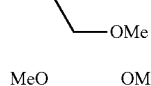 | 2'-MeO | H |
| 4-Cl | MeO OMe | 2'-MeO | H |
| 3-Cl | | H | H |

327
-continued

| R₁ | R₂ | R₃ | R₄ |
|---|---|---|---|
| 2-Cl |  | H | H |
| 4-Cl |  | 5'-Br | H |
| 4-Cl |  | 5'-Br | H |
| 3-Cl |  | 2'-MeO | H |
| 3-Cl | 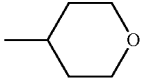 | 2'-MeO | H |
| 3-Cl | 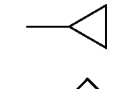 | 2'-MeO | H |
| 3-Cl |  | 2'-MeO | H |
| 3-Cl | 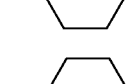 | 6'-CH₃ | H |
| 3-Cl | 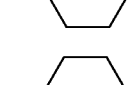 | 6'-CH₃ | H |
| 4-OCF₃ |  | 6'-CH₃ | H |
| 4-Cl |  | 2'-MeO | 7-F |
| 4-Cl |  | 6'-Me | 7-F |
| 4-Cl | 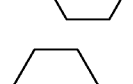 | 6'-Me | 7-F |
| 4-Cl | 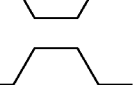 | 6'-Me | 7-F |
| 4-Cl | 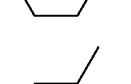 | 2'-MeO | 7-F |
| 4-Cl |  | 2'-MeO | 7-F |
| 4-Cl | 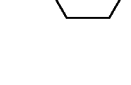 | 2'-MeO | 7-F |

328
-continued

| R₁ | R₂ | R₃ | R₄ |
|---|---|---|---|
| 4-Cl | 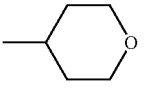 | 2'-MeO | 7-F |
| 4-Cl | 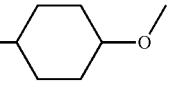 | 6'-Me | 8-F |
| 4-Cl | 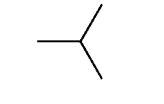 | 6'-Me | 8-F |
| 4-Cl | 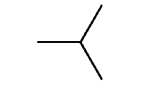 | 2'-MeO | 8-F |
| 4-Cl | 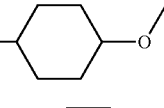 | 2'-MeO | 8-F |
| 4-Cl | 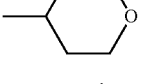 | 2'-MeO | 8-F |
| 4-Cl | 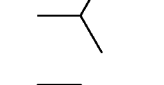 | 2'-MeO | 7-MeO |
| 4-Cl | 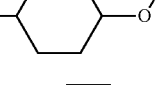 | 2'-MeO | 7-MeO |
| 4-Cl | 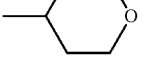 | 2'-MeO | 7-MeO |
| 4-Cl | 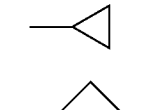 | 2'-MeO | 7-MeO |
| 4-Cl | 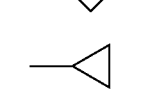 | 2'-MeO | 7-MeO |
| 3,4-dichloro |  | 6'-Me | H |
| 3,4-dichloro | 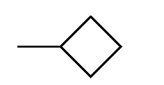 | 6'-Me | H |
| 3,4-dichloro | | 6'-Me | H |
| 3,4-dichloro | 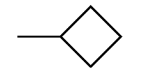 | 2'-MeO | H |
| 2,4-dichloro | 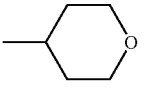 | 2'-MeO | H |
| 2,4-dichloro | | 2'-MeO | H |

329
-continued

| R₁ | R₂ | R₃ | R₄ |
|---|---|---|---|
| 3,4-dichloro | 4-methyltetrahydropyran | 6'-Me | 7-F |
| 3,4-dichloro | isobutyl | 6'-Me | 7-F |
| 3,4-dichloro | 4-methoxycyclohexylmethyl | 6'-Me | 7-F |
| 3,4-dichloro | isobutyl | 2'-MeO | 7-F |
| 3,4-dichloro | 4-methyltetrahydropyran | 2'-MeO | 7-F |
| 3,4-dichloro | cyclopropylmethyl | 2'-MeO | 7-F |
| 3,4-dichloro | cyclobutylmethyl | 2'-MeO | 7-F |
| 3,4-dichloro | isobutyl | 6'-Me | 8-F |
| 3,4-dichloro | cyclopropylmethyl | 6'-Me | 8-F |
| 3,4-dichloro | 4-methyltetrahydropyran | 6'-Me | 8-F |
| 3,4-dichloro | 4-methoxycyclohexylmethyl | 6'-Me | 8-F |
| 3,4-dichloro | isobutyl | 2'-MeO | 8-F |
| 3,4-dichloro | cyclopropylmethyl | 2'-MeO | 8-F |
| 3,4-dichloro | 4-methyltetrahydropyran | 2'-MeO | 8-F |
| 3,4-dichloro | 4-methoxycyclohexylmethyl | 2'-MeO | 8-F |
| 4-OCF₃ | 4-methoxycyclohexylmethyl | 2'-MeO | 8-F |
| 4-OCF₃ | cyclohexylmethyl | 2'-MeO | 8-F |

330
-continued

| R₁ | R₂ | R₃ | R₄ |
|---|---|---|---|
| 4-OCF₃ | isobutyl | 6'-Me | 8-F |
| 4-OCF₃ | cyclopropylmethyl | 6'-Me | 8-F |
| 4-OCF₃ | cyclohexylmethyl | 6'-Me | 8-F |
| 4-OCF₃ | 4-methoxycyclohexylmethyl | 6'-Me | 8-F |
| 4-Cl | isobutyl | 6'-Me | 8-MeO |
| 4-Cl | cyclopropylmethyl | 2'-MeO | 8-F |
| 4-Cl | 4-methoxycyclohexylmethyl | 6'-Me | 8-MeO |
| 4-Cl | cyclopropylmethyl | 6'-Me | 7-MeO |
| 4-Cl | cyclohexylmethyl | 6'-Me | 7-MeO |
| 4-OCF₃ | isobutyl | 2'-MeO | 7-F |
| 4-OCF₃ | cyclopropylmethyl | 2'-MeO | 7-F |
| 4-OCF₃ | cyclohexylmethyl | 2'-MeO | 7-F |
| 4-OCF₃ | 4-methyltetrahydropyran | 2'-MeO | 7-F |
| 4-OCF₃ | isobutyl | 6'-Me | 7-F |
| 4-OCF₃ | cyclohexylmethyl | 6'-Me | 7-F |
| 4-OCF₃ | 4-methoxycyclohexylmethyl | 6'-Me | 7-F |
| 4-NHAc | isobutyl | 2'-MeO | H |

-continued

| R₁ | R₂ | R₃ | R₄ |
|---|---|---|---|
| 4-NHAc | cyclopropyl | 2'-MeO | H |
| 4-NHAc | 4-methoxycyclohexyl | 2'-MeO | H |
| 4-NHAc | cyclohexyl | 2'-MeO | H |
| 4-NHAc | tetrahydropyran-4-yl | 6'-Me | H |
| 4-NHAc | tetrahydropyran-4-yl | 2'-MeO | H |
| 4-NHAc | 1,3-dimethoxypropan-2-yl | 2'-MeO | H |
| 4-NHAc | isopropyl | 6'-Me | H |
| 4-NHAc | 4-methoxycyclohexyl | 6'-Me | H |
| 4-NHAc | cyclopropyl | 6'-Me | H |
| 4-NHAc | cyclohexyl | 6'-Me | H |
| 4-COOCH₃ | isopropyl | 2'-MeO | H |
| 4-COOCH₃ | cyclopropyl | 2'-MeO | H |
| 3,4-difluoro | cyclopropyl | 2'-MeO | H |

-continued

| R₁ | R₂ | R₃ | R₄ |
|---|---|---|---|
| 3,4-difluoro | 4-methoxycyclohexyl | 2'-MeO | H |
| 3,4-difluoro | tetrahydropyran-4-yl | 2'-MeO | H |
| 3,4-difluoro | cyclopropyl | H | H |
| 3,4-difluoro | 4-methoxycyclohexyl | H | H |
| 3,4-difluoro | tetrahydropyran-4-yl | H | H |
| 4-F | isopropyl | 2'-MeO | 8-CN |
| 4-F | 4-methoxycyclohexyl | 2'-MeO | 8-CN |
| 4-F | tetrahydropyran-4-yl | 2'-MeO | 8-CN |
| 4-F | isopropyl | 6'-Me | 8-CN |
| 4-F | 4-methoxycyclohexyl | 6'-Me | 8-CN |
| 4-F | isopropyl | 2'-MeO, 6'-Me | H. |

4. A pharmaceutical composition comprising a therapeutically effective amount of the compound of claim 3 and a pharmaceutically acceptable excipient, adjuvant, carrier, buffer or stabilizer.

5. A compound selected from the group consisting of:
TBI-1002
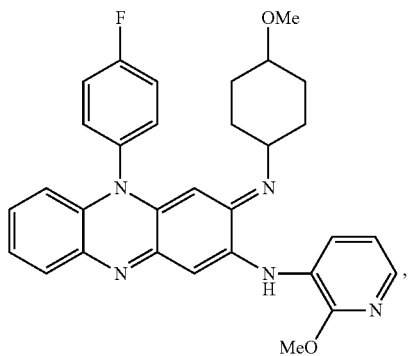
TBI-1004
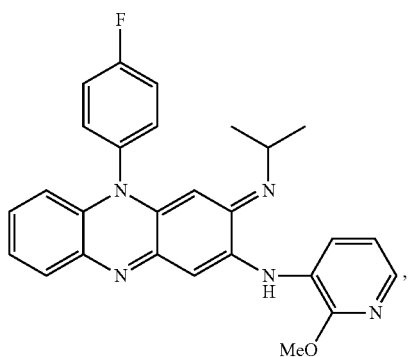
TBI-1010
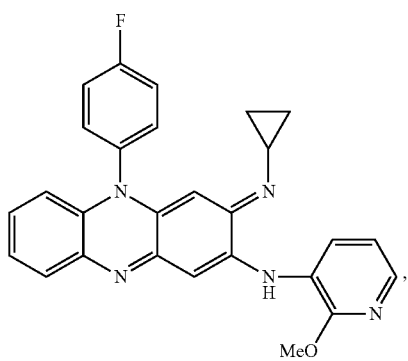
TBI-166
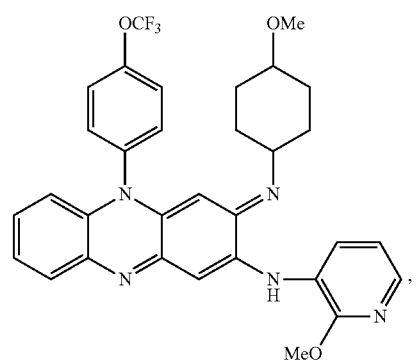
-continued
TBI-449
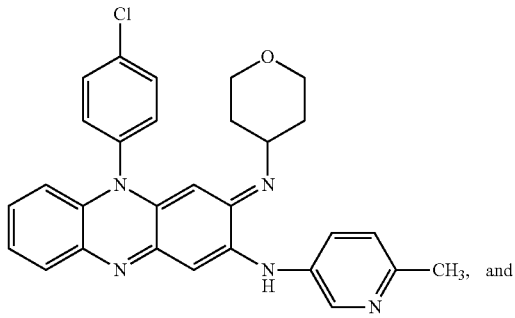
and
TBI-450
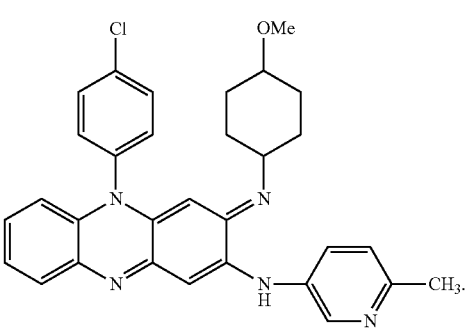
6. A compound selected from the group consisting of:
TBI-416
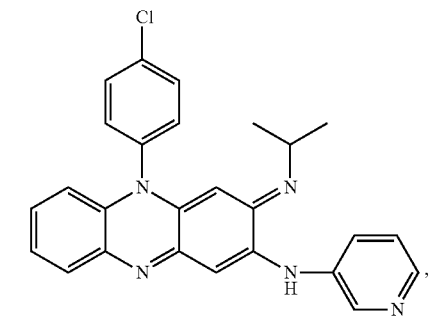
TBI-678
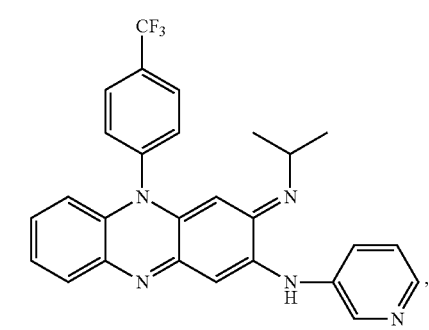

-continued
TBI-688
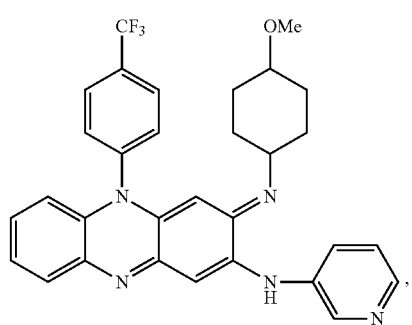
TBI-161
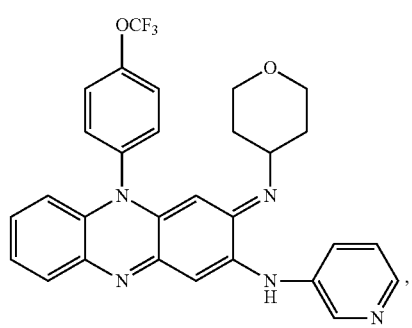
TBI-444
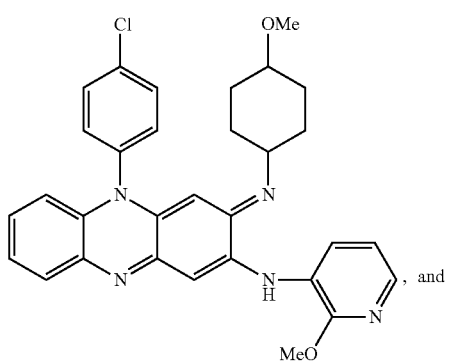
TBI-443
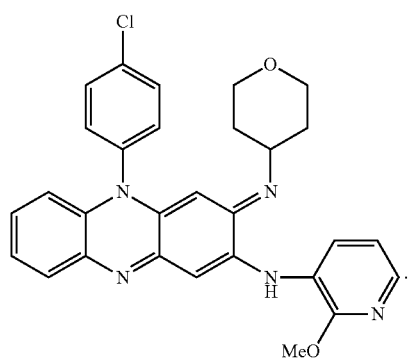
7. A compound selected from the group consisting of:
TBI-1004
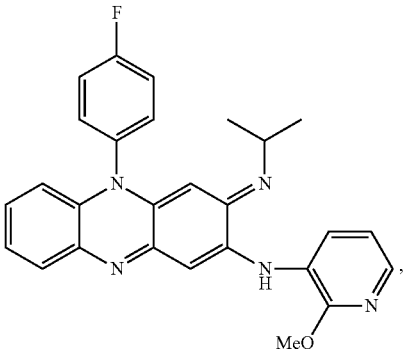
TBI-166
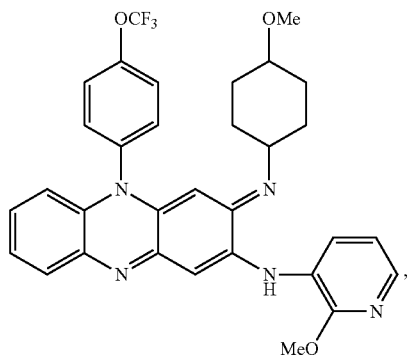
TBI-449
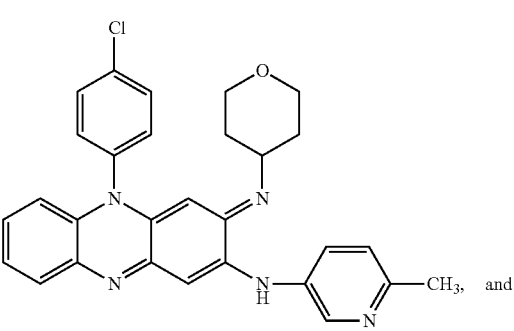
, and
TBI-450
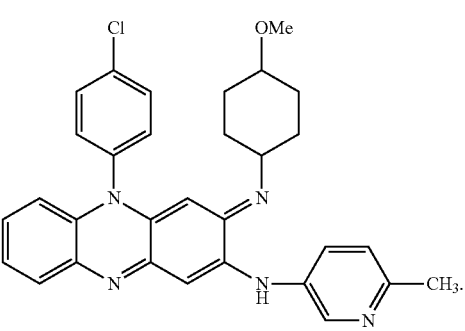
.
* * * * *